(12) United States Patent
Jain et al.

(10) Patent No.: US 11,789,837 B1
(45) Date of Patent: Oct. 17, 2023

(54) ADAPTIVE DATA COLLECTION IN CLINICAL TRIALS TO INCREASE THE LIKELIHOOD OF ON-TIME COMPLETION OF A TRIAL

(71) Applicant: VigNet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 17/592,440

(22) Filed: Feb. 3, 2022

Related U.S. Application Data

(63) Continuation-in-part of application No. 17/569,542, filed on Jan. 6, 2022, now Pat. No. 11,645,180, and a
(Continued)

(51) Int. Cl.
*G06F 11/30* (2006.01)
*G06F 11/34* (2006.01)
(Continued)

(52) U.S. Cl.
CPC ...... *G06F 11/3006* (2013.01); *G06F 11/3075* (2013.01); *G06F 11/3438* (2013.01); *G06F 18/22* (2023.01); *G16H 15/00* (2018.01)

(58) Field of Classification Search
CPC ............. G06F 11/3006; G06F 11/3075; G06F 11/3438; G06K 9/6215
See application file for complete search history.

(56) References Cited

U.S. PATENT DOCUMENTS 5,197,489 A * 3/1993 Conlan ................. G16H 15/00 600/595
5,545,186 A 8/1996 Olson et al.
(Continued)

FOREIGN PATENT DOCUMENTS

EP 2545468 1/2013
WO WO 1995012812 5/1995
(Continued)

OTHER PUBLICATIONS

Esposito, Massimo, et al. "A smart mobile, self-configuring, context-aware architecture for personal health monitoring." Engineering Applications of Artificial Intelligence 67 (2018): 136-156. (Year: 2018).*
(Continued)

Primary Examiner — Matthew J Brophy
(74) Attorney, Agent, or Firm — Fish & Richardson P.C.

(57) ABSTRACT

Methods, systems, and apparatus, including computer programs encoded on computer storage media, for managing and adapting monitoring programs. In some implementations, a system communicates with a set of remote devices involved in a monitoring program that involves collection of data from the remote devices over a communication network. The system determines a set of attributes associated with an outcome or condition that has occurred for multiple of the remote devices. The system generates parameters to adapt the monitoring program, and the system selects a second group of remote devices to involve in the adapted monitoring program based on profiles or sets of attributes of users associated with the remote devices. The system configures the remote devices in the selected second group to perform monitoring for the adapted monitoring program, including acquiring data for the adapted monitoring program
(Continued)

and providing the acquired data to a server over the communication network.

24 Claims, 49 Drawing Sheets

Related U.S. Application Data continuation-in-part of application No. 17/378,643, filed on Jul. 16, 2021, now Pat. No. 11,296,971, which is a continuation-in-part of application No. 17/324,098, filed on May 18, 2021, now Pat. No. 11,316,941, said application No. 17/569,542 is a continuation of application No. 17/233,356, filed on Apr. 16, 2021, now Pat. No. 11,281,553, application No. 17/592,440 is a continuation-in-part of application No. 17/233,103, filed on Apr. 16, 2021, now Pat. No. 11,586,524, and a continuation-in-part of application No. 17/185,954, filed on Feb. 25, 2021, said application No. 17/378,643 is a continuation-in-part of application No. 17/177,153, filed on Feb. 16, 2021, now Pat. No. 11,521,714, and a continuation-in-part of application No. 17/166,899, filed on Feb. 3, 2021, now Pat. No. 11,196,656, and a continuation-in-part of application No. 17/166,777, filed on Feb. 3, 2021, now Pat. No. 11,361,846.

(51) Int. Cl.
*G06F 18/22* (2023.01)
*G16H 15/00* (2018.01)

(56) References Cited

U.S. PATENT DOCUMENTS

| | | | |
|---|---|---|---|
| 5,547,878 A | 8/1996 | Kell | |
| 5,573,013 A * | 11/1996 | Conlan | G01P 1/127 600/595 |
| 5,832,474 A | 11/1998 | Lopresti et al. | |
| 6,029,144 A | 2/2000 | Barrett et al. | |
| 6,039,688 A | 3/2000 | Douglas et al. | |
| 6,260,022 B1 | 7/2001 | Brown | |
| 6,269,339 B1 | 7/2001 | Silver | |
| 6,514,200 B1 | 2/2003 | Khouri | |
| 6,574,622 B1 | 6/2003 | Miyauchi et al. | |
| 6,663,846 B1 | 12/2003 | McCombs et al. | |
| 6,865,580 B1 | 3/2005 | Bush | |
| 6,879,970 B2 | 4/2005 | Shiffman et al. | |
| 7,054,782 B2 | 5/2006 | Hartlaub | |
| 7,076,534 B1 | 7/2006 | Cleron et al. | |
| 7,113,917 B2 | 9/2006 | Jacobi et al. | |
| 7,170,993 B2 | 1/2007 | Anderson et al. | |
| 7,213,009 B2 | 5/2007 | Pstotnik et al. | |
| 7,246,069 B1 * | 7/2007 | O'Hanlon | G16H 40/63 600/528 |
| 7,251,609 B1 | 7/2007 | McAlindon et al. | |
| 7,330,717 B2 | 2/2008 | Gidron et al. | |
| 7,359,915 B1 | 4/2008 | Bush | |
| 7,415,447 B2 | 8/2008 | Shiffman et al. | |
| 7,427,920 B2 * | 9/2008 | Martin | A61B 5/002 340/286.07 |
| 7,447,643 B1 | 11/2008 | Olson et al. | |
| 7,730,063 B2 | 6/2010 | Eder | |
| 7,752,059 B2 | 7/2010 | Sweeney et al. | |
| 7,809,601 B2 | 10/2010 | Shaya et al. | |
| 7,809,660 B2 | 10/2010 | Friedlander et al. | |
| 7,930,262 B2 | 4/2011 | Friedlander et al. | |
| 7,937,275 B2 | 5/2011 | Schoenberg | |
| 8,019,618 B2 * | 9/2011 | Brown | G16H 50/20 600/300 |
| 8,032,545 B2 | 10/2011 | Setimi | |
| 8,065,180 B2 | 11/2011 | Hufford et al. | |
| 8,157,730 B2 | 4/2012 | LeBouef et al. | |
| 8,255,240 B2 * | 8/2012 | O'Hanlon | G16H 10/60 600/300 |
| 8,316,020 B1 | 11/2012 | Kleinmann | |
| 8,380,531 B2 | 2/2013 | Paty et al. | |
| 8,433,605 B2 | 4/2013 | Hufford et al. | |
| 8,527,486 B2 | 9/2013 | Wittig et al. | |
| 8,533,029 B2 | 9/2013 | Hufford et al. | |
| 8,583,453 B2 | 11/2013 | Plummer et al. | |
| 8,589,175 B2 | 11/2013 | Glauser et al. | |
| 8,606,595 B2 | 12/2013 | Udani | |
| 8,682,693 B2 * | 3/2014 | Rao | H04L 12/4641 705/2 |
| 8,684,922 B2 | 4/2014 | Tran | |
| 8,706,521 B2 | 4/2014 | Ramarajan et al. | |
| 8,707,392 B2 | 4/2014 | Birtwhistle et al. | |
| 8,825,775 B2 | 9/2014 | Bohner et al. | |
| 8,966,548 B2 | 2/2015 | Busse et al. | |
| 8,990,250 B1 | 3/2015 | Chowdry et al. | |
| 9,020,971 B2 | 4/2015 | Bayliss et al. | |
| 9,286,442 B2 | 3/2016 | Csoma et al. | |
| 9,361,011 B1 | 6/2016 | Burns | |
| 9,414,776 B2 * | 8/2016 | Sillay | A61B 5/14542 |
| 9,426,433 B1 | 8/2016 | Mazzarella | |
| 9,461,972 B1 | 10/2016 | Mehta | |
| 9,495,651 B2 | 11/2016 | O'Sullivan et al. | |
| 9,514,655 B1 | 12/2016 | Nusbaum et al. | |
| 9,595,123 B2 * | 3/2017 | Brayanov | G06T 11/206 |
| 9,659,254 B2 | 5/2017 | Achin et al. | |
| 9,753,618 B1 | 9/2017 | Jain et al. | |
| 9,754,081 B2 * | 9/2017 | Ghasemzadeh | G16H 50/50 |
| 9,813,318 B2 | 11/2017 | Iyoob et al. | |
| 9,844,725 B1 | 12/2017 | Durkin et al. | |
| 9,848,061 B1 | 12/2017 | Jain et al. | |
| 9,858,063 B2 | 1/2018 | Jain et al. | |
| 9,928,230 B1 | 3/2018 | Jain et al. | |
| 9,983,775 B2 | 5/2018 | Jain et al. | |
| 10,069,934 B2 | 9/2018 | Jain et al. | |
| 10,095,688 B1 | 10/2018 | Jain et al. | |
| 10,231,622 B2 | 3/2019 | Soyao et al. | |
| 10,255,274 B1 | 4/2019 | Schilling | |
| 10,304,000 B2 | 5/2019 | Birnbaum et al. | |
| 10,311,972 B2 * | 6/2019 | Kohlbrecher | G06F 11/3006 |
| 10,347,020 B2 * | 7/2019 | Brayanov | G06T 11/206 |
| 10,373,072 B2 * | 8/2019 | Britton | G06N 20/00 |
| 10,379,987 B1 * | 8/2019 | Chari | G06F 11/3495 |
| 10,452,816 B2 | 10/2019 | Kidd et al. | |
| 10,455,262 B2 | 10/2019 | Rieger et al. | |
| 10,510,438 B2 | 12/2019 | Frazier et al. | |
| 10,521,557 B2 | 12/2019 | Jain et al. | |
| 10,546,339 B2 | 1/2020 | Jiao et al. | |
| 10,561,321 B2 * | 2/2020 | Valys | A61B 5/7267 |
| 10,565,894 B1 | 2/2020 | Jain et al. | |
| 10,580,531 B2 | 3/2020 | Jiao et al. | |
| 10,621,550 B2 * | 4/2020 | Carey | G06F 21/6263 |
| 10,628,553 B1 | 4/2020 | Murrish et al. | |
| 10,636,525 B2 | 4/2020 | Jiao et al. | |
| 10,650,474 B2 | 5/2020 | Jiao et al. | |
| 10,672,519 B2 | 6/2020 | Jiao et al. | |
| 10,685,090 B2 * | 6/2020 | Petterson | G16H 10/20 |
| 10,692,589 B2 * | 6/2020 | Mueller-Wolf | G16H 80/00 |
| 10,756,957 B2 | 8/2020 | Jain et al. | |
| 10,762,990 B1 | 9/2020 | Jain et al. | |
| 10,775,974 B2 | 9/2020 | Jain et al. | |
| 10,795,795 B1 * | 10/2020 | Chari | G06F 11/3495 |
| 10,887,157 B1 | 1/2021 | Fletcher | |
| 10,938,634 B1 | 3/2021 | Cruise | |
| 10,938,651 B2 | 3/2021 | Jain et al. | |
| 10,956,950 B2 * | 3/2021 | Al-Ali | G06F 21/105 |
| 10,964,435 B2 * | 3/2021 | Bar | G16H 40/67 |
| 11,023,511 B1 | 6/2021 | Fletcher et al. | |
| 11,029,972 B2 * | 6/2021 | Vichare | G06F 11/3466 |
| 11,056,242 B1 | 7/2021 | Jain et al. | |
| 11,061,798 B1 | 7/2021 | Jain et al. | |
| 11,082,487 B1 | 8/2021 | Jain et al. | |
| 11,102,304 B1 | 8/2021 | Jain et al. | |
| 11,127,506 B1 | 9/2021 | Jain et al. | |
| 11,151,462 B2 | 10/2021 | Jain et al. | |
| 11,153,156 B2 | 10/2021 | Jain et al. | |

(56) References Cited

U.S. PATENT DOCUMENTS

| | | | |
|---|---|---|---|
| 11,157,823 B2 | 10/2021 | Jain et al. | |
| 11,158,423 B2 | 10/2021 | Jain et al. | |
| 11,196,656 B1 | 12/2021 | Jain et al. | |
| 11,210,606 B1* | 12/2021 | Morgan | G16H 40/20 |
| 11,237,937 B1* | 2/2022 | Chari | G06F 11/3419 |
| 11,240,329 B1 | 2/2022 | Jain et al. | |
| 11,253,188 B2* | 2/2022 | Tal Fass | A61B 5/4806 |
| 11,281,553 B1* | 3/2022 | Jain | G06F 18/22 |
| 11,296,971 B1 | 4/2022 | Jain et al. | |
| 11,316,941 B1 | 4/2022 | Jain et al. | |
| 11,521,714 B1 | 12/2022 | Jain et al. | |
| 11,522,703 B1* | 12/2022 | Jain | H04L 9/0894 |
| 11,586,524 B1 | 2/2023 | Jain et al. | |
| 2001/0019338 A1 | 9/2001 | Roth | |
| 2002/0010596 A1 | 1/2002 | Matory | |
| 2002/0022973 A1 | 2/2002 | Sun | |
| 2002/0095196 A1* | 7/2002 | Linberg | G16H 40/40 607/60 |
| 2002/0099570 A1 | 7/2002 | Knight | |
| 2002/0143563 A1 | 10/2002 | Hufford et al. | |
| 2002/0143595 A1 | 10/2002 | Frank et al. | |
| 2003/0065669 A1 | 4/2003 | Kahn et al. | |
| 2003/0130871 A1 | 7/2003 | Rao et al. | |
| 2003/0135391 A1* | 7/2003 | Edmundson | G16H 50/70 705/14.19 |
| 2003/0165954 A1 | 9/2003 | Katagiri et al. | |
| 2003/0182429 A1 | 9/2003 | Jagels | |
| 2004/0030424 A1 | 2/2004 | Corl et al. | |
| 2004/0059697 A1 | 3/2004 | Forman | |
| 2004/0172447 A1 | 9/2004 | Miller | |
| 2004/0175700 A1 | 9/2004 | Geesaman | |
| 2004/0203755 A1 | 10/2004 | Brunet et al. | |
| 2004/0210457 A1 | 10/2004 | Sameh | |
| 2005/0086587 A1 | 4/2005 | Balz | |
| 2005/0165626 A1 | 7/2005 | Karpf | |
| 2005/0182664 A1 | 8/2005 | Abraham-Fuchs | |
| 2005/0183143 A1* | 8/2005 | Anderholm | G06F 11/3438 726/22 |
| 2005/0186550 A1 | 8/2005 | Gillani | |
| 2005/0246304 A1 | 11/2005 | Knight et al. | |
| 2006/0041452 A1 | 2/2006 | Kukarni | |
| 2006/0107219 A1 | 5/2006 | Ahya | |
| 2006/0136240 A1 | 6/2006 | Cleveland et al. | |
| 2006/0184493 A1 | 8/2006 | Shiffman et al. | |
| 2006/0205564 A1 | 9/2006 | Peterson | |
| 2006/0206861 A1 | 9/2006 | Shenfield et al. | |
| 2006/0218533 A1 | 9/2006 | Koduru et al. | |
| 2006/0277295 A1 | 12/2006 | Masuda et al. | |
| 2007/0021984 A1 | 1/2007 | Brown | |
| 2007/0150314 A1* | 6/2007 | Abraham-Fuchs | G16H 40/20 705/3 |
| 2007/0172844 A1 | 7/2007 | Lancaster et al. | |
| 2007/0179361 A1 | 8/2007 | Brown et al. | |
| 2007/0231828 A1 | 10/2007 | Beachy et al. | |
| 2007/0250429 A1 | 10/2007 | Walser et al. | |
| 2007/0259351 A1 | 11/2007 | Chinitz et al. | |
| 2007/0276270 A1 | 11/2007 | Tran | |
| 2007/0281285 A1 | 12/2007 | Jayaweera | |
| 2007/0294110 A1 | 12/2007 | Settimi | |
| 2008/0005679 A1 | 1/2008 | Rimas-Ribikauskas | |
| 2008/0010945 A1 | 1/2008 | McKenna et al. | |
| 2008/0021287 A1* | 1/2008 | Woellenstein | G16H 50/30 600/300 |
| 2008/0109455 A1 | 5/2008 | Katz | |
| 2008/0127040 A1 | 5/2008 | Barcellona | |
| 2008/0140444 A1 | 6/2008 | Karkanias et al. | |
| 2008/0242221 A1 | 10/2008 | Shapiro et al. | |
| 2008/0243038 A1 | 10/2008 | Bennett | |
| 2008/0254429 A1 | 10/2008 | Woolf et al. | |
| 2008/0261191 A1 | 10/2008 | Woolf et al. | |
| 2008/0275985 A1* | 11/2008 | Kundu | G06Q 40/04 709/224 |
| 2008/0294459 A1 | 11/2008 | Angell et al. | |
| 2008/0311968 A1 | 12/2008 | Hunter | |
| 2009/0023555 A1 | 1/2009 | Raymond | |
| 2009/0024944 A1 | 1/2009 | Louch | |
| 2009/0031215 A1 | 1/2009 | Collier et al. | |
| 2009/0035733 A1 | 2/2009 | Meitar et al. | |
| 2009/0043689 A1 | 2/2009 | Yang | |
| 2009/0076856 A1 | 3/2009 | Darby et al. | |
| 2009/0125333 A1 | 5/2009 | Heywood et al. | |
| 2009/0163182 A1 | 6/2009 | Gatti | |
| 2009/0163183 A1 | 6/2009 | O'Donoghue et al. | |
| 2009/0170715 A1 | 7/2009 | Glinsky | |
| 2009/0172002 A1 | 7/2009 | Bathiche | |
| 2009/0198814 A1 | 8/2009 | Oono et al. | |
| 2009/0276771 A1 | 11/2009 | Nickolov et al. | |
| 2009/0299766 A1 | 12/2009 | Friedlander et al. | |
| 2010/0041378 A1 | 2/2010 | Aceves | |
| 2010/0082367 A1 | 4/2010 | Hains et al. | |
| 2010/0088245 A1 | 4/2010 | Harrison et al. | |
| 2010/0179833 A1 | 7/2010 | Roizen et al. | |
| 2010/0211941 A1 | 8/2010 | Roseborough | |
| 2010/0218132 A1 | 8/2010 | Soni et al. | |
| 2010/0250285 A1 | 9/2010 | Shelton | |
| 2010/0250341 A1 | 9/2010 | Hauser | |
| 2010/0262664 A1 | 10/2010 | Brown et al. | |
| 2011/0004110 A1* | 1/2011 | Shusterman | G16H 50/20 600/509 |
| 2011/0129130 A1* | 6/2011 | Avinash | G16H 50/70 382/128 |
| 2011/0129131 A1* | 6/2011 | Avinash | G16H 50/20 382/128 |
| 2011/0173308 A1 | 7/2011 | Gutekunst | |
| 2011/0184748 A1 | 7/2011 | Fierro et al. | |
| 2011/0200979 A1 | 8/2011 | Benson | |
| 2011/0230360 A1 | 9/2011 | Stephan et al. | |
| 2011/0273309 A1 | 11/2011 | Zhang et al. | |
| 2012/0035954 A1 | 2/2012 | Yeskel | |
| 2012/0036220 A1 | 2/2012 | Dare et al. | |
| 2012/0059735 A1 | 3/2012 | Su et al. | |
| 2012/0065987 A1 | 3/2012 | Farooq et al. | |
| 2012/0079096 A1 | 3/2012 | Cowan et al. | |
| 2012/0095352 A1* | 4/2012 | Tran | A61B 5/6803 600/490 |
| 2012/0102050 A1 | 4/2012 | Button | |
| 2012/0220835 A1 | 8/2012 | Chung | |
| 2012/0227046 A1* | 9/2012 | Park | G06F 11/3438 718/100 |
| 2012/0266251 A1 | 10/2012 | Birtwhistle et al. | |
| 2012/0272156 A1 | 10/2012 | Kerger | |
| 2012/0303798 A1 | 11/2012 | Crowell et al. | |
| 2012/0310670 A1 | 12/2012 | Pruitt | |
| 2013/0024207 A1 | 1/2013 | Anderson et al. | |
| 2013/0030258 A1* | 1/2013 | Cheung | G16H 20/30 600/301 |
| 2013/0030836 A1 | 1/2013 | Ackerson | |
| 2013/0060922 A1 | 3/2013 | Koponen et al. | |
| 2013/0110565 A1 | 5/2013 | Means | |
| 2013/0166494 A1 | 6/2013 | Davis | |
| 2013/0172774 A1 | 7/2013 | Crowder et al. | |
| 2013/0238686 A1 | 9/2013 | O'Donoghue | |
| 2013/0245389 A1* | 9/2013 | Schultz | A61B 5/0002 600/301 |
| 2013/0262140 A1 | 10/2013 | Friedlander et al. | |
| 2013/0329632 A1 | 12/2013 | Buyukkoc et al. | |
| 2014/0019191 A1 | 1/2014 | Mulji et al. | |
| 2014/0058755 A1 | 2/2014 | Macoviak et al. | |
| 2014/0067596 A1 | 3/2014 | McGovern et al. | |
| 2014/0088995 A1 | 3/2014 | Damani | |
| 2014/0100883 A1 | 4/2014 | Hamilton | |
| 2014/0156823 A1 | 6/2014 | Liu | |
| 2014/0181715 A1 | 6/2014 | Axelrod | |
| 2014/0184422 A1* | 7/2014 | Mensinger | G16H 40/67 340/870.02 |
| 2014/0195297 A1 | 7/2014 | Abuelsaad et al. | |
| 2014/0240122 A1 | 8/2014 | Roberts | |
| 2014/0257058 A1 | 9/2014 | Clarysse et al. | |
| 2014/0257852 A1 | 9/2014 | Walker et al. | |
| 2014/0273913 A1 | 9/2014 | Michel | |
| 2014/0278474 A1 | 9/2014 | McClure et al. | |

(56) References Cited

U.S. PATENT DOCUMENTS

| | | | |
|---|---|---|---|
| 2014/0297311 A1* | 10/2014 | Jackson | G06Q 30/0201 705/2 |
| 2014/0310398 A1 | 10/2014 | Zhou | |
| 2014/0316793 A1 | 10/2014 | Pruit | |
| 2014/0344208 A1 | 11/2014 | Ghasemzadeh et al. | |
| 2014/0350954 A1 | 11/2014 | Ellis et al. | |
| 2015/0019342 A1 | 1/2015 | Gupta | |
| 2015/0025917 A1 | 1/2015 | Stempora | |
| 2015/0025997 A1 | 1/2015 | Tilenius et al. | |
| 2015/0056589 A1 | 2/2015 | Zhang et al. | |
| 2015/0073830 A1 | 3/2015 | Hill et al. | |
| 2015/0126822 A1* | 5/2015 | Chavan | A61B 5/0205 600/595 |
| 2015/0134265 A1* | 5/2015 | Kohlbrecher | G16H 40/63 702/19 |
| 2015/0135160 A1 | 5/2015 | Gauvin | |
| 2015/0143470 A1 | 5/2015 | Stiekes et al. | |
| 2015/0148061 A1 | 5/2015 | Koukoumidis et al. | |
| 2015/0164438 A1* | 6/2015 | Halperin | G16H 20/10 340/573.1 |
| 2015/0178473 A1 | 6/2015 | Hufford et al. | |
| 2015/0178474 A1 | 6/2015 | Hufford et al. | |
| 2015/0193588 A1 | 7/2015 | Nemoto et al. | |
| 2015/0199490 A1 | 7/2015 | Iancu et al. | |
| 2015/0228041 A1 | 8/2015 | Naley et al. | |
| 2015/0294090 A1 | 10/2015 | Kodiyan | |
| 2015/0302539 A1* | 10/2015 | Mazar | G08B 21/02 705/3 |
| 2015/0347682 A1 | 12/2015 | Chen et al. | |
| 2015/0356582 A1 | 12/2015 | Turner, Jr. | |
| 2015/0356701 A1 | 12/2015 | Gandy et al. | |
| 2016/0048652 A1 | 2/2016 | Spivey et al. | |
| 2016/0058287 A1 | 3/2016 | Dyell | |
| 2016/0063210 A1 | 3/2016 | Bardi et al. | |
| 2016/0086505 A1 | 3/2016 | Hanlon | |
| 2016/0098541 A1 | 4/2016 | Haskell et al. | |
| 2016/0125171 A1 | 5/2016 | Finken et al. | |
| 2016/0140320 A1 | 5/2016 | Moturu et al. | |
| 2016/0140322 A1 | 5/2016 | Menon et al. | |
| 2016/0180053 A1 | 6/2016 | Fuertinger et al. | |
| 2016/0189317 A1 | 6/2016 | Papandrea | |
| 2016/0217266 A1* | 7/2016 | Damani | G16H 70/00 |
| 2016/0239620 A1 | 8/2016 | Lussier et al. | |
| 2016/0267238 A1 | 9/2016 | Nag | |
| 2016/0287166 A1* | 10/2016 | Tran | A61B 5/74 |
| 2016/0314257 A1 | 10/2016 | Nolan et al. | |
| 2016/0350671 A1* | 12/2016 | Morris, II | G05B 23/0229 |
| 2016/0357944 A1 | 12/2016 | Iyer et al. | |
| 2016/0378950 A1 | 12/2016 | Reiner | |
| 2017/0000422 A1 | 1/2017 | Moturu et al. | |
| 2017/0004260 A1 | 1/2017 | Moturu et al. | |
| 2017/0011200 A1 | 1/2017 | Arshad et al. | |
| 2017/0020444 A1 | 1/2017 | Lurie | |
| 2017/0039324 A1 | 2/2017 | Francois et al. | |
| 2017/0039341 A1 | 2/2017 | Shklarski et al. | |
| 2017/0046127 A1 | 2/2017 | Fletcher et al. | |
| 2017/0071671 A1 | 3/2017 | Neumann et al. | |
| 2017/0076049 A1 | 3/2017 | Miller | |
| 2017/0085444 A1 | 3/2017 | Hart et al. | |
| 2017/0124276 A1 | 5/2017 | Tee | |
| 2017/0132395 A1 | 5/2017 | Futch | |
| 2017/0147681 A1 | 5/2017 | Tankersley et al. | |
| 2017/0181645 A1* | 6/2017 | Mahalingam | A61B 5/74 |
| 2017/0200091 A1* | 7/2017 | Britton | G06N 20/00 |
| 2017/0213007 A1 | 7/2017 | Moturu et al. | |
| 2017/0235912 A1 | 8/2017 | Moturu et al. | |
| 2017/0262606 A1 | 9/2017 | Abdullah et al. | |
| 2017/0293538 A1 | 10/2017 | Seenappa | |
| 2017/0303187 A1 | 10/2017 | Crouthamel et al. | |
| 2017/0308669 A1 | 10/2017 | Apte et al. | |
| 2017/0311860 A1* | 11/2017 | Bar | A61B 5/16 |
| 2017/0323064 A1 | 11/2017 | Bates | |
| 2017/0330297 A1 | 11/2017 | Cronin et al. | |
| 2017/0372348 A1 | 12/2017 | Baluja | |
| 2018/0001184 A1 | 1/2018 | Tran et al. | |
| 2018/0024901 A1 | 1/2018 | Tankersley et al. | |
| 2018/0025125 A1 | 1/2018 | Crane et al. | |
| 2018/0036591 A1 | 2/2018 | King et al. | |
| 2018/0039726 A1 | 2/2018 | Boissel | |
| 2018/0052971 A1 | 2/2018 | Hanina et al. | |
| 2018/0056130 A1 | 3/2018 | Bitran et al. | |
| 2018/0060522 A1* | 3/2018 | Petterson | G16H 10/20 |
| 2018/0068083 A1 | 3/2018 | Cohen et al. | |
| 2018/0089159 A1 | 3/2018 | Jain et al. | |
| 2018/0089376 A1 | 3/2018 | Tucker et al. | |
| 2018/0096740 A1 | 4/2018 | Moturu et al. | |
| 2018/0116599 A1 | 5/2018 | Bastide et al. | |
| 2018/0121605 A1 | 5/2018 | Allen et al. | |
| 2018/0150523 A1 | 5/2018 | Shiffman et al. | |
| 2018/0176331 A1 | 6/2018 | Jain et al. | |
| 2018/0189046 A1 | 7/2018 | Kunisetty et al. | |
| 2018/0189856 A1 | 7/2018 | Lenhart et al. | |
| 2018/0197624 A1 | 7/2018 | Robaina et al. | |
| 2018/0206775 A1* | 7/2018 | Saria | A61B 5/6898 |
| 2018/0242860 A1 | 8/2018 | LeBouef et al. | |
| 2018/0247353 A1* | 8/2018 | Al-Ali | A61B 5/0205 |
| 2018/0267879 A1 | 9/2018 | Tsuda et al. | |
| 2018/0301205 A1 | 10/2018 | Mao | |
| 2018/0308002 A1* | 10/2018 | Kurian | G06F 11/00 |
| 2018/0308569 A1 | 10/2018 | Luellen | |
| 2018/0325385 A1* | 11/2018 | Deterding | A61B 5/14551 |
| 2018/0335939 A1 | 11/2018 | Karunamuni et al. | |
| 2018/0359281 A1 | 12/2018 | Ng et al. | |
| 2018/0365028 A1 | 12/2018 | Hosabettu | |
| 2018/0367560 A1 | 12/2018 | Mahaffey et al. | |
| 2018/0373462 A1 | 12/2018 | Childress et al. | |
| 2019/0000349 A1* | 1/2019 | Narayan | G16H 50/50 |
| 2019/0000350 A1* | 1/2019 | Narayan | G16H 50/50 |
| 2019/0002982 A1 | 1/2019 | Wang | |
| 2019/0006025 A1 | 1/2019 | Li | |
| 2019/0012434 A1 | 1/2019 | Frazier | |
| 2019/0019581 A1 | 1/2019 | Vaughan et al. | |
| 2019/0021650 A1 | 1/2019 | Lee et al. | |
| 2019/0038148 A1* | 2/2019 | Valys | A61B 5/7275 |
| 2019/0043501 A1 | 2/2019 | Ramaci | |
| 2019/0043610 A1 | 2/2019 | Vaughan | |
| 2019/0043619 A1 | 2/2019 | Vaughan et al. | |
| 2019/0046037 A1* | 2/2019 | Ramesh | G16H 50/20 |
| 2019/0073333 A1* | 3/2019 | Joshua | G06F 11/3051 |
| 2019/0074080 A1 | 3/2019 | Appelbaum et al. | |
| 2019/0076031 A1* | 3/2019 | Valys | A61B 5/02405 |
| 2019/0079846 A1 | 3/2019 | Shaik | G06F 11/302 |
| 2019/0080785 A1 | 3/2019 | Li | |
| 2019/0102670 A1 | 4/2019 | Ceulemans et al. | |
| 2019/0104951 A1* | 4/2019 | Valys | G16H 50/20 |
| 2019/0122266 A1 | 4/2019 | Ramer et al. | |
| 2019/0138656 A1 | 5/2019 | Yang et al. | |
| 2019/0140892 A1 | 5/2019 | Jain et al. | |
| 2019/0147043 A1 | 5/2019 | Moskowitz | |
| 2019/0160287 A1* | 5/2019 | Harrer | G16H 10/60 |
| 2019/0172588 A1 | 6/2019 | Tran et al. | |
| 2019/0180862 A1 | 6/2019 | Wisser et al. | |
| 2019/0201123 A1 | 7/2019 | Shelton et al. | |
| 2019/0206521 A1 | 7/2019 | Walpole et al. | |
| 2019/0207814 A1 | 7/2019 | Jain et al. | |
| 2019/0214116 A1 | 7/2019 | Eberting | |
| 2019/0227528 A1 | 7/2019 | Abbott et al. | |
| 2019/0243944 A1 | 8/2019 | Jain et al. | |
| 2019/0272925 A1 | 9/2019 | Barrett et al. | |
| 2019/0286086 A1 | 9/2019 | Gardner et al. | |
| 2019/0311803 A1* | 10/2019 | Kohlbrecher | G16H 40/63 |
| 2019/0313934 A1 | 10/2019 | Lee et al. | |
| 2019/0318818 A1 | 10/2019 | Chaudhuri et al. | |
| 2019/0320310 A1 | 10/2019 | Horelik et al. | |
| 2019/0373070 A1 | 12/2019 | Ramachandran et al. | |
| 2019/0373071 A1 | 12/2019 | Ramachandran et al. | |
| 2020/0019995 A1 | 1/2020 | Krishnan et al. | |
| 2020/0027565 A1* | 1/2020 | Poppe | G16H 50/70 |
| 2020/0058382 A1 | 2/2020 | Birnbaum et al. | |
| 2020/0065879 A1 | 2/2020 | Hu et al. | |
| 2020/0077942 A1 | 3/2020 | Youngblood et al. | |
| 2020/0082918 A1 | 3/2020 | Simhon et al. | |
| 2020/0105380 A1 | 4/2020 | Ennist et al. | |

(56) References Cited

U.S. PATENT DOCUMENTS

| | | | |
|---|---|---|---|
| 2020/0107733 A1* | 4/2020 | Valys | A61B 5/7282 |
| 2020/0107763 A1* | 4/2020 | Antunes | A61B 5/031 |
| 2020/0112479 A1 | 4/2020 | Jain et al. | |
| 2020/0119986 A1 | 4/2020 | Jain et al. | |
| 2020/0131581 A1 | 4/2020 | Jain et al. | |
| 2020/0135331 A1 | 4/2020 | Mohebbi et al. | |
| 2020/0145308 A1 | 5/2020 | Al Ramady et al. | |
| 2020/0160170 A1* | 5/2020 | Kursun | G06N 3/045 |
| 2020/0203012 A1* | 6/2020 | Kamath | A61B 5/002 |
| 2020/0211679 A1 | 7/2020 | Pellini et al. | |
| 2020/0211680 A1 | 7/2020 | Sablinski et al. | |
| 2020/0227152 A1 | 7/2020 | Moturu et al. | |
| 2020/0242557 A1* | 7/2020 | Carey | G16H 10/40 |
| 2020/0243167 A1 | 7/2020 | Will et al. | |
| 2020/0249962 A1* | 8/2020 | Vichare | G06F 9/5083 |
| 2020/0267110 A1 | 8/2020 | Nolan et al. | |
| 2020/0273567 A1* | 8/2020 | Petterson | G16H 10/20 |
| 2020/0281485 A9* | 9/2020 | Valys | G16H 40/67 |
| 2020/0303074 A1* | 9/2020 | Mueller-Wolf | A61B 5/7275 |
| 2020/0304387 A1* | 9/2020 | Pan | H04L 43/04 |
| 2020/0319877 A1* | 10/2020 | Glazer | G06F 9/44505 |
| 2020/0321116 A1 | 10/2020 | Neumann | |
| 2020/0342352 A1 | 10/2020 | Neumann | |
| 2020/0350041 A1 | 11/2020 | Li | |
| 2020/0357490 A1 | 11/2020 | Kartoun et al. | |
| 2020/0382395 A1 | 12/2020 | Kerry | |
| 2020/0387810 A1 | 12/2020 | Hodgson et al. | |
| 2020/0395124 A1* | 12/2020 | Karlin | G16H 30/40 |
| 2020/0410090 A1 | 12/2020 | Baker | |
| 2020/0411199 A1 | 12/2020 | Shrager et al. | |
| 2021/0004537 A1 | 1/2021 | Sapugay et al. | |
| 2021/0027136 A1* | 1/2021 | Hwang | G06N 20/20 |
| 2021/0043321 A1* | 2/2021 | Deterding | A61B 5/117 |
| 2021/0044579 A1 | 2/2021 | Nelson-Gal et al. | |
| 2021/0050098 A1* | 2/2021 | Sterner | G16H 40/20 |
| 2021/0057091 A1 | 2/2021 | Gutekunst et al. | |
| 2021/0081189 A1 | 3/2021 | Nucci et al. | |
| 2021/0134421 A1* | 5/2021 | Mousseau | G06F 21/6245 |
| 2021/0144058 A1 | 5/2021 | Jain | |
| 2021/0183512 A1* | 6/2021 | Van Dusen | G08B 21/0423 |
| 2021/0183516 A1* | 6/2021 | Chevalier | G16H 30/20 |
| 2021/0193316 A1 | 6/2021 | Krishnan et al. | |
| 2022/0076822 A1 | 3/2022 | Liu et al. | |

FOREIGN PATENT DOCUMENTS

| | | |
|---|---|---|
| WO | WO 2011112556 | 9/2011 |
| WO | WO 2013144769 | 10/2013 |
| WO | WO 2016110804 | 7/2016 |
| WO | WO 2016161416 | 10/2016 |
| WO | WO 2017106770 | 6/2017 |

OTHER PUBLICATIONS

Kakha, Priyanka, N. K. Tripathi, and Peerapong Kitipawang. "A real-time health monitoring system for remote cardiac patients using smartphone and wearable sensors." International journal of telemedicine and applications 2015 (2015): 8-8. (Year: 2015).*

Wan, Jie, et al. "Wearable IoT enabled real-time health monitoring system." EURASIP Journal on Wireless Communications and Networking 2018.1 (2018): 1-10. (Year: 2018).*

[No Author Listed] "Cancer Care Patient Navigation. A practical guide for community cancer centers," Association of Community Cancer Centers, 2009, retrieved on Jan. 2, 2018, retrieved from URL <https://www.accc-cancer.org/resources/pdf/Patient-Navigation-Guide.pdf>, 40 pages.

[No Author Listed] "Methods for JITAIs Just in Time Adaptive Intervention," Apr. 22, 2016, retrieved on Nov. 9, 2016, retrieved from URL<https://community.isr.umich.edu/public/Default.aspx?alias=community.isr.umich.edu/public/jitai&>.

addiction-ssa.org [online], "Ecological momentary assessment," May 12, 2017, retrieved on Mar. 21, 2022, retrieved from URL<https://www.addiction-ssa.org/commentary/emerging-research-methods-series-ecological-momentary-assessment>, 3 pages.

am.asco.org [online] "The Value of Patient Navigators as Members of the Multidisciplinary Oncology Care Team," Jun. 6, 2016, retrieved on Jan. 2, 2018, retrieved from URL <https://am.asco.org/value-patient-navigators-members-multidisciplinary-oncology-care-team>, 3 pages.

Atan et al., "Sequential Patient Recruitment and Allocation for Adaptive Clinical Trials," Proceedings of the 22nd International Conference on Artificial Intelligence and Statistics, Apr. 2019, 89:1-10.

Berry, "Adaptive Clinical Trials in Oncology," Nature Reviews, Apr. 2012, 9:199-207.

Biswas et al., "Processing of wearable sensor data on the cloud—a step towards scaling of continuous monitoring of health and well-being," Presented at 2010 Annual International Conference of the IEEE Engineering in Medicine and Biology, Buenos Aires, Argentina, Aug. 31-Sep. 4, 2010, pp. 3860-3863.

Bothwell et al., "Adaptive Design Clinical Trials: A Review of the Literature and ClinicalTrials.gov," BMJ Open, Feb. 10, 2018, 11 pages.

Boulos et al., "How smartphones are changing the face of mobile and participatory healthcare: An overview, with example from eCAALYX," Biomedical Engineering Online, Apr. 2011, 10:24, 14 pages.

Branch-Elliman et al., "Pragmatic, Adaptive Clinical Trials: Is 2020 the Dawning of a New Age?," Contemporary Clinical Trials Communications, Jul. 17, 2020, 19:1-3.

Braun et al., "Cancer Patient Navigator Tasks across the Cancer Care Continuum," J Health Care Poor Underserved, Feb. 1, 2012, 23(1):398-413.

businessinsider.com [online], "Latest Trends in Medical Monitoring Devices and Wearable Health Technology," Jan. 31, 2020, retrieved on Mar. 12, 2021, retrieved from URL<https://www.businessinsider.com/wearable-technology-healthcare-medical-devices>, 8 pages.

Cancer.gov [online], "NCI Dictionary of Cancer Terms," Jan. 9, 2020, retrieved on Mar. 13, 2020, retrieved from URL<https://www.cancer.gov/publications/dictionaries/cancer-terms/def/research-study>, 1 page.

cancer.org [online], "Patient Navigators Help Cancer Patients Manage Care," Feb. 24, 2017, retrieved on Jan. 2, 2018, retrieved from URL <https://www.cancer.org/latest-news/navigators-help-cancer-patients-manage-their-care.html>, 4 pages.

Chow et al., "Adaptive Design Methods in Clinical Trials—A Review," Orphanet Journal of Rare Diseases, May 2, 2008, 13 pages.

Coravos et al., "Modernizing and designing evaluation frameworks for connected sensor technologies in medicine," Digital Medicine 3, Mar. 13, 2020, 10 pages.

cordatahealth.com [online], "Automated Patient Navigation: Commission on Cancer and Other Requirements," Oct. 13, 2014, retrieved on Jan. 2, 2018, retrieved from URL<http://www.cordatahealth.com/blog/automated-patient-navigation-commission-on-cancer-and-other-requirements>, 4 pages.

Ctti-clinicaltrials.org [online], "Clinical Trials Transformation Initiative (CTTI) Recommendations: Advancing the Use of Mobile Technologies for Data Capture and Improved Clinical Trials," Jul. 2018, retrieved on Jan. 7, 2021, retrieved from URL<https://ctti-clinicaltrials.org/wp-content/uploads/2021/06/CTTI_Digital_Health_Technologies_Recs.pdf>, 32 pages.

Dias et al., "Wearable Health Devices—Vigtal Sign Monitoring, Systems and Technologies," Sensors, Jul. 25, 2018, 18(8):2414.

dicardiology.com [online], "Continuous Heart Monitoring Key to Identifying Cause of Cryptogenic Stroke," Nov. 16, 2015, retrieved on Mar. 12, 2021, retrieved from URL<https://www.dicardiology.com/article/continuous-heart-monitoring-key-identifying-cause-cryptogenic-stroke>, 4 pages.

Ekonomou et al., "An Integrated Cloud-based Healthcare Infrastructure," Presented at IEEE Third International Conference on Cloud Computing Technology and Science, Washington, DC, USA, Nov. 29-Dec. 1, 2011, pp. 532-536.

FDA.gov [online], "Enhancing the Diversity of Clinical Trial Populations—Eligibility Criteria, Enrollment Practices, and Trial Designs,"

(56) References Cited

OTHER PUBLICATIONS

Nov. 2020, retrieved on Jan. 31, 2022, retrieved at URL<https://www.fda.gov/media/127712/download>, 21 pages.
FDA.gov [online], "FDA Offers Guidance to Enhance Diversity in Clinical Trials, Encourage Inclusivity in Medical Product Development," Nov. 9, 2020, retrieved on Mar. 11, 2021, retrieved from URL<https://www.fda.gov/news-events/press-announcements/fda-offers-guidance-enhance-diversity-clinical-trials-encourage-inclusivity-medical-product>, 3 pages.
FDA.gov [online], "FDA Takes Action for Failure to Submit Required Clinical Trial Results Information to ClinicalTrials.gov," Apr. 28, 2021, retrieved on Apr. 31, 2022, retrieved from URL<https://www.fda.gov/news-events/press-announcements/fda-takes-action-failure-submit-required-clinical-trial-results-information-clinicaltrialsgov>, 3 pages.
FDA.gov [online], "FDA's Role: ClinicalTrials.gov Information," Apr. 28, 2021, retrieved on Jan. 31, 2022, retrieved from URL<https://www.fda.gov/science-research/clinical-trials-and-human-subject-protection/fdas-role-clinicaltrialsgov-information>, 4 pages.
Flatiron.com [online], "OncoTrials," May 14, 2018, retrieved on Mar. 13, 2020, retrieved from URL <https://flatiron.com/oncology/clinical-trials/>, 4 pages.
Flatiron.com [online], "Press Release: Flatiron Health Announces Three Publications Studying a Feasible, Reliable, Scalable and Meaningful Real-World Progression Endpoint for Oncology Research," Aug. 22, 2019, retrieved on Mar. 13, 2020, retrieved from URL<https://flatiron.com/press/press-release/real-world-progression-2019/>, 4 pages.
Forbes.com [online], "How Digital Technology Can Increase Diversity, Equity and Inclusion In Medical Research", May 12, 2021, retrieved on Oct. 28, 2021, retrieved from URL<https://www.forbes.com/sites/forbestechcouncil/2021/05/12/how-digital-technology-can-increase-diversity-equity-and-inclusion-in-medical-research/?sh=1dfa75252f7a>, 5 pages.
Foxnews.com [online], "FDA Issues Final Guidance to Improve Diversity in Clinical Trials", Nov. 9, 2020, retrieved on Mar. 11, 2021, retrieved from URL<https://www.foxnews.com/health/fda-issues-final-guidance-improve-diversity-clinical-trials>, 7 pages.
Gaydes et al., "Good Practices for Adaptive Clinical Trials in Pharmaceutical Product Development," Drug Information Journal, Sep. 2009, 43:539-556.
Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.
Grants.nih.gov [online], "Amendment: NIH Policy and Guidelines on the Inclusion of Women and Minorities as Subjects in Clinical Research", Nov. 28, 2017, retrieved on Mar. 3, 2022, retrieved from URL<https://grants.nih.gov/grants/guide/notice-files/NOT-OD-18-014.html>, 3 pages.
Grants.nih.gov [online], "NIH Policy and Guidelines on The Inclusion of Women and Minorities as Subjects in Clinical Research", Dec. 6, 2017, retrieved on Mar. 3, 2022, retrieved from URL<https://grants.nih.gov/policy/inclusion/women-and-minorities/guidelines.html>, 17 pages.
Grilo et al. "Pretreatment Patient Factors Predicting Attrition From a Multicenter Randomized Controlled Treatment Study for Panic Disorder," Comprehensive Psychiatry, Nov./Dec. 1998, 39(6):323-332.
Hammond et al., "Connecting Information to Improve Health", Health Affairs, Feb. 2010, 7 pages.
healthtechmagazine.net [online], "How Network Monitoring Keeps Healthcare Devices and Patients Safe," HealthTech, May 7, 2020, retrieved on Mar. 12, 2021, retrieved at URL<https://healthtechmagazine.net/article/2020/05/how-network-monitoring-keeps-healthcare-devices-and-patients-safe>, 7 pages.
Heron, "Ecological Momentary Intervention [EMI]: Incorporating mobile technology into a disordered eating treatment program for college women," Dissertation for the degree of Doctor of Philosophy, Syracuse University, College of Arts and Sciences, Jul. 2011, 202 pages.
hitconsultant.net [online], "Life Image, Medel.ai Integrates to Support AI-Driven Clinical Trails," Nov. 6, 2018, retrieved on Mar. 12, 2021, retrieved from URL<https://hitconsultant.net/2018/11/06/life-image-medel-ai-partner-ai-driven-clinical-trails/#.Xmr7yqhKhZc>, 4 pages.
Kadhim et al., "An Overview of Patients Health Status Monitoring System Based on Interner Things," Wireless Personal Communications, May 15, 2020, 114(3):1-28.
Kakria, "A Real-Time Health Monitoring System for Remote Cardiac Pateints Using Smartphone and Wearable Sensors," International Journal of Telemedicine and Applications, Nov. 12, 2015, vol. 2015, Article ID 373474, 11 pages.
khanacademic.org [online], "Khan Academy," Mar. 2, 2007, retrieved on Mar. 21, 2022, retrieved from URL<https://www.khanacademy.org/>, 4 pages.
Komen.org [online], "Types of Research Studies," Mar. 11, 2015, retrieved on Mar. 13, 2020, retrieved from URL<https://ww5.komen.org/BreastCancer/DifferentTypesofResearchStudies.html>, 5 pages.
Korn et al., "Adaptive Clinical Trials: Advantages and Disadvantages of Various Adaptive Design Elements", JNCI J Natl. Cancer Inst., Mar. 17, 2017, 109(6):1-6.
Lan et al., "WANDA: An end-to-end remote health monitoring and analytics systems for heart failure patients," Proceedings of the Conference on Wireless Health, Oct. 2012, 8 pages.
Med.Standford.edu [online], "Cohort Discovery," retrieved on Mar. 13, 2020, retrieved from URL <https://med.stanford.edu/starr-tools/cohort-discovery.html>, 3 pages.
Michaeljfox.org [online], "Fox Trial Finder," retrieved on Mar. 13, 2020, retrieved from URL<https://www.michaeljfox.org/trial-finder>, 4 pages.
Miksad et al., "Small But Might: The Use of Real-World Evidence to Inform Precision Medicine," Clinical Pharmacology & Therapeutics, Jul. 2019, 106(1):87-90.
Mixpanel.com [online], "The ultimate guide to cohort analysis: How to reduce churn and strengthen your product," available on or before Mar. 13, 2020, retrieved on Mar. 13, 2020, retrieved from URL <https://mixpanel.com/topics/cohort-analysis/>, 11 pages.
Murphy et al., "Visual Query Tool for Finding Patient Cohorts from a Clinical Data Warehouse of the Partners Healthcare System," Presented at Proceedings of AMIA Symposium, Los Angeles, CA, USA, Nov. 4-8, 2000, 2000:1174.
Nickelled.com [online], "Chapter 5: Top cohort analysis tools and resources," Dec. 12, 2018, retrieved on Mar. 28, 2022, retrieved from URL<https://www.nickelled.com/cohort-analysis/tools/>, 13 pages.
NPR.org [online], "Scientists Say The Rush To Do Covid Research Led To A Whole Lot Of Waste," Apr. 23, 2021, retrieved on Feb. 1, 2022, retrieved from URL<https://www.npr.org/sections/goatsandsoda/2021/04/23/988744818/scientists-say-the-rush-to-do-covid-research-led-to-a-whole-lot-of-waste>, 9 pages.
Obgyn.com [online], "Neural Networks", Apr. 14, 2014, retrieved on Mar. 21, 2022, retrieved from URL<http://www.obgyn.com.ac.uk/cam-only/statsbook/stneunet.html>, 34 pages.
Opb.org [online], "OHSU's Covid-19 Study Accused of Racial Bias", Jun. 6, 2020, retrieved on Mar. 11, 2021, retrieved from URL<https://www.opb.org/news/article/key-to-oregon-ohsu-covid-19-study-accused-of-racial-bias/>, 8 pages.
Oregonlive.com [online], "OHSU ends massive coronavims study because it underrepresented minorities, university says", Aug. 27, 2020, retrieved on Mar. 11, 2021, retrieved from URL<https://www.oregonlive.com/coronavirus/2020/08/ohsu-drops-massive-coronavirus-study-because-minorities-didnt-sign-up-university-says.html>, 4 pages.
otago.ac.nz [online], "Experience sampling and ecological momentary assessment with mobile phones," May 2015, retrieved on Mar. 21, 2022, retrieved from URL<http://www.otago.ac.nz/psychology/otago047475.pdf>, 4 pages.
Pallmann et al., "Adaptive Designs in Clinical Trials: Why Use Them, and How to Run and Report Them," BMC Medicine, Feb. 28, 2018, 16:29, 15 pages.
PaloAltoNetworks.com, "Monitor Device Health," Panorama Administrator's Guide Version 8.1, last updated Jun. 17, 2020, retrieved on Mar. 12, 2021, retrieved at URL<https://docs.paloaltonetworks.com/

(56) References Cited

OTHER PUBLICATIONS panorama/8-1/panorama-admin/manage-firewalls/device-monitoring-on-panorama/monitor-device-health.html>, 3 pages.
Park et al., "Critical Concepts in Adaptive Clinical Trials", Clinical Epidemiology, Mar. 23, 2018, 10:343-351.
Rogers et al., "Composer: Visual Cohort Analysis of Patient Outcomes," Applied Clinical Informatics, Mar. 2019, 10(2):278-285.
Runyan et al., "Virtues, ecological momentary assessment/intervention and smartphone technology," Front Psychol, May 6, 2015, 6:481, 24 pages.
Shen et al., "Learning for Dose Allocation in Adaptive Clinical Trials with Safety Constraints", Proceedings of the 37th International Conference on Machine Learning, Jul. 2020, 11 pages.
Simon et al., "Adaptive Enrichment Designs for Clinical Trials," Biostatistics, Sep. 2013, 14(4):613-625.
Smith et al., "Performance Measurement for Health System Improvement: Experiences, Challenges and Prospects," Presented at Proceedings of WHO European Ministerial Conference on Health Systems, Tallinn, Estonia Jun. 25-27, 2008, 28 pages.
Suh et al., "A remote patient monitoring system for congestive heart failure," Journal of Medical Systems, May 25, 2011, 35(5):1165-1179.
technologyreview.com [online], "Can "Digital Therapeutics" Be as Good as Drugs?," Apr. 7, 2017, retrieved on Mar. 21, 2022, retrieved from URL <https://www.technologyreview.com/s/604053/can-digital-therapeutics-be-as-good-as-drugs/>, 4 pages.
TheGuardian.com [online], "Five of the Best Health Monitoring Devices," Aug. 21, 2016, retrieved on Mar. 28, 2022, retrieved from URL<https://www.theguardian.com/technology/2016/aug/21/five-best-cardio-health-monitoring-devices>, 15 pages.
Thorlund et al., "Key Design Considerations for Adaptive Clinical Trials: A Primer for Clinicians," BMJ, Mar. 8, 2018, 5 pages.
Tourous et al., "Empowering the Digital Therapeutic Relationship: Virtual Clinics for Digital Health Interventions," NPJ Digital Medicine, May 16, 2018, 1(16):1-3.
U.S. Final Office Action in U.S. Appl. No. 16/800,952, dated Jan. 19, 2021, 24 pages.
U.S. Final Office Action in U.S. Appl. No. 17/166,777, dated Aug. 5, 2021, 9 pages.
U.S. Final Office Action in U.S. Appl. No. 17/177,153 dated Oct. 4, 2021, 38 pages.
U.S. Final Office Action in U.S. Appl. No. 17/233,103, dated Oct. 26, 2021, 30 pages.
U.S. Non Final Office Action in U.S. Appl. No. 17/166,777, dated Apr. 27, 2021, 26 pages.
U.S. Non Final Office Action in U.S. Appl. No. 17/166,899, dated Apr. 19, 2021, 25 pages.
U.S. Non Final Office Action in U.S. Appl. No. 17/177,153, dated Mar. 3, 2022, 34 pages.
U.S. Non Final Office Action in U.S. Appl. No. 17/177,153, dated May 27, 2021, 41 pages.
U.S. Non Final Office Action in U.S. Appl. No. 17/324,098, dated Aug. 2, 2021, 19 pages.
U.S. Non-Final Office Action in U.S. Appl. No. 16/800,952, dated Sep. 1, 2020, 17 pages.
U.S. Non-Final Office Action in U.S. Appl. No. 17/233,103, dated Feb. 16, 2022, 20 pages.
U.S. Non-Final Office Action in U.S. Appl. No. 17/233,103, dated Jul. 7, 2021, 20 pages.
U.S. Non-Final Office Action in U.S. Appl. No. 17/233,356, dated Jun. 15, 2021, 36 pages.
U.S. Notice of Allowance in U.S. Appl. No. 17/166,777, dated Feb. 4, 2022, 14 pages.
U.S. Notice of Allowance in U.S. Appl. No. 17/166,899, dated Aug. 4, 2021, 11 pages.
U.S. Notice of Allowance in U.S. Appl. No. 17/233,356, dated Oct. 5, 2021, 19 pages.
U.S. Notice of Allowance in U.S. Appl. No. 17/324,098, dated Dec. 15, 2021, 6 pages.
U.S. Notice of Allowance in U.S. Appl. No. 17/378,643, dated Nov. 10, 2021, 30 pages.
Wikipedia.org [online], "Clinical trial," Feb. 17, 2020, retrieved on Mar. 30, 2022, retrieved from URL<https://en.wikipedia.org/wiki/Clinical_trial>, 20 pages.
Wikipedia.org [online], "Digital therapeutics," Nov. 20, 2017, retrieved on Jan. 2, 2018, retrieved from URL<https://en.wikipedia.org/wiki/Digital_therapeutics>, 2 pages.
Wikipedia.org [online], "Observational study," Feb. 17, 2020, retrieved on Mar. 30, 2022, retrieved from URL<https://en.wikipedia.org/wiki/Observational_study>, 4 pages.
Wikipedia.org [online], "Research," Mar. 7, 2020, retrieved on Mar. 30, 2022, retrieved from URL<https://en.wikipedia.org/wiki/Research>, 16 pages.
Wired.com [online], "Patient Monitoring, Big Data, and the Future of Healthcare," Aug. 6, 2014, retrieved on Mar. 30, 2022, retrieved at URL<https://www.wired.com/insights/2014/08/patient-monitoring-big-data-future-healthcare/>, 6 pages.
Yin et al., "A health decision support system for disease diagnosis based on wearable medical sensors and machine learning ensembles," IEEE Transactions on Multi-Scale Computing Systems, Oct. 2017, 3(4):1-14.
ispor.com [online], "How mHealth technology is revolutionizing clinical research," Sep./Oct. 2018, retrieved on Apr. 1, 2022, retrieved from URL<https://www.ispor.org/docs/default-source/publications/value-outcomes-spotlight/september-october2018/ispor-vos-october-2018-toc-mhealth.pdf?slvrsn=5822a619_2>, 4 pages.
Notice of Allowance in U.S. Appl. No. 17/569,542, dated Dec. 21, 2022, 42 pages.
Office Action in U.S. Appl. No. 17/708,183, dated Sep. 29, 2022, 27 pages.

\* cited by examiner

| Study Criteria 510a | |
|---|---|
| Cohort Size: 100 | 511 |
| Study Length: 45 days | 512 |
| Study Region: Virginia | 513 |
| Requirements:<br>(1) Must make 3 Medical Office Visits per Month<br>(2) Must have a Smartphone | 514 |
| Inclusion Criteria:<br>(1) Must be between 30 and 50 years old<br>(2) Must be Diagnosed with High Blood Pressure | 515a |
| Exclusion Criteria:<br>(1) Can't have Diabetes<br>(2) Can't be Pregnant | 516 |
| Target Date: April, 2024 | 517 |

Diversity Analysis Results (Cohort Selection/Invitation) 520a

- Reference Population: 521 VA (2024 Estimated) – 49% (Group 1) / 24% (Group 2) / 24% (Group 3)
- Target Group Composition for Cohort: 522 50% (Group 1) / 25% (Group 2) / 25% (Group 3)
- Previous Participants: 523 915 (Group 1); 220 (Group 2); 200 (Group 3) - No Warning. Required Invitation Acceptance Rate is < 15%

Recommended Actions – Selecting Cohort 530a

Option 1 – (1) Send invitations to all previous study participants in Groups 1-3; (2) remove Inclusion Criteria 1 532
- Diversity Score: 0.91
- Target Group Composition: 50% / 25% / 25%
- Predicted Group Composition at Enrollment: 43% / 30% / 27%
- Predicted Group Composition at Study Completion: 51% / 23% / 26%

Option 2 - (1) Send invitations to all previous study participants; and (2) invite 20% more participants from Group 2 than Group 3 534
- Diversity Score: 0.85
- Target Group Composition: 50% / 25% / 25%
- Predicted Group Composition at Enrollment: 43% / 30% / 24%
- Predicted Group Composition at Study Completion: 54% / 23% / 23%

FIG. 5A

| Study Criteria 510b | |
|---|---|
| Cohort Size: 100 | 511 |
| Study Length: 45 days | 512 |
| Study Region: Virginia | 513 |
| Requirements:<br>(1) Must make 3 Medical Office Visits per Month<br>(2) Must have a Smartphone | 514 |
| Inclusion Criteria:<br>(1) Must be Diagnosed with High Blood Pressure | 515b |
| Exclusion Criteria:<br>(1) Can't have Diabetes<br>(2) Can't be Pregnant | 516 |
| Target Date: April, 2024 | 517 |

Diversity Analysis Results (Enrollment) 520b

- Target Group Composition: 522    50% / 25% / 25%
- Enrolled Group Composition: 524    48% / 27% / 24%
- Predicted Group Composition at Completion: 525    55% / 20% / 25%
- Anticipated Diversity Level at Completion: 526    0.83
- Warning: 527 Group Composition Outside of Target Composition Range!

Recommended Actions – Start of Study 530b

Option 1 – (1) Add taxi credit; and (2) Send new enrollment invitations to Group 2 candidates
536
- Diversity Score: 0.94
- Target Diversity levels: 50% / 25% / 25%
- Predicted New Group Diversity at Enrollment: 43% / 30% / 27%
- Predicted Group Diversity at Study Completion: 51% / 23% / 26%

Study Criteria *510b*

- Cohort Size: 100 *511*
- Study Length: 45 days *512*
- Study Region: Virginia *513*
- Requirements: *514*
  (1) Must make 3 Medical Office Visits per Month
  (2) Must have a Smartphone
- Inclusion Criteria: *515b*
  (1) Must be Diagnosed with High Blood Pressure
- Exclusion Criteria: *516*
  (1) Can't have Diabetes
  (2) Can't be Pregnant
- Target Date: April, 2024 *517*
- ⋮

Diversity Analysis Results (Enrollment) *520b*

- Target Group Composition: *522*    50% / 25% / 25%
- Enrolled Group Composition: *524*    48% / 27% / 24%
- Predicted Group Composition at Completion: *525*    55% / 20% / 25%
- Anticipated Diversity Level at Completion: *526*    0.87
- Warning: *527* Group Composition Outside of Target Composition Range!

Adjust Enrollment *540*

| Recommended Users to Improve Diversity | Recommended Users for Removal or Replacement |
|---|---|
| User S:<br>- Group(s): Group 2 (Underrepresented)<br>- Expected Participation Level: 76%<br>- Anticipated Diversity Level if Added: 0.91<br>INVITE | User D:<br>- Group(s): Group 1 (Overrepresented)<br>- Participation Level: 51%<br>- Anticipated Diversity Level if Removed: 0.90<br>REMOVE / REPLACE |
| User R:<br>- Group(s): Group 2 (Underrepresented)<br>- Expected Participation: 71%<br>- Anticipated Diversity Level if Added: 0.90<br>INVITE | User B:<br>- Group(s): Group 1 (Overrepresented)<br>- Participation Level: 59%<br>- Anticipated Diversity Level if Removed: 0.89<br>REMOVE / REPLACE |

| Study Parameters/Elements | Cluster 1 | | | ... | Cluster 2 | | | ... |
|---|---|---|---|---|---|---|---|---|
| | Effect on Compliance | Effect on Retention | Effect on Data Quality | | Effect on Compliance | Effect on Retention | Effect on Data Quality | |
| Blood Pressure Monitoring | +1 | 0 | +2 | ... | -1 | -1 | +1 | ... |
| Location Monitoring | -1 | -1 | +1 | ... | 0 | 0 | +2 | ... |
| Smartphone Usage | -2 | -1 | 0 | ... | 0 | +1 | +1 | ... |
| In-person Visits (Monthly) | -1 | -1 | +1 | ... | -1 | -1 | +2 | ... |
| In-person Visits (Weekly) | -3 | -3 | +2 | ... | +2 | +2 | +3 | ... |
| Communication (Email) | -3 | +2 | -1 | ... | -3 | -1 | -1 | ... |
| Communication (SMS) | +3 | ... | +3 | ... | ... | ... | +1 | ... |
| ... | ... | ... | ... | ... | ... | ... | ... | ... |

FIG. 10

PROFILE 1 (Based on Cluster 1) 1102

Profile 1 - Impact of Study Parameter(s)/Element(s) — 1104a

| Study Parameter/Element | Impact Scores |
|---|---|
| Location Monitoring | -1/-1/+1 |
| Smartphone Usage | -2/-1/0 |
| In-person Visits (Weekly) | -1/-2/+3 |
| ... | |

Profile 1 - Impact of Communication Type — 1104b

| Communication Type | Impact Scores |
|---|---|
| Email | -3/-3/-1 |
| SMS Messaging | +3/+2/+3 |
| Voice Call | -1/-2/+3 |
| ... | |

Profile 1 - Impact of Communication Frequency — 1104c

| Communication Frequency | Impact Scores |
|---|---|
| Daily | -2/-3/+1 |
| Weekly | +1/+1/0 |
| Monthly | +2/+3/-2 |
| ... | |

Profile 1 - Inclusion Criteria — 1106

| Parameter Type | Acceptable Value(s) |
|---|---|
| Race | Race A |
| Ethnicity | Ethnicity A, E, and/or S |
| Age | 17-25 |
| Sex | Male or Female |
| Pregnant | No |
| Residence | Suburban or Rural |
| Medical Condition | Diabetes |
| ... | |

Profile 1 - Member Behaviors and Attributes — 1108

| Behavior / Attribute | Percent |
|---|---|
| Study Completion | 45% |
| Study Compliance | 68% |
| Smart Phone Compliance | 76% |
| Invitation Acceptance | 34% |
| Access to Vehicle | 25% |
| Residence (Suburban) | 75% |
| Residence (Rural) | 25% |
| Sex (Male) | 66% |
| Sex (Female) | 34% |
| ... | |

FIG. 11

Program Elements 1610

- Cohort Size: 100  _1611_
- Program Length: 45 days  _1612_
- Protocol:  _1613_
  (1) Must make 3 Medical Office Visits per Month
  (2) Must have a Smartphone
- Inclusion Criteria:  _1614_
  (1) Must be Diagnosed with High Blood Pressure
- Exclusion Criteria:  _1615_
  (1) Can't have Diabetes
  (2) Can't be Pregnant
- Target Date: April, 2024  _1616_
- Diversity/Success Criteria: _1617_
  (1) Min. Group Size = 8
  (2) Min. Diversity Score = 0.8
  ...

Monitoring Group  _1620_

Cohort Participants:
 - User B: Diversity Group 2
 - User Z: Diversity Group 3
 - User F: Diversity Group 1
 - User H: Diversity Group 2
 ...

Diversity Analysis Results  _1630_

- Program-End Target Composition: 50% / 25% / 25%
- Current Group Composition: 48% / 27% / 24%
- Predicted Group Composition at Program-End: 55% / 20% / 25%
- Predicted Diversity Score at Program-End: 0.83
- Warning: Predicted Group Composition Outside of Target Composition Range!

Recommended Actions to Improve Program-End Diversity  _1640_

Option 1 – (1) Add taxi credit; and (2) Send new enrollment invitations to Group 2 subjects
 - Predicted Diversity Score at Program End: 0.94
 - Program-End Target Composition: 50% / 25% / 25%
 - Predicted Composition at Program-End: 51% / 23% / 26%
 ...

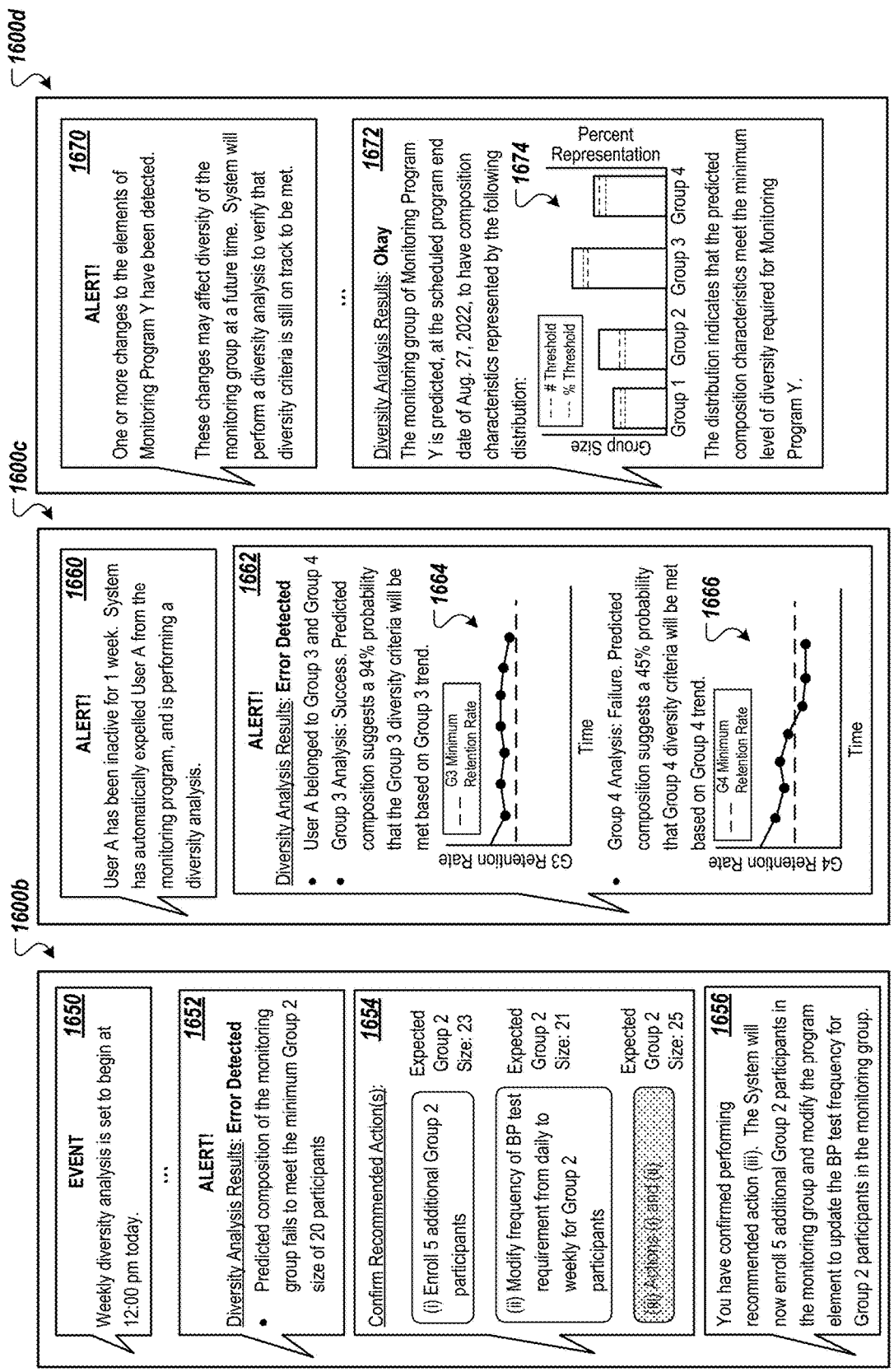

2140

Study Parameters 2160g
- Duration
- Objectives
- Incentives/compensation
- Adaptations permitted
- Adaptation constraints
- Accuracy & specificity targets
- ...

Participant Communication 2160h
- Communication types (e.g., reminder, challenge, data-driven insight, etc.)
- Content and appearance (e.g., complexity, level of detail, formatting, style, etc.)
- Media types used (e.g., text, audio, image, video, etc.)
- Communication mode (e.g., phone call, email, SMS text message, in-application notification, web portal, etc.)
- ...

Data Collection Methodology 2160e
- Types of data collected
- Surveys used
- Software used
- Devices & sensors used
- Data collection parameters (e.g., frequency, collection method, required compliance, required data quality, etc.)
- ...

Treatment/Intervention Parameters 2160f
- Medications used
- Medication dosages
- Medication frequency
- Number & type of different treatment groups or study "arms"
- ...

Eligibility Criteria 2160a
- Inclusion criteria
- Exclusion criteria
- ...

Cohort Characteristics 2160b
- Actual cohort size
- Target cohort size
- Number of cohorts
- Cohort membership
- ...

Program Availability 2160c
- Prioritization of participant attributes
- Availability or ranking on program gallery
- ...

Diversity & Representation Targets 2160d
- Categories or attributes to track
- Minimums or quotas
- Target Proportions
- ...

FIG. 21B

| Example conditions for identifying an opportunity for adapting a research study. E.g., for at least a minimum number of participants: |
|---|
| Desired effect detected |
| Desired effect not detected |
| Adverse event (e.g., side effects, toxicity, etc.) |
| High compliance with the study protocol |
| Occurrence of a predetermined condition or attribute (e.g., physiological, behavioral, psychological, etc.) |
| Data received or outcomes generated that match, or have a minimum level of similarity to, a predetermined pattern |
| Similarity identified in attributes, outcomes, events, or conditions monitored |
| Measured characteristic outside an expected range |
| Measured characteristic differs by a minimum amount from a target or typical level for the monitoring group |
| Cluster of participants identified having at least a minimum difference from other clusters |
| ... |

| Adaptation Viability & Suitability Assessment | | | |
|---|---|---|---|
| Criteria | Proposed Adaptation 1 | Proposed Adaptation 2 | ... |
| Number of affected participants satisfies a minimum threshold? | Yes | Yes | ... |
| Data needed to meet the objective can be collected with available methods? (e.g., available devices, software, surveys, etc.) | Yes | Yes | |
| Importance score satisfies a minimum threshold? | Yes | Yes | ... |
| Predicted retention of at least a minimum level? (Taking into account predicted enrollment rates, predicted attrition rates, etc.) | Yes | Yes | ... |
| Predicted compliance above a minimum level? | Yes | Yes | ... |
| Predicted data quality satisfies standards? | Yes | Yes | ... |
| Set of retained, complying participants at study-end predicted likely to provide minimum level of statistical power? | Yes | No | ... |
| Diversity criteria satisfied? (e.g., set of retained, complying participants at study end predicted likely to provide needed levels of diversity?) | Yes | No | ... |
| ... | ... | ... | |
| Study Adaptation Opportunity Selected for Recommendation or Implementation: | YES | NO | |

ADAPTIVE DATA COLLECTION IN CLINICAL TRIALS TO INCREASE THE LIKELIHOOD OF ON-TIME COMPLETION OF A TRIAL

CROSS-REFERENCE TO RELATED APPLICATIONS

This application is a Continuation-in-Part of U.S. patent application Ser. No. 17/378,643, filed on Jul. 16, 2021, which is a Continuation-in-Part of each of: (i) U.S. application Ser. No. 17/166,899 filed Feb. 3, 2021; (ii) U.S. application Ser. No. 17/166,777 filed Feb. 3, 2021; (iii) U.S. application Ser. No. 17/177,153 filed Feb. 16, 2021; and (iv) U.S. application Ser. No. 17/324,098 filed May 18, 2021. This application is also a Continuation-in-Part of U.S. patent application Ser. No. 17/569,542, filed on Jan. 6, 2022, which is a Continuation of U.S. patent application Ser. No. 17/233,356, filed on Apr. 16, 2021, now U.S. Pat. No. 11,249,875. This application is also a Continuation-in-Part of U.S. patent application Ser. No. 17/233,103, filed on Apr. 16, 2021. This application is also a Continuation-in-Part of U.S. patent application Ser. No. 17/185,954, filed on Feb. 25, 2021. The entire contents of each of the prior applications listed above are incorporated by reference herein.

BACKGROUND

Many systems rely on remote devices to perform monitoring. In many cases, monitoring performance fluctuates or varies over time and decreases in monitoring performance can jeopardize the success of a monitoring system. For example, when a large number of geographically distributed devices are used for monitoring, the performance may vary for devices in different locations and contexts so that devices in certain situations fail to provide the needed monitoring data.

SUMMARY

The disclosed system improves monitoring performance by assessing groups of remote devices and prioritizing adjustments to improve monitoring performance. The system can detect and respond to performance problems that affect different groups of devices differently, taking action to ensure that the objectives of monitoring are achieved. The system can prioritize the groups of remote devices based on the respective performance of the devices or impact on the overall monitoring, and the system dynamically makes adjustments to improve performance of devices in the group with the highest priority.

Over the course of a monitoring program, the system can incrementally or periodically make adjustments to improve monitoring performance. The system can limit the adjustments to only those groups with a high priority, or can perform the adjustments for the high-priority groups in order before making adjustments for other groups. By focusing adjustments on these high-priority groups, the system can increase the extent of the performance improvements realized and reduce the time required to realize performance improvements for the monitoring program as a whole (e.g., across the entire set of devices). Both of these effects improve the likelihood of a monitoring program meeting objectives, including targets for the diversity in devices and user monitored (e.g., achieving diversity among the attributes, contexts, data patterns, of devices and users involved). In many cases, the priorities of the groups are assigned so that the highest-priority groups are those that are underperforming and would be most likely lead to failure of the monitoring program to meet its objectives. As a result, improvements in performance among at least some devices in the highest priority groups significantly increases the likelihood of the meeting the requirements of the program.

The system can dynamically determine and perform adjustments for the high-priority groups. For example, the system can use historical data for the groups to determine what adjustments are anticipated to provide the greatest performance increase and when the adjustments should be performed to realize the maximum performance increase. The adjustments that the system makes can change how the system interacts with various remote devices in the monitoring program, such as by changing the communication characteristics between the system and devices in the high priority groups. The system can make various other adjustments that can be applied to the entire monitoring program, particular groups, or event particular participants or devices. In most cases, however, adjustments are made selectively for the specific devices and groups where performance improvements are determined by the system to be needed and most likely to be realized if attempted. In many cases, the adjustments increase power usage of battery-powered remote devices due to increased outputs, increased user interactions, higher frequencies of sensor measurements, and so on. As a result, there is a high incentive to maintain efficiency by limiting resource-intensive changes to the specific devices where the resulting benefit to monitoring performance (e.g., completeness, frequency, and accuracy of collected data) justifies the increased operations the adjustments cause.

Many systems rely on remote devices to perform monitoring. In many cases, monitoring performance fluctuates or varies over time and decreases in monitoring performance can jeopardize the success of a monitoring system. For example, when a large number of geographically distributed devices are used for monitoring, the performance may vary for devices in different locations and contexts so that devices in certain situations fail to provide the needed monitoring data or provide data that does not meet desired levels of data quality (e.g., accuracy, precision, etc.).

The disclosed system improves monitoring performance by assessing different groups of remote devices and prioritizing adjustments to improve performance. The system can detect and respond to performance problems affecting different groups of devices. The manner in which the system responds can be particular to the specific performance problem, to the device or type of device affected, or a combination of the performance problem and device or device type. The different responses may include the system applying different solutions in effort to correct the performance problem or account for the effect the performance problems have on the monitoring program. Alternatively, the system may apply the same solution to different degrees by applying different setting values, changes to setting values, or magnitude of changes to settings values. For example, if two groups of devices are experiencing poor sensor quality performance, the system may determine a solution for both groups of devices to increase the frequency at which sensor data is collected using the devices in both groups. However, the system may apply different degrees of changes to the frequency settings. In more detail, the system may modify the sensor data collection frequency for the first group of devices to be twice as frequent as the second group of devices due to the second group of devices having a slower processor than that in the first group of devices.

As part of determining which modifications to perform, the system prioritizes the groups of remote devices based on the respective performance of the devices or impact on the overall monitoring performance. For example, if two groups of devices are both experiencing similar performance problems, the system can prioritize a first group of devices among the two groups based on the number of devices in the first group being closer to a minimum number of devices required of the first group and, therefore, presenting a greater risk to the monitoring program's success. The system can identify responses dynamically as performance problems are identified. For example, poor performance in one of a multiple performance categories may trigger a performance analysis by the system. The results of the performance analysis can be used to prioritize groups of devices, individual devices, or particular responses for different groups of devices or individual devices. The groups of devices or individual device may be prioritized based on their performance and anticipated impact on the successful completion of the monitoring program.

Over the course of a monitoring program, the disclosed system can responsively or periodically make adjustments to improve monitoring performance. The system can determine when to make adjustments and which devices or groups of devices to make the adjustments for. The system can also determine the particular adjustments to make, selecting the adjustments that are most likely to result in the successful completion of the monitoring program. In making these adjustments, the system can use the previously determined priorities to determine what adjustments to make or which adjustments to prioritize. That is, after prioritizing particular groups of devices, the system can proceed to make adjustments for those highest priority groups of devices.

This system can provide a number of benefits that improve monitoring systems. For example, over the course of a monitoring program, the system can incrementally or periodically make adjustments to improve monitoring performance. In more detail, the system can perform adjustments on its own after determining what response is appropriate and which devices the response should be applied to. The system may determine what adjustments to make in response to a triggering event, such as the detection of sufficiently low performance in any one device or among a group of devices. Additionally or alternatively, the system may conduct a performance analysis periodically to identify what adjustments if any should be made at scheduled times throughout a study period. The adjustments may be determined to provide one or more benefits, such as to increase retention of a particular device or group of devices, to improve data quality obtained from a device or group of devices, or to increase the likelihood of successful completion of the monitoring program which may require data quality, compliance, and population minimums. By dynamically making adjustments, the disclosed system can quickly and efficiently react to and mitigate monitoring performance degradation. The system can most efficiently and effectively make these adjustments by limiting the adjustments to the highest priority groups of devices or individual devices, or by performing adjustments in order of the priority of the corresponding groups of devices or individual devices. Accordingly, in time-sensitive situations or situations where resources may be limited, the system can greatly improve the likelihood of monitoring program success by prioritizing adjustments for those groups of devices or individual devices that are most likely to fail monitoring program requirements or to prevent the monitoring program from meeting its objectives.

The system can also improve monitoring efficiency by determining and making adjustments for groups of devices that share one or more characteristics instead of for individual devices. For example, the system can reduce the amount of computing resources used for determining adjustments by limiting performance analysis to groups of devices that share one or more predetermined characteristics. In carrying out this analysis, the system can identify adjustments that are likely to improve the average performance of the devices in the group to account for performance issues that the group as whole is experiencing. Such an analysis would highlight the differences in performance between groups and allow the system to identify the minimum number or impact of monitoring adjustments need to achieve requirements for the monitoring program. Because the same adjustment would be applied to each device in a particular group of devices, the system can realize further efficiency benefits as the actions or outreach performed by the system in making the adjustments and managing the monitoring program would be simplified. Moreover, the shared characteristics among devices in each group may correspond to particular populations that are required to be represented in the monitoring program as an objective for the successful completion of the monitoring program, such as a target coverage for the monitoring program. By analyzing the performance of devices group-by-group, the system can more precisely and efficiently track the coverage of the monitoring program to ensure the monitoring program maintains or is on track for maintaining an appropriate amount of coverage for different coverage areas or diversity groups.

Through this mitigation by way of prioritized adjustments, the system can improve operation of monitoring programs that the system is managing and increase the likelihood of successfully completing those programs. In more detail, by making adjustments that specifically account for performance issues identified, the anticipated effect that the performance issues have on the likelihood of obtaining monitoring program success, the devices or type of devices present in a group of devices, or a combination thereof, the system can improve the likelihood of successfully completing a given monitoring program. By increasing the likelihood of successfully completing the program, the system can, thereby, reduce the chance of having to repeat or extend the duration of the monitoring programs. For example, the system may detect that insufficient sensor data quantity and quality is being collected from multiple remote devices enrolled in a monitoring program. This monitoring group of remote devices can include different subgroups that represent multiple categories of subjects, each defined by a set of attributes. The system can proceed to use data collected from the multiple remote devices to determine each of the subgroups' contributions to the detected performance degradation, and prioritize those subgroups based on their respective contributions so that the subgroup most responsible for the performance degradation is prioritized over the other subgroups. The system can then adjust the monitoring of the remote devices in the highest priority subgroups, or modify configurations for those remote devices. Making adjustments with respect to those devices that are primarily responsible for the degradation is anticipated to have the greatest, positive effect on the monitoring performance, and, therefore, is most likely to mitigate the degradation. Accordingly, in making adjustments for the highest priority subgroups of devices, the system improves operation of monitoring programs and increases the likelihood of successfully completing those programs.

In some systems there are constraints on the resources available to perform monitoring. For example, there are limited numbers of devices or limited resources to conduct repairs or provide replacements parts or devices, and so it is important to properly allocate the limited resources to achieve high performance.

The disclosed system uses prioritization of groups of remote devices to improve the allocation of resources among the overall set of devices. For example, the system can assess groups of devices representing different contexts and prioritize the groups with low performance or high impact on the aggregate performance. The system uses the priority levels for the groups to allocate limited resources where they will have the highest benefit or greatest improvement in monitoring performance.

The disclosed system can improve the operation and likelihood of successful completion of monitoring programs by intelligently allocating limited resources for specific subgroups of devices. As an example, these subgroups of devices can be those that present the largest hindrance to monitoring performance or are expected to present the largest hindrance to monitoring performance and, therefore, be prioritized for resource allocation. As an example, a set of five smartphones can be expected to improve monitoring performance due to having increased reliability and housing more precise sensors when compared to a particular subgroup of devices enrolled in a monitoring program. The system may detect that the accuracy of data received from the monitoring group fails to meet a minimum data quality threshold or is trending below the data quality threshold. An analysis of the collected data and subgroups of devices can reveal that the data collected from the particular subgroup of devices is consistently low quality and, in response, prioritize the particular subgroup of devices above the other subgroups. The system can proceed to allocate the five smartphones to the particular subgroup of devices, and schedule five devices in the subgroup of devices for replacement. In allocating the smartphones to the particular subgroup, the system can realize improved performance among the subgroup and an increased likelihood of successfully completing the monitoring program. By improving monitoring program operation and increasing the likelihood of successfully completing monitoring programs, the system can reduce the chance of having to repeat or extend the duration of the monitoring programs.

In one general aspect, a method includes: accessing, by the one or more computers, data describing a monitoring program that involves collecting data over a period of time from a monitoring group comprising geographically distributed devices involved in the monitoring program that provide sensor measurements over a communication network, wherein the monitoring program has a corresponding diversity target that specifies a level of diversity to achieve among multiple categories, wherein the accessed data includes (i) data collection requirements indicating types of data for the devices in the monitoring group to provide as part of the monitoring program and (ii) attributes associated with the devices in the monitoring group; classifying, by the one or more computers, the devices in the monitoring group into different groups corresponding to the categories based on the attributes associated with the devices; monitoring, by the one or more computers, performance of the different devices with respect to the data collection requirements for the monitoring program; evaluating, by the one or more computers, the performance of the different groups to determine a performance score for each group, wherein the performance score for a group is based on levels of compliance with the data collection requirements by the devices in the group; and adjusting, by the one or more computers, administration of the monitoring program for the devices based on the performance scores for the groups, the adjusting comprising performing one or more actions to improve diversity with respect to the categories for the monitoring performed for the monitoring program.

In some implementations, the method includes prioritizing the different groups based on the performance scores for the different groups; and wherein the administration of the monitoring program is adjusted based on the prioritization of the groups.

In some implementations, the method includes evaluating a level of diversity present for the monitoring program including determining, for each group, at least one of (i) an effect that the group has on the level of diversity or (ii) a likelihood that the group will meet the requirements for the group that are specified by the diversity target. Prioritizing the different groups includes prioritizing the different groups based on at least one of (i) the determined effects that the respective groups have on the level of diversity present for the monitoring program or (ii) the determined likelihoods that the respective groups will meet corresponding requirements for the groups.

In some implementations, the monitoring program has a predetermined minimum number of members for each group; evaluating the level of diversity for the monitoring program includes determining differences between current or predicted future amounts of enrolled, complying members of the groups and corresponding minimums for the groups, wherein the effect that each group has on the level of diversity or the likelihood of each group meets its requirements is based on the determined differences; and prioritizing the different groups includes prioritizing the different groups based on the differences.

In some implementations, determining the differences between amounts of members and the corresponding minimums includes: identifying, for each of the groups, a number of devices in the group; and calculating, for each of the groups, a difference between the identified number of devices and the minimum number of devices.

In some implementations, determining the differences includes: using the performance scores to predict, for each of the groups, a number of devices in the group that will comply with the data collection requirements at a future time; and calculating, for each of the groups, a difference between the predicted number of devices for the group at the future time and the minimum for the group.

In some implementations, the diversity target for the monitoring program has one or more predetermined ratios specifying desired composition characteristics of the monitoring group with respect to the different categories; evaluating the level of diversity for the monitoring program includes comparing a ratio involving of the devices in one or more groups with the one or more predetermined ratios, wherein the effect that each group has on the level of diversity or the likelihood of each group meeting corresponding requirements is based on the comparison of ratios; and prioritizing the different groups includes prioritizing the different groups based on the comparisons.

In some implementations, the method includes accessing profiles that define the categories. Classifying the devices in the monitoring group into the different groups corresponding to the categories includes: comparing the attributes associated with the devices with attributes or attribute ranges specified by the profiles; and based on the comparison, assigning each devices to at least one of the categories.

In some implementations, adjusting administration of the monitoring program includes: adjusting a composition of the devices in the monitoring group based on the performance scores; or selectively adjusting operation of a subset of devices that is selected from the monitoring group based on the performance scores.

In some implementations, the adjusting is performed in response to determining that the monitoring program (i) currently fails to meet or (ii) is predicted by the one or more computers to not meet the diversity target in the future, wherein the determination includes comparing the current or predicted level of diversity for the monitoring group to the level of diversity specified by the diversity target.

In some implementations, a server system manages monitoring programs that involve distributed monitoring using remote devices. The server system can improve the efficiency and effectiveness of monitoring by making adaptations to the monitoring programs, e.g., selectively changing monitoring parameters for specific individuals and groups of devices. For example, a monitoring program can involve a first group of remote devices that each separately make measurements with one or more sensors and report the data to the server system. From the monitoring data received, the server system can detect events and conditions that present opportunities for improvements in efficiency and effectiveness and adapt the monitoring program in response. The server system can then adapt the monitoring program, select additional remote devices to involve in the adapted monitoring program, and reconfigure the remote devices (the original first group of monitoring devices or the additional remote devices) to change their monitoring operations.

As an example, a few of the remote devices involved in a monitoring program may detect a particular condition, and the system may evaluate the monitoring data and determine that the particular condition justifies enhanced monitoring, e.g., to investigate the causes, effects, or rate of occurrence of the particular condition. The system can then cause the enhanced monitoring to be performed generally across the original group of devices or selectively for a subset of remote devices identified as most relevant to the particular condition of interest. The system may determine that a subset of the remote devices have a context that results in a high likelihood of experiencing the particular condition, while other remote devices do not. The system can then adapt the monitoring parameters for the original monitoring program to better detect the particular condition and related factors (e.g., by changing sensor operation, measurement frequency, precision or type of reported data, etc.). The system can then send updated software, updated firmware, configuration data, instructions, or other elements over a network to remotely alter operation of the remote devices in the subset to begin the new, enhanced monitoring program.

The system can be used to provide adaptive clinical trials and adaptations in other types of health research studies. The adaptive nature of the system also allows it to automatically investigate unusual conditions that occur, even if those conditions are not anticipated. From a first monitoring program with 1000 participants or devices, the system may detect an unusual result for some number of them, such as 7 of the participants. The unusual result could be a negative event (e.g., a disease symptom) or a positive event (e.g., high treatment effect of a medication). Even without a defined or predetermined reference specifying that the unusual result justifies further monitoring or adaptation, the system can detect that the result is significant based on comparison with the prior monitored history, patterns (e.g., trends, progressions, rates of change, etc.), distribution of results among devices, clustering of results, and other techniques.

The system can evaluate the factors in common among the devices and participants that reported the unusual result (e.g., aspects of location, attributes, history, environment, etc.) and determine which are shared or are most correlated with the result. This allows the system to generate a set of criteria for identifying individuals and devices for which the result is likely to occur, even if the result has not occurred yet for those devices. For example, the system may determine that certain locations (e.g., western United States) and environmental factors (e.g., temperature above 80 degrees) are correlated with a result. The system can use these factors to adapt a monitoring program, e.g., to expand representation of individuals and devices having the context or attributes identified with the result of interest.

When an opportunity for adapting a monitoring program is identified (e.g., a trend, correlation, anomaly, etc.), the system can validate whether the identified opportunity meets criteria demonstrating that an adaptation, if carried out, would be appropriate. If a proposed adaptation is predicted to provide sufficient additional value, the system can proceed with the adaptation. The system can then generate and distribute a software module, data package, configuration data, or other elements to cause devices to perform additional monitoring to better characterize contexts or attributes that are correlated with a result of interest. This additional monitoring, which may run in parallel or in addition to the original monitoring, may provide higher resolution and more complete data, e.g., measuring additional types of data, measuring more frequently, adding constraints on context or behavior, etc. This allows the system to automatically and efficiently supplement the base level of monitoring with targeted additional monitoring as monitoring data is. This enables the system to better characterize different conditions (e.g., determine the likelihood, magnitude, frequency of occurrence, factors predictive of occurrence, and so on) that develop over the course of monitoring in an efficient way, even if those results or the need for adaptation were not initially anticipated.

In one general aspect, a method of managing monitoring programs involving remote devices comprises: communicating, by one or more computers, with a set of remote devices involved in a monitoring program that involves collection of data from the remote devices over a communication network, wherein communicating with the remote devices comprises receiving, from each of the remote devices over the communication network, a series of messages including monitoring data collected by the remote device at different times for first types of data specified by the monitoring program; identifying, by the one or more computers, a pattern or similarity among monitoring data collected from a subset of the remote devices involved in the monitoring program; determining, by the one or more computers, that the identified pattern or similarity satisfies one or more criteria for initiating additional monitoring; in response to determining that the identified pattern or similarity satisfies the one or more criteria, determining, by the one or more computers, one or more parameters specifying second types of data to collect in the monitoring program; and configuring, by the one or more computers, one or more devices to perform monitoring for the monitoring program that includes including acquiring data for the second types of data and providing the acquired data to a server over the communication network.

In some implementations, configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In some implementations, the second types of data comprise user inputs as responses to surveys provided as part of the monitoring program.

In some implementations, the second types of data comprise the first types of data and one or more additional types of data.

In some implementations, the pattern or similarity among the monitoring data comprises a pattern or similarity among at least one of: compliance with a set of monitoring requirements; a monitored health outcome; measured values from one or more sensors; or user responses to surveys.

In some implementations, the method includes: storing data indicating predetermined conditions for adapting monitoring programs; and determining that the predetermined conditions are satisfied. The configuring can be performed in response to determining that the predetermined conditions are satisfied.

In some implementations, the predetermined conditions comprise at least one of minimum levels of importance, group size, relevance of the pattern or similarity, or magnitude of an effect indicted by the pattern or similarity.

In some implementations, determining the one or more parameters comprises determining selection criteria for selecting devices to involve in the second monitoring program, timing parameters to specify timing of data collection using the devices, or data collection techniques to specify techniques for collecting the second types of data.

In some implementations, the monitoring program is an adaptive clinical trial.

In some implementations, the method includes altering the study protocol of the monitoring program to obtain an altered study protocol for the monitoring program.

In another general aspect, a method includes: communicating, by one or more computers, with a first group of remote devices involved in a monitoring program that involves collection of data from the remote devices over a communication network, wherein communicating with the remote devices comprises receiving, from each of the remote devices over the communication network, a series of messages including monitoring data collected by the remote device at different times for first types of data specified by the monitoring program; determining, by the one or more computers and based on the data collected from the remote devices, a set of attributes associated with an outcome or condition that has occurred for multiple of the remote devices; generating, by the one or more computers, adapted parameters for the monitoring program, the parameters including selection criteria to select individuals or devices associated with the set of attributes to provide data in the monitoring program; selecting, by the one or more computers, a group of additional remote devices to involve in the monitoring program based on profiles or sets of attributes associated with the remote devices; and configuring, by the one or more computers, the remote devices in the selected additional remote devices to perform monitoring for the monitoring program, including acquiring data for second types of data specified by the second monitoring program and providing the acquired data to a server over the communication network.

In some implementations, the method includes: analyzing, by the one or more computers, the data collected from the remote devices in the first group to identify a pattern or similarity among monitoring data collected from a subset of the remote devices involved in the monitoring program; and determining, by the one or more computers, attributes associated with the respective devices in the subset. The selection criteria can be based on the attributes associated with the respective devices in the subset.

In some implementations, the attributes are attributes of the devices.

In some implementations, the attributes are attributes of users of the devices.

In some implementations, the attributes are attributes specified in a profile for a device or for a user of the device.

In some implementations, determining the selection criteria based on the attributes associated with the respective devices in the subset comprises: determining, for a particular attribute, a range of attribute values based on a range or distribution of attribute values for the particular attribute among the attributes associated with the respective devices in the subset; and determining the selection criteria to include devices or users having attribute values for the particular attribute in the determined range.

In some implementations, configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In some implementations, the method includes: providing, to a client device of a researcher associated with the monitoring program, program data for display on a user interface of the client device, the program data indicating characteristics of the adapted monitoring program, including at least one of the selection criteria, data indicating the members of the additional participants or devices or characteristics of the additional participants or devices, or the second types of data to be collected; and after providing the program data for display, receiving, from the client device, confirmation data indicating user input confirming that the monitoring program should be adapted as indicated in the user interface. Configuring the remote devices is performed in response to receiving the confirmation data.

In another general aspect, a method performed by one or more computers includes: after a monitoring program involving collecting data from a first group of remote devices has begun, receiving, by the one or more computers, input from a user associated with the monitoring program, the input indicating a request to adapt or evaluate potential for adapting the monitoring program; providing, by the one or more computers, a list of candidate items to monitor or candidate changes to make in the adapted monitoring program; receiving, by the one or more computers, user input indicating a selection from among the candidate items or candidate changes; generating, by the one or more computers, updated parameters that adapt the monitoring program to monitor the selected items or operate with the selected changes, the second monitoring program specifying data collection procedures to collect data to monitor the selected items or implement the selected changes; and configuring, by the one or more computers, one or more remote devices to perform monitoring for the adapted monitoring program, including acquiring data for second types of data specified by the adapted monitoring program and providing the acquired data to a server over the communication network.

In some implementations, the candidate items are topics, data types, or outcomes selected based on parameters of the monitoring program or data collected in the monitoring program.

In some implementations, the candidate items include variations of items monitored in the monitoring program.

In some implementations, generating the adapted monitoring program comprises applying a set of modifications to the monitoring program.

In some implementations, generating the adapted monitoring program comprises: selecting a set of items from a repository for generating monitoring programs; and integrating the selected set of items into a monitoring program template.

In some implementations, the method comprises accessing a database that maps the candidate items to data collection elements.

In some implementations, the data collection elements comprise surveys, device configuration settings, or device instructions.

In some implementations, the method includes configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In another general aspect, a method performed by one or more computers comprises: communicating, by one or more computers, with a first group of remote devices involved in a monitoring program that involves collection of data from the remote devices over a communication network, wherein communicating with the remote devices comprises receiving, from each of the remote devices over the communication network, a series of messages including monitoring data collected by the remote device at different times for first types of data specified by the first monitoring program; determining, by the one or more computers and based on the data collected from the remote devices, a set of attributes associated with an outcome or condition that has occurred for multiple participants involved in the monitoring program; generating, by the one or more computers, parameters to adapt the monitoring program including second types of data to be monitored in the adapted monitoring program; selecting, by the one or more computers, a set of devices for the adapted monitoring program, wherein the devices in the identified set of devices are each associated with a participant having the set of attributes; and configuring, by the one or more computers, remote devices to perform monitoring for the adapted monitoring program, including acquiring data for second types of data specified by the adapted monitoring program and providing the acquired data to a server over the communication network.

In some implementations, the method comprises selecting the remote devices from among devices involved in multiple different prior monitoring programs.

In some implementations, the method comprises accessing a database indicating devices and users involved in monitoring programs, the database storing attribute information specifying attributes of the devices and users. Selecting the remote devices comprises selecting, from among the respective sets of devices involved in the different prior monitoring programs, remote devices for the second group to include devices associated with the determined set of attributes.

In some implementations, the attributes are attributes of users of the devices.

In some implementations, the attributes are attributes specified in a profile for a device or for a user of the device.

In some implementations, configuring the one or more devices comprises distributing, to the one or more devices, a software module or configuration data that cause the one or more devices to initiate collection of the second types of data.

In some implementations, the second types of data comprise measurements made using one or more sensors of the one or more devices or of devices communicatively coupled to the one or more devices.

In some implementations, the measurements comprise one or more physiological or behavioral measurements.

In another general aspect, a method performed by one or more computers includes: accessing, by the one or more computers, data indicating characteristics for a monitoring program that involves data collection from a plurality of remote devices over a communication network, the characteristics including requirements that participants in the monitoring program need to satisfy during the monitoring program including data collection requirements specifying types of data to be acquired from the remote devices; identifying, by the one or more computers, a group of candidates for the monitoring program; based on outcomes of other monitoring programs, generating, by the one or more computers, a prediction for the group that indicates a predicted level of compliance of the group with the requirements of the monitoring program; based on the prediction for the group that indicates a predicted level of compliance of the group with the requirements of the monitoring program, generating, by the one or more computers, one or more scores indicative of whether the monitoring program will satisfy one or more predetermined conditions needed for successful completion of the monitoring program; and based on the generated one or more scores, identifying and applying an adaptation to the monitoring program that alters the monitoring program in a manner predicted to increase a likelihood that the adapted monitoring program will satisfy the one or more predetermined conditions.

In some implementations, the method includes providing, by the one or more computers, a notification over the communication network that is indicative of whether the monitoring program will satisfy one or more predetermined conditions.

In some implementations, the monitoring program involves repeated data collection from the plurality of remote devices over a period of time; the prediction for the group comprises a predicted amount of the candidates in the group that are predicted to comply with the requirements of the monitoring program through the end of the period of time; and the one or more scores are based on the predicted amount and a minimum amount of participants needed for the monitoring program.

In some implementations, generating the one or more scores comprises performing, by the one or more computers, a statistical power analysis for the monitoring program based on the predicted level of compliance.

In some implementations, the one or more scores comprise at least one of: a likelihood that the monitoring program, with the group of candidates as participants, would achieve a predetermined level of statistical power given the predicted level of compliance for the group; a statistical power value predicted to result, at the end of the monitoring program, from conducting the monitoring program with the group of candidates as participants; and a sample size for a set of participants at the beginning monitoring program that is predicted to result in at least a minimum level of statistical power at the end of the monitoring program after accounting for non-compliance at a level indicated by the predicted level of compliance of the group.

In some implementations, the predicted level of compliance of the group with the requirements of the monitoring program comprises a value indicating at least one of: a number of members of the group predicted to comply with the requirements of the monitoring program; a number of members of the group predicted to not comply with the requirements of the monitoring program; a proportion of the members of the group predicted to comply with the requirements of the monitoring program; or a proportion of the members of the group predicted to not comply with the requirements of the monitoring program.

In some implementations, generating the prediction for the group comprises predicting a level of enrollment, compliance, or retention for the group.

In some implementations, generating the prediction for the group comprises: accessing a database indicating attributes of the individual candidates in the group; and predicting a likelihood of compliance with the requirements of the monitoring program for each of the candidates in the group, each prediction being made based on the requirements of the monitoring program and the attributes of the corresponding candidate; wherein the prediction for the group is based on the set of likelihoods for the various individual candidates in the group.

In some implementations, the prediction for the group is generated based on output of one or more machine learning models trained to predict likelihoods of at least one of enrollment, compliance, retention, or data quality levels, the one or more machine learning models being trained using training data that includes (i) attributes of different individuals enrolled in monitoring programs that have different requirements for participants, (ii) the requirements for participant actions of the monitoring programs, and (iii) observed compliance results for the individuals, and the one or more machine learning models are trained to provide output indicating, for a group or individual, a likelihood or rate of enrollment, compliance, retention, or a minimum data quality level in response to receiving input feature data indicating (i) attributes of individuals or of groups and (ii) data indicating requirements of a monitoring program.

In some implementations, the one or more machine learning models comprise at least one of a neural network, a support vector machine, a classifier, a regression model, a clustering model, a decision tree, a random forest model, a genetic algorithm, a Bayesian model, or a Gaussian mixture model.

In some implementations, the data indicating requirements for the monitoring program comprise parameters entered by a user designing the monitoring program; and wherein the group of candidates is a group of devices or individuals that are enrolled to participate in the monitoring program or that are selected to be invited to participate in the monitoring program.

In some implementations, as the user changes parameters for the monitoring program or as changes are made to the group of candidates, repeatedly performing operations that include: generating the prediction that indicates a predicted level of compliance of the group; generating the one or more scores indicative of whether the monitoring program will satisfy one or more predetermined conditions; and evaluating the generated one or more scores with respect to the corresponding reference values; and determining, by the one or more computers and based on the evaluation, that a likelihood of the monitoring program satisfying the one or more criteria is less than a minimum level; and in response to the determination, providing a notification that the monitoring program has less than a minimum level of satisfying the one or more criteria.

In some implementations, the monitoring program is a proposed adapted monitoring program that the one or more computers generated from records for a primary monitoring program that was conducted or is in progress; the group of candidates includes participants in the primary research study; the method comprises determining, by the one or more computers, whether to recommend or implement the adaptations of the proposed adapted monitoring program based on evaluation of the one or more scores indicative of whether the primary monitoring program will satisfy one or more predetermined conditions.

In some implementations, the evaluation of the one or more scores comprises comparing the one or more scores to predetermined thresholds.

In some implementations, the monitoring program is a decentralized clinical trial, sometimes referred to as a digital trial or virtual trial, in which trial participants conduct most or all of the monitoring away from medical facilities (e.g., at home, at work, during day-to-day life) using mobile devices and other technology.

In some implementations, the monitoring program is an adaptive clinical trial.

In some implementations, the requirements include requirements in a study protocol for the sub-study.

In some implementations, the method includes: performing, by one or more computers, statistical power analysis to determine the likelihood of reaching statistical validity given the predicted level of compliance; and providing, by one or more computers and for presentation on the user interface, an indication of the likelihood of reaching statistical validity for the monitoring program. The indication can be provide for the original monitoring program, for the adapted monitoring program, or both.

The various models discussed herein can be machine learning models, for example, a neural networks or classifiers. Other types of models that may be used include support vector machines, regression models, reinforcement learning models, clustering models, decision trees, random forest models, genetic algorithms, Bayesian models, and Gaussian mixture models. Different types of models can be used together as an ensemble or for making different types of predictions. Other types of models can be used, even if they are not of the machine learning type. For example, statistical models and rule-based models can be used.

Other embodiments of these and other aspects disclosed herein include corresponding systems, apparatus, and computer programs encoded on computer storage devices, configured to perform the actions of the methods. A system of one or more computers can be so configured by virtue of software, firmware, hardware, or a combination of them installed on the system that, in operation, cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIGS. 5A-5C are diagrams that illustrate example diversity assessment and action selection interfaces.

FIG. 10 is a diagram that illustrates an example table that indicates impact scores corresponding to different clusters.

FIG. 11 is a diagram that illustrates an example profile.

FIGS. 16A-16D are diagrams that illustrate example interfaces for diversity prediction.

FIG. 21B is a diagram that illustrates various examples of aspects of a monitoring program that can be adapted by the system.

FIGS. 23B-23C are diagrams showing tables of information representing operations of the system and data used to evaluate and create monitoring programs.

Like reference numbers and designations in the various drawings indicate like elements.

DETAILED DESCRIPTION

Figure 1:
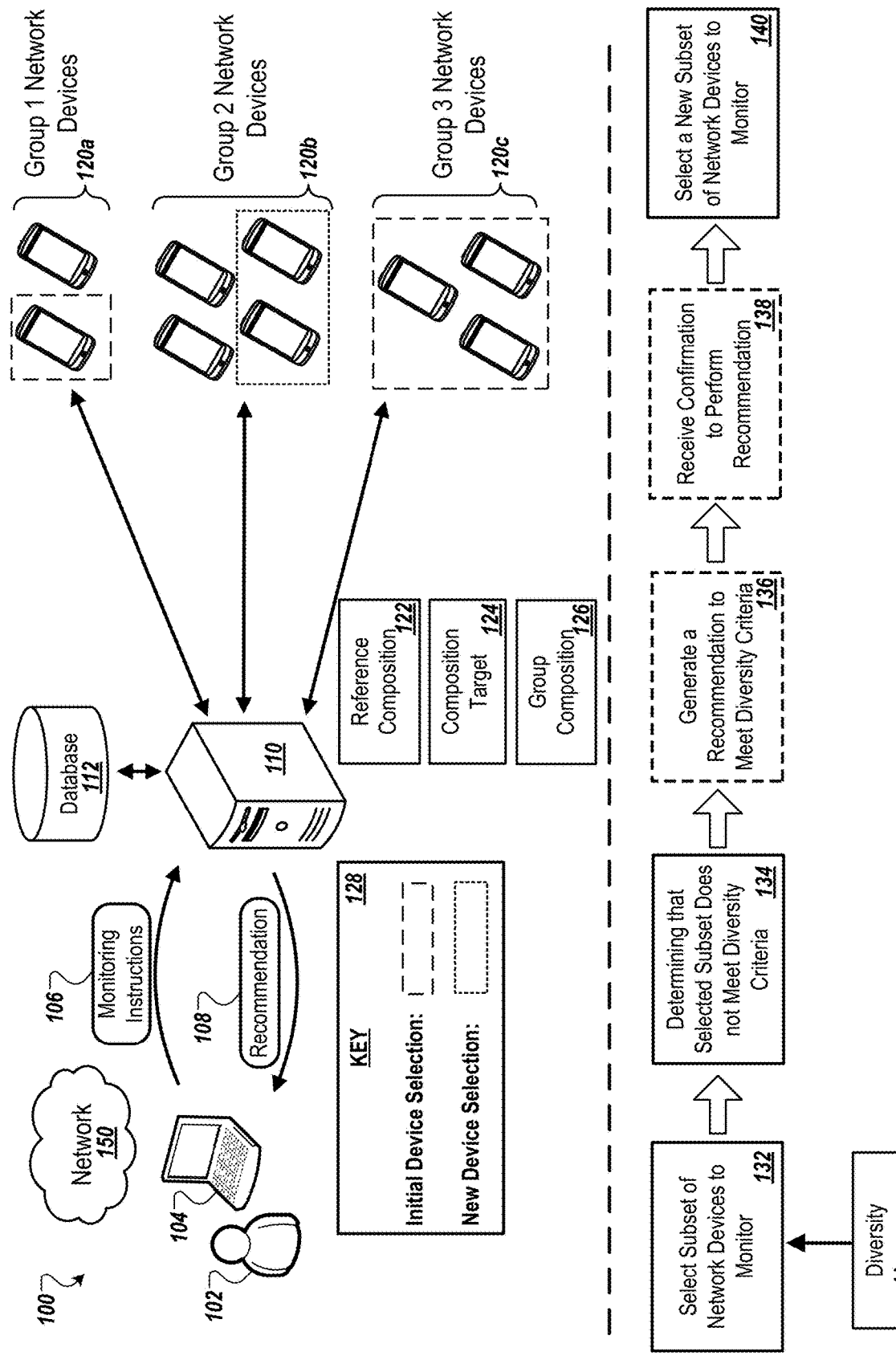
FIG. 1 is a diagram that illustrates an example system for assessing and selecting technologies to meet diversity requirements.

A computer system provides a platform for administering monitoring programs that involve customized data collection from groups of remote devices. The system enables different parties, e.g., organizations, administrators, third-parties, etc., to create or register monitoring programs to be distributed and managed by the system. For example, a server system can provide a multi-tenant system that provides functionality to create monitoring programs each tenant organization, select groups of devices and users to participate in the monitoring programs, and distribute the monitoring programs (e.g., including items such as software modules, configuration data, data collection instructions, interactive content, etc. so that groups of remote devices carry out the monitoring). The system can thus administer many different monitoring programs on behalf of different tenant organizations, with the system including servers that collect and process data from the remote devices as the monitoring programs are carried out over time. The systems and methods disclosed herein can include features as described in U.S. patent application Ser. No. 17/166,899, filed Feb. 2, 2021, U.S. patent application Ser. No. 17/166, 777, filed on Feb. 2, 2021, U.S. patent application Ser. No. 17/177,153, filed on Feb. 16, 2021, U.S. patent application Ser. No. 17/324,098, filed on May 18, 2021, all of which are incorporated herein by reference. The system can also make predictions as to whether objectives of the monitoring program are anticipated to be met. These objectives, e.g., monitoring program requirements, include diversity criteria that the computer system uses to predict whether the monitoring program will be successful. For example, the diversity criteria can correspond to a sufficiently high confidence that the results of a study will be viable and/or applicable. Accordingly, the success of the monitoring program as a whole can depend on having a monitoring group with at least a minimum level of diversity (e.g., amount of variation or variety in different attributes or categories) by the completion of the monitoring program, where devices and/or users for each of different profiles or contexts each comply with the required actions of the monitoring program over time.

As will be described in more detail below, in determining whether the diversity criteria is met, the computer system can make predictions that indicate future composition characteristics of the monitoring group or that the computer system uses to determine future composition characteristics of the monitoring group. These predictions can include predictions of compliance, retention, and/or data quality for a particular participant or group of participants represented in the monitoring group. The predictions can be based on the historical data collected during past monitoring programs for particular users or groups of users. These predictions can additionally or alternatively be based on the requirements of the monitoring program, such as other success criteria, protocols for the monitoring program, objectives for the monitoring program, parameters for the monitoring program, etc.

For example, a monitoring program may require a minimum level of diversity among its monitoring group to be considered successfully completed. The computer system may use attributes of the monitoring group(s) or their corresponding members, and the requirements of the monitoring program to predict whether the minimum level of diversity is likely to be met, e.g., by a scheduled end of the monitoring program, by a deadline set for the monitoring program, or at some future point in time. When a prediction indicates that a future composition of the monitoring group is anticipated to fail one or more diversity criteria of the monitoring program, e.g., prediction or corresponding value fails to meet a threshold confidence score, the computer system can recommend adaptations to the monitoring program and the corresponding monitoring group.

The diversity criteria can be set so that, when satisfied, the data collection outcomes for the study have sufficient real-world applicability or viability of monitoring program results. For example, if a group of participants who successfully complete a medical study fail to meet certain diversity criteria, the results of the study may have limited real-world applicability and the study would have to be repeated or extended. Thus, the system can significantly improve efficiency by using the diversity criteria to predict whether the results of the monitoring program will be viable or if there is a sufficiently high risk of the monitoring program producing unviable results, and to recommend actions anticipated to improve the viability of the monitoring program results when the results are predicted to be unviable or there is a sufficiently high risk of the results being unviable as indicated by the failure to meet one or more diversity criteria. The computer system can also use the results of the diversity analysis to reduce the monitoring program invitation or enrollment size for the monitoring group, and, thereby, improve efficiency by reducing the amount of resources used for and allocated to manage the monitoring group. That is, the computer system can avoid over-enrollment or significant over-enrollment if the predictions indicate that the monitoring group will have a minimum level of diversity by the end of the monitoring program. Similarly, the computer system can identify the most efficient way to improve diversity, e.g., modification to the requirements of a monitoring program or inviting only those participants to enroll in a monitoring program that have demonstrated the highest compliance and/or retention rates.

Accordingly, the computer system significantly improves effectiveness and efficiency by reducing or eliminating the need to repeat monitoring programs, reducing the length of monitoring programs or eliminating the need to extend monitoring programs, or reducing the size of monitoring group.

In general, diversity criteria can refer to values, ranges of values, data structures, or rules that define a standard or reference for determining whether there is sufficient variety among a monitoring group of participants (e.g., users and/or devices). That is, the diversity criteria for a monitoring program can define a minimum level of diversity required of that program. The values or ranges of values may define thresholds that correspond to sufficient or insufficient variety among the monitoring group, such as minimum thresholds and/or maximum thresholds that correspond to percent representations for multiple diversity groups in the monitoring group. Similarly, the values or ranges of values may define target values or ranges of values that correspond to sufficient variety among the monitoring group, such as target populations of diversity groups in the monitoring group. The data structures can include target distributions for the monitoring group, such as target population distribution and/or target percent representation distribution for multiple diversity groups in the monitoring group. The diversity criteria may also indicate the extent that predicted values for the monitoring group can vary from target values, such as a maximum number or percent change that a predicted number of participants in a group can deviate from a corresponding target value. The diversity criteria can also include a minimum diversity score, e.g., a single value that indicates a minimum level of diversity for a monitoring program. As will be described in more detail below, the computer system can predicted a diversity score using predicted composition characteristics for the monitoring group and proceed to compare to the predicted diversity score to the minimum diversity score.

Diversity of the monitoring group can be based on the variety of attributes among the participants in the monitoring group, and/or the variety of groups of participants (e.g., diversity groups that represent different categories of users) in the monitoring group. The diversity criteria is not limited to demographic attributes such as age, sex, race, socioeconomic status, and so on, but can also encompass diversity among physical characteristics, medical histories, genetic profiles, geographic locations, and many other attributes that are not demographic in nature.

In some cases, diversity of the monitoring group is also or alternatively based on the variety of behaviors of participants or groups of participants in the monitoring group. For example, diversity of the monitoring group can be based in part on observed or anticipated (e.g., based on historical data collected from past monitoring programs) behaviors of participants, such as participants' observed or expected reaction to different program elements, reaction to communications having particular attributes, health-related behaviors, atypical behaviors or those that have been found to have had a significant impact on meeting monitoring program protocols, etc. In more detail, the system may use collected data to determine that a particular participant typically demonstrates poor sleep hygiene. This behaviors may be stored by the system and associated with the participant. For example, this behavior may be stored as an attribute for the participant.

As will be described in more detail below, the computer system can assess the diversity of a monitoring group using the diversity criteria. To perform this assessment, the computer system may predict one or more characteristics of the monitoring group at a future time, such as at a set or anticipated completion of the monitoring program, and compare those characteristics to the diversity criteria to determine if the diversity criteria are met.

In general, composition characteristics refer to a set of features that describe a composition of the monitoring group. Composition characteristics can refer to either observed characteristics of the current composition of the monitoring group for a monitoring program, or to predicted characteristics of the composition of the monitoring group at a future time such as by a set or anticipated completion time for the monitoring program. As an example, the composition characteristics can include a size of the monitoring group, the size (e.g., population) of diversity groups in the monitoring group, and/or the percent representation of diversity groups in the monitoring group. The composition characteristics can also include an overall compliance rate for the monitoring group, an overall retention rate for the monitoring group, and/or an overall data quality for the monitoring group. Similarly, the composition characteristics can include compliance rates for each participant or group of participants (e.g., diversity group represented by a profile) in the monitoring group, retention rates for each participant or group of participants in the monitoring group, and/or data quality for each participant or group of participants in the monitoring group. The computer system can use the composition characteristics to determine if a monitoring program is on track to be successfully completed. For example, the computer system can predict composition characteristics for a particular monitoring program, and proceed to compare the predicted characteristics to the diversity criteria. Based on this comparison, the computer system can determine (i) that the diversity criteria is met and the results of the monitoring program are sufficiently likely to produce viable results, or (ii) that one or more diversity criteria are not met and the results of the monitoring program are not sufficiently likely to produce viable results.

When the computer system determines that one or more diversity criteria or other success criteria are not met or that there is a sufficiently high likelihood of one or more criteria not being met, the computer system can determine a set of remedial actions to address the anticipated failure or sufficiently high risk of failure. These actions can include changes to the elements of the monitoring program, the invitation of additional subjects to the monitoring program, the enrollment of additional participants in the monitoring program, and/or changes to the software configuration of remote devices used by the monitoring program's participants.

In general, monitoring program elements can refer to various features of the program, such as features that specify the operation of the computer system in initializing the program, managing the program, and interacting with remote devices during the program. In more detail, the monitoring program elements can include criteria used to identify eligible subjects. For example, the monitoring program elements can include inclusion criteria used to determine what subjects are eligible for enrollment, and exclusion criteria used to determine what subjects (e.g., otherwise eligible subjects) must be excluded from the monitoring program. The monitoring program elements can also include requirements/protocols for the monitoring program that define what actions and/or data is required of the program's participants. For example, the elements of a monitoring program can provide that all participants that belong to a first category of participants must visit with a medical professional once a week, and all participants that belong to a second category of participants must visit with a medical professional once every two weeks. The monitoring program elements can also include settings that define how the computer system manages the monitoring program and/or interacts with the participants in the monitoring group. For example, the elements can include different sets of communication parameters that the computer system uses to generate communications for different groups of participants in the monitoring program. The settings can also include event schedules and/or queues for the monitoring group, for different groups of participants in the monitoring group, and/or different participants in the group. The elements can also include the software configuration(s) for the monitoring program for the monitoring group as a whole, for particular participants, and/or for particular groups of participants. A software configuration for a monitoring program may specify, for example, how a monitoring program interface appears on remote devices, how notifications from the computer system appear on the remote devices, types of data to be collected by the remote devices, and/or a frequency or schedule for transmitting data from the remote devices to the computer system. Finally, the elements can also include the particular success criteria for the corresponding monitoring program, such as the diversity criteria for determining whether the monitoring group of the program will have a minimum level of diversity.

FIG. 1 is a diagram that illustrates an example system 100 for assessing and selecting technologies to meet diversity requirements. Among other uses, the system 100 can be used to identify and/or select devices and/or software to monitor to ensure that certain diversity criteria is being met. Similarly, the system 100 can be used to analyze device and/or software selections made by a user, and perform an action such as generating a recommendation to adjust the analyzed devices if the selected devices and/or software does not meet the diversity criteria or would not be expected to meet the diversity criteria by the end of a monitoring period. For example, if the selections made by the user would result in an insufficient number of devices associated with a particular group from being monitored, the system 100 may generate a warning to send to an administer with a recommendation to add a device from the underrepresented group, remove a device from one of the overrepresented groups, to add a device from the underrepresented group and remove a device form one of the overrepresented groups, or to perform one or more other actions such as to adjust the criteria for making a device and/or software selection.

Monitoring a set of devices or particular software running on a set of devices may include the system 100 collecting data from a distributed group of devices over a network. Data may be collected over a predetermined amount of time, until a goal is achieved, and/or until an event is detected. The frequency of data collection may be predetermined such that data is collected (e.g., requested and/or received) at predetermined intervals. Alternatively, data may be collected as it is produced, in response to certain goals or milestones being met, in response to certain events occurring or being detected, etc.

The system 100 can be used to, for example, identify (e.g., calculate) a target diversity level for a group of devices to be monitored (or a group of devices that are used to run software to be monitored), assess the current diversity of the group of devices (e.g., that have been selected for monitoring), and generate recommendations to reach or approach the target diversity level. The system 100 includes a client device 104 and a computer system 110 that includes functionality to make diversity assessments of devices and/or software selected for monitoring. The computer system 110 may further include functionality to select corresponding actions to perform or recommend in order to achieve the target diversity level.

It may be important to achieve and/or maintain a target diversity level for monitored devices to ensure the viability of data or results obtained during the monitoring period. For example, the computer system 110 may monitor how particular software performs on a variety of devices associated with different groups to determine how the software will perform when publicly released. If however, the monitored devices are not representative of the devices used by the general population, then data or results obtained from the monitoring of the devices may lack utility or otherwise have only limited applicability. For example, the data or results may fail to identify incompatibility between the monitored software and devices associated with a particular group when those devices are not included in the monitoring or are unrepresented (e.g., when compared to the use of those devices in the general population) to the point that statistically significant results regarding those groups of devices cannot be obtained or are sufficiently unlikely to be obtained.

Accordingly, in identifying a target diversity level and working to achieve or maintain the target diversity level, the computer system 110 can obtain improved data or results from the monitoring of multiple devices or software running on those devices. The improved data or results may be more comprehensive in that they correspond to a more diverse device pool.

In addition, in identifying a target diversity level and working to achieve or maintain the target diversity level, the computer system 110 can more efficiently conduct monitoring of multiple devices or software running on those devices. For example, the computer system 110 may determine that based on a reference population of devices (e.g., devices used in target region), the target diversity level should provide that no devices (or a very limited number of devices) that are Group 4 devices should be monitored. This may be based on, for example, the reference population of devices not including any (or a very limited number of) Group 4 devices. As such, the computer system 110 can improve efficiency by limiting the enrollment and monitoring of devices to those devices that are not Group 4 devices. That is, the computer system 110 can limit the enrollment and monitoring of devices to only those devices that will produce useful results (e.g., as may be indicated by the target diversity level). This has the added benefit of reducing computational burden on the computer system 110, reducing the amount of computing resources (e.g., CPU hours, RAM, etc.) that would have been otherwise spent monitoring the unnecessary devices (e.g., Group 4 devices), freeing up computing resources to perform other tasks, etc.

As illustrated in FIG. 1, the computer system 110 has access to a database 112 and also communicates with the client device 104 over a network 150. The computer system 110 can receive data from the client device 104 and can send data to the client device 104 as will be described in more detail below. For example, the computer system 110 can receive monitoring instructions 106 from the client device 104 indicating monitoring criteria and/or criteria for device selection, an indication of devices to select for monitoring, and/or an indication of software to monitor that is to be run on a cohort of devices. The computer system 110 may store the monitoring instructions 106, e.g., the criteria and/or device selections, in the database 112, perform a diversity analysis using the monitoring instructions 106, generate analysis results and/or recommendation(s) for the monitoring program, and/or transmit the analysis results and/or recommendation(s) to the client device 104. The computer system 110 may additionally or alternatively automatically perform one or more actions based on the results of the diversity assessment. For example, the computer system 110 may automatically adjust monitoring parameters, add or remove inclusion criteria for devices, add or remove exclusion criteria for devices, enroll or remove from enrollment one or more devices, etc.

Eligibility criteria such as inclusion criteria which dictates the minimum requirements that devices must meet to be enrolled in the monitoring program and exclusion criteria which dictates which devices must be excluded (e.g., even if they meet the inclusion criteria) may be used to determine which devices to enroll and, therefore, which devices to monitor. Sometimes eligibility criteria can have a detrimental effect on diversity as certain eligibility criteria may disproportionately impact certain groups of devices, e.g., a particular model of device, devices running a particular operating system (OS), devices running a particular OS version, a particular model or series of devices, devices having a particular hardware component, etc.

The client device 104 may be used by an administrator 102 to perform various actions with respect to the monitoring of devices. For example, the administrator 102 can use the client device 104 to create a new monitoring program (e.g., to test new software or a new version of software, such as a particular software module, a new operating system version, etc.), update a monitoring program (e.g., update parameters of a monitoring program, add or remove inclusion criteria for the devices, add or more exclusion criteria for the devices, enroll or remove devices from monitoring, etc.), and/or monitor the devices (e.g., monitor the performance of devices while running particular software, monitor the devices for errors or malfunctions, monitor the devices activity of participants, data collected from participants, review recommendations from the computer system 210, etc.). The client device 204 may be a computing device, such as a desktop computer, a laptop computer, a smartphone, a tablet, a cell phone, etc.

The computer system 110 may monitor a cohort of devices to, for example, test new or existing software. For example, the computer system 110 may, based on the monitoring instructions 106, determine that a new software program, Program A is to be tested on a cohort of devices to determine if minimum performance can be achieved across a variety of devices, to identify errors that are caused or might be caused as a result of running the Program A on a variety of devices such as system crashes, to determine if Program A causes any devices to overheat or experience other malfunctions, etc. The administrator 102 may initiate the monitoring of devices through the client device 104, e.g., in order to determine if new software is ready for release (e.g., to the public, to a particular country, to a particular region, to personnel of a particular business, to a particular group of persons, etc.), to determine if new or existing software is sufficient to meet the needs of a client (e.g., a particular business, a government entity, a particular group of persons, etc.), to determine if the new or existing software meets performance criteria (e.g., minimum loading times, minimum response times such as a render response time or a server response time, maximum battery life drain on underlying device, minimum throughput performance, minimum concurrency performance, maximum load times, latency requirements, maximum error rates, etc.).

The computer system 110 may monitor a cohort of devices to, for example, test the performance of the devices and/or test the hardware components of devices. For example, the computer system 110 may, based on the monitoring instructions 106, determine that devices with the latest CPU B should be tested to identify the performance benefits provided by CPU B. The administrator 102 may initiate the monitoring of devices through the client device 104, e.g., in order to start the monitoring of devices having CPU B during performance testing. The monitoring instructions 106 may indicate, for example, that the inclusion criteria for the monitoring program includes a requirement that all enrolled devices have the CPU B. Based on this, the computer system 110 may select a subset of available devices for performance testing, where each of the selected devices includes the CPU B. The computer system 110 may perform a diversity analysis on the selected subset of devices. The diversity analysis may reveal, for example, that one more additional devices should be included in the performance testing, such as one or more devices from varying groups of devices (e.g., the groups of devices corresponding to particular manufactures, particular hardware components, particular operating systems or other software, etc.).

The computer system 110 may communicate with the client device 104 and various devices, such as devices in a first group of network devices 120a, in a second group of network devices 120b, and/or in a third group of network devices 120c over a network 150. The network 150 can include public and/or private networks and can include the Internet. The network 150 may include wired networks, wireless networks, cellular networks, local area networks, wide area networks, etc.

The devices in the first group of network devices 120a, the second group of network devices 120b, and the third group of network devices 120c may include devices that may optionally be monitored. These candidate devices may be, for example, specifically used for testing, e.g., software and/or performance testing. For example, these devices may be part of a mobile device farm. These devices may include, for example, network-enabled computing devices, such as one or more desktop computers, laptop computers, smartphones, cell phones, tablets, etc.

A reference composition 122 is the group composition for a particular population of devices and is used by the computer system 110 to determine a composition target 124. That is, the reference composition 122 may reflect diversity for a particular set of devices (e.g., the set of devices used by the general public, used by a particular government agency, used by a particular business, used by a particular group of individuals that meet certain selection criteria such as being recently released or having particular hardware components, etc.). The reference composition 122 may be selected by the administrator 102, or determined by the computer system 110 based on information provided by the administrator 102 (e.g., provided in the monitoring instructions 106). For example, if the administrator 102 provides in the monitoring instructions 106 that a new software module is to be tested for a particular government agency, the computer system 110 may determine that the devices currently in use for the personnel of the government agency should be used as a reference population of devices. Based on this the computer system 110 may determine the reference composition 122 by, for example, accessing data from the database 112 or from remote storage that indicates that 70% of the personnel of the government agency use smartphones running OS A, and 30% of the personnel of the government agency use smartphones running OS B.

The computer system 210 may use the reference composition 122 to determine a composition target 124 for the set (e.g., cohort) of devices to be monitored. For example, the composition target 124 may be determined by removing one or more group of devices from the reference composition 122, by adjusting the reference composition 122 to account for trends (e.g., to estimate a new composition for a population of devices at a future point in time), etc. The composition target 124 may indicate the sought device diversity for monitoring, e.g., at an enrollment stage of monitoring or, more likely, at the conclusion of the conclusion of monitoring. As an example, if a selected set of devices to be monitored for performance over a period of one month is being performed for new devices that have not previously undergone performance tests, the computer system 110 may determine the composition target 124 by limiting the device population of the reference composition 122 to only those devices in the device population that are new models released in the last year and/or are models that have not previously undergone performance tests. The computer system 110 may use the reference composition 122 to identify the different group percentages for the composition target 124. The computer system 110 may similarly determine what devices to enroll in monitoring based on the cohort composition target 224, e.g., in an effort to have an observed/enrolled group composition 126 of devices at the end of the monitoring program match the composition target 124.

The composition target 124 may additionally or alternately indicate a quota that needs to be met for the different groups of devices. For example, the composition target 124 may additionally or alternatively indicate that there needs to be at least two devices from the Group 3 network devices 120c and at least one device from the Group 1 network devices 120a.

Continuing the earlier example, if the reference composition 122 provides for 70% Group 3 devices 120c and 30% Group 1 devices 120a and trend data (e.g., previously determined by the computer system 110 and stored in the database 112) indicates that there is a trend of a growing population of percent of Group 3 devices 120c relative to the population of Group 1 devices 120a, then the computer system 110 may calculate the composition target 124 based on the trend data as 75% Group 3 devices 120c and 25% Group 1 devices 120a.

The group composition 126 may represent the current composition of a relevant population of devices to be monitored. For example, at a time of enrollment, the group composition 126 may refer to the composition of a group of devices that have been enrolled by the computer system 110 in the monitoring program. Similarly, during the monitoring program, the group composition 126 may refer to the composition of a group of devices that are still undergoing monitoring. Some devices that were initially enrolled may no longer be monitored at this time due to, for example, errors, crashes, hardware failures, etc. As another example, some devices that were initially enrolled may have been removed by the computer system 110 from enrollment to meet diversity criteria. Accordingly, the computer system 110 may determine the group composition 126 multiple times through the monitoring program, e.g., at fixed time intervals, in response to errors or warnings being detected, when certain monitoring milestones are reached (e.g., tests regarding a particular performance parameter are completed).

The computer system 110 can also be used to automatically determine devices and/or software eligible for monitoring or to enroll in monitoring based on information provided by the administrator 102. For example, the administrator 102 may provide selection criteria that indicates parameters for monitoring (e.g., as part of the monitoring instructions 106), such as a length of time that the monitoring will take place for, a time of day that the monitoring will take place for, frequency of data requests to the monitored devices and/or data transmissions from the monitored devices, inclusion requirements for the devices or software that are used to determine eligibility, exclusion criteria for the devices or software that may dictate the automatic removal of any devices or software that meet one of the exclusion criteria (e.g., even if the devices or software meet the inclusion requirements), etc.

Where the selection criteria has or is predicted by the computer system 110 to have a disproportionately adverse effect on a particular group of devices (e.g., such that it is predicted that the diversity of devices at an end of the monitoring period will be outside of a target diversity device composition), the system 100 may generate a warning and/or a recommendation to adjust the selection criteria. In some cases, instead of generating a recommendation, the system 100 may perform one or more actions automatically.

The devices or software to be monitored may include, for example, computer devices, such as network enabled smartphones, tablet computers, laptop computers, desktop computers, etc. The devices or software may additionally or alternatively include particular software that is running on a device, a virtual machine, a container, a network environment, a virtual network environment, etc. For example, the computer system 110 may be used to monitor a particular type of OS software that it would like to test on multiple different devices (e.g., of different manufacturers, models, hardware specifications, CPU types, RAM amounts, etc.). The computer system 110 may receive an indication from the administrator 102 of the software to be monitored and selection criteria for the devices that are to run the software. The computer system 110 may determine a diverse group of devices to run the software, or determine that a group of devices selected by the administrator 102 does not meet diversity criteria (or is unlikely to meet the diversity criteria).

As illustrated in FIG. 1, the overall process of creating and carrying out a monitoring program may be broken down into different stages 132-140. In the first stage 132, the administrator 102 can select through the client device 104 a set of devices (e.g., cohort of devices) to monitor or the computer system 110 can select the set of devices based on the monitoring instructions 106. Continuing the earlier example, the computer system 110 may select three devices from Group 3 devices 120*c* and one device from the Group 1 devices 120*a* to monitor based on the monitoring instructions 106 and previously determined trend data. In response to the selection of the set of devices that are to be monitored, the computer system 110 may calculate diversity measures 130 to determine if the selected set of devices meets diversity criteria. The diversity measures 130 may include, for example, the current group composition 126 determined using the selected devices. For example, the computer system 110 may determine that group composition is 75% Group 3 devices 120*c* and 25% Group 1 devices 120*a* as indicated by the key 128. The diversity measures 130 may include the reference composition 122 or an update to the reference composition 122, the composition target 124 or an update to the composition target 124, and/or the results of a comparison of the group composition 126 (or a predicted group composition 126 for the end of the monitoring program) to the composition target 124. The diversity measures 130 may also include the calculation of new trend data or the updating of existing of trend data using new information.

As an example, in generating the diversity measures 130, the computer system 110 may determine, based on trends in one or more devices populations, that Group 2 devices have a fast growing population. Based on this, the computer system 110 may determine that the results of the monitoring program will have limited applicability if Group 2 devices are unrepresented or not included. As such, the computer system 110 may calculate a new composition target 124 that accounts for the growing use of Group 2 devices. For example, the computer system 110 may determine that the composition target 124 should be 20% Group 1 devices 120*a*, 40% Group 2 devices 120*b*, and 40% Group 3 devices 120*c*.

In the second stage 134, the computer system 110 determines that the selected subset (e.g., the initial device selection) does not meet diversity criteria. For example, the computer system 110 may determine that the diversity criteria is not met if the group composition 126 does not include or is predicted not to include by the end of the monitoring program a device from a device group in the composition target 124. Similarly, the computer system 110 may determine that the diversity criteria is not met if the group composition 126 deviates a threshold percent (e.g., for any one group of devices) or predicted to deviate by a threshold percent by the end of the monitoring program from the composition target 124. As another example, the computer system 110 may determine that the diversity criteria is not met if the group composition 126 or the predicted group composition at the end of the monitoring program is not within range (e.g., for any one group of devices) of a target diversity range (e.g., calculated based on the composition target 124).

In an optional third stage 136, the computer system generates a recommendation to meet the diversity criteria. For example, the computer system 110 may generate a recommendation 108 that it transmits to the client device 104. The recommendation may be to add a device from an underrepresented group of devices, remove a device from enrollment that is in an overrepresented group of devices, remove inclusion an inclusion criterion so that more devices may qualify for enrollment, remove an exclusion criterion so that less devices will be rejected from enrollment, etc. For example, if the inclusion criteria indicated that the device had to be one of a set of specific device models, the computer system 110 may recommend that the inclusion criteria be removed (e.g., as it may be overly restrictive for failing to account for new device models). Similarly, continuing the earlier example, the computer system 110 may recommend for two devices from the Group 2 devices 120*b* to be added and for one of the Group 1 devices 120*c* to be removed.

In an optional fourth stage 138, the computer system 110 receives confirmation from the client device 104 to perform the actions specified in the recommendation 108.

In some cases, the computer system 110 receives instructions to perform one or more different or modified actions compared to the actions in the recommendation 108.

In the fifth stage 140, the computer system 110 selects a new subset of devices to monitor. For example, in response to receiving a confirmation to perform the recommended actions provided in the recommendation 108, the computer system 110 may enroll two devices from the Group 2 devices 120b as indicated by the key 128. By doing this, the computer system 110 can update the group composition 126 so that the current group composition 126 or a predicted group composition at the end of the monitoring program will match (or be sufficiently close to) the composition target 124 and/or so that a minimum number of Group 2 devices 120b can be enrolled in the monitoring program. This would indicate that sufficient device diversity is predicted to be met based on the updates to the enrolled devices.

Other changes or modifications to the enrolled devices may be performed at other stages of the monitoring program. These changes or modifications may be made for diversity purposes based on newly determined diversity measures. These changes or modifications may be based on changes to the enrolled devices, a warning generated in response to new data indicating that the composition target 124 is unlikely to be met by the end of the monitoring program (e.g., new trend data, data indicating the a number of devices from a particular group of devices have been unenrolled, etc.), etc.

Figure 2:
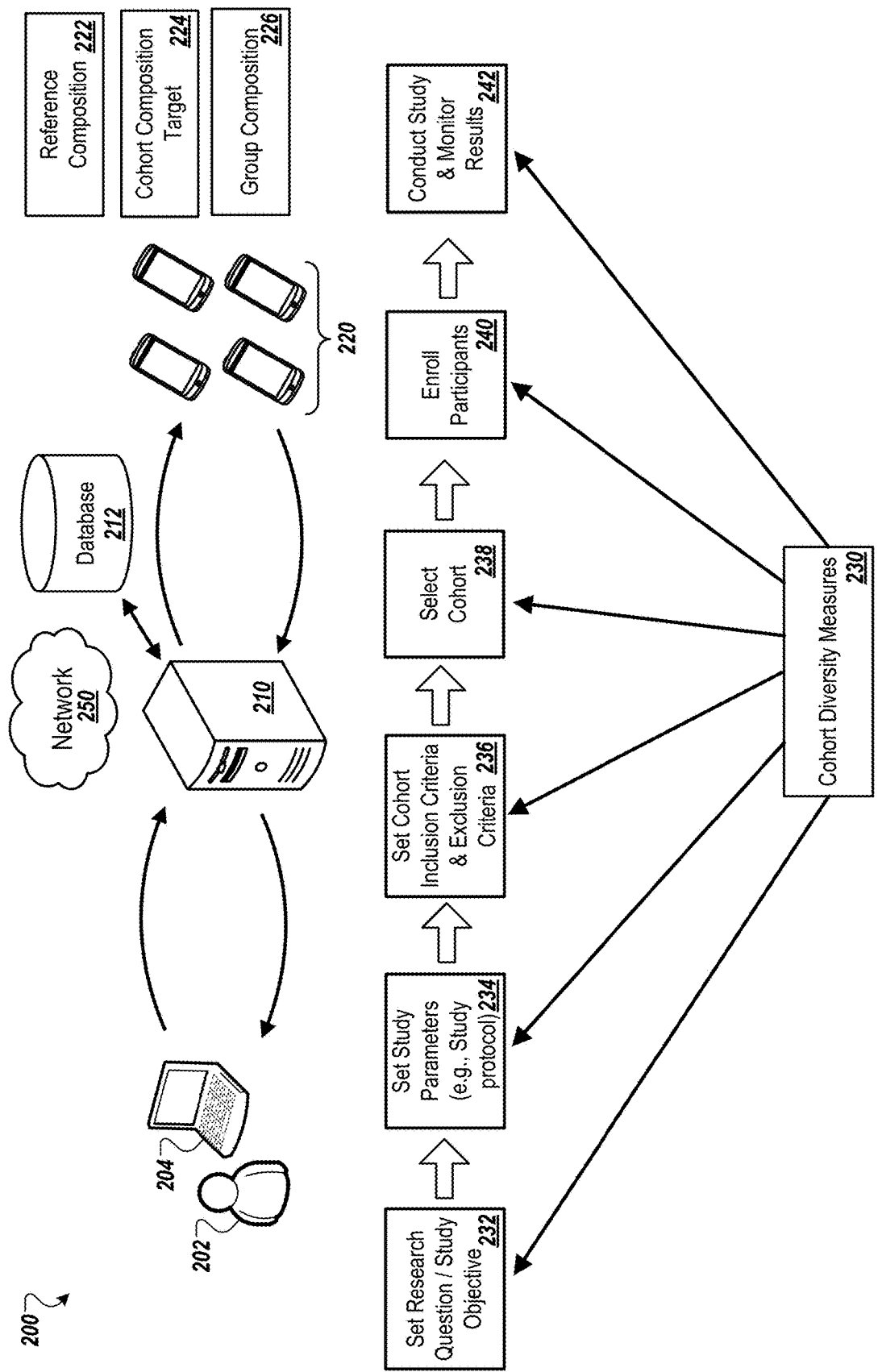
FIG. 2 is a diagram that illustrates an example system for performing diversity assessment and action selection.

FIG. 2 is a diagram that illustrates an example system 200 for performing diversity assessment and action selection. Among other uses, the system 200 can be used to assist in the creation and implementation of research studies (e.g., clinical trials, experimental studies, longitudinal studies, correlational studies, case studies, etc.), as well as adaptation of existing or ongoing studies. Specifically, the system 200 can be used to, for example, identify a target diversity level for a research study (e.g., based on one or more goals for the research study), assess the current diversity of the research study, and generate recommendations to reach or approach the target diversity level. The system 200 includes a client device 204 and a computer system 210 that includes functionality to make diversity assessments of one or more research studies and to select corresponding actions to perform or recommend. The numerous benefits discussed above with respect to the computer system 110 are applicable to the computer system 210.

The systems discussed herein, including the computer system 210, can be used to create, manage, adapt, and evaluate monitoring programs in many fields, including manufacturing quality control, environmental monitoring, health research, and many other areas where sampling is used to monitor a subset of a population. In the case of health research in particular, the system can be a multi-tenant system for administering clinical trials through remote devices. The system can create and adapt clinical trials that involve many users remotely collecting user input and sensor data through mobile devices. The system can create and administer studies for various different organizations, allowing the system to efficiently administer many clinical trials concurrently, each with their own separate monitoring groups (e.g., cohorts of participants with associated devices), objectives for monitoring, data collection and reporting procedures, and requirements for diversity in the monitoring groups.

The techniques described can be used to achieve various benefits. For example, by taking into account diversity at the onset and multiple times throughout a clinical study, numerous health benefits can be achieved. Notably, diversity in a research study can be monitored and actions performed in an effort to maintain a target level of diversity such that the results of the study are applicable to typically unrepresented segments of a population. With respect to new medications and treatments, the applicability of these new medication and treatments may be extended such that those belonging to the underrepresented segments can be safely administered the medications/treatments where there otherwise would have been significant doubt due to, for example, there being no data collected for these groups and/or an insufficient amount of data for the results to be statistically relevant for these groups. Similarly, negative interactions and side effects of new medications/treatments for those belonging to the underrepresented segments are more likely to be identified, thereby reducing the risk of injury or death.

As an example, many recent COVID-19 vaccine trials excluded pregnant women due to pregnant women being a high risk group. Unfortunately, by eliminating this group of participants from the vaccine trials, there is insufficient data to determine if many of the vaccines can be safely administered to pregnant women. The disclosed system may identify pregnant women as a group that should be included for a vaccine or medical trial as an underrepresented or excluded group of participants. This may be especially true for medications that are likely to be taken by pregnant women, such as those that are meant to address pregnancy issues, illness that commonly arise during pregnancy, medications that are typically taken by women between the ages 18 and 54, etc. The disclosed system may further account for the increased risks by, for example, making a researcher aware of the increased risks, recommending additional or more comprehensive monitoring during the study for this particular group of participants, recommending a lower dose of the medication or vaccine being tested for this particular group of participants, etc. In this way, important data can be collected on the underrepresented or excluded group of pregnant women while steps can be taken to reduce the risk presented to this group. The collected data may indicate whether it is safe to administer the vaccine to pregnant women, whether there are any side effects unique to pregnant women, whether there are any reactions to the vaccine associated with medications typically taken by pregnant women, etc. Accordingly, in recommending that this group of typically excluded or underrepresented participants be included in the study, the disclosed system can improve the safety afforded to those in the group.

In general, diversity or diversity level may refer to the type or amount of variety of groups or attributes represented in a set (e.g., a monitoring group for a monitoring program, a candidate pool, etc.). For example, a diversity level may be a value or a set of values (e.g., a distribution) that indicates the variety of groups of users represented in, or predicted to be represented in, a monitoring group of a monitoring program. One way to assess diversity is to assess distribution of members of a monitoring group across different groups, e.g., to determine whether the distribution of members into the different groups is sufficiently similar to the distribution of those groups among a reference population. This population may be a current population at a geographical region or an expected future population, a group that has been invited to participate in a research study, a group (e.g., cohort) that has enrolled in a research study, a group that has enrolled and remains active in a research study, a group that has a particular set of attributes (e.g., a disease relevant to a research study), etc. This population may additionally or alternatively be a subset of a larger reference population. Alternatively, diversity may be assessed without a reference population. For example, diversity may be assessed simply based on the amount of variation or difference present of groups of users and/or attributes of users represented in or predicted to be represented in the monitoring group (e.g., a number of different groups represented, size of the largest group, size of the smallest group, proportion of members outside the largest group, mean or median group size, and other measures) without comparison to a reference population.

The categories or profiles used as different groups to assess diversity may be defined using one or more attributes, including demographic and non-demographic characteristics. In many cases it is important to obtain diversity not only in demographics, but also in health status, lifestyle, location, context, medical history, and other factors to obtain a broad and effective monitoring. As an example, groups to be assessed during a research study may be defined to have certain combinations of attributes, with one group having a first set of attributes, a second group having a second set of attributes, and so on. The attributes used to define groups can include race, ethnicity, nationality (or nationality of relatives such as parents or grandparents), residence in a certain region (e.g., city, county, state, country, etc.), genomics data (e.g., having a particular gene variant or not having a particular gene variant), state of health (e.g., a body fat percentage of less than 25%), physiological attributes (e.g., weighing more than a threshold amount, weighing less than a threshold amount, having a RHR within a particular range, etc.), psychological attributes, and so on. The attributes can include behavior factors such as sleep, diet, exercise, and other behavior factors.

Other examples of characteristics that can be used to define a group may include ages, age ranges, medical conditions, medicines (e.g., that have been prescribed and/or are being taken by individuals), treatments (e.g., that individuals are undergoing), etc. For example, a first group of a particular population may correspond to all those in the population that have been diagnosed with diabetes, while a second group of the population may correspond to all those in the population that have not been diagnosed with diabetes, and a third group of the population may correspond to all those in the population between the ages of 20-40 regardless of whether they are diagnosed with diabetes It may be important to achieve and/or maintain a target diversity level for participants in a study to ensure the viability of data or results obtained during the study. For example, the computer system 210 may want to perform a research study to determine the effectiveness and safety of a new pharmaceutical. If however, the study participants are not representative of a reference population that is to use the new pharmaceutical, then data or results obtained from the study may lack utility or otherwise have only limited applicability. For example, if a target group composition cannot be achieved by the end of the study (or the target group composition cannot be achieved within a margin of error), the results of the study may fail to identify side effects of those in groups that are typically excluded from studies due to the higher risk they present (e.g., pregnant women, elderly persons, those with particular diseases or other serious ailments, etc.), of those in groups that are typically less likely to join or complete a study, those in groups that have difficulty meeting the requirements of a study (e.g., due to residential location, access to vehicles, access to computing devices, etc.), etc. Similarly, the data may be insufficient to determine if the medication can be safely administered to those groups.

The computer system 210 may access data corresponding to a particular reference population, such as a list of persons in the reference population. The computer system 210 may filter the reference population to those that have the characteristics corresponding to a particular group, and proceed to sample from the filtered list, e.g., in order to identify a manageable list of persons associated with first group. As will be described in more detail below, the computer system 210 can use this sampled list in a variety of ways. For example, the computer system 210 may simply invite the persons in the sample list. As another example, the computer system 210 may analyze the other characteristics of the persons in the sample list and use these characteristics to identify persons to be invited/enrolled in the study, and/or removed from consideration or enrollment for the study. In this way, the computer system 210 can enroll participants who more accurately represent the larger reference set (e.g., the reference population).

In general, study parameters may include the information that defines the protocol for a study. The study parameters may include, for example, one or more locations where the study is to be conducted, an expected number of participants for the study, a length of the study, an age range of participants for the study, a budget for the study, a target date for the release of a medication or treatment being studied, etc. The study parameters may also include requirements of the participants and/or for how the study is to be conducted. For example, a first parameter for a new research study may provide that participants will be required to attend three medical office visits per month, and a second parameters may provide that participants are required to have or obtain a smartphone. The study parameters may be set by a researcher 202 through the client device 204, by the computer system 210, or by a combination of the researcher 202's inputs and the computer system 210.

In general, eligibility criteria (also referred to as selection criteria) are used to identify devices and users that can appropriately participate in a monitoring study. The criteria may include inclusion criteria and exclusion criteria described in more detail below. Eligibility criteria may also refer to other requirements provided in the study parameters. For example, there may be an eligibility criterion that participants have access to a smartphone, laptop, or other network-enabled computing device due to the study parameters requiring the participants to make frequent telehealth visits. The system 210 ensures not only that eligibility criteria are satisfied for participants in a monitoring program, but that the desired level of diversity is present across the monitoring group as a whole, with diversity being tracked and achieved for each of the different types of attributes that are important for achieving the outcome of the monitoring program.

In general, inclusion criteria may refer to the minimum requirements that candidates must meet in order to be enrolled in study. The inclusion criteria may be based on the question (e.g., goal) of the study, e.g., provided by the researcher 202. For example, if a new study is designed to research the side effects of a new Drug X for the treatment of high cholesterol, then the inclusion criteria for the study may include a requirement that participants have high cholesterol. The inclusion criteria may be set by the researcher 202 using the client device 204. The computer system 210 may additionally or alternatively set the inclusion criteria. For example, based on information sent to the computer system 210 from the client device 204 indicating that the goal of the researcher study is to identify the side effects of a new Drug X for the treatment of high cholesterol, the computer system 210 may, based on this information, add a requirement that each participant have high cholesterol to the inclusion criteria or may generate a recommendation for the researcher 202 to add this criterion or confirm its inclusion. Other examples of inclusion criteria may include a particular age or age range (e.g., corresponding to a particular group of persons that are most likely to take Drug X).

In general, exclusion criteria may refer to attributes of candidates that prevent them from being enrolled in the study (e.g., even if they meet the inclusion criteria). The exclusion criteria may be based on and/or otherwise take into consideration risk factors. For example, the exclusion criteria may prevent those who are pregnant or over a certain age from participating in the study. The exclusion criteria may be based on the question (e.g., goal) of the study, e.g., provided by the researcher 202. For example, if a new study is designed to research the side effects of a new Drug X for the treatment of high cholesterol, then the exclusion criteria may include attributes that have known negative effects with Drug X. For example, the computer system 210 may refer to previous studies stored in a database 212 that indicates that Drug X cannot be safely administered to those with diabetes. In response, the computer system 210 may automatically add diabetes as an exclusion criterion for the research study, or generate a recommendation to add diabetes as an exclusion criterion and send the recommendation to the client device 204 to present to the researcher 202.

As illustrated in FIG. 2, the computer system 210 has access to the database 212 and also communicates with the client device 204 over a network 250. The computer system 210 can receive data from the client device 204 and can send data to the client device 204 as will be described in more detail below. For example, the computer system 210 can receive data from the client device 204 indicating a question and/or requirements for a study (e.g., to initiate a new research study). The computer system 210 may store question and/or requirements in the database 212, perform a diversity analysis using the questions and/or requirements, generate analysis results and/or recommendation(s) for the new study, and/or transmit the analysis results and/or recommendation(s) to the client device 204. The computer system 210 may additionally or alternatively automatically perform one or more actions based on the results of the diversity assessment. For example, the computer system 210 may automatically adjust study parameters, add or remove inclusion criteria, add or remove exclusion criteria, enroll or remove one or more participants, send invitations to enroll to one or more participants, etc.

The client device 204 may be used by a researcher 202 to perform various actions with one or more research studies. For example, the researcher 202 can use the client device 204 to create a research study, update a research study (e.g., update parameters of a research study, add or remove inclusion criteria of a research study, add or more exclusion criteria of a research study, enroll or remove participants of a research study, etc.), and/or monitor a research study (e.g., monitor activity of participants, data collected from participants, review recommendations from the computer system 210, etc.). The client device 204 may be a computing device, such as a desktop computer, a laptop computer, a smartphone, a tablet, a cell phone, etc.

The computer system 210 may communicate with the client device 204 and the participant devices 220 over a network 250. The network 250 can include public and/or private networks and can include the Internet. The network 250 may include wired networks, wireless networks, cellular networks, local area networks, wide area networks, etc.

The computer system 210 can also communicate with participant devices 220. The participant devices 220 may belong to users who have been invited to enroll in a research study, have enrolled in the research study, and/or are enrolled and active in the research study. The participant devices 220 may be computing devices. For example, the participant device 220 may include one or more desktop computers, laptop computers, smartphones, cell phones, tablets, etc.

A reference composition 222 is the group composition for a particular population and is used by the computer system 210 to determine a cohort composition target 224. That is, the reference composition 222 may reflect diversity for a particular population (e.g., for a particular region, a particular region at a future point in time, those having a particular medical condition, those taking a certain medication, those belonging to a particular age group, etc.). The reference composition 222 may be selected by the researcher 202, or determined by the computer system 210 based on information provided by the researcher 202. For example, if the researcher 202 provides that a study regarding a new cholesterol medication is to take place in Virginia and does not specifically indicate a reference population, the computer system 210 may use Virginia as a reference population. The computer system 210 may proceed to identify the group composition of the reference population. For example, the computer system 210 may look up and/or estimate the percentage of Virginia's population that have or are likely to experience high cholesterol, percentages corresponding to particular races or ethnicities, percentages corresponding to particular age ranges, etc.

The computer system 210 may use the reference composition 222 to determine a cohort composition target 224. For example, the cohort composition target 224 may be determined by removing one or more groups from the reference composition 222 (e.g., if you want to focus the study on only persons suffering from a particular medication), by adjusting the reference composition 222 to account for trends (e.g., to estimate a new composition for a population at a future point in time), etc. The cohort composition target 224 may indicate the desired diversity for a new research study, e.g., at enrollment or, more likely, at the conclusion of the research study. As an example, if a new research study is to study the effects of a new cholesterol medication, the computer system 210 may determine the cohort composition target 224 by limiting the population of the reference composition 222 to only those in the population that are suffering from high cholesterol or are likely to suffer from high cholesterol. The computer system 210 may use the reference composition 222 to identify the different group percentages for the cohort composition target 224. The computer system 210 may determine what candidates to invite and/or enroll based on the cohort composition target 224, e.g., in an effort to have a group composition 226 at the end of the study match the cohort composition target 224.

As an example, the reference composition 222 may indicate for a corresponding population that a first group corresponding to those of a first ethnicity makes up 55% of the population, that a second group corresponding to a second ethnicity makes up 20% of the population, that a third group corresponding to third ethnicity makes up 15% of the population, and that a fourth group corresponding to those that have or are likely to from high cholesterol makes up 43% of the population. In determining the cohort composition target 224, the computer system 210 may refer to the reference composition 222 to determine percentages for the first three groups when the population is limited to the fourth group. For example, the computer system 210 may use the reference composition 222 to determine that 52% of the individuals in the fourth group also belong to the first group, that 25% of the individuals in the fourth group also belong to the second group, and that 12% of the individuals in the fourth group also belong to the third group. The computer system 210 may proceed to set the cohort composition target 224 to 52% for the first group, 25% for the second group, 12% for the third group, and 11% to one or more other groups.

The group composition 226 may represent the current composition of a relevant population of the study. For example, the group composition 226 may refer to the composition of a group of candidates that were invited to enroll in a study and/or to a cohort of enrolled participants. The computer system 210 may determine the group composition 226 multiple times through the study, e.g., once for each stage of the research study. The group composition 226 may be calculated using different populations. For example, the group composition 226 may initially be calculated for the candidate pool of potential participants, to a group of candidates that were invited to enroll, to the cohort of enrolled participants (e.g., at one or more points throughout the study), etc.

As illustrated in FIG. 2, a research study may be broken down into different stages 232-242. In the first stage 232, the researcher 202 can use the client device 204 to set a research question or study objective. For example, the researcher 202 can initiate a new study through the client device 204 by submitting a study objective to study the side effects of a new Drug X for treating high cholesterol. In the second stage 234, the researcher 202 and/or the computer system 210 set parameters for the study, such as a study size, a region where the study is to take place, devices and/or sensors needed for the study, etc. As an example, the computer system 210 may generate one or more recommendations for study parameters, such as a recommended study size. In the third stage 236, the researcher 202 and/or the computer system 210 set cohort inclusion criteria and/or exclusion criteria. In the fourth stage 238, the researcher 202 and/or the computer system 210 select the cohort. Selecting the cohort may include identifying a group of candidates send enrollment invitation to. Alternatively, selecting the cohort may include identifying a group of candidates from an applicant pool to enroll. In the fifth stage 240, the cohort participants are enrolled. The computer system 210 may generate and send a notification to the participant devices 220 indicating that they have been enrolled. In the sixth stage 242, the study is conducted and the results are monitored. Data may be obtained from the participants through the participant devices 220. The data may be used to identify an activity or participation level of the participants, participants who are inactive, participants who have unenrolled, etc.

Each of the stages 232-242 of the research study may be based on cohort diversity measures 230. That is, the cohort diversity measures 230 may be used by the computer system 210 to confirm or modify how the research study is to proceed from one stage to the next. The cohort diversity measures 230 may include results of one or more diversity analyses, e.g., which may differ depending on the present stage of the research study. For example, with respect to the first stage 232, the cohort diversity measures 230 may include an indication of biases associated with the research question/study objective, or type of research question/study objective. Specifically, if the research study objective is set to study the effects of Drug X for the treatment of high cholesterol, the computer system 210 may access historical data and/or remote data of previous cholesterol research studies that shows that persons of Asian ethnicity are often unrepresented by 20% in cholesterol research studies. There may be relevant reasons for this, such as the possibility of persons of Asian ethnicity being significantly less likely to have high cholesterol. However, despite this, it may be critical to accurately represent the Asian ethnicity segment of the cohort composition target 224 to ultimately determine if Drug X can be safely administered to those of Asian ethnicity and/or to identify dangerous side effects which may disproportionately affect those of Asian ethnicity. More generally, the cohort diversity measures 230 may show that persons of a certain group are consistently underrepresented in clinical trials involving a new medication, such as pregnant persons, persons older than 70 years of age, persons with immune system disorders, etc.

The cohort diversity measures 230 may include one or more diversity levels calculated by the computer system 210. These diversity levels may correspond to a current level of diversity, e.g., present among previous participants (e.g., potential candidates), those invited to enroll in the study (e.g., candidates), those that have accepted to be enrolled in the study and/or are enrolled in the study (e.g., participants), etc. Additionally or alternatively, these diversity levels may correspond to a predicted level of diversity at a future point in time, such as the study completion.

A determined diversity level may indicate how close the predicated group composition at study completion is to the cohort composition target 224. The diversity level may be expressed as, for example, a diversity score. That is, the diversity level may be expressed a value (e.g., a number, a classification, etc.) that is indicative of how close the predicted group composition at study completion is to the cohort composition target 224 (e.g., a target group composition). In some cases, the score can indicate a magnitude of how far the distribution or composition of members of the cohort varies from the target distribution or composition. As an example, a diversity score of 1.0 may indicate that the predicted group composition at study completion matches the cohort composition target 224. Lower scores can indicate increasing differences from the target level, e.g., a score of 0.9 may indicate that the composition varies from the target by at least 5% in at least one category or attribute, a score of 0.8 may indicate that the composition varies from the target by at least 10% in one target or attribute, etc. The scoring can change linearly or nonlinearly with the amount of deviation from the target.

The diversity score for a monitoring group may be determined as an aggregate or composite of separate scores for different categories or profiles for which composition is tracked. For example, if there are 5 different types of participants needed, and only four of the 5 meet the requirements for the minimum number of participants, then the diversity score can be 80%. Separate scores may be determined for each category or group to be included, and those scores can be averaged (e.g., if group 1 has 100% of needed members, group 2 has 90% of needed members, and group 3 has 60% of needed members, the average of 83% can be used as a diversity score for the monitoring group as a whole).

The diversity score may be based on absolute measures, such as the numbers of participants in each group, or it may be relative measures, such as the amount in one group relative to the amount in another category or to the monitoring group as a whole (e.g., a ratio, proportion, fraction, percentage, etc.). A diversity score can also be determined relative to other references, such as a previously predicted group composition, a previously determined diversity score, a predicted group composition corresponding to one or more recommendations (e.g., predicated based on an assumption that the recommended actions will be performed), etc.

Diversity scores can be generated and provided for each of the different categories or attributes that are relevant to the monitoring program. For example, the system can determine, for each of various groups to be represented in the monitoring group, how close the subset representing that group is to the target level for the group. This can help indicate, for example, the specific groups or categories of devices and users where additional representation is needed in the monitoring group.

Additionally or alternatively, the diversity level may be expressed as a probability or confidence score indicating the expected results for the study, such as a likelihood that a minimum amounts or proportions of the different groups represented in the monitoring group will achieve compliance with the requirements until the end of the monitoring program. Because there are multiple different groups or categories of members in the monitoring group, set of probabilities or confidence scores can be determined, with one for each of the different groups or categories. In addition, multiple versions of the scores can be determined for different scenarios, e.g., one for the current state of the monitoring program and the current monitoring group, and others representing the expected likelihood(s) of success that would result after performing different actions corresponding to different recommendations.

The diversity level may indicate a level of confidence in achieving the cohort composition target 224, and/or achieving a group composition that is with an acceptable range (e.g., percent range or value range) of the cohort composition target 224. For example, a diversity score of 0.91 may indicate that the computer system 210 has determined that there is 91% possibility of the group composition at study completion being within a threshold percentage (e.g., 5%, 3%, 1%, etc.) of the cohort composition target 224. Or, if the cohort composition target 224 is expressed as one or more ranges, the score can indicate the likelihood of the composition having representation of groups that falling within the target ranges.

Diversity level may also or alternatively describe a group composition (e.g., a predicted group composition), or the difference between a group composition (e.g., current or predicted) and the cohort composition target 224. For example, a predicted group composition at study enrollment may be a first diversity level, a predicted group composition at study completion may be a second diversity level, and a difference (e.g., difference between two sets of values, absolute value of the difference between the two sets of values, etc.) the group composition at study completion and the cohort composition target 224 as a third diversity level.

In some cases, there are multiple diversity metrics used to assess the level of diversity. For example, a first diversity level may include a diversity distribution indicating different likelihoods of achieving the cohort composition target 224, and a diversity score may be second diversity level identified from the diversity distribution (e.g., as the value associated with the highest probability out of the all of the values).

The target diversity level described above and elsewhere may refer to a single diversity level or to a group of multiple diversity levels or metrics. For example, a target diversity level may require as a first level or metric a requirement that a cohort (e.g., monitored group) meets certain enrollment minimums (e.g., at least one subject from each diversity group). For example, the enrollment minimums may provide that for each medical condition in a list of particular medical conditions, there are at least two corresponding subjects that have the medical condition. The target diversity level may further require a diversity score metric. For example, the monitoring program may require a diversity score of 0.7 or greater by the end of the monitoring program. This diversity score may be calculated using a target group composition of subjects and an observed or anticipated (e.g., at the end of the monitoring program) composition of subjects (e.g., determined from the current or anticipated enrollment of subjects in the monitoring program). This diversity score can, for example, represent the difference between the actual (e.g., observed or anticipated) composition of subjects and the target composition (e.g., a composition having sufficient or ideal diversity). For example, the diversity score may be a value between 0 and 1. Here, 0 may correspond to complete or maximum divergence or difference between a vector (or array) representing an actual composition of subjects and a second vector (or array) representing the target composition of subjects. Similarly, 1 may correspond to no or minimum divergence or difference between the two vectors or the two arrays. The computer system 210 may, therefore, calculate a diversity score and/or a target diversity level by calculating the difference or divergence between two or more vectors. Similarly, the computer system 210 may, therefore, calculate a diversity score and/or a target diversity level by calculating the difference or divergence between two or more arrays.

In determining a diversity level such as a diversity score, the computer system 210 may sample from a larger reference set to obtain a makeup that is representative of the larger reference set (e.g., replicating, within a predetermined tolerance, the distribution of certain attributes or characteristics that are relevant to the monitoring program). That is, the computer system 210 may sample from a larger reference set so that the sample reflects the characteristics across the reference group. For example, the computer system 210 may access from the database 212 or from an external data storage, data that corresponds to persons having characteristics that define a first group, such as being of a specific race, being of a specific ethnicity, being of a specific nationality, living in a certain region (e.g., city, county, state, country, etc.), having particular genomics data (e.g., particular gene variant), having a particular state of health, having particular physiological attributes (e.g., weighing more than a threshold amount, weighing less than a threshold amount, having a RHR within a particular range, etc.), having a particular diet or having particular eating habits (e.g., vegetarian, vegan, etc.), having a particular occupation, having a particular level of education (e.g., high school diploma, two years of college, four years of college, graduate degree, etc.), etc. The computer system 210 may access this data, such as a list of persons in the reference population (e.g., used to determine the reference composition 222) that belong to this first group, and proceed to sample the data (e.g., in order to identify a manageable list of persons associated with first group).

The computer system 210 can use this sampled list in a variety of ways. For example, the computer system 210 may simply invite the persons in the sample list, or a subset of persons in the sampled list, to participate in the study. As another example, the computer system 210 may analyze the other characteristics of the persons in the sample list and use these characteristics to identify persons to be invited/enrolled in the study, and/or removed from consideration or enrollment for the study. For example, if the sample data indicates that 95% of users associated with Group 1 also have characteristic B and none of the users associated with Group 1 have characteristic C, the computer system 210 may set characteristic B as inclusion criteria for Group 1 participants, and characteristic C as exclusion criteria for Group 1 participants. In this way, the computer system 210 can enroll participants who more accurately represent the larger reference set (e.g., the reference population).

The computer system 210 may make various recommendations or take various actions based on the determined diversity level(s). These diversity measures may be, for example, compared by the computer system 210 to one or more thresholds that correspond to particular recommendations and/or actions.

As another example with respect to the first stage 232, the cohort diversity measures 230 may also include an indications of determinations made by the computer system 210 with respect to whether the question/objective is too limited. For example, the computer system 210 may generate a warning if it determines that a study objective set by the researcher 202 will result in a restrictive FDA label. The computer system 210 may also generate a recommendation or identify an action to perform as part of the cohort diversity measures 230. For example, if the objective is to study the effects of a particular treatment on a small population segment, the computer system 210 may generate a recommendation to modify the objective to take into account other population segments, such as similar population segments.

As another example, with respect to the second stage 234, the cohort diversity measures 230 may include indications of particular study parameters that disproportionately affect certain groups of the cohort composition target 224. For example, the computer system 210 may generate a warning for a study parameter that requires that participants have or use a smartphone upon determining that the study parameter is predicated to significantly reduce the enrollment of users belonging to an example Group A. The cohort diversity measures 230 may also include a recommendation for a revised study parameter, a replacement study parameter, a removal of the study parameter, or an addition of a study parameter (e.g., the providing a smartphone to users in Group A as part of the study). The recommendations may be specific to particular population groups. Instead of a recommendation, one or more of the actions may be automatically performed by the computer system 210. The cohort diversity measures 230 may additionally or alternatively include the reference composition 222 determined by the computer system 210 based on the study parameters.

As another example, with respect to the third stage 236, the cohort diversity measures 230 may include indications of particular study criteria that disproportionately affect certain groups of the cohort composition target 224. For example, the computer system 210 may generate a warning for an exclusion criterion that prevents those older than 65 years old from enrolling in the study upon determining that the majority of persons belonging to Group B that are likely to enroll are older than 65 years old and/or upon determining that persons belonging to Group B that are older than 65 years old are much more likely to be retained than those in Group B under 65 years old. Accordingly, the exclusion criterion may prevent or make it exceedingly difficult for the group composition 226 to reach the cohort composition target 224 by the end of the research study. The cohort diversity measures 230 may also include a recommendation for a revised inclusion criterion or exclusion criterion, a replacement inclusion criterion or exclusion criterion, a removal of an inclusion criterion or exclusion criterion, or an addition of an inclusion criterion or exclusion criterion. The recommendation may be specific to particular population groups. Continuing the earlier example, the computer system 210 may generate a recommendation to remove the age exclusion criterion for only those belonging to Group B (e.g., to account for the particular conduct of Group B participants while limiting the amount of risk introduced that comes from enrolling those of advanced age). The cohort diversity measures 230 may additionally or alternatively include the reference composition 222 determined by the computer system 210 based on the study parameters, the inclusion criteria, and/or the exclusion criteria.

As another example, with respect to the fourth stage 238, the cohort diversity measures 230 may include recommendations as to what candidates should be invited for enrollment in the study, and/or what candidates should be accepted for enrollment if there are a group of applicant candidates. The cohort diversity measures 230 may also include a determined group composition for the recommended invitees/applicants, for the predicted cohort of enrolled participants at the start of the study (e.g., based on a prediction of what percentage of invitees from the different groups are expected to enroll), and for the predicted cohort of enrolled participants at the end of the study (e.g., based on a prediction of what percentage of the invitees from the different groups are expected to enroll and expected to be retained/remain active). The recommendation may be specific to particular population groups. As an example, the computer system 210 may generate a recommendation to invite 25% more candidates from Group B than from Group A based on historical data indicating that those from Group A are 20% more likely to enroll than those from Group B. Instead of generating a recommendation to send to the client device 204, the computer system 210 may perform one or more actions automatically. For example, the computer system 210 may automatically determine which candidates from an applicant pool to enroll, and/or which candidates from a candidate pool (e.g., previous study participants, previous study applicants, previous study participants that completed their respective studies, etc.) to invite.

As another example, with respect to the fifth stage 240, the cohort diversity measures 230 may include an updated group composition 226 based on the enrolled participants and an updated prediction for the group composition 226 at the end of the study (e.g., based on the past behaviors and/or trends of the different groups). The cohort diversity measures 230 may include an indication of the results of a comparison between the updated prediction for the group composition 226 at the end of the study and the cohort composition target 224. For example, the cohort diversity measures 230 may include warning that indicates too many persons from Group A have enrolled relative to the number of persons from Groups B and C that have enrolled. The cohort diversity measures 230 may also include recommendations corresponding to the enrolled participants. For example, if more candidates from Group A enrolled than was anticipated, the recommendations may include removing one or more of the participants from Group A (e.g., those that have been identified as the least reliable/active from historical data and/or stored user profile information in the database 212), to send new invites to candidates of Groups B and C, and/or to revise the study parameters, the inclusion criteria, and/or the exclusion criteria in order to increase the retention of those in Groups B and C. As an example, due to a low enrollment of Group C participants and trend of poor retention of Group C participants when they are required to visit medical offices, the computer system 210 may determine as a recommendation a support option to account for the identified problem. For example, the computer system 210 may determine a first recommendation to provide Group C participants taxi fare to counter the known cause of the poor Group C retention, and a second recommendation to allow Group C participants to make their appointments through telehealth services.

In some cases, the fourth stage 238 and the fifth stage 240 are part of the same stage. For example, if there are pool of candidates who have applied, selecting the cohort from the applicant pool may include enrolling those selected as participants for the study.

As another example, with respect to the sixth stage 242, the cohort diversity measures 230 may include an updated group composition 226 based on the remaining enrolled participants and an updated prediction for the group composition 226 at the end of the study. For example, the computer system 210 can take into account participants that have left the study or that are no longer active. The cohort diversity measures 230 may include an indication of the results of a comparison between the updated prediction for the group composition 226 at the end of the study and the cohort composition target 224. For example, the cohort diversity measures 230 may include warning that indicates too many persons from Group B are at risk of being removed from the study due to low activity, and/or that it is unlikely that the cohort composition target 224 can be reached based on observed data for Group B and previously determined trends for Group B. The cohort diversity measures 230 may also include recommendations corresponding to the enrolled participants. For example, the computer system 210 may recommend adding one or more study parameters specific to participants in Group B that have previously worked to increase participation.

Many different research studies are conducted every year, including clinical studies for new treatments and medications. However, health care disparities are an issue plaguing various research studies that can arise due to a failure to take into account certain segments of a population. Particular segments of the population, such as older adults, pregnant women, children, and racial and ethnic minorities are affected in different ways but are often underrepresented in research studies. As a consequence, the results of these research studies may have limited applicability, particularly for those in the underrepresented segments of the population. This often leads to health care disparities such that there is incomplete or unreliable information as to how those segments of the population will be affected, which can prevent, for example, new medications and treatments from being safely administered to those segments of the population. Moreover, many current studies fail to take into account behavioral variation among the different segments of the population. This often leads to lower enrollment and retention of some segments of the population.

The techniques discussed herein enable the computer system 210 to detect and correct for bias and underrepresentation of different population segments at many stages throughout the research study process. As noted above, the computer system 210 can calculate diversity metrics and impacts of different factors in a study on different segments, when defining a research question (232), when setting study parameters (234), when setting cohort inclusion and exclusion criteria (236), when selecting members of cohorts (238), enrolling participants (240), and when conducting a research study and monitoring results (242). At each stage, the computer system 210 can assess levels of representation to verify that the needed diversity is present both for the current study data and cohort, as well as for the ultimate outcomes for the study (e.g., for the group within the cohort that is retained to completion of the study, and the data set obtained by the end of the study). At each stage, the computer system 210 can assess diversity and alert a study administrator if the composition deviates from a target composition by more than a predetermined amount (e.g., exceeds a threshold level of difference for at least one segment of interest). The computer system 210 can also identify and recommend actions, e.g., changes to the study parameters or group of individuals selected as a cohort that will improve the distribution or composition of the cohort toward target levels representing the desired level of diversity.

Figure 3:
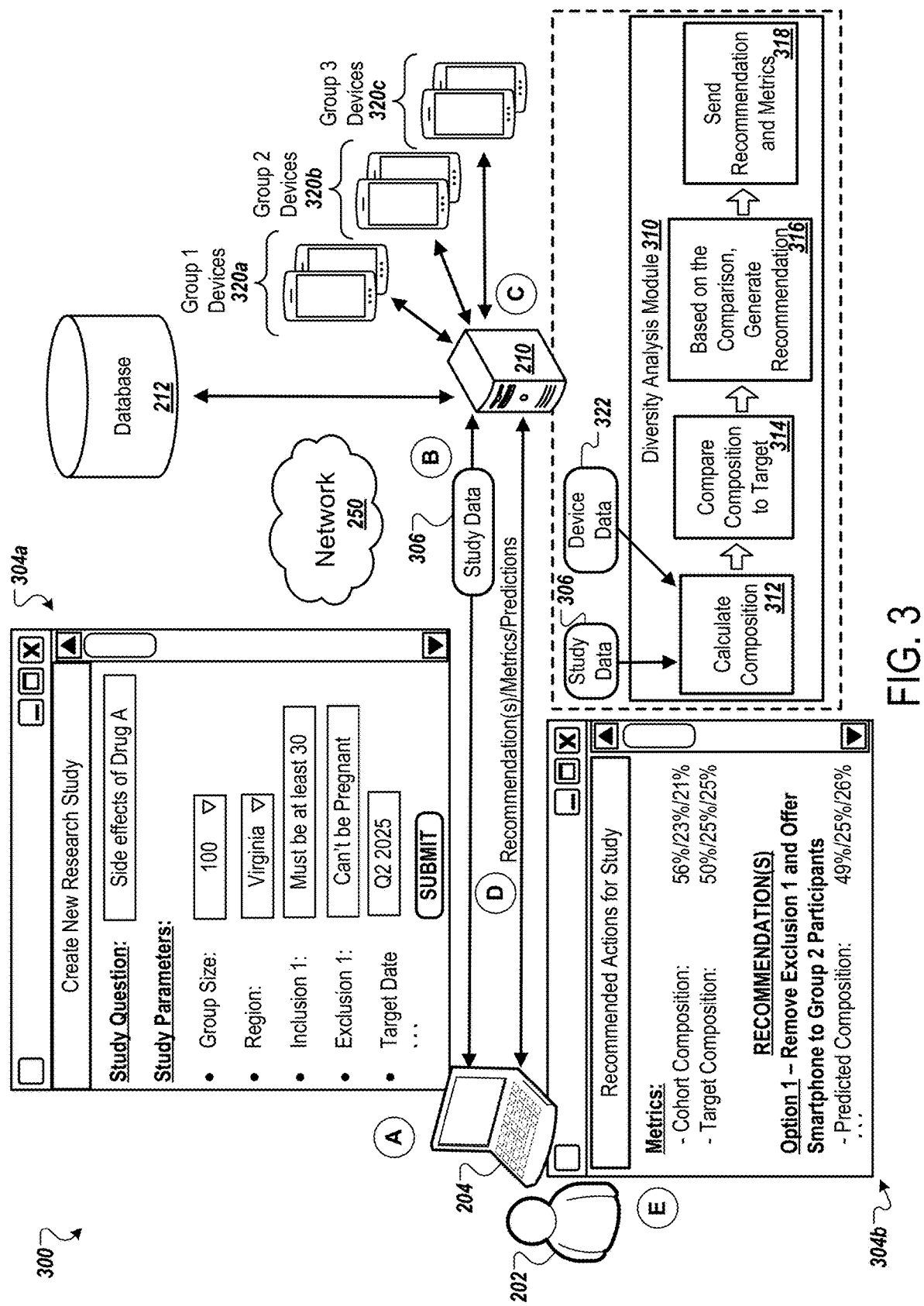
FIG. 3 is a diagram that illustrates an example system and process for performing diversity assessment and action selection for a new research study.

FIG. 3 is a diagram that illustrates one or more components of the system 200 and a process for performing diversity assessment and action selection for a new research study.

In general, FIG. 3 illustrates the researcher 202 initiating a research study through the client device 204. The computer system 210 can use the information received from the client device 204 to calculate one or more diversity measures, such as the reference population for the study, the reference composition, and the target composition. The computer system 210 may also invite users to enroll in the study and/or enroll users in the study based on the received information. Based on the users that enrolled and their associated groups, the computer system 210 may generate and transmit to the client device 204 a recommendation to improve the diversity of the study participants.

FIG. 3 illustrates various operations and flows of data represented as stages (A)-(E), which can be performed in the order shown or in a different order. For example, one or more of the stages (A)-(E) can occur concurrently.

As illustrated, in stage (A), the researcher 202 may be presented an interface 304a of the client device 204 to create a new research study and/or to set a new research question. The researcher 202 may interact with one or more interface elements in the interface 304a to set a study question, to set study parameters, to set inclusion criteria, and/or to set exclusion criteria.

In stage (B), after providing the study question and/or the corresponding study parameters, the researcher 202 may submit the new study to the computer system 210. For example, in response to receiving an indication that the researcher 202 has selected a "Submit" interface element, the client device 204 may generate and transmit study data 306 to the computer system 210 over the network 250.

The study data 306 may include, for example, a study question or research objective, study parameters, inclusion criteria, and/or exclusion criteria. In some cases, the study data 306 may only include the study question or research objective. The computer system 210 may automatically select the study parameters, inclusion criteria, and/or exclusion criteria based on the study question/research objective and/or based on default values. Alternatively, the researcher 202 may set the study parameters, the inclusion criteria, and/or the exclusion criteria at a later time, e.g., after the computer system 210 has performed a diversity analysis of the study question or research objective.

In stage (C), in response to receiving the study data 306, the computer system 210 may perform a diversity analysis using the study data 306. In performing the diversity analysis, the computer system 210 may calculate the cohort diversity measures 230 discussed above with respect to FIG. 2. The computer system 210 may, for example, use a diversity analysis module 310 to perform the diversity analysis based on the study data 306 and/or device data 322, to generate recommendations based on the diversity analysis, and/or to perform one or more actions based on the diversity analysis. The device data 322 may include data received from or generated for Group 1 devices 320a that correspond to a first group of users (e.g., candidates or enrolled participants), Group 2 devices 320b that correspond to a second group of users (e.g., candidates or enrolled participants), and/or Group 3 devices 320c that correspond to a third group of users (e.g., candidates or enrolled participants). The Group 1 devices 320a, the Group 2 devices 320b, and the Group 3 devices 320c may represent three groups of devices whose corresponding users are candidate participants for the study. As an example, these devices may represent all users (e.g., previous study participants; previous study applications; current study applications; etc.) who meet the inclusion criteria and do not meet the exclusion criteria. Similarly, these devices may represent users who the computer system 210 has invited to enroll in the study. As another example, these devices may represent the users who have enrolled in the study.

The device data 322 may indicate, for example, data received from at least a subset of the Group 1 devices 320a, the Group 2 devices 320b, and/or the Group 3 devices 320c. For example, the device data 322 may include response to invitations to enroll in the study. The device data 322 may, therefore, indicate each of the users that have been invited to enroll in the study and have agreed to enroll in the study. Similarly, the device data 322 may include data indicating which users have enrolled in the study. The device data 322 may also or alternatively indicate other information such as which invitations to enroll have successfully been transmitted to the users (e.g., to their corresponding device), which users have viewed an invitation to enroll (e.g., but have not yet responded), the percent of users by group that have responded positively to an invitation to enroll, the percent of users by group that have responded negatively to an invitation to enroll, etc.

As part of the diversity analysis, the diversity analysis module 310 of the computer system 210 may perform an operation 312 of calculating a composition to use for the study based on the study data 306 and/or the device data 322. The composition may be current group composition or a predicted composition at a future point in time, such as at the end of the study (e.g., determined based on machine learning models or statistical data indicating the predicted compliance or retention levels for different groups). The composition may be, for example, the group composition 226 shown in FIG. 2. As an example, the diversity analysis module 310 may use the device data 322 indicating which devices (and their corresponding users) have responded positively to an invitation to enroll in the study. That is, the device data 322 may indicate which users have enrolled in the study. The diversity analysis module 310 may use the device data 322 to determine the current group composition (e.g., participants who are currently enrolled), or a predicted group composition (e.g., at the time of enrollment, or at the time of study completion).

In some cases, the diversity analysis module 310 may use the device data 322 to update the database 212. For example, the diversity analysis module 310 may simply store the device data 322 on the database 212. As another example, as explained in more detail below with respect to FIG. 4 and FIGS. 6A-6B, the diversity analysis module 310 may use the device data 322 to update trend data associated with different user groups. This trend data may be stored in the database 212, and used by the diversity analysis module to make predictions and/or recommendations. For example, the diversity analysis module 310 may update trend data in the database 212 corresponding to the likelihood of a Group 1 users accepting invitations to enroll in a study based on the number of invitations successfully transmitted to the Group 1 devices 320a and the number of positive responses received from the Group 1 devices 320a as provided in the device data 322.

The diversity analysis module 310 performs a second operation 314 of comparing the group composition to a composition target, such as the cohort composition target 224 shown in FIG. 2. The composition target may be set by the researcher 202 and be part of the study data 306. Alternatively, the computer system 210 may determine the cohort composition target based on the study data 306. For example, the computer system 210 may first determine a reference composition based on the study data 306. As an example, the computer system 210 may use the region parameter (Virginia) and the target date parameter (Q2 2025) to determine the reference composition. Specifically, the computer system 110 may use the two parameters and corresponding data stored in the database (e.g., trend data, population data, etc.) to estimate the population composition in the region at the target date (e.g., the ethnic population composition of Virginia in the year 2025). The computer system 110 may proceed to set this estimated population composition as the reference composition.

From the reference composition, the diversity analysis module 310 may determine the cohort composition target. For example, the diversity analysis module 310 may use the inclusion criteria of must be at least 30 and the exclusion criteria of cant be pregnant to limit the population of the reference composition to only those who are over 30 and/or are not pregnant. The diversity analysis module 310 may calculate the cohort composition target 224 from the reference composition using the identified subset of the population. In some cases, the diversity analysis module 310 may detect diversity issues, such as that the inclusion criteria and/or the exclusion criteria are too limiting (e.g., to specific groups). For example, the diversity analysis module 310 of the computer system 210 may generate a warning if the updated population to use for the cohort composition target 224 excludes or significantly reduces the representation of certain segments in the reference population.

In comparing the group composition to the composition target, the diversity analysis module 310 may determine if the group composition matches the composition target, is within a threshold percent (e.g., for any one group) of the composition target, and/or falls within an acceptable target diversity range (e.g., calculated based on the composition target).

The diversity analysis module 310 performs a third operation 316 of generating a recommendation to send to the client device 204 based on the results of the comparison. In generating a recommendation, the diversity analysis module 310 may perform a statistical analysis to identify one or more actions to include in the recommendation. The statistical analysis may be based on identified correlations between different parameters, criteria, and/or actions and certain participant groups and/or group trends. For example, historical data may indicate that past participants associated with Group C have a very low percentage of attending medical appointments, and that previously performed actions of providing taxi credits was typically effective at improving the visit attendance of participants in this group. Accordingly, if the diversity analysis module 310 identifies an issue where participants of Group C are not attending medical appointments, the computer system 210 may recommend that the researcher 202 provide the Group C participants with a taxi credit. The computer system 210 may also make this recommendation prior to any attendance issue being observed, to prevent such an issue from arising.

Additionally or alternatively, in generating the recommendation, the diversity analysis module 310 may use one or more machine learning models to select one or more actions to recommend. As an example, the diversity analysis module 310 may provide an input vector describing the characteristics of the study, such as the cohort composition target, as input to a machine learning model. The diversity analysis module 310 may additionally or alternatively provide a second input vector describing the current characteristics of the cohort, such as the group composition 226, as input to the machine learning model. The output of the machine learning model may be a vector containing a series of values. Each value may correspond to a particular action such that a relatively higher value indicates that a particular action corresponding to the value is better suited for recommendation and/or performance given the input data.

As an example, the diversity analysis module 310 may determine that the exclusion criterion of preventing those who are pregnant from joining the study will be too detrimental to certain population groups. If reference population of the calculated composition may correspond to persons who are likely to take "Drug A" for the treatment of a certain condition and the diversity analysis module 310 determines that a large percentage of persons who are anticipated to take Drug A are pregnant women, then the diversity analysis module 310 may generate update the cohort composition target to include pregnant women as a first group. The diversity analysis module 310 may proceed to generate a diversity warning based on a comparison of the group composition containing no pregnant women to the updated cohort composition target that now includes pregnant women as a group. In response to the warning, the diversity analysis module 310 may provide an input vector describing the characteristics of the study, the updated cohort composition target, and the group composition to a set of machine learning models. The output of the machine learning models may indicate one or more recommended actions to perform in order to achieve the cohort composition target. For example, the output of the machine learning models may correspond to a an action of removing the exclusion criterion of preventing pregnant women from joining the study, as this has the most significant and detrimental effect on the group composition 226 with respect to pregnant women and prevents the cohort composition target from being achieved. Be removing this exclusion criterion, pregnant women will be permitted to join the research study which may allow the cohort composition target that includes pregnant women to be achieved.

The diversity analysis module 310 may also calculate metrics corresponding to a recommendation. For example, the diversity analysis module 310 may calculate the potential effects of the recommendation on group enrollment (e.g., likelihood of enrollment), of group composition (e.g., at start of study, at the end of the study, etc.), on the likelihood of reaching the cohort composition target, etc.

In stage (D), the diversity analysis module 310 performs a fourth operation 318 of generating instructions for the computer system 210 to send the recommendation and corresponding metrics to the client device 204 over the network 250. The metrics may also include the calculated reference composition, the cohort composition target, a current group composition, and/or a predicated group composition at a future point in time (e.g., at the end of the study).

In stage (E), the client device 204 presents a recommendation interface 304b to the researcher 202. The recommendation interface 304b may depict the diversity metrics such as the cohort/group composition and the cohort composition target. The recommendation interface 304b may also present one or more recommendations, and their corresponding effects on cohort diversity. If multiple recommendations are presented, the recommendations may be presented in an order corresponding to what actions or groups of actions are most likely to succeed in reaching the cohort composition target 224, or most likely to get sufficiently close to the cohort composition target 224.

As discussed in some detail above, the diversity analysis module 310 may use one or more algorithms to perform the diversity analysis, generate the diversity measures 130, and/or generate recommendations. For example, the diversity analysis module 310 may use one or more static algorithms to calculate the group composition at a future point in time using previously obtained data or previously determined trends (e.g., generated using previously obtained data) for those groups of users (e.g., indicating the expected or average percentage of users in a particular group completing a study). The diversity analysis module 310 may additionally or alternatively use one or more machine learning algorithms trained to predict the group composition at a future point in time, and/or trained to select actions to perform and/or predict the diversity effects of those actions. The one or more machine learning algorithms may be trained using historical data that indicates the behavior of past study participants (e.g., an indication as to whether they completed or unenrolled from a study, an activity level of the participant during the study, etc.), the groups that the participants belong to, and/or the study parameters (e.g., inclusion criteria, exclusion criteria, other requirements or study parameters).

As input (e.g., an input vector), the one or more machine learning algorithms may receive an indication of the participants currently enrolled in the study and/or the group composition (e.g., group composition 226), and the current study parameters (e.g., including inclusion criteria and exclusion criteria). Other input may include an indication of the observed activity levels of users and/or groups for this study, and/or an enrollment trend of users and/or groups for this study.

With respect to machine learning algorithms configured to predict the group composition at the end of the study, the output (e.g., an output vector) of the machine learning algorithm may include a vector of values that correspond to different group composition possibilities. The highest value may indicate the most likely group composition that will be observed at the end of the study.

With respect to machine learning algorithms configured to select actions and/or predict the effects of actions, the output (e.g., an output vector) of the machine learning algorithms may include a vector of values corresponding to different actions and/or different combinations of actions. The highest value may indicate the highest recommended action or combination of actions, corresponding to the action or combination of actions that is most likely to result in achieving the cohort composition target, getting sufficiently close to the cohort composition target, and/or getting closer to the cohort composition target than other actions or combinations of actions.

Figure 4:
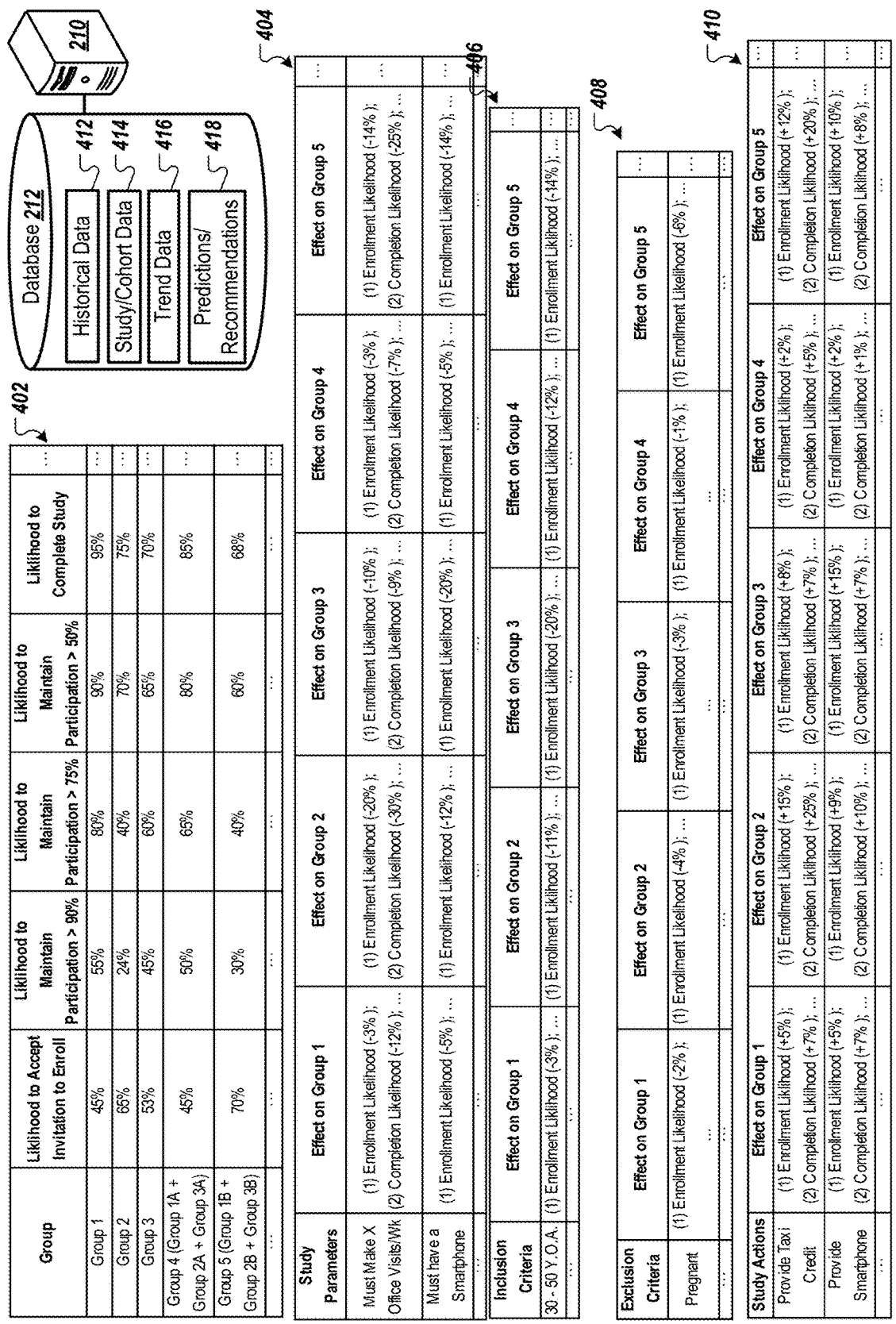
FIG. 4 is a diagram that illustrates example tables used for diversity assessment and action selection.

FIG. 4 is a diagram that illustrates example tables 402-410 used for diversity assessment and action selection. The tables 402-410 may be generated, updated, and referenced by the computer system 210. The computer system 210 may use the information in the tables 402-410 to perform a diversity analysis, calculate diversity measures (e.g., including diversity levels), and generate recommendations. The computer system 210 may store the tables 402-410 in the database 212.

Importantly, the tables 402-410 indicate the different effects that different monitoring program parameters have on the actions of individuals in different groups. For example, one element, such as a requirement of an in-person visit, may have a high negative effect on enrollment or compliance of members of one group but may have a less negative effect, or a neutral or positive effect on enrollment or compliance of members of another group. The computer system 210 analyzes the records of prior actions to characterize or profile the correlations between different factors and the resulting observed outcomes. This allows the system to quantify the potential bias that different factors cause on enrollment, compliance, and retention. It also provides the source data that the system 210 can use to trace the causes of low enrollment, compliance and retention in monitoring programs and signals to the system 210 the opportunities to address factors that may be harming monitoring program outcomes. For example, the system 210 can detect that compliance among a particular group is low, identify from the tables a data collection action that is correlated with low compliance, and then select an alternative method of collecting the data that the tables indicate has a higher likelihood of compliance As an example, the tables 402-410 may be generated by the computer system 210 using historical data 412 and study/cohort data 414 (e.g., data collected from study participants, diversity analyses during a study, etc.). The tables 402-410 may represent determined trend data 416 and/or predictions/recommendations 418 corresponding to different participant groups.

As illustrated, different groups of participants may be associated with different behaviors during a research study, and/or are likely to react differently to particular actions, study parameters, inclusion criteria, and/or exclusion criteria. By identifying how different groups are likely to behave and/or react, a study can be generated and conducted in a manner to ensure (or significantly increase the likelihood) of achieving a set cohort composition target by the end of the study.

A first table 402 indicates example trends in activities levels and study completion rates for different groups. The computer system 210 may generate the first table 402 using historical data 412. The historical data 412 may include, for example, enrollment data from one or more past studies, participation data from one or more past studies, participant profiles corresponding to participants in one or more past studies, etc. The participant profiles may include data that indicates one or more groups associated with the participants, such as demographic and/or non-demographic information of the participants. The participant profiles may include enrollment data (e.g., an indication of how many studies that the participant has been invited to join, has applied for, has enrolled in, etc.) and/or participation data (e.g., average participation level of the participant, how often the participant remained an active participant, etc.).

The computer system 210 may update the table 402 using study/cohort data, which may include, for example, data measured, observed, or received during a research study such as one currently being conducted.

The first table 402 may be part of trend data 416 that is generated by the computer system 210 based on the historical data 412 and/or the study/cohort data 414. The computer system 210 may refer to the table 402 in order to generate predictions and/or recommendations 418.

A second table 404 indicates the predicted effects of particular study parameters on different groups. The effects may include, for example, anticipated changes to study enrollment, participation, and/or completion likelihood for each group. The second table 404 may be generated by the computer system 210 using the historical data 412. The second table 404 may be updated by the computer system 210 using the study/cohort data 414.

The second table 404 may be part of trend data 416 that is generated by the computer system 210 based on the historical data 412 and/or the study/cohort data 414. The computer system 210 may refer to the table 404 in order to generate the predictions and/or recommendations 418.

A third table 406 indicates the predicted effects of particular inclusion criteria on different groups. The effects may include, for example, anticipated changes to study enrollment, participation, and/or completion likelihood for each group. The third table 406 may be generated by the computer system 210 using the historical data 412. The third table 406 may be updated by the computer system 210 using the study/cohort data 414.

The third table 406 may be part of trend data 416 that is generated by the computer system 210 based on the historical data 412 and/or the study/cohort data 414. The computer system 210 may refer to the third table 406 in order to generate the predictions and/or recommendations 418.

A fourth table 408 indicates the predicted effects of particular exclusion criteria on different groups. The effects may include, for example, anticipated changes to study enrollment, participation, and/or completion likelihood for each group. The fourth table 408 may be generated by the computer system 210 using the historical data 412. The fourth table 408 may be updated by the computer system 210 using the study/cohort data 414.

The fourth table 408 may be part of trend data 416 that is generated by the computer system 210 based on the historical data 412 and/or the study/cohort data 414. The computer system 210 may refer to the fourth table 408 in order to generate the predictions and/or recommendations 418.

A fifth table 410 indicates the predicted effects of particular study actions on different groups. The effects may include, for example, anticipated changes to study enrollment, participation, and/or completion likelihood for each group. The fifth table 410 may be generated by the computer system 210 using the historical data 412. The fourth table 408 may be updated by the computer system 210 using the study/cohort data 414.

The fifth table 410 may be part of trend data 416 that is generated by the computer system 210 based on the historical data 412 and/or the study/cohort data 414. The computer system 210 may refer to the fifth table 410 in order to generate the predictions and/or recommendations 418.

The computer system 210 may generate the predictions and/or recommendations 418 for a particular study by applying the trend data 416 to the measured study/cohort data 414. For example, based on the likelihood of Group 2 participants enrolling in a study being higher than Group 3 participants, the computer system 210 may recommend that less Group 2 participants be invited to enroll in the study if the same number of participants from Groups 2 and 3 are being sought.

FIGS. 5A-5B are diagrams that illustrate example diversity assessment interface and action selection interfaces 502a-502c. These interfaces 502a-502c may be presented on the client device 204 of the researcher 202. The client device 204 may present the interfaces 502a-502c at one or more stages of the study based on information received from the computer system 210. As will be described in more detail below, the interfaces 502a-502c may present diversity measures calculated by the computer system 210, the results of a diversity analyses performed by the computer system 210, and/or recommendations generated by the computer system 210. The researcher 202 can interact with the interfaces 502a-502c to make various selections, such as the selections of recommendations, to make modifications (e.g., modifications to a recommendation), or to initiate one or more actions to take (e.g., one or more actions that were not recommended by the computer system 210 that the researcher 202 indicates that the computer system 210 should perform).

As will be discussed in more detail below, the recommendations may be ranked and presented in an order corresponding to their rank. The researcher 202 may interact with the interface 502a to select actions to finalize a monitoring program, adjust a monitoring program, select recommended actions to adjust a monitoring group, or make other adjustments.

FIG. 5A illustrates example diversity assessment and action selection interface 502a during a cohort selection stage of a study. The interface 502a may be presented on the client device 204. As an example, the interface 502a may be presented on the client device 204 after (e.g., in response to) the researcher 202 submitting a research question or study objective (e.g., optionally along with other study information initially submitted by the researcher 202). The interface 502a may present various diversity metrics calculated by the computer system 210 and recommendations generated by the computer system 210. The researcher 202 may interact with the interface 502a to, for example, select a recommendation for the computer system 210 to perform, adjust study parameters, select users to enroll in a study, select users to be invited to the study, etc.

The interface 502a includes a monitoring program elements section 1610, a diversity analysis results section 520a, and a recommendation section 530a. The researcher 202 may, for example, use the interface 502a to review recommendations generated by the computer system 210 at a beginning stage of the study. The researcher 202 may, through the interface 502a, select one or more recommended actions to be performed.

The researcher 202 may be able to also use the interface 502a to indicate one or more actions to be performed, e.g., that may not have been recommended. For example, the researcher 202 may, through the interface 502a, add or remove an exclusion criterion to or from the exclusion criteria 516.

As shown, the monitoring program elements section 1610 may include various parameters for a given study. For example, the monitoring program elements section 1610 may include a cohort size 511, a study length 512, a study region 513, study requirements 514, and a target date 517.

In addition to study parameters, the study criteria 510a may also include inclusion criteria 515a that enrolled participants are required, at a minimum, to meet, and exclusion criteria 516. If a candidate happens to meet any of the exclusion criteria 516, that candidate is automatically excluded from consideration, e.g., even if they meet the inclusion criteria 515a and any other requirements in the study criteria 510a. Similarly, if new information is obtained that indicates that an enrolled participant meets an exclusion criterion, the computer system 210 may automatically remove the participant from enrollment.

However, in some cases, the computer system 210 generates a warning indicating the problem, and transmit the warning to the client device 204. The computer system 210 may refrain from removing the participant until it receives a confirmation or instructions to do so from the client device 204. The computer system 210 may, however, change how it interacts with the participant. For example, if the study involves taking a new drug, the computer system 210 may send a notice to the participant to immediately stop taking the drug, to contact their doctor, to go to the hospital, etc. Depending on the possible severity associated with the exclusion criteria (e.g., increased likelihood of a serious allergic reaction by 500%), the computer system 210 may contact a doctor for the participant and/or emergency services for the participant (e.g., if the participant does not respond to an initial message with a threshold amount of time).

The study criteria may be set by the researcher 202, the computer system 210, or a combination of the researcher 202 and the computer system 210.

The diversity analysis results section 520a depicts the results of a diversity analysis performed by the computer system 210 at the start of a study. The diversity analysis presented may be based on a research question provided by the researcher 202 and/or the study criteria 510a. This diversity analysis may reflect a diversity analysis performed before any participants have been enrolled in the study, and/or before any candidates have been invited to participate in the study.

As shown, the diversity analysis may include a determined reference population 521, a target group composition 522 (e.g., for the enrolled participant at the completion of the study), and identified previous participants 535. The identified previous study participants 523 may be all participants that are relevant to the study. For example, if the study calls for monitoring participants from Group 1, Group 2, and Group 3, the previous study participants 523 may include all previous participants of those groups. As another example, the previous study participants 523 may include only those participants that meet the study criteria 510a, e.g., meet the requirements 514, meet the inclusion criteria 515a, don't meet any of the exclusion criteria 516, live in or sufficiently near the study region 513, etc.

In some cases, the previous study participants 523 may also include participants who have registered for a study (e.g., registered for this current study) but have not necessarily participated in or completed a previous study.

The recommendation section 530a may include one or more recommendations generated by the computer system 210 using the diversity analysis results. The computer system 210 may generate one or more recommendations using the diversity analysis results in order to achieve the target group composition 522.

As shown, a first recommendation option 532 is displayed in the interface 502a and has been selected (e.g., by the researcher 202). This recommendation option 532 includes a modification to the study criteria 510a. Specifically, the recommendation option 532 provides for removing one of the inclusion criterion from the inclusion criteria 515a. The recommendation option 532 also provides that invitations to enroll will be sent to all previous study participants 523, which includes, for example, 915 participants from Group 1, 211 participants from Group 2, and 201 participants from Group 3. The previous study participants 523 may be limited to those participants that have successfully completed a study, that completed a study with an average activity level that meets a threshold activity level, that maintained an activity level above a threshold activity level, that participated in a threshold number of previous studies, that completed a threshold number of previous studies, etc.

The recommendation section 530a also includes a second recommendation option 534. The computer system 210 may provide for presenting the recommendation option 532 above the recommendation option 534 based on an anticipated diversity level associated with the recommendation option 532 being greater than an anticipated diversity level associated with the recommendation option 534. That is, the computer system 210 may rank the different recommendation options and display the different recommendations options in accordance with their respective ranks.

The diversity level may indicate how close the predicated group composition at study completion is to the target group composition. The diversity level may be, for example, a diversity score. That is, the diversity level may be a single value that is indicative of how close the predicted group composition at study completion is to the target group composition. As an example, a diversity score of 1.0 may indicate that the predicted group composition at study completion matches the target group composition 522. The diversity score may be absolute, or it may be relative, e.g., relative to a previously predicted group composition at study completion or relative to the predicted group composition at study completion of one or more other recommendation options. Additionally or alternatively, the diversity level may be, for example, a calculated distribution (e.g., probability distribution). This diversity distribution may, for example, indicate probabilities of achieving the target group composition 522 (e.g., after performing actions corresponding to a particular recommendation option) and/or probabilities associated with different possible group compositions at study completion.

The diversity level can indicate a level of confidence in achieving the target group composition 522, and/or achieving a group composition that is with an acceptable range (e.g., percent range or value range) of the target group composition 522. For example, a diversity score of 0.91 may indicate that the computer system 210 has determined that there is 91% possibility of the group composition at study completion being within a threshold percent (e.g., 5%, 3%, 1%, etc.) of the target group composition 522 provided that the actions corresponding to the recommendation option 532 are performed.

Diversity level may also or alternatively describe a group composition, or the difference between a group composition (e.g., current or predicted) and the target group composition 522. For example, a predicted group composition at study enrollment may be a first diversity level, a predicted group composition at study completion may be a second diversity level, and a difference (e.g., difference between two sets of values, absolute value of the difference between the two sets of values, etc.) the group composition at study completion and the target group composition 522 as a third diversity level.

In some cases, there are multiple diversity levels (e.g., diversity metrics) that include both one or more singular values, and one or more distributions. For example, a first diversity level may include a diversity distribution indicating different likelihoods of achieving the target group composition 522, and a diversity score may be second diversity level identified from the diversity distribution (e.g., as the value associated with the highest probability out of the all of the values).

As discussed above, the computer system 210 may rank the recommendations based on one or more diversity metrics (e.g., diversity levels) calculated for the recommendations. For example, the computer system 210 may rank the recommendations presented in the recommendation section 530a according to a calculated anticipated diversity score for each of the recommendations (e.g., that indicates the anticipated diversity of the cohort at the end of the study should the actions in the corresponding recommendation be performed). The anticipated diversity score is likely to be higher if the actions in a recommendation are predicted to produce a group composition that matches or gets sufficiently close (e.g., with respect to the performance of actions in other recommendations) to the target group composition 522. The computer system 210 may provide instructions to the client device 204 to have the recommendations presented on the interface 502c according to their rank. For example, the computer system 210 may provide instructions to the client device 204 to present the recommendation option 532 above the recommendation option 534 based on the anticipated diversity score (e.g., at the end of the study) associated with the recommendation option 532 being greater than the anticipated diversity score associated with recommendation option 534. By ranking the recommendations according to their influence in achieving the target group composition 522 and, therefore, their influence in on the study's ability to produce viable data, the computer system 210 can (i) more efficiently present its recommendations to the researcher, and/or (ii) take greater advantage of the limited screen space available on the client device 204 (or a display connected to the client device 204).

In some implementations, computer system 210 may only recommend a threshold number of recommendation options (e.g., for display on the client device 204) and/or only send a threshold number of recommendation options to the client device 204. For example, the computer system 210 may only recommend the two, three, or four highest ranking recommendation options for display on the client device 204. The threshold may be selected by the researcher 202 or may be automatically determined by the computer system 210. As an example, the computer system 210 may determine the threshold based on diversity scores associated with the different recommendations, and/or based on the difficulty of the actions in the recommendation options. In more detail, the computer system 210 may generate instructions to present less recommendation options if there are significant diversity score differences (e.g., greater than 5%, 10%, or 20% divergence with respect to the top three, four, or five highest ranking recommendation options) between the different recommendation options such that there are recommendation options that are clearly superior to other recommendation option, or may present more recommendation options if there are insignificant diversity score differences between the different recommendation options (e.g., less than 2%, 5%, or 10% divergence with respect to the top three, four, or five highest ranking recommendation options) such that there are multiple recommendation options that are likely to produce similar diversity results. By presenting only a subset of recommendations, the computer system 210 can (i) more efficiently present the key recommendations to the researcher, and/or (ii) take greater advantage of the limited screen space available on the client device 204 (or a display connected to the client device 204) by removing the need to devote screen space to recommendations that are unlikely or less likely to achieve the diversity needs of the study.

Prior to recommending a set of actions, the computer system 210 may first ensure that the corresponding prospective recommendation meets certain criteria. For example, the computer system 210 may first apply a minimum anticipated diversity level threshold to the recommendation before it can be presented on a display of the client device 204 and/or sent to the client device 204. For example, the computer system 210 may apply a static threshold of 0.90 to the anticipated diversity level. This would have the effect of permitting only the first recommendation option 532 from being displayed in the interface 502a. The diversity level threshold may instead be dynamic, e.g., based on a current anticipated diversity level, based on historical data for the groups being invited to participate in the study, based on the trends for the groups being invited to participate in the study, etc. For example, the computer system 210 may only allow recommendations that result in the anticipated diversity level improving by at least 5% with respect to a current anticipated diversity level at completion. By presenting only a subset of recommendations that meet certain quality criteria, the computer system 210 can (i) more efficiently present the key recommendations to the researcher that are likely to have a minimum beneficial effect on meeting the diversity needs of the study, and/or (ii) take greater advantage of the limited screen space available on the client device 204 (or a display connected to the client device 204) by removing the need to devote screen space to recommendations that are unlikely or less likely to achieve the diversity needs of the study.

The recommendations determined by the computer system 210 may also include recommendations to mitigate risks presented by the inclusion of high risk groups in the study. The inclusion of these high risks groups can benefit the diversity of the study so that the study can achieve its diversity needs (e.g., the target group composition 522, a minimum number of participants from Group 1, a minimum number of participants from Group 2, a minimum number of participants from Group 3, a minimum activity level for each of the participants or minimum average activity level for each group of participants, etc.). However, the inclusion of these high risk groups can also present additional risks that may need to be mitigated in other ways, such as through the addition, removal, or modification of study parameters (or for the provision other study actions) for those participants in these at risk groups.

The computer system 210 may identify a group of persons as at risk based on the group being tagged or preprogrammed as at risk in the database 212 (e.g., tagged by the researcher 202 or tagged by a previous researcher) such as elderly persons, based on historical data showing disproportionately high incidents (e.g., side effects from pharmaceuticals, hospitalizations, death, etc.) for those in the at risk group, etc. After determining that one or more participants in the at risk group are to be enrolled in the study or invited to enroll in the study, the computer system 210 may generate one or more recommendations to mitigate the risks presented to these groups, such as a recommendation to provide additional monitoring for those in the at risk group, a recommendation for more frequent data collection for those in the at risk group, a recommendation to reduce the medication dosage for those in the at risk group to spread the vaccine administration over a longer period of time for those in the at risk group, a recommendation for the medication or vaccine to be administered only by a doctor, a recommendation for the medication or vaccine to be administered only by a doctor in a hospital, etc.

FIG. 5B illustrates example diversity assessment and action selection interface 502b during a participant enrollment stage of a study. The interface 502b may be presented on the client device 204. As an example, the interface 502b may be presented on the client device 204 at an enrollment stage of the study. Specifically, the interface 502b may be presented after (e.g., in response to) all or threshold percent of users have responded to enrollment invitations, after a threshold amount of time has passed since enrollment invitations were sent out, after a threshold number of users have enrolled, etc. The interface 502b may present various diversity metrics calculated by the computer system 210 and recommendations generated by the computer system 210 for this stage of the study. The researcher 202 may interact with the interface 502b to, for example, select a recommendation for the computer system 210 to perform, adjust study parameters, select new users to enroll in a study, select new users to be invited to the study, select users to remove from enrollment, select users to have their invitations revoked, etc.

The interface 502b includes an updated study criteria section 510b, a diversity analysis results section 520b, and a recommendation section 530b. The researcher 202 may, for example, use the interface 502b to review recommendations generated by the computer system 210 at an enrollment stage of the study. The researcher 202 may, through the interface 502b, select one or more recommended actions to be performed.

The researcher 202 may be able to also use the interface 502b to indicate one or more actions to be performed, e.g., that may not have been recommended. For example, the researcher 202 may, through the interface 502b, add or remove an inclusion criterion to or from the inclusion criteria 515b.

As shown, the study criteria section 510b may include various parameters for a given study. For example, the study criteria section 510b may include a cohort size 511, a study length 512, a study region 513, study requirements 514, and a target date 517.

In addition to study parameters, the study criteria 510b also include updated inclusion criteria 515b and exclusion criteria 516. The inclusion criteria 515b has been updated based on a selected recommendation so that an inclusion criterion has been removed. This has the effect of increasing the candidate pool of potential participants.

The diversity analysis results section 520b depicts the results of a diversity analysis performed by the computer system 210 at an enrollment stage the study. The diversity analysis presented may be based on a research question provided by the researcher 202, the study criteria 510b, the candidates invited to enroll and/or the candidates that have applied to enroll, and/or the actual enrollment of the study.

As shown, the diversity analysis results section 520b may include the target group composition 522 (e.g., for the enrolled participant at the completion of the study), an enrolled group composition 524 (e.g., indicating the diversity of participants who have actually enrolled in the study), and a predicted diversity at completion 525. The computer system 210 may determine the predicted diversity at completion 525 based on, for example, a combination of historical data or trends determined from historical data, and the enrolled group composition 524.

The computer system 210 may compare the predicted diversity at completion 525 to the target group composition 522. If the predicted group composition 525 falls outside of a target composition range (e.g., based on the target group composition 522), then the computer system 210 may generate a warning 527 indicating that it is anticipated that the target group composition 522 will not be achieved.

As another example, the warning 527 may be generated by the computer system 210 in response to determining that the diversity level 526 does not meet a threshold diversity level. For example, the computer system 210 may compare the diversity level 526 to a threshold diversity level of 0.90. Based on the diversity level 526 being below the threshold diversity level, the computer system 210 may generate the warning 527 or a similar warning (e.g., indicating low diversity level and/or that the target group composition is unlikely to be achieved by study completion), and transmit the warning to the client device 204.

In some cases, the computer system 210 may compare the diversity level 526 to multiple thresholds. These thresholds may correspond to different actions performed by the computer system 210. For example, if the diversity level does not meet a first threshold but does meet a second threshold, the computer system 210 may generate a low priority warning and transmit it to the client device 204. However, if the diversity level does not meet the first threshold and the second threshold, the computer system 210 may generate a high priority warning, transmit the warning to the client device 204, and automatically perform one or more actions to account for the low diversity level. For example, the computer system 210 may determine one or more actions to take to improve the diversity level, such as invite persons to enroll from an underrepresented group, remove persons from an overrepresented group, remove or modify inclusion or exclusion criteria, adjust the study parameters, etc.

The recommendation section 530b may include one or more recommendations generated by the computer system 210 using the diversity analysis results indicated in the diversity analysis results section 520b. The computer system 210 may generate one or more recommendations using the diversity analysis results in order to achieve the target group composition 522. Specifically, the computer system 210 may determine a first recommendation option 536 based on or in response to the warning 527. The first recommendation option 536 may be a recommendation to perform one or more actions so that the predicated diversity at completion 525 will match the target group composition 522 or will be within a target diversity range (e.g., that is based on the target group composition 522).

FIG. 5C illustrates example diversity assessment and action selection interface 502c during a participant enrollment stage of a study. The interface 502c may be presented on the client device 204. As an example, the interface 502c may be presented on the client device 204 at an enrollment stage of the study. Specifically, the interface 502c may be presented after (e.g., in response to) all or threshold percent of users have responded to enrollment invitations, after a threshold amount of time has passed since enrollment invitations were sent out, after a threshold number of users have enrolled, etc. The interface 502c may present various diversity metrics calculated by the computer system 210 and recommendations to adjust enrollment generated by the computer system 210 for this stage of the study. The interface 502c may include various interface elements that allow a user to quickly consider and act on recommendations to invite or enroll new users in the study, remove users from enrollment, or replace users who are currently enrolled. The researcher 202 may interact with the interface 502c to, for example, select new users recommended by the computer system 210 to enroll in a study, select new users recommended by the computer system 210 to be invited to the study, select users recommended by the computer system 210 for removal from enrollment, select users recommended by the computer system 210 for replacement, select users recommended by the computer system 210 for having their invitations revoked, etc.

As another example, the interface 502c may be presented on the client device 204 at one or more later stages of the study (e.g., after some of study data has been obtained from the participant devices). Specifically, the interface 502c may be presented after (e.g., in response to) a participant leaving the study, a participant's activity level dropping below a threshold activity level, a diversity score falling below a diversity score threshold, etc.

The interface 502c includes the updated study criteria section 510b, the diversity analysis results section 520b, and an enrollment section 540. The researcher 202 may, for example, use the interface 502c to adjust the enrollment for the study at the start of the study or at one or more later points in time during the study.

As shown, the study criteria section 510b may include various parameters for a given study. For example, the study criteria section 510b may include a cohort size 511, a study length 512, a study region 513, study requirements 514, and a target date 517. In addition to study parameters, the study criteria 510b also include updated inclusion criteria 515b and exclusion criteria 516.

The diversity analysis results section 520b depicts the results of a diversity analysis performed by the computer system 210 at an enrollment stage the study. The diversity analysis presented may be based on a research question provided by the researcher 202, the study criteria 510b, the candidates invited to enroll and/or the candidates that have applied to enroll, and/or the actual enrollment of the study.

As shown, the diversity analysis may include the target group composition 522 (e.g., for the enrolled participant at the completion of the study), the enrolled group composition 524 (e.g., indicating the diversity of participants who have actually enrolled in the study), and the predicted diversity at completion 525. The computer system 210 may determine the predicted diversity at completion 525 based on, for example, a combination of historical data or trends determined from historical data, and the enrolled group composition 524.

As discussed above, using the target group composition 522 and at least one of the enrolled group composition 524 and the predicted group composition 525, the computer system 210 calculates a diversity level 526. As shown, the diversity level 526 is an anticipated diversity level at study completion, e.g., that is indicative of the difference (e.g., actual or percent difference) between the predicted group composition 525 and the target group composition 522.

The computer system 210 may compare the predicted diversity at completion 525 to the target group composition 522. If the predicted group composition 525 falls outside of a target composition range (e.g., based on the target group composition 522), then the computer system 210 may generate the warning 527 indicating that it is anticipated that the target group composition 522 will not be achieved.

As another example, the warning 527 may be generated by the computer system 210 in response to determining that the diversity level 526 does not meet a threshold diversity level. For example, the computer system 210 may compare the diversity level 526 to a threshold diversity level of 0.90. Based on the diversity level 526 being below the threshold diversity level, the computer system 210 may generate the warning 527 or a similar warning (e.g., indicating low diversity level and/or that the target group composition is unlikely to be achieved by study completion), and transmit the warning to the client device 204.

In some cases, the computer system 210 may compare the diversity level 526 to multiple thresholds. These thresholds may correspond to different actions performed by the computer system 210. For example, if the diversity level does not meet a first threshold but does meet a second threshold, the computer system 210 may generate a low priority warning and transmit it to the client device 204.

However, if the diversity level does not meet the first threshold and the second threshold, the computer system 210 may generate a high priority warning, transmit the warning to the client device 204, and automatically perform one or more actions to account for the low diversity level. For example, the computer system 210 may determine one or more actions to take to improve the diversity level, such as invite persons to enroll from an underrepresented group, remove persons from an overrepresented group, remove or modify inclusion or exclusion criteria, adjust the study parameters, etc.

The enrollment section 540 may present more detail information on the currently enrolled participants, and/or may present options, such as recommended options, for adjusting the enrollment of the study. As shown, the enrollment section 540 may include a table 542 that includes a first column the displays that displays users that the computer system 210 recommends to be invited for enrollment and/or added to enrollment, and a second column that displays users that the computer system 210 has marked for possible removal or replacement.

Factors for recommending users for invitation, addition, removal, or replacement may include the group(s) associated with the user and an expected participation for the user. The computer system 210 may recommend the addition of users that are associated with an unrepresented group or a group that is anticipated to be unrepresented at study completion. Similarly, the computer system 210 may recommend the remove or replacement of users that are associated with an overrepresented group or a group that is anticipated to be overrepresented at study completion. As an example, the computer system 210 may be more likely to recommend Group 2 users based on the predicted group composition 525 indicating that the anticipated enrollment of Group 2 participants will be significantly lower than that indicated in the target group composition 522. The computer system 210 may also recommend users that have a higher expected participation as they will be more likely to provide data and/or consistently provide data required for a study, and/or more likely to complete the study.

The table 542 may also indicated the predicted effect that the addition, removal, or replacement of the specific users may have on the study. As an example, the computer system 210 may determine the anticipated diversity level at study completion should the corresponding user be added, removed or replaced. For example, the addition of the User S to the study is anticipated to raise the diversity level from 0.87 to 0.91.

The researcher 202 may interact with the table 542 to select one or more users to add/invite. Similarly, the researcher 202 may interact with the table 542 to select one or more users to remove or replace. If the researcher 202 select to replace a user, they the client device 204 may prompt the researcher 202 to select a replacement user to invite/add.

The recommendation for the addition, invitation, removal, or replacement of participants may further be based on the past studies that the participants have previously been a part of. For example, candidates may be more likely to be recommended for invitation and/or addition (e.g., addition may be an option if the participant has already agreed to enrolled or applied to enroll) if the participants have enrolled in a previous research study, have completed a previous research study, have enrolled in a relatively high number of research studies (e.g., compared to other candidates, enrolled participants, etc.), have completed a relatively high number of research studies, and/or have completed a threshold percent of research studies that they previously enrolled in. In contrast, enrolled participants may be more likely to be marked for removal or replacement if, for example, they have not enrolled or completed a previous research study (e.g., which would introduce a great deal of uncertainty such that there may be, for example, insufficient information to anticipate whether the participant will complete the study and/or the expected participation of the participant), have enrolled in or completed a relatively low number of studies, and/or have a low study completion percentage.

The expected participation of the candidates and the enrolled participants may be determined using information obtained from past studies. For example, the computer system 210 may access a previously calculated expected participation for an enrolled participant from a user profile for the participant. As another example, the computer system 210 may access study data stored and associated with a user, and calculated, based on the study data, an expected participation level of the user. The expected participation level may be based on, for example, a user's task completion percentage, task completion time, inquiry response time, data upload consistency, etc.

The computer system 210 may rank the users that it recommends for invitation, enrollment, removal, or replacement. For example, the users may be ranked based on the anticipated diversity level calculated by the computer system 210 should the recommendation be acted on. The effects of a user being added or invited to a study on the anticipated diversity level are likely to increase more significantly if the user belongs to a currently underrepresented group or anticipated unrepresented group (e.g., anticipated to be unrepresented by the end of the study, such as the Group 2 participants that are currently overrepresented but are anticipated to be underrepresented) than if the user belongs to a currently overrepresented or anticipated overrepresented group (e.g., Group 1 participants that are currently underrepresented but anticipated to be overrepresented by the end of the study). Additionally or alternatively, the users may be ranked based on their expected activity level in the study (e.g., based on historical data indicating their past activity levels, past study completion rates, etc.). This however may be taken into account by the anticipated diversity level since the anticipated diversity level may correspond to the predicted group composition 522 at the end of the study and a lower expected activity level associated with a user would indicate a higher likelihood of the user not completing the study and/or not producing sufficient data needed for the study.

The computer system 210 may provide instructions to the client device 204 to have the recommended users presented in the interface 502c according to their rank. For example, as shown, User S may be presented above User R based on the anticipated diversity level of 0.94 (e.g., by the end of the study) for inviting or enrolling User S being greater than the anticipated diversity level of 0.93 for inviting or enrolling User R. By ranking the user recommendations according to their influence in achieving the target group composition 522 and, therefore, their influence in on the study's ability to produce viable data, the computer system 210 can (i) more efficiently present its recommendations to the researcher, and/or (ii) take greater advantage of the limited screen space available on the client device 204 (or a display connected to the client device 204).

In some cases, the client device 204 may present the user recommendations as a list that is not necessarily organized by the recommended action. The list may instead be ordered based on the anticipated diversity level and/or the expected participation level. For example, the client device 204 may present a list of user recommendations starting with inviting User S (e.g., based on being associated with the highest diversity level), followed by inviting User R (e.g., based on being associated with the second highest diversity level), followed by removing or replacing User D (e.g., based on being associated with the third highest diversity level), and followed by removing or replacing User B (e.g., based on being associated with the fourth highest diversity level).

Similarly, the computer system 210 may only recommend a subset of the available users based on their determined ranks. For example, the computer system 210 may only recommend a threshold number of user recommendations (e.g., a total of only three, four, or six user recommendations are initially presented to the researcher 202 on the client device 204 unless the researcher 202 requests additional recommendations) or a threshold number of user recommendations for each specific action (e.g., a maximum of three invitation or enrollment recommendations are presented on the client device 204, and a maximum of two removal or replacement recommendation are presented on the client device 204) selected accordingly to their respective ranks. The thresholds may be selected by the researcher 202 or may be automatically determined by the computer system 210. As an example, the computer system 210 may determine the thresholds based on the total number of participants currently enrolled in the study and/or on a target number of participants for the study. By presenting only a subset of user recommendations, the computer system 210 can (i) more efficiently present the key recommendations to the researcher, and/or (ii) take greater advantage of the limited screen space available on the client device 204 (or a display connected to the client device 204) by removing the need to devote screen space to recommendations that are unlikely or less likely to achieve the diversity needs of the study.

The computer system 210 may apply additional criteria to the user recommendations. For example, the computer system 210 may apply one or more thresholds that indicate the maximum number of recommendations presented on the interface 502c. However, the computer system 210 may first apply a minimum anticipated diversity level threshold to the recommendation before it can be presented on a display of the client device 204 and/or sent to the client device 204. For example, the computer system 210 may apply a static threshold of 0.90 to the anticipated diversity level. This would have the effect of only the recommendations of inviting User S, inviting User R, and removing or replacing User D being displayed on the interface 502c. The diversity level threshold may instead be dynamic, e.g., based on the current anticipated diversity level at completion 526, based on historical data for the groups and/or participants enrolled in study, based on the trends for the groups and/or participants enrolled in the study, etc. For example, the computer system 210 may only allow user recommendations that result in the anticipated diversity level improving by at least 5% with respect to the current anticipated diversity level at completion 526. By presenting only a subset of user recommendations that meet certain quality criteria, the computer system 210 can (i) more efficiently present the key recommendations to the researcher that are likely to have a minimum beneficial effect on meeting the diversity needs of the study, and/or (ii) take greater advantage of the limited screen space available on the client device 204 (or a display connected to the client device 204) by removing the need to devote screen space to recommendations that are unlikely or less likely to achieve the diversity needs of the study.

The computer system 210 may apply similar thresholds to the expected participation level. For example, the computer system 210 may apply a first static or dynamic threshold (e.g., relative to the activity level of other candidates, of currently enrolled users, activity level of other candidates in the same group as the recommended user, of currently enrolled users in the same group as the recommended user, etc.) that indicates a minimum expected participation level to be recommended by the computer system 210 for an invitation to enroll in the study or to be enrolled in the study. Similarly, the computer system 210 may apply a second static or dynamic threshold (e.g., relative to the activity level of other candidates, of currently enrolled users, activity level of other candidates in the same group as the recommended user, of currently enrolled users in the same group as the recommended user, etc.) that indicates a maximum expected participation level to be recommended by the computer system 210 for removal or replacement. Again, by presenting only a subset of user recommendations that meet certain quality criteria, the computer system 210 can (i) more efficiently present the key recommendations to the researcher that are likely to have a minimum beneficial effect on meeting the diversity needs of the study, and/or (ii) take greater advantage of the limited screen space available on the client device 204 (or a display connected to the client device 204) by removing the need to devote screen space to recommendations that are unlikely or less likely to achieve the diversity needs of the study.

In some cases, a similar interface to the interface 502c is presented at one or more points throughout the study. For example, a similar interface may be presented at the user's request to modify an enrollment of participants in the study. As another example, a similar interface may be prepared and/or presented in response to certain research milestones being met, in response to a diversity warning or error being generating (e.g., due to participants associated with particular groups leaving the study; participants of particular groups not being sufficiently active in the study; etc.

Although various examples described throughout this disclosure provide for a target group composition or target group diversity including one or more target percentages for one or more groups of devices or users, the target group composition or target group diversity may alternatively provide, for each of multiple categories or types of devices or users, a target number for that category or type (e.g., a quota representing a total or minimum number to include). For example, the target group composition 522 may include a first quota of at least five-hundred users from Group 1, a second quota of at least two-hundred and fifty users from Group 2, and a third quota of at least two-hundred and fifty users from Group 3. In these examples, the relative composition of the group populations may not matter or may be a secondary factor when compared to the goal of meeting the quotas.

In some cases, there is a target group composition and one or more quotas that must be met. For example, the computer system 210 may set the target group composition 522 to 50% for Group 1 participants, 25% for Group 2 participants, and 25% for Group 3 participants, and set an acceptable target composition range as 48-52% Group 1 participants; 24-26% Group 2 participants, and 24-26% Group 3 participants. However, the computer system 210 may also set quotas for each of the groups. The target group composition and the quotas may be set in order to ensure the viability of the study results. For example, the target group composition and the quotas may be set in order to ensure (or significantly increase the likelihood) that statistically relevant results can be obtained from the study.

In some cases, the interfaces 502a-502c present different options and/or functionality depending on the current stage of the study, detected events, and/or obtained data. For example, the interface 502a may be presented at a study parameter stage of the study (e.g., the second stage 234 shown in FIG. 2), an inclusion and exclusion criteria stage of the study (e.g., the third stage 236), or a select cohort stage of the study (e.g., the fourth stage 238). In contrast, the interface 502b and/or the interface 502c may be presented at an enroll participants stage of the study (e.g., fifth stage 240). Based on the different stages associated with the interfaces, the client device 204 may present (e.g., based on instructions provided by the computer system 210) different options for the researcher 202 to interact with. For example, the client device 204 may present options in the interface 502a for the researcher 202 to select, modify, add, and/or remove study parameters. In contrast, in the client devices 204 may not immediately present these options in the interfaces 502b and 502c (e.g., although the researcher 202 may be able to still access them). Instead, the client device 204 may present in the interfaces 502b and 502c different options to view details of those currently enrolled in the study, to invite or enroll new users, to remove or replace enrolled users, to view details of candidates such as historical data of previous study participants, to view in real-time or substantially real-time the effects of different user selection scenarios (e.g., to see the effects on a calculated diversity score, on the anticipated group composition 522 at the end of the study, on anticipated participation level by group by the end of the study, on an anticipated participation level by group over the course of the study, on an anticipated group composition over the course of the study, etc.), etc.

Figure 6A:
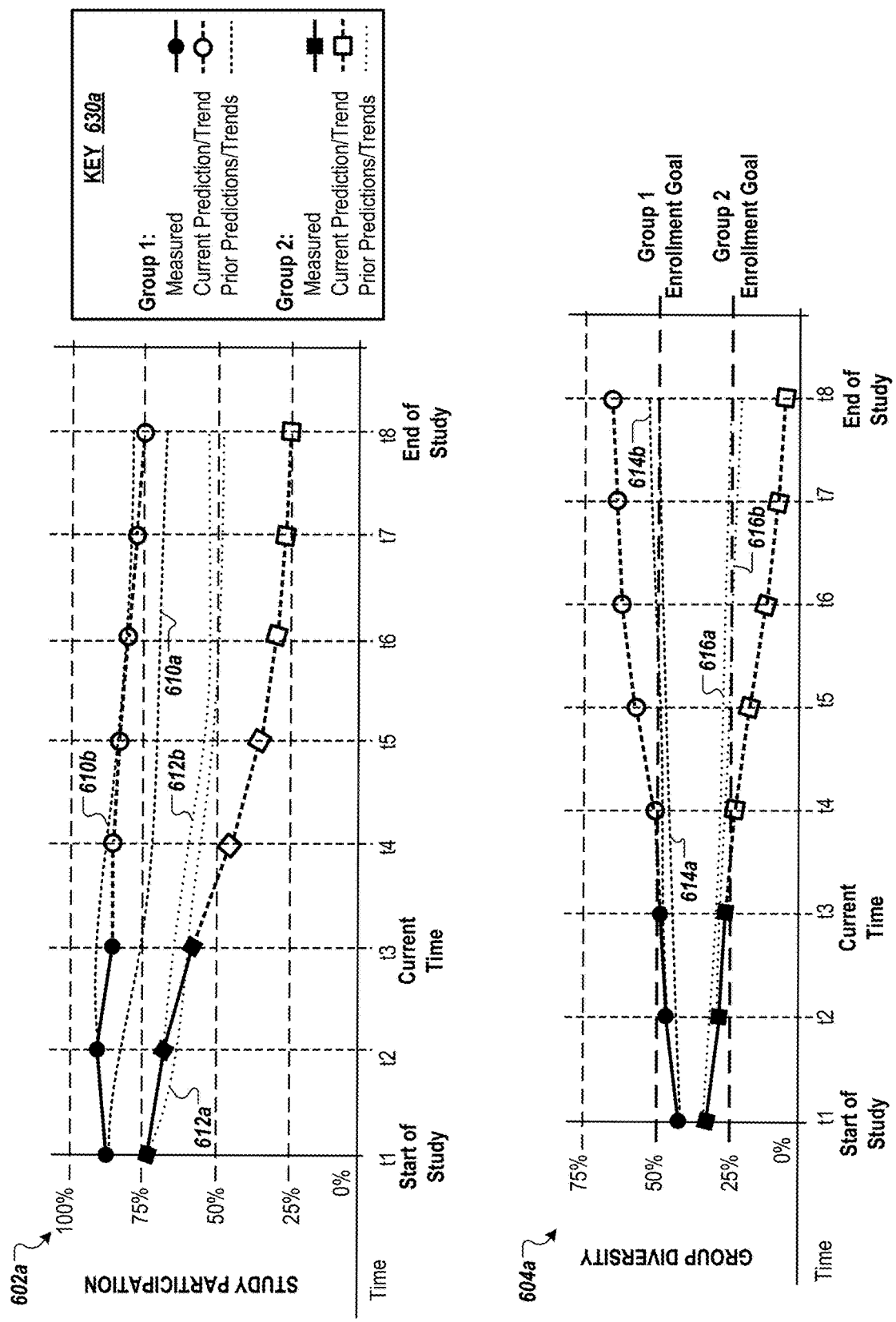
FIGS. 6A-6B are diagrams that illustrate group predictions for a research study.
Figure 6B:
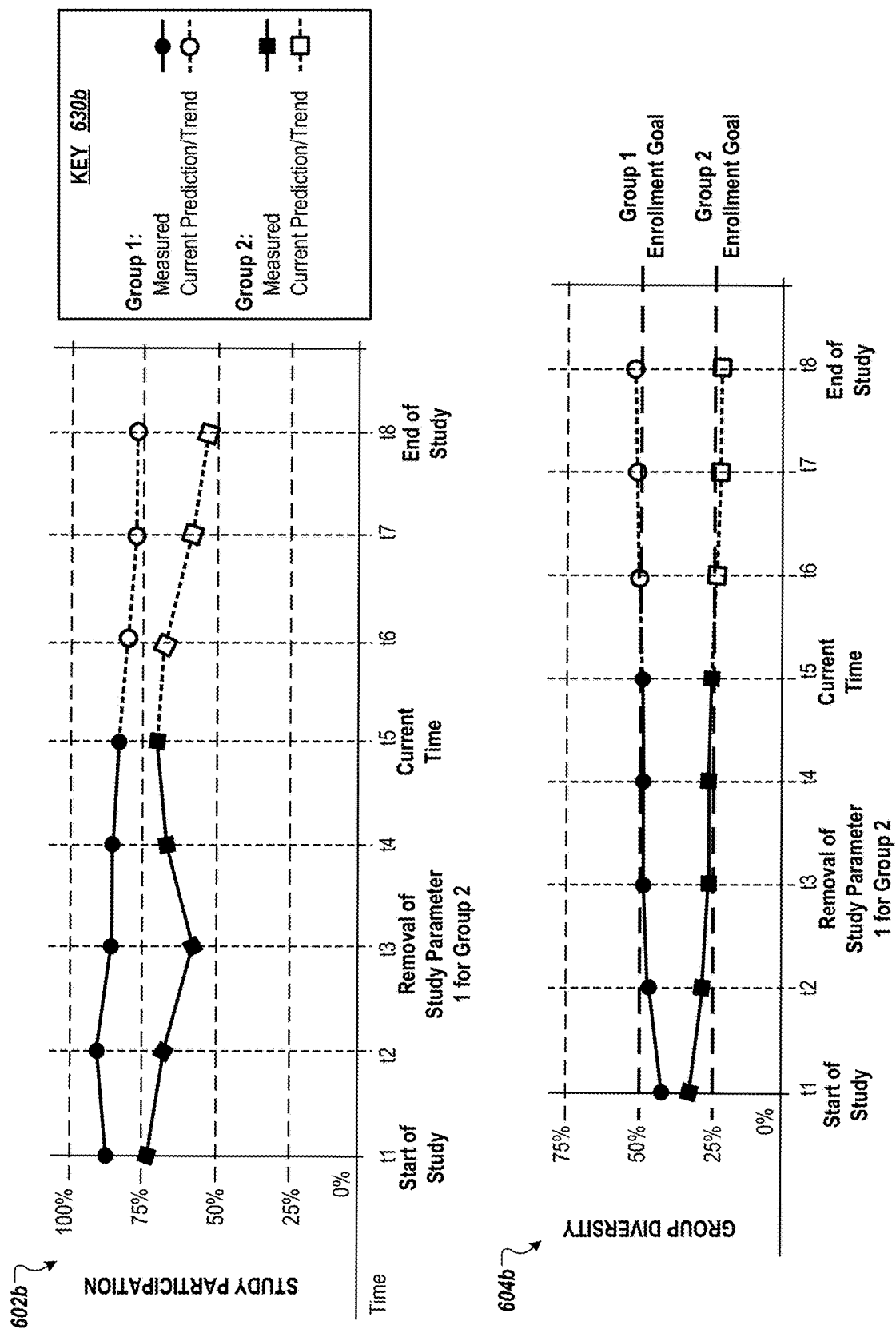

FIGS. 6A-6B are diagrams that illustrate group predictions for a research study. These predications may be generated by the computer system 210 during the performance of diversity analyses. In generating the predictions, the computer system 210 may access the table data shown and described above with respect to FIG. 4. Specifically, the computer system 210 may use previously determined trend data to make predications regarding specific groups of participants. The computer system 210, may also make predications for specific participants. These predictions can be used to update or modify the predications or the prediction calculations for the groups that the specific participants belong to.

FIG. 6A is a diagram that illustrates group predictions for a research study, such as a clinical trial, or other monitoring program. The predictions may be made by the computer system 210 described above with respect to FIGS. 2-4. The computer system 210 may use the predications to determine the predicted group composition at a future time, such as at study completion.

A first graph 602a indicates measured and predicted group participation levels. As illustrated by a key 630a, the graph 602a depicts measured or observed study participation levels, previous predictions made or trends corresponding to a time before the current time (t3), and a current prediction or trend corresponding to the current time (t3). For example, the computer system 210 may have, based on one or more data points corresponding to a start of study time (t1) and known trends for Group 1 participants (e.g., as indicated in the trend data 416 shown in FIG. 4, such as the table 402), generated a prediction 610a corresponding to the start of study time (t1). The prediction 610a indicates, for example, that anticipated study participation levels of Group 1 participants at one or more future points in time with respect to the start of study time (t1). For example, the prediction 610a indicates that the Group 1 participants are most likely to have a study participation level of 66% by the end of the study (t8). The prediction 610a may be a trend line for Group 1 that is applied to one or more observed data points, such as a measured participation level of 87% at the start of the study.

Similarly, the computer system 210 may have, based on one or more data points corresponding to a start of study time (t1) and known trends for Group 2 participants (e.g., as indicated in the trend data 416 shown in FIG. 4, such as the table 402), generated a prediction 612a corresponding to the start of study time (t1). The prediction 612a indicates, for example, that anticipated study participation levels of Group 2 participants at one or more future points in time with respect to the start of study time (t1). For example, the prediction 612a indicates that the Group 2 participants are most likely to have a study participation level of 49% by the end of the study (t8). The prediction 612a may be a trend line for Group 1 that is applied to one or more observed data points, such as a measured participation level of 74% at the start of the study.

The computer system 210 may have, based data measured (e.g., received, observed, and/or collected) over the time range of t1-t2 and known trends for Group 1 participants (e.g., as indicated in the trend data 416 shown in FIG. 4, such as the table 402), generated a second prediction 610b corresponding to a second time (t2). The prediction 610b indicates, for example, that anticipated study participation levels of Group 1 participants has significantly changed such that the Group 1 participants are now anticipated to have a study participation level of 78% by the end of the study (t8). The computer system 210 also determines an updated prediction 612b for the Group 2 participants indicating a new anticipated participation level of Group 2 participants of 55% by the end of the study.

Finally, the computer system 210 may have, based on data measured from the start of the study (t1) to the current time (t3) generated a current study prediction for the Group 1 participants and the Group 2 participants. The new prediction for the Group 1 participants indicates modest changes to the anticipated study participation levels that does not raise any alarms. In contrast, a significant dip in the measured study participation levels for the Group 2 participants (and/or other indicators) has resulted in the predicted study participation levels of Group 2 participants to drop significantly. The computer system 210 may generate a warning in response to the current prediction for the Group 2 participants. For example, the computer system 210 may generate a warning based on a slope of a current prediction trend line, based on anticipated participation levels of the Group 2 participants dropping below one or more threshold study participation levels that correspond to one or more different times, etc.

As an example, participants may be automatically unenrolled from a study if there participation drops below a certain threshold (e.g., 40%). As such, because the most recent prediction for the Group 2 participants indicates an average study participation level below 40% at one or more points (e.g., before or at the end of the study), the computer system 210 may, in response, generate a warning to transmit to the client device 204. The warning may be accompanied with one or more recommendations on how to address the low study participation of Group 2 participants. Alternatively, the computer system 210 may automatically perform one or more actions in attempt to address the identified issues. As will be discussed in more detail with respect to FIG. 6B, the computer system 210 may remove a study parameter from the study for Group 2 participants that, for example, the historical data 412 has shown to have a negative effect on the participation levels (e.g., and therefore the enrollment) of Group 2 participants. This cause and effect may be depicted, for example, in table 404 of FIG. 4. The study actions recommended or performed by the computer system 210 may be depicted for example, in table 410 of FIG. 4.

In general, trend lines determined and/or applied to make predictions for group participants based on various factors. For example, a trend line applied for a particular group may be determined for and/or otherwise specific to a particular time or stage of a study (e.g., particular percentage of the study that is complete), such that there may be multiple different or possible trend lines for a given group of participants. Similarly, different group trend lines may additionally or alternatively correspond to different ranges of observed or measured values. For example, the computer system 210 may apply a first trend line for study participation of Group 1 participants if a measured data point for the start of study time falls between 80% and 90% participation, and a second trend line if the measured data point for the start of study time falls between 70% and 80% participation. Accordingly, here, the computer system 210 may apply the first trend line to the Group 1 start of study measured data point(s) to generate the prediction 610a.

The computer system 210 may make new predictions at different points throughout the study. For example, the computer system 210 may make a new prediction after a threshold amount of time has passed, after a particular study completion percentage is reached or added since a last prediction was made (e.g., prediction is made every time is determined that the current study completion percentage is 5% closer to 100% from a prior study completion percentage corresponding to when an immediately preceding prediction was made), in response to new data being collected or received (e.g., from the study participants), after a milestone in the study is reached, and/or after a stage or phase of the study changes. For example, the graphs 602a and 604a may be generated in response to receiving measuring new data from the study participants, and/or weekly based on data received and/or collected from study participants over the last week.

A second graph 604a indicates measured and predicted group diversity levels (e.g., diversity of enrolled participants). As shown, the most recent group diversity predictions indicate very low retention of Group 2 participants such that it is very unlikely that the target cohort diversity will be achieved. This low retention of Group 2 may be based, at least in part, on the low study participation levels observed and/or predicted. As an example, the computer system 210 may generate the group diversity prediction based, at least in part, on the measured and/or predicted study participation of the different groups.

As an example, the computer system 210 may have, based on one or more data points corresponding to a start of study time (t1) and known trends for Group 1 participants (e.g., as indicated in the trend data 416 shown in FIG. 4, such as the table 402), generated a prediction 614a corresponding to the start of study time (t1). The prediction 614a indicates, for example, an anticipated Group 1 enrollment relative to one or more other groups in the study. For example, the prediction 614a indicates that the Group 1 participants are most likely to make up about 50% of the study enrollment by the end of the study (t8), e.g., which is in line with a Group 1 enrollment goal to achieve the cohort composition target 224 by the end of the study. The prediction 614a may be a trend line for Group 1 that is applied to one or more observed data points, such as a measured enrollment percentage of Group 1 participants of 42% at the start of the study.

Similarly, the computer system 210 may have, based on one or more data points corresponding to a start of study time (t1) and known trends for Group 2 participants (e.g., as indicated in the trend data 416 shown in FIG. 4, such as the table 402), generated a prediction 616a corresponding to the start of study time (t1). The prediction 616a indicates, for example, an anticipated Group 2 enrollment relative to one or more other groups in the study. For example, the prediction 616a indicates that the Group 2 participants are most likely to make up about 25% of the group composition 225 by the end of the study (t8), e.g., which is in line with a Group 2 enrollment goal to achieve the cohort composition target 224 by the end of the study. The prediction 616a may be a trend line for Group 2 that is applied to one or more observed data points, such as a measured enrollment percentage of Group 2 participants of 33% at the start of the study.

The computer system 210 may have, based data measured (e.g., received, observed, and/or collected) over the time range of t1-t2 and known trends for Group 1 participants (e.g., as indicated in the trend data 416 shown in FIG. 4, such as the table 402), generated a second prediction 614b corresponding to a second time (t2). The prediction 614b indicates, for example, that anticipated study participation levels of Group 1 participants has modestly changed such that the Group 1 participants are now anticipated to make up roughly 53% of the group composition 226 by the end of the study. The computer system 210 also determines an updated prediction 616b for the Group 2 participants that the Group 2 participants are now anticipated to make up 23% of the group composition 226 by the end of the study. These changes may, in some cases, be enough to trigger the computer system 210 to generate a warning, to determine one or more recommendations, and/or to automatically perform one or more actions.

Finally, the computer system 210 may have, based on data measured from the start of the study (t1) to the current time (t3) generated a current study prediction for the Group 1 participants and the Group 2 participants. The new predictions for the Group 1 and Group 2 participants indicates significant changes to the group composition 226, such that the computer system 210 may, in response, generate a warning. Notably, the current prediction indicates that the enrollment of Group 2 participants is expected to deviate significantly from the Group 2 enrollment goal of 25%, and that, relatedly, the enrollment of Group 1 participants is expected to deviate significantly from the Group 1 enrollment goal. The computer system 210 may generate a warning in response to the current prediction for the Group 1 and Group 2 participants. For example, the computer system 210 may generate a warning based on a slope of a current prediction trend line, based on an anticipated group composition 226 at the end of the study (t8), based on the enrollment percentage of the Group 2 participants dropping below a threshold at one or more current and/or future points in time, based on the enrollment percentage of the Group 1 participants exceeding a threshold at one or more current and/or future points in time, etc.

FIG. 6B is a diagram that illustrates updated group predictions for a research study. The predictions may be made by the computer system 210 described above with respect to FIGS. 2-4. The computer system 210 may use the predications to determine the predicted group composition at a future time, such as at study completion.

As illustrated in FIG. 6B and by the key 630b, time has elapsed and the predictions have been updated accordingly when compared to FIG. 6A. The updated prediction may have been made by the computer system 210. During the elapsed time, (e.g., at the time t3) a study action of removing "Study Parameter 1" for the Group 2 participants has been performed. This study action may have been automatically performed by the computer system 210, or may have been part of a recommendation generated by the computer system 210 that was accepted by a researcher of the study. As shown, the performance of the study action has had a significant effect on the observed and predicted data (e.g., diversity related data) for the study with respect to Group 2 participants.

The first graph 602b indicates updated measured and predicted participation levels of study participants by group last updated at a time t5. As shown, the performance of the study action to remove a study parameter for Group 2 participants has had a significant effect (here an improvement) on the participation levels of Group 2 participants.

A second graph 604a indicates updated measured and predicted group diversity levels (e.g., diversity of enrolled participants). The measured and predicated group diversity levels were in this example last updated at a time t5. As shown, the most recent group diversity predictions indicate a significantly improved group diversity predictions such that the expected group diversity at the end of the study is now expected to be within 3% of the target cohort diversity.

Figure 8A:
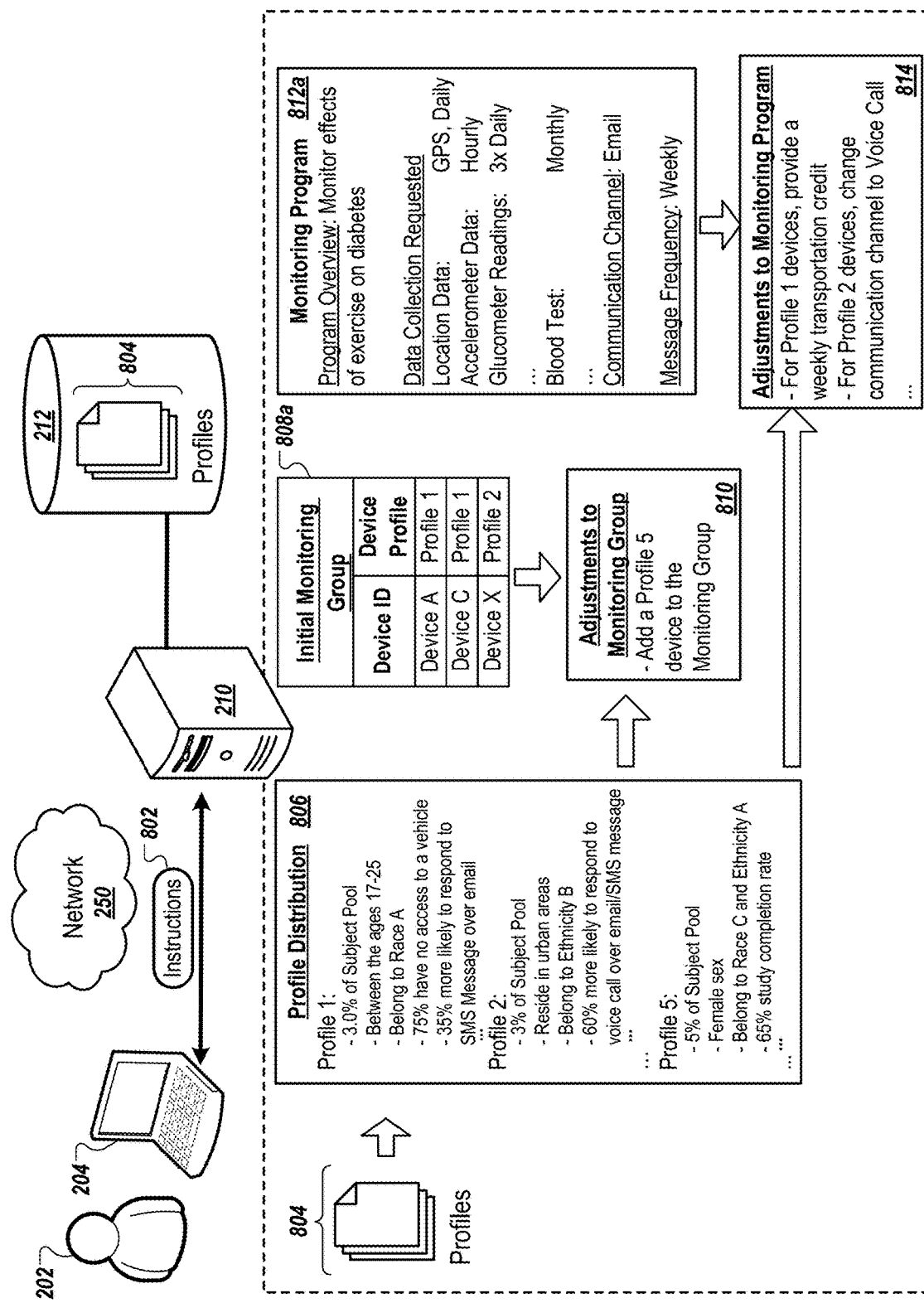
FIGS. 8A-8B are diagrams that illustrate an example system for customizing monitoring programs involving remote devices.
Figure 8B:
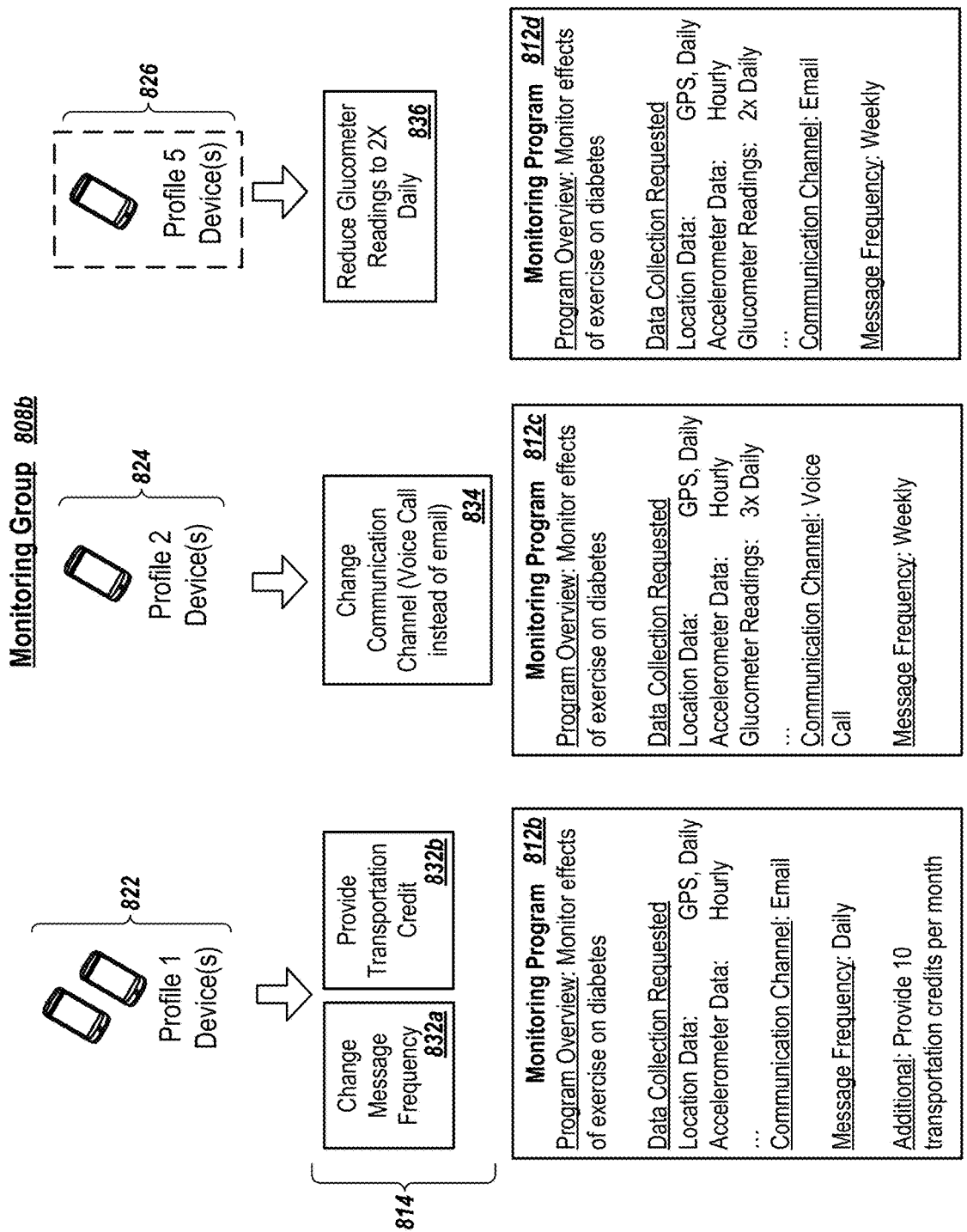

FIGS. 8A-8B are diagrams that illustrate one or more components of the system 200 and a process for customizing monitoring programs involving remote devices. In customizing monitoring program, the computer system 210 of the system 200 can assess and adjust the composition of groups for a monitoring program 812a or the monitoring program 812a using a set of profiles 804. The computer system 210 may distribute adjusted monitoring program 812 to multiple remote devices.

The computer system 210 may be configured to distribute software for a monitoring program to devices that are to be monitored. The monitoring program may indicate times when data is to be obtained from, requested from, or sent to the monitored devices. The monitoring program may also indicate the type of data or the specific data that is to be obtained from, requested from, or sent to the monitored devices. The data obtained or requested from the monitored devices may include sensor data collected using sensors of the monitored devices or sensor devices electronically connected to the monitored devices. The data sent to the monitored devices may include instructions to collect sensor data, or updates to the monitoring program or a portion of the monitoring program on the devices. In updating the monitoring program or a portion of the monitoring program on the devices, a configuration of the monitored devices can be adjusted to, for example, change what data is monitored or how the data is monitored.

The computer system 210 can adjust the monitoring program for particular groups of devices or users. These groups may correspond to different profiles generated by the computer system 210. The computer system 210 may assign each of the monitored devices to at least one profile based on attributes of the devices or attributes of users of the devices. For example, a first profile may indicate that a device must include a GPS unit and a heartrate monitor, and that the user of the device must live in an urban environment and must be between the ages of 25 and 30 years of age. If a first device of the group of device meets the device requirements of the profile criteria and has a user that meets the user requirements of the criteria, the computer system 210 may classify the first device as belonging to the first profile.

The computer system 210 may generate the profiles based on previously observed outcomes. For example, the computer system 210 may generate profiles based on observed outcomes of a currently running and/or previously performed monitoring programs. The observed outcomes may include the compliance of the devices or their users with the requirements of the monitoring program, and the retention of the devices or their users in the monitoring program. As another example, the computer system 210 may generate profiles based on attributes of devices or users in a candidate pool. The attributes may include, for example, sensors that the devices include, sensor devices that are compatible with the devices, models of the devices, operating systems of the devices, etc. The attributes may also include demographic or non-demographic information that describes the users. The users may include, for example, users that have previously participated in a monitoring program, that are currently participating in a monitoring program, have indicated that they want to participate in a monitoring program, or that are eligible for a monitoring program.

The computer system 210 may generate the profiles using a machine learning model or a group of machine learning models. As an example, the computer system 210 may using a clustering machine learning model to cluster different devices or users based on observed outcomes. Similarly, as another example, the computer system 210 may use a clustering model to cluster different groups of devices or users based on attributes of the devices or users. The model may use all attributes available to the model in performing the clustering. Alternatively, the model may use a subset of attributes corresponding to key attributes to perform the clustering. These key attributes may be determined using another machine learning model or a group of other machine learning models, using a static algorithm or group of static algorithms, or based on input from an administrator or researcher.

In general, a monitoring program refers to a set of elements that define how to conduct a monitoring program of multiple devices and/or persons. The elements may include parameters for the monitoring program. These parameters may, for example, define inclusion criteria for persons or devices in the monitoring program, and/or exclusion criteria for persons or devices in the monitoring program. The elements may also include a definition of the monitoring program or an indication of what type of studies the monitoring program has (i) previously been used for, and/or (ii) is applicable to. The elements may also include an indication of the particular data that is to be requested and/or received during a program, a schedule that indicates when data is to be requested and/or received, and/or a frequency of data collection or reception. The elements may further define one or more conditions for determining the end of the monitoring program. For example, an element may indicate that sessions of the monitoring program are (e.g., by default) to be run for six months. As another example, an element may in dictate that sessions of the monitoring program are to be run until a set of particular conditions are met (e.g., enough data is collected from each of the participants). Similarly, the elements may define conditions for determining one or more milestones of the monitoring program.

The elements may define or otherwise indicate other information of the monitoring program, including other communication information. For example, the elements may indicate a default communication channel, a default word choice (e.g., vocabulary) for communication, a default sentence structure (e.g., formal, semi-formal, informal, etc.).

Figure 7:
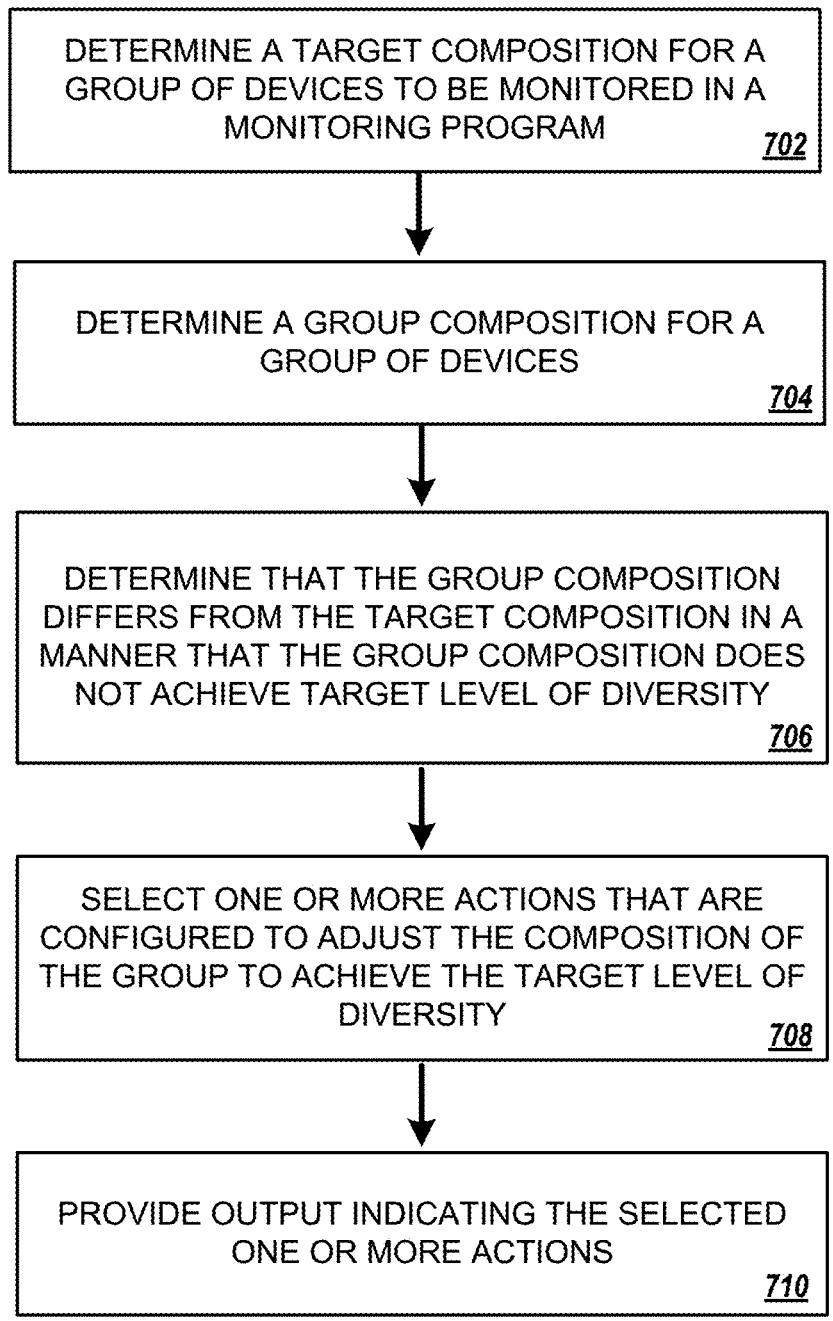
FIG. 7 is a flowchart diagram that illustrates an example process for diversity assessment and action selection.

FIG. 7 is a flowchart diagram that illustrates an example process for diversity assessment and action selection. The process 700 may be performed by the computer system 110 shown in FIG. 1. The process 700 may be performed by the computer system 210 shown in FIGS. 2-4.

In many cases, the administrator of a monitoring program, such as a researcher conducting a clinical trial, cannot determine whether the monitoring group provide sufficient diversity to achieve the needs of the monitoring program. Beyond simply whether a sufficient total number of participants are enrolled, it is difficult to determine whether the makeup of the monitoring group provides the right variety in participant backgrounds. Further, the effective level of diversity can be diminished through the lack of compliance that disproportionately affects some groups over others. The process 700 helps the system determine and inform an administrator whether a monitoring group has sufficient diversity, as well as to indicate what adjustments should be made to obtain the proper diversity representation level if it is not present.

Briefly, the system can identify a reference population for the monitoring program (e.g., population at large, or a group most likely to use a drug or product) and determine a diversity goal that reflects the characteristics of the reference population. The system can also determine diversity metrics for a monitoring group (e.g., a clinical trial cohort) and provide the diversity metrics to the administrator, indicating whether the current and expected future monitoring group characteristics will meet the target level of diversity. For example, the system can compare the diversity metrics for the cohort to the goal levels (e.g., thresholds, ranges, minimums, etc.), determine that the diversity metrics are outside a desired range, and then select actions to improve diversity in the monitoring group.

The process 700 includes determining a target composition for a group to be monitored in a monitoring program (702). In some cases, the system provides a user interface through which a researcher or other administrator can specify the target composition. In other cases, the system determines the target composition, calculating an appropriate target from data describing a reference population and other data.

As discussed above, the target composition can be based on a reference population, such as a set of devices or users in a particular geographical area. The target composition can be based on other populations or subgroups. For example, for a research study about diabetes, the target composition may be based on the set of people in the United States that have diabetes, and so the target composition represents the characteristics of that population rather than the general population. The system can receive input indicating the location or general population of interest, and then retrieve population data (e.g., census data, survey data, etc.) specifying the makeup of the population. The system then sets the target composition to have characteristics (distribution of profiles or attributes) that are the same as or are based on the characteristics in the population data.

The target composition can be defined with respect to attributes that are specified by a user as relevant to the study or as inferred by the system as relevant to the study. The dimensions used for assessing composition and diversity can be different from one monitoring program to another. Some monitoring programs may define composition in terms of a desired distribution across each of age, sex, and race. Other monitoring programs may additionally or alternatively use other attributes, such as whether a person has a certain health status or not (e.g., high blood pressure, obesity, diabetes, cancer history, etc.), a certain genetic profile, or whether the user has a certain behavior pattern. Thus, the dimensions for which diversity can be assessed and achieved can be well beyond simple demographics.

The target composition can be expressed in different ways, and even with multiple types of constraints for a single monitoring program. One is a relative measure for different groups or profiles (e.g., 10% from group 1, 20% from group 2, etc.). Another is a set of minimums or quotas for each of different groups (e.g., at least 10 from group 1, at least 25 from group 2, etc.). Another is a set of ranges, thresholds, or constraints. For example, the target may be expressed as amounts or percentages of the monitoring group for each of different attribute values (e.g., a minimum of 40% male, a minimum of 40% female, a minimum of 30 individuals that have diabetes and a minimum of 30 individuals that do not have diabetes, no more than 40% Caucasian participants, at least 15% for each of multiple different racial backgrounds, etc.)

The process 700 includes determining a group composition for a group of devices or users for the monitoring program (704). The group can be a monitoring group of enrolled devices or users that have registered or subscribed to participate in the monitoring program. As another example, the group can be a group of candidates selected to invite to participate, or a candidate pool from which candidate participants can be selected. In health research studies, the group can be an actual cohort of individuals enrolled in a research study. Similarly, at the creation of the research study, before the study has begun, the group can be a candidate pool or a selected prospective cohort (e.g., a set of prospects identified as meeting the selection criteria which may not yet have enrolled).

The system can determine the measures of composition of the group for each of the different constraints or measures of diversity used to define the target. For example, if the target is a set of quotas for different participant types or profiles (e.g., defined by age, race, sex, or other attributes), the system can determine the number of people in the assessed group that meet each type or profile. Similarly, if the target is expressed in terms of percentages for different types or profiles, the group composition can also be determined as the percentages for the different types or profiles. In general, the group composition can indicate the amounts of members in different categories and the distribution of different attribute values among the group, in absolute or relative terms.

The process 700 includes determining that the group composition differs from the target composition in a manner that the group composition does not achieve the target level of diversity (706). The system can store user profiles that describe the attributes, history, medical history, and other characteristics of individuals. The system can compare the group composition with the target composition and determine whether the group composition is within a threshold level of the target composition. This can involve comparing the amounts of participating devices or users in different categories to the respective amounts indicated by the target composition data. This may also include generating a diversity score, for the group as a whole or for different categories of participants, and determining whether the difference is less than a predetermined threshold (e.g., less than 5% different, etc.). In many cases, a difference of at least the predetermined magnitude for any one of various categories or groups (e.g., less than the minimum needed for any of group 1, group 2, group 3, etc.) or for any of the predetermined attributes for which diversity is needed (e.g., age, sex, race, diabetes status, location, mental health history, etc.) can trigger the system to take corrective actions to bring the monitoring group back to the composition needed.

Notably, the system can assess diversity for not only the nominal membership of the monitoring group (e.g., the set enrolled or invited to enroll), but also the set of members actually complying with (or predicted to comply with) the requirements of the monitoring program. For example, for a clinical trial, 1000 participants may be enrolled, but only 850 may be complying with the requirements of the study protocol. These requirements may be for data collection (e.g., completing a survey, acquiring sensor data, etc.) or for other actions separate from data collection (e.g., taking a medication, performing a needed amount of exercise, sleeping according to study guidelines, etc.). As a result, the system can assess the composition and diversity of the set of the 850 complying participants to provide a more accurate indicator of the results of the study. Because compliance and attrition can vary for different participant backgrounds and different participant attributes, the system's assessment of the complying set can provide an early indicator where compliance problems for some groups may decrease the effective diversity among the valid, usable data sets for the study. Participants that do not comply with the requirements may be considered withdrawn from participation for the purposes of the calculation showing the diversity status, even if the participants continue to be enrolled and outreach is made to bring them back into compliance.

In many cases, administrators may enroll an appropriately diverse group of participants at the beginning of the study, but poor quality data collected, incomplete data collection, lack of compliance with participant disproportionately affects participants in one or more groups, which can put the entire research study at risk of cancellation. This, of course, risks wasting all of the resources expended on the study, at the servers of the system as well as at all of the many remote devices. The system can compare the collected data for individual participants with the requirements of the monitoring program they participate in to determine compliance, on a repeated or ongoing basis. This then gives the system the ability to determine the composition and diversity status of the subset of the monitoring group that is complying with the requirements.

The system can be a multi-tenant system that manages many different monitoring programs each with their own requirements for diversity and their own target compositions. The system can monitor the compliance of individuals in each monitoring group with respect to the particular requirements of the corresponding monitoring programs. This allows the system to track, in real time or substantially in real time, whether each monitoring program is meeting its own objectives for composition and diversity.

The process 700 includes selecting one or more actions that are configured to adjust the composition of the group to achieve the target level of diversity (708). When the desired diversity level is not met, the system can identify the participant categories or participant attributes that are underrepresented and determine actions to bring levels for those categories or attributes up to the levels needed to meet the target composition. For example, the system can determine that within a monitoring group, a first category is represented by only 7 participants while the target is 10 individuals. In response, the system can search the user profile database and identify at least three additional individuals in the first category that meet the eligibility criteria for the monitoring program. The identified candidates may then be added to monitoring group (e.g., invited to enroll, added as participants, etc.) to bring the composition and diversity level to the needed state.

The selection of actions can include actions determined to increase the compliance with study requirements for participants in specific categories or with specific attributes that are underrepresented. For example, if 10 participants are needed for category 2, but only 8 out of the 10 enrolled participants in that category are complying with the data collection requirements, then the system can select actions that are calculated to increase the compliance of the two non-complying participants and/or to increase future compliance for all participants in that category. The tables shown in FIG. 4 can be used by the system to identify additional elements to add to the monitoring program to increase compliance (e.g., those associated with positive effect on compliance or at least lower negative effects). The system can also change the manner of communicating with those participants, add additional participants for underrepresented categories or take other actions to improve the diversity level.

The process 700 provides output indicating the selected actions (710). This can include providing the output to a device associated with a researcher or other administrator for the monitoring program, for display in a user interface on the administrator's device. The user interface may include interactive controls, and in response to the controls the system can carry out one or more recommended actions to improve the composition and diversity level for the monitoring group toward the target composition.

In addition, the system may carry out the one or more selected actions, in some cases automatically without requiring specific user input or confirmation. In these cases, the system can carry out adjustments to the monitoring groups (e.g., inviting or enrolling new participants in categories that are underrepresented or are effectively underrepresented when compliance is taken into account), adjusting monitoring program elements for unrepresented groups (e.g., adding or substituting interactions, survey elements, configuration data, etc.), changing the form or content of communications to underrepresented groups, and so on. The system can identify and carry out various types of actions to improve the level of diversity among enrolled and complying members of the monitoring group. This includes providing customized support or interaction to customized for the needs or preferences of different groups. Depending on the participant's background, some may respond better to being provided a credit for taxi service, providing a mobile phone, changing manner of interactions in the study, etc. Similarly, the system may broaden inclusion criteria (e.g., remove limitations to joining the monitoring group) to encompass more of people of the needed backgrounds. Similarly, the system can reduce or remove exclusion criteria to similarly encompass more candidates when needed. As discussed further below, various actions can add additional participants to the cohort from underrepresented groups or may communicate with participants to restore compliance with program requirements. In addition, the system may determine a reason that diversity metrics are out of target ranges, such as identifying one or more factors in the study that are resulting in a bias to enrollment, compliance, or retention. For example, for certain groups, one or more requirements may be disproportionately missed, signaling a need to change that requirement or add additional support for those groups. For each of various potential changes, the system can determine a candidate pool or predicted outcome as if the change was carried out, then select the actions with the best results predicted (e.g., scored as providing the least disruption, highest improvement to diversity, etc.)

In addition to assessing effective level of diversity among participants currently complying with program requirements, the system can assess the diversity among the set of participants projected or predicted to comply with the requirements. This can be useful at the creation of a study, to assess how the requirements of a new study may disproportionally affect the compliance or retention of one group over another. Using the analysis of FIG. 4, the system can identify the elements that have the negative effect and propose substitute elements with better outcome profiles and/or recommend additional elements to compensate for the effect. Similarly, the predictions of compliance rates and retention rates for different groups can be used while a study is ongoing, showing that although current compliance is acceptable, historically the compliance or retention by the end of the study may be worse and may remove the diversity level currently seen.

FIGS. 8A-8B are diagrams that illustrate one or more components of the system 200 and a process for assessing and adjusting the composition of groups for a monitoring program 812*a* or the monitoring program 812*a* using a set of profiles 804.

The disclosed systems can be used to achieve number benefits. For example, the computer system 210 can provide numerous benefits to realize and improved program monitoring and distribution system.

Notably, other systems often, if not always, fail to start with an appropriate set of subjects to monitor. That is, these systems are incapable of checking if a set of subjects, such as a set of devices or device users, will provide the overall set of data and the diverse context to be able to capture the variety of data required in the monitoring program. Often these systems are simply provided a pre-selected group subjects or randomly select a group of subjects that are bound to produce, or have an unacceptably high likelihood of producing, unviable results or results that fail one or more other goals of the monitoring program.

In contrast, the computer system 210 can address this issue by selecting a group of subjects to invite or enroll in a monitoring program that are predicted to meet the set goals for the monitoring program. In more detail, the computer system 110 may select a diverse group of subjects to enroll or invite to the monitoring program such that the composition of the group meets certain diversity requirements. By including a diverse group of subjects at the outset of the monitoring program, the computer system 210 can at least improve the likelihood of obtaining viable results from the monitoring program. As an example, many medical studies today fail to produce viable results or produce results having severely limited applicability due to a failure to include or maintain a diverse set of participants. Diversity may refer to diversity among various subject attributes, including both demographic and non-demographic attributes.

The computer system 210 may also take into account other attributes of the subjects when selecting a group of subjects to enroll or invite to a monitoring program. For example, the computer system 210 may take into account historical data, trends in the historical data, and, optionally, trends among certain populations to select subjects that are likely to meet the requirements of the study. The historical data or trends may indicate past or anticipated retention rates for subjects or groups of subjects, past or anticipated compliance rates for subjects or groups of subjects, or past or anticipated data quality obtained from subjects or groups of subjects. For example, the historical data may indicate that a particular subset of subjects is likely to have low compliance with a particular requirement of a monitoring program. In response to this determination, the computer system 210 may avoid enrolling or inviting those subjects to the monitoring program.

However, if those subjects are necessary to achieve certain minimum diversity criteria or other goals for the monitoring program, the computer system 210 can modify the elements of the monitoring program for that particular subset of subjects to improve compliance. Modifying the elements may include modifying or removing requirements of the monitoring program, or adding remedial elements. For example, if the particular subset of subjects is determined by the computer system 210 to generally not have access to a vehicle and, as a result, have low compliance with required medical office visits, the system 210 may add taxi credit to a new version of the monitoring program for those subjects as a remedial measure to improve compliance rates for those subjects with respect to office visits.

In selecting subjects at an outset of a monitoring program or determining how to modify the elements of a monitoring program to improve, the computer system 210 may use various profiles that represent categories of subjects. These profiles may be used to determine how particular subjects are likely to respond to certain monitoring program requirements, and, therefore, to determine if they should be enrolled to the monitoring program or if the monitoring program needs to be adjusted for one or more particular groups of subjects. These profiles may additionally or alternatively be used to improve the diversity of a monitored group or to determine if a monitored group has a sufficient diversity. For example, the computer system 110 may identify the profiles corresponding to a monitoring group and use the profiles to determine if there is sufficient diversity, at the outset or predicted diversity at completion of the monitoring program. If diversity is insufficient, the computer system 210 may use the profiles to identify unrepresented or underrepresented profiles, and proceed to enroll or invite subjects from categories represented by those unrepresented or underrepresented profiles.

By selecting at the outset of a monitoring program a group of subjects that will likely provide the overall set of data and the diverse context to be able to capture the variety of data needed for the monitoring program, the computer system 210 is able to significantly reduce computational inefficiencies. Notably, this selection improves the likelihood of obtaining viable results for the monitoring program as a whole, which greatly reduces. As such, the computer system 210 is able to significantly reduce the computational load on the system and the remote devices and the CPU hours of the system and the remote devices.

As shown in FIG. 8A, in response to receiving instructions 802 from the client device 204, the computer system 210 may access the profiles 804 from the database 212 and use the accessed profiles 804 to determine adjustments to make to the monitoring program 812a or to a group composition selected for the monitoring program 812a.

The instructions 802 may also include other information. For example, the instructions 802 may indicate an initial monitoring group 808a. That is, the instructions 802 may include or point to an initial list of devices and/or persons that have been invited to, selected for, or enrolled in the monitoring program.

The instructions 802 may also or alternatively include or otherwise indicate the elements of the monitoring program 812a. In response to receiving the instructions 802, the computer system 210 may generate the monitoring program 812a, may select an existing monitoring program that includes the elements in the instructions 802, or may update an existing monitoring program to include the elements in the instructions 802.

The instructions 802 may include data that the computer system 210 uses to initiate a monitoring program 812a. Specifically, the instructions 802 may include an indication of the specific monitoring program that should be selected for a new monitoring program (e.g., from a list of available monitoring programs).

Alternatively, the computer system 210 may select the initial monitoring group 808a from a candidate pool of devices and/or users based on the instructions 802. As an example, the instructions 802 may include criteria, such as diversity criteria, for a monitoring program that is to be performed. The computer system 210 may use this criteria to select devices and/or people for the monitoring program to place into the initial monitoring group. As an example, the instructions 802 may include diversity criteria indicating an exact or minimum number of devices or persons there needs to be in the monitoring program that are associated with specific profiles. Specifically, the monitoring instructions 802 may indicate that the monitoring group 808a must include at least one device assigned to Profile 1, and at least one device assigned to profile 2. Similarly, the instructions 802 may indicate exact, minimum, and/or maximum percentages that represent the population of devices or persons associated with specific profiles in the monitoring group 808a. For example, the monitoring instructions 802 may indicate that at least 50% of the devices in the monitoring group 808a should be assigned to Profile 1 and that at least 25% of the devices in the monitoring group 808a should be assigned to Profile 2.

Each of the profiles in the profiles 804 may correspond to a subgroup of devices and/or persons. Specifically, each profile may correspond to a subgroup or a distinct (e.g., non-overlapping) subgroup of devices and/or persons that share at least one of the same key attributes, similar attributes, or demonstrate the same or similar behaviors. That is, each profile may represent a category of devices and/or candidates. As will be discussed in more detail with respect to FIGS. 9A-9B, the computer system 210 can generate the profiles using previously observed outcomes (e.g., behaviors) and/or attributes attributed candidates for inclusion in the monitoring group. The computer system 210 may generate the profiles using one or more machine learning models, such as one or more clustering algorithms.

The profiles 804 may be previously generated and stored in the database 212. Alternatively, the profiles 804 may be generated or updated in response to the computer system 210 receiving instructions 802 from the client device 204. For example, in response to receiving the instructions, the computer system 210 may generate the profiles 804 or may update the profiles 804 using the most recently available monitoring data.

A profile distribution 806 indicates example information that defines a number of example profiles. The information in the profile distribution 806 may include criteria for determining if a device or person is eligible for assignment to the profile, e.g., inclusion criteria. For example, the criteria for Profile 1 indicates that a subject must be between the ages of 17-25 and belong to Race A to be eligible. The information may also include outcome information (e.g., anticipated behaviors such as retention, compliance, and quality of data) associated with subjects (e.g., devices and/or persons) associated with the profile. As will be discussed in more detail with respect to FIGS. 9A-9B, this outcome information may be determined for each of the profiles by analyzing outcome information associated with previous subjects or current subjects in a category of subjects corresponding to each of the profiles. As an example, 75% of the subjects in Profile 1 do not have access to a vehicle and 25% of the subjects are more likely to respond to SMS message when compared to an email message. The profile distribution may also contain various other data such as a population percentage that the subjects of each of the profiles represent of the total candidate pool. For example, 3.0% of the subjects in the candidate pool are associated with Profile 1. The candidate pool may include all subjects that have previously or are currently enrolled in a monitoring program. Alternatively, the candidate pool may include all active subjects, e.g., those that are currently enrolled in a monitoring program or are available for enrollment in a monitoring program.

In some cases, a subject may be associated (e.g., assigned to) multiple profiles. For example, a subject may meet the inclusion criteria for multiple profiles and, therefore, be associated with the multiple profiles.

In some cases, a subject is associated with only a single profile. For example, if a subject has been assigned to a first profile, they may be prevented from being assigned to a second profile.

The computer system 210 may reassign subjects to different profiles (e.g., determine that they belong to different categories of subjects) over time based on the monitored actions of the subjects. For example, a particular subject may initially demonstrate a smartphone compliance rate below 60% over the first three monitoring programs they participate in, and, as a result, be assigned by the computer system 210 to a first profile of the profiles 804. However, if over the next three monitoring programs they improve their overall compliance rate to 75%, the computer system 210 can reassign the subject to a second profile of the profiles 804.

The computer system 210 may use the profile distribution 806 to adjust the monitoring group (810). The computer system 210 may use the profile distribution 806 to adjust the initial monitoring group 808a at the outset of the monitoring program for the monitoring program 812a. In more detail, the computer system 210 may use the profile distribution 806 to identify categories of devices or persons that are underrepresented in the initial monitoring group 808a. For example, the computer system 210 may use the profile distribution 806 and the initial monitoring group 808a to determine that a device corresponding to Profile 5 should be added to the monitoring group 808. The computer system 210 may make this determination based on diversity reasons, e.g., in order to have at least one device from each profile or from each profile in one or more subsets of profiles. The computer system 210 may make this determination based on one or more determinations or predications. For example, the computer system 210 may use the profile distribution 806 to select a Profile 5 device based on the higher study completion rate of the profile 5 subjects in order to boost efficiency, increase likelihood that study will be successful (e.g., if an analysis of the initial monitoring group reveals that there is a higher than acceptable chance of study failure), etc. As another example, the computer system 210 may determine to add a Profile 5 device based on the percentage of the candidate pool. Specifically, the computer system 210 may add devices associated with unrepresented or underrepresented profiles for each profile that corresponds to at least threshold percent (e.g., 3%) of the candidate pool. Accordingly, the computer system 210 may determine to add a Profile 5 subject to the monitoring group 808 based on the Profile 5 population meeting the threshold percent.

After determining to add a Profile 5 subject to the monitoring group 808, the computer system 210 may automatically enroll a Profile 5 subject in the monitoring program, or may generate and send an invitation to a Profile subject to enroll in the monitoring program. As an example, the computer system 210 may take into consideration one or more factors to determine which subject to enroll or invite to the monitoring program. These factors may include, for example, the retention rates associated with the subject, the compliance rates associated with the subject, quality of data previously obtained from the subject or otherwise associated with the subject, the experience of the subject (e.g., number of monitoring program the subject has previously participated in), the activity level of the subject (e.g., how recent the subject has participated in a monitoring program), invitation acceptance rate of the subject, trends in factors (e.g., trends in the retention rates, compliance rates, activity level, etc. of the subject), etc. For example, a subject that has participated in at least one monitoring program over the last year and has a retention rate of 78% may be selected by the computer system 210 for enrollment over a subject that has not participated in at least one monitoring program over the last year and/or has a retention rate less than 70% despite both subjects corresponding to Profile 5.

After determining to add a Profile 5 subject to the monitoring group 808, the computer system 210 may generate and send a recommendation to the researcher 202 to enroll a Profile 5 subject or to send an enrollment invitation to a Profile 5 subject. The recommendation may include multiple subjects recommended by the computer system 210. The multiple subjects may be arranged in an order that corresponds to a recommendation order, such that the subject that the computer system 210 recommends most is shown first or highest in a list of subjects. The computer system 210 may wait to receive a response from the researcher, e.g., wait to receive a response from the client device 204, to enroll or invite one or more of the recommended subjects. Alternatively, the computer system 210 may wait for a predetermined amount of time after transmitting the recommendation to the client device 204. If a response is not received by this point, the computer system 210 can automatically enroll a Profile 5 subject in the monitoring program, or generate and send an invitation to a Profile subject to enroll in the monitoring program.

The computer system 210 may also use the profile distribution to adjust the monitoring program 812a (814). That is, the computer system 210 can determine adjustments to make to the monitoring program 812a using information in the profile distribution 806 corresponding to profiles associated with subjects in the monitoring group 808. The adjustments may include one or more changes to elements of the monitoring program 812a. As an example, these adjustments may include one or more of the following: modifications to the inclusion criteria for the monitoring program; modifications to the exclusion criteria for the monitoring program; modifications to the type, source, schedule, or frequency of data collection; modifications to the type, source, schedule, or frequency of data requests; modifications to monitoring program events or other requirements; modifications to communication methods, content, schedule, and/or frequency; and/or the addition of support features.

The adjustments may correspond to particular profiles of the profiles 804. For example a first set of adjustments may be particular to the Profile 1 subjects while a second set of adjustments may be particular to the Profile 2 subjects. That is, the computer system 210 may customize the monitoring program 812a for one or more profiles, e.g., based on the information contained in or associated with the profiles as indicated by the profile distribution 806. As shown, the computer system 210 uses the profile distribution 806 to customize the monitoring program 812 for the Profile 1 devices and the Profile 2 devices. Specifically, for the Profile 1 devices, the computer system 210 adjusts the monitoring program 812 to provide a weekly transportation credit to those Profile 1 devices based on, for example, the profile distribution 806 indicating that 75% of Profile 1 subjects do not have a vehicle and the monitoring program 812 requiring weekly medical office visits. Similarly, the computer system 210 adjusts the monitoring program 812 for the Profile 2 devices to update the communication channel from email to voice call based on the profile distribution 806 indicating that Profile 2 subjects are 60% more likely to respond to voice call over email and SMS message.

The computer system 210 can automatically make the adjustments to the monitoring program 812 or, alternatively, can generate a recommendation that includes the proposed adjustments. The computer system 210 may transmit the recommendation to the client device 204.

The computer system 210 may update the monitoring program for one or more groups of devices to improve efficiency and/or the likelihood of success of the monitoring program. That is, the computer system 210 may update the monitoring program 812a to improve the outcomes of the monitoring program (e.g., improve likelihood of subject compliance, compliance rates, retention rates, and/or quality of data obtained).

The adjustments to the monitoring program 812 may be temporary for the particular monitoring program. Alternatively, the adjustments to the monitoring program 812 may be permanent so as to update the default elements of the monitoring program.

FIG. 8B illustrates the adjustments made by the computer system 210 to the monitoring group 808 and to the monitoring program 812 for different categories of subjects. As shown, the computer system 210 has updated the monitoring group 808a which included a first subgroup 822 of devices that belong to a first category of subjects (e.g., subjects that correspond to Profile 1 of the profiles 804) and a second subgroup 824 of devices that belong to a second category of subjects (e.g., subjects that correspond to Profile 2 of the profiles 804) to the monitoring group 808. The monitoring group 808b includes the first subgroup 822 of devices, the second subgroup 824 of devices, and a third subgroup 826 of devices that belong to a third category of subjects (e.g., subjects that correspond to Profile 5 of the profiles 804).

Based on determinations made using the profile distribution 806 and the monitoring group 808b, the computer system 210 generates customized monitoring programs 812b, 812c, and 812d for each subgroup of devices 822, 824, and 826, respectively. The changes 814 indicate the changes that the computer system 210 made to the initial monitoring program 812a to generate each of the customized monitoring programs 812b, 812c, and 812d. The changes 814 made to the initial monitoring program 812a for the different subgroups of subjects may be made to improve predicted outcomes for the study. For example, the changes 814 may be made by the computer system 210 in an effort to improve retention of the subjects in the different subgroups, improve compliance with the requirements of the monitoring program, improve the likelihood of obtaining a minimally acceptable amount of data (e.g., to get results from the monitoring program that are statistically relevant, or that meet some other viability measure), improve the likelihood of obtaining at least a minimum level of data quality (e.g., to get results from the monitoring program that are statistically relevant, or that meet some other viability measure), etc.

For the subgroup 822 subjects, the changes 814 include a change 832a to message frequency, and an addition of an assistive element 832b to the monitoring program 812 to provide transportation credit 832b. As an example, Profile 1 of the profiles 804 may indicate that the Profile 1 subjects respond better to more frequent communication (e.g., may indicate higher compliance and/or retention rates with more frequent event reminders). The computer system 210 may use this information to increase the default message, e.g., from weekly to daily.

For the subgroup 824 subjects, the changes 814 include a change 834 to the communication channel. As an example, Profile 2 of the profiles 804 may indicate that the Profile 2 subjects demonstrate higher compliance when voice calls are used over other communications channels. The computer system 210 may use the information in Profile 2 to change the default communication channel, e.g., from email to voice call.

For the subgroup 826 subjects, the changes 814 include a change 836 to the communication channel. As an example, Profile 5 of the profiles 804 may indicate that the Profile 5 subjects have significantly lower retention rates when monitoring programs require the subjects to submit test results more than two times a day when compared to the retention rates for Profile 5 subjects when they are required to submit test results two times a day or less frequently. The computer system 210 may use the information in Profile 5 to modify the glucometer reading requirement, e.g., form requiring three readings per day to two readings per day.

Figure 9A:
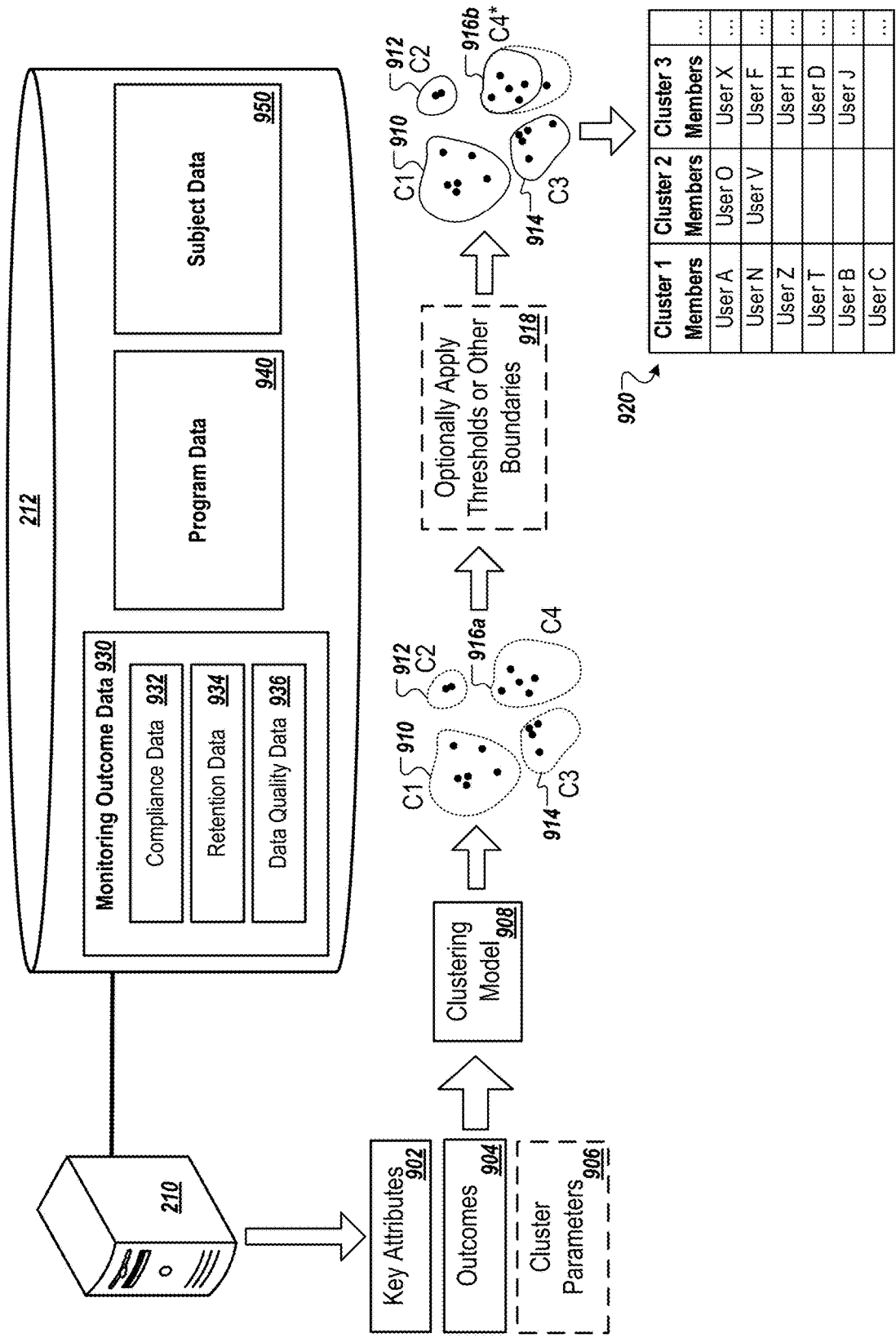
FIGS. 9A-9B are diagrams that illustrate an example system for generating profiles.
Figure 9B:
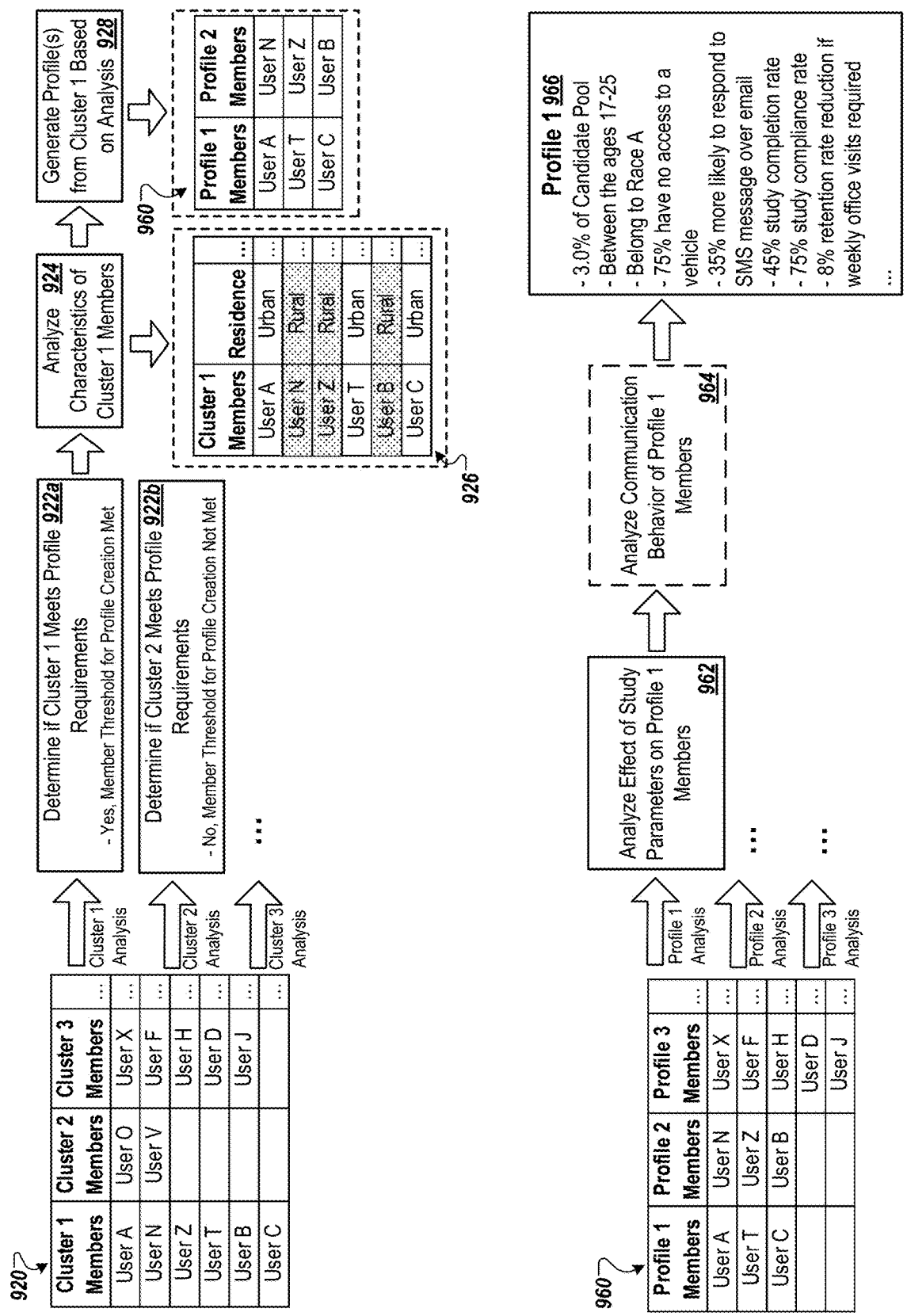

FIGS. 9A-9B are diagrams that illustrate one or more components of the system 200 an example system for generating profiles.

As shown in FIG. 9A, the computer system 210 may generate profiles using outcome data 940, program data 940, and/or subject data 950 stored in the database 212.

The monitoring outcome data 940 may include compliance data 932 (e.g., that indicates previously observed compliance rates for past subjects), retention data 934 (e.g., that indicates previously observed compliance rates for past subjects), and data quality data 936 (e.g., that indicates the quality of data that was obtained from past subjects). The monitoring outcome data 930 may be organized based on the individual subjects. For example, different portions of the compliance data 932, the retention data 934, and the data quality data 936 may correspond to a specific subject. The portion of the compliance data 932 associated with the specific subject may indicate, for example, the overall compliance of the subject across all requirements for all previous monitoring programs or all monitoring programs that are sufficiently recent, the compliance of the subject for particular requirement categories (e.g., smartphone compliance, office visit compliance, etc.) across all previous monitoring programs or all monitoring programs that are sufficiently recent, etc.

The program data 940 may describe the requirements of each monitoring program. For example, the program data 940 may include the default elements of each monitoring program. As was described in more detail with respect to FIGS. 8A-8B, these elements may be removed or modified based on profile data associated with the monitored group. Similarly, elements may be added to monitoring programs based on profile data associated with the monitored group.

More specifically, the program data 940 may include instructions to acquire or request specific data or types of data from subjects, instructions for subjects to perform particular actions, instructions as to the channel of communication and/or the frequency of communication between the computer system 210 and the subjects, instructions to provide accommodations (e.g., taxi credits), etc.

The program data 940 may also include various data packets corresponding to different monitoring programs. These data packets may include, for example, installation files for programs that are to be run on devices to be monitored in a monitoring program.

The subject data 950 may include the attributes, history, behavior, and other tracked data for monitored subjects. As an example, the attribute information in the subject data 950 may include demographic as well as non-demographic information for each of the monitored subjects (e.g., previously monitored subjects or currently monitored subjects), such as race, ethnicity, age, sex, residential area (e.g., city, state, country, etc.), type of residential area (e.g., urban, suburban, or rural), medical conditions, surgeries (e.g., type of surgery and date of surgery), prescriptions, etc. The history information may include information indicating the past monitoring programs that the subject has participated in or completed, and/or the past monitoring programs used during those sessions. The behavior information may indicate the particular subject's observed responses or compliance with certain monitoring program requirements (e.g., elements). As an example, the behavior information may indicate that the subject is 50% less likely to be retained if the monitoring program requires him to make weekly doctor visits. The behavior information may also include or point to portions of the compliance data 932, the retention data 934, and/or the data quality data 936 associated with that particular subject.

In generating the profiles, the computer system 210 may first use one or more machine learning models to cluster subjects from a set. The set may include, for example, subjects that have previously participated in a monitoring program, have previously completed a monitoring program, are currently participating in a monitoring program, have previously participated in a monitoring program that was held sufficiently recent, or have previously completed a monitoring program that was held sufficiently recent. The computer system 210 may use a clustering model 908 to generate different clusters of subjects or eligible subjects based on certain input.

As shown, the computer system 210 may provide one or more of key attributes 902 or outcomes 904 as input to the clustering model 908. The computer system 210 may optionally provide cluster parameters 906 as input to the clustering model 908. In addition, the clustering model 908 may have access to the monitoring outcome data 930, the program data

940, and/or the subject data 950, or may be provided the monitoring program data 930, the program data 940, and/or the subject data 950 as input.

The key attributes 902 may include a list of types of attributes that the clustering model 908 can use to cluster the subjects. For example, the key attributes 902 may include a list of attribute types that are found in the subject data 950. The key attributes 902 may be selected by the researcher 202, may correspond to a particular monitoring program selected for a monitoring program, and/or may be determined by the computer system 210. For example, a researcher 202 may indicate, for diversity purposes, that the key attributes 902 should include race, ethnicity, and medical conditions of the subjects. Based on this, the clustering model 908 may cluster the subjects based on the key attributes 902 or based in part on the key attributes 902 (e.g., clustering model 908 may also take into account the outcomes 904 or other data in the subject data 950).

The key attributes 902 may additionally or alternatively include a subset of the subject data 950. That is, the key attributes 902 may include a portion of the attribute information in the subject data 950 corresponding to the type of attribute selected.

The outcomes 904 may include a list of types of outcomes that the clustering model 908 is to cluster the subjects based on. For example, the outcomes 904 may include a list of outcome types that are found in the monitoring outcome data 930. The outcomes 904 may be selected by the researcher 202, may correspond to a particular monitoring program selected for a monitoring program, and/or may be determined by the computer system 210. For example, a researcher 202 may indicate that subjects should be clustered based on smartphone compliance during monitoring programs.

The outcomes 904 may additionally or alternatively include all or a portion of the monitoring outcome data 930. For example, the outcomes 904 may include all or a portion of the compliance data 932, the retention data 934, or the data quality data 936.

The cluster parameters 906 may include additional criteria for the clusters. For example, the cluster parameters 906 may specify a minimum cluster size, a maximum cluster size, the number of clusters, a minimum number of clusters, a maximum number of clusters, etc.

The clustering model 908 uses the key attributes 902, the outcomes 904, and/or the cluster parameters 906 to generate the clusters 910, 912, 914, 916a. Each of the clusters contain at least one subject of the subject pool. As an example, the key attributes 902 may include medical conditions or a particular set of medical conditions. Based on this, the clustering model 908 may generate the clusters 910, 912, 914, and 916a such that each includes subjects that generally have the same or similar medical conditions. As another example, the clustering model 908 may additionally or alternatively cluster subjects in the subject pool based on outcome data associated with the subjects. That is, the clustering model 908 may group subjects that have the same or similar monitoring program compliance rates, monitoring program retention rates, data quality, or health outcomes (e.g., degree of recovery or management of a disease, occurrence of side effects, etc.).

Clustering by the clustering model 908 may be performed in a number of ways. As discussed above, clustering may be primarily based on the attributes of the subjects, such as demographic and/or non-demographic information stored for subjects as part of the subject data 950. In this example, the clustering model 908 may generate clusters of subjects where each cluster includes a group of subjects that have a number of attributes in common (e.g., same ethnicity, same race, same medical conditions, etc.), have a number of similar attributes (e.g., similar or otherwise related medical conditions that fall into the same category of medical conditions, a height that falls within a particular height ranged determined by the clustering model, etc.), have a number of the key attributes 902 in common, and/or have a number of similar attributes of the key attributes 902. In more detail, the clustering model 908 may cluster subjects based on subjects in each of the groups having the highest number of attributes in common or the highest number of the key attributes 902 in common for that particular cluster when compared to the subjects assigned to other clusters.

Another way that the clustering model 908 can generate the clusters 910-916 is by clustering based on the outcome data 930. For example, the clustering model 908 can generate clusters of subjects based on those that perform similarly. In more detail, the clustering model 908 may generate the clusters 910-916 that each correspond to different groups of subjects that have the same or similar retention rates, the same or similar study completion rates, the same or similar compliance rates (e.g., smartphone compliance, office visit compliance, etc.), etc. Accordingly, the computer system 210 can use profiles generated from these clusters to predict how a subject is likely to perform in a current monitoring program if they meet the eligibility criteria for the profiles. Determining on the number of subjects that are assigned to the different profiles, the computer system 210 may determine that more subjects need to be enrolled in the current monitoring program (e.g., due to the profiles indicating a low retention rate and/or completion rate), ideally those that correspond to a profile which indicates a high completion rate, retention rate, and/or compliance rate.

In assigning subjects to clusters, the clustering model 908 may determine a set of attribute values or ranges that serve as criteria for the clusters. For example, the clustering model may determine that the second cluster 912 requires that the subjects belong to Race B, be over thirty-five years old, and have diabetes. Based on subjects O and V meeting these criteria, the clustering model 908 may determine that the second cluster 912 includes subjects O and V. This criteria may be used to generate a profile corresponding to the second cluster 912. For example, the same criteria may be used as eligibility criteria for determining if a corresponding profile is applicable to a subject in a current monitoring program, and/or the criteria may be modified (e.g., by an administrator) before being used as eligibility criteria for determining if a corresponding profile is applicable to a subject in a current monitoring program. Clustering in this manner can be used to achieve clusters of subjects that can be used to meet certain diversity criteria. That is, clusters of subjects can be formed where each cluster includes subjects having particular attributes. Accordingly, in conducting a new monitoring program, profiles generated from these clusters can be used to determine if certain diversity criteria is being met or may be used a substitute for diversity criteria. For example, if it is determined that no subjects in a current monitoring program belong to a first profile corresponding to the cluster 910, then additional subjects should be invited to join the monitoring program in order to improve the diversity of the monitoring program and, thereby, improve the applicability of the results and/or improve the likelihood of the results being valid.

Alternatively, the clustering model 908 may generate a set of attribute values or ranges after determining the clusters from the attributes of the subjects in the determined clusters.

For example, after generating the clusters 910-916, the clustering model 908 may determine for each of the clusters eligibility criteria for the cluster using the attributes of subjects assigned to each of the clusters. In more detail, for the second cluster 912, the clustering model 908 may access a subject of the subject data 950 corresponding to the subjects O and V based on the subjects O and V having been assigned to the cluster 912. The clustering model 908 may use this subset of data to generate eligibility criteria for the cluster 912 and/or eligibility criteria for a profile based on the cluster 912. The types of attributes used to generate the criteria may be those that are indicated in the key attributes 902. For example, if the key attributes 902 indicate that clustering should take into account the ethnicity of the subjects, then the ethnicity of the subjects assigned to the cluster 912 should differ from the ethnicity of the subjects assigned to the other clusters. Accordingly, the computer system 210 can access from the subject data 950 the ethnicity data corresponding to the Subjects O and V and use that data to generate the criteria. Additionally or alternatively, the clustering model 908 may determine what attributes of the subjects assigned to the cluster 912 are unique with respect to the other clusters. For example, the clustering model 908 may determine that the cluster 912 is the only cluster to include subjects over thirty-five years old. Accordingly, the clustering model 908 may determine that the criteria corresponding to the cluster 912 should include a requirement of a subject being over thirty-five years old.

Thresholds or other boundaries may be optionally applied to one or more of the generated clusters (918). For example, thresholds or other boundaries set by the researcher 202 may be applied to one or more of the clusters 910, 912, 914, and 916a. Applying the thresholds or other boundaries can result in removing clusters, splitting a cluster into two or more new clusters, removing a subject from a cluster or otherwise dissociating the subject with the cluster, etc. As an example, the threshold or other boundaries may include inclusion criteria for the clusters generated by the computer system 210 or set by the researcher 202. The computer system 210 may apply this inclusion criteria to the clusters. As an example, the computer system 210 may apply an inclusion criterion that all subjects in the cluster 916a must be older than 30 years of age. As such, the computer system 210 may update the cluster 916a to disassociate any subjects that were 30 years of age or younger.

The subjects associated (e.g., assigned to) each of the clusters 910, 912, 914, and 916 may be considered members of their respective clusters. A table 920 includes example members of the first cluster 910, the second cluster 912, and the third cluster 914.

As shown in FIG. 9B, the computer system 210 may use the different clusters to generate profiles. In more detail, the computer system 210 may generate one or more profiles from the clusters. Additionally or alternatively, the computer system 210 may determine that one or more of the clusters are not eligible for profile generation, e.g., due to not meeting eligibility requirements (e.g., minimum member size; minimum subject population representation; minimum diversity level; etc.). For example, the computer system 210 may analyze each of the clusters to determine if they meet certain requirements for profile generation. As an example, a cluster may only be eligible for profile creation if it represents a threshold percentage of the subject pool or eligible subject pool.

In generating the profiles, the computer system 210 may analyze each of the previously determined clusters. For example, the computer system 210 may perform a first analysis on the cluster 910. In this analysis, the computer system 210 may determine if the cluster 910 meets the requirements for a profile (922a). Here, the profile requirements include a requirement that the number of members in the cluster meet a member threshold (e.g., at least three members, at least ten members, at least one-hundred members, etc.). The computer system 210 may compare the number of members in the cluster 910 to the member threshold to determine that the member threshold is met, and, therefore, that the cluster 910 meets the profile requirements.

After determining that a cluster meets the profile requirements, the computer system 210 can analyze the characteristics of the cluster's members (924). For example, the computer system 210 may obtain the demographic and non-demographic corresponding to the members of the cluster 910. For example, the computer system 210 may generate a table 926 from subject data obtained from the database 212. After obtaining this information, the computer system 210 may use the information to identify shared or common attributes among the members (e.g., race, religion, ethnicity, sex, residence area, level of education, health conditions, prescriptions, past surgeries, etc.), calculate various statistics for the members (e.g., percentage of members that live in a rural area, percentage of members that have access to a vehicle, etc.), and determine likelihoods of particular outcomes (e.g., likelihood of completing a study, meeting a minimum compliance rate, providing sufficient data for monitoring program/session requirements, etc.) and behaviors (e.g., smartphone compliance, attending medical appointments, responding to reminders, etc.).

The computer system 210 may also identify trends or patterns in the obtained subject data. For example, the computer system 210 may recognize that those cluster 910 members that reside in rural areas tend to have similar and distinct smartphone compliance rates when compared to the cluster 910 members that reside in urban areas.

The computer system may proceed to generate profiles 960 from the cluster based on the analysis results (928). For example, the computer system 210 may use the shared or common attributes among the members to generate inclusion criteria for the profile. Similarly, the computer system 210 can include the calculated statistics and determined likelihoods in the profile(s) corresponding to the cluster 910.

In generating profile(s) from the cluster, the computer system may generate multiple from the cluster. For example, the computer system 210 may generate a first profile corresponding to a first subset of the cluster 910 members and a second profile corresponding to a second subset of the cluster 910 members. The subset of members may be determined by the computer system 210, e.g., based on identified trends or patterns in the subject data. Alternatively, the computer system 210 may determine the subsets based on input from the researcher 202. For example, the researcher 202 may indicate one or more attributes that must be shared among profile members. In more detail, the input from the researcher 202 may indicate that all profile members must share the same residence type. Based on this, the computer system 210 may split the cluster 910 members into a first subgroup corresponding to a first profile for members that reside in urban areas, and a second subgroup corresponding to a second profile for members that reside in rural areas.

If the computer system 210 generates multiple profiles from a single cluster, the computer system 210 may analyze each of the multiple profiles. The computer system 210 may do this to (i) determine if the profiles meet the profile requirements (e.g., computer system 210 may eliminate one of the multiple profiles if it does not meet the member threshold) and (ii) analyze the characteristics of the profile members. The computer system 210 may use the determined shared or common attributes among the profile members to generate inclusion criteria for the profile. Similarly, the computer system 210 may include the resulting statistics and likelihoods in the profiles.

In some cases, in generating the profiles, the computer system 210 uses the clustering model 908 to perform another round of clustering. For example, the computer system 210 may use the clustering model 908 to perform another round of clustering based on a different set of attributes (e.g., a set of attributes other than the key attributes 902) and/or based on the outcomes 904. The computer system 210 may perform this second round of clustering before analyzing the clusters, such that the resulting clusters are analyzed to determine if they meet the cluster requirements.

After generating the profiles 960, the computer system 210 may perform an analysis on each of the profiles. In performing the analysis, the computer system 210 may analyze the effect of study parameters on the profile members (962). For example, the computer system 210 may use the subject data 950 to calculate the effects of different parameters (e.g., monitoring program requirements such as required tests that must be performed by subjects, frequency of tests that must be performed subjects, office visits that subjects must attend, morning office visits, afternoon office visits, etc.) on the outcomes of subjects (e.g., retention rates, compliance rates, sufficient data quality rates, etc.). As an example, based on this analysis, the computer system 210 can determine that Profile 1 subjects are 35% more likely to comply (e.g., respond to) with SMS message over communications sent by email. Similarly, based on this analysis, the computer system 210 can determine that the retention rate of Profile 1 subjects is reduced by 8% when subjects are required to attend weekly office visits.

In some cases, the computer system 210 may analyze the communication behavior of the members of a profile (964). This analysis may be a separate analysis from analyzing the effect of study parameters, or may be part of that analysis. In analyzing the communication behavior, the computer system 210 may determine the preferred communication channel, communication frequency, communication time, communication content, communication vocabulary (e.g., word choice), or communication sentence structure for the profile's members. The computer system 210 may further determine the effects of particular communication attributes (e.g., channel, frequency, time sent, etc.) on the outcomes of the profile's members, e.g., when compared to other communication attributes. For example, the computer system 210 may determine that the Profile 1 subjects prefer communication by SMS text message over email. The computer system 210 may analyze the subject data 950 to determine that, when compared to email, the Profile 1 subjects are 35% more likely to respond to SMS text message.

The computer system 210 may update profiles over time using monitored data. For example, the computer system 210 may reanalyze the effects of study parameters on profile members using updated subject data. The computer system 210 may perform this analysis after a triggering event is detected, such as the passing of a predetermined amount of time, after a threshold amount of monitored data is collected, after a monitoring program ends, etc. Similarly, the computer system 210 may use the clustering model 908 to cluster subjects after a triggering event is detected (e.g., after a predetermined amount of time has passed, after a threshold amount of monitored data is collected, after a threshold number of new subjects have appeared/joined, etc.). The computer system 210 may proceed to analyze the clusters in the manner described above. Additionally or alternatively, the computer system 210 may avoid additional analysis of a cluster (e.g., to improve efficiency, reduce processor load, increase processing speed, etc.) if it is determined that the members for a particular cluster match the membership for a previously determined cluster.

The computer system 210 may reassign users to different profiles overtime. For example, the computer system 210 may reassign users using the clustering model 908 (e.g., if the output of the model indicates that the users now belong to a cluster not associated with their current profile(s)). As another example, the computer system 210 may automatically assign users to profiles and/or reassign users to different profiles if the corresponding subject data indicates that they (i) meet the inclusion criteria for one or more profiles that they are currently not assigned to, and/or (ii) they no longer meet the inclusion criteria for one or more profiles that they are currently assigned to (e.g., current age indicates that they are no longer in a particular age range required for a first profile).

FIG. 10 is a diagram that illustrates an example table 1000 that includes impact scores corresponding to different clusters 1002 and 1004. In more detail, the table 1000 indicates the impact that different study parameters and other elements are anticipated to have on different clusters of subjects 1002 and 1004.

The impact scores may indicate a quantified impact on one or more outcomes of a monitoring program, such as the retention of subjects, compliance of subjects (e.g., overall compliance, or compliance with particular requirements), data quality, etc. An impact on retention of subjects may indicate an anticipated increase or decrease to the retention rate for a group of subjects (e.g., based on stored historical data) that is attributable to one or more particular study parameters or other elements. As another example, an impact on retention may indicate an anticipated increase or decrease to the likelihood of a minimum number or percent of subjects being retained by the end of the monitoring program with respect to those subjects in the cluster or assigned to the corresponding profile.

Similarly, an impact on compliance of subjects may indicate an anticipated increase or decrease to the compliance rate for a group of subjects (e.g., based on stored historical data) that is attributable to one or more particular study parameters or other elements. As another example, an impact on compliance may indicate an anticipated increase or decrease to the likelihood of a minimum acceptable compliance rate for the monitoring program (e.g., for study data viability) with respect to those subjects in the cluster or assigned to the corresponding profile.

An impact on data quality may indicate an anticipated increase or decrease to the data quality (e.g., determined based on whether required or requested data was received, the accuracy of data received, the accuracy of the sensor(s) used to acquire the data, the time spent by a subject to produce the data (e.g., did subject spend the time to read and accurately respond to a set of questions), the quantity of data received, the response time of receiving data after requested, etc.). As another example, an impact on data quality may indicate an anticipated increase or decrease to the likelihood of a minimum acceptable data quality (e.g., for study data viability) being achieved (e.g., by the end of the study) with respect to those subjects in the cluster or assigned to the corresponding profile.

The impact scores may correspond to percentages. For example, a "−1" impact score on retention may indicate that it is anticipated that about 10% (e.g., a value rounded to the nearest decimal place and assigned a positive or negative indicator based on the effect of the parameter) of the cluster 1 subjects will not be retained during the study session (e.g., based on historical data of the subject data 950). The percentages may be particular to the effect. For example, a "+2" impact score on effect of data quality may indicate that it is anticipated that there will be about a 15% increase in data quality as a result of the inclusion of the particular study parameter or element in a monitoring program. In contrast, a "+2" effect on retention may indicate that it is anticipated that there will be about a 10% increase in retention as a result of the inclusion of the particular study parameter or element in a monitoring program.

The impact scores may correspond to percentage ranges. For example, a "−1" may indicate a decrease of 10% or less, a "−2" may indicate a decrease of 25% or less, and a "−3" may indicate a decrease of greater than 25%. The percentage ranges may be set by the researcher 202 or may be determined by the computer system 210. For example, an impact of "±1" may indicate small impact as defined by the researcher 202, an impact of "±2" may indicate medium impact as defined by the researcher 202, and an impact of "±3" may indicate a large impact as defined by the researcher 202. As previously mentioned, the impact scores may be particular to the effect such that percentage ranges differs between effect on compliance, effect on retention, and/or effect on data quality.

The computer system 210 may calculate the impact scores in the table 1000. For example, the computer system 210 may calculate the impact scores when analyzing the effects of study parameters on profile members (962) described above with respect to FIG. 9B.

Instead of impacts on clusters of subjects, the table 1000 may additionally or alternatively indicate the anticipated impact of different study parameters and other elements on different groups of subjects that correspond to particular profiles. For example, the impact information in the table 1000 corresponding to the cluster 1002 may actually correspond to Profile 1 of the profiles 960. Similarly, the impact information in the table 1000 corresponding to the cluster 1004 may actually correspond to Profile 2 of the profiles 960.

FIG. 11 is a diagram that illustrates an example profile 1102.

As shown, the profile 1102 includes a number of tables 1104a, 1104b, and 1104c that indicate the impact of different study parameters or other elements on the compliance, retention, and data quality. The profile 1102 includes a first table 1104a that indicates the anticipated impact of different study parameters and/or other elements on the compliance, retention, and data quality during a given monitoring program. For example, if a monitoring program requires weekly in-person visits, the computer system 210 can anticipate a small reduction to Profile 1 subject retention (e.g., compared to their typical retention rate), a moderate reduction to Profile 1 subject compliance (e.g., compared to their typical compliance rate), and a significant improvement to Profile 1 subject data quality (e.g., compared to their typical data quality provided).

The profile 1102 also includes a second table 1104b that indicates the anticipated impact of different communication types on the compliance, retention, and data quality during a given monitoring program, and a third table 1104c that indicates the anticipated impact of different communication frequencies on the compliance, retention, and data quality during a given monitoring program.

The information in the tables 1104a, 1104b, and 1104c can be determined by the computer system 210. For example, the computer system 210 may calculate the impact scores of the various study parameters and other elements when it analyzes the effect of study parameters on profile members (962) described in more detail above.

The profile 1102 also includes a fourth table 1106 that indicates the inclusion criteria to determine if subjects belong to a category of subjects represented by the profile 1102. The inclusion criteria may include both demographic and non-demographic information. For example, the inclusion criteria in the fourth table 1106 may require that all Profile 1 subjects be between the ages of 17-25 but also require them to being diagnosed with the medical condition, diabetes.

The profile 1102 also includes a fifth table 1108 that includes the determined behaviors and attributes for those subjects associated with the profile 1102. For example, the computer system 210 may determine these behaviors and/or attributes using the subject data 950. The behaviors may include, for example, an overall retention rate (e.g., study completion rate), an overall compliance rate, one or more particular compliance rates (e.g., corresponding to particular requirements of a monitoring program, such as a smart phone compliance rate if a monitoring program requires subjects to use a smart phone and/or collect sensor data with a smart phone), etc. The attributes may include a subset of attributes that are determined to be unusual (e.g., significantly deviate from subject averages). For example, it may be unusual that only 25% of Profile 1 subjects have access to a vehicle (e.g., where 55% of subjects on average have access to a vehicle).

Figure 12:
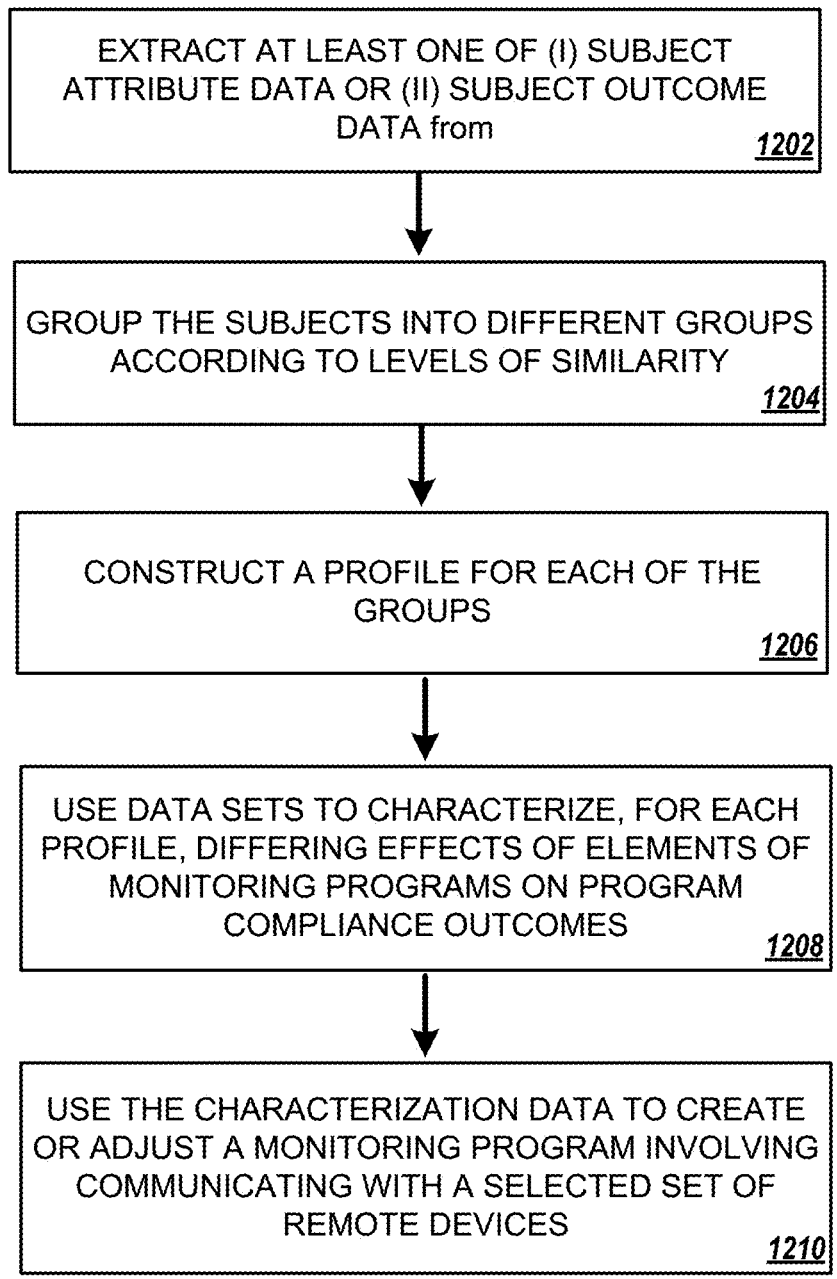
FIG. 12 is a flowchart diagram that illustrates an example process for customizing monitoring programs involving remote devices.

FIG. 12 is a flowchart diagram that illustrates an example process 1200 for customizing monitoring programs involving remote devices. The process 1200 may be performed by one or more computers, such as the computer system 210 shown in various figures including FIG. 2. The operations of the process 1200 may be distributed among one or more servers, one or more client devices, and/or other computing systems. For example, the operations of the process 1200 may be performed by a management and distribution system, such as the system 210, that includes one or more servers, one or more client devices, and/or other computing systems.

The process 1200 includes extracting at least one of (i) subject attribute data or (ii) subject outcome data (1202). Subjects may include at least one of devices or users. For example, a group of subjects selected for a monitoring program may include a diverse set of devices, such as a set of different smartphones. Prior to monitoring the subject devices, the computer system 210 may distribute software for the monitoring program to the subject devices. The subject devices may proceed to install the software. The software may specify the collection of data using sensors of the subject devices or devices connected to the subject devices (e.g., according to a set schedule or in response to receiving particular requests from the computer system 210), provide for a channel of communication between the computer system 210 and the subject devices (e.g., a secure channel of communication, such as an encrypted communication channel), a user interface through which one or more users of the subject devices can interact (e.g., to respond to messages or notifications sent to the subject devices from the computer system 210), etc.

Subjects may additionally or alternatively include a set of users. The users may include users that have participated in one or more previous monitoring programs or monitoring programs. In some cases, the users may include users that are new and have not participated in any monitoring programs or monitoring programs. Prior to monitoring the subjects, the computer system 210 may distribute software for the monitoring program to remote devices that the subject users have access to. The software may be installed in these remote devices and specify, for example, the collection of data of the subject users using sensors of the devices (e.g., according to a set schedule or in response to receiving particular requests from the computer system 210), provide for a channel of communication between the computer system 210 and the devices (e.g., a secure channel of communication, such as an encrypted communication channel), a user interface through which one or more of the subject users can interact with the devices (e.g., to respond to messages or notifications sent to the subject devices from the computer system 210), etc.

Where the subject is a device, extracting subject attribute data describing characteristics of a subject may include, for example, extracting an identifier assigned to the subject device, a manufacturer of the device, a model of the device, a software version running on the device, a CPU speed of the device, a memory size of the device, an indication of sensors installed in the device (e.g., fingerprint scanner, GPS unit, Lidar, accelerometer, etc.), etc. Similarly, where the subject is a user, extracting subject attribute data describing characteristics of the subjects may include, for example, extracting a name of the user, an identifier assigned to the user, demographic information of the user (e.g., age, race, ethnicity, gender, marital status, income, education, employment, residential state, etc.), non-demographic information of the user (e.g., past surgeries, medical conditions, genetics, lifestyle patterns, environmental factors, access to health care, etc.), an indication of what devices and/or sensors that user has access to, etc. As will be described in more detail below, the computer system 210 may use the attribute data of the subjects to categorize the subjects. As an example, with respect to FIG. 9A, the subject attribute data may be part of the subject data 950.

Extracting the subject outcome data can include extracting subject outcome data including results from monitoring programs that involved the subjects. The results may include, for example, compliance data for the subjects, retention data for the subjects, and data quality data for the subjects. As an example, with respect to FIG. 9A, the subject outcome data may include the compliance data 932, the retention data 934, and the data quality data 936. The computer system 210 may determine the subject outcome data using, for example, monitored results of subjects during the past monitoring programs. The monitored results may be stored, at least initially, as part of the subject data 950. The computer system 210 may extract the relevant information from the subject data 950, such as response times, response content, sensor data, etc., to determine the subject outcome data.

The compliance data may include, for example, compliance rates such as an overall compliance rate for each of the subjects or for each category of subjects with respect to monitoring program requirements of past monitoring programs and/or monitoring programs that the subjects have participated in. However, the compliance data may also or alternatively include compliance rates for particular areas, such as the subjects' compliance with device usage (e.g., smartphone compliance, blood pressure device compliance, heart rate monitor compliance, etc.), with responsiveness (e.g., does the subject on average respond within thirty minutes of receiving a message or notification, within one hour of receiving a message or notification, within one day of receiving a message or notification, etc.; does the subject consistently provide required test results; does the subject consistently perform required tasks; etc.), with office visits (e.g., medical visits scheduled as part of the monitoring program), etc. In determining a compliance rate for a subject, the computer system 210 may average all of the relevant compliance rates (e.g., overall compliance rate, or subject-specific compliance rate) for the subject across their past monitoring programs.

The retention data may include, for example, a retention rate for each of the subject or for each category of subjects over their past monitoring programs sessions. As an example, the computer system 210 may determine a retention rate for each subject using the number of monitoring programs the subject has previously participated in, and the number of monitoring program the subject successfully completed. As an example, the computer system 210 may determine that a subject was not retained in (e.g., did not complete) a particular monitoring program if they stopped responding, if their compliance rate(s) fell below threshold compliance rate(s), if they failed to perform one or more tasks (e.g., perform tests, upload tests results, attend medical office visits, fill out surveys, meet dietary restrictions, perform required exercises, etc.), or if they indicated that they were withdrawing from the monitoring program. The computer system 210 may keep track of the subject retention rates as part of the retention data 934. The computer system 210 may optionally determine and track retention rates of subjects in particular monitoring programs or types of monitoring programs. For example, if a particular subject has participated in three monitoring programs of a monitoring program (e.g., potentially different versions of the monitoring program including customized versions), the computer system 210 may determine and track a retention rate for the subject with respect to this particular monitoring program. The computer system 210 may similarly track the subject's compliance data and data quality data that correspond to this monitoring program.

The data quality data may include, for example, an indication of data quality for each of the subjects or for different categories of subjects. Additionally or alternatively, the data quality data may include data quality rates that indicate, for each of the subjects or for each category of subjects, the percent of data that meets minimum data quality requirements. The computer system 210 may use various factors to determine data quality or which may be used to set minimum data quality requirements. These factors can include response times (e.g., where relatively quick response times and/or relatively long response times may correspond to low data quality), sensor data accuracy (e.g., based on the sensor and/or device used to collect the sensor data), sensor data consistency (e.g., based on the sensor and/or device used to collect the sensor data, and/or the other sensor data values collected using the same sensor and/or device or the same sensor type and/or device type), response content (e.g., text input that is relatively short or that is below a threshold word count may correspond to low data quality; text input that is relatively long or that is above a threshold word count may correspond to high data quality; etc.), etc. The computer system 210 may use one or more algorithms to determine a data quality score or a data quality rate, e.g., for a particular monitoring program and/or across all monitoring programs. As an example, the computer system 210 may calculate a data quality score for each monitoring program of each subject or each category of subjects, and average the data quality scores to obtain an overall data quality score for the subject or the group of subjects.

Extracting at least one of the subject attribute data or the subject outcome data can include extracting at least one of the subject attribute data or the subject outcome data from a database. The database may store data sets for multiple different subjects, such as data sets for different devices and/or data sets for different users. The data sets can include attribute data for the different subjects. For example, where the subject is a device, a corresponding data set may include an identifier assigned to the device, make of the device, a model of the device, a software version running on the device, a CPU speed of the device, a memory size of the device, an indication of sensors installed on the device (e.g., fingerprint scanner, GPS unit, Lidar, accelerometer, etc.), etc. The computer system 210 may extract all or a portion of this information from the data sets. Similarly, where the subject is a user, a corresponding data set may include the name of the user, an identifier assigned to the user, demographic information of the user (e.g., age, race, ethnicity, gender, marital status, income, education, employment, residential state, etc.), non-demographic information of the user (e.g., past surgeries, medical conditions, genetics, lifestyle patterns, environmental factors, access to health care, etc.), an indication of what devices and/or sensors that user has access to, etc. The computer system 210 may extract all or a portion of this information from the data sets.

The data sets may include results of monitoring performed for the subjects using one or more remote computing devices. For example, the data sets may include an indication of messages sent to the subjects, responses received from the subjects, sensor data received from the subjects, etc. The data sets may additionally include information determined from received data and/or responses, such as subject outcomes. For example, the data sets may include response times, response frequency, message compliance or compliance rates for the user, an indication of user retention or retention rates for the user, indications of data quality, etc.

Extracting at least one of (i) the subject attribute data or (ii) the subject outcome data can include using metadata to identify the data in one or more data sets that should be extracted. For example, the computer system 210 may use an identifier or data type to extract attribute data from the database 212. Similarly, the computer system 210 may use a different identifier or data type to extract outcome data from the databased 212.

Extracting at least one of (i) the subject attribute data or (ii) the subject outcome data can include parsing through stored, monitored subject data to identify at least one of the subject attribute data or the subject outcome data. For example, the computer system 210 may store the monitored data in the database 212. In response to receiving instructions to start a new monitoring program, receiving instructions to update the profiles or groups, determining that monitoring data has been collected on one or more new subjects, and/or detecting a different event, the computer system 210 may parse through the data sets in the database 212 to identify the subject attribute data and/or the subject outcome data.

The process 1200 includes grouping the subjects into different groups according to levels of similarity (1204). The levels of similarity can be levels of similarity among the attributes of the subjects and/or the monitored outcomes for the subjects. As an example, with respect to FIG. 9A, the computer system 210 may determine or receive an indication of the key attributes 902 and the outcomes 904. The key attributes 902 may include a subset of particular subject attributes extracted by the computer system 210 from the subject data 950. Similarly, the outcomes 904 may include a subset of particular monitored outcomes for the subjects extracted by the computer system 210 from the monitoring outcome data 930. The computer system 210 may proceed to use at least one of the key attributes 902 and the outcomes 904 to group the subjects into different groups.

In grouping the subjects, the computer system 210 may group subjects based on the extracted attributes, the extracted outcomes, or a combination of the attributes and outcomes. As an example, the computer system 210 may use the extracted attributes to identify those subjects that share the same or a similar subset of subject attributes. In grouping the subjects, the computer system may additionally or alternatively identify those subjects that have demonstrated the same or similar outcomes. For example, the computer system 210 may identify those subjects that tend to have similar overall compliance rates (e.g., compliance rate are within a range of multiple ranges of compliance rates), similar device compliance rates, similar retention rates, produce similar data quality, etc. The computer system 210 may then further organize the subjects by those that have similar medical conditions or that share other attributes to identify multiple groups of subjects. For example, the computer system 210 may identify a first group of subjects that have diabetes and a compliance rate above 60%, a second group of subjects that have diabetes and a compliance rate below 60%, a third group of subjects that do not have diabetes and a compliance rate above 60%, and a fourth group of subjects that do not have diabetes and have a compliance rate below 60%.

In grouping the subjects, the computer system 210 may use one or more static or machine learning algorithms. For example, in some implementations, grouping the subjects into different groups according to levels of similarity includes grouping the subjects into different groups using one or more machine learning models. The one or more machine learning models can include a clustering machine learning model. For example, the computer system 210 can provide the key attributes 902 and/or the outcomes 904 to the clustering model 908 as input. The clustering model 908 may proceed to cluster the subjects (e.g., previous monitoring program participants) based on the key attributes 902 and/or the outcomes 904 into multiple groups of subjects. The clustering model 908 can cluster the subjects according to a subset of subject attributes and/or particular outcomes (e.g., desirable outcomes, undesirable outcomes, or certain types of outcomes, such as compliance rates, retention rates, or data quality).

Where a clustering machine learning model is used to group the subjects, the clustering model may be one of following models: a density clustering model, a connectivity clustering model, a centroid clustering model, distribution clustering model, a subspace clustering model, a group clustering model, a graph clustering model, signed-based clustering model, or a neural network model. In some cases, multiple machine learning models are used. As an example, two or more clustering models may be used to group the subjects.

In some implementations, the machine learning model(s) used for grouping subjects are trained (e.g., supervised) using input data sets and expected outputs for those data sets. The data sets may include, for example, subject attribute data and/or subject outcome data. The expected outputs for those data sets may include an indicator for each of the subjects that specifies which group that the subject belongs to. For example, the expected outputs may include values corresponding to subjects that fall within a first range of values corresponding to a first group of subjects, values corresponding to other subjects that fall within a second range of values corresponding to a second group of subjects, etc.

In some implementations, the machine learning model(s) used for grouping subjects are not-trained (e.g., unsupervised). For example, the machine learning model(s) may include an unsupervised k-means clustering algorithm that does not require ground truth in order to group the data points of the input data into distinct subgroups.

The output of the machine learning model may indicate a group that each of the subjects belong to. For example, the output of the machine learning model may include a value for a first subject that falls within a first range of values corresponding to a first group of subjects, and a second value for a second subject that falls within a second range of values corresponding to a second group of subjects. The output of the machine learning model may indicate one or more value ranges or thresholds that define the different groups. As another example, the output of the machine learning model may include a value for each subject, where the value corresponds to a particular group that the subject is placed in. In more detail, the output value may indicate the centroid that each subject was assigned to during grouping (e.g., clustering).

In some implementations, additional input is provided to the machine learning model. For example, with respect to FIG. 9A, the computer system 210 may provide cluster parameters 906 to the clustering model 908. The cluster parameters 906 may define a number of clusters, a minimum or maximum cluster size, a number of clustering iterations, a centroid change threshold, etc.

In some implementations, in grouping the subjects, the machine learning model performs multiple grouping iterations. For example, the machine learning model may be a k-means clustering algorithm that performs multiple clustering iterations until there is no change to the centroids or until the change to the centroids is below a threshold value.

The process 1200 includes constructing a profile for each of the groups (1206). A profile may represent a category of subjects. A profile may be constructed using one of the different groups of subjects. The resulting profile may represent a category of subjects that corresponds to one of the different groups of subjects. For example, after grouping the subjects into the different groups, the computer system 210 may construct corresponding profiles for the different groups. Each profile may be constructed using subject data from one of the different groups of subjects.

In some implementations, a profiles is constructed using two or more groups of subjects of the different groups. For example, the computer system 210 may combine multiple of the different groups of subjects, and used the combined groups to construct the profile such that the profile corresponds to multiple groups of the different groups of subjects.

Similarly, in some implementations, a profile is constructed using only a portion of one of the different groups. For example, the computer system 210 may split a group of subjects into two or more subgroups (e.g., based on input from a researcher or an administrator). The computer system 210 may proceed to use one of these subgroups to construct the profile such that the profile corresponds to the subgroup but does not correspond to all subjects in the larger group of subjects.

The computer system 210 may use subject data corresponding to one or more of the different groups to construct each of the profiles. The computer system 210 may use subject attribute data (e.g., not necessarily limited to the extracted subject attribute data) and subject outcome data (e.g., not necessarily limited to the extracted subject outcome data) to construct the profiles for each of the groups. In more detail, in constructing the profiles, the computer system 210 may use the subject attribute data and/or the subject outcome data to define inclusion criteria for each category of subjects corresponding to one of the different groups. For example, for a particular group of subjects, the computer system 210 may determine based on the attribute data that each subject in the group is over the age of 37, lives in an urban environment, and has been diagnosed with high blood pressure. Based on this, the computer system 210 may, in constructing a profile to represent a category of subjects corresponding to this group, set inclusion criteria for the group to require that subjects be above the age of 35, reside in an urban environment, and be diagnosed with high blood pressure or are observed to have at least 7/10 indicators for high blood pressure (e.g., based on a preliminary test, entry survey, etc.).

The set criteria may include a broader range of values than observed values, e.g., to make the group more inclusive. Alternatively, the set criteria may include a range of values that is the same range as the observed values. Similarly, the set criteria may include a range of values that is less than the observed values, e.g., to make the group more exclusive and/or to account for outliers in the group. Finally, the set criteria may include a combination of different range of values that are greater than, less than, and/or the same as the observed values.

In some implementations, the computer system 210 filters the different groups to identify a subset of groups in the different groups that meet criteria for profile construction. For example, in order to be used for profile construction, each of the different groups may need to include a minimum number of subjects. The groups may also need to meet other profile criteria, such as minimum diversity requirements. The profile criteria may be set by a researcher or an administrator. After determining the subset of groups in the different groups that meet the criteria for profile construction, the computer system 210 may use each of the groups in the subset of groups to construct corresponding profiles.

In some implementations, the inclusion criteria is used to determine which subjects correspond to which profiles. For example, although the subjects were previously assigned to groups, the inclusion criteria may differ from the observed values of the group. Accordingly, the computer system 210 may compare the inclusion criteria against the attribute data and/or outcome data of the subjects to determine or verify which subjects correspond to which profiles. The attribute data and/or outcome data of the subjects used by the computer system 210 used to determine or verify which subjects correspond to which profiles may include attribute data and/or outcome data of active subjects (e.g., subjects that have participated in a monitoring program or monitoring program over the last year, have participated in a monitoring program or monitoring program over the last two years, are listed as active, etc.). In contrast, the attribute data and/or outcome data used to construct the profiles may include attribute data and/or outcome data of all subjects in a subject pool (e.g., for which monitored data has been collected), including active and inactive subjects.

In some implementations, information is added to the profiles that is not used as inclusion criteria. For example, the computer system 210 may include subject attribute data and/or attribute data statistics in the profile. In more detail, the computer system 210 may include the number or percent of subjects in the profile that have a particular attribute (e.g., percent of subjects that have high blood pressure, that are of a first ethnicity, that have a college education, etc.), and/or that demonstrate the same or similar outcomes (e.g., that have a retention rate greater than 75%, that have a retention rate between 50% and 75%, and that have a retention rate less than 50%). The computer system 210 may also determine and include in the profile an indication of the number of subjects in the category of subjects, or a percent of the total or active subject pool that the category of subjects represents. For example, the computer system 210 may compare the number of subjects in a category of subjects represented by a profile to the total number of subjects or to a total number of active subjects to determine that the category of subjects represents 4.2% of the subject pool or of the active subject pool.

The process 1200 includes using data sets to characterize, for each profile, differing effects of elements of monitoring programs on program compliance outcomes (1208). The data sets may be stored in a database by, for example, the computer system 210. The data sets may include monitored subject data over multiple monitoring programs. In determining the different effects of elements of monitoring programs, such as tasks (e.g., tests, appointments, exercises, etc.), message content, message frequency, message time, task or event schedule, etc., on subjects' outcomes, the computer system 210 may use the program data 940 to identify various monitoring program elements and use the monitoring outcome data 930 to identify the effects of those program elements on the different categories of subjects. In more detail, for a particular monitoring program element, the computer system 210 may determine which subjects have encountered that element before and in which past monitoring program(s), and use a portion of the outcome data 930 corresponding to those past monitoring programs and subjects to determine what effect on subject outcomes, if any, the particular element had on those subjects.

For example, if three subjects assigned to a first profile are determined to have encountered the requirement for weekly office visits in one or more prior monitoring programs, the computer system 210 may obtain a portion of the monitoring outcome data 930 corresponding to those monitoring programs for the first profile subjects. The computer system 210 may proceed to use the portion of the outcome data 930 and the corresponding subject data 950 to determine (e.g., to see if there was a deviation or a statistically significant deviation from the first profile subject's typical behavior) if the weekly office visits had a negative, positive, or neutral effect on compliance rates, retention rates, and/or data quality for the first profile subjects, and the magnitude of that effect on those subject outcomes. The computer system 210 may proceed to include the effect (e.g., direction and magnitude) as part of the profile As discussed above, the effect of a monitoring program element on subject outcomes may be in the form of calculated impact scores as shown and described above with respect to FIGS. 10-11. An impact score may be an absolute or relative score. This score may represent a percentage or a percentage range. The percentage or percentage range that the impact score represents may depend on the magnitude of the impact score and/or on the corresponding outcome (e.g., larger percent range for compliance rates than, for example, retention rates which are likely to fluctuate to a lesser degree than compliance rates).

In some implementations, the computer system 210 analyzes the communication behavior of the subjects of a profile. This analysis may be a separate analysis from analyzing the effect of study parameters, or may be part of that analysis. In analyzing the communication behavior, the computer system 210 may determine the preferred communication channel, communication frequency, communication time, communication content, communication vocabulary (e.g., word choice), or communication sentence structure for the profile's subjects. The computer system 210 may further determine the effects of particular communication attributes (e.g., channel, frequency, time sent, etc.) on the outcomes of the profile's subjects, e.g., when compared to other communication attributes. For example, the computer system 210 may determine that the Profile 1 subjects prefer communication by SMS text message over email. The computer system 210 may analyze the subject data 950 to determine that, when compared to email, the Profile 1 subjects are 35% more likely to respond to SMS text message.

The computer system 210 may update profiles over time using monitored data. For example, the computer system 210 may reanalyze the effects of study parameters on profile subjects using updated subject data obtained in one or more ongoing monitoring programs or results from recently completed monitoring programs. The computer system 210 may perform this analysis after a triggering event is detected, such as the passing of a predetermined amount of time, after a threshold amount of monitored data is collected, after a monitoring program ends, etc. Similarly, the computer system 210 may use the clustering model 908 to cluster subjects after a triggering event is detected (e.g., after a predetermined amount of time has passed, after a threshold amount of monitored data is collected, after a threshold number of new subjects have appeared/joined, etc.). The computer system 210 may proceed to analyze the clusters in the manner described above. Additionally or alternatively, the computer system 210 may avoid additional analysis of a cluster (e.g., to improve efficiency, reduce processor load, increase processing speed, etc.) if it is determined that the members for a particular cluster match the membership for a previously determined cluster.

In some implementations, the computer system 210 analyzes the effects of each element of every monitoring program that has been run in a sessions. Because various monitoring programs and monitoring programs may include all or a portion of the same elements, the computer system 210 does not necessarily need to analyze each and every element of each monitoring program (or version of monitoring program) separately.

In some implementations, the computer system 210 analyzes the effects of only a subset of elements of the monitoring programs that have been run in one or more monitoring programs. For example, the computer system 210 may choose to analyze the effects of only those elements for which sufficient monitored data has been collected on. In more detail, the computer system 210 may choose to only analyze the effects of those elements that have been in at least three monitoring programs, for which there have been at least six months of data collected for, for which at least twenty unique subjects experienced, etc.

In analyzing the effects of the monitoring program elements on subject outcomes, the computer system 210 may extract, for each profile, the relevant information from the database 212, and analyze the extracted data together. That is, instead of analyzing the effects on a subject by subject basis, the computer system 210 may collect, for each of the profiles, all of the relevant subject data and analyze the collected data as a whole. This has the benefit if reducing computational burden by reducing the number of processes the CPU(s) of the computer system 210 need to perform, and further increases efficiency by speeding up the processing time.

After analyzing the effects of the monitoring program elements on subject outcomes, the computer system 210 may update the profiles to include the corresponding analysis results. For example, if it is determined that subjects in a category of subjects represented by Profile 1 are twice as likely to not complete a study if it requires blood to be drawn daily, the computer system 210 may update Profile 1 to include an impact score of −5 (e.g., to represent −50% effect on retention rate) for retention for the monitoring program element, "blood drawn" with a frequency of "daily."

The computer system 210 may organize the different effects of different elements into different categories or hierarchies within the profiles. For example, with respect to FIG. 11, the computer system 210 may organize the data in the table 1104b and the table 1104c under a communication category.

The process 1200 includes using the characterization data to create or adjust a monitoring program involving communicating with a selected set of remote devices (1210). The computer system 210 may identify the profiles that are present among a monitoring group selected for a monitoring program, compare the elements of the selected monitoring program to the element effect information in the profiles, and, based on the comparison, determine one or more adjustments to the monitoring program for the different categories of subjects. The adjustments made by the computer system 210 may include removing or modifying an element of a monitoring program (e.g., reduce number of tests that user must complete if this is determined to significantly lower retention rates), adjusting communication attributes (e.g., communication channel, frequency, time, content, sentence structure, etc.), or adding an element (e.g., account for subjects not having access to a device, account for subject not having access to transportation by providing transportation credit, etc.). For example, if an element of a monitoring program is anticipated to reduce compliance with subjects assigned to a second profile, the computer system 210 may adjust that element using information in the second profile to mitigate the anticipated reduced compliance.

The computer system 210 can automatically make the adjustments for the one or more groups of subjects enrolled in the monitoring program. For example, if the computer system 210 determines that a particular adjustment should account for an anticipated lower retention rate among Profile 1 subject due to an element of the monitoring program, the computer system 210 may generate a new version of the monitoring program and distribute this new version to only remote devices corresponding to the Profile 1 subjects.

The computer system 210 can generate a recommendation to make one or more adjustments and transmit the recommendation to a researcher or an administrator. The recommendation may include multiple recommended adjustments to the monitoring program, such as one or more recommended adjustments for each unique profile present among the selected subjects for the monitoring program. The recommendation may include the most recommended adjustments, such as the five or ten most recommended adjustments. Similarly, the computer system 210 may generate a recommendation that includes at least two recommendations (e.g., two most recommended adjustments) for each of the profiles present among the selected subjects. The computer system 210 may rank the recommended adjustments, e.g., based on predicted effect at achieving a successful monitoring program (e.g., obtaining viable data). For example, the adjustments predicted by the computer system 210 to have the largest remedial effect (e.g., for expected negative outcomes, such as low retention, low compliance, low data quality, etc.) may be ranked above adjustments that are predicted to have less significant effects. Similarly, adjustments that are predicted by the computer system 210 to have a higher likelihood of producing a remedial effect may be ranked by the computer system 210 above adjustments whose beneficial effect is more speculative.

The computer system 210 may wait for a response from the researcher or administrator before proceeding with the monitoring program. The response may include a confirmation (e.g., if it included one recommended adjustment, or one recommended adjustment for each category of subjects represented in the monitoring group). Alternatively, the response may include one or more selections, e.g., that correspond to adjustments selected by the researcher or administrator. The computer system 210 may use the confirmation or response to generate one or more additional versions of the monitoring program, each specific to a particular category of subjects (e.g., corresponding to a particular profile).

In some implementations, if the computer system 210 does not receive a response within a predetermined amount of time, the computer system may implement one or more recommended adjustments itself. For example, for each profile, the computer system 210 may generate a version of the monitoring program where the most recommended adjustment has been made (e.g., if there are recommended adjustments). If there were no recommended adjustments for a particular category of subjects, the computer system 210 may send the default monitoring program to the remote devices of those subjects.

Using the characterization data to create or adjust the monitoring program may also include using the characterization data to adjust the enrolled subjects. For example, if the characterization data indicates that a subset of the enrolled subjects are predicted to have insufficient compliance rates through a session due to the monitoring program requirements (e.g., if the program requirements cannot be adjusted or cannot be adjusted to the extent needed), the computer system 210 may replace the subset of the enrolled subjects with a different set of subjects who are anticipated to produce outcomes that are sufficient with the monitoring program's requirements. The computing system 210 may automatically enroll the other subjects, or may send invitations to the other subjects to enroll.

As another example, the computer system 210 may use the profiles to determine that additional subjects need to be added to the monitoring group due to one or more profiles not being represented. That is, the profiles may be used as a diversity metric. The computer system 210 may, for example, determine that one or more additional subjects should be enrolled or invited to the monitoring program based on the size of the category of subjects that is not represented. For example, the computer system 210 may automatically enroll or generate a recommendation for enrollment of a subject that is in a category of subjects (e.g., corresponding to a particular profile) that represents more than 3%, 5%, or 7% of the subject pool and is not represented in the monitoring group for the current monitoring program. Similarly, certain categories of subjects may be marked as necessary for monitoring program representation for other reasons, such as for meeting diversity criteria required for the monitoring program and/or for obtaining viable results.

Communication with a selected set of remote devices may take place over a communication network such as a wireless internet network (e.g., Wi-Fi), a cellular network (e.g., 5G network), etc. The computer system 210 may form a secure communication channel, such as an encrypted channel between the remote devices and the computer system 210 to protect the transfer of sensitive data such as medical records, medical information, health data, photographs, etc. between the remote devices and the computer system 210.

Prior to starting a monitoring program, the computer system 210 may distribute software to the remote devices. Alternatively, the remote devices may access the software through a website or mobile application. However, the accessed software may be customized to the specific remote device based on it or its user corresponding to a particular subject profile. The software may provide for the configuration of a secure communication channel between a remote device and the computer system 210, and/or for a user interface through which a subject can interact to, for example, respond to messages, provide feedback, provide text input, submit photographs, submit test results, etc. using touch input, keyboard input, voice input, or a combination of different input types.

As previously mentioned, the computer system 210 may customize the monitoring program for different categories of subjects corresponding to different profiles. In doing this, the computer system 210 may generate and distribute different software versions. The different software versions may provide for different and possibly unique interactions between devices of subjects corresponding to a first profile, and devices of subjects corresponding to a second profile. For example, the two different software versions corresponding to the same base monitoring program may provide for a different frequency of data collection, using a different sensor to collect the data, a different channel of communication to send request or message, etc.

In some implementations, the remote devices are the subjects for a monitoring program.

Figure 13:
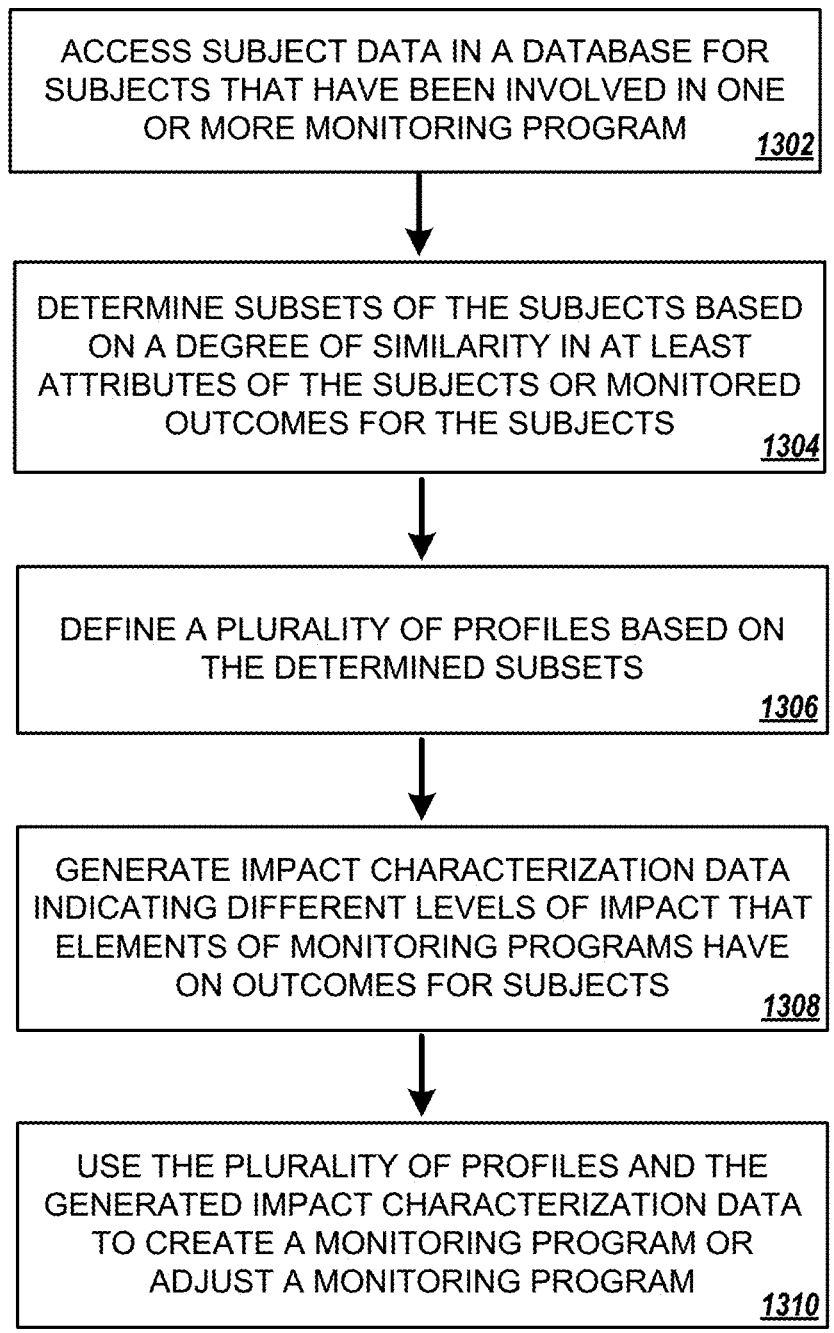
FIG. 13 is a flowchart diagram that illustrates an example process for customizing monitoring programs involving remote devices.

FIG. 13 is a flowchart diagram that illustrates an example process 1200 for assessing and selecting technologies. The process 1300 may be performed by one or more computers, such as the computer system 210 shown in various figures including FIG. 2. The operations of the process 1300 may be distributed among one or more servers, one or more client devices, and/or other computing systems. For example, the operations of the process 1300 may be performed by a management and distribution system, such as the system 210, that includes one or more servers, one or more client devices, and/or other computing systems.

The process 1300 includes accessing subject data in a database for subjects that have been involved in one or more monitoring program (1302). For example, with respect to FIG. 9A, the computer system 210 may access the subject data 950 from the database 212. The subject data 950 may include attributes for subjects in a subject pool that have participated in one or more previous monitoring programs, and/or are currently enrolled in an ongoing monitoring program. The subject data 950 may also include other data, such as historical data, including response times, response content, compliance data, uploaded data, indication of past and/or present monitoring programs that subject has participated in, etc.

The process 1300 includes determining subsets of the subjects based on a degree of similarity in at least attributes of the subjects or monitored outcomes for the subjects (1304). For example, with respect to FIG. 9A, the computer system 210 may use key attributes 902 (e.g., a subset of particular subject attributes selected by the computer system 210 or a researcher) and/or outcomes 904 (e.g., one or more particular outcomes selected by the computer system 210 or a researcher). The computer system 210 may group the subjects using the key attributes 902 and/or the outcomes 904. As an example, the computer system 210 may provide the key attributes 902, the outcomes 904, and subject data for a subject pool to the clustering model 908 as input. The clustering model 908 may proceed to organize the subjects in the subject pool based on the key attributes 902 if that is provided as input, based on the particular outcomes (e.g., data quality, overall compliance rates, compliance rates in a particular category, retention rates, etc.) in the outcomes 904 if that is provided as input the clustering model 908, or based on the key attributes 902 and the outcomes 904 if both are provided as input to the clustering model 908.

The output of the clustering model 908 may include an indication of which cluster each of the subjects in the subject pool belongs to. For example, the output of the clustering model 908 may be an indication of which centroid each subject was assigned to.

The process 1300 includes defining a plurality of profiles based on the determined subsets (1306). For example, the computer system 210 may use each of the groups of the subjects (e.g., the clusters) to a profile that represents a category of subjects. In generating the profiles, the computer system 210 may retrieve information from the subjects in the groups and use the information to define inclusion criteria for the different profiles. The inclusion criteria may be defined by the computer system 210 such that it is mutually exclusive with respect to the inclusion criteria of the other profiles, such that the a subject cannot be assigned to multiple profiles. However, in some cases, a subject may be assigned to multiple profiles.

The process 1300 includes generating impact characterization data indicating different levels of impact that elements of monitoring programs have on outcomes for subjects (1308). The computer system 210 may identify the profiles that are present among a monitoring group selected for a monitoring program, compare the elements of the selected monitoring program to the element effect information in the profiles, and, based on the comparison, determine one or more adjustments to the monitoring program for the different categories of subjects. The adjustments made by the computer system 210 may include removing or modifying an element of a monitoring program (e.g., reduce number of tests that user must complete if this is determined to significantly lower retention rates), adjusting communication attributes (e.g., communication channel, frequency, time, content, sentence structure, etc.), or adding an element (e.g., account for subjects not having access to a device, account for subject not having access to transportation by providing transportation credit, etc.). For example, if an element of a monitoring program is anticipated to reduce compliance with subjects assigned to a second profile, the computer system 210 may adjust that element using information in the second profile to mitigate the anticipated reduced compliance.

The process 1300 includes using the plurality of profiles and the generated impact characterization data to create a monitoring program or adjust a monitoring program (1310). For example, the computer system 210 may customize a monitoring program selected by a researcher to improve the likelihood of viable data being produced as a result of the monitoring program, and/or other goals of the monitoring program being obtained (e.g., such as diversity goals to increase the applicability of the results of the monitoring program). The computer system 210 may create and/or customize a monitoring program for each profile among the enrolled monitoring program subjects. Accordingly, the computer system 210 may first identify what profiles are present among the monitoring group, prior to (i) adjusting the monitoring group and/or (ii) the elements of the monitoring program.

Figure 14:
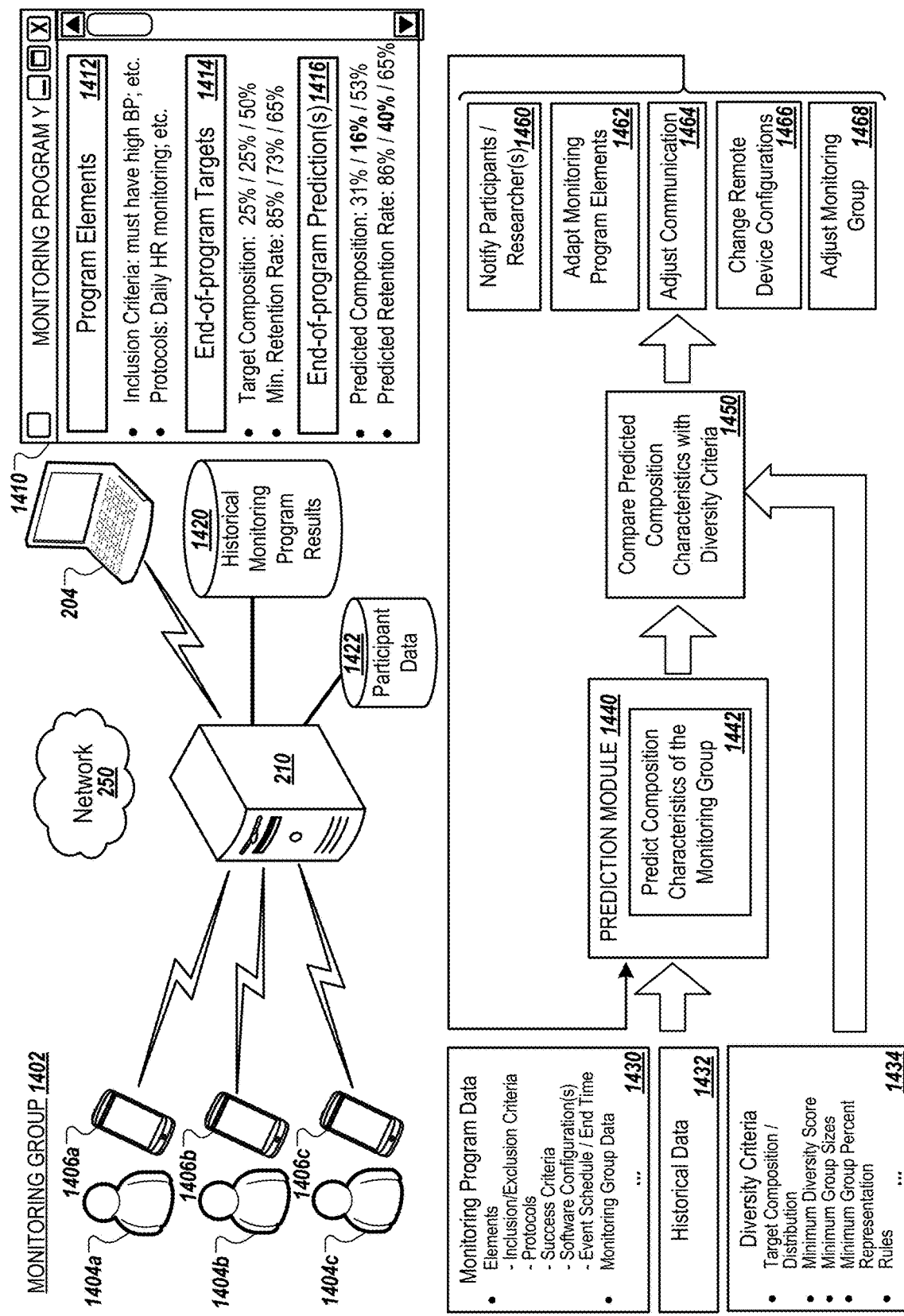
FIG. 14 is a diagram that illustrates an example system for predicting diversity for monitoring programs.

FIG. 14 is a diagram that illustrates one or more components of the system 200 and a process for predicting group diversity for monitoring programs. The computer system 210 can use a prediction module 1440 to make various predictions for a monitoring group 1402, including predictions of the group 1402's composition and/or diversity in the future. In making these predictions, the computer system 210 can obtain and use information that includes characteristics of the monitoring group 1402 and of the particular monitoring program that the monitoring group 1402 is participating in. The computer system 210 may also use other information to make these predictions, including historical data collected during past monitoring programs from other monitoring groups. The computer system 210 can provide this information as input to the prediction module 1440, and, in response, receive output that includes or indicates predicted characteristics of the monitoring group 1402. The system 210 may compare the characteristics to corresponding criteria to determine if the monitoring group 1402 is predicted to have sufficient diversity at a future time, such as a predetermined future milestone or a known or anticipated end of the monitoring program.

The predictions can help the computer system 210 determine whether the monitoring program will be successfully completed and/or, more specifically, whether the monitoring program will produce viable results. Where the predictions indicate that the monitoring group 1402 will lack sufficient diversity for the monitoring program to produce viable results (e.g., results that are sufficiently applicable to a target population, results that have a sufficiently low probability of producing false-negatives, results that have the ability to meet a required level of statistical significance, etc.), the computer system 210 can determine one or more actions to improve the anticipated diversity of the monitoring group 1402. As a result of performing these actions, the computer system 210 can significantly improve the likelihood of the monitoring program producing viable results, and, therefore, improve the likelihood of successfully completing the monitoring program. These actions have the added benefit of reducing the likelihood of the computer system 210 needing to repeat or extend the length of the monitoring program, and, therefore, reduce the amount of resources spent on or allocated to managing the monitoring program and producing viable results.

As shown, the monitoring group 1402 may include a set of participants 1404a, 1404b, and 1404c and corresponding participant devices 1406a, 1406b, and 1406c. The participant devices 1406a-1406c can communicate with the computer system 210 over the network 250. The computer system 210 may send software packets to each of the participant devices 1406a-1406c. The software packet sent to each of the devices 1406a-1406c can be based on the particular monitoring program that the monitoring group 1402 is participating in, on the attributes of the corresponding participant, and/or on the participant group(s) that the corresponding participant belongs to.

For example, based on a researcher using the client device 204 to initialize a "Monitoring Program Y", the computer system 210 may identify a default software configuration for the Monitoring Program Y, generate a corresponding data packet used to install the software configuration on one or more remote computing devices, and distribute the data packet to the devices 1406a-1406c. In this example, each of the devices 1406a-1406c may receive a data packet from the computer system 210 that provides for installing software with the same configuration as the other devices in the monitoring group 1402.

As another example, the computer system 210 may use additional information to customize the default software configuration and/or to select a different version of the software. In more detail, the computer system 210 may use participant data stored in the participant database 1422 and/or the historical monitoring program data stored in the monitoring program database 1420 to identify changes to the default software configuration and/or versions of the software configuration that have been shown per the historical data to improve the compliance, retention, and/or data quality of participants having particular attributes or belonging to particular participant groups. The computer system 210 may proceed to distribute customized software configurations and/or select versions of the software to the devices 1406a-1406c based on the attributes of the participants 1404a-1404c and/or the participant groups that the participants 1404a-1404c belong to. In this example, each of the devices 1406a-1406c may receive a data packet from the computer system 210 that provides for installing software with a different configuration compared to that installed on the other devices in the monitoring group 1402.

Although the monitoring group 1402 is depicted having the three participants 1404a-1404c and participant devices 1406a-1406c, the monitoring group 1402 may include additional participants and corresponding participant devices that are not shown. For example, the monitoring group 1402 may include hundreds or thousands of participants and/or participant devices.

In some implementations, the monitoring group 1402 includes only the participant devices 1406a-1406c. Alternatively, in some implementations, the monitoring group 1402 includes only the participants 1404a-1404c. In this example, the computer system 210 can communicate with the participants 1404a-1404c through one or more remote devices, such as a remote computer that the participants 1404a-1404c can use to log into corresponding user profiles.

The monitoring program database 1420 can store monitoring program data collected over past monitoring programs and/or ongoing monitoring programs. As will be discussed in more detail below with respect to FIG. 17, the collected data can include or be stored with the protocols for monitoring programs for which data is being collected, other elements for the monitoring programs for which data is being collected (e.g., communication attributes used to generate communications for particular monitoring groups, groups of participants, and/or individual participants), and/or diversity criteria determined for the monitoring programs. The collected data can also include information received from participant devices, such as participant responses, test results, and/or sensor data. The monitoring program data can also include information that is generated by the computer system 210 using the collected data, such as metrics used to determine whether a monitoring program was or is likely to be successful. For example, the computer system 210 may store with the collected data corresponding metrics calculated using the collected data such as a compliance rates, retention rates, and average data quality for particular monitoring groups, groups of participants, and/or participants. Similarly, the computer system 210 can determine and store with the collected data a diversity score and/or composition characteristics for the monitoring groups, such as the final, observed composition characteristics of each of the monitoring groups at an end of their corresponding monitoring program.

The monitoring program database 1420 can be updated to include additional data collected for one or more monitoring programs. For example, the database 1420 can be updated periodically based on default settings or those set by an administrator of the system 210. Additionally or alternatively, the database 1420 can be updated in response to certain events. For example, the database 1420 can be updated in real-time or near real-time in response to the computer system 210 collecting monitoring program data while managing one or more monitoring programs.

The participant database 1422 can store participant data collected during participant registration and/or over past and ongoing monitoring programs. As will be discussed in more detail below with respect to FIG. 17, the participant data collected can include attributes of the participants, such as their age, sex, medical conditions, prescriptions, etc. or other information that may be relevant to analyzing the diversity of the monitoring group 1402. Other participant data collected can include participant responses, test results, sensor data, etc. that the computer system 210 can use to determine compliance rates, retention rates, and/or data quality metrics for the particular participants, for participant groups that the corresponding participants belong to, and/or for the monitoring group as a whole. The participant data collected can also include attributes of the participant devices, such as a make, model, software version, CPU speed, CPU core size, RAM size and/or speed, and/or memory size of the participant devices.

The participant database 1422 can be updated to include additional data collected for one or more monitoring programs. For example, the database 1422 can be updated periodically based on default settings or those set by an administrator of the system 210. Additionally or alternatively, the database 1422 can be updated in response to certain events. For example, the database 1420 can be updated in real-time or near real-time in response to the computer system 210 collecting participant data while managing one or more monitoring programs.

As shown, during the creation or initialization of a monitoring program, an interface 1410 can be presented on a display of the client device 204. The interface 1410 can present information to assist a user of the client device 204 to configure a monitoring program ("Monitoring Program Y"). For example, the interface 1410 can present diversity information that the user can use to adjust the elements of the Monitoring Program Y. The diversity information can be generated by the computer system 210 based on the program elements in the section 1412 that are associated with Monitoring Program Y and/or have previously been selected by a user of the client device 204. In more detail, the interface 1410 can include a program elements section 1412 that includes the current elements for the Monitoring Program Y.

The interface 1410 also includes an end-of-program targets section 1414 that specifies diversity criteria and/or other success criteria required for the Monitoring Program Y. The end-of-program targets may have been previously selected for the Monitoring Program Y, or may be set or updated by a user of the client device 204. Alternatively, the computer system 210 may determine the end-of-program targets based on various factors such as a determined minimum level of diversity required for the program (e.g., based on a target population that the results of the Monitoring Program Y will be applied to, such as to a country's population when a pharmaceutical being studied is planned to be distributed in the country.) and the historical data in the database 1420.

The interface 1410 also includes an end-of-program prediction(s) section 1416. The section 1416 can include predictions such as diversity predictions made by the computer system 210. As will be discussed in more detail below with respect to FIGS. 15A-15D, the computer system 210 can use various different techniques to make the end-of-program predictions. As an example, the computer system 210 can use the program elements in section 1412 for the Monitoring Program Y, current composition characteristics for the monitoring group 1402, and/or the historical data in the database 1420 to predict composition characteristics of the monitoring group 1402 at the a scheduled or anticipated end of the Monitoring Program Y.

The computer system 210 may also make other predictions, such as predictions regarding the compliance rate, retention rate, and/or level of data quality expected from the monitoring group 1402, participant groups in the monitoring group 1402 (e.g., different diversity groups represented by one or more participants in the monitoring group 1402), and/or individual participants in the monitoring group 1402 based on the historical data in the database 1420 and/or the participant data in the database 1422. The computer system 210 can use these predictions to predict the composition characteristics for the monitoring group 1402 or to more accurately predict the composition characteristics for the monitoring group 1402.

The predictions in the section 1416 include a predicted composition of the monitoring group 1402. As shown, the predicted composition indicates that by a future time (e.g., scheduled end of the Monitoring Program Y) the monitoring group 1402 will be composed of 31% participants belonging to a first diversity group (e.g., Group 1), 16% participants belonging to a second diversity group (e.g., Group 2), and 53% participants belonging to a third diversity group (e.g., Group 3). The interface 1410 may visualize distinguish predictions that fail to meet the success criteria in section 1414, e.g., based on a determinations made by the computer system 210. These predictions may be highlighted, may have a different color applied to them, may appear in bold text, may appear as a different size text, or may appear as a different font. For example, the "16%" has been displayed on the interface 1410 in bold text based on the computer system 210 determining that this value deviates too far from the corresponding target composition value of 25% (e.g., predicted representation value is at least 20% less than the corresponding target value). Similarly, the computer system 210 may send instructions to the client device 204 to visually distinguish the predicted retention rate of 40% for the second diversity group based on this value failing to meet the corresponding minimum retention rate of 73%.

The predictions displayed in section 1416 of the interface 1410 may correspond to a particular time that is either known or anticipated. For example, where the Monitoring Program Y has a scheduled end time, the prediction may be made for the scheduled end time. However, there may be cases where there is no set or scheduled end time. For example, the computer system 210 may determine a time when all of the end-of-program targets and/or other success criteria in the section 1414 is sufficiently likely to be met. If the computer system 210 identifies such a time, e.g., a time when the Monitoring Program is anticipated to meet all of the success criteria and, therefore, be successfully completed, the predictions made by the computer system 210 can correspond to this time. Similarly, if the computer system 210 determines that there is no future time (e.g., out to threshold point, such as a year from the start date of the Monitoring Program Y) when all of the success criteria is sufficiently likely to be met, the computer system 210 may make predictions for a default time in the future (e.g., three months from current time, three months from start date, one month from current time, one month from start date, etc.) and/or generate and transmit a notification to the client device 204 that the Monitoring Program Y is predicted to fail.

The section 1416 can also include predictions if one or more recommended actions are performed by the computer system 210. For example, as will be discussed in more detail below with respect to FIG. 16A, the computer system 210 may make predictions that assume one or more changes to the program elements, to the monitoring group 1402, and/or to software configurations of the participant devices in the monitoring group 1402. These predictions may indicate which of the recommended actions are anticipated to have the most desirable effects on the diversity of the monitoring group 1402 and/or assist a user of the client device 204 make a better informed selection of actions in a recommended set of actions that the computer system 210 should perform.

In making the predictions found in the section 1416, the computer system 210 may use a prediction module 1440. In more detail, the computer system 210 may obtain monitoring program data 1430, corresponding historical data 1432, and corresponding diversity criteria 1434 and proceed to provide all or a portion of the data to the prediction module 1440 as input. Depending on the data available and/or the data the prediction module 1440 receives as input, the prediction module 1440 may use one or more different techniques for predicting composition characteristics of the monitoring group 1402 at a future time. For example, if the prediction module 1440 only receives the monitoring program data 1430 and the corresponding historical data 1432 as input, the prediction module may use a first technique (e.g., a particular workflow, series of workflows, etc. that call on specific models such as particular machine learning models). In contrast, if the prediction module 1440 only receives the diversity criteria and the monitoring program data 1430, the prediction module 1440 may instead use a second technique different from the first technique. The techniques used by the prediction module 1440 may differ in whether they use statistical models or machine learning (ML) models, and/or in the particular statistical and/or ML models that they use to make the predictions. The techniques may also differ in other ways, such as the information required as input and/or the predictions produced using the techniques.

For example, different techniques used by the prediction module 1440 may differ in that they are used to predict different composition characteristics of the monitoring group 1402 and/or they are used to make predictions for different participant groups (e.g., diversity groups) present in the monitoring group 1402.

As another example, different techniques used by the prediction module 1440 may differ in how they arrive at a diversity prediction. For example, as will be discussed in more detail below with respect to FIGS. 15A-15D, some techniques may rely on predicting completion rates for different diversity groups whereas other techniques rely on predicting a likelihood of meeting the diversity criteria 1434.

The computer system 210 may obtain the monitoring program data 1430 from local storage, from the database 212 or one of the other databases, and/or from the client device 204. For example, all or a portion of the monitoring program data 1430 from the client device 204 in response to a user of the device 204 creating and/or submitting the Monitoring Program Y through the interface 1410 or another interface of the device 204. The monitoring program data 1430 can include the current elements of the monitoring program (e.g., which may be updated over time to account for predicted diversity problems), and monitoring group data for the monitoring group 1402. The monitoring group data 1402 may include an indication of the participants and/or participant devices invited to or enrolled in the monitoring group 1402. For example, the monitoring group data 1430 can include identifiers for the participants 1404a-1404c that the computer system 210 can later use to retrieve stored attribute data for the participants 1404a-1404c from the participant database 1422. As another example, the computer system 210 can retrieve the attributes for the participants and/or participant devices in the monitoring group 1402 and include the attribute information in the monitoring program data 1430 that it provides to the prediction module 1440.

The computer system 210 may obtain historical data 1432 from the historical monitoring program database 1420. The historical data 1432 retrieved from the database 1420 can be a subset of the historical data stored in the database 1420. For example, the computer system 210 may request from the database 1420 only that portion of the stored historical data that corresponds to past monitoring programs that one or more of the participants 1404a-1404c have previously participated in (or are currently participating in) and/or that corresponds to past monitoring programs that included participant groups that are also represented in the monitoring group 1402. For example, based on a determination that the participant 1404a belongs to a Group 1 diversity group, the computer system 210 may retrieve all historical data (or all historical data that is sufficiently recent, such as all historical data collected over the past two years, three years, five years, etc.) for monitoring programs that had monitoring groups that included (e.g., at an outset of the respective programs) a participant belonging to Group 1.

The computer system 210 may obtain and/or determine diversity criteria 1434 for the monitoring program. For example, the computer system 210 may receive the diversity criteria 1434 from the client device 204 in response to a user of the device 204 submitting the Monitoring Program Y that includes user-defined diversity criteria, such as a target composition.

Additionally or alternatively, the computer system 210 may determine its own diversity criteria, e.g., that is in addition to the user-specified criteria or in place of user-specified criteria. The computer system 210 may take into account the program elements (e.g., which may indicate a type of monitoring program, goals for the monitoring program, etc.), the monitoring group 1402, and/or a target population in determining the diversity criteria. For example, based on the Monitoring Program Y being a clinical study for a particular pharmaceutical and a target population that is anticipated to be prescribed the pharmaceutical, the computer system 210 can determine rules such that diversity groups found in the target population (e.g., meeting a certain minimum size or minimum representation) must also be represented in the monitoring group 1402 and minimum group sizes for each of the diversity groups calculated using statistical rules (e.g., rules to provide for the possibility of finding statistically significant results given the allowable error for a pharmaceutical study) and/or industry standards for clinical studies.

In determining the diversity criteria, the computer system 210 may also rely on historical data from the database 1420. This historical data may suggest particular composition characteristics of different monitoring groups that typically produced unviable results (e.g., results that have limited or no applicability due to the corresponding monitoring group having too low of a sample size with respect to one or more required diversity groups), or that produced viable results.

The computer system 210 can provide the diversity criteria 1434 as input to the prediction module 1440. Alternatively, the computer system 210 may refrain from providing the diversity criteria 1434 to the prediction module 1440. For example, the computer system 210 may provide the monitoring program data 1430 (or a portion of the monitoring program data 1430 such as the monitoring group data) and the corresponding historical data 1432 as input to the prediction module 1440, and use the diversity criteria 1434 only to compare the output of the prediction module 1440 with.

The prediction module 1440 can use the monitoring program data 1430, the historical data 1432, and/or the diversity criteria 1434 to predict composition characteristics of the monitoring group 1402 at a future time (1442), such as at the end of the monitoring program. The computer system 210 may choose to provide only portions of the monitoring program data 1430, the historical data 1432, and/or the diversity criteria 1434 to the prediction module 1440. Alternatively, the prediction module 1440 may use only a subset of the data that it receives.

In predicting the composition characteristics, the prediction module 1440 can use one or more statistical or ML models that are included in the prediction module 1440 or that the prediction module 1440 can call upon. The models can output metrics that represent predicted composition characteristics and/or that can be used by the prediction module 1440 to determine predicted composition characteristics of the monitoring group 1402. These techniques and others will be described in more detail below with respect to FIGS. 15A-15D.

The future time that the prediction module 1440 makes prediction for can include a set or anticipated end of the monitoring program. For example, if the monitoring program is scheduled to end in six months, the predictions generated by the prediction module 1440 can include predicted composition characteristics for the monitoring group 1402 six months from a current time and/or date. However, the future time can include other times that are not the set or anticipated end of the monitoring program. For example, the future time for predictions generated by the prediction module 1440 may be set for a month, three months, or a year from the current time and/or date.

In some implementations, the computer system 210 may generate and send a request to the client device 204 requesting that a user of the client device 204 (e.g., researcher or admin) enter or select a future time for the prediction module 1440 to perform predictions for. For example, based on the request transmitted to the client device 204 from the computer system 210, the client device 204 may present an interface that includes a list of upcoming dates or times to perform the diversity analysis for. The list may include a date/time corresponding to the set end of the monitoring program, dates/times corresponding to different milestones such as anticipated milestone completion dates, dates/times corresponding to different deadlines for the monitoring program, etc. The interface may also optionally present a field where a custom date/time can be entered. A researcher can interact with the interface to select one or more of the presented dates and times for the prediction module 1440 to generate predictions for. The client device 204 can transmit an indication of the selection(s) to the computer system 210. The computer system 210 can, in response, provide the selection(s) to the prediction module 1440.

As another example, the computer system 210 can automatically determine the future time based on one or more factors, such as when the monitoring program is scheduled or anticipated to be completed, how long ago the monitoring program started, if there are any upcoming milestones for the monitoring program, past predictions, etc. For example, the computer system 210 may use rules that provide if the monitoring program is to end one year or more from the current date, predictions should be made for six months from the current date. The rules can also provide that if the monitoring program is to end less than one year from the current date, predictions should be made three months from the current date unless the monitoring program is scheduled to end in less than three months in which case the predictions should be made for the scheduled end of the monitoring program.

As another example, for each diversity analysis, the predication module 1440 may predict composition characteristics for the monitoring program at multiple times/dates in the future. In more detail, the prediction module 1440 may start with a time that is sufficiently near the current time for a first set of predictions, and proceed to extend the time from the current time until the predictions indicate that the predicted composition characteristics do not meet the diversity criteria 1434 or sufficiently diverge (e.g., diverge more than a threshold percent from the diversity criteria 1434). That is, the prediction module 1440 may extend the time from the current time until it identifies a time when failure to meet the diversity criteria is sufficiently likely (e.g., the point where the predicted composition characteristics do not meet the diversity criteria 1434, or the point where the predicted composition characteristics indicate that there is a sufficient likelihood of not meeting the diversity criteria 1434). The predictions outputted by the prediction module 1440 can be those that correspond to the identified time.

The computer system 210 can proceed to compare the predicted composition characteristics with the diversity criteria 1434 (1450). In making the comparison, the computer system 210 may identify problematic composition characteristics. This may include predicted composition characteristics that do not match or diverge sufficiently far from a corresponding target (e.g., target value, target range, target distribution, etc.) specified in the diversity criteria 1434. Other problematic composition characteristics can include those that do not meet a threshold included in the diversity criteria 1434, or that are not within or outside a particular range of values specified in the diversity criteria 1434.

Based on the comparison, the computer system 210 can determine a set of actions to improve the predicted diversity of the monitoring group. For example, the computer system 210 can determine the set of actions in response to the predicted composition characteristics failing to meet at least one of the diversity criteria in the diversity criteria 1434. Where the comparison indicates that all criteria are anticipated to be met, the computer system 210 may either refrain from determining a set of actions or, e.g., if there remains a significantly high likelihood of one or more of the diversity criteria not being met, proceed to determine a set of actions to improve the likelihood of the diversity criteria 1434 being met.

Based on the comparison, the computer system 210 may determine that an action 1460 of notifying participants and/or researchers is likely to improve the diversity of the monitoring group 1402 at the monitoring program's completion. For example, if the comparison reveals the expected Group 2 size at the end of the monitoring program does not meet a minimum Group 2 size in the diversity criteria 1434 due to a low expected compliance rate among the Group 2 participants, the computer system 210 can use the historical data 1432 or other historical data in the database 1420 to determine that notifying Group 2 participants of their low compliance or risk of low compliance typically improves their compliance. The computer system 210 can determine that it should recommend and/or perform an action of notifying Group 2 participants because this action is anticipated to improve the Group 2 compliance rate and, therefore, the expected Group 2 size in the predicted monitoring group 1402 at the end of the monitoring program.

Based on the comparison, the computer system 210 may determine that an action 1462 of adapting monitoring program elements is likely to improve the diversity of the monitoring group 1402 at the monitoring program's completion. For example, if the comparison reveals the expected Group 2 size at the end of the monitoring program does not meet a minimum Group 2 size in the diversity criteria 1434 due to a low expected compliance rate among the Group 2 participants, the computer system 210 can use the historical data 1432 or other historical data in the database 1420 to determine that changing the monitoring program elements for the Group 2 participants by adjusting a required test frequency tends to improves the compliance rate of Group 2 participants. The computer system 210 can determine that an action of adjusting the program elements is likely to improve the Group 2 compliance rate and, therefore, the expected Group 2 size in the predicted monitoring group 1402 at the end of the monitoring program.

Based on the comparison, the computer system 210 may determine that an action 1464 of adjusting communications between the computer system 210 and at least a portion of the monitoring group 1402 is likely to improve the diversity of the monitoring group 1402 at the monitoring program's completion. For example, if the comparison reveals the expected Group 2 size at the end of the monitoring program does not meet a minimum Group 2 size in the diversity criteria 1434 due to a low expected compliance rate among the Group 2 participants, the computer system 210 can use the historical data 1432 or other historical data in the database 1420 to determine that Group 2 participants typically exhibit higher compliance rates when a frequency of communication is increased and informal vocabulary is used. The computer system 210 can determine that an action of adjusting the communications (e.g., adjusting the communication attributes that the communications must comply with and/or that the computer system 210 uses to make the communications) between the computer system 210 and the Group 2 participants in the monitoring group 1402 is likely to improve the Group 2 compliance rate and, therefore, the expected Group 2 size in the predicted monitoring group 1402 at the end of the monitoring program.

Based on the comparison, the computer system 210 may determine that an action 1466 of changing remote device configurations for at least a portion of the participant devices in the monitoring group 1402 (or participant devices that are to be added to the monitoring group 1402) is likely to improve the diversity of the monitoring group 1402 at the monitoring program's completion. For example, if the comparison reveals the expected Group 2 size at the end of the monitoring program does not meet a minimum Group 2 size in the diversity criteria 1434 due to a low expected compliance rate among the Group 2 participants, the computer system 210 can use the historical data 1432 or other historical data in the database 1420 to determine that Group 2 participants typically exhibit higher compliance rates when their devices are configured to collect additional sensor data and when incoming messages are accompanied by an alert. The computer system 210 can determine that an action of adjusting a software configuration for the Group 2 participant devices to collect the additional sensor data and to add audio/visual alerts for messages coming from the computer system 210 is likely to improve the Group 2 compliance rate and, therefore, the expected Group 2 size in the predicted monitoring group 1402 at the end of the monitoring program.

Based on the comparison, the computer system 210 may determine that an action 1468 of adjusting the monitoring group 1402 is likely to improve the diversity of the monitoring group 1402 at the monitoring program's completion. For example, if the comparison reveals the expected Group 2 size at the end of the monitoring program does not meet a minimum Group 2 size in the diversity criteria 1434 due to a low expected compliance rate among the Group 2 participants, the computer system 210 can calculate a number of additional Group 2 participants needed for the predicted Group 2 size to meet the corresponding diversity criteria. The computer system 210 can determine that an action of inviting additional Group 2 participants to or enrolling additional Group 2 participants in the monitoring program is likely to improve the Group 2 compliance rate and, therefore, the expected Group 2 size in the predicted monitoring group 1402 at the end of the monitoring program.

The computer system 210 may use a recommendation module to determine the set of actions to recommend and/or perform. For example, the computer system 210 may use a recommendation module that includes or can call upon one or more statistical or ML models. The computer system 210 may provide as input to the recommendation module the historical data 1432 which may indicate past monitoring program elements and/or changes to monitoring program elements that had beneficial effects on the diversity of monitoring groups. The computer system 210 can also provide all or a portion of the monitoring program data 1430 as input to the recommendation module. The recommendation module can use the monitoring program data 1430 to identify relevant portions of the historical data 1432, to identify potentially problematic elements, and/or identify potentially problematic composition characteristics of the current monitoring group 1402. Importantly, the computer system 210 can also provide the recommendation module the results of the comparison between the predicted composition characteristics and the diversity criteria 1434. The recommendation module can use the comparison results to identify program modifications that have historically resulted in improvements to the particular composition characteristics that fail to meet one or more of the diversity criteria.

The computer system 210 is not limited to determining, recommending, and/or performing the actions depicted, and may determine other types of actions to recommend and/or to perform. For example, the computer system 210 may determine an action to update the diversity criteria 1434 for the monitoring program to reduce the minimum group size for a particular participant group. This action may be in response to, for example, the prediction module 1440 indicating a low likelihood of achieving the minimum group size for a particular group but also indicating a high likelihood of higher than anticipated data quality from the particular group, making the previous minimum group size unnecessary (e.g., unnecessary to achieve the success criteria for the monitoring program, unnecessary for the results of the monitoring program to have statistical significance, etc.).

As another example, this action may be in response to, for example, the prediction module 1440 indicating a low likelihood of achieving the minimum group size for the particular group, and other actions failing to produce sufficient enrollment, compliance, and/or retention for participants in the particular group. That is, the action of adjusting the diversity criteria 1434 may be based on a determination that there is sufficiently low likelihood of meeting one or more of the criteria despite the action(s) taken by the computer system 210. In this situation, the computer system 210 may determine the effects on the results of the monitoring program due to changing the diversity criteria 1434. These effects could include a lower likelihood of the program's results being applicable for one or more populations, e.g., due to a reduced probability of the results being statistically significant for a particular population as a result of small sample size, limited data quantity, and/or poor data quality that correspond to the changes made to the diversity criteria 1434 (e.g., broadening of criteria and/or elimination of criteria).

In general, the diversity analysis can include all or a portion of the described actions performed by the computer system 210. For example, the diversity analysis can include providing at least a portion of the monitoring program data 1430, the historical data 1432, and/or the diversity criteria 1434 as input to the prediction module 1440 and obtaining the predicted composition characteristics as an output of the prediction module 1440. The diversity analysis can also include additional actions, such as determining the diversity criteria 1434, comparing the predicted composition characteristics to the diversity criteria 1434, and/or determining recommended actions to perform.

The computer system 210 may repeat all or a portion of the diversity analysis multiple times. For example, after performing one of the actions 1460, 1462, 1464, 1466, and/or 1468, the computer system 210 may perform the diversity analysis again using the updated monitoring program data 1430. In more detail, the computer system 210 may continue to make additional predictions on an ongoing basis, e.g., periodically or in response to detected events. Accordingly, the computer system 210 can track the anticipated monitoring group composition to determine, for example, if intervening actions are needed to successfully complete the monitoring program, the accurateness of predictions previously made by the prediction module 1440, or if past intervening actions are having their anticipated effect on the monitoring group 1402.

The computer system 210 may perform the described diversity analysis a single time, or at multiple times. For example, the computer system 210 can perform the diversity analysis when a researcher or admin uses the client device 204 to submit a monitoring program. As another example, the computer system 210 may perform a diversity analysis at particular stages of the monitoring program, such as when a group of subjects has been invited to enroll in the monitoring program and/or have been enrolled in the program, when an enrollment period has ended, and/or at one or more set times during the study.

The computer system 210 may perform the diversity analysis in response to detecting particular events. For example, the computer system 210 may perform the analysis in response to determining that a participant has left the monitoring group 1402, is sufficiently unlikely to meet the success criteria for the program, or cannot meet the success criteria (e.g., due to having too low of compliance from which they cannot recover to successfully complete the program; and/or due to having too low of data quality from which they cannot recover to successfully complete the study). Similarly, the computer system 210 may perform the analysis in response to detecting changes to the monitoring program, such as a changes made by researchers or made by the computer system 210. These changes can include changes to the monitoring program elements, changes to the monitoring group 1402, and/or changes to the software configurations of the participant devices in the monitoring group 1402.

The computer system 210 may automatically schedule diversity analysis to be performed, such as periodically and/or in response to detected events as described above. For example, the computer system 210 may schedule a diversity analysis to be performed every month and every time a modification to the monitoring program is made (e.g., manually by a user of the client device, by a participant leaving the monitoring group 1402, and/or by the computer system 210 performing a recommended action). However, the frequency for diversity analyses or changes to the frequency of diversity analyses may depend on the extent that predictions generated by the prediction module 1440 diverge from the diversity criteria 1434. For example, if predictions made by the prediction module 1440 indicate that that there is sufficiently low likelihood of the diversity criteria 1434 being met, the computer system 210 can update the frequency of performing diversity analyses from once a month to once a week. The frequency for diversity analyses or changes to the frequency of diversity analyses can depend on the extent that predictions generated by the prediction module 1440 diverge from the diversity criteria 1434.

FIGS. 15A-15D are diagrams that illustrate one or more components of the system 200 for predicting group diversity for monitoring programs. The diagrams demonstrate that the computer system 210 can use a multitude of different techniques to predict composition characteristics and/or a level of diversity for the monitoring group 1402. The different techniques may require using different information to make the predictions, using a different type or number of models/modules to generate outputs that the computer system 210 uses to make the predictions, and/or using different techniques to interpret the outputs of models/modules. After making these predictions, the computer system 210 can use the predictions to make further insights of the monitoring group 1402 and/or to generate a set of actions to improve the diversity of the monitoring group 1402.

In some implementations, the computer system 210 uses multiple techniques to generate the predictions. For example, the computer system 210 may use a first technique to predict particular composition characteristics, and a second technique to predict other composition characteristics based on the first technique typically producing more accurate predictions with respect to the particular composition characteristics and/or the second technique typically producing more accurate predictions with respect to the other composition characteristics. As another example, the computer system 210 may use multiple techniques to make the same type of predictions. The computer system 210 can use the predictions made through the different techniques to generate a combined prediction (e.g., by averaging the results, averaging weighted results, or using an algorithm to combine the results) that is, for example, more likely to be accurate than the predictions made through a single technique.

Figure 15A:
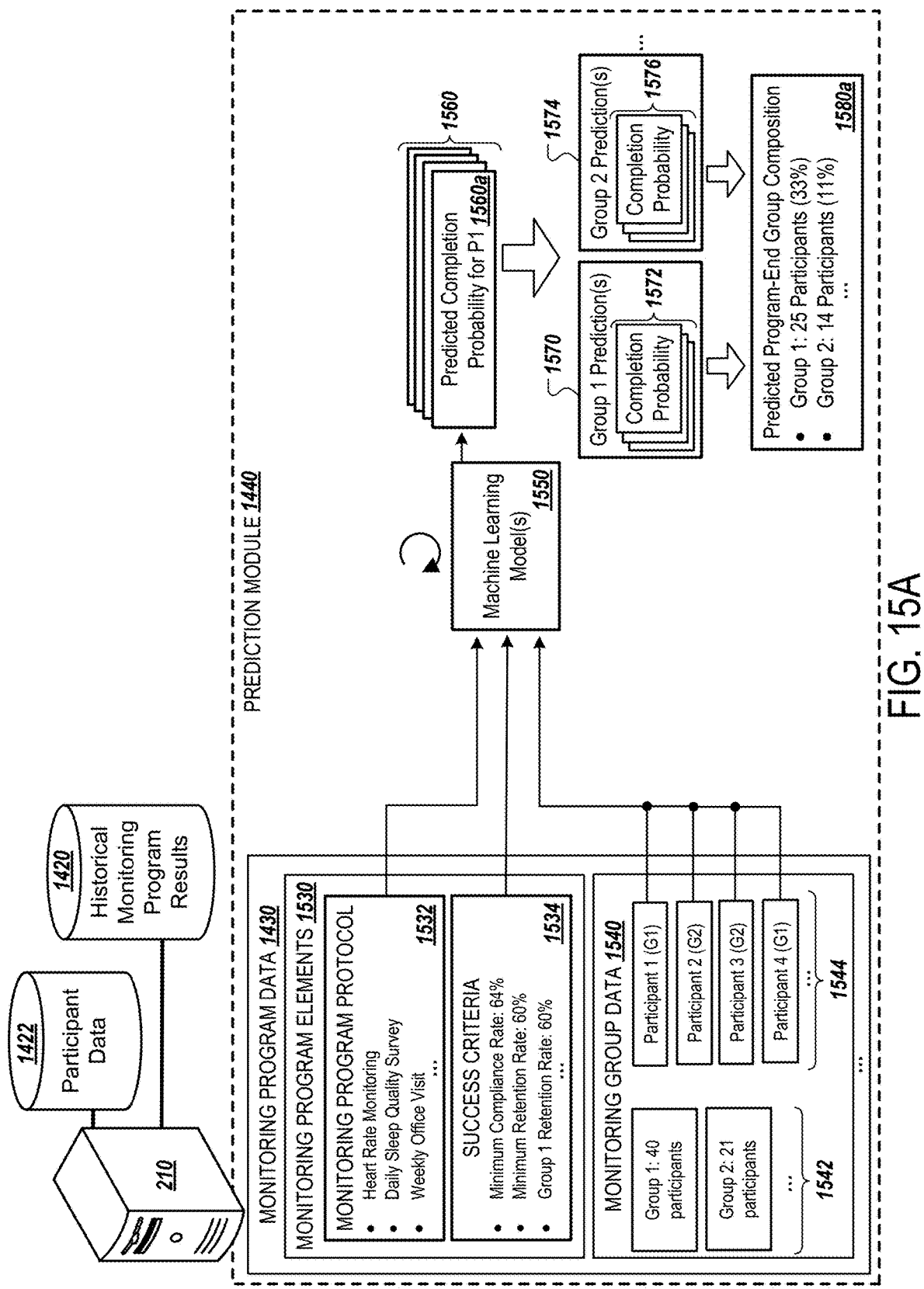
FIGS. 15A-15D are diagrams that illustrate example systems for predicting diversity for monitoring programs.

In FIG. 15A, the prediction module 1440 uses a set of one or more machine learning models 1550 to generate predictions. The machine learning models 1550 can generate monitoring group 1402 predictions based on received portions of the monitoring program data 1430. In more detail, the prediction module 1440 provides at least a portion of the monitoring program elements 1530 and the monitoring group data 1540 as input to the machine learning models 1550. The machine learning (ML) models 1550 may use this input data to generate outputs 1560 that are, or indicate, predicted completion probabilities for the monitoring group 1402's participants. More generally, the models 1550 and other models can trained to predict future compliance for some future period, for example, for a certain amount of time (e.g., the next day, week, month, etc.) or to a future milestone point, or to another time that may not be the completion or end of the program. In some implementations, the compliance predicted can refer to at least a minimum level of participation (e.g., collecting the minimum amount of data that is acceptable for the monitoring program) occurring for the duration from the current time to the future time. If a survey is required to be completed each day in order to not invalidate results, then the prediction of compliance can involve a prediction whether a participant will submit the survey each day until the future time corresponding to the prediction.

The ML models 1550 can include one or more types of ML models or algorithms. For example, the ML models 1550 can include one or more of a supervised learning model, an unsupervised learning model, a hybrid-learning model, or a reinforcement learning models.

The ML models 1550 may be trained using training data sets generated from historical data stored in the database 1420. Specifically, the computer system 210 can train the ML models 1550 using monitoring program data from previous monitoring programs. This monitoring program data can include monitoring group data for previous monitoring programs such as the starting and ending enrollment data for the previous monitoring groups, protocols for the previous monitoring programs, and/or success criteria for the previous monitoring programs.

The ML models 1550 may be trained with the goal of minimizing a loss function based on the differences between predicted completion probabilities for participants and the observed completion rate. The loss may be defined at the participant group level instead of the individual participant level. For example, the computer system 210 can train the ML models 1550 using monitoring program data for a Monitoring Program X that started with five participants from Group 1. If initial predictions generated by the ML models 1550 indicate an average completion rate of 40% for the Group 1 participants but the observed completion rate for the Group 1 participants turned out to be 60%, the difference of 20% may be used as a loss, used to determine a loss (e.g., a squared loss), and/or used for calculating a mean square error (MSE) for training the ML models 1550. As an example, the ML models 1550 here may include a regression loss models, a classification model, or a neural network. More generally, any of the ML models 1550 or any of the other machine learning models discussed herein may be may be, for example, a neural network, a support vector machine, a classifier, a regression model, a reinforcement learning model, a clustering model, a decision tree, a random forest model, a genetic algorithm, a Bayesian model, or a Gaussian mixture model.

The ML models 1550 may be trained with the goal of correctly specifying whether participants will successfully complete a monitoring program or not. The ML models 1550 may be trained for individual participants and output a classification such as binary value for each of the participants. For example, the computer system 210 can train the ML models 1550 using monitoring program data for a Monitoring Program X that started with ten participants from multiple participant groups. The ML models 1550 can generate an output such as a binary output for each of the ten participants that indicates whether each of the participants are predicted to successfully complete the Monitoring Program X. The computer system 210 can proceed to compare the ten predictions with the actual results that indicate which of those participants successfully completed the Monitoring Program X. The ML models 1550 can be trained to reduce the number/percent of incorrect predictions. As an example, the ML models 1550 here may include a classification model (e.g., binary classification, decision tree(s), etc.) or a neural network.

The ML models 1550 may be trained using all historical data available. For example, the computer system 210 may convert all historical data in the database 1420 into training data sets and proceed to train the ML models 1550 with them. Alternatively, the ML models 1550 may be trained using only the historical data that the computer system 210 determines meets certain criteria. For example, the computer system 210 may convert only the historical data in the database 1420 that is sufficiently recent (e.g., acquired over the past five years, three years, two years, etc.) into training data sets and proceed to train the ML models 1550 with them.

In some implementations, the ML models 1550 include multiple ML models or algorithms that are used by the prediction module 1440 for different purposes or scenarios. For example, the ML models 1550 may include a ML model for each group of participants. The prediction module 1440 may use a portion of the ML models 1550 that correspond to those groups of participants that are present in the monitoring group 1402, e.g., as indicated by the monitoring group data 1540. Each of these group-specific ML models may be trained using a portion of the historical data in the database 1420 that corresponds to that group of participants.

In making diversity predictions, the prediction module 1440 may first identify a subset of the monitoring program data 1430 to provide as input to the ML models 1550. In more detail, the prediction module 1440 may extract from the monitoring program data 1430 a portion of the monitoring program elements 1530 and a portion of the monitoring group data 1540. The prediction module 1440 can proceed to provide the extracted data as input to the ML models 1550.

Specifically, the prediction module 1440 can obtain the monitoring program protocol 1532 that specifies a set procedure for the monitoring program. This procedure may specify required actions that participants in the monitoring group 1402 must perform and/or specify rules for how the computer system 210 must conduct the monitoring program. For example, the protocol 1532 may specify that participants in the monitoring group 1402 must perform heart rate monitoring and submit heart rate tests daily, fill out and submit a daily sleep quality survey, and attend a weekly office visit to be evaluated by a doctor. As another example, the protocol 1532 may specify a schedule for when the computer system 210 is to send notifications, such as reminders or data requests, to the participant devices in the monitoring group 1402. Similarly, the protocol 1532 may specify rules for communicating with the participants and/or researchers, such as rules that dictate the form and timing of notifications when a participant fails to timely perform a required action.

The prediction module 1440 can also obtain success criteria 1534 that specifies the criteria used by the computer system to determine if participants and/or the monitoring group 1402 successfully completed the monitoring program. The success criteria 1534 obtained may be limited to success criteria other than diversity criteria. Similarly, the success criteria 1534 obtained may be a subset of the success criteria that specifies the success criteria for individual participants, such as a minimum compliance rate required for each participant or for each participant in a particular group of participants.

In some implementations, in obtaining the monitoring program protocol 1532, the prediction module 1440 accesses the monitoring program data 1430 in the database 212 and retrieves the monitoring program protocol 1532 from the database 212.

The prediction module 1440 can also obtain the participant attribute data 1544 that includes attribute information for each of the participants in the monitoring group 1402. As will be described in more detail below with respect to FIG. 17, the participant attribute data 1544 can include demographic and non-demographic information collected on each of the participants in the monitoring group 1402. This information can include names for the participants, identifications assigned to the participants, ages for the participants, known medical conditions of the participants, medications that have been prescribed to the participants, etc. Similarly, this information can include behaviors that the participants have previously demonstrated or have otherwise indicated, such as difficulty keeping a dosage schedule, difficulty complying with dietary restrictions, or difficulty performing particular types of exercises. The participant attribute data 1544 may also include monitoring program related information for the participants, such as indications of the monitoring programs that they have participated in and/or successfully completed, the number of monitoring programs that they have participated in and/or successfully completed, their overall successful completion rate, date(s) for their most recent program completion(s), etc.

The participant attribute data 1544 can include an indication of the participant groups that each participant belongs to. Alternatively, the computer system 210 or the prediction module 1440 can determine which participant groups that each of the monitoring group 1402's participants belong to using the participant group data 1542 of the monitoring group data 1540. For example, the participant group data 1542 may include, for each of the groups, a list of participants that belong to the corresponding group. The computer system 210 or the prediction module 1440 may proceed to compare the names or identifiers in the participant attribute data 1544 to the lists to identify which groups the participants belong to, or the lists may be limited to those participants in the monitoring group 1402. As another example, the participant group data 1542 can include a profile for each of the groups that defines inclusion criteria for each of the participant groups. The computer system 210 or the prediction module 1440 can compare the inclusion criteria to the participant attribute data 1544 to determine the participant group(s) that each of the participants in the monitoring group 1402 belong to, and/or to determine the number or percent of participants in the monitoring group 1402 that belong to each of the participant groups.

In some implementations, in obtaining the participant attribute data 1544, the prediction module 1440 accesses the monitoring program data 1430 in the database 1422 and retrieves the participant attribute data 1544 from the database 1422.

In some implementations, the prediction module 1440 does not obtain the monitoring program protocol 1532, the success criteria 1534, and the participant attribute data 1544. For example, the prediction module 1440 may obtain only the protocol 1532 and the participant attribute data 1544 to provide as input to the ML models 1550. The ML models 1550 can be configured to generate outputs using the protocol 1532 and the participant attribute data 1544 without the success criteria 1534. In this example, the ML models 1550 may be trained using data sets that indicate which participants successfully completed the past monitoring programs and which did not, which would allow the ML models 1550 to accurately predict successful completion without the need for success criteria 1534. However, potentially more accurate predictions can be made by the ML models 1550 when using the current success criteria 1534 when predicting whether participants will successfully complete a monitoring program.

After obtaining the subset of the monitoring program data 1430, the prediction module 1440 can provide the obtained data as input to the ML models 1550. Specifically, the prediction module 1440 can provide the monitoring program protocol 1532, the success criteria 1534, and the participant attribute data 1544 as input to the ML models 1550. The prediction module 1440 can provide the entirety of the input data to the ML models 1550 at once, or it can provide the input data in separate datasets. For example, the prediction module 1440 can first provide a dataset that includes the monitoring program protocol 1532 and participant attribute data for Participant 1 as input to the ML models 1550 before providing a second dataset that includes the monitoring program protocol 1532 and participant attribute data for Participant 2 as input to the ML models 1550.

In some implementations, the ML models 1550 process different datasets sequentially. For example, the prediction module 1440 may provide different datasets corresponding to each of the participants in the monitoring group 1402 as input to the ML models 1550 (e.g., as they are created, one dataset at a time, all at once, etc.). The ML models 1550 may process the multiple datasets sequentially, e.g., in the order that they are received and/or in a queue order.

In some implementations, the ML models 1550 process different datasets in parallel. For example, the ML models 1550 may process two or more datasets corresponding to two or more participants in the monitoring group 1402 in parallel. The prediction module 1440 may place the datasets in one or more queues for the ML models 1550 to draw from.

Using the input data, the ML models 1550 can generate output data 1560. The output data 1560 can include an output for each of the participants present in the monitoring group 1402. For example, when the diversity analysis is performed at the start of the monitoring program, the monitoring group 1402 may include a first participant and, therefore, the ML models 1550 would generate a corresponding output for that first participant. However, if the first participant leaves or is removed from the monitoring program before a second diversity analysis is performed, the ML models 1550 would not generate another output for the first participant as they are no longer part of the monitoring group 1402.

The output data 1560 may include for each participant a predicted completion probability. For example, the output data 1560 can include a first output 1560*a* for Participant 1 that indicates the determined likelihood of Participant 1 successfully completing the monitoring program (e.g., the probability of Participant 1 meeting the success criteria of the monitoring program data 1430).

The prediction module 1440 can use the output data 1560 to make predictions for each group of participants in the monitoring program. For example, using the participant group data 1542 and/or the participant attribute data 1544, the prediction module 1440 can organize the output data 1560 into different sets, one for each group of participants present in the monitoring group 1402. For example, the prediction module 1440 may place the predicted completion probability 1560*a* in a first set of outputs 1572 for Group 1 based on the participant group data 1542 indicating that Participant 1 is in Group 1. The prediction module 1440 may similarly generate other sets of outputs for the other groups present in the monitoring group 1402, including a second set of outputs 1576 for Group 2.

The prediction module 1440 can use the different sets of outputs to generate corresponding predictions for the different participant groups. For example, the prediction module 1440 can use the first set of outputs 1572 to generate a first set of predictions 1570 for Group 1. Similarly, the prediction module 1440 can use the second set of outputs 1572 to generate a second set of predictions 1574 for Group 2. The sets of predictions 1570 and 1574 can each include, for example, an overall completion probability for the respective participant group. For example, the prediction module 1440 can calculate an overall completion probability for Group 1 by averaging the completion probabilities in the first set of outputs 1572. The prediction module 1440 can treat the overall completion probability for each of the participant groups as, for example, a predicted retention rate for that respective participant group.

The prediction module 1440 can use the different sets of outputs to generate other predictions. For example, after determining an overall completion probability for Group 1, the prediction module 1440 can apply the probability to the current number of Group 1 participants in the monitoring group 1402 (e.g., as indicated by the participant group data 1542) to predict the number of Group 1 participants there will be in the monitoring group 1402 at the monitoring program's completion.

The prediction module 1440 can use the predictions generated using the output data 1560 to determine a predicted group composition 1580*a*. The group composition 1580*a* can include predicted composition characteristics of the monitoring group 1402 at a future time, such as a set or anticipated end of the monitoring program. As shown, the predicted group composition 1580*a* includes a predicted population and percent representation for each participant group that is currently represented in the monitoring group 1402. As an example, if the first set of predictions 1570 indicates that twenty-five Group 1 participants are predicted to successfully complete the monitoring program and other sets of predictions indicate that fifty-one other participants are expected to successfully complete the monitoring program, the prediction module 1440 can calculate that the percent representation of the Group 1 participants is expected to be 33% and include that value in the predicted group composition 1580*a*. As another example, if the first set of predictions 1570 indicates that the overall completion probability for Group 1 is 62.5%, then the prediction module 1440 can calculate the number of Group 1 participants expected to be in the monitoring group 1402 at the monitoring program's completion is twenty-five.

The predicted group composition 1580*a* can also include other predicted composition characteristics of the monitoring group 1402. For example, the predicted group composition 1580*a* can include a predicted diversity score for the monitoring group 1402 at the future time. The diversity score may be calculated using an algorithm that takes into account various other predicted composition characteristics and/or diversity criteria. For example, the diversity score may be calculated using the anticipated sizes for each of the groups present in the monitoring program 1402. As another example, the diversity score may be calculated using an anticipated total size for the monitoring group 1402, the predicted percent representations for each of the groups present in the monitoring group 1402 (or present at the start of the monitoring program), and/or minimum percent representations for each of the groups as indicated in the diversity criteria 1434.

The predicted group composition 1580*a* may be represented as a distribution. The computer system 210 can later use the predicted distribution to compare with a target distribution in the diversity criteria 1434.

After generating the predicted group composition 1580*a*, the prediction module 1440 can output the predicted group composition 1580*a* one or more other systems or modules of the computer system 210. The computer system 210 may use the predicted group composition 1580*a* to compare to the diversity criteria 1434 as described above with respect to FIG. 1.

The prediction module 1440 can also output other information to other system or modules of the computer system 210. For example, the predication module 1440 can output the output data 1560, the first set of outputs 1572, first set of predictions 1570, etc. to a recommendation module of the computer system 210.

As another example, the output data 1560 may include for each participant a classification and/or binary value that indicates whether the corresponding participant is predicted to successfully complete the monitoring program or not. For example, the ML models 1550 may output a value of "1" to indicate that a particular participant in the monitoring group 1402 is anticipated to successfully complete the monitoring program, and output a value of "0" to indicate that a particular participant is not anticipated to successfully complete the monitoring program.

Continuing this example, the first set of outputs 1572 can include the binary values corresponding to each participant of the monitoring group 1402 that is in Group 1, and the second set of outputs 1576 can include the binary values corresponding to each participant of the monitoring group 1402 that is in Group 2. The prediction module 1440 can use the sets of binary values to determine an overall completion probability or retention rate for each group of participants. For example, the prediction module 1440 can average the binary values in the first set of outputs 1572 to calculate an overall completion probability for Group 1. The prediction module 1440 can proceed to use this value to calculate a predicted Group 1 size and/or percent representation.

Figure 15B:
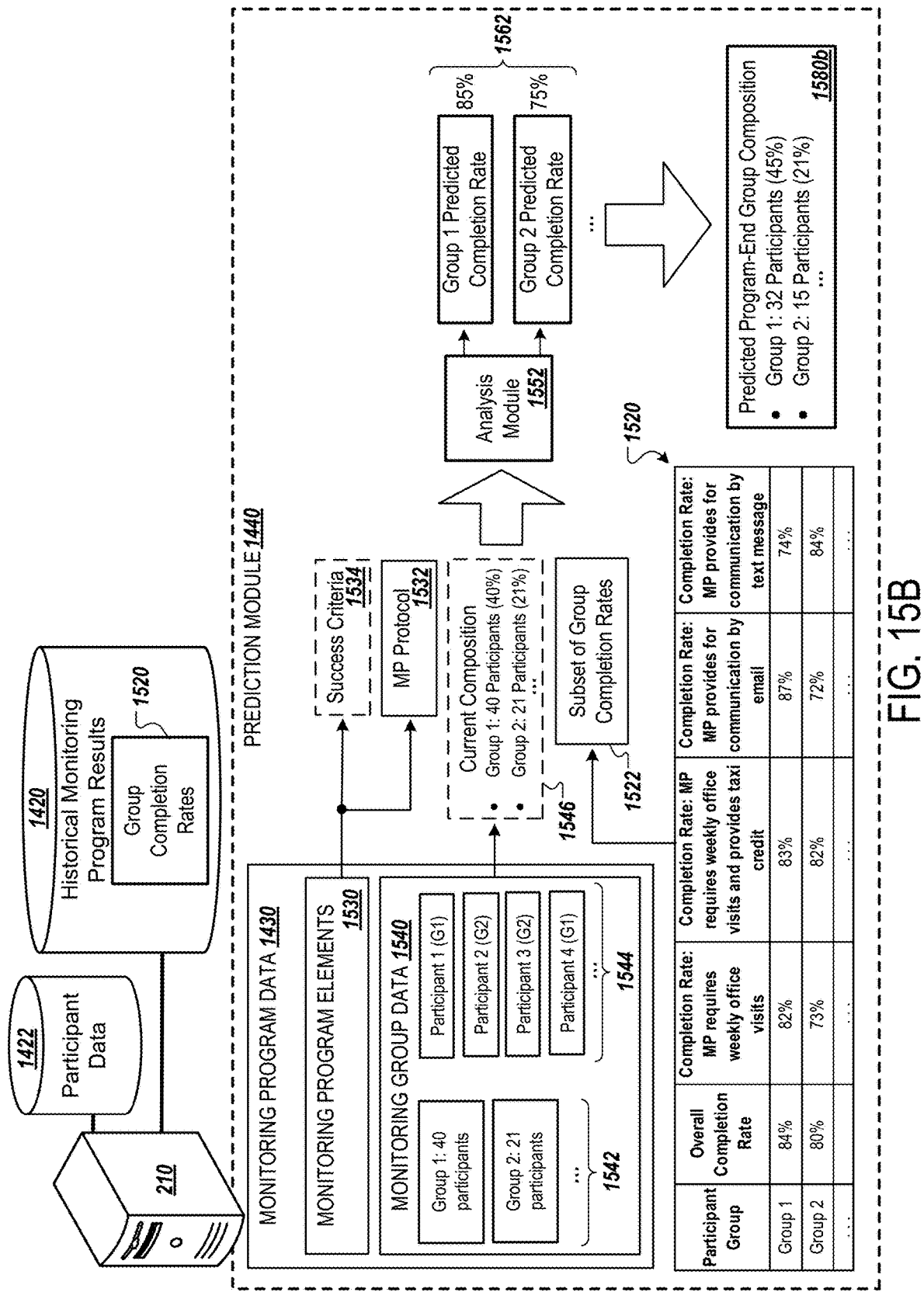

In FIG. 15B, the prediction module 1440 uses an analysis module 1552 to generate predictions. The analysis module 1552 can generate monitoring group 1402 predictions based on received portions of the monitoring program data 1430 and historical data. In more detail, the prediction module 1440 provides at least a portion of the monitoring program elements 1530, the monitoring group data 1540, and group completion rates stored in the database 1420 as input to the analysis module 1552. The analysis module 1552 may use this input data to generate outputs 1562 that are, or indicate, predicted completion probabilities for the monitoring group 1402's participants.

The analysis module 1552 can include statistical models (e.g., statistical algorithms), machine learning models, or a combination of statistical and machine learning models. The machine learning models optionally included in the analysis module 1552 can include one or more of a supervised learning model, an unsupervised learning model, a hybrid-learning model, or a reinforcement learning models.

In some implementations, the analysis module 1552 only includes a statistical model. For example, the analysis module 1552 can calculate anticipated completion rates using only one or more static algorithms without relying on any machine learning.

In some implementations, where the analysis module 1552 includes an ML model, the ML models may be trained using training data sets generated from historical data stored in the database 1420. Specifically, the computer system 210 can train the ML model using monitoring program data from previous monitoring programs.

The prediction module 1440 may obtain the monitoring program protocol 1532, the success criteria 1534, and the monitoring group data 1540 as described above with respect to FIG. 15A.

From the obtained monitoring group data 1540, the prediction module 1440 can determine a current composition 1546 for monitoring group 1402. The current composition 1546 can indicate composition characteristics present among the monitoring group 1402. The prediction module 1440 can use the participant attribute data 1544 and/or the participant group data 1542 in the monitoring group data 1540 to determine a current size and percent representation of each of the participant groups in the monitoring group 1402. For example, at the time the diversity analysis is imitated, the monitoring program 1402 may include one-hundred participants, forty of which belong to Group 1 and twenty-one of which belong to Group 2. The prediction module 1440 may extract this information from the monitoring group data 1540 and (i) include the information in the current composition 1546 and (ii) use it to determine a percent representation for each of the groups to include in the current composition 1546.

The prediction module 1440 can also obtain historical data stored in the database 1420. Alternatively, the prediction module 1440 can receive the historical data 1432 that was previously acquired from the database 1420. The historical data obtained by the prediction module 1440 can include all or a subset of group completion rates 1520 for various participant groups. As shown, the group completion rates 1520 can include multiple completion rates (e.g., retention rates) for each participant group for different monitoring program elements, such as particular monitoring group protocols. The group completion rates 1520 may also include a baseline rate for each of the participant groups that, for example, indicates an overall completion rate for the respective participant group. The analysis module 1552 may use the baseline rate for a participant group to determine if a particular program element (e.g., protocol entry) will have a beneficial or negative effect on the completion rate for that participant group.

The prediction module 1440 can identify from the group completion rates 1520 the subset of group completion rates 1522. The subset of group completion rates 1522 may include only those rates that correspond to a participant group represented in the monitoring program 1402 as indicated by the participant group data 1542, and that corresponds to at least one element in the monitoring program elements 1530. The subset of group completion rates 1522 can also include one or more baseline rates for each of the participant groups. For example, based on the participant group data 1542, the prediction module 1440 may filter the group completion rates 1520 to remove all rates that do not correspond to participant groups present in the monitoring group 1402. The prediction module 1440 can proceed to use by comparing the entries in the protocol 1532 to the remaining group of completion rates to identify a subset of group completion rates that match one or more entries of the protocol 1532. The prediction module 1440 may form the subset of group completion rates by filtering, from the remaining group of completion rates, all rates that are not a baseline rate (e.g., overall completion rate) and that were not identified as matching one or more entries of the protocol 1532.

The prediction module 1440 may provide the subset of group completion rates 1522 as input to the analysis module 1552 along with the other obtained data.

The analysis module 1552 can use the input data to generate output data 1562. The output data 1562 can include predicted completion rates for each participant group present in the monitoring group 1402. The analysis module 1552 can determine the predicted completion rates in variety of different ways. For example, the analysis module 1552 can identify and extract a single completion rate for each participant group from the subset of group completion rates 1522. Alternatively, the analysis module 1552 can use multiple completion rates to determine the effect of different monitoring program elements for each of the participant groups, and apply the effects to a corresponding baseline completion rate for each of the participant groups.

In more detail, in determining the outputs data 1562, the analysis module 1552 may identify a single completion rate from the subset of group completion rates for each participant group to include in the output data 1562. For example, the analysis module 1552 can compare the protocol 1532 to descriptions for different completion rates in the subset of group completion rates 1522 to identify a set of completion rates having a description that matches or is substantially similar to the protocol 1532. The analysis module 1552 can extract from the set of completion rates a completion rate for each participant group.

As another example, in determining the outputs data 1562, the analysis module 1552 can use multiple completion rates. Specifically, the analysis module 1552 may match different sets of completion rates (e.g., columns) in the subset of group completion rates 1522 to corresponding monitoring program elements such as entries in the protocol 1532. The module 1552 may proceed to determine the effect of the different protocol entries on the completion rates for each of the participant groups present in the monitoring program 1402 by comparing the completion rates to corresponding baseline completion rates (e.g., overall completion rate). For example, the analysis module 1552 may determine that the protocol entry of requiring weekly office visits is expected to reduce the completion rate for Group 1 participants by 2% (e.g., calculated by subtracting the completion rate of 82% for Group 1 participants when protocol requires weekly office visits from Group 1 baseline completion rate of 84%) and the completion rate for Group 2 participants by 7%.

Continuing this example, the analysis module 1552 may proceed to determine the effect that each of the protocol 1532 entries are likely to have on the baseline completion rate for each of the participant groups, and, from these sets of effects, calculate an predicted completion rate for each participant group.

After generating the output data 1562 by calculating a predicted completion rate for each participant group present in the monitoring group 1402, the prediction module 1440 can use the predicted completion rates to determine a predicted group composition 1580b. The prediction module 1440 can use the techniques described above with respect to FIG. 15A to generate the predicted group composition. As an example, the prediction module 1440 may apply the predicted completion rates to the current composition 1546 to obtain predicted sizes for each of the participant groups. The prediction module 1440 can then use the predicted sizes to calculate percent representations for each of the participant groups and/or to generate a predicted distribution.

The predicted group composition 1580b can also include other predicted composition characteristics, such as a diversity score as described in more detail above.

In some implementations, the prediction module 1440 does not provide the current composition 1546 as input to the analysis module 1552. The analysis module 1552 may use other information to predict completion rates for different participant groups. The prediction module 1440 can proceed to apply these predicted completion rates to the starting composition to determine the predicted group composition 1580b.

In some implementations, the predicted group composition 1580b is the output of the analysis module 1552. For example, when the prediction module 1440 provides the current composition 1546 as input to the analysis module 1552, the analysis module 1552 can first determine the output data 1562, and apply the output data 1562 that includes predicted completion rates to the current composition 1546 to obtain the predicted group composition 1580b.

In some implementations, the prediction module 1440 generates the subset of group completion rates 1522 from the historical data 1432. For example, the prediction module 1440 may identify monitoring programs that have the same monitoring program protocol as the monitoring program protocol 1532, or that have a substantially similar protocol (e.g., monitoring programs having protocols that include all or a threshold percent of the protocol entries found in the protocol 1532). The prediction module 1440 can proceed to extract or calculate completion rates for each participant group in the previous monitoring groups that is also represented in the monitoring group 1402. After extracting or calculating these completion rates from the historical data for the different participant groups, the prediction module 1440 can combine them to generate a single completion rate for each participant group. The prediction module 1440 can combine the various completion rates by averaging them, or by calculating a weighted average where, for example, a higher weight is afforded to more recent monitoring programs and/or to monitoring programs having protocols that more closely match the protocol 1532.

Figure 15C:
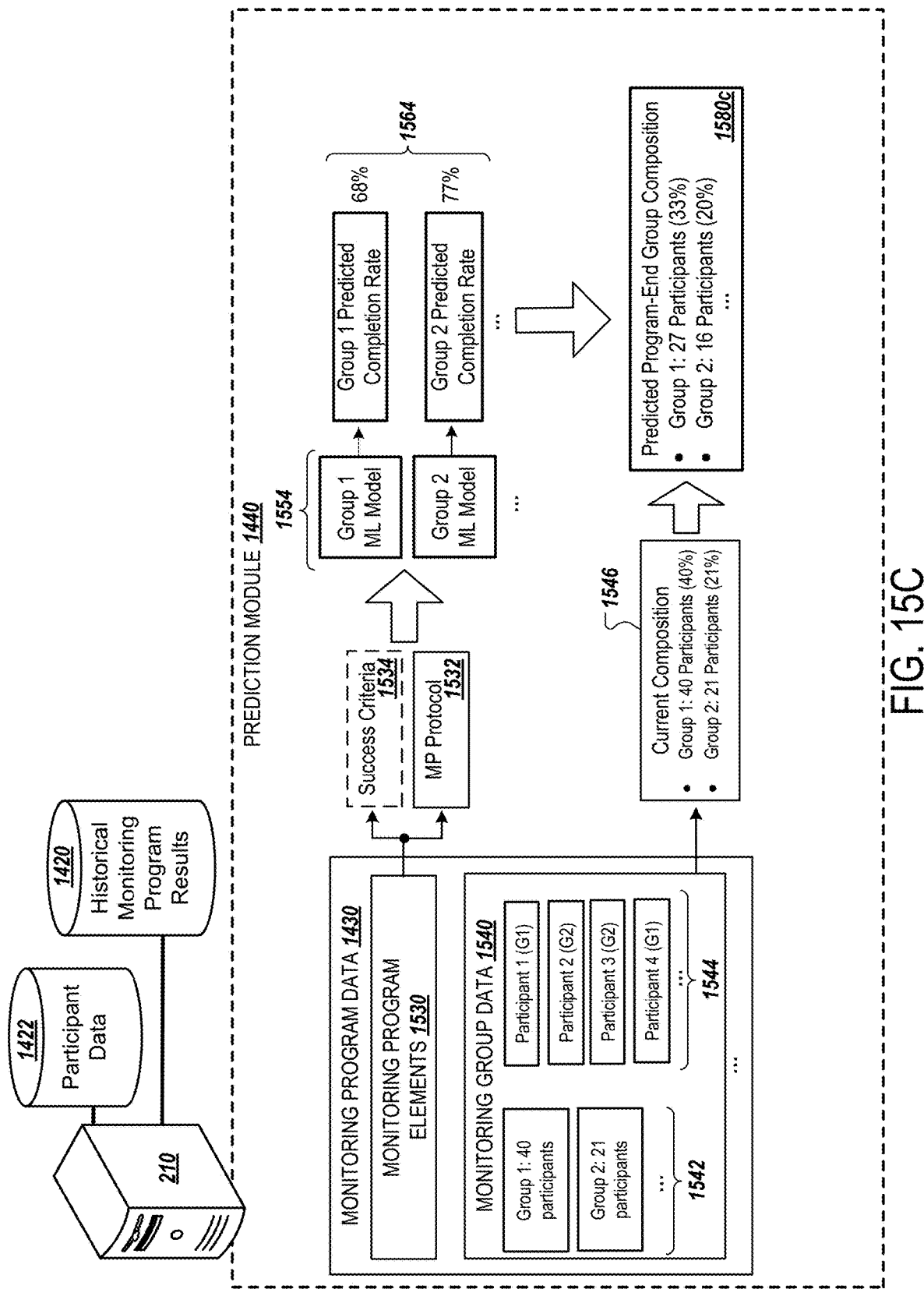

In FIG. 15C, the prediction module 1440 uses a set of multiple machine learning models 1554 to generate predictions. The ML models 1554 can generate monitoring group 1402 predictions based on received portions of the monitoring program data 1430. In more detail, the prediction module 1440 provides at least a portion of the monitoring program elements 1530 as input to the ML models 1554. The ML models 1554 can use this input data to generate outputs 1564 that are, or indicate, predicted completion probabilities for the participant groups present in the monitoring group 1402.

The ML models 1554 can include one or more types of ML models or algorithms. For example, the ML models 1554 can include one or more of a supervised learning model, an unsupervised learning model, a hybrid-learning model, or a reinforcement learning models.

The ML models 1554 may be trained using training data sets generated from historical data stored in the database 1420. Specifically, the computer system 210 can train the ML models 1554 using monitoring program data from previous monitoring programs. This monitoring program data can include protocols for the previous monitoring programs and/or success criteria for the previous monitoring programs.

As described above with respect to the ML models 1550 in FIG. 15A, the ML models 1554 may be trained to reduce a loss. The computer system 210 can determine the loss using predicted completion rates generated by the ML models 1554 for each participant group and corresponding actual completion rates for those participant groups as indicated by the historical data in the database 1420. As an example, the ML models 1554 can include regression loss models, classifiers (e.g., that outputs a value that corresponds to a particular classification represented by a particular completion rate percent or range of percent), and/or neural networks.

The prediction module 1440 can provide the protocol 1532 as input to each of the multiple ML models 1554. The prediction module 1440 may also provide the success criteria 1534 for the monitoring program as input to all or a subset of the ML models 1554.

As an example, if there is sufficient historical data to use for training a particular participant group, the prediction module 1440 may determine that it is not necessary to provide the success criteria 1534 as input to the ML models 1554. Similarly, if there is insufficient historical data to use for training a particular participant group, the prediction module 1440 may determine that it is necessary to provide the success criteria 1534 as input to the ML models 1554.

In some implementations, when the success criteria 1534 is not provided as input to the ML models 1554. The ML models 1554 may retrieve default success criteria for the monitoring program or for monitoring programs in general.

The ML models 1554 can use the input data to generate output data 1564. The output data 1564 can include, for example, a predicted completion rate for each participant group present in the monitoring group 1402. That is, each of the ML models in the ML models 1554 can generate a corresponding completion rate for their respective participant group.

In determining the completion rates for the different participant groups, the ML models 1554 may use similarities between the protocol 1532 and the protocols of past monitoring programs to determine the effect (e.g., effect on the completion rate) that the protocol 1532 is expected to have on participant retention in each of the participant groups. The ML models 1554 may use the success criteria 1534 to more accurately predict the completion rates. For example, if the historical data indicates that 75% of Group 1 participants from a previous monitoring program (e.g., having a matching or similar protocol to the protocol 1532) successfully completed the previous monitoring program but the success criteria for that program differs substantially from the success criteria 1534, then a ML model for Group 1 in the ML models 1554 (or the prediction module 1440) may first determine the completion rate for the past monitoring program for the Group 1 participant had the success criteria 1534 been applied to that program. Continuing the example, the Group 1 ML model may determine that the completion rate for the Group 1 participants would have only been 65% had the success criteria 1534 been used. The Group 1 ML model may proceed to use this value to determine the effects of the protocol 1532 on the completion rate for the Group 1 participants.

After the ML models 1554 output the predicted completion rates for the multiple participant groups present in the monitoring group 1402, the prediction module 1440 use the monitoring group data 1540 to determine a predicted group composition 1580c. For example, the prediction module 1440 can determine the current composition 1546 from the participant group data 1542. The prediction module 1440 can proceed to apply the predicted completion rates for each of the participant groups to corresponding group sizes in the current composition 1546 to determine predicted group sizes for each of the participant groups. After determining the predicted sizes, the prediction module 1440 can use the predicted sizes to determine percent representations for each of the participant groups and/or a predicted distribution.

As discussed above with respect to FIGS. 15A-15B, the predicted composition 1580c can include other predicted composition characteristics for the monitoring group 1402 such as a diversity score.

In some implementations, the ML models 1554 output a value for each participant group that corresponds to a particular classification. The prediction module 1440 may apply the values to a key to identify a classification for each of the participant groups. As an example, the classifications can correspond to 5% ranges where an output value of 0.5 corresponds to a classification for a 50% completion rate, and an output value of 0.57 corresponds to a classification for a 55% completion rate.

Figure 15D:
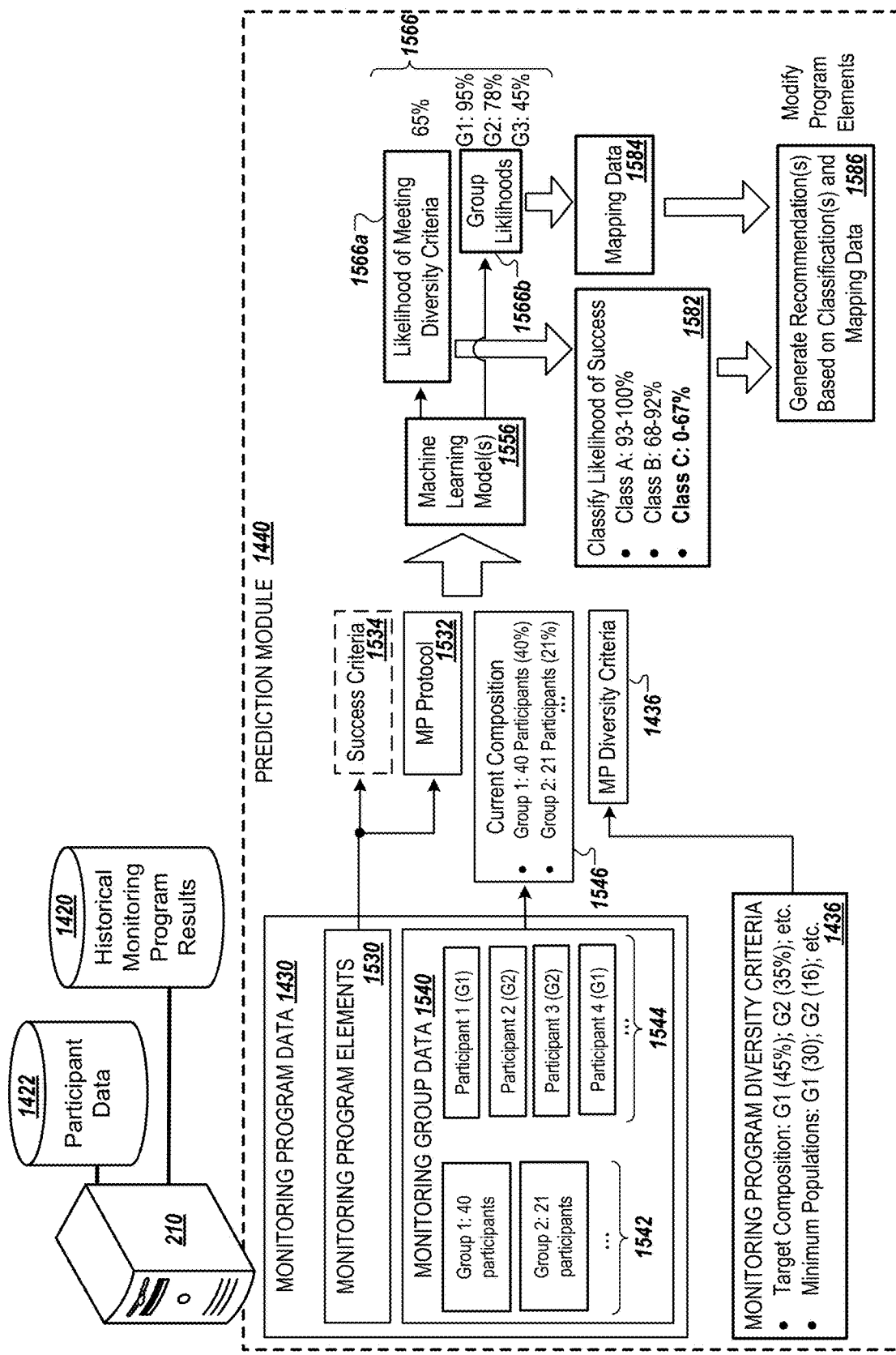

In FIG. 15D, the prediction module 1440 uses one or more machine learning models 1556 to generate predictions. The ML models 1556 can generate monitoring group 1402 predictions based on received portions of the monitoring program data 1430 and the diversity criteria 1436. In more detail, the prediction module 1440 provides at least a portion of the monitoring program elements 1530, the monitoring group data 1540, and the diversity criteria 1436 as input to the ML models 1556. The ML models 1556 can use this input data to generate outputs 1566 that are, or indicate, likelihoods for meeting the diversity criteria 1436.

The ML models 1556 can include one or more types of ML models or algorithms. For example, the ML models 1556 can include one or more of a supervised learning model, an unsupervised learning model, a hybrid-learning model, or a reinforcement learning models.

The ML models 1556 may be trained using training data sets generated from historical data stored in the database 1420. Specifically, the computer system 210 can train the ML models 1556 using monitoring program data and diversity criteria from previous monitoring programs. This monitoring program data can include protocols for the previous monitoring programs, success criteria for the previous monitoring programs, and/or the monitoring group data for previous monitoring programs.

As described above with respect to the ML models 1550 in FIG. 15A and the ML models 1554 in FIG. 15C, the ML models 1556 may be trained to reduce a loss. The computer system 210 can determine the loss using predicted likelihoods generated by the ML models 1556 (e.g., overall likelihood of meeting diversity criteria and/or likelihood of each participant group meeting diversity criteria) and corresponding observed likelihoods as indicated by the historical data in the database 1420. As an example, the ML models 1556 can include regression loss models, classifiers (e.g., that outputs a value that corresponds to a particular classification represented by a particular likelihood percentage or range of percentages), and/or neural networks.

In some implementations, the ML models 1556 include a ML model for each participant group. For example, the ML models 1556 can include a first ML model for Group 1 and a second ML model for Group 2. Each of the multiple models may be trained using different data sets that correspond to their respective participant group. Each of the multiple models can be configured to predict a likelihood of corresponding participant group meeting the diversity criteria 1436 for the monitoring program.

The prediction module 1440 can provide the protocol 1532, the current composition 1546, and the diversity criteria 1436 as input to each of the ML models 1556. The prediction module 1440 may also provide the success criteria 1534 for the monitoring program as input to the ML models 1556.

As an example, the ML models 1556 can use the input data to generate group likelihoods 1566b for each participant group represented in the monitoring group 1402. The prediction module 1440 can use the resulting group likelihoods 1566b of the output data 1566 to calculate an overall likelihood 1566a of the monitoring group 1402 meeting the diversity criteria. For example, an algorithm in the ML models 1556 may be used to calculate the overall likelihood 1566a from the group likelihoods 1566b by averaging the group likelihoods 1566b or using a weighted average of the 1566b where the weight applied corresponds to current or predicted percent representation of each of the participant groups in the monitoring group 1402.

The prediction module 1440 can classify the output data 1566 and use the classifications to generated recommendations. For example, the prediction module 1440 can apply classifications 1582 to the overall likelihood 1566a to determine a warning level for the monitoring program at its current stage. As shown, based on the overall likelihood 1566a being 65%, the prediction module 1440 can determine that the most-at-risk warning level (e.g., Class C) applies to the monitoring programs. The different warning levels can correspond to different recommended actions, different variable values for recommended actions (e.g., number of participants recommended to be enrolled in the monitoring program, the amount of taxi credit provided to participants, etc.), and/or different number of recommended actions.

For example, based on an overall likelihood meeting the least-at-risk warning level (e.g., Class A), the prediction module may determine that recommended actions are limited to 1-2 actions and that the recommended actions should not include modifications to the monitoring program elements. In contrast, based on the overall likelihood 1566a meeting the most-at-risk warning level, the prediction module may determine that at least two recommended actions should be performed and that the recommended actions should include at least one modification to the monitoring program elements.

The prediction module 1440 may similarly apply mapping data 1584 to the group likelihoods to identify the participant groups that are anticipated to cause the most problems with respect to the diversity criteria 1436. As an example, the mapping data 1584 can include likelihoods or ranges of likelihoods for different participant groups, and corresponding recommended actions or sets of recommended actions that are anticipated to improve those likelihoods. The prediction module 1440 can proceed to match the individual likelihoods in the group likelihoods 1566b to corresponding values or ranges in the mapping data 1584 to identify a set of one or more recommended actions for each of the participant groups.

As another example, the mapping data 1584 can include various recommendations and sets of recommendations and their corresponding effect on group likelihoods for different groups. The prediction module 1440 can determine, e.g., based on the diversity criteria, a minimum group likelihood needed for each of the participant groups or for all participant groups. Once the minimum likelihood(s) are determined, the prediction module 1440 can find a difference between the minimum likelihoods and the likelihoods in the group likelihoods to identify the likelihood difference that needs to be made up for each of the groups. The prediction module 1440 can use the likelihood differences for each of the participant groups to identify recommended actions and/or sets of recommended actions for the corresponding participant group. For example, if the minimum likelihood for each of the groups is determined to be 80%. The prediction module 1440 may determine that no actions need to be taken with respect to Group 1 participants, that recommendations corresponding to a difference of 2% need to be taken with respect to Group 2 participants, and that recommendations corresponding to a difference of 35% need to be taken with respect to Group 3 participants. Based on this, the mapping data 1584 may indicate that additional or more significant actions need to be taken with respect to the Group 3 participants based on the significant difference between the predicted likelihood for Group 3 and the minimum likelihood.

The mapping data 1584 selected can be based on the classification determined for the overall likelihood 1566a. For example, the mapping data 1584 that the prediction module 1440 applies to the group likelihoods 1566b may be for when the monitoring group 1402 is most-at-risk of not meeting the diversity criteria 1436. The recommended actions and/or sets of recommended actions in the mapping data 1584 may include those that have an additional number of recommendations and/or larger variable values so that the effect of the actions on the monitoring program is more significant.

The mapping data 1584 can be generated by the computer system 210 using historical data in the database 1420. For example, the computer system 210 can identify from the historical data monitoring programs with matching or similar protocols to the protocol 1532, and map the effects of different actions or monitoring program elements on different participant groups in those monitoring programs.

In some implementations, the mapping data 1584 is specific to the diversity criteria 1436. For example, the mapping data 1584 may be generated (e.g., from default mapping data or otherwise existing mapping data) to take into account the diversity criteria 1436 for the monitoring program. If, for example, the diversity criteria is particularly strict, then the mapping data 1584 may indicate that additional actions are needed and/or actions with larger variable values are needed (e.g., more participants to be invited and/or enrolled in the monitoring program than what would be recommended with less strict diversity criteria).

Based on the application of the classifications 1582 to the overall likelihood 1566a and the mapping data 1584 to the group likelihoods to the mapping data 1584, the prediction module 1440 can determine a set of one or more actions 1586 to recommend. The recommended actions 1586 may include those in the mapping data 1584 that have been shown to improve the likelihoods to the extent needed for different participant groups. The recommended actions 1586 may include different actions or sets of actions for different participant groups. For example, based on only Group 2 and Group 3 having a predicted likelihood less than a minimum ally acceptable likelihood, the recommended actions may include only a first set of actions to improve the likelihood for Group 2 and a second set of actions to improve the likelihood for Group 3. The prediction modules may uses the actions in the first set and the actions in the second set to form recommendations, where recommendations include at least one action from the first set corresponding to Group 1 and one action from the second set corresponding to Group 2.

The prediction module 1440 may also verify that a set of recommended actions is anticipated to produce an overall likelihood 1566a that is in the leas-at-risk warning level, or that at least removes the overall likelihood 1566a from the most-at-risk warning level. For example, the prediction module 1440 may perform additional diversity analyses that each assume a corresponding set of recommended actions has been performed.

In some implementations, the prediction module 1440 uses both monitoring group data for the current monitoring group 1402 and monitoring group data for a starting monitoring group. For example, after predicting completion rates for different participants or groups of participants, the prediction module 1440 can use the starting composition for the monitoring program 1402 to calculate a predicted retention rate for each participant or group of participants.

As demonstrated throughout FIGS. 15A-15D, the results or output of the prediction module 1440 may vary based on the technique(s) implemented by the prediction module 1440. In some cases, the prediction module 1440 may perform multiple analyses using different techniques and then combine the respective results to obtain a more accurate result. For example, the prediction module 1440 may perform a first diversity analysis using the ML models 1550 in FIG. 15A to obtain the predicted group composition 1580a and perform a second diversity analysis using the analysis module 1552 (e.g., at substantially the same time) to obtain the predicted group composition 1580b. The prediction module 1440 can proceed to average the predicted group sizes for each of the participant groups and use the updated group sizes to calculate updated percent representations for each of the participant groups. The computer system 210 can use the resulting predicted group composition to compare to the diversity criteria 1434, and use to determine a set of recommended actions.

In some implementations, the computer system 210 determines to perform multiple analyses when certain conditions are met. For example, the computer system 210 may allow the prediction module 1440 to use multiple techniques when load or user traffic on the system 210 is below a threshold amount (e.g., in an off-peak time period), when load or user traffic on the system 210 is anticipated to be below a threshold amount (e.g., in an anticipated off-peak time period). Similarly, the computer system 210 may permit the use of multiple techniques when sufficient resources are available, but then limit the prediction module to a single technique when resources are more limited.

In some implementations, the computer system 210 selects which of the multiple techniques to have the prediction module 1440 perform based on detected server conditions. For example, based on the load on the system 210 and/or the amount of resources that are available for use, the computer system 210 may permit the prediction module 1440 to use techniques that require additional processing power or resources or may limit the prediction module 1440 to those techniques that require the least amount of processing power or resources. Specifically, during high-load times, the computer system 210 may limit the prediction module 1440 to use of the analysis module 1552 shown in FIG. 15B which may require less processing power due to using, in some examples, statistical models instead of machine learning models.

FIGS. 16A-16D are diagrams that illustrate example interfaces for diversity prediction. The interfaces can be used to communicate predictions made by the computer system 210 to a user of the client device 204, such as a researcher or an administrator. This information can help the users of the client device 204 quickly understand the health of the monitoring program. In more detail, the interfaces can be presented on the client device 204 based on notifications generated and sent by the computer system 210 in response to detecting events, such as a predicted lack of diversity in the monitoring group 1402 of the corresponding monitoring program. For example, the computer system 210 may perform a diversity analysis periodically or in response to detecting particular events to verify that the monitoring group 1402 is on track to achieve a minimum level of diversity in the future. The notifications sent to and displayed on the client device 204 can include a variety of information, including, for example, an indication that a particular event has occurred that has triggered a diversity analysis or that a scheduled diversity analysis has been started. More detailed notifications can include the results of the diversity analysis which can include various predictions made by the computer system 210 and, in some implementations, details as to how the computer system 210 made the predictions, such as information that the computer system 210 relied on to make the predictions. This additional insight can provide users of the client device 204 a better understanding of how the computer system 210 is making its predictions, which can help the users identify causes for inaccurate predictions and/or explain away divergences between the users' expectations the system 210's predictions. Moreover, the more detailed information may also educate users as to how to better configure a monitoring program to achieve particular outcomes, such as to avoid certain elements when participants from particular diversity groups are included in the program.

The interfaces can also be used to facilitate user interactions to improve diversity of monitoring groups. For example, the computer system 210 can communicate a set of one or more recommended actions that it predicts will improve the diversity of the monitoring group 1402. The client device 204 may receive a notification that indicates that the system 210 will perform at least one of the recommended actions automatically, or, alternatively, can receive a notification that requests a user to select an action from the set for the system 210 to perform. The interfaces can also prompt the users for other information such as the selection (or verification) of particular subjects to add to the monitoring group 1402, the addition of a program element, the removal of a program element or selection of program element recommended for removal, the entering or selection of values for program settings (e.g., data request frequency, etc.). The computer system 210 can use the user interactions to improve its decision making in the future. For example, the computer system 210 can use the selections made by the users of the client device 204 and/or the values provided by the users of the client device 204 to train the prediction module 1440, train one or more modules used to determine recommended actions, and/or update user preferences. This training and/or updates can have the beneficial effects of improving the predictions made by the system 210, improving the recommended actions generated by the system 210, and/or reducing the need for user input or the extent of input required in the future.

The interfaces can be configured in a variety of ways based on, for example, a software configuration corresponding to the particular monitoring program, and/or preferences associated with the client device 204 or associated with particular users of the client device 204. For example, the computer system 210 may provide the client device 204 a particular software package that corresponds to the monitoring program and/or a particular admin/researcher for the monitoring program. The software package may dictate how notifications are presented on a display of the client device 204, the form and/or type of notifications that are sent to the client device 204, and/or how a mobile application corresponding to the monitoring program is displayed on a display of the client device 204.

FIG. 16A illustrates example diversity assessment and action selection interface 1600a during a monitoring group selection stage of a monitoring program. The interface 1600a may be presented on the client device 204. For example, the interface 1600a may be presented on a display of the client device 204 after a researcher cohort selection stage of a study. The interface 502a may be presented on the client device 204. As an example, the interface 1600a may be presented on the client device 204 after (e.g., in response to) the researcher 202 submitting a research question or study objective (e.g., optionally along with other study information initially submitted by the researcher 202). The interface 1600a may present various diversity metrics calculated by the computer system 210 and recommendations generated by the computer system 210, such as the recommended actions 1586 shown in FIG. 15D. The researcher 202 may interact with the interface 1600a to, for example, select or confirm a recommendation of the computer system 210 for the computer system 210 to perform, adjust monitoring program elements such as a monitoring program protocol and monitoring program parameters, select users to enroll in a study, select users to invite to the study, confirm the enrollment or invitation of users recommended by the computer system 210, etc.

The interface 1600a includes a monitoring program elements section 1610, a monitoring group section 1620, a diversity analysis results section 1630, and a recommendation section 1640. The researcher 202 may, for example, use the interface 1600a to review recommendations generated by the computer system 210 at different times in the study. The researcher 202 may interact with the interface 1600a to select or confirm the performance of one or more recommended actions.

In some implementations, the researcher 202 does not need to make a selection or confirmation of recommended actions. For example, the recommendation section 1640 may instead serve as a notification area to notify the researcher 202 of the actions that have or will be taken by the computer system 210, and/or to provide insight as to the computer system 210's predicted effects of actions on the composition of the monitoring group 1402.

The researcher 202 may be able to also use the interface 1600a to indicate one or more actions to be performed by the computer system 210, e.g., that may not have been recommended. For example, the researcher 202 may, through the interface 1600a, modify the monitoring program elements. Specifically, the researcher 202 can use the interface 1600a to update a protocol for the monitoring program, change diversity or success criteria for the monitoring program, etc.

As shown, the monitoring program elements section 1610 may include various program elements for a particular monitoring program. For example, the monitoring program elements section 1610 may include a monitoring program size 1611, a monitoring program length 1612, a monitoring program protocol 1613, inclusion criteria 1614, exclusion criteria 1615, a target date 1616, and diversity/success criteria 1617.

The monitoring program elements in the section 1610 can be set by the researcher 202, the computer system 210, or a combination of the researcher 202 and the computer system 210.

The monitoring group section 1620 includes information for the participants enrolled in the monitoring program, or participants that have been or are to be invited to the monitoring program. As an example, the section 1620 may display the monitoring group data 1540 or the participant attribute data 1544 described above with respect to FIGS. 15A-15D. As shown, the section 1620 includes a name or identifier for each participant that has been enrolled in or invited to the monitoring program. For example, the section 1620 can include the names or identifiers for each participant in the monitoring group 1402. The section 1620 can also display other information such as an indication of the diversity groups that each participant corresponding to the monitoring program belongs to, and/or attributes for each of the participants. For example, as shown, a first participant enrolled in the monitoring group for the monitoring program belongs to the Group 2 diversity group.

The diversity analysis results section 1630 depicts the results of a diversity analysis performed by the computer system 210 prior to the end of the monitoring program. The results of the diversity analysis presented may have been generated by the prediction module 1440. The diversity analysis results section 1630 can include predicted composition characteristics for a monitoring group. For example, as shown, the section 1630 includes percent representations for different diversity groups (e.g., participant groups) in the monitoring group at the end of the monitoring program and a predicted diversity level (e.g., diversity score) for the monitoring group at the end of the monitoring program.

The section 1630 can present other information related to predicted composition characteristics for the monitoring group. Specifically, the section 1630 may present diversity criteria, such as a program-end target composition for the monitoring group. The section 1630 can also present current monitoring group data such as a current group composition of the monitoring group. The section 1630 may also present warnings or alerts generated as a result of the diversity analysis. For example, based on the computer system 210 determining that the predicted group composition diverges beyond a threshold percentage from the target composition, the computer system 210 can send instructions to present a warning that the predicted group composition is outside of target composition range. The computer system 210 can identify and generate instructions to present other alerts or warnings, such as alerts when the predicted diversity level does not meet a minimum diversity level and/or when a predicted diversity group size does not meet a minimum group size.

The recommendation section 1640 can include one or more actions or sets of actions recommended by the computer system 210 based on the diversity analysis results presented in section 1630. The computer system 210 may determine the recommended actions using the techniques described above with respect to FIGS. 14 and 15A-15D. For example, the computer system 210 can determine a set of recommended actions to improve diversity of the monitoring group at a future time based on predicted composition characteristics generated by the prediction module 1440 for the monitoring group 1402. Similarly, the prediction module 1440 can generate an output that indicates the recommended actions to perform to improve the diversity of the monitoring group 1402 at a future time.

The recommended actions may be selected by the computer system 210 based on the computer system 210 determining that the effects the recommended actions will have on the monitoring group will result in the diversity/success criteria 1617 being met or in improvement to the likelihood of the diversity criteria 1617 being met at a future time such as at the end of the monitoring program.

For each set of recommended actions, the computer system 210 may perform a diversity analysis that assumes that the corresponding set of recommended actions have been performed. The computer system 210 may use the results of the diversity analysis to rank different sets of one or more recommended actions. As described in more detail below, the sets of recommended actions may be presented on the interface 1600a in an order corresponding to their rank. Similarly, only a subset of the sets of recommended actions may be presented on the interface 1600a, such as the highest ranking set, the top three highest rankings sets, etc.

As an example, the computer system 210 determine a first set of recommended actions that includes adding taxi cred and sending enrollment invitations to additional eligible Group 2 subjects (e.g., Group 2 subjects that are not currently enrolled in the monitoring program, were not previously enrolled in the monitoring program, and/or are active). The computer system 210 may predict, e.g., using the prediction module 1440, that should the first set of recommended actions be performed, the predicted diversity score will be improved so that it meets the minimum diversity score as required by the diversity/success criteria 1617. The computer system 210 may also predict that the group composition of the monitoring group is anticipated to substantially match or diverge less than a threshold percentage from the target composition at the end of the monitoring program.

The diversity level (e.g., diversity score) may indicate the extent that the predicated composition characteristics of the monitoring group meet the diversity/success criteria 1617, and/or the likelihood of the monitoring program successfully meeting the diversity/success criteria 1617 at a future time, such as at program completion. The diversity level may be, for example, a diversity score. As an example, the diversity level may be a single value that is indicative of how close the predicted group composition for the monitoring group at program completion is to the target group composition. As an example, a diversity score of 1.0 may indicate that the predicted group composition at program completion matches the target group composition. The diversity score may be absolute, or it may be relative, e.g., relative to a previously predicted group composition at program completion or relative to the predicted group composition at program completion of one or more other recommendation options. Additionally or alternatively, the diversity level may be, for example, a calculated distribution (e.g., probability distribution). This diversity distribution may, for example, indicate probabilities of achieving the target group composition or other diversity criteria (e.g., after performing actions corresponding to a particular recommendation option).

The diversity level can indicate a level of confidence in achieving the diversity/success criteria 1617. For example, the diversity level can indicate a level of confidence in the monitoring group achieving the target group composition, and/or achieving a group composition that is with an acceptable range (e.g., percent range or value range) of the target group composition. For example, a diversity score of 0.91 may indicate that the computer system 210 has determined that there is 91% possibility of the group composition of the monitoring group at program completion being within a threshold percent (e.g., 5%, 3%, 1%, etc.) of the target group composition provided that the actions corresponding to the recommendation option are performed.

In some implementations, the computer system 210 calculates multiple diversity scores for different diversity criteria in the diversity/success criteria 1617. The computer system 210 may use these different scores to generate the diversity level, e.g., by taking the average or weighted average of the different scores.

In some implementations, there are multiple diversity levels (e.g., diversity metrics) that include both one or more singular values, and one or more distributions. For example, a first diversity level may include a diversity distribution indicating different likelihoods of achieving the target group composition 522, and a diversity score may be second diversity level identified from the diversity distribution (e.g., as the value associated with the highest probability out of the all of the values).

As discussed above, the computer system 210 may rank the recommendations based on one or more diversity metrics (e.g., diversity levels) calculated for the recommendations. For example, the computer system 210 may rank the recommendations presented in the recommendation section 1640 according to a predicted diversity score for each of the sets of recommend actions (e.g., that indicate the anticipated diversity of the monitoring group at the end of the monitoring program should the actions in the corresponding recommendation be performed). The predicted diversity score is likely to be higher if the actions in the recommended set of actions are predicted to produce a group composition that matches or gets sufficiently close (e.g., with respect to the performance of actions in other recommendations) to the target group composition. The computer system 210 may provide instructions to the client device 204 to have the recommendations presented on the interface 1600a according to their rank. By ranking the sets of recommended actions according to their influence in achieving the diversity/success criteria 1617 and, therefore, their influence in on the study's ability to produce viable data, the computer system 210 can (i) more efficiently present its recommendations to the researcher, and/or (ii) take greater advantage of the limited screen space available on the client device 204 (or a display connected to the client device 204).

In some implementations, computer system 210 may only recommend a threshold number of sets of recommended actions (e.g., for display on the client device 204) and/or only transmit a threshold number of sets of recommended actions to the client device 204. For example, the computer system 210 may only recommend the two, three, or four highest ranking sets of recommended actions for display on the interface 1600a of the client device 204. The threshold may be selected by the researcher 202 or may be automatically determined by the computer system 210. As an example, the computer system 210 may determine the threshold based on diversity scores associated with the different sets of recommended actions, and/or based on the difficulty of the actions in the sets of recommended actions.

Prior to recommending a set of actions, the computer system 210 may first ensure that the corresponding prospective sets of recommended actions meet certain criteria. For example, the computer system 210 may first apply a minimum anticipated diversity level threshold to each set of recommended actions before it can be presented on a display of the client device 204 and/or sent to the client device 204. For example, the computer system 210 may apply a static threshold of 0.90 to the predicted diversity score. The diversity level threshold may instead be dynamic, e.g., based on a current predicted diversity level at the end of the monitoring program, based on historical data for the diversity groups being invited to participate in the monitoring program or enrolled in the monitoring program, based on the trends for the groups being invited to participate in the study, etc. By presenting only a subset of the sets of recommended actions that meet certain quality criteria, the computer system 210 can (i) more efficiently present the key recommendations to the researcher that are likely to have at least a minimum beneficial effect on meeting the diversity needs of the monitoring program by the program's completion, and/or (ii) take greater advantage of the limited display space available on the client device 204 (or a display connected to the client device 204) by removing the need to devote space to recommendations that are unlikely or less likely to achieve the diversity needs of the monitoring program.

FIG. 16B illustrates example interface 1600b for communicating diversity assessment information. The interface 1600b may be presented on the client device 204. However, the interface 1600b may be presented on other devices, such as those belonging to participants in the monitoring group 1402, those belonging to other researchers, or other devices of the researcher 202.

As shown, the interface 1600b may first display an event notification 1650 that indicates that a scheduled diversity analysis has been initiated or set to begin in the near future. The interface 1600b next presents an alert notification 1652 that indicates that the diversity analysis was performed but an error was detected. As an example, the computer system 210 may have detected an error based on the predicted composition of the monitoring group failing to meet certain diversity criteria corresponding to a particular diversity group.

The interface 1600b may next presents an interactive notification 1654 that requests that a user confirm the performance of at least one recommended actions. A user can make selections of interface elements presented in the notification 1654. For example, a user can interact with different interface elements that correspond to individual recommended actions or to sets of recommended actions. The user can select one or more of the interface elements. In response to the selection, the client device 204, for example, can generate instructions for the computer system 210 to perform the one or more actions corresponding to the selection(s) made. As shown, a user has selected an interface element that correspond to the performance of both a first recommended action and a second recommended action.

The notification 1654 can also present other information such as predicted effects that the different recommendation options will have on the monitoring program, or predicted composition characteristics of the monitoring group should the recommendation options be performed. For example, the notification 1654 can display next to each recommendation option a corresponding predicted group size for the particular diversity group should the recommendation option be performed by the computer system 210.

The interface 1600*b* may next display a confirmation notification 1656 that confirms the selection of the recommendation option. In some implementation, the notification 1656 may include an interface element or a temporary interface element that allows a user to undo the confirmation of the recommendation option.

FIG. 16C illustrates example interface 1600*c* for communicating diversity assessment information. The interface 1600*c* may be presented on the client device 204. However, the interface 1600*c* may be presented on other devices, such as those belonging to participants in the monitoring group 1402, those belonging to other researchers, or other devices of the researcher 202.

As shown, the interface 1600*c* may first display an alert notification 1660 that indicates that an event has been detected and that a diversity analysis has been, or will be, performed in response to the detected event. As an example, the detected event may be that a participant in a monitoring group has been active for a threshold amount of time. Other events that may trigger a diversity analysis can include, for example, detected modifications to the elements of a monitoring program, and changes to the enrollment of a monitoring program.

The interface 1600*c* next presents an alert notification 1662 that indicates that the diversity analysis was performed but an error was detected. As an example, the computer system 210 may have detected an error based on predictions for a particular diversity group indicating that there is an insufficient likelihood of diversity criteria for the diversity group being met by the end of the monitoring program. In more detail, based on a participant (User A) no longer being compliant with the protocol for the monitoring program and belonging to two diversity groups (Group 3 and Group 4), the computer system 210 may generate predictions for the two diversity groups to determine if corresponding diversity criteria is on track to be met by the end of the monitoring program without the participant. As shown, the computer system 210 may use a trend 1664 for the first of the two diversity groups to determine that the first diversity group in the monitoring group is still on track to meet corresponding diversity criteria by an end of the monitoring program, such as a minimum retention rate for the first diversity group. However, the computer system 210 may use a second trend 1666 for the second of the two diversity groups to determine that the second diversity group in the monitoring group is no longer on track to meet the corresponding diversity criteria by the end of the monitoring program, such as a minimum retention rate for the second diversity group.

The alert notification 1662 can include additional information including other prediction made by the computer system 210. For example, the alert notification 1662 can include a likelihood corresponding to first diversity group analysis that indicates the probability that diversity criteria corresponding to the first diversity group will be met by the end of the monitoring program. The alert notification 1662 can include a similar likelihood for the second diversity group.

FIG. 16D illustrates example interface 1600*d* for communicating diversity assessment information. The interface 1600*d* may be presented on the client device 204. However, the interface 1600*d* may be presented on other devices, such as those belonging to participants in the monitoring group 1402, those belonging to other researchers, or other devices of the researcher 202.

As shown, the interface 1600*d* may first display an alert notification 1670 that indicates that an event has been detected and that a diversity analysis has been, or will be, performed in response to the detected event. As an example, the event may be that the computer system 210 has modified an element of the monitoring program or has detected a modification to the monitoring program.

The interface 1600*d* next presents a diversity analysis notification 1672 that indicates that the diversity analysis was performed and no errors were detected. The notification 1672 may include other information such as predicted composition characteristics of the monitoring group that were generated during the diversity analysis, and/or a future time corresponding to the prediction (e.g., a set time for program's end). For example, the notification 1672 can include a predicted distribution 1674 for the monitoring group at scheduled program end date. The distribution 1674 can be displayed with diversity criteria overlain on the distribution 1674 to show, in this example, that the distribution 1674 met the corresponding diversity criteria. For example, the notification 1672 may overlay the distribution 1674 with minimum sizes for each diversity group and minimum percent representation for each diversity group. As another example, the notification 1672 may overlay the distribution 1674 with a target distribution of the diversity criteria.

The distribution 1674 and corresponding diversity criteria in the notification 1672 can assist a user by signaling to them which diversity groups in the monitoring program are most likely and the least likely of meeting the diversity criteria. The notification 1672 may also provide other information that can assist a user in understanding the techniques used by the computer system 210 in performing the diversity analysis, such as the trends 1664 and 1666 described above with respect to FIG. 16C.

Figure 17:
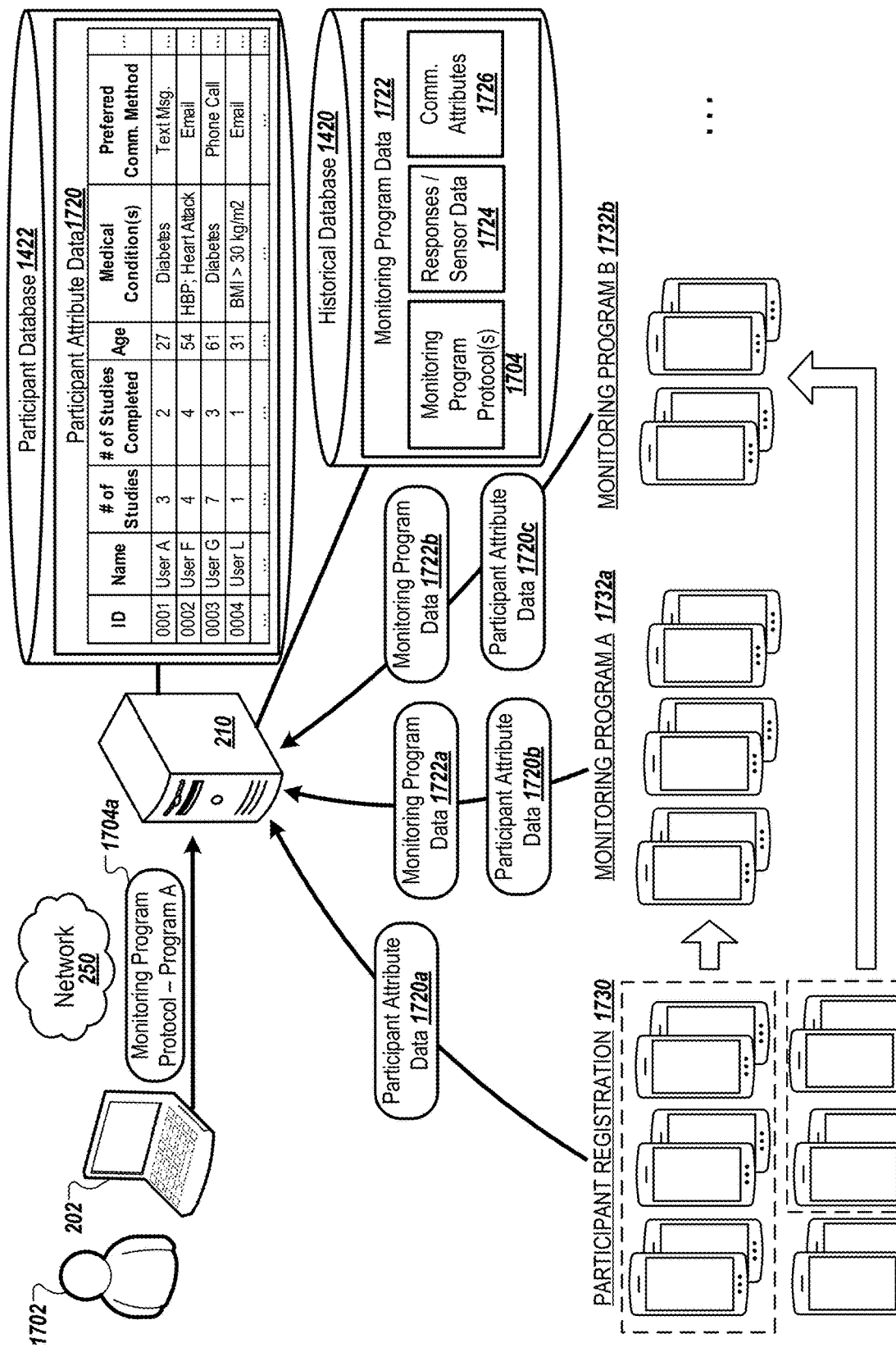
FIG. 17 is a diagram that illustrates an example system for managing monitoring programs.

FIG. 17 is a diagram that illustrates one or more components of the system 200 for managing monitoring programs. The diagram depicts how the computer system 210 can collect various types of information from participants at different stages in the computer system 210's management of monitoring programs. The computer system 210 can also collect information from multiple monitoring groups corresponding to different, ongoing monitoring programs. Using the collected data, the computer system 210 can update information stored in its databases, such as the participant attribute data 1720 stored in the participant database and historical monitoring program data 1722 stored in the historical database 1420. The updated information can be used to improve later predictions made in the ongoing monitoring programs. For example, the computer system 210 may update the databases 1420 and 1422 in real-time or near real-time as information is collected from the remote devices and processed. By quickly processing and storing the collected information, the computer system 210 can improve the accuracy of predictions made and the number of predictions that are made using the most up-to-date information.

As shown, the database 1420 can store the monitoring program data 1722 from multiple monitoring programs. The monitoring program data 1722 can be limited to previous monitoring programs that have concluded. Alternatively, the monitoring program data 1722 can also include information collected from monitoring programs that are ongoing. The monitoring program data 1722 can include protocols 1702 for multiple monitoring programs, responses and sensor data 1724 collected from participant devices in multiple monitoring groups, and communication attributes 1726. The communication attributes 1726 can include characteristics of notifications sent to the participant devices used in the multiple monitoring programs. For example, the communication attributes 1726 can include indications of communication channels, word choices, sentence structures, message types, responses requested, response types, message content, transmission times, message sizes, etc. sent by the computer system 210 to the participant devices.

The database 1422 can store participant attribute data 1720. The participant attribute data 1720 can include demographic and non-demographic attributes for each participant that has enrolled in at least one monitoring program, or that has registered with the computer system 210 so that they can be invited or enrolled in future monitoring programs. As shown, the participant attribute data 1720 can include identifiers assigned by the computer system 210 to the participants, names for the participants, an indication of the number of studies the participants have enrolled in, an indication of the number of studies the participants have successfully completed, an age of the participants, medical conditions of the participants, and preferences of the participants such as preferred communication channels, times, or frequencies. The attribute data 1720 can include other attribute information for the participants such as atypical or notable behaviors for the participants, or trends corresponding to the users. For example, the attribute data 1720 can indicate those participants that typically fail to take prescribed medication consistently. The computer system 210 may use this information to, for example, avoid enrolling those participants in pharmaceutical studies, or those pharmaceutical studies where an inconsistent dosage schedule could result in a serious health risk and/or invalidation of the results for that participant.

The computer system 210 can collect information used to update the information stored in the databases 1420 and 1422 at different times from multiple, different devices. The computer system 210 may receive monitoring program protocols from different researcher devices in response to them generating a new monitoring program or modifying a monitoring program. For example, the computer system 210 can receive the monitoring program protocol 1702a over the network 150 after the researcher has submitted a Monitoring Program A using the client device 204. The computer system 210 can proceed to update the monitoring program protocol 1702 using the protocol 1702.

The computer system 210 may collect participant attribute data 1720 at various stages. For example, the computer system 210 may collect participant attribute data 1720a when a group 1730 of one or more users registers to become monitoring program participants. In more detail, in registering, the computer system 210 may provide to devices of the group 1730 a form to fill out that includes fields that correspond to different types of attribute data. The computer system 210 can proceed to update the attribute data 1720 using the attribute data 1720a.

After participants have registered, they may be enrolled in different monitoring programs. The computer system 210 may proceed to collect additional information for the participants during the monitoring programs in addition to monitoring program data. For example, during a first monitoring program 1732a, the computer system 210 may collect additional monitoring program 1722a and participant attribute data 1720b from the participant devices in the corresponding monitoring group for the program 1732a. The computer system 210 may simultaneously or at a different time collect monitoring program data 1722b and participant attribute data 1720c for a second monitoring program 1732b that the computer system 210 is also managing. The computer system 210 can proceed to use the program data 1722a and 1722b to update the monitoring program data 1722.

Similarly, the computer system 210 can proceed to use the attribute data 1720b and 1720c to update the attribute data 1720.

The computer system 210 can update the database 1420 and 1422 in real-time or substantially real-time. Alternatively, the computer system 210 may have scheduled update times, such as once a day during an off-peak time. Scheduled update times may allow the computer system 210 more freedom to select ideal times to process the collected data before storage. For example, with a scheduled update time, the computer system 210 may wait until certain criteria is met before processing the collected data. This criteria can include a threshold amount of resources becoming available, a number of active users being below a threshold number, etc.

Figure 18:
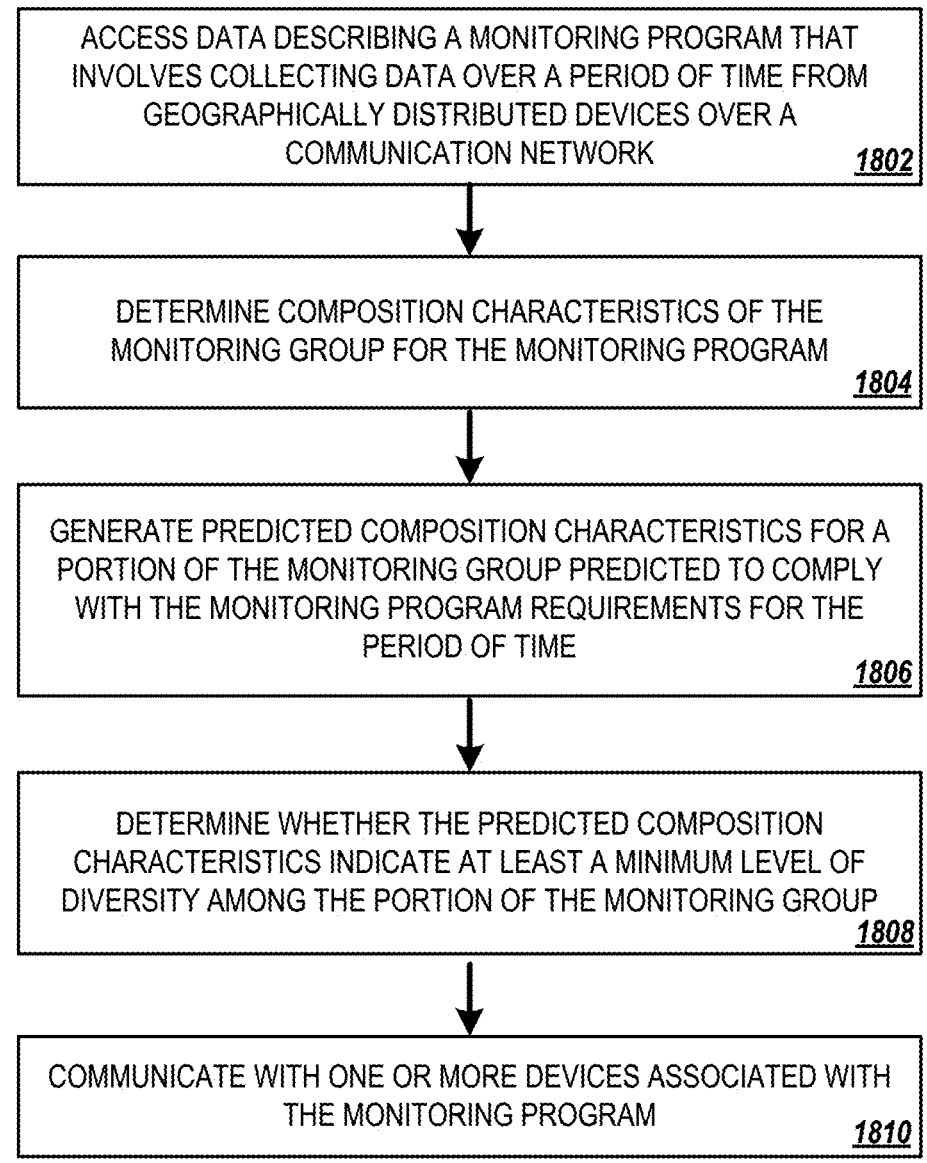
FIG. 18 is a flowchart diagram that illustrates an example process for predicting diversity for monitoring programs.

FIG. 18 is a flowchart diagram that illustrates an example process for predicting diversity for monitoring programs. The process 1800 can be used to monitor and improve research studies, such as clinical trials. The process 1800 enables the system 210 to generate predictions, before the end of a clinical trial, about the amount of diversity that is predicted to be present in a cohort at the end of the clinical trial, such as at a predetermined time in the future. The system 210 uses historical information about the rates at which individuals in different groups enroll in studies when invited, complete studies they are enrolled in, comply with study requirements, provide adequate data quality, and otherwise act in research studies. The system 210 uses this data to predict how different categories or groups within the cohort will perform during a clinical trial. In other words, the system 210 takes into account that cohort members with different backgrounds have different typical behavior profiles and different rates of attrition and noncompliance over the course of a clinical trial. The system 210 can use the predictions (e.g., predicted attrition levels, predicted noncompliance rates) for different groups to make predictions whether goals or requirements for the research study as whole will be satisfied. For example, the system 210 can predict characteristics of or behavior of the cohort, to estimate whether the cohort will include a sufficient number of participants that comply with research study requirements and whether the set will have needed composition characteristics (e.g., diversity or representation among various groups or categories of interest).

Different groups or categories of individuals have different preferences and propensities, so that a monitoring program or parts of it (e.g., some requirements or some types of participant actions or data collection steps) are less likely to be completed successfully by some groups than others. The system 210 can observe and determine the different trends and patterns that occur for the different groups by analyzing records of monitoring programs, such as results of prior clinical trials indicated by research literature or data for clinical trials that the system 210 manages or supports. The system 210 can determine the differential impact that different program elements have on different groups, and thus the differences in rates of expected successful completion for different groups or categories of individuals. In many cases, the rates of successful completion vary based on the attributes of the individual and the nature of the study (e.g., the specific requirements that participants need to meet). For example, people in an age range of 20-60 may be highly likely to complete surveys on a mobile phone, while individuals over 60 years old may have a lower likelihood of completing the surveys. The system 210 can determine the historical differences in compliance for people in different groups or categories (e.g., groups in which members have certain attribute values or attribute combinations). The system 210 can also train machine learning models based on examples of the different outcomes, e.g., outcomes for individuals in different categories in different studies, to predict likelihoods of compliance and/or expected rates of compliance.

The ability to achieve and maintain diversity is an important aspect of clinical research for many researchers today. In August 2020, for example, Oregon Health & Science University cancelled a large coronavirus research study called the "Key to Oregon" study primarily because minorities were underrepresented. See "OHSU ends massive coronavirus study because it underrepresented minorities, university says," The Oregonian, Aug. 27, 2020, https://www.oregonlive.com/coronavirus/2020/08/ohsu-drops-massive-coronavirus-study-because-minorities-didnt-sign-up-university-says.html The study was meant to track coronavirus symptoms for 100,000 people. However, after selecting and engaging many participants and making several million dollars of investment, the study was canceled because various racial groups were underrepresented.

The present technology can give researchers an accurate view of the diversity status of their studies, not only based on current enrollment but with accurate predictions of diversity status that will be achieved at the end of the study. This visibility gives researchers the confidence to proceed with important health research and avoid costly errors such as proceeding with studies that ultimately cannot provide the diversity needed to provide valid, generalizable results. The evaluation of diversity status and expected diversity status at study-end can be performed repeatedly, allowing the system 210 to provide early indications when conditions change and the risk of failing to meet diversity targets increases. The system 210 can quantify the likelihoods, providing metrics such as the expected composition of complying cohort members at the end of the study or a likelihood that a study when completed will achieve diversity targets. Just as important, the system 210 can identify and implement actions to improve diversity. The predictions and estimates of the system 210 enable the system 210 to pinpoint which groups are at greatest risk of being underrepresented and which requirements are likely to be most problematic for those groups. Importantly, the predictive capabilities of the system 210 raise issues early, even before problems with non-compliance or low data quality arise, allowing the system 210 to take corrective action to mitigate problems or even avoid them altogether. Thus, beyond simply identifying that a study is at risk for low diversity and quantifying the likely outcome, the system 210 can actively monitor and manage studies to maintain diversity, preemptively acting to increase compliance and other measures of success for groups that have historically had lower compliance. These features enable the system 210 to avoid study cancellation and to achieve study data collection objectives, making the overall research process faster, more efficient, and yielding results more broadly applicable to diverse populations.

Using the historical records for other research studies and the predictions of machine learning models, the system 210 can infer or predict whether a research study may later become unable to meet its goals or requirements for cohort composition or diversity. Many cohorts begin with an appropriate number of participants and a sufficient diversity, but over time attrition and non-compliance disproportionately affect some groups more than others, which can alter the composition of the set of participants who are providing usable data. Using historical data and predictive modeling, the system 210 can predict which studies are at risk of failing to collect data from a sufficiently diverse group of participants and quantify the likelihood and severity of the problem. This allows the system 210 to detect that a study has a high likelihood of failing to meet a diversity target, even if the current composition of the cohort for the study and even data collection so far or data collection trends do not indicate a problem.

For example, a study may begin with 100 participants enrolled in the cohort, with 50 men and 50 women. Targets or requirements for the final data set to be generated for the study can be set, such as collecting data with a minimum level of compliance and quality from 80 participants over a certain duration, such as three months. The targets or requirements can include requirements for diversity based on various attributes, in this example, based on sex. For example, the study may require at least 35 men and 35 women to complete the study, or for neither men nor women to make up more than 60% of the total set of complying participants.

Even though the beginning cohort composition meets the requirements, various factors could result in collecting data sets that are more heavily weighted toward one group or another. For example, differences in compliance for different groups can cause the study-end data sets collected to have diversity metrics that are very different from those of the initially selected cohort. If a larger proportion of women comply with study requirements than men, then the effective cohort composition at the end of the study (e.g., the portion of the cohort in which participants successfully met the minimum requirements of the study) may be much more heavily weighted toward women than men. The collected data may fail to meet the diversity requirements of the study, e.g., by having fewer than 35 men completing the study or having women make up more than 60% of the total that complete the study.

The system 210 can assess and predict the likelihood that a study will provide needed levels of diversity in the study-end collected data sets. The system 210 predicts how the various diversity groups (e.g., men and women in this example) are expected to perform over the duration of the study. The system 210 can determine expected rates at which successful participation is likely to occur (e.g., being retained in the study, complying with study requirements to at least a minimum acceptable level, providing data of appropriate quality, and continuing to do so for the duration of the study) for each of the diversity groups of interest. This may be done using a machine learning model trained to predict rates of successful completion for different groups or likelihoods of meeting a target composition among the study-end set of successfully-completing participants. Another technique is to use the historical outcomes for other studies to provide estimates of future completion rates, especially when using studies selected because they have similar characteristics to the current study (e.g., similar duration, similar data collection requirements, similar participant activities, etc.).

With the predictions, the system 210 can determine, even before a study begins, whether the study and cohort as designed is likely, if conducted, to meet the goals or requirements for diversity and other characteristics by the end of the study. For example, the system 210 may predict success rates that show 50% of the men will finish successfully and 80% of the women will finish successfully. From this, the system 210 can determine that the likely result would not meet the diversity requirements of the study, e.g., because data for 25 men, not the minimum of 35, would be collected successfully, and because the collected data sets would overrepresent women since they would be more than 60% (e.g., 40 out of 65 or 61%) of the total.

At any stage in the study, from before it begins up to completion, the system 210 can generate predictions about the future performance of the cohort, including determining the likely characteristics (e.g., total size, data quality level, distribution among different groups or categories, etc.) of the complying portion of the cohort and determining if those characteristics meet the goals or requirements for the study. These can be expressed in different forms, such as estimated characteristics of the complying portion of the cohort at the end of the study, estimated compliance rate or number of complying participants for each group of interest, likelihoods that different groups or the study as a whole will meet different requirements, a classification of the cohort (e.g., high, medium, or low likelihood of success in meeting diversity requirements, total number of complying participants, or other requirements), etc.

Depending on the implementation, the system 210 can use different levels of customization in generating predictions. Some implementations are generalized, while other have varying degrees of customization for the specific cohort selected or the specific elements or requirements of a monitoring program. For example, to generate an estimated compliance rate for men for a study (e.g., estimated proportion of the men that will meet the minimum compliance requirements), a generalized approach can look at overall success rates for men in various studies. A more customized approach may factor in the specific requirements of the current study, such as daily survey completion about sleep and ongoing step count tracking. The result can be more tailored and thus more accurate by being based on, or by more heavily weighting, the results for studies that include those requirements or similar types of activities. So far, these types of predictions can be made in a general sense for a cohort, without the characteristics of the specific individuals in the cohort being used. At another level of customization, the system 210 can generate predictions based on the characteristics of individuals in a cohort or set of candidates (e.g., a proposed cohort or candidate pool). For example, the system 210 can consider, for the group of men in the cohort, the distribution of attributes within the group (e.g., age, race, occupation, residence location, etc.) and account for how these factors affect compliance rates in the historical data. Thus, the predictions can use the breakdown or aggregation of characteristics that are not specifically measured for purposes of diversity requirements to more accurately predict how this group of men in the cohort will behave, rather than making a prediction about men in general. Finally, for an even more customized and accurate approach, the system 210 can use the characteristics of each individual to determine that individual's likelihood of successful completion, and from the likelihoods for individuals determine an overall expected rate. This approach may customize the prediction based on both the characteristics of individuals and the characteristics of the study itself (e.g., elements such as duration, data collection requirements, participant activities required, etc.).

The system 210 can notify researchers and administrators when predictions for a monitoring program indicate a low likelihood of success in meeting the requirements for diversity or other characteristics, e.g., when a predicted likelihood is less than a threshold or when the estimated study-end characteristics do not meet the desired levels. This provides an early warning to researchers that can save millions of dollars of investment in studies that would, if conducted, most likely fail for lack of diversity or lack of compliance with study requirements. However, beyond informing of issues, the system 210 can identify and implement changes to improve the eventual performance of the cohort and the overall set of data collected in the study. The system 210's early detection of actual, currently-present or potential, future-arising lack of diversity enables the system 210 to generate corrections and changes in the administration of the study that will improve the diversity and other composition characteristics for the collected data. As an example, the system 210 can adjust communication with remote devices of participants to change interaction settings for participants in groups that are at greatest risk of not being adequately represented, e.g., to increase reminder frequency, to change user interface layout, to change the communication channels used (e.g., text message, e-mail message, phone call, mobile device notification, etc.), change the media types used (e.g., text, image, video, audio, etc.), and so on. The system 210 can identify and change the data collection scheme applied for the study, for some or all groups within the cohort. For example, for individuals in low-compliance groups (e.g., groups predicted to have less than a certain likelihood, e.g., 80%, 60%, 50%, etc., of meeting their minimum amount of complying members through the end of the study), the system 210 can implement additional data collection redundancy. For example, rather than collect exercise data through a survey alone, the system 210 can instruct devices of users in low-compliance groups to also automatically generate step count or other exercise data. In many cases, the system 210 can identify and implement the changes automatically or can make recommendations and carry out changes after a researcher approves. Other actions that the system 210 can take, including changing device configurations and operation of remote devices used in monitoring, are discussed further below.

As another example, the system 210 can use a database having user profiles for candidates for the study and, even after the study has begun, the system 210 can identify changes to the cohort that would increase the number or percentage of complying participants in groups most likely to not meet their diversity goals. For example, if men are predicted to be underrepresented in the data set at the end of the study, the system 210 can select, from a candidate pool, additional men that meet cohort selection requirements for the study (e.g., at least a minimum age, no excluded health conditions, etc.). The system 210 can automatically score and rank the candidates, such as to choose those that have the best expected compliance based on the attributes indicated in their user profiles. The system 210 can identify a number of candidates that would be needed to increase the study-end representation of men to a desired level, given the predicted rates of attrition and non-compliance that are expected for the group of for these candidates specifically. The system 210 can then select this determined number of additional male candidates to add to the cohort, and can automatically invite them (e.g., sending, an email, a text message, a notification through an application, etc.) to enroll. The system 210 may alternatively recommend to the researchers for the study to add more men, and potentially indicate the recommended number and/or the set of individuals recommended, and can receive confirmation of the recommendation through the researcher's interaction with a user interface. Whether done automatically or in response to a researcher's confirmation or instruction, the system 210 can send messages to the remote devices of the new candidates that are invited, causing their devices to provide interactive elements (e.g., a notification, a button, a URL, an application user interface, etc.) that are selectable to initiate the process of enrolling the user (e.g., indicating consent to participate, downloading configuration data or a software module for the study to the device, configuring the device to automatically capture sensor measurements and report results to a server over a network, configuring the device to initiate user interactions with the new participant, and so on).

Before the process 1800 or as part of the process 1800, the system 210 can generate or train models based on historical data for prior monitoring programs (e.g., clinical trials) to learn how different participant attributes affect likelihoods of outcomes such as enrollment and consent, retention or study completion, compliance with different requirements, data quality levels achieved (e.g., quantity, accuracy, precision, consistency, reliability), and so on. Different types of models can be used, for example, statistical models, rule-based models, machine learning models, etc. Any of the machine learning models discussed herein may be may be, for example, a neural network, a support vector machine, a classifier, a regression model, a reinforcement learning model, a clustering model, a decision tree, a random forest model, a genetic algorithm, a Bayesian model, or a Gaussian mixture model. Combinations of multiple models can be used together, for example, in an ensemble configuration so that multiple models or even multiple models together are used to make a prediction, with outputs of the different models being combined (e.g., averaged, weighted, maximum or minimum value taken) to generate the overall output.

The training data can indicate the attributes and history of individual participants (e.g., demographic attributes, physiological attributes, behavioral attributes, health status, and more). The training data can also indicate outcomes for each individual with respect to retention, compliance, data quality, and so on. Different types of training data can be used depending on the type of model and the level of precision desired.

For example, a model may be configured to predict the likelihood of an outcome, such as compliance with a requirement, for an individual. This type of model can be configured to receive information indicating attributes of the individual (e.g., age, sex, physiological measurements, etc.) and the model would similarly would be trained using training examples that include attribute values for individuals of the same types of attributes provided as input to the model.

Other models may be generalized based on groups of individuals or for cohorts as a whole, and so may use training data sets that indicate characteristics at this more general level. Still further, some models can be trained to predict overall compliance for a group or category of participants generally, without taking into account other participant attributes. For example, groups may be defined based on race or ethnicity or other types of attributes. Training data can indicate the compliance rates achieved for the different groups for different studies, whether through information about the attributes of individuals and their outcomes or summary information about total information by group.

The models can be machine learning models, such as neural networks or reinforcement learning models, that iteratively learn through exposure to examples. For each model, a set of input feature types is defined, which sets the types of variables that the model will account for in making predictions, typically including an identification of the group of interest and/or the attribute values that distinguish one group from another. For a model that predicts future compliance by individuals with specific participant actions based on individual attribute values, the input can include (i) values for a predetermined set of attributes of an individual, (ii) an indication of the group the individual is in (e.g., a group identifier or attribute values indicating the characteristics that place the individual in the group), and (iii) one or more values indicating the requirement(s) for which compliance is being predicted (e.g., daily survey responses, wearing an activity tracker, providing heart rate data, etc.

Many variations are possible. For example, rather than provide input that would indicate the group to be predicted, different models may be generated based on examples for different groups, and the group-specific models would not need input of group-indicating information. Similarly, rather than indicate a type of action about which compliance is predicted, there can be different models for different types of actions, e.g., one model for predicting compliance in responding to a survey, another model for predicting compliance in providing heart rate data, and so on. These models, like the other discussed, can be generated to predict the rates and likelihoods of compliance for repeated action over time (e.g., performed daily, hourly, weekly, or at another frequency for a certain duration e.g., a week, a month, a year, etc.), not just to predict whether a single event occurs or not. Any of the models can be configured to generate predictions for a set of multiple individuals (e.g., a subset of a cohort that represents one diversity group) and aggregate information about the set of individuals (e.g., averages, distributions, minimum, maximum, number of individuals, etc.) can be provided instead of individual attribute values. In some cases, models can make predictions about a group or category overall, independent of the makeup in a specific cohort or candidate pool, in which case indicating only the group identifier or attributes common to the group can inform the model of the type of prediction needed.

The training data for a model have multiple training examples that include each of the types of information provided as input to the model, with additional indications of observed outcomes. During training, the system 210 can derive from each training example an input vector of feature values and a training target related to the outcome. The system 210 can then use backpropagation of error or other training techniques to iteratively adjust values of internal parameters of the model (e.g., node weights and biases of a neural network). In particular, the training target derived from the outcome of the example can be used to incrementally train the model to make a more accurate prediction (e.g., an output closer to the training target). Other model types, such as reinforcement learning models, may learn from the pattern of data or aggregate set of data, even without a specific target outcome being defined.

Various examples herein focus on measuring and predicting compliance by participants with actions or activities that participants are requested to perform as part of a study, e.g., data collection actions (e.g., responding to surveys, interacting with an application or other device, providing tracked movement data or location data, providing physiological measurements, providing other sensor data, etc.) and other patient activities (e.g., taking medication as directed, exercising as directed, sleeping as directed, etc.). Nevertheless, the analysis performed and the models trained and used can assess other outcomes, such as enrollment, retention, study completion, achieving adequate data quality, and so on. Models can additional be trained to predict combinations of these, such as overall success rate or success likelihood that an individual or group will enroll, be retained, and comply with data collection and data quality requirements consistently to the end of the study.

The process 1800 can include accessing data describing a monitoring program that involves collecting data over a period of time from geographically distributed devices over a communication network (1802). The system 210 uses this information to customize the predictions and assessments for the particular monitoring program. As discussed below, the system 210 can use these to give early warning that lack of diversity or other problems with data collection may arise in the future. The system 210 can also can preemptively make corrections and adjustments to improve the data collection for the program as a whole and to increase the likelihood that diversity and other data collection requirements are met at the conclusion of the monitoring program.

The predictions and actions of the system 210 can be based on data such as the composition of the monitoring group, the specific requirements that participants need to satisfy, and the goals or requirements for the study. With information about the monitoring program, the system 210 can predict with respect to the study's specific goals (e.g., the diversity targets specifically for that monitoring program). The system 210 also obtains high accuracy in predicting compliance and other outcomes by taking into account the how specific program elements (e.g., types of data to be collected, types of activities required, accuracy needed, duration of the program, etc.) affect the likelihoods. For example, a monitoring program with a complicated or burdensome set of requirements on participants can be predicted, based on historical evidence and/or trained models, to have lower compliance than one with simpler or fewer requirements. The information about the monitoring group can be used to assess diversity and other characteristics, as well as to determine how the different requirements of the study may have different effects on different groups or types of participants, such as with some requirements disproportionately certain categories of participants.

The system 210 can maintain a database with information about each of the various monitoring programs that are being designed or are ongoing. The information can include many items about the studies, including: selection criteria for selecting the devices or participants to monitor; enrollment data about the devices or participants in a monitoring group or candidate pool; data collection to be performed, e.g., types of data to collect (e.g., heart rate, step count, daily calories consumed, types of sensor data used), frequency of collection, mode of collection (e.g., daily survey, automatic passive sensing, phone vs. watch, in-person visit, bio-specimen, user input vs. medical device reporting), etc.; other activities that participants are requested to perform (e.g., exercise, taking medication, etc.); standards for acceptable data quality and compliance (e.g., accuracy of measurements needed, thresholds or rules for how consistently participant data must be provided to be used in the study); goals and requirements for each monitoring program (e.g., minimum size of the monitoring group, minimum level of diversity in the monitoring group, etc.); monitoring program characteristics (e.g., duration, when and whether new participants can be added, etc.). This type of information typically varies from one monitoring program to another. For clinical trials and other research studies, much of this information can be stored in or obtained from a study protocol for the study.

The system 210 can use various types of information about the monitoring program in different ways. For example, the system 210 can obtain information indicating the makeup of the monitoring group, e.g., summary information about the number of participants and/or devices in different diversity groups, or data identifying the specific participants and/or devices to be monitored. This information can be a set of individuals that are enrolled, or invited, or proposed to be invited, or even for the candidate pool overall. The information can include identifiers for specific individuals, user profile data for the individuals, or other information that the system 210 can use to determine which individuals and or devices correspond to different diversity groups, and to retrieve the attribute information for the individuals and diversity groups.

The system 210 can also obtain information about the requirements and activities involved in the monitoring program. This can include information in a study protocol that specifies items such as the methodology for a study, types of data to be collected, devices and software to be used, and more. The system 210 uses this information to determine the activities and requirements involved in the monitoring program to better estimate the likelihood of proper compliance with those requirements.

The system 210 can obtain information indicating the goals, targets, and requirements for the monitoring program as a whole. These can be constraints or requirements that need to be met in order for data collection of the monitoring program to be successful. In this sense, success of the study refers to adequately collecting the data desired to be collected, e.g., successfully collecting the needed type, amount, and quality of data, over a sufficiently long duration, from a sufficiently large and diverse monitoring group. Typically, success of a monitoring program in this sense is not based on whether the data collected in this manner proves a hypothesis or achieves a desired health outcome (e.g., whether a drug is safe or effective at managing a disease), although in some implementations, constraints and predictions for these additional factors can also be considered.

In particular, the monitoring program can have one or more diversity goals or requirements. Diversity can be measured with respect to certain attributes of interest that are specified for the monitoring program. As discussed above, diversity considerations can include but are not limited to demographic attributes such as age, sex, race, socioeconomic status, and so on, but can also encompass diversity among physical characteristics, medical histories, behavior patterns, genetic profiles, geographic locations, and many other attributes that are not demographic in nature. Some monitoring programs specify that they need diversity in sex the participants, other programs need diversity in the locations of participants, other programs need diversity across different variants of a gene, and so on.

The diversity goals or requirements can specify the attributes for which diversity is needed, as well as the amount or level of diversity needed for those attributes. In other words, the diversity goal can specify not simply that certain groups should be each be represented, but also amounts of representation needed for each group. The goals or targets can be expressed in any of various different ways, including: minimum numbers for certain groups (e.g., those including individuals with certain attribute values, attribute ranges, profiles); target proportions or relative amounts for different groups; rules or conditions that should be met; quotas for different groups; and so on. Various models trained with broad-based training data sets can be used to provide predictions of outcomes. For each monitoring program, the system 210 determines whether the predicted outcomes would meet the specific diversity goals or requirements for that monitoring program.

Other information is also collected, maintained, and accessed by the system 210, such as data collected over the course of the monitoring program. The system 210 can track, for each participant or device enrolled in a monitoring program, the data collection events that occur and those that are missed. The actual data received can be stored and analyzed, as well as context or metadata for the collection (e.g., time, location, device used, etc.). The system 210 can score the data quality of the collected data as well, to determine if the proper accuracy, precision, quantity, timing, and other parameters are provided. This enables the system 210 to determine whether individuals are meeting the requirements of the monitoring program, as well as to determine compliance rates for the groups or categories that need to be monitored to meet the diversity requirements.

In some implementations, the system 210 factors in the compliance of individuals and groups in its predictions. For example, the system 210 can adjust or determine predictions of future compliance using the history, patterns, trends, and progression over time of tracked compliance for individuals, groups within a monitoring group, as well as the monitoring group as a whole. The data can be used in various ways. One is to remove consider individuals removed from a cohort if inconsistency or lack of compliance exceeds a predetermined amount. If there are Another technique is to identify patterns or trends in monitoring data and to apply an adjustment or weight to predictions based on it. For example, as learned from examples of prior studies that a repeated week-over-week decline in compliance rate (e.g., proportion of complying participants) for a group can indicate further decline, and so compliance estimates can be reduced (e.g., by a predetermined amount, an average of the previous two declines, etc.).

In some cases, information about the observed compliance in the current study (e.g., the most recent data collection event, a recent window, or history for the entire monitoring program so far) can be provided as input to a machine learning model trained to receive this information along with other input feature values (e.g., indicating participant attributes, study requirements, etc.). The machine learning model can thus be trained to recognize not only how the attributes of an individual, diversity group, or monitoring group are predictive of future compliance, but also how current or previous compliance is predictive of future compliance. Thus the rates, patterns, and changes in compliance over time can factored in to improve the accuracy of the model. This may show that, in some cases, a cohort with low but improving compliance may have a better predicted outcome than a cohort with high but declining compliance. Models can be trained with examples that show different levels of compliance, or different patterns, trends, or progressions of compliance, including time series of collection events (e.g., daily pattern of 1, 1, 1, 0, 1, 1, 0, . . . where "1" indicates successful completion of a requirement on a day and "0" indicates failure to complete the requirement that day).

The process 1800 can include determining composition characteristics of the monitoring group for the monitoring program (1804). To evaluate the potential success of data collection in a monitoring program, the system 210 can start by assessing the current composition of the monitoring group, taking into account any attrition and non-compliance that has occurred so far. To predict the characteristics of the portion of the monitoring group that will comply through to the end of the monitoring program, the system 210 starts by assessing the current state of the monitoring group, which may be different from the characteristics at the beginning of the monitoring program. For example, some participants may have withdrawn from the monitoring program, while others may have been added. Similarly, some participants may be effectively excluded due to no longer complying with the selection criteria, or may be non-compliant to an extent that they already cannot be used in the study.

The determined composition characteristics thus provide a starting point from which predictions about future compliance and outcomes can be made. In some cases, the composition characteristics are of the same type as the requirements for the monitoring group. For example, if a minimum number of participants is set for each of different diversity groups, the system 210 can determine the number of participants in each diversity group. As noted above, the system 210 can filter out participants that have characteristics or behavior patterns that would disqualify them from the monitoring group, such as noncompliance with requirements of the monitoring program extensive enough that it cannot be corrected. Other characteristics can also be determined, such as the total number of participants, proportions of participants in different diversity groups, distribution of participants within each diversity group among different attributes or outcomes (e.g., a histogram of attribute values or compliance results so far), and so on.

The composition characteristics provide an initial reference for the analysis of the monitoring program. The system 210 can use the determined composition characteristics to verify that the monitoring program meets diversity requirements at the current time. For example, the system 210 can compare determined characteristics for each diversity group with corresponding minimums or thresholds for the diversity group. If the current number of participants for a diversity group is already less than the minimum, then the system 210 can identify that the monitoring program already fails to meet the requirements. More commonly, the number of participants in different diversity groups or proportions of the monitoring group in different diversity groups can provide a base value from which predictions about future behavior can be applied. For example, as discussed below, the numbers of participants in the diversity groups can then be discounted or adjusted using estimated rates of future compliance for the diversity groups.

The process 1800 can include generating predicted composition characteristics for a portion of the monitoring group predicted to comply with the monitoring program requirements for the period of time (1806). For example, the system 210 can predict the level of diversity that will be present, at the end of the monitoring program, among the members of the monitoring group that meet the requirements for ongoing compliance, data quality, and so on. One way that the system 210 can do this is to determine predicted outcome rates (e.g., for attrition, compliance, data quality, etc.) for different diversity groups, and apply those to the determined characteristics of the cohort.

As an example, a clinical trial may require a minimum of at least 70 participants continuing to the end of the study. The clinical trial may also have a target for diversity among three different groups or categories, group 1 ("G1"), group 2 ("G2"), and group 3 ("G3"). The groups may be defined based on one or more types of attributes, e.g., ranges or combinations values for age, sex, race, ethnicity, health status, medical history, etc. The clinical trial may require a minimum of 25 people from each group to achieve goals of the study, such as the statistical validity needed to generate results for a population. For the collected data to be valid and usable, participants need to comply with daily requirements and activities of the study. Beyond being nominally enrolled, the clinical trial may require participants to consistently provide data over a predetermined period, such as three months, for example, in the form of survey responses, automatic sensor data collection (e.g., from a phone, watch, or other mobile device), interactions with devices, and potentially other forms (e.g., in-person visits, bio-specimen samples, etc.). The clinical trial may have certain standards defined for acceptable compliance of participants, such as missing no more than two days of data collection per week and not missing more than one day in a row. Failure of participants to meet the requirements (or deviating by at least a certain amount from the requirement) may render a participant's data unreliable or unusable for the clinical trial, effectively removing the participant from the group of active, complying participants.

The system 210 may determine in step 1804 that, one month into the study after starting with an initial cohort of 100 individuals, the current numbers of participants still active in the study include 30 in G1, 32 in G2, and 27 in G3. The historical outcomes for compliance, data quality, and so on may be different for people in the different diversity groups, as evidenced by different compliance rates in prior clinical trials or other monitoring programs. The system 210 takes into account the different levels of incidence of attrition, non-compliance, low data quality, and so on for the different groups and can determine, e.g., that the success rate over the remaining two months of the study is 85% for G1, 95% for G2, and 70% for G3. As a result, the system 210 can estimate that at the end of the clinical trial, the resulting data set will provide complete data sets for roughly 25 individuals in G1, 30 individuals in G2, and 19 individuals in G3. From this, the total number of individuals is expected to successfully participate to the end of the clinical trial is above the minimum (e.g., 74 compared to a minimum of 70), and groups G2 and G2 are expected to meet their minimum targets for representation. However, with the lower expected success rate for members in G3, this category of participant is expected to be underrepresented and not meet the minimum for the category (e.g., 19 compared to a minimum of 25 needed). Thus, even if the current characteristics of the cohort meet the requirements for the clinical trial, the system 210 can determine that future characteristics of the cohort would not.

The system 210 may use any of various techniques to make the predictions about future outcomes for the monitoring group and the future characteristics of the monitoring group. One technique is to use statistical techniques to take historical data (e.g., from prior monitoring programs), identify examples of individuals that would be included the different diversity groups (e.g., G1, G2, G3), and then determine this historical success rate. For example, across the set of examples for people whose attributes would classify them into G1, the success rate can be a fraction of those meeting requirements out of the total, e.g., 1523 out of 1792 for an 85% rate. For better accuracy, the examples chosen can be selected for similarity to the context or situation of the current monitoring program. For example, rather than consider all examples of individuals that would be classified into G1, the system 210 can select a subset that were in studies that had similar requirements to that of the current study, so the examples used are more reflective of the requirements that participants of the current study would need to meet. The system 210 may optionally can determine a different prediction for success with respect to different requirements, e.g., 95% expected to provide daily survey responses, 86% expected to provide daily step count data, 85% expected to provide the appropriate level of data quality (potentially making different estimates for different aspects of data quality), and so on. The system 210 may combine the expected rates (e.g., with the combined uncertainty leading to a lower success rate than any of the individual rates) or in some cases as a simplification take the lowest expected success rate to use. As another example, the system 210 can determine examples of behavior occurring over consistent periods or may normalize measures to account for differences. For example, the system 210 can predict a attrition rate per month based on non-compliance, poor data quality, or other factors. For G1 that may be an expected attrition of 8% per month, as prior studies that have similar characteristics to those of the present study may show. Thus, over the remaining two months of the clinical trial, the total attrition would include 0.92*0.92=0.85 expected successful completion. These types of calculations can be performed for each of the different monitoring groups, to account for each different group's characteristics.

Beyond simply using examples of individuals that would be classified into the same groups, the system 210 can account for the similarities or differences between the composition of the subset the monitoring group in G1 and the examples. Within a diversity group, perhaps those in a certain age range and the same race, tendencies and preferences are not homogenous and behavior can still tend to vary according to other factors, such as whether a person is near the upper or lower ends of the age range, whether the person is male or female, the level of experience and comfort the person has with using a smart phone or other technology, the residence location of the person, and so on. Accordingly, to improve accuracy of the predicted success rates (e.g., reflecting one or more of retention, compliance, data quality, etc.), the system 210 can select or weight the data used to generate expected success rates according to similarity with the distribution of attributes present in the G1 members in the monitoring group. As a result, if the members in G1 in the monitoring group are predominantly on the younger end of the age range, then historical data for others that with those characteristics can be used. The system 210 can optionally determine subgroups for different attributes or attribute combinations (e.g., subdividing male vs female historical outcomes, outcomes for different geographical areas, etc.) to tailor the estimated rates for the subgroups even if the subgroups are defined based on attributes not related to the diversity requirements.

The use of data from prior studies enables the system 210 to make accurate predictions about future compliance, data quality, and other outcomes before a monitoring program even begins. This is a significant advantage because it can account for differing likelihoods of attrition and non-compliance among different diversity groups very early, at the stage of selecting the initial cohort or even assessing viability of creating a study, when the study and the cohort can be changed to improve the likelihood of success. Once the monitoring program does begin, and data collection and other events can be assessed, the system 210 can use the trends observed to predict future outcomes. For example, the system 210 can extrapolate behavior over the first week or month (e.g., a rate of steady participation, or declining participation, or other pattern) for future time periods. However, this may not account for non-linear effects, such certain fractions of participants failing to ever begin participation (e.g., skewing metrics for an initial period) or for fatigue or disinterest to set in later for some participants (e.g., for some consistent participants to reduce engagement after 2 months), or for these effects to be more less pronounced for different types of participant requirements. As a result, in addition to or instead of simply extrapolating the trend of behavior or outcomes observed, the system 210 can match patterns or progressions of compliance that have occurred with similar patterns observed in historical data. For example, although participation has stayed high for the first month, given that other studies with similar participant requirements experienced a drop in participation in the second and third months, the system 210 can predict that a similar drop will occur based on the similarity to other patterns, even if the data received so far and the current compliance trend do not yet show any decline.

The system 210 can also use trained machine learning models to predict the future outcomes. One example is a model that predicts a success rate (e.g., either overall or for specific factors such as compliance, data quality, etc.) for a group based on the group's characteristics and the characteristics of monitoring program. For example, the input vector can include values indicating the characteristics shared by the members of the group (e.g., attributes that, when present, cause a participant to be classified into G1). If G1 represents Hispanic males, then values indicating those characteristics can be input. In some cases, instead of indicating attributes that define the group, certain groups may be pre-defined before or during training of the model so that the model associates the group with a particular identifier. In that case, an identifier for the group (e.g., a G1 identifier) can be provided instead of the characteristics of the group. The input vector can also include values indicating characteristics of the study (e.g., remaining duration of the study, which types of data are collected, which types of devices or software are used by participants, frequency of data collection needed, level of precision needed, medication adherence required, etc.). In particular, data values indicating participant actions required or data quality characteristics required can be provided. Training of the model is based on the data for many different studies, including many different examples of how people that fit the profile of G1 and other groups respectively have behaved, across a variety of different participant requirements and study characteristics, including for different combinations of them. This allows the model to learn how different factors for study To allow the model to provide even more accurate predictions, the model may be configured to receive and be trained to use additional information about the distribution of attributes in a diversity group. For example, regardless of the attributes to define G1, the input vector for G1 may indicate a mean or median age of those in G1 in the monitoring group, a percentage of those in G1 in the monitoring group that are male or female, and so on. The model can be trained with these attribute values being input also, so the model learns how different characteristics of a group of individuals affect the ultimate success rates for different studies.

Other types of models can similarly be trained and used. For example, different models can be determined for different diversity groups, e.g., a model for G1 trained based on G1 examples, a model for G2 trained based on G2 examples, and so on, so that the characteristics of the group need not be input. Similarly, models for specific requirements can be determined, e.g., one model for predicting compliance with daily surveys, another model for prediction of compliance with sensor data collection for exercise data, etc. so that input of the requirement(s) for which compliance is predicted need not be input for each prediction.

As another example, a model may be configured to predict the likelihood that an individual reaches an outcome, such as compliance with one or more requirements. This type of model can be configured to receive information indicating (i) attributes of the individual (e.g., age, sex, residence location, physiological measurements, etc.) and (ii) an indication of one or more study characteristics or requirements for which a likelihood is predicted (e.g., data quality requirements, participant activities, participant data collection activities, study duration, etc.). The model would similarly would be trained using training examples that include attribute values for individuals and study characteristics or requirements of the same types of attributes provided as input to the model. The input may include group identifiers or indications of the attributes that cause individuals to be classified into the diversity groups of interest. Because the training data examples additionally indicate the observed outcomes for many different individuals facing various different requirements, the model can learn how different participant attributes and different study characteristics and requirements affect outcomes for compliance, data quality, and so on.

With a model that predicts individual likelihoods of success, the system 210 can determine the overall predicted compliance rate for a group by aggregating the individual probabilities for different members of a group. For example, G1 for the clinical trial may include various individuals that have likelihoods of compliance to the end of the study of 0.45, 0.80, 0.70, and so on. To determine the expected rate of compliance for the cohort, as a simple technique, the system 210 may determine an arithmetic mean of the different probabilities for the individuals. This average can serve as an expected proportion of the group that would comply with the requirements of the study. Other forms of combining predictions for individuals may also be used.

Optionally, the models can be configured to receive and use information about historical performance of a diversity group or an individual about which prediction is being performed. For example, for predicting the likelihood of an individual completing study requirements, the percentage of compliance or even a binary value whether the individual has completed one or more different requirements so far can be provided to the model. The model can use this recent context to provide a more accurate prediction. During training, information about longitudinal performance of individuals can be broken into segments. For example, information about an individual over three months can be broken into three training examples each covering one month of participation and using data from the previous month(s) as context when available.

So far, the example with G1, G2, and G3 assumes that the diversity groups are mutually exclusive, so no individual is part of multiple diversity groups. However, that is not a requirement and diversity predictions can be made using the same techniques. Nevertheless, with overlap in group membership, predictions for the total monitoring group may be done separately from the group analysis, rather than aggregating results for different groups, to avoid potentially double counting individuals.

The process 1800 can include determining whether the predicted composition characteristics indicate at least a minimum level of diversity among the portion of the monitoring group predicted to comply with the monitoring program requirements (1808). Using the data retrieved for the monitoring program, the system 210 determines whether the diversity goals, targets, or requirements are likely to be met, e.g., to be met a future time such as at the end of the study. The predicted composition characteristics can be obtained as discussed above by applying the predictions about future success rates (e.g., based on compliance, data quality and other factors) to the current monitoring group characteristics, showing how the numbers and proportions for different diversity groups are expected to change. The system 210 can then compare the predicted composition characteristics with the diversity requirements.

In the example discussed above, the system 210 estimates that at the end of the clinical trial, the resulting data set will provide complete data sets for roughly 25 individuals in G1, 30 individuals in G2, and 19 individuals in G3. Because a minimum of 25 individuals is needed for each of the three groups, this indicates that the group G2 is solidly above the minimum, G1 may meet the target but is at risk for falling below the minimum, and G3 is expected to not meet the minimum. The system 210 can compare the expected numbers and proportions of study-end complying individuals for different groups with the requirements for the study, however they are defined (e.g., as quotas, ranges, minimums, proportions, relative measures for one group relative to another or to the total, etc.).

As shown above, the system 210 can determine whether the expected value or estimated characteristics that are most likely will meet the diversity requirements. The system 210 can additionally or alternatively generate values indicating a confidence score or likelihood that the monitoring group as a whole will meet all diversity requirements, and/or a confidence score or likelihood for each group whether it will meet its requirement. For example, the calculated probabilities that G1, G2, and G3 will meet their requirements may be 50%, 85%, and 10%, respectively. The probabilities can be determined by aggregating probabilities for the success and compliance of the various individuals within the groups, e.g., determining the probability that at least the minimum of 25 participants remain engaged and successful based on the independent probabilities calculated for the different individuals. The likelihood for the entire study meeting all diversity goals being about 4% (e.g., 0.5*0.85*0.1=0.0425). In this case, the result indicates that the clinical trial currently has a very low likelihood of succeeding with all of the diversity goals, and that various changes to the clinical trial, the cohort, and interaction with the participants is needed to improve the likelihood of achieving the needed representation in G1 and G3.

The process 1800 can include communicating with one or more devices associated with the monitoring program based on results of the determination whether the predicted composition characteristics indicate at least the minimum level of diversity (1810). This can involve communicating with devices of researchers and administrators as well as with remote devices of participants used for data collection. The system can provide various types of information to a researcher about the current and predicted future diversity status. This information can be provided over a communication network for a user interface of an application, a web application, a web page, etc., or in another kind of message (e.g., text message, e-mail, mobile device notification, etc.). In some cases, the data is provided for display in a user interface such as a dashboard for monitoring study progress or a workspace for designing a study. Thus, the system 210 can provide data that informs or alerts a researcher to the effects of current trends or even changes that the researcher makes (e.g., changes by adding or removing requirements for data collection or other participant actions, adding or removing cohort members, etc.)

The system 210 can provide indications of the predicted future composition characteristics, e.g., providing the expected outcomes of 25, 30, and 19 complying participants for G1, G2, and G3, respectively. These can be provided with information indicating the corresponding minimums, e.g., 25 participants each, for display also. The system 210 can also indicate the likelihoods of the different groups or the study as a whole meeting the corresponding diversity targets, e.g., probabilities of 50%, 85%, 10%, and 4% respectively.

In some implementations, the system 210 recalculates the expected future diversity status periodically or in response to certain triggers. This check can be done repeatedly as a monitoring program proceeds to detect when data collection results or other factors cause predicted diversity to decline. For example, each time a researcher loads an interface, or when additional data is collected, or daily, the system 210 can perform the process 1800 with updated data. The system 210 can have certain thresholds or criteria for initiating notifications and corrective actions. For example, the system 210 may have a threshold to notify researchers when the probability that a study will meet its diversity goals falls below 80%. This can trigger notifications on a user interface when a user logs in, notifications pushed to a device or sent through email or text message, or other forms.

In addition, the system 210 can identify various preemptive actions to improve the likelihood of successful completion of the monitoring program with the needed diversity characteristics. One example is changing the communication with different groups of subjects (e.g., changing the timing, content, and quantity of reminders and data collection requests to better suit different groups). Another example is changing the composition of the monitoring group (e.g., identifying, inviting, and enrolling additional participants that would be in groups that are predicted to not have the minimum amount of retained, complying participants with appropriate quantity and quality of collected data). Another example is to change elements of the monitoring program, such as to add supportive elements (e.g., educational media and user interfaces, reminders, travel benefits such as taxi credits) targeted for participants in groups at greatest risk of not meeting their minimums, and so on. Another example is to provide software or configuration data over network to add redundancy or increase the frequency of data collection attempts. All of these are informed by the analysis of the different groups, so that changes are made for and intensity of support and interaction can be increased for participants and devices corresponding to the groups (e.g., G3 and G1) most in need of improvement to reach a desired confidence or probability of reaching their corresponding targets.

In some implementations, the system 210 uses the indication of low likelihood of meeting diversity requirements as a trigger to select different digital health technologies for individual users or for a diversity group (e.g., G3) as a whole. The system 210 can use any of the techniques discussed in U.S. patent application Ser. No. 16/877,162, filed on May 18, 2020, which is incorporated herein by reference. This can include predicting compliance for different technology items and identifying, recommending, and implementing use of substitutes or complementary technology items that are expected to produce better compliance.

Another type of change that the system 210 can make or recommend is to change the monitoring group. The system 210 can identify, based on user profiles for candidates indicated in the database, additional members that would meet the criteria for the groups that have higher than desired probabilities of being underrepresented, e.g., G1 and G3, and which also meet the cohort selection criteria. Optionally, the system 210 can evaluate the new candidates identified for these different groups and predict the likely compliance of each. From these the system 210 can score or rank candidates to select those in the groups where more representation is needed that are most likely to comply and succeed in meeting study requirements. Alternatively new candidates can be randomly or pseudo-randomly selected. The system 210 can identify a number of candidates that would be needed to increase likelihood of reaching the target representation (for the group or for the study as a whole) at study end to the desired level, such as 80%. This can be done by simulating additions, predicting the changes, and then iteratively adding until the likelihood threshold is met or exceeded. The system 210 can then select this determined number of additional candidates in G1 and G3 to add to the cohort, and can automatically invite them (e.g., sending, an email, a text message, a notification through an application, etc.) to enroll. Researchers can be recommended which individuals to add or which groups in which to add individuals, and may be given the opportunity to confirm or approve first.

The changes that the system 210 identifies to improve compliance and diversity can be made by the system automatically, e.g., to preemptively increase survey reminders to members of G3 when the system 210 determines that the predicted survey response compliance rate is low. In some implementations, changes can be recommended to a researcher or other administrator and performed in response to receiving confirmation. For example, a user interface for the researcher can be populated with user interface controls, based on data sent by the system 210, that the researcher can select to initiate the various actions identified for improving diversity.

In some cases, the system 210 is used to assist in initial selection of a cohort or to assess whether a study is viable with a certain pool of candidates. The cohort for the study may be generated by selecting individuals whose profiles meet the selection criteria for the clinical trial. For example, an administrator may select candidates to invite to participate in the clinical trial or the system can select candidates using user profiles in a database. Even before the clinical trial begins, the system can use historical outcomes and/or predictions to assess the likelihood that the set of candidates to invite will yield a cohort that will provide the needed compliance among a sufficiently large and diverse set of participants. For example, an administrator may select a group of 120 candidates, with 40 candidates in each of groups G1, G2, and G3.

The system 210 can determine, for each group, an estimated rate of conversion, e.g., a proportion of those that enroll out of the total invited. This rate can be determined based on records for previous clinical trials indicating invitations made, enrollment outcomes (e.g., which individuals enrolled and which did not), and user profiles for the users (e.g., to determine which groups the individuals would correspond to). The system 210 may use statistics for the groups directly (e.g., use the historical rates calculated for the groups), use a trained machine learning model to predict the rates, or generate a more complex rate based on likelihood of enrollment for each individual (e.g., using a trained machine learning model to predict an enrollment outcome for each candidate and using the likelihoods to generate an overall predicted rate for the candidates in a group).

As the system 210 receives data collection results from remote devices, the system 210 uses the results to update and continue training the various models. In addition, as the system 210 recommends and makes changes to improve outcomes and future diversity status, the system 210 tracks the results achieved for the different interventions it performs. As a result, the system 210 can learn which interventions are most effective for different diversity groups and for different situations, allowing the system 210 to select and perform more effective preemptive and corrective actions in the future for the same or different monitoring programs.

The process 1800 can include causing each of one or more remote devices to carry out monitoring using one or more changed parameters or software modules selected to provide better compliance or data quality. This can include distributing configuration data corresponding to one or more programs identified for the one or more remote devices using the adapted scoring process. Distributing the configuration data can include transmitting, to each of the one or more devices, configuration data configured to adjust operation of the remote devices to set or change sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements.

Distributing the configuration data can include transmitting, to each of the one or more devices, configuration data configured to adjust operation of the remote devices to set or change data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements.

Distributing the configuration data can include transmitting, to each of the one or more devices, configuration data configured to adjust operation of the remote devices to set or change network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data.

The configuration data can cause remote devices to perform various changes or configuration actions, often without requiring user action once the user enrolls in the program. The actions can include: enabling or disabling a sensor of the remote device or a device communicatively coupled to the remote device; setting or changing sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements; setting or changing data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements; setting or changing network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data; setting or changing power usage parameters of the remote device, including changing a device power state or sleep setting of the remote device; altering a user interface of an application installed at the remote device, including changing a set of interactive user input controls presented in the user interface; setting or changing interactive content to be presented by the remote device as part of the program, the interactive content including at least one survey, prompt, or electronic form; or setting or changing parameters for presenting the interactive content that includes at least one of timing, frequency, format, triggers, or contexts for providing the interactive content.

FIGS. 19A-19D are diagrams that illustrates one or more components of the system 200 and a process of prioritizing monitored groups, participants, and/or devices for adjustments. The system 200 can prioritize the in the groups, that are the least likely to meet diversity criteria for a monitoring program or other program requirements. Similarly, the system 200 can prioritize the groups according to which groups are most likely to prevent the successful completion of the monitoring program.

Figure 19A:
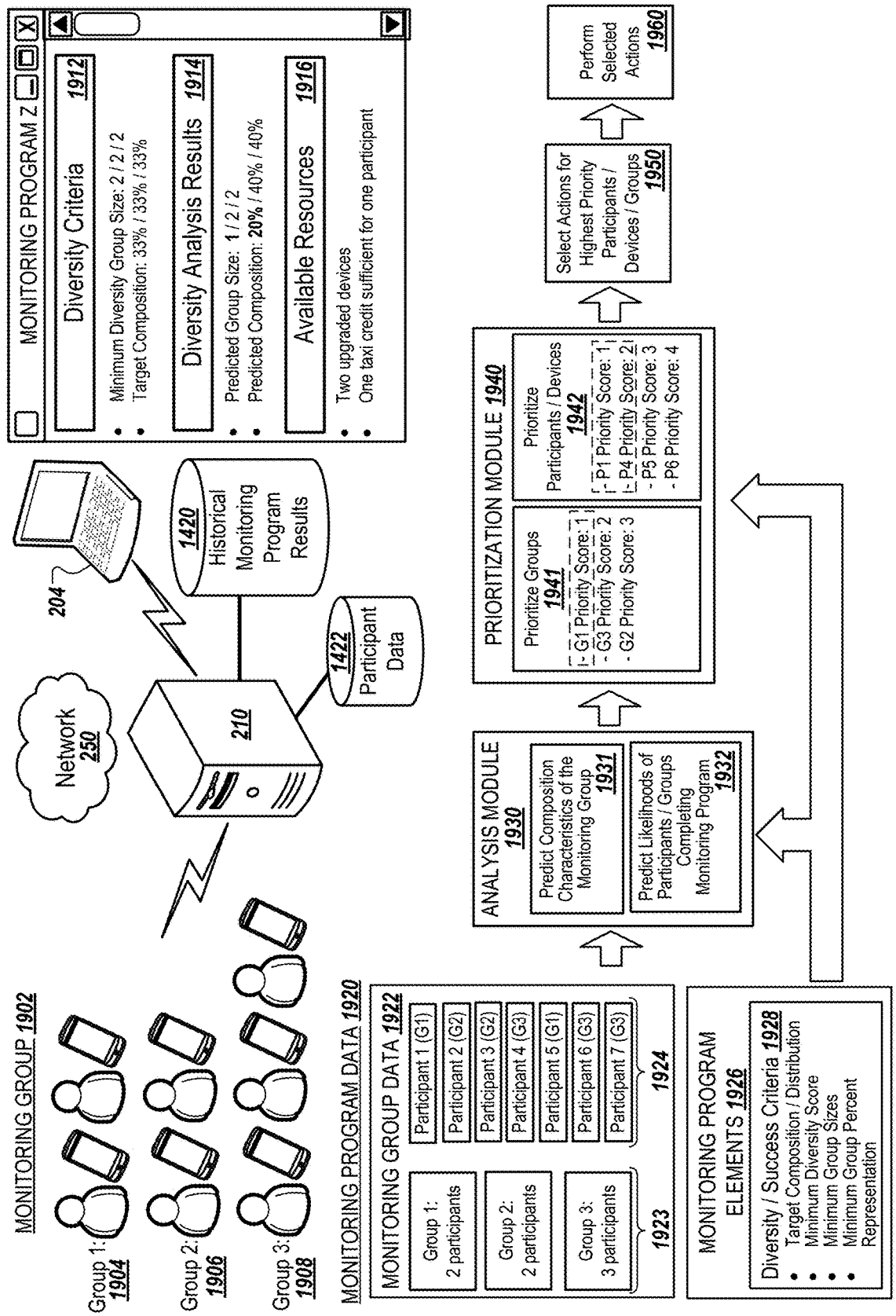
FIGS. 19A-19D are diagrams that illustrate an example system for prioritizing intervention to improve monitoring performance for groups in a monitoring program.

As illustrated in FIG. 19A, the computer system 210 can use an analysis module 1930 to make various determinations or predictions for a monitoring group 1902 enrolled in a monitoring program, such as likelihoods of different groups or participants successfully completing the monitoring program. The computer system 210 can use a prioritization module 1940 to generate priority scores for different groups or participants in the monitoring group 1902 based on the analysis module 1930's determinations or predictions. The priority scores may indicate likelihoods of different groups or participants successfully completing the monitoring program, or an impact that each of the groups or participants have on a likelihood of the monitoring program being successfully completed. The prioritization module 1940 can rank the groups or participants according to their priority scores. The system 210 can use the rankings to identify a subset of the groups or participants in the monitoring group 1902 with the highest ranking (e.g., highest priority) for which there is the greatest need of a change to meet the overall objectives of the monitoring program.

In many cases, the groups or devices that need attention and changes in monitoring may not be immediately apparent from performance measures alone. For example, the individuals or groups that have the lowest monitoring performance (e.g., lowest completion rates or lowest accuracy) may not necessarily be the ones that have the greatest impact on the monitoring program as a whole. For example, in a first group and second group may respectively have 70% and 80% of devices enrolled providing the data needed. However, the first group may be far oversubscribed relative to its minimum (e.g., with 11 devices enrolled with a minimum of 6 devices needed), while the second group is not (e.g., 12 devices enrolled with a minimum of 10 devices needed). As a result, even though the second group is performing better by many objective measures—having more devices involved and with higher success rates for those devices—the second group can still be assigned a higher priority so that adjustments to the monitoring program support and improve the performance of the second group. In this way, the system 210 selectively applies changes to target the groups and devices that will provide the greatest improvement to the objectives of the overall monitoring program, which in some cases are the ones that are most at risk of jeopardizing the success of the overall monitoring scheme.

In a similar manner, adjustments made for individual devices and users are also weighed and prioritized for the effect on current and future performance. Rather than simply make changes for target devices with the lowest performance, the system 210 considers the groups that devices are in and how potential improvement would affect the objectives of the monitoring program. For example, three devices might have measurement completion rates of 40%, 70% and 80%, where a minimum of 75% is needed for a data set to be valid, and otherwise the device's data needs to be removed entirely from the study. While focusing on improving the lowest performing devices may be the right choice in some cases, it is not necessarily the best to ensure the study is effective. For example, although the device with 80% measurement completion currently meets the minimum standard, it may actually have the highest priority if is in a group where other devices in the group are not meeting the standard or if the group size is at or below the minimum level. In other words, maintaining acceptable performance from this device in a group at high risk of non-compliance may be more important than improving performance of devices in groups that already have met their minimums of complying members. Similarly, for the other two devices, the one with the 70% completion rate may be prioritized over the one with 40% completion, since the device with 70% may be determined to be closer to and thus more likely to be able to achieve the required 75% standard. Whether considering current performance relative to the standard or not, the system 210 can estimate, based on the attributes, history, and patterns observed for a device and user as well as other devices and users, which are most likely to improve performance in response to an adjustment and by how much. For example, the system 210 can determine that available changes to the monitoring program are expected to add 20% to monitoring completion rate of the device with a current 40% rate, while they are expected to add 15% to the monitoring completion rate of the device with a current 70% rate. In this case, the first device would still fail to reach the required 75% standard, while the second device is expected to meet the standard, making the second device a better fit and higher priority to receive targeted changes to improve monitoring performance.

In many cases, a system may attempt to improve monitoring performance for as many devices as possible. However, this may not be efficient or possible in all cases. For example, enrolling some additional devices and users in a research study may be desirable and even necessary in some instances, but doing so adds to processing loads, data storage requirements, network traffic, and cost. If the added devices or users are not needed, or do not address the actual weaknesses in monitoring performance (e.g., adding to a group that is fully represented and performing well), then the additional load and bandwidth is not justified and can be wasteful. In some cases, a monitoring program may set an upper limit that the system 210 needs to respect, such as a maximum of 200 enrolled devices or users. If a monitoring program has 175 enrolled but still has a high risk of not meeting the overall diversity requirements and other objectives, the system 210 needs to select how best to enroll the remaining 25 to achieve the needed monitoring performance for each of the diversity groups. Other limits can apply and make prioritization important. If there are only 150 units of a medical device available for a monitoring program, then the system 210 needs to allocate these in a manner that is sufficiently likely to meet the objectives of the monitoring program (e.g., to the appropriate distribution of users, locations, etc.), and adding more devices may not be an option. Similar issues can arise when participation requires use of software that has limited numbers of software licenses available, when physical capacity at certain sites is limited (e.g., when in-person visits or laboratory tests are required), and so on.

In addition, the system 210 itself has limited processing capacity and often manages many different monitoring programs concurrently, e.g., potentially dozens, hundreds, or thousands of different monitoring programs, each requiring ongoing interactions with its separate monitoring groups of remote devices. The servers of the system 210 have limited memory, computational capabilities, and network bandwidth, and so attempting every possible improvement for every remote device of every monitoring program simply is not feasible. Even if it were, it would still be important to prioritize the changes that have the most impact on the monitoring programs, to make those changes first and verify whether the desired improvements are obtained, before turning to the many less important changes that are not important or impactful to the objectives of the monitoring programs.

The system 210 considers the unique requirements, objectives, monitoring group composition, and monitoring results of each monitoring program in making adjustments. This allows the system 210 to adaptively adjust the administration of each monitoring program to maintain at least a minimum likelihood that different objectives of the program, such as obtaining a valid data set from a sufficiently diverse set of devices and users, are met. The system 210 repeatedly monitors the performance of individual users and devices over the course of the monitoring program, and also examines the performance and collected data set characteristics for different sub-groups of devices and users, e.g., different diversity groups for which minimum amounts of representation are desired. The system 210 uses the monitored performance and status of the groups to control interactions with individual devices, selectively targeting communications, configuration changes, user interactions, and other interactions to specific devices based on their individual performance and group membership to improve monitoring performance where the system 210 predicts it will have the greatest benefit in increasing the likelihood of achieving the overall monitoring objectives for the monitoring program.

The system 210 can initiate changes that the system 210 selects from of a variety of types of changes. For example, the system 210 can send instructions to change the parameters for measurements and sensor data collection performed using sensors of remote devices and connected devices. Many of the remote devices involved in monitoring programs are smartphones, and these include sensors such as microphones, cameras, accelerometers, GPS sensors, compass sensors, and more. Smartphone can also interact with other devices, such as smartwatches, smart rings, wearable devices, and medical devices (e.g., medical monitoring or treatment devices such as glucometers, blood pressure cuffs, weight scales, thermometers, pulse oximeters, drug delivery systems, telehealth equipment, respiratory equipment (e.g., continuous positive airway pressure machines, ventilators, oxygen concentrators, etc.), and more). The system 210, upon determining that a device is not providing the type of measurement needed, or that the accuracy or measurement frequency is too low, can send instructions to activate a sensor, deactivate a sensor, change the duration or intensity of activation, change the frequency at which measurements occur, change the triggers for activation (e.g., contexts, inputs, times, locations, etc. that cause a device to acquire and record a new measurement), and so on. In some cases, the remote device is instructed to change the types of data collected, the types of sensors used, or whether to collect data with its own sensor or with a connected device or both. As an example, the instruction from the system 210 can cause a remote device to increase the number of times that measurements are attempted, e.g., from once and hour to every 15 minutes, to increase the likelihood that valid measurements will be acquired. Of course, the increased measurement rate would increase power usage and reduce battery life of a user's smartphone, and so this type of change is best performed selectively, for the devices where it is needed to meet the monitoring program objectives rather than performed for all devices.

Accordingly, the system 210 can selectively make adjustments targeted to provide the most benefit to the monitoring program, e.g., to improve monitoring performance (e.g., diversity, data collection completeness, data collection frequency, reliability, efficiency, accuracy, and data quality) by addressing the groups or participants that are least likely to complete the monitoring program or that have the most detrimental impact on the successful completion of the monitoring program.

For the analysis module 1930 to make determinations or predictions, the computer system 210 may first obtain information that the analysis module 1930 uses to make these determinations or predictions. This information can include characteristics of the monitoring group 1902 and requirements for the monitoring program. The analysis module 1930 can also use other information, such as information collected from devices in the monitoring group 1902 over the duration of the monitoring program and historic data from previous monitoring programs.

The determinations or predictions made by the analysis module 1930 can indicate whether the monitoring program will be successfully completed and/or, more precisely, whether the monitoring program will produce viable results. That is, the determinations or predictions can take into account the requirements for the monitoring program or can be compared with the requirements for the monitoring program to determine success of the monitoring program or a likelihood of success for the monitoring program. These requirements can include diversity criteria that define a level of diversity for the monitoring program sufficient to produce viable results (e.g., results that are sufficiently applicable to a target population, results that have a sufficiently low probability of producing false-negatives, results that have the ability to meet a required level of statistical significance, etc.). When prioritizing groups, the prioritization module

1940 may prioritize groups in the monitoring group 1902 failing to meet diversity criteria or that are not anticipated to meet the diversity criteria. Similarly, when prioritizing participants, the prioritization module 1940 may prioritize participants in the monitoring group 1902 that belong to particular diversity groups that are failing to meet diversity criteria or that are not anticipated to meet the diversity criteria. It follows that the adjustments selected and performed by the system 210 for the prioritized groups/participants can include actions to improve diversity among the monitoring group 1902, thereby expanding the section of a target population that the monitoring program's results will be applicable to or, similarly, increasing the number of populations the monitoring program's results will be applicable to. By performing these adjustments, the computer system 210 can significantly improve the likelihood of the monitoring program producing results having real-world viability, reducing the need to repeat or extend the length of the monitoring program.

As shown, the monitoring group 1902 may include a first group 1904 that belongs to a first diversity group, a second group 1906 that belongs to a second diversity group, and a third group 1908 that belongs to a third diversity group. Each of the groups 1904 can include one or more participants and corresponding participant devices. The participant devices can communicate with the computer system 210 over the network 250. The computer system 210 may send software packets to each of the participant devices in the monitoring group 1902. The software packet sent to each of the participant devices can be based on the particular monitoring program that the monitoring group 1902 is participating in, on the attributes of the participant device, on the attributes of the corresponding participant, and/or on the diversity group(s) that the devices or corresponding participants belong to.

The participant devices in the monitoring group 1902 can be geographically distributed. That is, the participant devices may be located remotely with respect to the computer system 210 and/or with respect to each other.

In general, a diversity group refers to a group of subjects (e.g., participants or devices that have (i) registered for monitoring programs and/or (ii) enrolled in a monitoring program) that represent a particular category of subjects. Each category of subjects can be defined by a particular profile that specifies a set of attributes for determining subject inclusion. As an example, the set of attributes can include values or ranges of values for different diversity dimensions, such as an age or age distribution dimension, sex dimension (e.g., male or female), race dimension, ethnicity dimension, geographic dimension (e.g., country, state, and/or city of residence), medical condition dimension (e.g., genetic conditions, diseases, past surgeries, pregnancy, etc.), medication dimension (e.g., prescriptions), etc. For a monitoring program to meet a minimum level of diversity, multiple participants from multiple diversity groups may need to be enrolled in the monitoring program and comply with the program's requirements.

In some cases, subjects are represented by a single profile. For example, each participant in the monitoring group 1902 may be represented by a particular profile. In more detail, the first group 1904 of participants may belong to a first diversity group represented by a first profile, the second group 1906 may belong to a second diversity group represented by a second profile, and the third group 1908 may belong to a third diversity group represented by a third profile. The three profiles may have different inclusion requirements that the computer system 210 can compare to participant attribute information to determine, for each participant, a single diversity group that the respective participant should be assigned to.

In some cases, subjects are represented by one or more profiles. For example, each participant in the monitoring group 1902 may be represented by, potentially, multiple profiles. In more detail, the first group 1904 of participants can belong to a first diversity group represented by a first profile. However, one of the participants in the first group 1904 may also belong to a second diversity group represented by a second profile. Similarly, the other one of the participants in the first group 1904 may belong to a third diversity group represented by a third profile. The three profiles may have different or overlapping inclusion requirements that the computer system 210 can compare to participant attribute information to determine, for each participant, one or more diversity groups that the respective participant should be assigned to.

Other types of attributes can be used to define diversity groups. For example, with respect to devices, the set of attributes can include values or ranges of values for different diversity dimensions, such as a device model dimension, a device manufacturer dimension, a device performance dimension (e.g., minimum CPU speed, range of CPU speeds, minimum batter life etc.), a sensor dimension (e.g., requirement of a HR monitor, requirement of an accelerometer that has a pitch and roll accuracy of 0.1 degrees RMS or less, etc.), a component dimension (e.g., CPU core size, RAM size, memory size, battery cells, battery capacity, etc.), etc.

In some cases, each group in a monitoring group only includes one or more participants. For example, the monitoring group 1902 may include multiple participants. The participants may communicate with the computer system 210 using at least one computing device that is/are used by the multiple participants and/or is/are shared by the multiple participants.

In some cases, each group in a monitoring group only includes one or more devices. For example, the monitoring group 1902 may include multiple remote computing devices. These devices may belong to different users. These devices may be part of a device farm. These devices may be geographically distributed (e.g., remote) with respect to the computer system 210 and/or with respect to one another.

In the examples shown in FIGS. 19A-19D, various major functions are performed by the system 210, including (A) accessing and evaluating information for a monitoring program, (B) classifying devices and corresponding users, (C) monitoring and evaluating performance in the monitoring program, (D) prioritizing groups, (E) selecting actions to improve monitoring performance, and (F) implementing selected actions. These and various other functions are discussed in more detail below.

A. Accessing and Evaluating Monitoring Program Information

The computer system 210 can access data to provide to the analysis module 1930 and/or the prioritization module 1940. The computer system 210 can access this data from one or more databases that are local or remote with respect to the computer system 210. For example, the computer system 210 can access historic monitoring program data from the database 1420 and participant attribute data from the database 1422.

In accessing data to provide to the modules 1930 and/or 1940, the computer system 210 can access data collected from devices in a monitoring group over a period of time. For example, the computer system 210 can access data collected by the devices in the monitoring group 1902 over a period of time. The period of time may be the time from the start of the monitoring program and the current time. Similarly, the period of time may be a time since data was first transmitted from one of the devices in the monitoring group 1902 to the computer system 210 until a time when data was last transmitted from one of the devices in the monitoring group 1902 to the computer system 210. That is, the accessed data can include data collected from the monitored devices since a start of the monitoring program. Alternatively, the period of time can be the entire duration or expected duration of the monitoring program. Accordingly, the accessed data can include any data collected from the monitored devices over the duration of the monitoring program.

The accessed data can also or alternatively include data collected from monitored devices over different periods of time. For example, the accessed data can include data collected from monitored devices since the devices and/or their corresponding participants were first registered. Similarly, the accessed data can include data collected from monitored devices during one or more past monitoring programs.

The computer system 210 can access various types of data collected from monitored devices. For example, the computer system 210 can access registration information that includes attribute information for the device and/or a user of the device (e.g., a participant). The collected data can include sensor data obtained by the devices and/or participant input entered through the devices. For example, the collected data accessed by the computer system 210 can include sensor data obtained by the remote devices (e.g., using one or more component sensors of the devices), test results generated using sensor data and/or participant input entered through the devices, survey information generated using participant input, among other information.

As an example, the monitoring program's protocol can provide that all participants must perform five exercises a day while wearing or holding their device, and fill out a quick survey that asks the participants how they feel after completing each exercise. The devices in the monitoring group 1902 may collect GPS data, accelerometer data, and heart rate (HR) data from the participants while they are performing the exercises, and proceed to transmit the sensor data to the computer system 210. The devices can also proceed to use the collected data to score performance tests for the participants, and transmit the test scores for each of the participants to the computer system 210. The devices may use timers or obtained sensor data to determine when participants have completed (or stopped) an exercise, and proceed to prompt the participants to fill out corresponding surveys. The devices may proceed to transmit the survey results and/or the survey to the computer system 210. The computer system 210 can store the collected data and associate the data with the monitoring program, with the corresponding participants, and/or with diversity groups that the corresponding participants belong to.

In accessing data to provide to the modules 1930 and/or 1940, the computer system 210 can access historic data from previous monitoring programs. The historic data can include the results, monitoring group data, and/or protocol information from previous monitoring programs. For example, the historic data can include the names of participants that were enrolled in a previous monitoring program at the start of the program, the names of participants that successfully completed the previous monitoring program, the populations of diversity groups represented in the monitoring group of the previous program at enrollment, the populations of diversity groups represented in the monitoring group at the end of the previous program, the protocol for the previous monitoring program including the requirements (e.g., success criteria/diversity criteria) for the program, and an indication of whether the monitoring program was successfully completed. The historic data can also include data collected from monitored devices during previous monitoring programs and/or during device or participant registration.

The historic data can include data objects generated by the computer system 210 using previously collected data. For example, the computer system 210 can assign collected data to one or more diversity groups using attribute information associated with the collected data, and use the different groups of assigned data to generate data objects for the diversity groups. The data objects can include, for example, average compliance rates and/or retention rates observed for subjects in the different diversity groups over time. As another example, the data objects can include average compliance rates and/or retention rates corresponding to a particular monitoring program elements (e.g., protocol elements, requirements such as success/diversity criteria, etc.) or combinations of elements. For example, the historic data can include a table that indicates that a compliance rate for Group A subjects is observed to be 80% when a monitoring program requires monthly office visits and 66% when a monitoring program requires weekly office visits.

The computer system 210 can use the generated data objects to identify trends for the different diversity groups. As will be discussed in more detail below, the computer system 210 can use these trends to make various predictions.

In accessing data to provide to the modules 1930 and/or 1940, the computer system 210 can access monitoring program data 1920. The monitoring program data 1920 can include monitoring group data 1922 that can indicate, for example, the participants or devices currently enrolled in the monitoring program, the diversity groups represented in the monitoring group 1902, and/or performance metrics for the participants or the groups. For example, the monitoring group data 1922 can include participant group data 1923 that indicates the various groups in the monitoring group 1902 that correspond to different diversity groups, and the current population of each of the groups. The monitoring group data 1922 can also contain participant attribute data 1924 that includes attribute information for each of the participants currently enrolled in the monitoring group 1902 (e.g., active in the monitoring group 1902), such as an indication of the diversity group(s)/profile(s) that each participant belongs to or the diversity group(s)/profile(s) that most closely match each participant. As an example, the participant attribute data 1924 can include an ID such as a name or ID number for each participant and performance metrics for each participant.

The performance metrics can include, for example, a current overall compliance rate for each participant or group. For example, the participant group data 1923 can include and/or multiple compliance rates for different areas of the monitoring program (e.g., requirements or protocol elements of the monitoring program, or types of requirements or protocol elements of the monitoring program). As an example, a first participant in the monitoring group 1902 can have an acceptable overall compliance rate of 76% while demonstrating poor compliance of 45% for attending office visits specified in the monitoring program's protocol. The participant attribute data 1924 can include both the overall compliance rate and the category-specific compliance rate.

Other performance metrics can include retention rates and levels of data quality for the participants or groups. For example, the computer system 210 can determine current retention rates for each of the groups by comparing the number of participants in each group at the start of the monitoring program to the number of active participants currently in each of the groups. The levels of data quality can indicate an overall data quality provided by the participants or participant devices, and/or an amount of data provided by the participants or participant devices. For example, a level of data quality for a first participant in the monitoring group may reflect the precision or accuracy of the participant's device sensors used to collect sensor data, the percent of surveys and tests that the participant completes, and the average answer time for the participant (e.g., where too short of an answer time may correspond to low data quality as the participant likely did not have enough time to read the question).

In some implementations, the computer system 210 uses accessed data to generate performance metrics for the participants or groups in a monitoring group. For example, the computer system 210 can access sensor data and participant responses, compare the accessed data to the monitoring program elements 1926, and use the comparison results to calculate an overall compliance rates for each of the participants. The computer system 210 can use these compliance rates and information indicating the diversity groups for each participant to calculate the current, average compliance rate for the first group 1904, the second group 1906, and the third group 1908.

The monitoring program data 1920 can also include monitoring program elements 1926 for the current monitoring program, such as a protocol for the monitoring program and/or requirements of the program. For example, the monitoring program elements 1926 can include the diversity/ success criteria 1928 for the monitoring program. The criteria 1928 can include, for example, target compositions or distributions for populations of diversity groups represented in the monitoring group 1902, a minimum diversity score or level for the successful completion of the monitoring program, minimum group sizes, minimum group percent representations, among other possible criteria. The monitoring program data 1920 can also include For example, the computer system 210 can access attribute information for the participants and/or devices in the monitoring group 1902 from the database 1422.

All or a portion of the monitoring program elements 1926 may be predetermined for the particular monitoring program or for all monitoring programs. For example, all monitoring programs may require the same minimum diversity score or may, before further determinations are made by the computer system 210, start with a preset minimum diversity score.

All or a portion of the monitoring program elements 1926 may be determined by the computer system 210 for the current monitoring program. For example, the computer system 210 may access preset diversity/success criteria and proceed to adjust the criteria for the particular monitoring program, e.g., based on the protocol for the monitoring program, based on the number of participants that enrolled in the monitoring program, and/or based on the number or populations of diversity groups represented in the monitoring group 1902.

In accessing data to provide to the modules 1930 and/or 1940, the computer system 210 can access information from the monitoring program elements 1926. This information can include a protocol for the monitoring program that specifies the actions that participants in the monitoring group 1902 are tasked with completing. The monitoring program elements 1926 can also include timing elements for the monitoring program, such as a set or anticipated duration for the monitoring program, start dates for the program, and/or end dates for the program. Notably, the monitoring program elements can include the diversity/success criteria 1928. The computer system 210 can use the information accessed from the monitoring program elements 1926, particularly the criteria 1928, to make determinations and predictions surrounding the monitoring program's chances of success.

B. Classifying Devices and Users

After accessing data, the computer system 210 can use the accessed data to classify devices or participants into different diversity groups. For example, the computer system 210 can use profiles that represent different diversity groups and the monitoring group data 1920 to classify each of the participants or participant devices enrolled in the monitoring program to at least one of the diversity groups. In more detail, the computer system 210 can match attribute values for each of the participants or devices to corresponding values in the profiles, determine if the attribute values fall in ranges of values in the profiles, and/or determine if the attribute values meet minimum or maximum values in the profiles.

In some implementations, the computer system 210 classifies participants or devices to diversity groups by identifying which profiles best represent the participants or devices. For example, the profiles can include target attribute values. The computer system 210 can compare these target attribute values to the attribute values of the monitoring group 1902 to identify, for each participant or participant device, the profile that most closely matches the corresponding set of attributes. One way that the computer system 210 can accomplish this calculating arithmetic means by taking differences between the attribute values for the monitoring group 1902 and the target values in the profiles and, for each participant or device, averaging the differences to calculate a set of averages for each participant or device. These averages can indicate how closely each participant or devices matches each of the profiles. The computer system 210 can proceed to classify each participant and/or device using the profile that corresponds to the lowest average in the set of averages for the participant. The computer system 210 can also use geometric techniques to classify the participants or devices. For example, the computer system 210 can treat attribute or attribute type as dimension in a coordinate system and proceed to identify or calculate a geometric center for each of the profiles. The computer system 210 can proceed to map the participants or devices in the coordinate system using their corresponding attribute values and determine, for each participant or devices, Euclidean distances from a point representing the participant or device to each of the profile centroids. The computer system 210 can proceed to classify each participant or device using the profile that is the shortest Euclidean distance from the participant or device. Using these techniques, the computer system 210 can classify participants or devices even when they have attribute values that do not match or meet corresponding values or ranges of values in the profiles. That is, the computer system 210 can use these techniques to identify the diversity group that is the best fit for each of the participants or devices.

The computer system 210 can also or alternatively use thresholds to classify the participants or devices. A threshold may be defined by a particular magnitude from a target value, or a particular percent difference from a target value. For example, where the attribute information for a device indicates that it has a processor with a speed of 2.4 GHz and a profile for a first diversity group has a target processor speed of 2.5 GHz, the computer system 210 may determine that the processor speed for the device meets the corresponding target speed when the threshold for the processor speed attribute is set to (i) a magnitude of 0.1 GHz or less or (ii) a percent difference of 4% or less.

In some implementations, the thresholds for classifying the participants or devices are static. For example, as described above, a threshold may be a preset percentage of the target value.

In some implementations, the thresholds for classifying the participants or devices are dynamic. The factors for dynamically adjusting the thresholds can include factors that are specific to the participant or the device, such as a number of diversity groups that the participant or device has been classified in and the number of classification attempts that have been made with respect to the participant or the device. For example, the computer system 210 can set the percentage thresholds for all attributes in a profile to be 5% from corresponding target values for a participant when the computer system 210 determines that this is the first classification attempt for the participant (e.g., across all profiles). However, if after the first classification attempt the participant is not classified in any diversity groups represented by the profiles, the computer system 210 can update the percentage thresholds for all attributes in the profile to be 10% from corresponding target values for the participant during a second classification attempt.

In addition to target values or ranges of values, the profiles can include inclusion criteria that a participant or device must meet to be classified in the corresponding diversity group. That is, the profiles can include values, ranges of values, or thresholds that are not optional (e.g., must be matched or met). For example, a profile for a first diversity group can include a set of target values for the age, height, and weight of participants. However, the profile can also include inclusion criteria such as requirements that all participants be female, reside in the United States, and must be diagnosed with type II diabetes. When attempting to classify participants in the monitoring group 1902 using the profile, the computer system 210 may first filter out participants that are not female, that reside outside of the U.S., and that do not have type II diabetes. The computer system 210 can proceed to compare the ages, heights, and weights of the remaining participants with the target age, height, and weight in the profile to determine which, if any, of the remaining participants should be classified in a diversity group represented by the profile.

In some implementations, when a participant or device cannot be classified to a diversity group for failing to meet the inclusion criteria of all applicable profiles, the computer system 210 treats the inclusion criteria of the profiles as a set of targets. For example, in response to determining that a participant fails to meet the inclusion criteria of each of a set of profiles (e.g., selected for the monitoring program based on a type of study being performed and/or on a target population), the computer system 210 can convert the inclusion criteria for the set of profiles to target values. The computer system 210 can proceed to use those target values along with the other attribute values, ranges of values, or thresholds in the set of profiles to identify the profile(s) that best fits the participant's attributes. The computer system 210 can classify the participant to the diversity group(s) that are represented by those profile(s).

In some implementations, the computer system 210 identifies subgroups of participants or devices in monitoring groups that are expected to behave similarly. For example, the computer system 210 may use a different set of profiles that correspond to participant or device performance to identify subgroups of participants or devices in the monitoring group 1902 that typically perform similarly and/or are expected to perform similarly. The computer system 210 may use these profiles and/or subgroups to make more accurate predictions as to how particular participants or devices will continue to perform in a monitoring program, e.g., at a future time, after one or more adjustments are made to improve diversity, etc. The computer system 210 may use these profiles and/or subgroups in other ways, such as to identify actions or adjustments for groups or particular participants/devices that have been prioritized on the basis of diversity.

As an example, the computer system 210 can use a performance profile that corresponds to a prioritized participant to identify a set of actions or adjustments that will likely improve the performance for that participant, e.g., improve the compliance rate of the participant, improve the likelihood of retaining the participant, and/or improve the level of data quality provided by the participant. The profiles can include or be used by the computer system 210 to look up performance trends and/or an expected performance measures for the participants or devices in categories represented by the profiles (e.g., overall performance measures and/or performance measures that correspond to particular monitoring program requirements or protocols). For example, the computer system 210 can use the performance profile to lookup expected compliance rates—for participants in a category represented by the performance profile—that correspond to different monitoring program protocols. From these compliance rates, the computer system 210 may identify a particular monitoring program protocol element that corresponds to low compliance among participants in the performance category and is found in the protocol for the current monitoring program.

In determining actions to perform with the prioritized participant (e.g., to improve the diversity for the monitoring program), the computer system 210 may first identify the participant's problematic performance area(s) (e.g., performance areas that led to the participant being prioritized) and use the performance profile to identify causes or solutions for the particular performance area(s). In this case, if the participant's low compliance or predicted low compliance form the basis for the prioritization (or significantly contributed to the prioritization), the computer system 210 may use the performance profile to identify the protocol element and proceed to modify or eliminate the protocol element. The modification may be applicable to the entire monitoring group 1902. Alternatively, the modification may be limited to the prioritized participant, the diversity group(s) that the prioritized participant belongs to, and/or the performance group that the prioritized participant belongs to.

The computer system 210 can use a machine learning model to identify the subgroups of participants or devices. For example, the computer system 210 can use one or more clustering models to group participants or devices from ongoing or past monitoring programs according to their performance, such as their compliance with program requirements, compliance with particular program requirements or protocol elements, enrollment rate, retention rate, average data quality, etc. The computer system 210 can use the resulting clusters of participants or devices to generate performance profiles. The inclusion criteria for the performance profiles can include performance measures (e.g., participants must demonstrate an average compliance rate between 65% and 72%), particular behaviors (e.g., participants must demonstrate a behavior of failing to take their prescribed medications more than 50% of the time), and/or particular attributes (e.g., participants must be paraplegic).

The computer system 210 may update the monitoring group data 1922 to include the classifications for the participants or devices. For example, the participant group data 1923 can be updated to reflect the number of participants in the monitoring group 1902 that belong to each of the diversity groups. Similarly, the participant attribute data 1924 can be updated to indicate the diversity group that each participant belongs to.

C. Monitoring and Evaluating Performance in the Monitoring Program

After classifying the participants or devices, the computer system 210 can evaluate the monitoring performance of the monitoring group 1902. The computer system 210 can use a variety of techniques to evaluate the monitoring performance. These techniques can include evaluating the current monitoring performance, and/or evaluating a predicted monitoring performance for a future time. The computer system 210 can consider a variety of performance metrics to evaluate the monitoring performance, such observed or predicted compliance rates, retention rates, and data quality levels. These performance metrics be determined for different diversity groups. For example, the computer system 210 can calculate the observed compliance rates, retention rates, and data quality levels for the groups 1904, 1906, and 1908 using portions of the monitoring group data 1922 that each correspond to one of the groups 1904, 1906, and 1908. From these calculated metrics, the computer system 210 can generate performances scores for the groups 1904, 1906, and 1908 that the prioritization module 1940 can use to prioritize and rank the groups and/or participants.

As shown, the computer system 210 can use the analysis module 1930 to evaluate the monitoring performance. The analysis module 1930 can include or leverage statistical models, machine learning (ML) models, or a combination of statistical and machine learning models. The analysis module 1930 can be configured to perform any of the techniques described above with respect to FIGS. 15A, 15B, 15C, and 15D. For example, the analysis module 1930 can use one or more models to predict completion probabilities for each participant in the monitoring group 1902, and/or to predict completion rates for groups in the monitoring group 1902 that correspond to different diversity groups. The analysis module 1930 can similarly use one or more models to determine a likelihood of the monitoring program meeting the diversity/success criteria 1928 and/or to determine likelihoods of the different groups in the monitoring group 1902 meeting corresponding portions of the diversity/success criteria 1928 (e.g., specific to particular groups, applicable to all participants or devices, applicable to all groups, etc.). The analysis module 1930 can treat all or a portion of these predictions as performance metrics for evaluating the monitoring performance. For example, the analysis module 1930 can treat predictions specific to particular groups as performance metrics for those groups, and then use those predictions to determine an overall monitoring performance indicator or score for the monitoring group 1902, such as a predicted likelihood of successfully completing the monitoring program.

In evaluating the monitoring performance, the analysis module 1930 can predict composition characteristics of a monitoring group (1931). That is, the analysis module 1930 can be configured to predict composition characteristics for the monitoring group 1902 at a future time based on the monitoring group data 1922 and other information, such as historical data for the different diversity groups obtained from the database 1420. The composition characteristics can include, for example, a predicted distribution of the monitoring group 1902 among the different groups and/or a predicted percent representation of each of the groups at a future time.

The analysis module 1930 can use a variety of techniques to predict the composition characteristics, such as those discussed above with respect to FIGS. 15A, 15B, and 15C. In performing these techniques, the analysis module 1930 can use one or more statistical models, machine learning (ML) models, or a combination of ML and statistical models. As an example, the analysis module 1930 can obtain historical data that corresponds to different diversity groups represented in the monitoring program, and use a statistical model to identify performance trends in the historical data for each of the diversity groups such as trends in participant retention for the different groups. The analysis module 1930 can proceed to apply these trends to the monitoring group data 1922 to predict a group size for each of the groups in the monitoring group 1902 at a future time.

The analysis module 1930 can use the composition characteristics to make monitoring performance predictions or more accurate monitoring performance predictions. For example, the analysis module 1930 can compare a predicted distribution for the monitoring group 1902 to minimum group sizes in the criteria 1928 to identify differences between the predicted distribution and the minimums. The analysis module 1930 can proceed to use these differences to determine (i) likelihoods of each of the groups completing the monitoring program (e.g., probability of the groups meeting the minimum group sizes and, possibly, other applicable criteria in the criteria 1928), and/or (ii) a likelihood of successfully completing the monitoring program (e.g., probability of all of the criteria 1928 being met).

In some implementations, in predicting the composition characteristics, the analysis module 1930 makes predictions for particular participants in a monitoring group. For example, the analysis module 1930 can use a portion of the monitoring group data 1922 corresponding to a particular participant and historical data of that participant to determine a likelihood of the participant completing the monitoring program. If the likelihood fails to meet a threshold likelihood (e.g., 50%, 60%, 75%), the analysis module 1930 may predict that participant will not complete the monitoring program. The analysis module 1930 may repeat this process for each participant to generate, for example, a predicted distribution of the monitoring group 1902 at the end of the program.

In evaluating the monitoring performance, the analysis module 1930 can determine likelihoods of participants or groups successfully completing the monitoring program (1932). In more detail, the analysis module 1930 can predict a likelihood for each group or participant in the monitoring group 1902 meeting applicable portions of the criteria 1928 by the end of the monitoring program. The analysis module 1930 can use the monitoring group data 1922 and the criteria 1928 to make these predictions. For example, the analysis module 1930 can use information collected from the participant devices during the monitoring program to predict the monitoring performance for the different groups at the end of the program. The analysis module 1930 can proceed to compare the predicted performance to the criteria 1928 to determine the likelihoods of each group completing the program.

The analysis module 1930 can use additional information to determine these likelihoods, such as a protocol for the monitoring program, relevant historic data obtained from the database 1420, previously collected participant information obtained from the database 1422, and/or profiles that define the diversity groups represented in the monitoring group 1902 (or that are required to be represented as specified in the criteria 1928). As an example, the analysis module 1930 can use the monitoring group data 1922 to identify an observed compliance rate for each group in the monitoring group 1902. The analysis module 1930 can proceed to obtain historic data for (i) previous monitoring programs that included protocol elements found in the protocol for the monitoring program and (ii) diversity groups represented in the monitoring group 1902. From this historic data, the analysis module 1930 can identify compliance trends for the different groups given particular protocol elements of the monitoring program. The analysis module 1930 can proceed to apply the identified trends to current compliance rates of the groups to predict a compliance rate for each of the groups at a future time. The analysis module 1930 can compare these predicted compliance rates to corresponding a minimum compliance rate in the criteria 1928 needed to maintain active participation, and, based on the comparison, predict a number of participants in each of the groups expected to complete the monitoring program. The analysis module can proceed to determine a likelihood of each of the groups completing the monitoring program based on a comparison of the predicted group sizes with corresponding minimum group sizes in the criteria 1928.

As will be discussed in more detail below, the prioritization module 1940 can use the likelihoods of the different groups completing the monitoring program to prioritize and rank the groups. For example, the prioritization module 1940 can use the likelihoods to generate priority scores for each of the groups that indicate how at risk each of the groups are of not meeting the criteria 1928. Similarly, the module 1940 can use the likelihoods to generate priority scores for each group that indicate the impact that each group has on the chances of the monitoring program meeting the criteria 1928.

The determined likelihoods of the participants or groups can represent performance scores for the participants or groups, or be used by the analysis module 1930 to generate performance scores for the participants or groups. For example, based on a prediction that the first group 1904 has 60% likelihood of completing the monitoring program, the analysis module 1930 can assign a performance score of 0.60 to the first group 1904. As will be discussed in more detail below, a performance score that indicates the likelihood of a group completing the monitoring program can be considered an overall performance score for that group that is used by the prioritization module 1940 to generate a priority score for that group. However, the analysis module 1930 may determine other types of performance scores for the participants and/or groups that are (i) used by the analysis module 1930 to determine an overall performance score for the participant/group, and/or (ii) used by the prioritization module 1940 to prioritize and rank the participants/groups.

As another example, the analysis module 1930 can take the average or weighted average of determined likelihoods for participants in each of the groups 1904, 1906, and 1908 to calculate a performance score for each of the groups 1904, 1906, and 1908. In more detail, if the analysis module 1930 determines that there is a 50% likelihood of a first participant in the group 1904 completing the program and an 80% likelihood of a second participant in the group 1904 completing the program, the analysis module 1930 can calculate a retention type performance score of 0.65 for the first group 1904. The analysis module 1930 can provide this performance score as output to the prioritization module 1940 and/or to calculate an overall performance score for the first group 1904.

The analysis module 1930 can determine likelihoods of the different groups or participants meeting other criteria. For example, using the techniques discussed, the analysis module can determine a first set of likelihoods of the groups 1904, 1906, and 1908 meeting corresponding minimum group sizes specified in the criteria 1928 and a second set of likelihoods of the groups 1904, 1906, and 1908 meeting corresponding minimum percent representations specified in the criteria 1928. The analysis module 1930 can use these likelihoods to determine the likelihood of each group/participant completing the monitoring program. The analysis module 1930 can also or alternatively use these likelihoods to generate performance scores for the groups/participants. That is, the analysis module 1930 can use these likelihoods to determine multiple performance scores for each group/participant that correspond to different performance categories such as compliance, group size, percent representation, retention, data quality, etc.

Continuing the earlier example, from the first set of likelihoods, the analysis module can determine a group size performance score for each of the groups 1904, 1906, and 1908. Similarly, from the second set of likelihoods, the analysis module 1930 can determine a percent representation performance score for each of the groups 1904, 1906, and 1908. In more detail, based on determining that there is a 55% likelihood of the first group 1904 meeting a minimum group size of two participants by the end of the program and a 65% likelihood of the first group 1904 meeting a minimum representation of 33%, the analysis module 1930 can assign a group size performance score of 0.55 and a percent representation group score of 0.65 to the first group 1904. The analysis module 1930 can proceed to use the multiple performance scores for each of the groups to calculate an overall performance score for each of the groups. For example, the analysis module 1930 can average the two performance scores for the first group 1904 to calculate an overall performance score of 0.60 for the first group 1904. As will be discussed in more detail below, the prioritization module 1940 can later use the group size performance score, the percent representation performance score, and/or the overall performance score for the first group 1904 to generate a priority score for the first group 1904.

The performance scores generated by the analysis module 1930 can take into account the criteria 1928. For example, if the criteria 1928 provides that the minimum group size is two participants for the first group 1904 and is four for the second group 1906, then the analysis module 1930 may determine different group size performance scores for the two groups 1904 and 1906 when they include the same number of participants. In more detail, the analysis module 1930 may generate a score of 0.5 for the first group 1904 indicating that the group is at significant risk of the not meeting the minimum group size of two by the end of the program. In contrast, the analysis module 1930 may generate a score of 0 for the second group 1906 indicating that, absent any adjustments, the group cannot meet the minimum group size of four participants by the end of the program.

In evaluating the monitoring performance, the analysis module 1930 can determine a likelihood of successfully completing the monitoring program. The analysis module 1930 can use previously made predictions made for participants or groups and the criteria 1928 to determine a likelihood of the monitoring program being successfully completed. As an example, the analysis module 1930 can use the previously determined likelihoods of each group and/or participant completing the monitoring program to calculate a likelihood of the monitoring program being successfully completed (e.g., when all criteria in the criteria 1928 is met). In more detail, the analysis module 1930 may provide the previously determined likelihoods of each group and/or participant as input to a ML model trained on previously collected monitoring program data from prior monitoring programs. The output of the ML model may be or indicate a probability of the monitoring program being successfully completed.

In determining the likelihood of successfully completing the monitoring program, the analysis module 1930 can determine or track the impact that each of the groups have on this likelihood. For example, the analysis module 1930 may determine a performance score for each group in the monitoring group 1902 that indicate the impact that the groups have on the likelihood of successfully completing the monitoring program. The impact that each group has on the likelihood of completion may be a calculated or estimated change in likelihood. For example, the analysis module 1930 may determine test likelihoods of program success for different scenarios, and proceed to compare the test likelihoods to previously determined likelihood of success to identify differences between the test likelihoods and the determined likelihood of success. These differences can represent the impact that each group's performance has on the likelihood of success.

As an example, the analysis module 1930 can determine a "test" likelihood that corresponds to the first group 1904 by creating a scenario where the first group 1904 has a 100% likelihood of completing the program. Alternatively, in making this determination, the analysis module 1930 can create a scenario where the first group 1904 is ignored by, for example, temporarily removing or modifying a portion of the criteria 1928 that is applicable to the first group 1904. The analysis module 1930 can take the difference between the test likelihood and previously determined likelihood of success for the program to identify an impact that the first group 1904's performance has on the likelihood of success. For example, where the test likelihood is 85% and the determined likelihood is 70%, the analysis module 1930 may determine that the performance of first group 1904 has a negative 15% effect on the likelihood of success. The analysis module 1930 can determine a performance score (e.g., impact score) of 0.425 for the first group 1904 by, for example, scaling negative effects to a range of 0 (e.g., 100% negative impact) to 0.5 and positive effects to a range of 0.5 to 1 (e.g., 100% positive impact). As will be discussed in more detail below, the computer system 210 may use these impact type performance scores (e.g., among other possible performance scores) to prioritize and rank the groups and/or participants.

Alternatively, the analysis module 1930 can estimate an impact that each of the groups or participants have on the likelihood of success. For example, the analysis module 1930 treat the likelihood of each of the groups completing the monitoring program as an estimate of the impact that the group will have on the likelihood of success. In more detail, if the analysis module 1930 determines that the first group 1904 has a 60% likelihood of completing the program, the module 1930 can proceed to generate an impact performance score of 0.60 for the first group 1904. Another, similar technique that the analysis module 1930 can implement to estimate the impact of the groups/participants is to compare the likelihoods of the groups/participants completing the monitoring program each other and generate impact performance scores for the different groups/participants based on the comparison. For example, the analysis module 1930 can average the likelihoods of the groups 1904, 1906, and 1908 completing the monitoring program and proceed to generate impact scores for those groups based on differences between the completion likelihoods and the average. In more detail, if the likelihood of the first group 1904 completing the program is 60% and the average likelihood across the three groups is 70%, the analysis module 1930 can estimate that the effect of the first group 1904's performance on the likelihood of completing the program to be negative 10%. The analysis module 1930 can proceed to convert this effect to an impact performance score of 0.4 for the first group 1904 using the example scaling method discussed above.

In some implementations, the analysis module 1930 determines the impact of group or participant performance on the monitoring program meeting other criteria. For example, using the techniques described above, the analysis module 1930 can determine an impact that each of the group's performance has on the likelihood of the program meeting all minimum group sizes by the end of the program. The prioritization module 1940 can use these impact scores to generate priority scores for each of the groups and/or the participants in the monitoring group 1902.

In some implementations, the computer system 210 stops prioritizing monitored groups and participants for adjustments based on the output of the analysis module 1930. For example, in response to the analysis module 1930 predicting the monitoring program will be successful or that there is a sufficient likelihood of the monitoring program being successful (e.g., greater than 80%, 85%, or 90% probability), the computer system 210 can suspend or stop the current workflow of prioritizing monitored groups and participants in the monitoring group 1902 for adjustments. The computer system 210 can restart or resume prioritizing monitoring groups and participants for adjustments at a later time. For example, the computer system 210 may wait a preset amount of time, wait until a scheduled time, or wait until a particular event is detected (e.g., a participant in the monitoring group 1902 has become dropped out or become inactive) to initiate a new workflow for prioritizing monitored groups and participants in the monitoring group 1902 for adjustments.

Although many of the examples discussed above describe the analysis module 1930 determining likelihoods and performance scores for groups corresponding to different diversity groups, the analysis module 1930 can also determine likelihoods and performance scores for individual participants in a monitoring group. For example, the analysis module 1930 can calculate an overall performance score for each participant in the monitoring group 1902 based on the current compliance rate and level of data quality for each of the participants determined from the monitoring group data 1922. As will be discussed in more detail below, the prioritization module 1940 can use these participant performance scores to generate priority scores for each of the participants and/or each of the groups 1904, 1906, and 1908.

In some implementations, the analysis module 1930 generates other performance metrics. For example, the module 1930 may determine a binary value for each group in the monitoring group 1902 that indicates whether the group is predicted to complete the program. The module 1930 may use these binary values to generate an overall performance score for the monitoring program. For example, the module 1930 can use previously determined performance scores or likelihoods for the groups 1904, 1906, and 1908 to determine binary values for each of the groups 1904, 1906, and 1908. If the module determines a value of 0 for the group 1904 (e.g., indicating that the group 1904 is predicted not to complete the program) and a value of 1 for the groups 1906 and 1908 (e.g., indicating that those groups are predicted to complete the program), the module 1930 may calculate a performance score for the program to be 2/3 or a scaled performance score of 0.67. As will be discussed in more detail below, the prioritization module 1940 may use these performance metrics to generate priority scores for the groups, participants, and/or devices in the monitoring group 1902. The module 1940 may also use these metrics to avoid prioritizing particular groups, participants, or devices, such as those that are performing adequately.

D. Prioritizing Groups

The prioritization module 1940 can prioritize groups in a monitoring group using the output of the analysis module 1930 (1941). To prioritize the groups, the prioritization module 1940 can generate priority scores for each group in a monitoring group and use the priority scores to rank the groups in an order that indicates their priority for actions to improve monitoring performance, including changing device settings, updating software, sending communications to users (e.g., reminders, incentives, educational material, etc.). The prioritization module 1940 use a set of priority factors to generate the priority scores. The priority factors can include information extracted from the output of the analysis module 1930 such as performances scores for the groups. The priority factors can include other information such as information extracted from the criteria 1928, the monitoring group data 1922, and/or historic data.

As an example, the prioritization module 1940 may generate a priority score for the first group 1904 by taking a weighted average of the group 1904's compliance performance score, group size performance score, retention performance score, and data quality performance score. The prioritization module 1940 may apply a particular weight to each of these priority score factors before averaging the weighted values. The prioritization module 1940 may proceed to generate priority scores for the other groups in the monitoring group 1902 using the same set of priority factors and weights.

The prioritization module 1940 can use information other than or in addition to the performance scores to generate priority scores. For example, the prioritization module 1940 can treat other outputs of the analysis module 1930, such as likelihoods of the groups completing the monitoring program, as priority factors when calculating the priority scores. Similarly, the prioritization module 1940 can use historic trends or rates for the different groups, such as historic compliance rate, as factors when calculating the priority scores. The prioritization module 1940 can also look up other information that was not previously obtained.

As an example, the prioritization module 1940 can consider the availability of subjects from different diversity groups when generating the priority scores. In more detail, a priority factor can include the number of available subjects in each diversity group represented in the monitoring group 1902 that can be enrolled or invited to enroll in the monitoring program. If there are five subjects for a first diversity group corresponding to the group 1904 that are available to enroll in the program and ten subjects for a second diversity group corresponding to the group 1906 that are available to enroll in the program, a priority score factor that considers subject availability would weigh in favor of giving the group 1904 priority over the group 1906. That is, if all other priority score factors for the groups 1904 and 1906 end up being equal, the priority scores generated by the prioritization module 1940 would indicate that the group 1904 is prioritized over the group 1906. This prioritization can reflect the higher chance of the computer system 210 not being able to add or replace participants in the first group 1904 when compared to the second group 1906, and, therefore, indicate that more care needs to be taken to retain the participants in the first group 1904.

After generating priority scores for each group in a monitoring program, the prioritization module 1940 can rank the groups according to their priority score. The resulting order of the groups can indicate which groups the computer system 210 should prioritize. As will be discussed in more detail below, the computer system 210 can refer to these rankings to determine which groups in the monitoring group 1902 should be prioritized for particular actions (e.g., that may be time-sensitive) and/or allocation of limited resources.

Continuing the earlier example, the prioritization module 1940 can use the rankings to determine that the first group 1904 is prioritized for intervention to improve monitoring before the second group 1906. Based on this, the computer system 210 can proceed to identify and perform actions for the participants in the group 1904 in order to improve the general performance of the group 1904 or to improve the performance of the group 1904 in one or more particular areas. For example, based on the group 1904 having a low retention performance score, the computer system 210 may identify and perform one or more actions known to improve participant retention generally or previously shown to improve participant retention for the diversity group represented by the group 1904.

The prioritization module 1940 can also prioritize participants or devices in a monitoring group for outreach (e.g., communication) and other interventions using the output of the analysis module 1930 (1942). Similar to the techniques used for prioritizing groups, the prioritization module 1940 can generate priority scores for each participant in a monitoring group and proceed to rank the participants using the priority scores. As an example, the prioritization module 1940 can calculate priority scores using multiple priority factors. These participant priority factors can include priority factors that the prioritization module 1940 used to calculate the group priority scores, such as performance scores in the output of the analysis module 1930. Other participant priority factors used by the prioritization module 1940 to generate the participant priority scores can include the group priority scores or rankings.

As an example, the prioritization module 1940 may generate a priority score for a participant by taking a weighted average of the priority score determined for the group that the participant belongs to, the observed compliance rate for the participant as indicated in the monitoring group data 1922, and output of the analysis module 1930 that includes the likelihood of the participant completing the program. The prioritization module 1940 can proceed to calculate priority scores for the other participants in the monitoring group 1902, and rank all of the participants according to their priority scores.

In some implementations, the prioritization module 1940 only generates priority scores for a subset of the participants or devices in a monitoring group. The subset of participants or devices selected by the prioritization module 1940 for prioritization may belong to groups with the lowest performance, e.g., the groups that are least likely to complete the monitoring program and/or have the largest negative impact on the likelihood of completing the monitoring program. For example, the prioritization module 1940 may apply a group threshold to the group rankings to identify the threshold number of highest ranking groups. As another example, the prioritization module may apply a score threshold to the identify groups with a sufficiently low priority score. The prioritization module 1940 may proceed to generate priority scores and rank only those participants that belong to identified groups.

In more detail, the prioritization module 1940 may identify the first group 1904 and the third group 1908 as the two highest ranking groups from the group rankings or as the groups having a priority score of 2.5 or less. The prioritization module 1940 can proceed to generate priority scores for the participants in the first group 1904 and the second group 1908, and rank that subset of participants according to the generated priority scores.

The subset of participants or devices selected by the prioritization module 1940 may be those participants or devices that have demonstrated poor performance in a monitoring group. For example, the prioritization module 1940 may use participant performance scores generated by the analysis module 1930 to select a subset of participants from the monitoring group 1902 to prioritize. To select the participants with the lowest performance, the prioritization module 1940 may apply a threshold or a percent threshold to the participants in the monitoring group 1902 after they have been ordered according to their performance. For example, the prioritization module 1940 may rank the participants according to their overall performance (e.g., lowest overall performance ranked first) and apply a percent threshold of 45% to the ranked participants, resulting in three participants of the monitoring group 1902 being selected for prioritization.

The prioritization module 1940 may omit participants or devices from prioritization if the likelihood of them completing the monitoring program is too low. As an example, the prioritization module 1940 may recognize based on the collected data and the output of the module 1930 that some participants or devices (e.g., from those selected for prioritization based on their poor performance) have below a threshold likelihood of completing the program or improving their performance to the extent needed to become compliant. The likelihood for a particular participant or device may be previously determined by the module 1930 or determined by the module 1940, e.g., using the output of the module 1930. Alternatively, the likelihood for a particular participant or device may be estimated based on other information such as performance scores. For example, the module 1940 may select all participants in the monitoring group 1902 for prioritization who have a compliance score below 6 but above 2 based on historic data indicating that those with a compliance score of 2 or less are 90% likely to fail the program even when actions are taken to improve their compliance.

In some implementations, the prioritization module 1940 omits particular groups from prioritization. The prioritization module 1940 may apply thresholds or other criteria to the performance metrics for each of the groups in a monitoring program to determine which groups should be prioritized. As an example, the module 1940 may determine that only those groups that are predicted to not complete the program should be prioritized. In more detail, the module 1940 may require that groups eligible for prioritization have a binary value of 0 assigned by the module 1930, indicating that they are not predicted to complete the program. In applying this criteria to the groups 1904, 1906, and 1908, the module 1940 may determine that only the group 1904 is eligible for prioritization due to have a binary value of 0. If the module 1940 determines that one of the groups are ineligible for prioritization, the module 1940 may also omit prioritizing participants or devices in the ineligible group.

By omitting participants or devices from prioritization, the module 1940 can greatly improve efficiency of the system 210. As will be explained in more detail below, omitting participants or devices from prioritization can reduce the load on the computer system 210 by reducing the number of computations that need to be made for generating priority scores and identify actions to take with respect to those participants or devices. Moreover, omitting participants or devices that have little chance of becoming compliant further improves efficiency by reducing waste of resources (e.g., computational resources, tangible resources such upgraded devices or sensors, etc.). That is, due to the low likelihood of the computer system 210 realizing returns in the form of performance (e.g., compliance, retention, and/or data quality needed for program completion) on resources allocated to these participants or devices, the module 240 can better utilize the resources by allocating them to participants or devices that have more than a de minimis probability of improving their performance to the extent needed to complete the program.

In generating the priority scores, the prioritization module 1940 may use statistical techniques such as taking the average or weighted average of multiple priority factor values. The prioritization module 1940 may instead use machine learning techniques for generating the priority scores. For example, the prioritization module 1940 may select a first ML model for determining group priority scores. The ML model selected by the prioritization module 1940 may be based the elements 1926 of the monitoring program, such as the protocol for the program and the criteria 1928. For example, the module 1940 may select a first ML model for monitoring programs that require the completion of daily tests and attendance of weekly office visits. The ML model may be trained on historic data collected from monitoring programs whose protocol included requirements for daily tests and weekly office visits. The ML model selected may alternatively be selected based on the particular group being analyzed. For example, the module 1940 may select a first ML model for a first diversity group that the group 1904 belongs to. This ML model may be trained on historic data collected from participants or devices belonging to the first diversity group.

Continuing the example, the module 1940 may provide priority factor values as input to the selected ML model and, in response, receive an output from the ML model. In more detail, the module 1940 may provide as input an overall performance score for the group 1904, a likelihood of the group 1904 completing the monitoring program, an average compliance of participants or devices in the group 1904, and an indication of the number of participants or devices in the group 1904 greater than the minimum group size in the criteria 1928. The output of the ML model may be the priority score for the group 1904 or be used by the module 1940 to generate a priority score.

As another example, in using ML models to generate priority scores, the module 1940 may select ML models that correspond to particular priority factors, and use outputs from multiple ML models to generate the priority scores. For example, the module 1940 may select a first ML model that corresponds to participant compliance. The module 1940 may provide as input to the first ML model an indication of the diversity groups that each of the groups 1904, 1906, and 1908 belong to, the compliance performance scores for each of the groups 1904, 1906, and 1908, and a minimum compliance rate from the criteria 1928. The module 1940 may also select a second ML model that corresponds to data quality. The module 1940 may provide as input to the second ML model an indication of the diversity groups that each of the groups 1904, 1906, and 1908 belong to, the average level of quality of data collected from devices in each of the groups, the average quantity of data collected from devices in each of the groups, an indication of an expected quantity and level of quality from the program's protocol or the criteria 128. Each of the ML models may provide three outputs, one for each of the groups 1904, 1906, and 1908. The module 1940 may generate priority scores for the three groups by taking an average or weighted average of each group's two outputs.

In some implementations, the prioritization module 1940 does not prioritize individual participants in a monitoring group. For example, the prioritization module 1940 may generate priority scores for groups in the monitoring group 1902 and forgo generating priority scores for individual participants.

Whether the prioritization module 1940 will prioritize participants or devices may be predetermined as a setting for the monitoring program. Alternatively, the prioritization module 1940 can make a determination of whether participants or devices should be prioritized. For example, the prioritization module 1940 may determine that participants (or a subset of participants) should be prioritized if any groups have a priority score below a threshold priority score. In more detail, in response to determining that the group 1904 has a priority score less than 1.5, the prioritization module 1940 can generate priority scores for all participants in the group 1904 and rank those participants according to their scores. This technique can be used to identify those individuals or devices that present the greatest risk to the success of the monitoring program, and allow the computer system 210 to tailor interactions for those problematic participants or participant devices.

The prioritization module 1940 may make the determination whether to prioritize participants or devices based on other factors. For example, the prioritization module 1940 can consider the processing resources available to the computer system 210 and/or the current or anticipated load on the computer system 210 when determining whether to prioritize participants. In more detail, the prioritization module 1940 may determine to generate priority scores for participants and devices if the current date is a weekday and the time is after 9:00 pm or before 9:00 am, when the load on the computer system 210 is typically below a threshold load level.

Eliminating or reducing prioritization of participants or devices can improve the efficiency of the computer system 210. Although the example depicted shows a small number of participants and devices, the number of participants or devices in a given monitoring program may be significantly greater than the number of diversity groups represented in the monitoring program. Accordingly, by determining not to prioritize the participants or devices, the prioritization module 1940 may significantly reduce the number of calculations that need to be made by the computer system 210 in generating priority scores. Moreover, as will be discussed in more detail below, the process of selecting actions may be simplified when only the groups are prioritized. For example, selecting actions can include evaluating the effect of actions on the highest ranking group(s) represented in the monitoring group 1902. Those actions that are predicted to produce the most positive results may be selected by the computer system 210 and applied to all participants or devices in the highest ranking group(s). However, when participants or devices are prioritized in addition to groups, the process of selecting actions may include evaluating actions on a participant-by-participant or device-by-device basis that requires significantly more processing resources. Accordingly, by determining not to prioritize participants or devices, the prioritization module 1940 can improve the efficiency by reducing the computational load on the computer system 210. The prioritization module 1940 can achieve similar benefits by prioritizing only select subsets of the participants or devices.

The prioritization module 1940 may apply the techniques described above for determining not to prioritize participants or devices to other decisions. For example, the prioritization module 1940 may make apply these techniques when determining whether to prioritize all or only a subset of the participants or devices (e.g., the poorest performing participants or devices).

In some implementations, the prioritization module 1940 determines what priority factors to use to generate the priority scores. The priority factors used may be based on the predictions made by the analysis module 1930. For example, the module 1940 may select priority factors that are related to the current or predicted performance of the monitoring program. In more detail, if the output of the analysis module 1930 indicates that none of the groups 1904, 1906, and 1908 are at risk of not meeting corresponding minimum group sizes in the criteria 1928, the prioritization module 1940 can avoid selecting certain priority factors that are based on group size for generating the priority scores. However, if the output of the analysis module 1930 indicates that the groups 1904, 1906, and 1908 each have compliance performance scores below a threshold score or below a threshold percentage of a target score, the module 1940 can select a priority factor that is or uses the compliance performance scores to generate the priority scores.

In some implementations, the priority factors used to generate the priority scores are different for different groups, participants, or devices. The priority factors selected for a particular group, participant, or device may be based on an observed or predicted performance of the group, participant, or device. Similarly, the priority factors selected for a particular group, participant, or device may be based on an observed or predicted performance impact the group, participant, or device has on the likelihood of completing the monitoring program or meeting a particular criterion in the criteria 1928.

As an example, in generating a priority score for a device, the module 1940 may compare different performance scores of the device to corresponding thresholds. The module 1940 may proceed to use priority factors that correspond to the particular performance areas where the device's performance did not meet the threshold scores. In more detail, a device may be a remote weather buoy that includes a temperature sensor, a GPS sensor, a wind speed sensor, and a transceiver. The output of the analysis module 1930 may determine that device has a data collection compliance score of 8/10, a data transmission compliance score of 6/10, a location data quality score of 9/10, a temperature data quality score of 5/10, and a wind speed data quality score of 7/10. The module 1940 may receive these scores and apply a score threshold of 6.5 to each of the scores to determine that the devices is exhibiting poor performance in the areas of data transmission compliance and temperature data quality. In response, the module 1940 may use the data transmission compliance score as a first priority factor and the temperature data quality score as a second priority factor in calculating the priority score for the device. In contrast, for a second device (e.g., another weather buoy that is a different model, has a different manufacturer, is newer, etc.), the module 1940 can determine that the second device is performing adequately in the area of temperature data quality and, in response, avoid using the temperature data quality score as a factor for calculating the priority score for the second device.

E. Selecting Actions to Improve Monitoring Performance

After the groups, participants, or devices have been ranked, the computer system 210 may select actions to improve the performance of the highest ranking groups, participants, or devices (1950). The computer system 210 can determine actions that are anticipated to have the best desired effect on those groups, participants, or devices, such as the largest increase in overall performance or performance in a particular area. For example, based on the group 1904 being the highest ranking group due to poor compliance, the computer system 210 can select a set of actions to perform with the group 1904 to improve compliance of participants in the group 1904. The set of actions selected by the computer system 210 can be those that have historically produced the largest increase in compliance among participants belonging to the first diversity group when compared to other actions or sets of actions.

In determining the actions to perform, the computer system 210 can refer to a table that includes actions or sets of actions and their expected effects. The table may be generated using historic data stored in the database 1420, and updated using data collected during monitoring programs. The table may be organized according to diversity groups and/or protocol elements of the monitoring program. For example, the table can indicate that performing a particular action such as providing a new software configuration is anticipated to produce different effects for the different diversity groups represented in the monitoring group 1902. Transmitting configuration files to the participant devices and reconfiguring the devices may, for example, be expected to increase compliance in the group 1904 while reducing retention and data quality in the group 1906. The table used by the computer system 210 may be specific to the monitoring program, e.g., created based on the protocol for the monitoring program and/or the criteria 128. Alternatively, the table used by the computer system 210 may be specific to a particular diversity group. For example, based on the first group 1904 being the highest ranking group, the computer system 210 may access a table that includes the anticipated effects of different actions on participants in the first diversity group that the group 1904 belongs to.

The computer system 210 may make predictions to determine actions to perform for a particular group, participant, or device. For example, the computer system 210 may use a ML model to predict updated performance metrics or performance scores for groups when a protocol element of the monitoring program is modified. In more detail, the computer system 210 may provide as input to the ML model an indication of the diversity group that the group 1904 belongs to, the previously observed or predicted retention rate for the group 1904, and the updated protocol for the monitoring program. The output of the ML model may be a new retention rate expected from the group 1904 should the change to the program's protocol be made.

Prior to selecting any actions, the computer system 210 may determine which groups, participants, or devices that actions should be selected for based on the rankings. For example, the computer system 210 may apply a first threshold to the group rankings and a second threshold to the participant rankings to identify the groups and participants that actions should be selected for. In more detail, as shown, the computer system 210 may apply a first threshold of 1 to the group rankings to identify the group 1904 as the only group that actions should be selected for, and a second threshold of 2 to the participant rankings to identify the participants P1 and P4 as the only participants that actions should be selected for. As will be described in more detail below, the actions selected for the group 1904 may be applied to all participants in the group 1904. Alternatively, the actions selected for the group 1904 may be applied only to participants in the group 1904 that are also identified as highest ranking participants.

The computer system 210 may apply other criteria in addition to or in place of thresholds when determining which groups, participants, or devices that actions should be selected for. As an example, the computer system 210 may apply a threshold of 1 to the group rankings to identify the group 1904 as the only group eligible for actions. The computer system 210 may proceed to apply a second threshold of 2 to the participant rankings and filter from these highest ranking participants those participants that do not belong to the group 1904 (e.g., the highest ranking group). In applying these techniques, the computer system 210 may identify the participant P1 as the only participant that actions should be selected for. However, the computer system 210 may still select actions for the group 1904 generally that may be applied to all participants in the group 1904, not necessarily just the participant P1. The computer system 210 may also or alternatively select actions anticipated to improve the performance of the participant P1 particularly.

The actions selected by the computer system 210 can include adjustments to the monitoring group 1902, such as enrolling or inviting to enroll other participants or devices. For example, after having identified the group 1904 as the highest ranking group, the computer system 210 may select an action to enroll additional participants in the group 1904. The selection of this action may be based on the computer system 210 determining that the group 1904 has a current size that is below or too close to a minimum group size in the criteria 1928 (e.g., current size is less than 5%, 8%, or 10% greater than the minimum group size). Similarly, the selection of this action may be based on the computer system 210 identifying from the output of the analysis module 1930 that the group 1904 has poor performance in the area of group size or that the predicted size of the group 1904 at the end of the program is below or too close to the minimum group size for the group 1904 (e.g., predicted size is less than 1%, 5%, or 10% greater than the minimum group size). By enrolling or inviting to enroll other participants or devices belonging to a particular diversity group into a group of the monitoring program, the computer system 210 can improve the likelihood of meeting the minimum group size for the group.

Enrollment can also improve the likelihood of meeting other criteria of a monitoring program. For example, enrolling additional participants or devices from particular diversity groups can improve the likelihood of matching a target distribution for the program and, similarly, meeting a minimum diversity score required for the program.

The computer system 210 may use attribute information to determine a set of subjects to enroll in the monitoring program or to invite to enroll in the program. For example, the computer system 210 may use participant data from the database 1422 to identify five subjects that belong to the first diversity group, that are available to be enrolled in a program, and have the highest overall compliance rates among the available first diversity group subjects.

The actions selected by the computer system 210 can include allocation of limited resources to particular groups, participants, or devices. The limited resources can include tangible resources such as replacement devices (e.g., upgraded smart phones or upgraded wearables), replacement sensors, or supplemental devices or sensors (e.g., smart watch or other wearable that interfaces with a mobile computing device). The limited resources can also include intangibles, such as software licenses and credits (e.g., taxi credits). For example, there may be a limited number of licenses for upgraded software available for a particular study. The upgraded software may, for example, provide a more user-friendly interface, more consistent sensor collection, more consistent data transmission, improved data analysis functions, etc. Based on the rankings and there being five software licenses for upgraded software available, the computer system 212 may select the five highest ranked devices to distribute the upgraded software to. By distributing resources based on the rankings, the computer system 210 can ensure that the resources are being provided to those groups, participants, and/or devices (i) with the greatest need for the resources and/or (ii) that can make the best use of the resources.

The computer system 210 can also select other types of actions. For example, the computer system 210 can modify the software configuration of a subset of participant devices based on the rankings or priority scores. In modifying the software configuration, the computer system 210 may generate software packages to be transmitted to and installed on the subset of participant devices. The new configuration may modify the way that notifications from the computer system 210 are presented on the interface of the participant devices, change the way that sensor data or other data is collected by the participant devices, and/or change how collected data is processed by the participant devices. As an example, based on the group 1904 being the highest ranked group, the computer system 210 may determine a set of actions to perform with the group 1904. The computer system 210 may predict that changing the configurations of the devices in the group 1904 to modify the sensors used to collect position data will produce the largest improvement to the quality of data collected by the devices in the group 1904. The computer system 210 may generate configuration data packets that change the configuration for these devices so that they will collect GPS data in addition to the current inertial measurement unit (IMU) data that they currently collect, and transmit the data packets to each of the devices in the group 1904.

As another example, the computer system 210 can make adjustments to elements of the monitoring program. In more detail, the computer system 210 can adjust the protocol for the monitoring program based on the prioritization module 1940's rankings or priority scores. The computer system 210 may use the rankings to identify the most at-risk groups, participants, or devices in the monitoring group 1902 and proceed to determine adjustments to the protocol that are anticipated to improve the performance of those identified. The computer system 210 can also customize protocols for different groups, participants, or devices based on the rankings or priority scores. For example, based on the group 1904 being the highest ranked group, the computer system 210 may determine modifications to the protocol that historically increase compliance of subjects in the first diversity group. Upon determining that compliance of subjects in the first diversity group typically increases when submission deadlines are changed from morning to afternoon, the computer system 210 can modify the protocol that is applied to the group 1904 to change the time when participants in the group 1904 are required to submit surveys or sensor data. However, the protocol applied to the groups 1906 and 1908 may remain the same.

Other modifications to the elements of the monitoring program can include changes to communication content or settings between the computer system 210 and the participant devices. These changes can include changes to communication formality, communication channel, structure of communication, content of communications, and timing of communications. For example, based on the participants P1 and P4 being the highest ranking participants, the computer system 210 may determine a set of actions to improve the performance, such as the compliance, of these participants. In evaluating different actions and their possible effect on P1 and P4's performance, the computer system 210 may determine that changing the formality of communications for P1 from formal and informal should improve P1's compliance by 7% and changing the frequency of communication for P2 from one reminder per event to two reminders per event should improve P2's compliance by 10%. The computer system 210 can proceed to update the communication settings for P1 and P2 according to these determinations, without affecting the communication settings for the other participants in the monitoring group 1902.

The computer system 210 may select various other actions to perform. As an example, the computer system 210 may use the rankings or priority scores from the module 1940 to schedule maintenance or updates for a set of devices. The updates may be a software update. For example, based on the group 1904 being the highest ranked group, the computer system 210 may check the software version of each of the devices in the group 1904. If any devices in the group 1904 are not using the most up-to-date software, the computer system 210 may push the necessary software updates to those devices or may schedule a time for the devices to be updated.

As mentioned above, the selected actions can also include scheduling maintenance for a set of devices in a monitoring program. For example, the monitoring program can be a study that includes the collection of data from various autonomous or semi-autonomous vehicles. Based on the group 1904 being the highest ranked group and the performance scores for the group indicating poor data quality, the computer system 210 may schedule maintenance for the vehicles in the group 1904 (e.g., inspection, sensor diagnostic, ECM reset, etc.). In scheduling the maintenance, the computer system 210 may send instructions to the vehicles that instruct the vehicles to travel to a particular location at a particular time (e.g., autonomously travel to maintenance address) or to enter a limited-use state for a particular time period (e.g., an off or suspended to prevent users from operating or moving the vehicles). The maintenance may be performed by one or more workers who the computer system 210 notifies of the maintenance task. Additionally or alternatively, the computer system 210 may use remote diagnostic software to perform maintenance on the vehicles remotely or to identify the type of maintenance the vehicles need.

F. Implementing Selected Actions

After selecting actions to perform for the highest ranking groups, participants, or devices, the computer system 210 can perform the selected actions (1960). For example, after determining that the software configuration for the group 1904 devices should be modified, the computer system 210 can generate and distribute data packages to the devices in the group 1904. The devices can proceed to import the data in the data packages and process the imported data, resulting in the configurations of each of the devices being modified.

In some implementations, the computer system 210 generates a recommendation using the selected actions and waits to perform the selected actions until a response is received. For example, the computer system 210 may generate a recommendation to enroll two additional participants and participant devices in the group 1904 and to allocate replacement devices to the participants P1 and P4. The computer system 210 may transmit the recommendation to the client device 204. Using the client device 204, an administrator or researcher can confirm all or a portion of the recommendation. For example, a researcher may confirm enrolling two additional participants but only approve allocating a replacement device to the participant P1.

The administrator or researcher may also make modifications to the selected actions or further define the actions that should be taken. For example, a recommendation can include an action to enroll additional participants belonging to the first diversity group. The client device may provide the researcher an interface showing available subjects that belong to the first group. The researcher can proceed to interact with this interface to select specific subjects that should be enrolled as participants in the monitoring program and be added to the group 1904. An indication of which subjects to enroll may be transmitted from the client device 204 to the computer system 210.

In some implementations, after performing the selected actions, the computer system 210 performs or schedules an analysis of the monitoring program. For example, the computer system may schedule an analysis of the monitoring program 1 week, 2 weeks, or 1 month from the date that the selected actions are first performed. The analysis can include determining the likelihood of completing the monitoring program and/or determining the performance of the groups in the monitoring program. The computer system 210 may compare the results of the analysis to the previous outputs of the analysis module 1930 to determine if the previously selected actions are having their anticipated effect. As an example, in performing the analysis, the computer system 210 may perform the actions described above from collecting data during the monitoring program through the analysis module 1930 generating output(s). The computer system 210 may compare the new output of the analysis module 1930 to the previous output of the analysis module 1930 to determine that three of four selected actions are having their intended effect. The one selected action not having its intended effect may be a software reconfiguration of group 1904 devices where compliance was predicted to improve by 10% but only 5% compliance has been realized. The computer system 210 may proceed to select one or more additional actions to perform predicted to further improve the compliance of the group 1904 participants.

The analysis performed by the computer system 210 after performing the selected actions can include a diversity analysis described in more detail above. As an example, a set time after performing the actions, the computer system 210 may perform a diversity analysis by predicting the composition of the monitoring group 1902 at an end of the monitoring program. The computer system 210 can use the predicted composition characteristics to calculate a predicted diversity score for the monitoring program at this future time. The computer system 210 may determine that the selected actions have succeeded or that further actions are needed by comparing the predicted diversity score to a minimum diversity score in the criteria 1928.

Figure 19B:
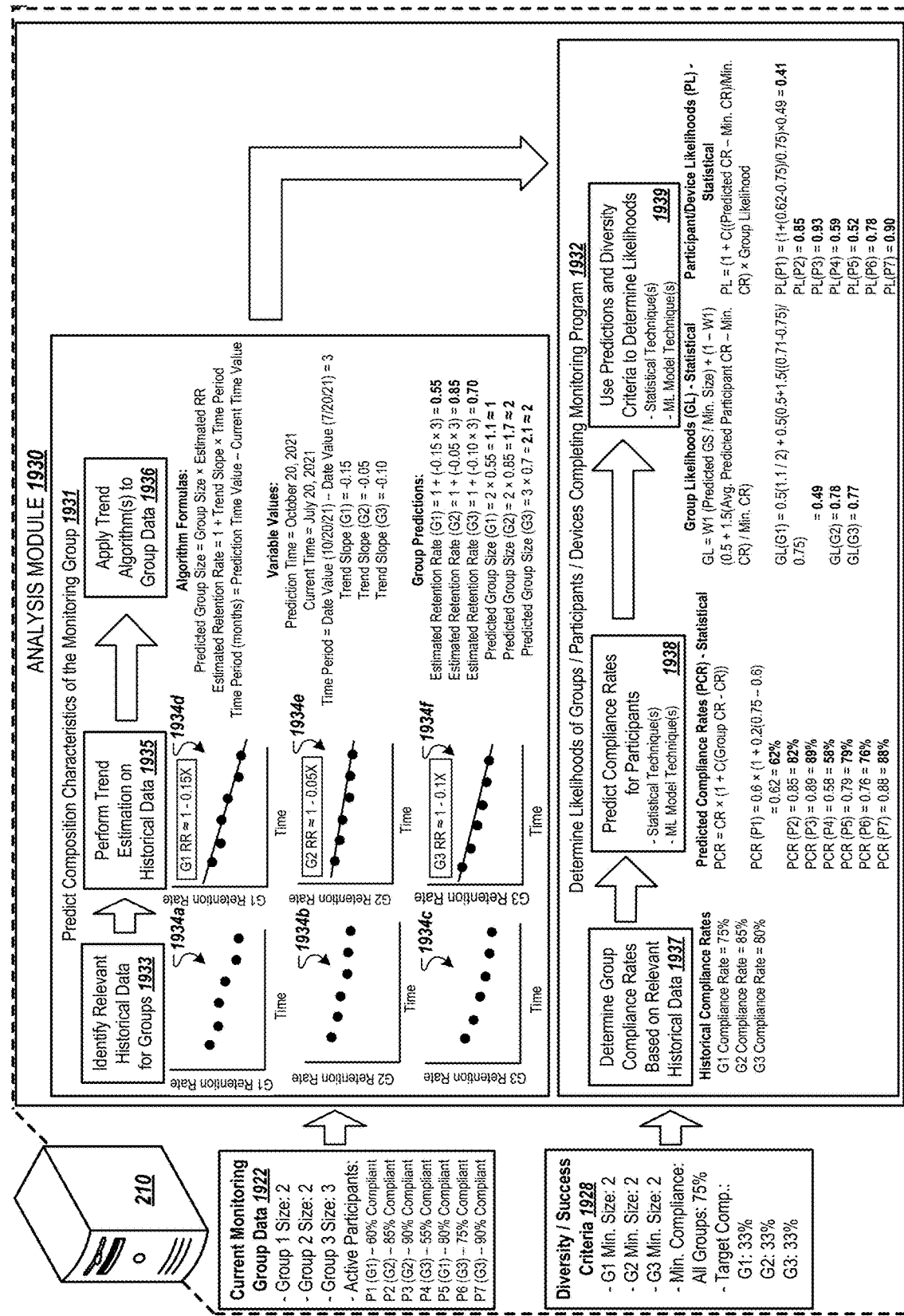

FIG. 19B illustrates using the analysis module 1930 to evaluate the performance of the monitoring group 1902. By evaluating the performance of the monitoring group 1902, the analysis module 1930 can help identify underperforming groups, participants, or devices and the particular areas where they are underperforming. The performance evaluation can also indicate the impact that the performance of the groups, participants, or devices have on the likelihood of completing the monitoring program. As will be described in more detail below, the prioritization module 1940 can use the results of the performance evaluation to prioritize the groups, participants, and/or devices in the monitoring group 1902 according to those with the greatest need for intervention, that need intervention the soonest, and/or that need the highest amount of intervention. Moreover, the computer system 210 can later use the results of the performance evaluation to identify possible causes and solutions for underperformance when selecting actions to perform with high priority groups, participants, or devices.

In evaluating the performance of the monitoring group 1902, the analysis module 1930 may make various determinations for the monitoring group 1902 or select portions of the monitoring group 1902. These determinations can include, for example, predicted composition characteristics, likelihoods of completing the monitoring program or becoming compliant with particular success/diversity criterion, and/or performance scores. The determinations may be for the monitoring group 1902 as a whole or for particular groups, participants, or devices in the monitoring group 1902. As will be described in more detail below with respect to FIG. 19C, the prioritization module 1940 may use these predictions to calculate priority scores for the groups, participants, and/or devices in the monitoring group 1902.

In some implementations, the analysis module 1930 makes predictions of the monitoring group 1902 for a future time. The future time may be an anticipated or scheduled end of the monitoring program. For example, the monitoring program may be a study using new wearable medical devices and their efficacy in helping to identify signs of heart attacks or strokes before they occur. The study may be initially scheduled to end one year from a start date of the study. When making predictions, the analysis module 1930 may use the difference in time between the current date and the scheduled end date. For example, the analysis module 1930 may provide the difference in time as an input, among multiple inputs, to a machine learning model that use the inputs to generate a likelihood of a group being compliant with the criteria 1928 at the end date. As another example, the analysis module 1930 may apply multiple trends corresponding to different diversity groups to the current monitoring group data 1922 and the difference in time to make various predictions. In more detail, the analysis module 1930 may identify a trend among compliance rates for subjects in the first diversity group. The analysis module 1930 may apply the trend to the current compliance rate for the group 1904 out to the difference in time to predict the compliance rate for the group 1904 at the end-of-program time.

In some implementations, the analysis module 1930 does not make predictions. For example, the analysis module 1930 may make determinations that are not predictions for a future time. These determinations can include performance scores for the groups, participants, or devices in the monitoring group 1902 based on their current performance. For example, the computer system 210 can use the current compliant rates for all participants in the group 1904 to identify an overall compliant rate for the group 1904. The computer system 210 can compare this rate with a minimum compliance rate of the criteria 1928 and/or with the average compliance rate for subjects in the first diversity group, and use the results of the comparison to calculate a compliance performance score for the group 1904. These determinations can also include determining likelihoods of the groups, participants, or devices completing the monitoring program or meeting particular diversity/success criterion based on the data 1922 and the criteria 1928.

As shown, the computer system 210 may provide the current monitoring group data 1922 and the diversity/success criteria 1928 as input to the analysis module 1930. The computer system 210 may also provide other data, such as historic data extracted from the database 1420.

The analysis module 1930 may use the received data to predict composition characteristics of the monitoring group (1931). The composition characteristics may include, for example, the predicted size of each of the different groups found in a monitoring group (e.g., each belonging to a particular diversity group). For example, the analysis module 1930 may use the received data to predict a size for each of the groups 1904, 1906, and 1908 at scheduled end of the monitoring program.

In predicting the composition characteristics, the analysis module 1930 may identify relevant historic data groups (1933). For example, the analysis module 1930 may request historic data from the database 1920 for the different diversity groups represented in the monitoring group 1902 and/or for previous monitoring programs that have the same or similar (e.g., multiple matching protocol elements) protocol as the current monitoring program. The analysis module 1930 can organize the historic data by group and/or performance type. For example, the analysis module 1930 may identify, from the historic data, the retention rates for the first diversity group (e.g., corresponding to the first group 1904) over program duration time. The analysis module 1930 may use this data for the first diversity group to generate the data object 1934a. The analysis module 1930 may repeat this process for the other groups represented in the monitoring group 1902. For example, the analysis module 1930 may further identify, from the historic data, the retention rates for the second diversity group (e.g., corresponding to the second group 1906) and the third diversity group (e.g., corresponding to the third group 1908) over program duration time. The analysis module 1930 may use this data to generate the data objects 1934b and 1934c.

In predicting the composition characteristics, the analysis module 1930 may perform trend estimation on the historic data groups (1933). For example, the analysis module 1930 may apply one or more trend estimation techniques to identify trends in each of the data objects 1934a, 1934b, and 1934c. The trends identified may be represented by, for example, a linear, exponential, polynomial, logarithmic, or power formula. The analysis module 1930 may generate the data objects 1934d, 1934e, and 1934f by updating the data objects 1834a, 1934b, and 1934c respectively to include trend lines for the identified trends. The resulting formulas and trend lines may indicate a trend for a particular diversity group and performance type. For example, the trend line in the data object 1934d estimates the retention rate for subjects in the first diversity group over the duration of a monitoring program.

The analysis module 1930 may apply trend algorithms to the group data (1936). For example, the analysis module 1930 may use the formula for the trend line in the data object 1934d to estimate the retention rate for the group 1904. In more detail, the analysis module 1930 may use a difference between the current time corresponding to the data 1922 and a time when the monitoring program is expected to end. In the example shown, this difference in time is three (3) months. Inputting this time into the formula for the first diversity group's retention rate, the analysis module 1930 can identify a predicted retention rate of 0.55 for the first group 1904. The analysis module 1930 may then apply this retention rate to the current size of the group 1904 found in the data 1922 to estimate a future size of one (1) participant for the first group 1904. The analysis module 1930 may repeat this process for each diversity group represented in the monitoring group 1902 or represented in the monitoring group 1902 at an outset of the monitoring program. For example, after repeating this process for the second diversity group corresponding to the group 1906 and the third diversity group corresponding to the group 1908, the analysis module 1930 predicts that the size of the second group 1906 will remain two (2) participants and that the size of the third group 1908 will be reduced to two (2) participants. The analysis module 1930 may output the predicted group sizes to the prioritization module 1940, which may use them to generate priority scores for the groups, participants, or devices.

In some implementations, the analysis module 1930 uses machine learning models to predict the composition characteristics. For example, instead of performing trend estimation on historical data and apply statistical algorithms, the computer system 210 may provide portions of the current monitoring group data 1922 and the criteria 1928 as input to a machine learning model. The output of the machine learning model may be a number that indicates the size of one or more of the groups at the end of the program.

The analysis module 1930 may determine likelihoods of groups or participants completing the monitoring program (1932). The analysis module 1930 may employ various techniques to make these predictions as discussed in more detail above with respect to FIG. 19A and FIGS. 14A-14D. As shown, the analysis module 1930 can employ various statistical techniques to determine likelihoods of the group, participants, and/or devices completing the monitoring program.

In determining the likelihoods, the analysis module 1930 may make analyze the performance of the monitoring group 1902 and/or make performance predictions. For example, the analysis module 1930 may determine group compliance rates based on relevant historical data (1937). The analysis module 1930 may accomplish this by extracting all historic data from the database 1420 collected from subjects in diversity groups represented in the monitoring group 1902, or all historic data from the database 1420 collected from subjects in diversity groups represented in the monitoring group 1902 and from previous monitoring programs that have protocol elements that match or are similar to those of the current monitoring program. The analysis module 1930 can then calculate the average compliance rates for each of the diversity groups from the extracted data. In some cases, the analysis module 1930 may weigh newer data from more recent monitoring program more heavily than older data from later monitoring programs when calculating the average compliance rates. The analysis module 1930 may also calculate other performance metrics such as historic retention rates and data quality levels for the different groups.

The analysis module 1930 may predict compliance rates for participants (1938). As an example, the analysis module 1930 may use similar techniques described above with diversity groups to identify the historical performance metrics for individual participants and devices, such as the historic compliance rate for each participant or device. The historic compliance rates may be treated as a predicted compliance rates. Alternatively, the analysis module 1930 may use the current compliance rates for the participants with other information to calculate predicted compliance rates. For example, the analysis module 1930 may use a formula to calculate the predicted compliance rate for each participant. The formula may take into account the current compliance rate for a participant and their corresponding historical diversity group compliance rate. The formula may also include one or more constant values used to weight the current participant compliance rate, the historical group compliance rate, and/or the difference between the two rates.

The analysis module 1930 may use the predictions and the success/diversity criteria 1928 to determine the likelihoods of completing the monitoring program (1939). The analysis module 1930 may calculate the likelihoods using statistical techniques. For example, the analysis module 1930 may use a first formula to calculate likelihoods of groups completing the monitoring program, and a second formula to calculate likelihoods of participants or devices completing the monitoring program. The first formula may include variables for the corresponding predicted group size previously determined by the analysis module 1930, minimum group size from the criteria 1928, current average compliance rate among participants in the group, and a minimum compliance rate from the criteria 1928. Similarly, the second formula may include variables for the corresponding predicted participant compliance rate, minimum compliance rate from the criteria 1928, and group likelihood calculated using the first formula. The analysis module 1930 may provide these likelihoods as output to the prioritization module 1940, which can use them to generate priority scores for the groups, participants, or devices.

In some implementations, the analysis module 1930 predicts likelihoods of groups or participants meeting specific criterion. For example, the analysis module 1930 may predict a likelihood of each of the groups in the monitoring group 1902 meeting corresponding minimum group sizes in the criteria 1928. Similarly, the analysis module 1930 may predict a likelihood of each of the participants in the monitoring group 1902 meeting the minimum compliance rate in the criteria 1928.

The analysis module 1930 may generate performance scores for the groups, participants, or devices in a monitoring group. For example, the analysis module 1930 may convert previously determined likelihoods for the groups, participants, and/or devices into performance scores as discussed in more detail above with respect to FIG. 19A. The analysis module 1930 may output the performance scores to the prioritization module 1940, which may use the performance scores to generate priority scores for the groups, participants, or devices.

In some implementations, the analysis module 1930 uses machine learning models to predict likelihoods of groups, participants, or devices completing the monitoring program or meeting particular criterion. For example, instead of using statistical formulas to determine group and participant likelihoods for completing the monitoring program, the analysis module 1930 may use multiple machine learning models that correspond to different diversity groups (e.g., trained using historic data collected from subjects in the different diversity groups). The analysis module 1930 may provide portions of the current monitoring group data 1922 and the criteria 1928 that correspond to the first diversity group as input to a machine learning model that also corresponds to the first diversity group. The output of the machine learning model may be a number that indicates the likelihood of the group completing the monitoring program.

Figure 19C:
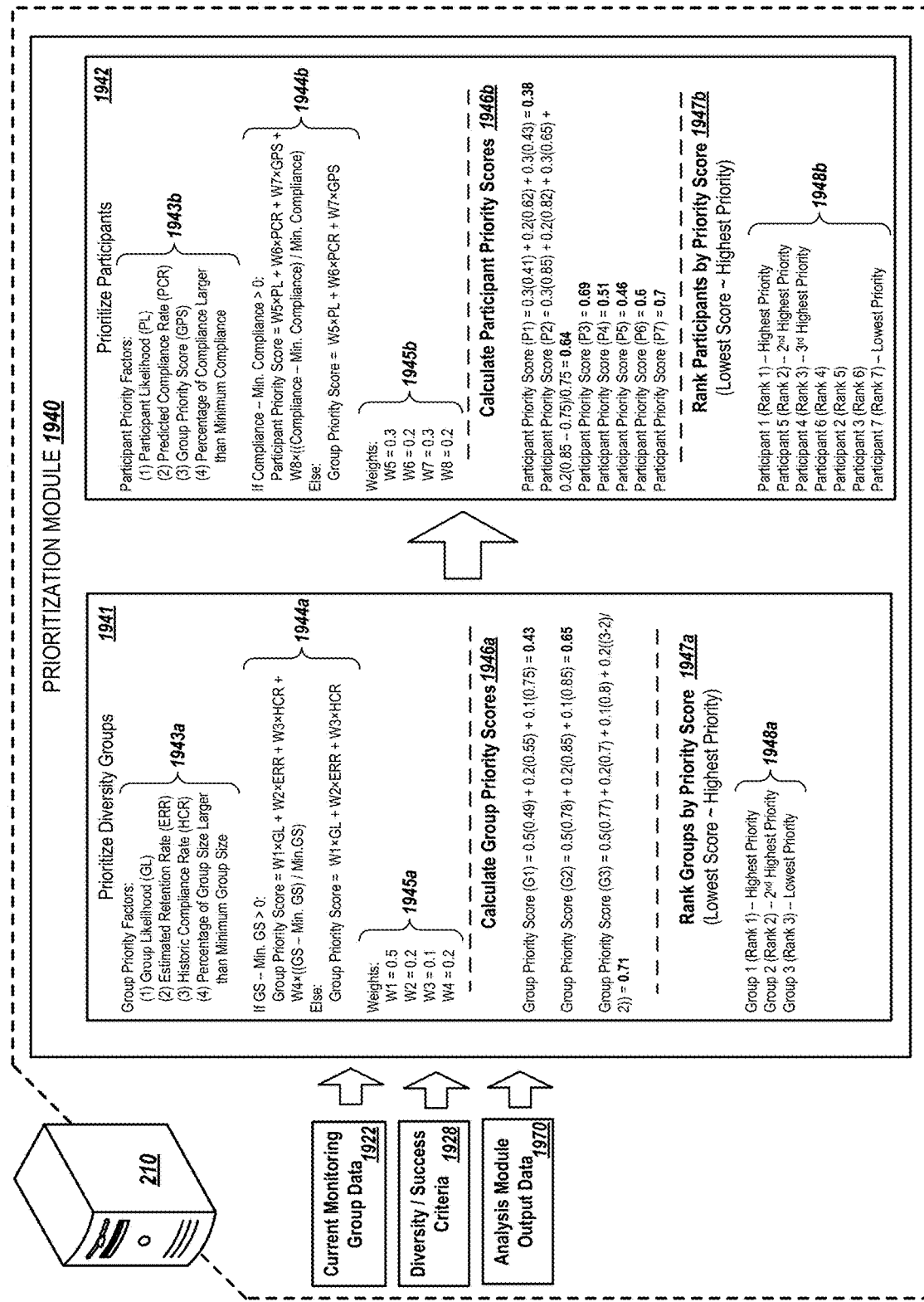

FIG. 19C illustrates using the diversity module 1940 to prioritize groups, participants, and/or devices in the monitoring program. The groups, participants, and/or devices may be prioritized according to those that have the greatest need for intervention to improve performance. For example, the prioritization module 1940 may use performance information from the analysis module 1930 to determine which groups are the least likely to complete the monitoring program or particular success/diversity criterion and prioritize these groups for intervention over other groups (e.g., groups that are not underperforming, or groups that are not underperforming to the extent the higher priority groups are). The module 1940 may prioritize the groups, participants, and/or devices based on their overall performance or performance in certain areas, such as those areas that the monitoring program is failing to meet minimum criteria for. The module 1940 may prioritize the groups, participants, and/or devices wholly or in-part on other factors.

As an example, the module 1940 may additionally or alternatively prioritize the groups, participants, and/or devices based on the performance that is observed and/or predicted to occur. In some cases, this enables prioritization according to which groups, devices, or participants are at greatest risk of failing to achieve the monitoring performance needed for the monitoring performance. Similarly, the prioritization can be performed based on which groups, devices, or participants need the most improvement, e.g., which groups have performance measures that are furthest below minimum levels or and/or have the least margin above the minimum levels of performance. These and other techniques for prioritization can indicate which groups, devices, and participants need intervention the soonest (e.g., most urgently) and/or to the greatest extent (e.g., in magnitude or amount of intervention) in order to bring current performance or predicted future performance up to a desired level.

For example, the output of the analysis module 1930 may indicate that a set of participants are approaching deadlines for data collection, and the module 1940 may prioritize these participants based in-part on these approaching deadlines. The deadlines may be preset as part of the monitoring program, such as weekly deadlines to complete surveys or collect sensor data. The deadlines may be predicted times when, for example, insufficient time remains to collect the minimum amount of data needed to comply with the monitoring program.

The module 1940 may additionally or alternatively prioritize the groups, participants, and/or devices according to those that need the greatest amount of intervention to improve monitoring. That is, those groups, participants, and/or devices that are anticipated to need the most amount of actions selected and/or performed with can be prioritized over other groups, participants, and/or devices in the monitoring program. For example, the output of the analysis module 1930 may indicate that a set of devices in the monitoring program are performing poorly in multiple performance areas, such as compliance, data quality, and data quantity. The prioritization module 1940 may prioritize these devices over other devices in the monitoring group 1902 due to their poor performance in the multiple areas. In more detail, this poor performance can indicate to the computer system 210 that more actions and/or different types of actions must be selected and performed to improve the devices' performance across the multiple areas.

In performing prioritization, the prioritization module 1940 can greatly improve the efficiency of the computer system 210 in conducting the monitoring program. For example, through prioritization, the module 1940 helps to quickly identify which groups, participants, and/or devices the computer system 210 should use resources on or allocate resources to. This can improve efficiency by reducing the number of groups, participants, and/or devices that the computer system 210 needs to select actions for and perform actions with. As a result, the amount of processing resources that the computer system 210 must use on selecting and performing actions is reduced. As discussed in more detail above, by prioritizing the groups, participants, and/or devices, the periodization module 1940 can identify those in the monitoring program that can make best use of limited resources, further improving efficiency. Moreover, as a result of identifying those with the greatest need for intervention to improve performance and/or that need intervention the soonest, the selected actions performed by the computer system 210 are more likely to improve the performance of those identified groups, participants, and/or devices. This reduces the likelihood of the success/diversity criteria not being met and, therefore, improves the likelihood of successfully completing the monitoring program, thereby reducing the chances of needing to extend or repeat the monitoring program.

The prioritization module 1940 can use a variety of information to determine how the groups, participants, and/or devices should be prioritized. This information can include performance information generated by the analysis module 1930. For example, the module 1940 can request or receive output data 1970 generated by the analysis module 1930. This output data 1970 can include likelihoods, performance scores, and/or predicted composition characteristics described in more detail above. The prioritization module 1940 can also use other information such as the current monitoring group data 1922 and the diversity/success criteria 1928 to prioritize the groups, participants, and/or groups.

As shown, the prioritization module 1940 prioritizes groups corresponding to different diversity groups (1941). One technique that the prioritization module 1940 can use to prioritize groups is to generate priority scores for each of the groups in a monitoring group using a formula that includes multiple variables that represent different priority factors. For example, the module 1940 can use the group priority factors 1943*a* to generate the group priority scores. The priority factors 1943 include, for example, group likelihoods extracted from the output data 1970, estimated retention rates extracted from the output data 1970, historic compliance rates extracted from the output data 1940 or calculated by the module 1940 from accessed historical data, and the percent difference between the current group size extracted from the group data 1922 and the minimum group size extracted from the criteria 1928. However, this example is not limiting and the module 1940 may use various other types of data metrics as priority factors for generating group priority scores, such as performance scores generated by the analysis module 1930 for the different groups and/or for the participants in each of the groups.

The prioritization module 1940 may use one or more formulas 1944*a* to calculate the diversity scores. The particular formula that the module 1940 applies may be based on particular circumstances involving the performance of the monitoring program, such as a likelihood of the monitoring program being completed, the overall performance scores for the groups, the lowest performance scores among the groups, or performance areas that all or the majority of groups are performing poorly in. However, other criteria may be used by the module 1940 to select which formula to apply. As an example, the module 1940 may apply a first formula when the current group size for a group is greater than a corresponding minimum group size, and a second formula when the current group size for the group is less than or equal to the corresponding minimum group size.

The formulas 1944*a* may include one or more weights 1945*a* that are applied to the group priority factors 1943*a*. As an example, each weight in the weights 1945*a* may be applied to a particular priority factor in the group priority factors 1943*a*. These weights may be updated over time by the computer system 210 or by a user, such as researcher or administrator. In some implementations, the weights 1945*a* are set by a machine learning model. The model may be a regression model configured to output one or more of the weights 1945*a* based on different inputs, such as the protocol elements for the monitoring program, the output data 1970, the group data 1922, and/or the criteria 1928. The model may be trained to reduce the difference between calculated priority scores and/or the resulting group rank and ground-truth data that indicates an ideal priority score and/or group rank.

Using the formulas 1944, the prioritization module 1940 can calculate the group priority scores (1946*a*). In FIG. 19C, the lower the group priority score, the higher the priority of the corresponding group, so lower group priority scores in the example correspond to an increased need for intervention to improve monitoring performance. As shown, the calculated group priority score 0.43 for the first group 1904 is less than the group priority scores for the second group 1906 (e.g., 0.65) and the third group 1908 (e.g., 0.71). The priority score for the group 1904 may be less than the other two group priority scores a result of the small group size of the group 1904 (e.g., a size of two compared to the minimum group size of two needed for that category) and the low compliance demonstrated by the participant P1 (e.g., one of the group 1904's two participants) which puts the group 1904 in jeopardy of not meeting corresponding portions of the criteria 1928 and completing the monitoring program.

After generating the group priority scores, the prioritization module 1940 may use the group priority scores to rank the groups in a monitoring program (1947*a*). For example, the module 1940 may generate rankings 1948*a* according to the calculated group priority scores. The rankings 1948*a* show that the groups 1904, 1906, and 1908 are ranked in first, second, and third respectively.

In some implementations, as discussed above with respect to FIG. 19A, the module 1940 may select a subset of the highest ranking groups that the computer system 210 should select action for. As an example, the module 1940 may apply a threshold or a percent threshold to the rankings 1948*a* to identify a subset of the highest rankings groups, e.g., those groups that are most in need of intervention to improve monitoring performance.

As shown, the prioritization module 1940 may use similar techniques to prioritize participants (1942). The formulas 1944*b* used by the module 1940 for generating participant priority scores may use a set of priority factors 1943*b* different from the group priority factors 1943*a*. For example, the participant priority factors 1943*b* include the group priority scores previously calculated by the module 1940 for the groups 1904, 1906, and 1908. However, in some cases, the participant priority factors 1943*b* share one or more factors with the group priority factors 1943*a*. Similarly, the formulas 1944*b* may use a different set of weights 1945*b* that are applied to the participant priority factors 1943*b*.

The module 1940 may proceed to calculate the participant priority scores (1946*b*). For example, the module 1940 may use the participant priority factors 1943*b* and the formulas 1944*b* to calculate a priority score for each of the participants in the monitoring group 1902. The participant P1 may have the lowest participant priority score which may reflect the poor compliance demonstrated by P1, the low likelihood of P1 completing the monitoring program, and P1 belonging to the highest priority group, the group 1904.

After calculating the participant priority scores, the module 1940 may rank the participants by their priority scores (1947*b*). For example, P1 may be ranked first due to having the lowest priority score, followed by P5 being ranked second due to having the second lowest priority score.

In some implementations, the prioritization module 1940 prioritizes devices using the techniques described above. The prioritization module 1940 may prioritize devices in the monitoring group 1902 in addition to or in place of prioritizing the monitoring group 1902's participants.

The module 1940 may output the priority scores and rankings that can be used by other components of the computer system 210. The module 1940 may output only the rankings, only the priority scores, or both the rankings and the priority scores. The module 1940 may filter out particular groups, participants, and/or devices from its output. For example, as described above, the module 1940 may apply a threshold or percent threshold to the rankings. In more detail, the module 1940 may apply a percent threshold of 33% to identify the group 1904 and the participants P1 and P5. The module 1940 may proceed to generate an output that includes the priority scores for the group 1904, P1, and P5 and their corresponding rankings. In response to other components of the computer system 210 receiving this information, the computer system 210 may start selecting actions for those highest ranking groups and participants.

Figure 19D:
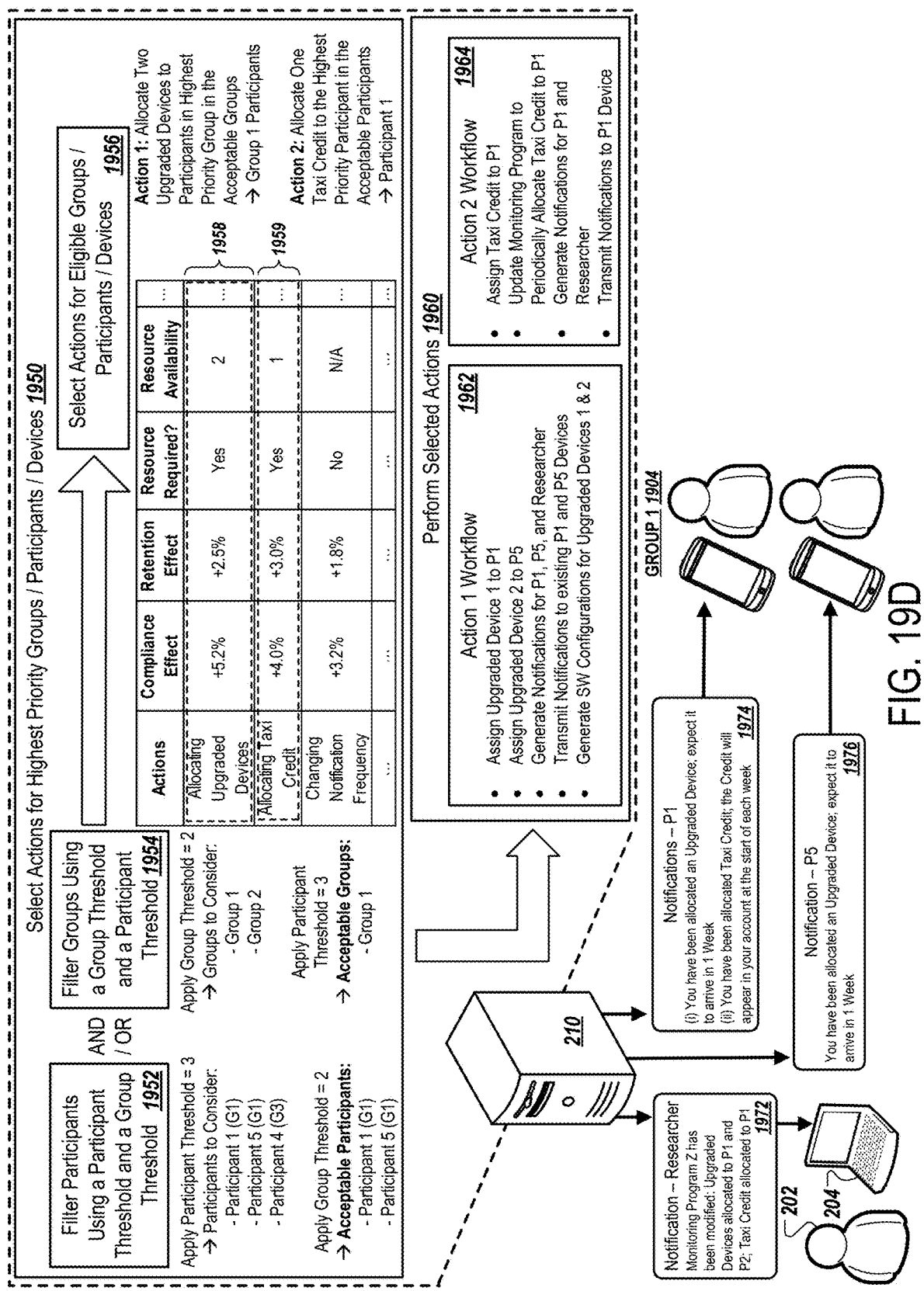

FIG. 19D illustrates selecting actions for the highest priority groups, participants, and/or devices and performing the selected actions. The computer system 210 may use the rankings from the prioritization module 1940 to identify the highest priority groups, participants, and/or devices in the monitoring group 1902 that have, for example, the greatest need for intervention in the form of actions performed by the computer system 210 to improve monitoring performance. The computer system 210 may use a variety of techniques described in more detail above and below to identify actions that will improve the performance of the highest ranking groups, participants, and/or devices and, thereby, increase the likelihood of completing the monitoring program. By successfully completing the monitoring program so that the criteria 1928 met, the computer system 210 can ensure or improve the likelihood that a minimum level of diversity is obtained and that the results of the program will be viable for their intended purpose (e.g., their intended population).

In selecting actions, the computer system 210 may optionally filter participants using a participant threshold and a group threshold (1952). As an example, the computer system 210 may apply a participant threshold of three (3) to the participant rankings to identify the participants P1, P5, and P4 as the three highest ranking participants. The computer system 210 may further apply a group threshold of two (2) to the group rankings to identify the first group 1904 and the second group 1906 as the highest ranking groups. The computer system 210 may filter the identified participants using the identified groups. For example, the computer system 210 may determine that only the participants P1 and P5 are eligible to perform actions with based on both participants belonging to the highest rankings groups, the first group 1904 and the second group 1906. Because the participant P4 does not belong to one of highest ranking groups, the computer system 210 may determine that no actions need to be selected for P4 at this time.

In selecting actions, the computer system 210 may optionally groups using a group threshold and a participant threshold (1954). As an example, the computer system 210 may apply a group threshold of two (2) to the group rankings to identify the first group 1904 and the second group 1906 as the two highest ranking groups. The computer system 210 may further apply a participant threshold of three (3) to the participant rankings to identify the participants P1, P5, and P4 as the highest rankings groups. The computer system 210 may filter the identified groups using the identified participants. For example, the computer system 210 may determine that only the first group 1904 is eligible to perform actions with based on there being no second group 1906 participants in among the three highest ranked participants.

In some implementations, the computer system 210 uses similar techniques to identify the highest ranking devices in a monitoring program. For example, in a study of various medical devices, the computer system 210 may use rankings for the devices to identify those that are failing to meet minimum sensor accuracy requirements, battery length requirements, and/or connectivity requirements for the monitoring program. After identifying these devices, the computer system 210 may select actions for the devices such as device or battery replacement, scheduled maintenance, and/or software updates.

The computer system 210 may select actions for eligible groups, participants, or devices (1956). As an example, the computer system 210 may refer to one or more data objects, such as tables, that relate different actions to different anticipated performance effects. Each entry of the data object may correspond to a particular action that the computer system may select for the highest ranking groups, participants, or devices. Each data entry in the data object may include anticipated effects on overall performance or on a particular performance area. For example, the data object includes a first entry 1958 that indicates that performing the action of allocating upgraded devices is anticipated to have a +5.2% effect on compliance and a +3.5% effect on retention. The computer system 210 may select from the available actions the actions that are anticipated to have the greatest positive effect on performance. For example, using the data object, the computer system 210 may select to perform the two actions corresponding to the data entries 1958 and 1959 due to them being anticipated to provide the greatest improvement to compliance and retention.

As shown, the data object may also indicate other information about selectable actions such as whether a particular resource such as a limited resource is required to perform the action. If a limited resource is required, the data object can also include an indication of the number of resources that are available. After allocating limited resources, the computer system 210 may update the data object to reflect the updated resource availability. Once all resources for a type of limited resource are used, the computer system 210 may determine that any corresponding actions are no longer selectable for the highest ranking groups, participants, or devices. For example, in response to the computer system 210 allocating two upgraded devices to the participants P1 and P5 in accordance with the action of the entry 1958, the computer system 210 may update the resource availability in the entry 1958 to 0. Afterwards, the computer system 210 may be prevented from selecting the action of the entry 1958 to perform with any other participants in the monitoring group 1902 unless additional upgraded devices are acquired.

The data object may be generated by the computers system 210 from trends among the historical data collected over past monitoring programs. Alternatively, the data object may be generated by the computer system 210 machine learning models to make different predictions for the effects that a particular action will have. The data object may be specific to particular diversity groups, participants, or devices. Additionally or alternatively, the data object may be specific to a set of protocol elements that match or are substantially similar to the protocol elements of the monitoring program.

An action selected by the computing system 210 may not always be the action that is anticipated to have largest improvement to overall performance. The computing system 210 may take into account other information that can provide that performance improvements in a particular area is more desirable than, for example, improvements to overall performance or other performance areas. For example, the output 1970 of the analysis module may indicate that the group 1904 had a performance score of 6/10 for compliance and a performance score of 4/10 for retention. Based on this and the group 1904 being the highest ranked group, the computer system 210 may select the action for the entry 1959 over the action for the entry 1958 due to (i) the performance scores for the group 1904 indicating that retention is the more critical performance area and (ii) the action for the entry 1959 predicted to improve retention to a greater extent than the action for the entry 1959.

The computer system 210 may select the action for certain eligible groups, participants, or devices. For example, the computer system 210 may select the action of allocating upgraded devices for all participants in the group 1904. As another example, the computer system 210 may select a second action of allocating taxi credit for only the participant P1 due to them being the highest ranking participant and there being only one resource for this action available.

After selecting actions to perform with the eligible groups, participants, and/or devices, the computer system 210 may perform the selected actions (1960). The computer system 210 may perform the selected actions once, periodically, in response to events, and/or over the duration of the monitoring program. The extent to which the computer system 210 repeats actions may depend on the action selected and on the needs of the group, participant, or device the action is selected for. As an example, one of the selected actions can include modifying the computer system 210's management of the monitoring program to provide additional reminders to the participants P1 and P5 for upcoming surveys. However, based on the compliance score for the participant P1 being lower than the compliance score for the participant P5, the computer system 210 may determine that it should send four reminders to the P1 device for every upcoming survey and one reminder to the P5 device for every upcoming survey.

One technique for performing the actions can include the computer system 210 generating a workflow for each of the selected actions. Each workflow may be generated to include a set of tasks for accomplishing one of the selected actions. The computer system 210 may schedule a particular time for the workflow to start or specify another type of trigger to initiate the workflow, such as the detection of a particular event (e.g., next test result received from participant device). As an example, the computer system 210 may generate a first workflow 1962 to perform the action of allocating upgraded devices to the group 1904's participants, and a second workflow 1964 to perform the action of allocating taxi credit to the participant P1.

After generating the workflows 1962 and 1964, the computer system 210 may initiate the workflows 1962 and 1964 to perform all or a portion of the tasks in each of the workflows 162 and 1964. For example, in performing the workflows 1962 and 1964, the computer system 210 may generate notifications 1972, 1974, and 1976 to notify the participants in the group 1904 and the researcher 202 of the actions being performed. For example, the notification 1974 may include an indication that the participant P1 has been allocated an upgraded device as well as a taxi credit. The notification 1974 may also include other information, such as particular timing information. For example, the notification 1974 can include an indication of when the upgraded devices will arrive and an indication of how often the participant P1 will receive taxi credit.

As described in more detail above with respect to FIG. 19A, after performing the selected actions, the computer system 210 may reanalyze the performance of the monitoring group 1902. The computer system 210 may compare the results of the most recent analysis to the immediate preceding analysis to determine the effect on the performance the actions have had on the monitoring group 1902 overall, the groups, the participants, and/or the devices.

Figure 20:
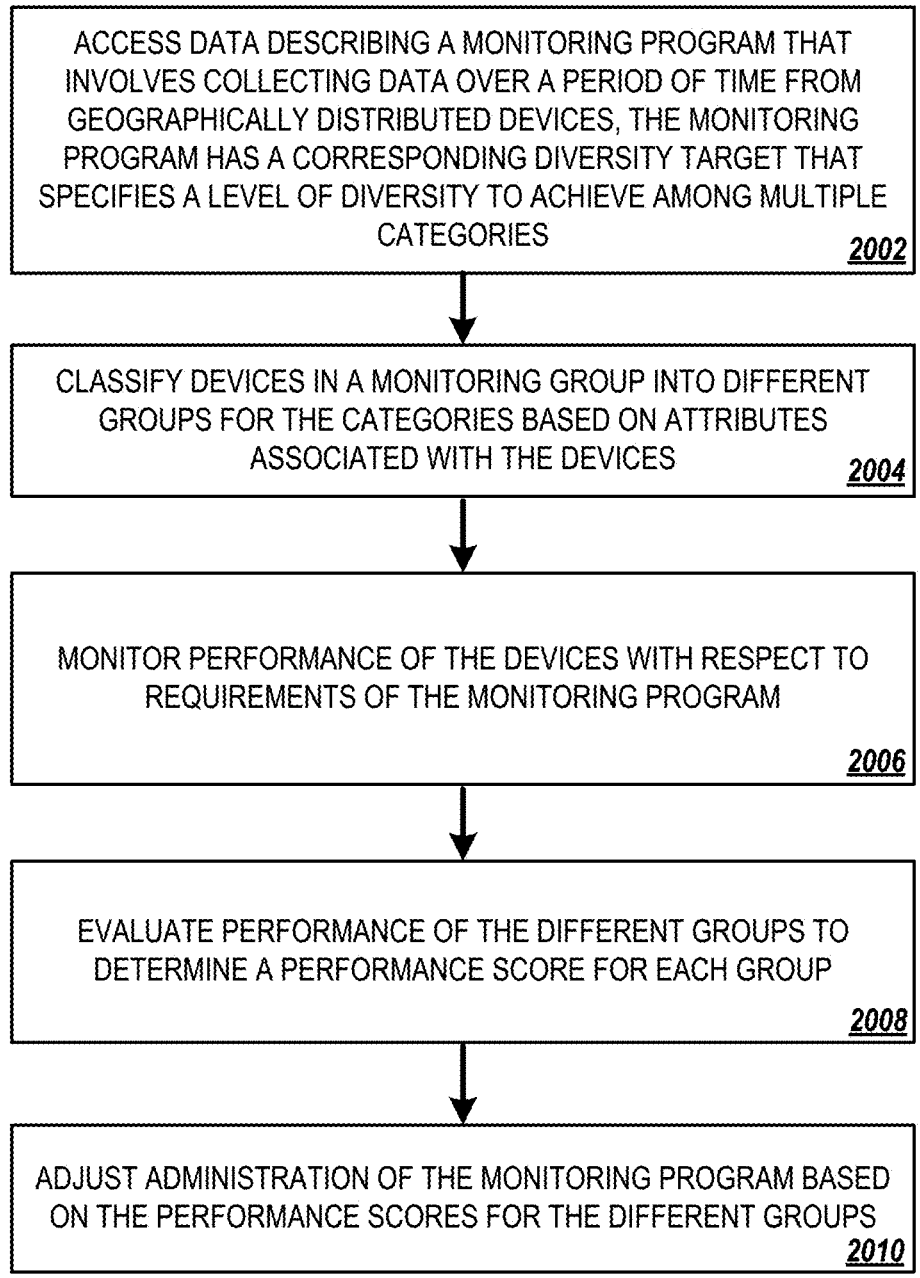
FIG. 20 is a flowchart diagram that illustrates an example process for improving monitoring performance for groups in a monitoring program.

FIG. 20 is an example process 2000 for monitoring and improving performance of remote devices involved in monitoring program. The process 2000 can be performed by one or more computers, such as the system 210.

The process 2000 includes accessing data describing a monitoring program (2002), for example, one of many that is supported or managed by a server system. Often, a server system can manage and monitor many different monitoring programs with different monitoring groups, with different procedures and data collection being done for each. The server system can be a multi-tenant system in which each monitoring program can be a different tenant, each with its own separate procedures and isolated (e.g., access-controlled and protected) data. Each can have separate procedures that the server system enforces for data collection, data validation, reporting results, logging events, and so on. The monitoring program can be a research study such as a clinical trial. For example, decentralized clinical trials or digital clinical trials typically involve participants that perform measurements and provide survey responses with devices such as smartphones, laptop computers, smart watches and other wearable devices, medical devices, and so on. Participants may additionally provide biospecimens (e.g., blood samples, urine samples, etc.) but in many cases participants may never need to travel to a health clinic or visit a doctor in person. Through user interactions with an application on a device, and through sensor measurements of one or more of a user's devices, the data needed for clinical trials can be effectively and efficiently collected.

The monitoring program involves repeatedly collecting data over a period of time (e.g., days, weeks, months, or years) from a monitoring group comprising geographically distributed devices involved in the monitoring program. Often, each device has a single corresponding user. For example, a smartphone often has a single primary user or owner, and the devices in the monitoring group can be smartphones of participants that have enrolled and consented to be participants in a particular clinical trial. As a result, the references to the devices and groups of devices involved in a study also refer to the individual participants or groups of participants associated with those devices. In other words, the monitoring group can be considered to be the group of devices that capture and transmit data for their corresponding participants, but a monitoring group may alternatively be considered to be the set of participants enrolled in the monitoring program (e.g., the cohort for a clinical trial) that the devices are providing physiological and behavioral measures about.

The devices in the monitoring group provide sensor measurements over a communication network, such as the Internet. The devices also provide user inputs received (such as survey responses from users), information about user interactions with the devices, environmental data (e.g., ambient noise levels, light levels, etc.), and other information. Each monitoring program has a predetermined set of data collection requirements indicating types of data for the devices in the monitoring group to capture and provide to the server as part of the monitoring program. For example, one monitoring program may specify to measure resting heart rate once every 8 hours, sleep duration every day, and daily step count total every day using sensors of a phone or wearable device, and also that a responses for a first survey should be collected once a week and responses for a second survey should be collected three times a week each at least one day apart. The data collection requirements for a monitoring program are stored in a profile or data set for monitoring program and can include more than just the types of data to be collected. For example, the requirements can specify the data quality needed (e.g., accuracy, precision, reliability, etc.), the rate or frequency of data collection needed, the total amount of data needed (e.g., number of measurements), the timing of measurements (e.g., time of day, spacing between measurements, timing with respect to other user activities such as eating, sleeping, or medication ingestion), the sources or techniques for collecting the different types of data (e.g., types of sensors or devices used), constraints on contexts or conditions for providing the data (e.g., times, locations, or activities that are allowed or disallowed for different measurements), and more.

In many research studies, there is a study protocol that sets forth the data collection procedures for the study. The data collection requirements can include or be derived from the study protocol. Beyond requirements for data collection, the monitoring program and its study protocol can also specify other requirements for devices or their corresponding users, such as to adhere to a medication regimen, to perform certain tasks or activities (which may be separate from the data collection), to maintain physiological parameters such as weight within certain boundaries, and so on. The system can evaluate whether these non-data-collection requirements are met, and use them to assess diversity and to prioritize groups and actions to improve diversity, just as it does for monitoring data collection performance. In general, a study protocol describes how a clinical trial will be conducted (e.g., the objective(s), design, methodology, statistical considerations, and organization of a clinical trial) and provides constraints and requirements to ensure the safety of the trial subjects and integrity of the data collected.

The data collection requirements can also specify the standards or thresholds that define a minimum acceptable data collection performance. For example, a device or participant may be required to continue for at least a minimum duration of longitudinal monitoring (e.g., at least 2 months consecutively), or continue to at least a certain milestone (e.g., to a scheduled end data for the clinical trial, until a certain health status is reached, etc.). Similarly, a minimum amount of the requested data collection may need to be performed, e.g., each of the data types to be collected need to be successfully collected weekly with at least 80% of the requested instances, no gaps in monitoring greater than a day, etc.

In many cases, data collection is less than perfect (e.g., with participants missing submissions on some days or occasionally providing inaccurate measurements), but when mostly complete the data can still be acceptable for use in the monitoring program. However, if the minimum standards are not met (e.g., a gap in measurement for more than a certain duration), the data from the device or participant may be unusable in the monitoring program, potentially causing the entire series of data collection for the device or participant to be excluded. This, in turn, may result in the diversity of monitoring performed failing to meet desired levels. For example, a study beginning with 10 men and 10 women as participants may initially meet diversity requirements, but if half of the men exhibit poor compliance or provide poor quality data, then the resulting data set may fail to provide have the diversity characteristics needed (e.g., a target composition with a minimum of at least 8 men and 8 women, and/or neither group constituting less than 40% of the total participants, etc.). In other words, through poor performance (which may result from poor participant compliance, poor data quality, participant attrition, hardware or software errors and incompatibility, and other factors), the effective composition and diversity of participants represented in the valid set of data collected may be less than is initially expected or indicated from the cohort membership.

To enable monitoring programs to meet their objectives, the system 210 can perform ongoing monitoring and adjustment, as discussed further below, to identify areas where monitoring performance is lowest or most likely to jeopardize reaching the objectives of the monitoring program. Even before the performance of any of the monitoring groups falls below minimum levels, the system 210 can identify the groups or categories least likely to meet their corresponding targets. The system 210 can proactively take actions to selectively adjust how the monitoring program is administered, to address the different ways that different groups or categories need to be supported to improve monitoring outcomes. In effect, the system 210 uses a form of ongoing closed-loop feedback to control various aspects of the monitoring program and adapt as monitoring performance changes. The system 210 can adjust the composition of the monitoring group (e.g., which devices and participants are involved), adjust the interactions with devices, adjust the configurations and software of the devices, adjust the schedule and types of measurements and other data collection events that are performed, adjust sensor parameters used to collect data, adjust user interface parameters, and more.

The analysis and corrective adjustments can be performed in an automated manner by the system 210. For example, the system 210 can automatically detect or anticipate performance problems for different groups that that matter for achieving the diversity or monitoring group composition targets for the monitoring program. The system 210 can also automatically select and implement adjustments to improve performance and thus the ultimate level of diversity represented in the final collected data set.

For each monitoring program, the system 210 stores a corresponding diversity target that specifies a desired level of diversity. This diversity can be specified with respect to multiple categories, which are based on attributes of devices or their users. For example, the target can specify desired diversity among attributes of participants including age, race, ethnicity, gender, geographic location, genetic or genomics (e.g., diversity among whether participants have different gene variants), health status, physiological measures (e.g., across different ranges of values for resting heart rate, blood pressure, respiration rate, blood glucose levels, etc.), behavioral measures (e.g., sleep, physical activity, travel, etc.), environmental conditions (e.g., noise levels, light levels, air quality, etc.), occupation, marital status, or others. Similarly, the categories can be based on attributes of devices, such as age, location, hardware capabilities, device model, sensor capabilities, network capabilities, or others. Diversity among device attributes can be helpful to avoid systematic measurement errors (e.g., biases that affect certain device models more than others), reduce risks due to incompatibilities, minimize the likelihood that all devices had a flaw such as poor battery life or low sensor accuracy that could affect data quality, and so on.

For each type of attribute for which diversity matters for a monitoring program, there may be various different categories of classes tracked. For geography, for example, each state in the United States may be a different category. For the attribute of race, for example, there may be different categories for Asian, Black, White, etc., each of which has a target amount, proportion, or other measure in the diversity target for the monitoring program overall. The attributes of interest can be assessed separately (e.g., at least 10 men, at least 10 women, at least 15 participants using a first model of activity tracker, at least 5 participants using a first model of smartphone, etc.), so that different potentially overlapping subgroups are assessed individually. The attributes may additionally or alternatively be assessed in combination (e.g., at least 10 men with diabetes, at least 10 men without diabetes, at least 10 women with diabetes, at least 10 women without diabetes, etc.). As discussed above, target compositions for diversity can be expressed in other ways, such as proportions (e.g., percentages, ratios, etc.) ranges of amounts, absolute amounts, relative amounts, and so on.

The system 210 can store information in a database that indicates the attributes associated with the various devices in the monitoring group. The attributes associated with a device can be attributes of the user of the device, e.g., values for attributes of the participant for which the device is used to monitor the participant's physiology, behavior, mental state, emotional state, environment, social interactions, etc. The system 210 can store a user profile for each of many individuals in a database, with the profiles including information from electronic health records (EHR), self-reported survey results, medical history, demographic information (e.g., age, sex, residence location, etc.), current health status, and more. Each user profile can also have information about the attributes of the user's device, e.g., smartphone model, device age, software installed and versions of the software, capabilities of the device, whether the user has other devices such as activity trackers and other wearable devices available, and so on. The system 210 can use the information in these profiles to classify devices and users to determine which categories and attributes they respectively contribute for the diversity analysis. Similarly, the system 210 can compare the information in the use profiles with selection criteria or other eligibility criteria, in order for the system 210 to select additional participants to include in the monitoring program that are determined by the system 210 to provide the greatest benefit to the overall ability (e.g., likelihood) of the monitoring program to meet its diversity target or other objectives. Similarly, when determining the predicted monitoring performance for a user or device, the system 210 can use the information in the user profiles to compare with historical outcomes (e.g., enrollment, retention, compliance, data quality, etc.) for other users and devices. Thus, based on the attributes of a user or device, the system 210 can more accurately predict, for individuals and groups within the monitoring group, the likelihoods of key outcomes (e.g., whether enrollment, retention, compliance with requirements, satisfactory data quality, etc.). Similarly, as monitoring data is obtained for individuals, the user profile information can be used as part of the training data to train machine learning models to obtain predictions.

Among the data that the system 210 stores for each monitoring program is a set of selection criteria specifying which users and/or devices are able to participate in the monitoring program. This can include inclusion criteria that specifies attributes or characteristics that users or devices need to have to be eligible for participating in the monitoring group. In addition or as an alternative, the selection criteria can include exclusion criteria indicating attributes or events that disqualify a user or device from participating in the monitoring program. The system 210 can retrieve and apply the selection criteria to, for example, verify initially and/or on an ongoing basis whether users or devices meet eligibility requirements, including detecting when a member of the monitoring group becomes ineligible and so needs to be removed. Similarly, the system 210 can use the selection criteria to determine adjustments to improve performance, including to identify which candidates would be eligible to be added to the monitoring group to improve overall diversity characteristics.

The process 2000 incudes classifying the devices in the monitoring group into different groups corresponding to the categories (2004). As discussed above, the categories represent the different attributes or attribute combinations that are desired to obtain the target level of diversity. For each category that is important for achieving the diversity target, the system 210 can identify the users or devices in the monitoring group that fit that category. In some cases, a profile is defined for each category, and users or devices are matched to the different categories based on how well their attributes fit the different profiles. For example, if categories are specified for each of the different states in the United States, the system 210 can use the stored user profiles to identify which users or devices are located in each of the different states. These would be different groups that the system 210 can analyze to determine if each group has the right amount or proportion of members, e.g., a group for users or devices in California, a group for users or devices in New York, etc. Similarly, if categories are based on participant age and sex, then the system 210 can use the information in the user profiles to determine, for each of the users or devices in the monitoring group, which categories the respective users should be classified in, thus resulting in different groups where the members of each group have certain attribute values in common.

In many cases, the membership of a device or user in one category or another is based on static of slowly changing characteristics, and so may be essentially fixed for the duration of a monitoring program. However, in other cases, the status of a user or device may change during the monitoring program. For example, a user may switch to a different devices with different capabilities, a user that was healthy may contract a disease that puts them in a different category based on health, a user's weight may change which puts them in a different one of various weight-based categories, and so on. As a result, the system 210 can periodically re-evaluate which devices or users are assigned to or labeled as being in different categories, and can update the classifications. As additional monitoring data or other data about participants and devices is received, this may also prompt the system 210 to re-evaluate group membership and potentially re-classify one or more of the devices or users.

For example, a monitoring program may set a diversity target for different groups based on participant age (e.g., with three attribute value ranges: 20-40 years, 41-60 years, and 61-80 years) and sex (e.g., with two different attributes: male and female). One way to classify users and devices may be to define categories for different permutations, so that there are six categories, one for each combination of age range and sex (e.g., men aged 20-40, women aged 20-40, men aged 41-60, women aged 41-60, etc.). For each of these six categories, there can be one or more measures specifying the desired amount or proportion of the monitoring group that the category should fill. For example, the diversity target may be that the monitoring group have at least 10 members from each of the six categories, and that each category be between 12% and 20% of the total membership of the monitoring group. As another example, for the same participant age and sex attributes, there may be two separate diversity targets and analysis, with two sex categories (e.g., male and female), and three participant age categories for the three different ranges. As a result, the diversity target may specify that at least 30 men and 30 women should be included in the monitoring program, with each group being between 40% and 60% of the total. Also, at least 20 members from each of the three age ranges should be included, with no age group representing more than 40% of the total in the monitoring group. Additional constraints or other formulations of the diversity targets can be used.

The process 2000 incudes monitoring performance of the different devices with respect to the data collection requirements for the monitoring program (2006). The monitoring can include receiving and assessing data from each of the different devices and users in a monitoring group. The data collected from a device can include the values of measured items (e.g., measurement results, sensor data, survey responses, user interaction data, etc.), as well as metadata, context data, and other related information. The system 210 can analyze the received information to characterize the monitoring that has been performed. This can include identifying properties of individual data points, data over certain time periods or time ranges (e.g., a day, a week, etc.), as well as patterns and trends over time.

Performance can refer to various characteristics of data collection, including whether needed data collection occurred, the quality and quantity of data obtained, the conditions and context under which data collection occurred, the source of the data (e.g., the type of sensor or device that provided the data), completeness of the data obtained, the reliability and consistency of data collection and transmission to the system 210 over time, and so on. Many aspects of performance can be measured with respect to the data collection requirements for the monitoring program, so that performance is indicated at least in part on the degree to which the data collection requirements are met by a device or user.

The monitoring can include passive monitoring by the system 210, such as receiving data sent automatically by the clients without each measurement or data collection event being initiated or instructed by the system 210. For example, the data can be collected locally at a client and then submitted to the system 210 over the network upon collection at the remote device or a batch on a reporting schedule. Each device involved in monitoring can have an application and one or more modules or configuration data packages that cause the device to perform measurements on a schedule, based on user interaction, in response to detecting a context of the device, and so on. For example, for health research such as a clinical trial, the system 210 can store and transmit a data package (e.g., a configuration data package, a software module, etc.) to remote devices. The remote devices can each have an application installed on the remote devices, where the application self-configures software and settings based on received data packages to perform the measurements and interactions (e.g., sensor data capture, survey presentation, etc.) directed by the data package. Although some or all of the different remote devices may receive the same data package that instructs the same behavior, the settings and data collection parameters used can be individual adapted over time. The server 210 can instruct changes to the data collection parameters that are targeted to individual users or devices to improve performance, and those changes can be made in a way that prioritizes increasing monitoring performance for the users or devices in specific groups (e.g., diversity groups having members associated with specific attributes combinations of attributes) that have the greatest need to improve monitoring performance.

The monitoring can be performed actively by the server 210, with the server 210 sending requests to the respective devices for devices to provide device and software status, event logs, usage statistics, collected data, metadata, context data, and more. The server 210 can monitoring different remote devices differently, for example, requesting data more frequently from devices that are predicted to provide data less reliably or which have historically provided data less reliably. In some cases, the server 210 may instruct or prompt specific measurements or other data collection from specific devices through communication over the network, and use the results of the interaction (e.g., whether the device was available and responded, whether the measurement was performed and the data received, etc.) to determine if the device is performing monitoring appropriately.

The system 210 determines, based on the data collection requirements for the monitoring program, which types of data are expected to be provided and with what timing. The system 210 then tracks, for each user or device in the monitoring group, whether the needed data collection was performed. This can involve comparing a desired schedule or pattern of data collection events, as specified by the data collection requirements for the monitoring program, with the actual record or pattern of data collection events that occur, and indicated by the collected data received by the system 210 over the network or by data in a log created a user's device or by the system 210. By tracking which data collection events occur and which do not, the system 210 can identify gaps in collection for different users or devices. The system 210 can thus determine how well a user or device has successfully provided certain data types (e.g., heart rate, step count, etc.) and complied with different data collection procedures (e.g., surveys, passive sensing, active sensing, sensing by different devices, etc.). The system 210 can also determine an overall rate at which the user or device provided needed data (e.g., 70% of the total measurements over the last week; or 67%, 75%, and 82% respectively for three different types of data or different types of interactions or measurements). With these measures, the system 210 can compare the level of data collection performance achieved with the full requested level or the minimum acceptable level of data collection.

The server 210 can also assess the quality of data received over the course of monitoring. For example, in addition to tracking which of the requested measurement events occurred for a device, the server 210 can evaluate and generate scores indicating the accuracy, precision, completeness, reliability, consistency, and other characteristics of the data obtained. To do this, the system 210 can examine collected data for inconsistencies, for example, detecting excessive variation from prior measurements or patterns, detecting conflicts between different measurements or data sources (e.g., a user survey stating high physical activity, but measured step count showing low physical activity), determining if received values are within a predetermined range of what would be considered a reasonable or valid result, and so on. The server can use metadata and context data in this analysis also. For example, the system 210 can examine device status information to verify that a remove device is operating properly when measurements are made or detect when measurements are made under conditions that limit accuracy. The operating status of a device or its software can be one of the various factors examined in determining the level of performance that is achieved.

The process 2000 includes evaluating the performance of the different groups to determine a performance score for each group (2008). With performance monitored and tracked (e.g., stored and maintained over time to show the patterns over time) for the various individual devices, the system 210 then evaluates the performance at the diversity group level. For example, based on the classifications of devices and users into groups for different categories of interest, the system 210 aggregates the tracked performance by group. For example, if there are six different diversity groups representing different attribute values for age range and sex of device users, then the system 210 can determine the performance for each group based on the set of devices and users in each group.

The performance score can characterize the performance of the group and can be expressed in various different ways. In some cases, measures of performance for individual devices or users in a group are combined and used to generate the performance score for the group. For example, the performance score may be an average percentage of data collection performed, such as an average of the percentages of data collection successfully performed by individual users or devices. The performance score can be a mean, median, minimum, or other measure taken across the set of performance measures for individual devices or users. Multiple performance scores can be determined for a group, such as a score for performance in collecting heart rate data, another for performance in collecting sleep duration data, and so on.

In many cases, the performance score is based on levels of compliance with the data collection requirements by the devices in the group. As another example, the performance score for the group can be a number of members of the group that are complying with the data collection requirements of the monitoring program (e.g., for amount, timing, accuracy, and so on for data collection), or more generally, are complying with all minimum requirements of the monitoring program.

In some implementations, the system 210 uses the tracked performance to determine scores indicative of predicted outcomes for the groups. For example, using the patterns and trends of data collection and the performance measures for individual devices and users over time (e.g., time series data indicating performance), the system 210 can calculate likelihoods that individuals or groups of individuals will provide a needed type, amount, and quality of data collection over a period of time that extends at least partially into the future. For example, the system 210 can determine, based on individual performance history, a likelihood that an individual will reach the end of the monitoring program (e.g., at a set milestone or end time for the end of a health research study) with a compliant level of data collection. This may be made using a projection, extrapolation, regression, or other technique. Similarly, the system 210 may generate a prediction for a percentage or number of members of the group that will reach the end of the monitoring program with a compliant level of data collection. This can be based on extrapolating from the time series or trend of performance scores for the group.

In some implementations, the system 210 uses other techniques to improve the accuracy of predictions. For example, the system 210 can use machine learning models trained based on examples of attributes of users and devices (e.g., values for attributes that may include or be different from those used to define the categories) and the corresponding histories and data collection outcomes. In the training, the attributes and current and previous outcomes are used to generate input feature values, and the outcomes actually achieved are used to define training labels or "ground truth" indications as training targets for a model. For example, training data examples may show that men age 20-40 tend to have a gradual decline in engagement and data collection performance from month to month, while women aged 41-60 show a more stable pattern. Similarly, the examples may show that individuals with one model of smartphone have high rates of providing step count while individuals with a second model of smartphone have lower rates of providing the step count.

Based on the training data examples, the system 210 may train a classifier, neural network, decision tree, or other machine learning model to generate values indicating predicted outcomes such as quality of data, rate of data collection, consistency of data collection, likelihood of completing a specific data collection requirement or combination of requirements, and so on. These can be predicted generally (e.g., for all data types and data collection), for different types of data (e.g., heart rate vs. sleep duration), for different data sources or collection procedures (e.g., surveys vs. automatic sensing), and so on. As a result, based on the training, the machine learning model is configured to (i) receive input feature values (e.g., a feature vector) that indicate attributes of a device and/or the device user (e.g., device model, device type, sensor capabilities, device age, etc.; participant age, race, residence location, health status, etc.), as well as potentially data about historical outcomes (e.g., performance measures of the device or user over the last day, week, month, etc.), and (ii) output in response a predicted value indicating the predicted amount of data collection, quality of collected data, likelihood of meeting one or more data collection requirements, and so on. Of course, other techniques for prediction can be used instead of or in addition to machine learning models, including statistical analysis, rule-based models, and so on. The various techniques discussed above for FIGS. 1-19D for predicting future compliance and other outcomes can be used in the process 2000 to generate scores, including group performance scores or individual performance scores, for prioritizing groups and individuals for intervention to improve monitoring.

The system 210 can use the performance scores (e.g., indicating current and/or predicted future performance) for the groups to prioritize the groups. This can include ranking the groups according to their performance scores. In some cases, the performance scores can represent how close a group is to a target level or minimum level of data collection for that diversity group. For example, a monitoring program may have three diversity groups, each with a diversity target of 10 participants providing valid data, and the groups may have 15, 18, and 20 members respectively. The performance scores for the three groups may indicate the current number (or predicted future number) of participants from the current membership of the groups that meet the data collection requirements, e.g., 12, 9, and 15 respectively. These may also be expressed as a percentage of the target or minimum amount for each, e.g., 1.2, 0.9, 1.5. Based on these performance scores, the second group has the highest priority or ranking, because it has the lowest amount of current or expected performance relative to its target level. Of course, the target levels may be different for different groups and this can be accounted for by generating the scores in a manner that is relative to or normalized for the differing numbers needed per group.

In many cases, the timing of intervention to improve performance matters. In particular, it can be important to intervene early in the occurrence of low or declining performance, before devices or participants reach a level of non-compliance that is uncorrectable. For example, a gap in monitoring of one day may be acceptable for a monitoring program, but a gap of two consecutive days may disqualify a participant's entire data set from consideration. As a result, the system 210 can prioritize interventions for users and devices early in the incidence of noncompliance—and even before any non-compliance when there is a predicted high likelihood of future non-compliance or trend indicative of future noncompliance (e.g., low consistency in timing of submissions). Nevertheless, even if non-compliance is correctable, it may not be significant to improve performance for a device or user in a group that is well above its target representation in the monitoring group, and so the system 210 can forgo intervention and instead devote resources to interventions that will improve the likelihood of the monitoring program meeting its objectives. The system 210 can thus prioritize interventions for individuals by both group-level and individual-level factors to quickly address the performance problems that (1) are most urgent to correct or are most able to be corrected, and (2) will provide the greatest impact in improving the ability of the monitoring program as a whole to reach its objectives, including the diversity target.

With the performance scores and rankings of the groups, the system 210 can then use those scores and rankings to determine scores and rankings to prioritize individuals. For example, the system 210 can generate an individual priority score for a device or user that is a weighted average of (i) one or more group measures, such as, the group performance score that the device or user is a member of, and (ii) one or more individual measures, such as an individual performance measure indicating the percentage or amount of data collection performed by the device or user. As a result, low group performance and low individual performance can combine to indicate a low combined performance that indicates that a device or user has a high need of intervention. The combined score can be adjusted (e.g., with different weights, offsets, penalties, etc.) based on the other factors discussed herein, such as a penalty (e.g., adding to the score to show less importance or urgency in intervening) if the data collection is so poor that intervention has a low likelihood of bringing the user or device into compliance.

In some cases, the different groups for different categories of interest are not mutually exclusive. For example, there may be groups for different age ranges and separate groups based on participant sex, so that a device or user corresponds to two different groups that each have different corresponding diversity targets. In these cases, a combined score for an individual can be based on the performance score for each group that the user or device is included in. As a result, the combined scores for users and devices can reflect a priority boost from each group where improved performance is needed. To normalize the scoring in the case that different users and devices fit into different numbers of categories (e.g., some being in three groups, some in two groups, etc.), the group scores can be averaged or the lowest group performance score can be used. Or, to reflect that a device or user would contribute to multiple aspects of diversity needed, the effective group component can be lower than the single lowest performance score. If the group scores are 1, 1, and 1, for three different groups a user or device is classified in, then the effective group performance score may be lowered, such as to 0.7, to reflect that the benefit to the monitoring program (or urgency for improving performance for this device or user) exceeds that of second user that is in a single group with a score of 1, because the second user would provide a diversity benefit across multiple of categories that have high priority instead of only one.

The process 2000 incudes adjusting administration of the monitoring program for the devices based on the performance scores for the groups (2010). This can involve changes in the way the system 210 communicates with devices, using any of the techniques discussed above for step 1810 of the process 1800. The adjustments made can include actions to improve diversity with respect to the categories needed for the monitoring program. The effective level of diversity can be improved in various ways, especially to improve monitoring performance to maintain or improve compliance with the data collection requirements for members of the groups most at risk of not meeting their diversity targets. This can include including increasing the quality of data provided by certain devices (e.g., by changing device settings, network configuration, sensor operation, etc.), increasing the amount or rate of data collection (e.g., through changes to device operation as well as prompting better and more consistent user interaction), changing the composition of the monitoring group (e.g., by adding devices or users selected to add monitoring in groups that have the lowest levels of current or predicted monitoring relative to their target levels), etc.

The interventions or types of adjustments that the system 210 selects can be performed automatically by the system 210 in some implementations, for example, to repeatedly and incrementally adjust the communication to different users in different ways (e.g., changing the times and locations that surveys are initiated, changing the frequency and content of reminders to acquire measurements, etc.) and to repeatedly and incrementally adjust device operation and configuration in different ways for different users (e.g., to instruct different devices to increase the frequency that sensors activate to take certain measurements, to increase the accuracy or precision measured or recorded, to increase the frequency of reporting results over a network, etc.). Other interventions, such as changing the composition of the monitoring group, can also be performed automatically by the system 210, for example, to automatically identify a set of candidates that would increase diversity among active monitoring that occurs and to send communications to invite those users or devices to participate. In the case where users have previously indicated interest or consent to participate (e.g., are waiting on a waiting list for an oversubscribed program), the system 210 may automatically initiate monitoring actions for one or more users or devices.

The system 210 may also provide recommendations of interactions to individuals, such as to electronic addresses or devices for researchers involved in a monitoring program. The system 210 may require authorization or approval of some adjustments, and may provide alerts or user interface data to inform the researchers and enable them to indicate approval to trigger the system 210 to carry out the interventions. Similarly, some changes to interaction with participants in a monitoring program, including changes to devices of the users, may be recommended or requested of the users, but the system 210 or the application on the user's device may wait for approval to make the change. For example, for a device that is not providing sufficiently accurate location data, the system 210 may instruct a device to monitor its location via GPS receiver every 15 minutes rather than once every hour.

In some implementations, and possibly based on the user's settings in the application, the application on the user's phone may automatically make the change without requiring approval from the user. In other implementations, the application on the phone may trigger display of a user interface that requests the user's permission to increase the monitoring frequency. For many changes to sensor operation and even for changing notification preferences, the changes that the system 210 instructs may increase power consumption and thus decrease battery life of the device. Accordingly, when the change is needed to improve monitoring performance, but may have adverse impact on the user (e.g., such as by lower battery life of the device), the system 210 or local software on the device may request approval.

Of course, not all changes to improve monitoring performance require increased power and other resources. Some changes the system 210 instructs may be made to conserve battery life. For example, when a device is not providing consistent data throughout the data due to running out of power or needing to be plugged in to charge for significant durations (and thus not being worn by the user while charging, so sensing of the user is not available during that time), the system 210 may instruct for the device to activate certain sensors less frequently, to conserve power and enable monitoring with lower frequency but spanning a longer duration each day.

The prioritization of groups and individual users or devices can be used to adjust the order and timing in which interventions are provided. For example, individuals in higher-priority groups can have interventions initiated before those of other lower-priority groups. The prioritization also helps allocate limited resources, such as to distribute devices, software, taxi credit vouchers, or other resources to the groups and individual users or devices where they will have the greatest impact in reaching the level of diversity needed. The prioritization also helps determine which groups and devices have any intervention made at all. When the system 210 determines that the need for performance improvement is low or would not significantly change the ability of the monitoring program to meet its diversity objectives, the system 210 may determine not to make adjustments for those devices or users (e.g., where the group has plenty of other devices providing data beyond the minimum level, or where performance of an individual device is already above the performance minimum and so no change is needed).

The prioritization allows for various types of differential treatment of members of one group compared to another. As an example, the system 210 may make adjustments such as applying a rule that increases communication with users through their devices if the group's performance is less than a certain threshold, but not if the performance for the group is above the threshold. Similarly, the system 210 can apply various rule-based changes, where a condition or trigger for taking an action is based on the value of the performance score for the group or for the combined score (based on both group-level performance and individual performance) for an individual.

In some cases, the system 210 can consider the diversity among the results monitored in the monitoring program. For example, a monitoring program may be configured to measure blood oxygen level (e.g., SpO2). The system 210 can have create ranges or clusters based on the results and evaluate how members of the monitoring group are distributed. For example, the monitoring program may be created to require diversity among SpO2 values, with at least some members monitored in the groups of 97-100 SpO2, 94-96 SpO2, 91-94, SpO2, and so on. If there are no members in one of the categories, or not sufficient distribution across the categories, the system 210 can identify the lack of representation of that condition (e.g., having a SpO2 in a certain range), and can take action to add participants having the needed characteristics.

Another reason for prioritizing interventions is to be able to more appropriately focus on incremental adaptations for the user or devices in groups where performance improvement is most needed. The system 210 can select an intervention for the users or devices in high-priority groups, and then continue to monitor whether and to what extent performance improves as a result of the intervention. If performance does not improve sufficiently, the system 210 can continue to make additional interventions for the members of the high-priority groups. Focusing interactions on repeatedly addressing the devices most in need of improvement, and/or for which improvement is most attainable, can achieve the fastest and best improvement outcomes.

The system 210 can store a database or other repository of different interventions, with different ways that a monitoring program can be adjusted to correct for different types of poor performance. For example, the system 210 can store a library of different interventions and corresponding conditions that can correct for the different indictors or causes of poor monitoring performance. For failure to complete a survey, the library can indicate sending reminders to the user, increasing the frequency that the survey is taken (e.g., every three days rather than once a week), changing the font size and layout of the survey, breaking the survey into multiple shorter interactions spaced apart over time (e.g., in the case that user has started a survey but does not complete it), and so on. For failure to obtain a sensor measurement, examples of interventions include increasing the frequency that the measurement is attempted (e.g., every 15 minutes rather than once per hour), attempting to obtain data from another device (e.g., requesting step count measures from a watch in addition to or instead of the user's phone), sending instructions or configuration data to change settings of the sensors or of the application that handles the measurements, scheduling the measurements for different times, setting triggers to perform the measurement when certain conditions are reached (e.g., when a certain user activity, location, etc. is detected), and so on.

For the various adjustments or interventions that are available, the repository can also store metadata that specifies when each is most appropriate. For example, the repository can store data indicating how effective different interventions have to improve data collection for different types of data (e.g., heart rate, sleep duration, etc.), for users of different attributes (e.g., by age, by sex, by race, by location, etc.), for devices of different types or models (e.g., for different models of smartphones, for phones vs. watches, etc.), and so on. With this effectiveness data, the system 210 can personalize the adjustments it makes by selecting, for each high-priority device or user, the intervention predicted to be most likely to improve monitoring performance and/or predicted to provide the greatest amount of improvement in monitoring performance. In some implementations, the system 210 can train, store, and use a machine learning model trained to predict which interventions are best suited for different device types, user types, and/or situations. For example, the model can receive input feature values indicating attributes of a device and its user, as well as potentially values characterizing the past monitoring performance or the problem with monitoring performance that has occurred (e.g., which measurement type was omitted, the level of data quality that was achieved, etc.). The model can then output one or more scores, for each of various different interventions, indicating the likelihood of improvement and/or magnitude of improvement that is expected in monitoring performance if the intervention is implemented. From these scores, the system 210 can select one or more interventions that are predicted to best improve monitoring performance for an individual device and/or user, for the areas of monitoring that the device or user is most in need of improvement.

The system 210 can also use the scores for past effects or predicted effects to determine when the expected benefit of interventions is too low to justify carrying out the change. The system can omit intervention in those cases where the historical or predicted value of amount or likelihood of improvement is less than a predetermined threshold. In other words, the system 210 selectively assigns interventions based on the level of need for performance improvement and the expected level of improvement. The system 210 may thus determine not to make interventions when the need for improvement or support for maintaining the current level of performance is low, and/or where a device or user is not in a high-priority group.

The system 210 has a range of interventions, discussed extensively above. These interventions include communications to cause devices to change their configurations, settings, software, network configurations, sensor operation, and so on to improve the rate and quality of measurements and survey responses. The interventions also include changes to user interfaces as well as sending reminders, notifications, alerts, and other communications to users. These interactions, targeted to the highest-priority individuals and groups, can help increase monitoring performance (through improved user action as well as device operation) where a change to improve monitoring performance is most needed and most urgently needed, whether that is to correct non-compliance that has already begun, to preemptively avoid non-compliance that is predicted to be likely, or to support maintained compliance for the groups and individuals where performance is most at risk of falling below the minimum levels needed for the respective diversity groups.

The interventions can include changing the composition of the monitoring group, by adding new devices or users to the monitoring group. The new devices or users can be selected, based on profiles in the database, as having the attributes for the categories where improved monitoring performance is most needed. The system 210 also applies the participant selection criteria and device capability requirements to select users that are eligible who also have devices capable of performing the needed monitoring actions (e.g., appropriate screen size, sufficient memory and processor speed, supported operating system version or other software version, correct sensor types and configuration, supported device model, etc.). To add new devices or users, the system 210 can identify the devices or users that would provide the greatest benefit (e.g., have attributes to be included in the highest-priority group(s)). From this set, the system 210 can also predict which candidates have the highest likelihood of compliance with the requirements of the monitoring program, which can be predicted based on the attributes of the candidates and historical interactions or outcomes for the candidates (e.g., pattern of data collection in previous studies). The system 210 can use predictive models, trained based on examples of individuals and devices from multiple different research studies and their outcomes, to predict future compliance and thus suitability for adding to the monitoring program. It is desirable that the system 210 institute interventions that will have significant positive effects, and adding individuals and devices that are have the appropriate attributes to improve diversity but that are not likely to comply with the data collection requirements ultimately would not be effective.

The system 210 can identify various preemptive actions to improve the likelihood of successful completion of the monitoring program with the needed diversity characteristics. One example is changing the communication with members of different groups (e.g., changing the timing, content, and quantity of reminders and data collection requests to better suit different groups). Another example is changing the composition of the monitoring group (e.g., identifying, inviting, and enrolling additional participants that would be in groups that are predicted to not have the minimum amount of retained, complying participants with appropriate quantity and quality of collected data). Another example is to change elements of the monitoring program, such as to add supportive elements (e.g., educational media and user interfaces, reminders, travel benefits such as taxi credits) targeted for participants in groups at greatest risk of not meeting their minimums, and so on. Another example is to provide software or configuration data over network to add redundancy or increase the frequency of data collection attempts. All of these are informed by the analysis of the different groups, so that changes are made for and intensity of support and interaction can be increased for participants and devices corresponding to the groups (e.g., G3 and G1) most in need of improvement to reach a desired confidence or probability of reaching their corresponding targets.

In some implementations, the system 210 uses the indication of low likelihood of meeting diversity requirements as a trigger to select different digital health technologies for individual users or for a diversity group (e.g., G3) as a whole. The system 210 can use any of the techniques discussed in U.S. patent application Ser. No. 16/877,162, filed on May 18, 2020, which is incorporated herein by reference. This can include predicting compliance for different technology items and identifying, recommending, and implementing use of substitutes or complementary technology items that are expected to produce better compliance.

Beyond the selection and recommendation of technologies, the system 210 can implement the changes to improve monitoring performance, by for example, initiating acquisition or shipment of a new device to an individual, sending different software, instructing configuration changes, and more.

Another type of change that the system 210 can make or recommend is to change the monitoring group. The system 210 can identify, based on user profiles for candidates indicated in the database, additional members that would meet the criteria for the groups that have higher than desired probabilities of being underrepresented, e.g., G1 and G3, and which also meet the cohort selection criteria. Optionally, the system 210 can evaluate the new candidates identified for these different groups and predict the likely compliance of each. From these the system 210 can score or rank candidates to select those in the groups where more representation is needed that are most likely to comply and succeed in meeting study requirements. Alternatively new candidates can be randomly or pseudo-randomly selected. The system 210 can identify a number of candidates that would be needed to increase likelihood of reaching the target representation (for the group or for the study as a whole) at study end to the desired level, such as 80%. This can be done by simulating additions, predicting the changes, and then iteratively adding until the likelihood threshold is met or exceeded. The system 210 can then select this determined number of additional candidates in G1 and G3 to add to the cohort, and can automatically invite them (e.g., sending, an email, a text message, a notification through an application, etc.) to enroll. Researchers can be recommended which individuals to add or which groups in which to add individuals, and may be given the opportunity to confirm or approve first.

The changes that the system 210 identifies to improve compliance and diversity can be made by the system automatically, e.g., to preemptively increase survey reminders to members of G3 when the system 210 determines that the predicted survey response compliance rate is low. In some implementations, changes can be recommended to a researcher or other administrator and performed in response to receiving confirmation. For example, a user interface for the researcher can be populated with user interface controls, based on data sent by the system 210, that the researcher can select to initiate the various actions identified for improving diversity.

In some cases, the system 210 is used to assist in initial selection of a cohort or to assess whether a study is viable with a certain pool of candidates. The cohort for the study may be generated by selecting individuals whose profiles meet the selection criteria for the clinical trial. For example, an administrator may select candidates to invite to participate in the clinical trial or the system can select candidates using user profiles in a database. Even before the clinical trial begins, the system can use historical outcomes and/or predictions to assess the likelihood that the set of candidates to invite will yield a cohort that will provide the needed compliance among a sufficiently large and diverse set of participants. For example, an administrator may select a group of 120 candidates, with 40 candidates in each of groups G1, G2, and G3.

The system 210 can determine, for each group, an estimated rate of conversion, e.g., a proportion of those that enroll out of the total invited. This rate can be determined based on records for previous clinical trials indicating invitations made, enrollment outcomes (e.g., which individuals enrolled and which did not), and user profiles for the users (e.g., to determine which groups the individuals would correspond to). The system 210 may use statistics for the groups directly (e.g., use the historical rates calculated for the groups), use a trained machine learning model to predict the rates, or generate a more complex rate based on likelihood of enrollment for each individual (e.g., using a trained machine learning model to predict an enrollment outcome for each candidate and using the likelihoods to generate an overall predicted rate for the candidates in a group).

As the system 210 receives data collection results from remote devices, the system 210 uses the results to update and continue training the various models. In addition, as the system 210 recommends and makes changes to improve outcomes and future diversity status, the system 210 tracks the results achieved for the different interventions it performs. As a result, the system 210 can learn which interventions are most effective for different diversity groups and for different situations, allowing the system 210 to select and perform more effective preemptive and corrective actions in the future for the same or different monitoring programs.

In the process 2000, adjusting the administration of the monitoring program can include causing each of one or more remote devices to carry out monitoring using one or more changed parameters or software modules selected to provide better compliance or data quality. This can include distributing configuration data corresponding to one or more programs identified for the one or more remote devices using the adapted scoring process. Distributing the configuration data can include transmitting, to each of the one or more devices, configuration data configured to adjust operation of the remote devices to set or change sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements.

Distributing the configuration data can include transmitting, to each of the one or more devices, configuration data configured to adjust operation of the remote devices to set or change data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements.

Distributing the configuration data can include transmitting, to each of the one or more devices, configuration data configured to adjust operation of the remote devices to set or change network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data.

The configuration data can cause remote devices to perform various changes or configuration actions, often without requiring user action on the device being changed. For example, devices of users that are enrolled in a monitoring program can have parameters for network communication, sensor measurement, user interface characteristics, and other aspects changed automatically. The configuration actions can include: enabling or disabling a sensor of the remote device or a device communicatively coupled to the remote device; setting or changing sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements.

The configuration actions can include setting or changing data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements.

The configuration actions can include setting or changing network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data; setting or changing power usage parameters of the remote device, including changing a device power state or sleep setting of the remote device.

The configuration actions can include altering a user interface of an application installed at the remote device, including changing a set of interactive user input controls presented in the user interface; changing the size, layout, formatting, and arrangement of user interface content; changing the media type (e.g., among text, images, videos, animations, graphics, charts, graphs, etc.); setting or changing interactive content to be presented by the remote device as part of the program, the interactive content including at least one survey, prompt, or electronic form; or setting or changing parameters for presenting the interactive content that includes at least one of timing, frequency, format, triggers, or contexts for providing the interactive content.

Figure 21A:
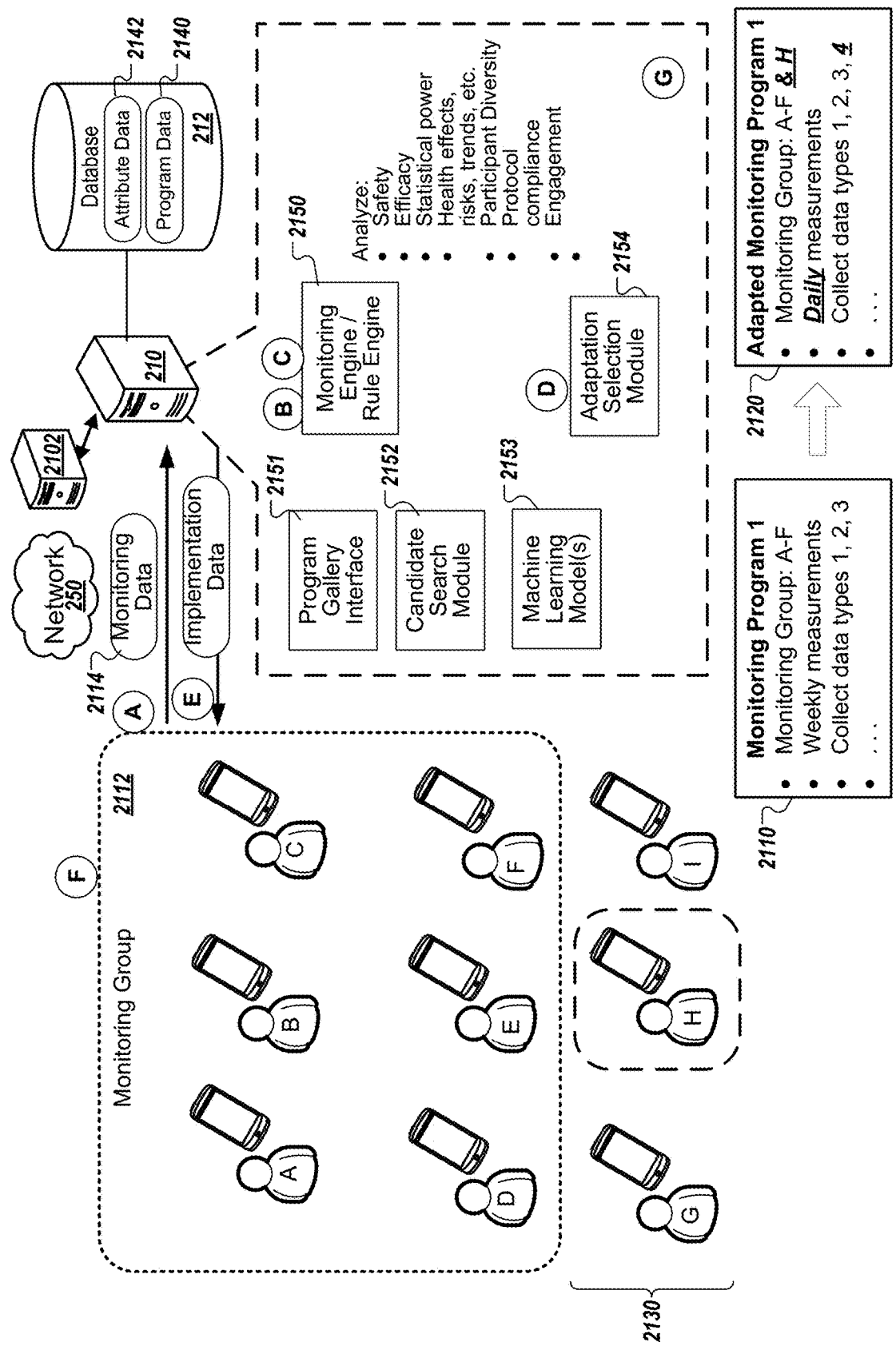
FIG. 21A is a block diagram that illustrates an example of the system configured to create and manage adaptive monitoring programs.

FIG. 21A is a block diagram that illustrates an example of the system configured to create and manage adaptive monitoring programs. In this example, the computer system 210 is configured to adapt or adjust any of various different aspects or characteristics of a monitoring program while the monitoring program is ongoing. For example, the computer system 210 can administer or conduct adaptive clinical trials and other adaptive health research studies. After a clinical trial has begun, the computer system 210 can automatically detect conditions that present an opportunity to improve or enhance the trial. The computer system 210 can evaluate these opportunities, select changes that are predicted to improve results of the trial, and recommend and/or implement the changes to the trial. The capability of the computer system 210 to detect and respond to opportunities for adapting trials allows frequent, small course corrections at early stages, which maximize the likelihood that a trial will achieve its objectives.

In the example, the computer system 210 is shown performing operations to manage and adapt a single monitoring program 2110. Nevertheless, the computer system 210 can operate concurrently manage and adapt many ongoing monitoring programs of many independent organizations and teams of researchers. For example, the computer system 210 can operate as a multi-tenant system, providing functionality as software-as-a-service (SaaS), and the database 212 can store information about many different adaptive clinical trials, their participants, and their results.

The adaptive capabilities provided by the computer system 210 can be used to change a trial in a way that maintains or increases diversity among participants. As discussed above, the diversity can be assessed and monitored by the computer system 210, for diversity in demographic attributes (e.g., age, sex, race, ethnicity, geographic location, etc.) as well as diversity in other types of attributes (e.g., physiological attributes, genomics, behavior, health status, disease status, comorbidities, personal medical histories, family medical histories, and so on). Many types of changes to an ongoing trial can improve diversity. For example, as discussed above, ongoing recruiting can be performed in targeted manner to add additional participants in categories that are underrepresented. The computer system 210 can identify the categories or user attributes that are underrepresented, and then search for and identify specific individuals that have the background that matches the categories or attributes needed. The computer system 210 can then invite and enroll those users, also providing the software and configuration data over the communication network 250 to cause devices of those users to begin collecting sensor data, survey responses, and other monitoring data. As another example, the computer system 210 can adjust the eligibility criteria for a study (e.g., inclusion criteria, exclusion criteria, etc.) to expand or contract the scope of participants that are permitted to participate in the trial. In addition or as an alternative, the computer system 210 can adjust the prioritization of recruitment of participants for a trial, so that individuals in certain categories that the computer system 210 identifies can be emphasized or over-weighted among new participants added. For example, the computer system 210 can change the way a trial is ranked in a program gallery interface that participants see, to increase the score or ranking of the trial for individuals that are in categories most needed in the study and to decrease the score or ranking of the trial for individuals that are not in the needed categories.

The adaptive capabilities provided by the computer system 210 can also be used to change trials in ways other than supporting diversity. For example, the computer system 210 can adapt trial properties to improve data quality for collected data, increase statistical power of findings in the study, test additional or different treatment regimens, and so on. As monitoring data is received, the computer system 210 can detect trends, anomalies, and patterns based on the monitoring data, then adapt data collection parameters and participant interactions to improve the trial's capability to assess those items. For example, analysis of monitoring data and participant health records (e.g., EHR) by the computer system 210 can reveal that a particular factor (e.g., a behavior, physiological characteristic, genomic characteristic, a biomarker, etc.) is correlated with a health outcome (e.g., positive response to treatment, a side effect of a medication, a reported symptom, etc.). In response, the computer system 210 can adapt the trial to alter monitoring to detect the factor and/or the health outcome (e.g., by initiating collection of additional types of data selected for the item to be monitored, or changing data collection frequency or other parameters). The computer system 210 may additionally or alternatively alter the recruiting priorities for the trial (e.g., to prioritize addition of new participants that have the particular factor), or identify, invite, and enroll specific individuals that are determined to have the factor of interest. In some cases, the computer system 210 may assess the overall set of participants to determine whether appropriate statistical power is present to characterize the suspected relationship (e.g., to prove or disprove with a desired degree of certainty), either generally or for specific groups or categories of individuals. When the computer system 210 determines that additional participants are needed to characterize the new relationship, the computer system 210 can expand recruiting to bring in the amount and types of participants needed.

Adaptation can be done across multiple different levels. For example, adaptation can be done for a monitoring program as a whole (e.g., the entire monitoring group 2112), or for individuals or groups within the monitoring group 2112. In doing so, the computer system 210 can apply adaptations based on aggregated or combined data across multiple individuals. For example, individuals in one category of participants in the monitoring group 2112 may show a certain symptom, and as a result the computer system 210 may add data collection or monitoring for that symptom not just for the people that experienced it, but for the larger category and/or for the entire monitoring group 2112. Similarly, if one category of participant needs additional time to collect data to reach a desired level of certainty for a finding, the duration of the study may extended for all participants. In this manner, while adaptations can be made for individuals, targeted for their preferences, responses, and health outcomes, adaptations can also be made based on data of a few participants for larger groups of participants that may not have exhibited the same preferences, responses, and health outcomes. As a simple example, in some cases, a prevalence of a side effect among 5% or 10% of a monitoring group 2112 may lead to an adaptation to enhance monitoring for all members of the monitoring group 2112, or to adjust the treatment parameters for all members of the monitoring group 2112.

The computer system 210 also benefits from the results and monitoring done for many different research studies, enabling the computer system 210 to learn over time which adaptations to a clinical trial are most successful and the conditions in which different changes succeed. As clinical trials provide data, and as adaptations are made, the computer system 210 can learn to distinguish between conditions under which adaptations are needed and those when adaptations are not, as well as to select or classify which changes are most appropriate when adaptation is beneficial. To do this, the computer system 210 can use any of a variety of approaches, including defining and updating rules or algorithms to detect and change monitoring programs, as well as maintaining and updating a database or repository of monitoring program elements that can be selectively brought into a trial to perform adaptations. The computer system 210 can perform training and updating of machine learning models used for adapting trials, such as machine learning models used to assess the suitability of or need for a change to a trial, as well as machine learning models used to assess the suitability of different types of changes. For example, based on historical data about the progression of different clinical trials, models can be trained and repeated updated over time to predict the likelihood that different types of changes (e.g., adding participants, adding a particular type of new data collection, employing one type of sensor or another, using a particular survey instrument, etc.) will positively affect one or more items of interest (e.g., compliance with a study protocol, retention at study end, meeting diversity targets, improving statistical power of a certain relationship, etc.). The rules, algorithms, and models that the computer system 210 uses to detect conditions for triggering adaptation and to select the specific adaptations to apply can be used across many different trials, and can be based on the monitored outcomes of many different trials.

Some adaptive clinical trials or adaptive design clinical trials are created with predetermined types of allowable changes defined in the study protocol or other information about the trials. While the computer system 210 enables adaptation at predetermined times and predetermined types of changes, the operation of the computer system 210 is not limited to this. Indeed, the computer system 210 can be used to adapt clinical trials and other monitoring programs even without the adaptation specified in advance. In many cases, the computer system 210 can perform repeated, incremental adjustments to monitoring programs that is responsive to conditions detected in the monitoring data, based on procedural or operational characteristics (e.g., current cohort size, compliance levels, diversity levels, etc.) or substantive health outcomes (e.g., physiological measurements, symptoms reported, positive or negative treatment outcomes, etc.).

As an example, the computer system 210 can dynamically adjust the priority of recruitment for different categories of participants. If there are three groups of participants G1, G2, G3, with each group representing a different category or set of attributes, the relative priority may initially be (1, 1, 1) indicating equal weighting for new recruitment into the respective groups. On a day-to-day basis (or more or less often, depending on the implementation), the computer system 210 can evaluate the diversity characteristics of the cohort and the needs of the research study. While computer system 210 determines that the cohort meets the diversity target for the research study, the equal weighting may be maintained. However, when the computer system 210 determines that compliance levels have fallen for group G1, or that predicted completion rates have dropped, the computer system 210 may increase the priority for that group, e.g., with weightings of (3, 1, 1) by group (e.g., so that 3 out of 5 new participants are in group G1), or even limiting recruiting to only group G1 until the right proportion or number is reached. As another example, new information from the monitoring data or an outside source (e.g., published research from other researchers, CDC reports, etc.) may indicate that group G3 has a higher risk or higher rate of infection for a disease, and so the computer system 210 may also prioritize recruitment from that group, setting relative priorities at (3, 1, 3). These priorities can adjust the score or ranking that the study receives for individuals, e.g., with individuals that would have the characteristics of groups G1 or G3 being shown the option for the study ranked much more highly (e.g., being boosted in score or ranking) relative to other studies in gallery interface. The computer system 210 may additionally or alternatively search the database 212 to identify specific candidates that have the characteristics to be included in groups G1 or G3, then present those candidates to a researcher or automatically invite and enroll them into the study.

The example of FIG. 21A shows the computer system 210, the network 250, and the database 212. The computer system 210 manages and adapts a monitoring program 2110, which in this case is an adaptive clinical trial. The computer system 210 facilitates data collection from a monitoring group 2112, which in the example is a cohort of participants enrolled in the adaptive clinical trial. Remote devices (e.g., cellular phones, tablet computers, desktop computers, etc.) of participants A-F provide monitoring data 2114 (e.g., sensor data, survey responses, behavior tracking data, self-reported outcomes such as disease symptoms, etc.) as part of the adaptive clinical trial, through an installed application, a web application, or other software.

The computer system 210 analyzes the received monitoring data 2114, as well as other data about the monitoring program 2110 and the monitoring group 2112, to detect when a change to the monitoring group 2112, data collection methodology, or other study parameters (e.g., objective, duration, treatment regimens, structure or design of the study, etc.) is appropriate or needed. When an appropriate condition for causing adaptation is detected, the computer system 210 selects one or more changes to make to the monitoring program 2110 and can carry out updates to administer the adapted monitoring program 2120 with the determined changes. The computer system 210 can indicate the need for a change and the recommended change to a researcher 202 (see FIG. 3) in a notification, user interface, web-based portal, application, or in another form on a client device 204 of the researcher 202. The recommendation can be provided along with data causing interactive user interface elements to be displayed, along with the recommendation, enabling the researcher 202 to select to confirm that the change should be made, deny the change, or modify the change (e.g., accept only part of the recommended change, replace the recommendation with a different change, or vary parameters such as size of cohort expansion). The computer system 210 receives and acts on the user input provided through the interactive controls to carry out adaptations as the researcher 202 authorizes. As discussed above and further below, the computer system 210 can also carry out determined changes to change cohort characteristics and other aspects of the study automatically.

In some implementations, the computer system 210 is granted authorization to make certain types of changes or changes within a limited degree or extent automatically, without requiring explicit confirmation or authorization from a researcher 202 for each change. For example, a researcher 202 may set a size range for participants in a study and ranges or targets (e.g., minimum amounts, minimum proportions, etc.) for each of different diversity categories for a cohort, and allow the computer system 210 to automatically vary recruitment parameters to maintain or adjust participant recruitment within those constraints. For example, the researcher 202 may specify that a clinical trial should have between 500 and 1000 participants, and that four demographic categories should make up at least 20% of the cohort. Acting within these constraints, the computer system 210 may then automatically vary parameters used to add new participants to the cohort, responding as needed changing conditions (e.g., attrition of participants, increases or decreases in compliance with the study protocol, new trends in health results monitored, new correlations or risk factors detected, and so on). Thus, the computer system 210 can respond to varying conditions, and can alter parameters of the monitoring program 2110 frequently as needed (e.g., day-to-day, week-to-week, month-to-month, or at another frequency). As an example, the computer system 210 can automatically change parameters that set the membership in the active cohort of participants, e.g., changing the set of candidate attributes that the computer system 210 uses to generate targeted invitations to participate in the study, and/or varying the scoring and ranking with which the monitoring program 2110 is presented to candidates in a program gallery. The computer system 210 can select and send program modules, configuration data, and other appropriate data packages that are configured to cause devices of newly enrolled participants to begin monitoring (e.g., presenting surveys, monitoring sensor outputs, reporting data to the computer system 210, etc.).

As another example, the computer system 210 automatically alter other aspects of a monitoring program. For example, the computer system 210 can be given authorization to automatically and dynamically customize the sensor data collection performed, the set of surveys presented to participants, and other data collection procedures. These changes can be made within certain guidelines, such as a maximum limit of no more than 10 surveys per participant per week and no more than two per day, or limiting sensor data collection to data collection using approved device(s) or software item(s). As symptoms and other health effects are detected, the computer system 210 can automatically change data collection to monitor them. For example, once a minimum prevalence of a symptom, such as fatigue, is reported, the computer system 210 can enable further data collection to monitor related parameters, such as heart rate, respiration rate, and so on. The computer system 210 can assess the characteristics and contexts in which the effect is reported, and may limit changes to the relevant groups, at least initially. For example, if fatigue is reported in participants over age 60, or for participants above a certain body mass index (BMI), the computer system 210 can detect this commonality or pattern and can target the adaptation in the data collection procedure directly for the group in which the risk is highest. This adaptation and targeting can be done using the techniques that U.S. Pat. No. 11,249,875 describes for detecting opportunities for new sub-studies and creating new sub-studies, although the adaptation for part of or an entire cohort, without the need to explicitly define a new sub-study. To the extent that participants each have a device with sensors capable of the appropriate measurements (e.g., an activity tracker for heart rate and actigraphy data, a cell phone for location data, etc.), the computer system 210 can communicate with the devices of participants over the network 250 to push data packages (e.g., software modules, configuration settings, instructions, commands, code, etc.) that can seamlessly initiate the data collection by the remote devices, using passive and/or active sensing, or otherwise adjust operation of the devices (e.g., running background processes, changing sleep timing, etc.).

The computer system 210 can have significant flexibility to enable and disable data collection at a fine-grained level as a study progresses. The original study protocol for the monitoring program 2110 may specify that participants complete a survey, such as a PHQ9 survey to assess depression symptoms, once a week. The computer system 210 may detect a condition that relates to this data type. For example, the computer system 210 may determine that results exceed a threshold level of variability, and thus that quality or reliability of the data is low. In response, the computer system 210 may automatically cause the survey to be presented more often, may initiate use of a different survey instead, and/or may instruct other indicators of depression symptoms to be measured. As another example, the computer system 210 may detect, through interim analysis of monitoring data 2114, that the health outcomes have at least a minimum level of correlation with the depression survey results received, signaling that the depression results have increased in importance to the study. The computer system 210, in response, can increase the frequency of the survey (e.g., to a daily survey, for a more detailed day-to-day view). The computer system 210 may also initiate new surveys or data collection, such as beginning use of an anxiety survey to allow analysis of potentially related factors or distinguish confounding factors, or engaging location monitoring on participants' mobile devices or begin automated tracking of social interactions as corroborating measures of depression.

As another example, the computer system 210 can monitor survey completion rates and patterns for individuals, groups within a cohort, and for a cohort as a whole, and the computer system 210 can adjust which surveys are presented and when. As discussed above, the computer system 210 can characterize how different elements of a study, including different surveys and data collection requirements, are received by different categories of participants and in different contexts. From this characterization data determined across many studies, and based on the specific patterns observed in the monitoring data 2114 of the current monitoring program 2110, the computer system 210 can determine to change survey types and content to improve compliance and data quality. For example, in response to a decrease in survey completion (whether for an individual, a particular set of participants or category of participants, or for the entire set of participants), or predictively to forestall a predicted or likely decrease over time, the computer system 210 can vary the survey instruments used, decrease the length, split a survey into smaller discrete interactions, decrease the complexity, change visual properties (e.g., change formatting, color scheme, layout, size, etc.), or perform other changes that the characterization data indicates will increase likelihood of completion.

As additional examples, the computer system 210 may adjust the duration of a monitoring program (e.g., from a planned 3 months of monitoring to 4 months). As another example, the computer system 210 may change the set of treatment regimens tested (e.g., from three study "arms" respectively testing 10 mg, 15 mg, and 20 mg doses of a drug plus a control group not taking the medication, to five study arms respectively testing 5 mg, 7.5 mg, 10 mg, 15 mg, and 20 mg doses and a control group). The computer system 210 may create or end testing of certain treatment regimens, or dynamically shift the amounts or proportions of participants in the different treatment regimens (e.g., to shift a greater proportion of participants to a treatment group for a treatment that has shown positive results, or to a treatment group where more participants are needed for statistically valid conclusions, or to remove from a treatment group participants having attributes discovered after the beginning of the study to increase a health risk such as a medication side effect or progression of a disease). The dynamic adjustments by the computer system 210 can be applied to all forms of patient interactions, where different sub-groups or cohorts within a monitoring program may have different communication settings, different behavioral constraints (e.g., parameters for diet, exercise, sleep, etc.), different digital therapeutics applied, different instructions or education provided, and so on.

The computer system 210 may also automatically adjust the structure of a monitoring program 2110 or its monitoring group 2112. For example, the computer system 210 may segment, or adjust the segmentation, of participants into different sub-cohorts, sub-studies, ancillary studies, and so on, each of which may have varied study protocols, treatments provided, data collection procedures, and so on. For example, the computer system 210 can be authorized to recommend, and even to automatically create and begin, sub-studies and ancillary studies, using the techniques discussed in (i) U.S. patent application Ser. No. 17/233,356, filed on Apr. 16, 2021, now U.S. Pat. No. 11,249,875; (ii) U.S. patent application Ser. No. 17/233,103, filed on Apr. 16, 2021; and (iii) U.S. patent application Ser. No. 17/185,954, filed on Feb. 25, 2021, each of which is incorporated by reference herein.

Figure 22:
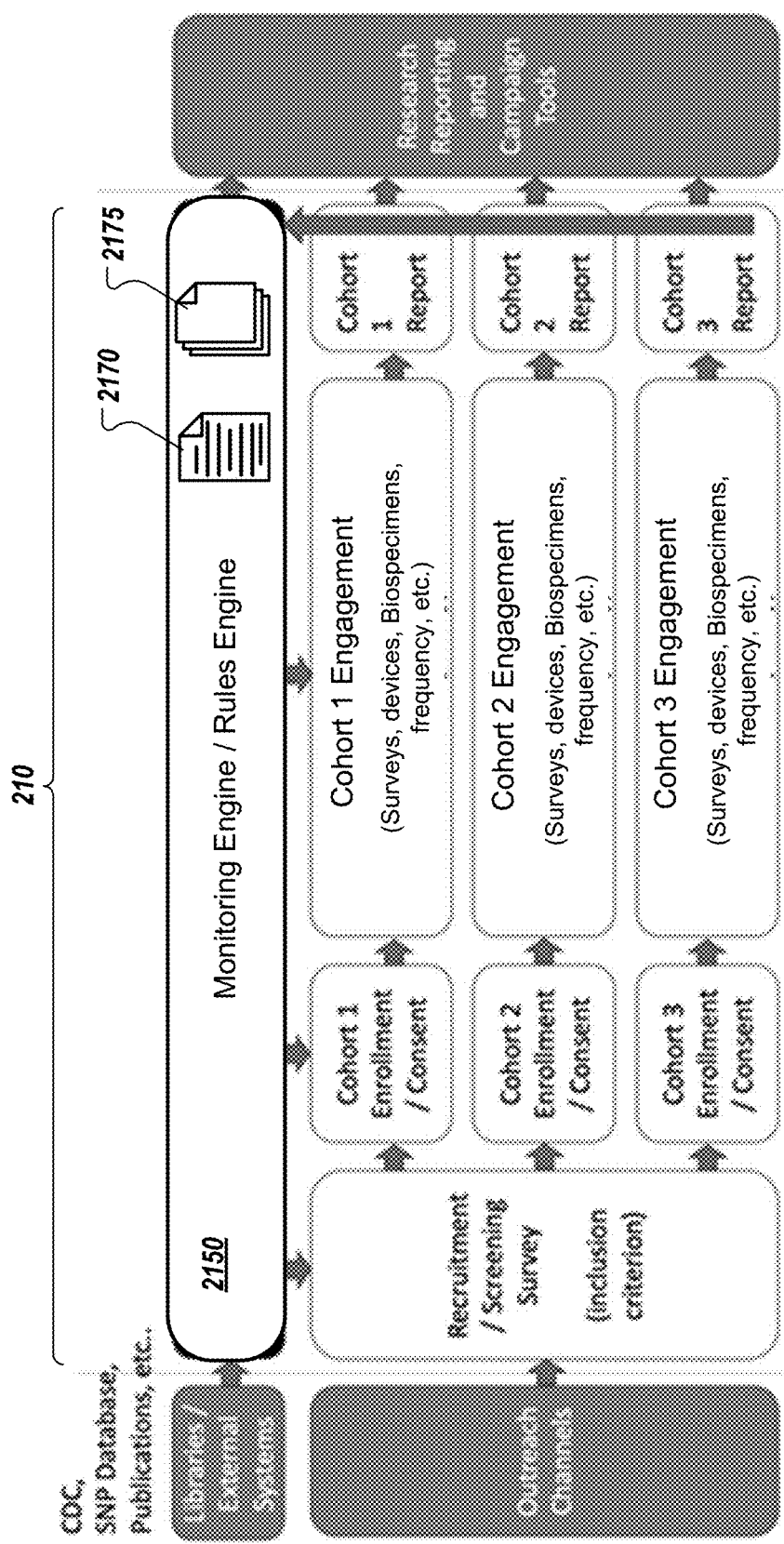
FIG. 22 is a block diagram that illustrates another example of the system managing adaptive monitoring programs.

The example of FIG. 21A shows a single main monitoring group 2112, but as discussed with respect to FIG. 22, a monitoring group or cohort can be formed of smaller cohorts, which may be sub-cohorts, subsets of the main cohort, participant categories for diversity tracking, or other groups. The monitoring group for a monitoring program may be, in effect, a "cohort of cohorts," where a collection of smaller groups or cohorts, each with separate versions of protocols and consent forms, together can be assessed by the computer system 210 collectively as well as individually. The computer system 210 can adapt the procedures and composition of each of these smaller cohorts or groups, such as making different changes for each to respond to each group's detected health trends, health correlations, adverse events or emerging risks, protocol compliance, communication preferences, and so on. In addition, the computer system 210 can determine how to adapt the monitoring program as a whole, based on the aggregate data across all the groups. To do this, the computer system 210 can consider the averages, distributions, and other measures for a combined or composite view across multiple or all of the groups. The computer system 210 can also make adaptations that transfer or apply procedures and study elements used for one group to another group or to the entire set of participants. For example, in the course of adapting data collection procedures for one category of participants, the computer system 210 may determine a strong correlation between a participant attribute or behavior and a positive or negative effect of a drug. When the monitoring data for a first category of participants provides at least a predetermined level of confidence in the correlation, the computer system 210 can import the data collection parameters needed to assess that correlation to one or more other groups or to the entire monitoring group 2112. This can enable the computer system 210 to gather the data needed to validate or confirm the correlation for other categories of participants or in a population generally. Other types of adaptations (e.g., procedures, data collection, study parameters, etc.) may be transferred or imported from one group or cohort to another within a monitoring program 2110. For example, the monitoring results for one group may suggest that a risk or health effect has wider applicability than initially expected, leading the computer system 210 to expand the age range for participant eligibility for all categories of participants, not just the one in which the monitoring data revealed the relationship.

The example of FIG. 21A shows a series of stages labelled (A) to (G) that show a flow of data in the system. At the start of the process, the monitoring program 2110 is active and the participants A-F in the monitoring group 2112 have been enrolled to participate. Enrollment can include steps such as a user opting in or selecting to participate, providing consent, registering for the study, being evaluated and found eligible to participate, etc. Each participant also has one or more devices that are configured, through a downloadable application, configuration data package, device or software settings, etc. to provide the interactions and data collection of the monitoring program 2110. The state of the monitoring program 2110 may be the initial state, as specified in the initial study protocol, or it may have already been adapted one or more times.

The database 212 stores program data 2140, which describes various information about the monitoring program 2140, such as the objectives of the monitoring program, eligibility criteria for participants (e.g., inclusion criteria, exclusion criteria), study duration (e.g., a planned period of time to collect data for the study), diversity targets or requirements, data collection procedures, and so on. The program data can include information from the study protocol. Other information, such as authorization for or constraints on adaptation that the computer system 210 can perform can also be included, and the computer system 210 can refer to this information to select or limit its adaptations.

The database 212 also stores attribute data describing information about individuals, including participants in the monitoring group 2112 as well as additional individuals 2130 that are not enrolled in the monitoring program 2130, but which are in pool of candidates (e.g., potential future participants). The attribute data can describe, for each person, demographic characteristics (e.g., age, sex, race, ethnicity, location, etc.), physical characteristics (e.g., physiological measurements), behavioral characteristics, mental health characteristics, current state of health, diseases or chronic conditions, personal medical history, family medical history, genomic data, and so on. The attribute data can include current and historical information, and may include EHR data for the individuals described.

In stage (A), the computer system 210 collects data from the remote devices of the participants in the monitoring group 2112. The monitoring program 2110, e.g., an adaptive clinical trial, has begun and ongoing monitoring of the participants A-F is being performed. For example, repeated, periodic data collection is performed using surveys and sensor data collection.

In stage (B), the computer system 210 analyzes the monitoring data 2114, along with the attribute data 2142 for participants and the program data 2140 for the program, along with potentially other information. For example, an analysis module, such as the monitoring engine or rules engine 2150, can apply a set of rules or criteria to detect opportunities for an adaptation that meet a threshold level of improvement or added value to the monitoring program 2110. The monitoring data 2114 can reveal significant information about the status of the monitoring group 2112 and likelihood that the monitoring program 2110 will achieve its objectives. Various types of information can be assessed, including safety, efficacy, statistical power, health effects, health risks, participant diversity, protocol compliance, participant engagement, and more. The computer system 210 can determine trends, patterns, correlations, and other relationships or effects from the monitoring data 2114.

In stage (C), the computer system 210 detects a condition that provides an opportunity for an adaptation. based on the analysis, the computer system 210 can evaluate the various patterns, correlations, health outcomes, anomalies, outliers, or events, and can use various thresholds and references to detect a condition for providing adaptation. For example, the computer system 210 can perform pattern matching to see if conditions detected match those of prior studies where adaptations were performed and/or led to successful outcomes. The computer system 210 can perform comparison and matching of contexts, such as comparing the trends in compliance and health outcomes with reference parameters or reference trends. The computer system 210 can apply various rules, developed based on the effects of different study parameters or study adaptations, to determine when a rule indicating a condition for applying a new adaptation has occurred. In some cases, the computer system 210 uses a machine learning model to classify whether the current state of the monitoring program 2110 and/or monitoring group 2112 is appropriate for an adaptation. Models can be trained to predict whether each of various different types of adaptations are appropriate, e.g., with different models or outputs respectively indicating scores or classifications whether it is appropriate to extend the duration of the study, add cardiac monitoring, add respiratory monitoring, expand the cohort size, etc. As discussed extensively above, the computer system 210 can assess diversity and likelihood of achieving desired cohort size and other characteristics at the end of the study, and can make adaptations base on that analysis. The computer system 210 can also obtain information from a third-party system 2102, such as to obtain updated disease information from government sources or to correlate study findings with genomics databases, which may indicate further directions for study or may change the emphasis of which items to monitor or the types of attributes that participants should have.

In stage (D), the computer system 210 selects an adaptation for the monitoring program 2110. This can include any of various types of adaptations discussed herein. An adaptation selection module 2154 can be used to assess various different adaptation options and to select the changes that the computer system 210 predicts will provide the greatest improvement in data collection completeness, data quality, addressing the research question or other objectives of the study, and so on. The computer system 210 may provide an indication of or recommendation of the adaptation to a researcher for the program 2110, and may request confirmation or approval to make the adaptation.

In stage (E), the computer system 210 implements the adaptation selected. This results in the adapted monitoring program 2120, which incorporates several changes. In the example, the changes include adding the new participant H to the monitoring group and communicating with the mobile device of the participant to begin data collection operations, e.g., presenting surveys and receiving responses, generating sensor data to measure user physiological characteristics and behaviors, detecting contexts (e.g., monitoring environmental factors and user behavior) to trigger conditional interactions such as contextually-triggered ecological momentary assessments (EMAs), performing on-demand interactions instructed by the computer system 210 over the network 250, and so on. The adaptations include increasing measurement frequency for all participants, from weekly measurements to daily measurements. The adaptations also include collecting an additional type of data (e.g., data type 4) from all participants.

The computer system 210 can implement the adaptations in various ways. For data collection changes, the computer system 210 can send implementation data to devices of participants, e.g., software modules, configuration data, instructions, etc., that cause the devices to change their monitoring or interactions with participants. To change cohort membership, the computer system 210 can adjust parameters used by a program gallery interface 2151 to change how the adapted monitoring program is scored, ranked, or made available to candidates. The computer system 210 can also use a candidate search module 2152 to search through or filter candidates 2130 and select specific individuals with the needed set of attributes to directly invite to participate.

In stage (F), the computer system 210 and the remote devices perform additional monitoring for the adapted monitoring program 2120. For example, the updated cohort, with participants A-F and H all provide data with survey results and sensor measurements, at the new daily measurement frequency and for the new set of data types to collect. The computer system 210 analyzes this additional monitoring data received to detect when other adaptation becomes appropriate.

In stage (G), the computer system 210 update the process of detecting adaptation opportunities and selecting adaptations in the future, for the current monitoring program 2120 or others. Based on the monitoring data that continues to be received, which indicates protocol compliance, health outcomes, and other properties, the computer system 210 can assess how changed parameters contributed to or detracted from desired outcomes (e.g., meeting diversity targets, meeting a desired level of statistical power, reaching a conclusion within a desired timeframe, etc.). With many examples, the computer system 210 can train or update the machine learning models 2153 to better predict when adaptation is appropriate, and which specific adaptations are appropriate for specific types of studies and conditions (e.g., types of trends, patterns, etc.). Similarly, the computer system 210 can use statistical measures or specific examples (including identified clusters of similar studies or similar results) to define or update the rules used by the rules engine 2150.

Many adaptive clinical trials and adaptive design trials are limited to making changes in response to predetermined conditions, or are limited to making a limited set of types of changes or making changes only at certain times or milestones. The computer system 210 can provide greater efficiency and effectiveness in adaptive clinical trials by providing an expansive set of possibilities, with conditions where different types of adaptation are appropriate being learned from effects of prior program elements and program adaptations. This allows the collective learning from many different studies and adaptation decisions to be applied effectively for other monitoring programs.

FIG. 21B is a diagram that illustrates various examples of aspects of a monitoring program that can be adapted by the system. The diagram shows various types of program data 2140 that can be stored to describe the monitoring program 2110. Various items 2160a-2160h are shown, representing parameters, settings, characteristics, and other aspects of the monitoring program 2110. Many or all of these items 2160a-2160h may be defined in a study protocol For example, values for each of the items 2160a-2160h listed can be stored in the database 212 for the monitoring program 2110, and similar information for other monitoring programs the computer system 210 administers can also be stored. The computer system 210 can use the items 2160a-2160h to analyze the status of the monitoring program 2110 and determine whether adaptation is needed and in what manner to adapt the monitoring program 2110. For example, using the current cohort status and information from the program data 2140 (e.g., objectives of the program, diversity targets, cohort size targets or constraints, etc.), the computer system 210 can determine whether to change the cohort size, and in what manner, such as whether to add participants, remove participants, which categories of participants are needed, how many participants to add, etc. Similarly, study parameters indicating desired level of confidence in study results can be used to determine when data collection procedures need to be changed to increase applicability of results, confirm a study finding, improve reliability or data quality, and so on.

In addition to using the items 2160a-2160h to make adaptations, the computer system 210 can be configured to adapt monitoring programs as needed to make changes for the dimensions represented by any or all of the items 2160a-2160h. For example, the computer system 210 can use a diversity target to determine when the monitoring group 2112 has failed to meet or is at risk of failing to meet the diversity target, to prompt adaptation to change cohort membership (and/or data collection procedures, communication with participants, or other parameters) to increase the diversity in the areas needed. In addition, the computer system 210 may evaluate the diversity target itself and may make an adaptation to change the diversity target. For example, after beginning a study with equal proportions of participants among three categories, the monitoring data or data from external sources (e.g., other research, CDC reports, etc.) may indicate that a fourth category of individual, not initially tracked for diversity, is at high risk for infection or severe disease outcomes. As a result, the computer system 210 may adjust the diversity target (e.g., minimums, proportions, distribution, etc.) to set a target level for the fourth category. The computer system 210 can automatically assess and track the updated set of four categories and adjust cohort membership and study characteristics to achieve the new target.

Diversity targets can be adjusted by the computer system 210 for other reasons, such as determining that the makeup of a reference population has changed, with the diversity target being adjusted to align with the new population characteristics. This can be particularly important in longitudinal studies, which may continue for months or years, during which demographic shifts can occur. Similarly, the computer system 210 may adjust diversity targets to align with a different geographic area. For example, a study may be initially focused on a particular state or county may be expanded to represent a larger area, such as a nation-wide or multi-national region, and the computer system 210 can adjust the diversity targets to match the characteristics of the new geographic area of relevance. The computer system 210 can also adapt diversity targets to match predicted future population characteristics, as estimated by the computer system 210 from trends in population demographics, such as to align diversity targets to a level predicted to be present in 5 years rather than a current level present.

As noted above, diversity can be tracked and adjusted not just for demographic attributes, but for aspects of health, behavior, and history as well. A study may begin with diversity targets for demographics, but during the study the computer system 210 may determine that diversity should be tracked across other dimensions also (e.g., presence of different comorbidities, such as diabetes, heart disease, etc.; for ranges of height, weight, etc.; and so on). The addition of, or adjustment of, diversity monitoring and diversity targets along physiological and behavioral dimensions can be triggered by analysis by the computer system 210 of monitoring data 2114 collected in the study, correlated with the attribute data 2142 for the participants in the study. This analysis can reveal patient attributes and behaviors that emerge as newly discovered relevant factors in the safety and efficacy of interventions or with respect to health risks and health outcomes. Consequently, as the computer system 210 determines that the magnitude of correlation or significance rises above a particular level or threshold, the computer system 210 can adjust diversity targets to provide diversity among those factors, adjust cohort composition to represent members with and/or without those factors, add new cohorts (e.g., sub-studies, ancillary studies, diversity groups, etc.), and adjust monitoring to measure those factors and related indicators.

The eligibility criteria 2160a include values of parameters specifying whether individuals are eligible to participate, such as inclusion criteria a participant is required to satisfy and exclusion criteria that, if satisfied, would block an individual from participating. The computer system 210 uses these values in assessing whether to invite potential candidates or display the monitoring program in the gallery interface. Similarly, the computer system 210 can adapt these parameters, such as by changing the inclusion criteria to encompass a wider set of participants. This can be done in response to determining, based on monitoring data 2114 or data from third-party sources, that the study is relevant to a greater set of individuals. For example, the original inclusion criteria might require participants to have an age between 50 and 70 years, but during the study the computer system 210 can determine that relevance may extend beyond this range. For example, the results may show little or no variation in safety and/or effectiveness of a drug based on age, and so the computer system 210 may expand the permitted age range in response. This can be done in a single step, e.g., expanding to 30 to 90 years, or may be done incrementally in stages, e.g., at first to 45-75 years, then 40-80 years, then 35-85 years, and so on. With the incremental approach, the computer system 210 can obtain monitoring data for a period of time after each adaptation, and check that the reason for further adaptation still holds (e.g., the new members in the expanded age continue to show no age-dependent change in safety or efficacy) before taking the next adaptation step.

Other changes to eligibility criteria 2160a can be made by the computer system 210, such as to add exclusion criteria to exclude patients with certain factors (e.g., a particular chronic disease, a particular genetic sequence, etc.) when monitoring data 2114 or other data indicates that the factor increases a health risk or is correlated with negative outcomes. The computer system 210 can also adjust the eligibility criteria to address new or adjusted research goals, such as to expand the range of participants so that study findings can be generalized to a larger population. In some cases, the computer system 210 can adapt the eligibility criteria when needed to reach other targets (e.g., diversity levels, minimum cohort size, desired level of statistical power, etc.). This can be done in response to tracking cohort status and trends over time, so that eligibility criteria is expanded when rate of enrollment or retention fails to reach a needed level, or when the computer system 210 analyzes the candidate pool and determines that expanding the range of eligibility is needed to reach a cohort size target within a predetermined amount of time (e.g., a month, or another target time). In some cases, when recruitment is occurring faster than anticipated, the computer system 210 may narrow eligibility criteria to target groups that provide better data or will be better participants. For example, the computer system 210 may add inclusion criteria requirements that a patient have genomic data or EHR data available, making them more valuable participants. Or, the computer system 210 may assess the likelihood of compliance by patients with different characteristics, and may require attributes that have been associated with high levels of compliance in previous studies.

The computer system 210 can also adapt cohort characteristics 2160b, by changing the actual cohort size (e.g., adding or removing participants), changing the target cohort size (e.g., increasing from 200 to 300 in response to a detected need to increase statistical power or capture additional dimensions of diversity), changing a number of cohorts or groups of participants represented in the study, and generally adjusting cohort membership (e.g., making invitations to specific candidates).

The computer system 210 can also adapt program availability 2160c, such as settings that affect how a program is offered to candidates. This can involve adjusting the program profile for a program, as well as adjusting the algorithms and rules for scoring and ranking programs relative to each other. Programs can be presented and recommended in a program gallery, as well as be scored and ranked, as described in U.S. patent application Ser. No. 17/224,315, filed on Apr. 7, 2021, which is incorporated by reference herein. The adaptations can include adjusting the prioritization of different participant attributes, to boost or penalize the relevance scores for certain participants, depending on whether they have attributes needed for eligibility or have attributes that would place them in a category in which further representation is needed. As a result, the computer system 210 can adjust whether a monitoring program is available to certain types of individuals that view a program gallery, and how the monitoring program is ranked. This can be done by setting parameters that cause the program gallery to customize the prominence or availability of the monitoring program for each individual that accesses the program gallery, based on that individual's attributes and the priorities set by the computer system 210.

The computer system 210 can also adapt diversity and representation elements 2160d. In addition to adapting the membership in the monitoring group 2112 as needed to achieve diversity targets, the computer system 210 can change the diversity targets themselves. This can include changing the categories of individuals or user attributes that are tracked and for which cohort membership is adjusted. Similarly, the diversity targets themselves, e.g., minimum amounts of people in different categories, quotas for diversity groups, target proportions of a cohort, etc., can be adjusted. As discussed above, these change may be made for a variety of reasons, such as in response to changes in a reference population, expanding a reference population for the study, determination that study outcomes or studied health aspects have increased relevance or impact on certain categories of participants, and so on.

The computer system 210 can also adapt data collection methodology 2160e. This can include adaptively changing the types of data collected, e.g., adding or removing collection of data for certain areas of health (e.g., sleep, exercise, diet, mental health, etc.), for certain physiological parameters (e.g., resting heart rate, peak heart rate, respiration rate, blood pressure, weight, blood glucose level, blood oxygenation level, etc.), for certain behavioral measures (e.g., step count, frequency and duration of inactive periods, sleep duration, sleep quality, etc.). Adjusting the data to be collected can include changing the surveys used, such as to add new surveys that the computer system 210 selects from a library or repository of survey instruments that are each associated with the types of data collected. The computer system 210 can also adjust which software, devices, and sensors are used by participants. The computer system 210 can also adapt data collection parameters, including frequency of data collection, the method of collection (e.g., survey 1 vs survey 2; device 1 vs. device 2; collection by device or by survey; etc.), the level of compliance required to remain in the study, set of data quality characteristics needed, and so on.

Adaptations to data collection methodology 2160e can be made to increase or change the types of substantive data collected, but can also be done to improve data quality (e.g., accuracy, precision, reliability, repeatability, etc.) and protocol compliance (e.g., increase consistency of collection, avoid gaps in monitoring, promote proper use of health monitoring devices, etc.). For example, in response to detecting data collection levels below a threshold (e.g., for a participant, group of participants, or an entire monitoring group 2112). As discussed above, different adaptations can be made for different groups of participants, guided by the analysis of how different study elements have historically affected compliance rates of participants in different categories. As a result, when various groups have low compliance, one group may have communication adjusted to increase reminders, another group may have the interactions of the data collection activity changed (e.g., a simplified survey, interactions broken up into multiple steps, etc.), another group may have a substitute data collection method applied (e.g., automated step count tracking and reporting by a device rather than user-entered data), and another group may simply increase the frequency that the data collection activity occurs.

The computer system 210 can also adapt treatment and intervention parameters 2160f. This can include changing the medications used, the dosages of the medications, the frequency of taking the medication, and other aspects of medication administration (e.g., time of day, whether taken with food, etc.). In a similar manner, the computer system 210 can adjust the types of digital therapeutics provided, the frequency and intensity that digital therapeutic interactions occur, and so on. Any interventions to affect the health and behavior of a participant can potentially be adapted. This includes changing the number and type of different treatment groups or "study arms" that respectively test different treatment regimens.

The computer system 210 can adapt other study parameters 2160g. This includes altering the duration of the study, such as to increase study duration when additional monitoring is needed to validate findings, or to decrease study duration (e.g., to end early) if a study has already reached a desired level of confidence for findings or if it becomes impossible to answer the research question. The computer system 210 can adapt the objectives of the study, for example, to add the testing of certain new correlations discovered based on the monitoring data 2114, or to change the target scope of applicability of the study findings to a new or altered population. The computer system 210 can adapt the set of incentives, compensation, and participant support elements (e.g., reimbursements, travel credits, etc.) as needed to support the desired level of diversity.

Based on the design of the study, certain types of adaptations may be permitted and/or constraints can be placed on the type or extent of adaptations permitted. The computer system 210 can store and check these parameters, keeping adaptations within the specified boundaries. When appropriate, the computer system 210 can identify and recommend other recommended adaptations and provide them to a researcher 202 for approval, even if they exceed the scope of adaptations that the computer system 210 is authorized to perform automatically without confirmation. Similarly, the monitoring program 2110 may have certain targets for statistical power, accuracy, specificity, and so on. For example, the computer system 210 may have targets for levels of false positives or false negatives to validate in a testing approach. The computer system 210 can adjust data collection parameters, cohort size and composition, study duration, and other parameters to meet these targets. In some cases, the computer system 210 may adjust the targets themselves, for example, to increase the target level of accuracy or validation after reaching an initial target early.

The computer system 210 can adapt parameters for participant communication 2160h, such as adjusting the types of communication provided (e.g., reminders, challenges, insights or results from monitoring, etc.), adjusting the content and appearance of communications (e.g., complexity, level of detail, formatting, style, etc.), adjusting the media types used (e.g., text, audio, image, video, etc.), or adjusting the communication mode (e.g., phone call, email, SMS text message, in-application notification, web portal, etc.). These changes can be made for the monitoring group 2112 as a whole, but can also be made separately for individuals or groups of participants. As discussed above, participants in different categories may respond differently to different communication types. Thus, the computer system 210 can adjust communications to customize them for each category of participant, based on outcomes predicted or observed following communications, to achieve the highest engagement and best level of compliance and data quality for participants in that category.

Figure 21C:
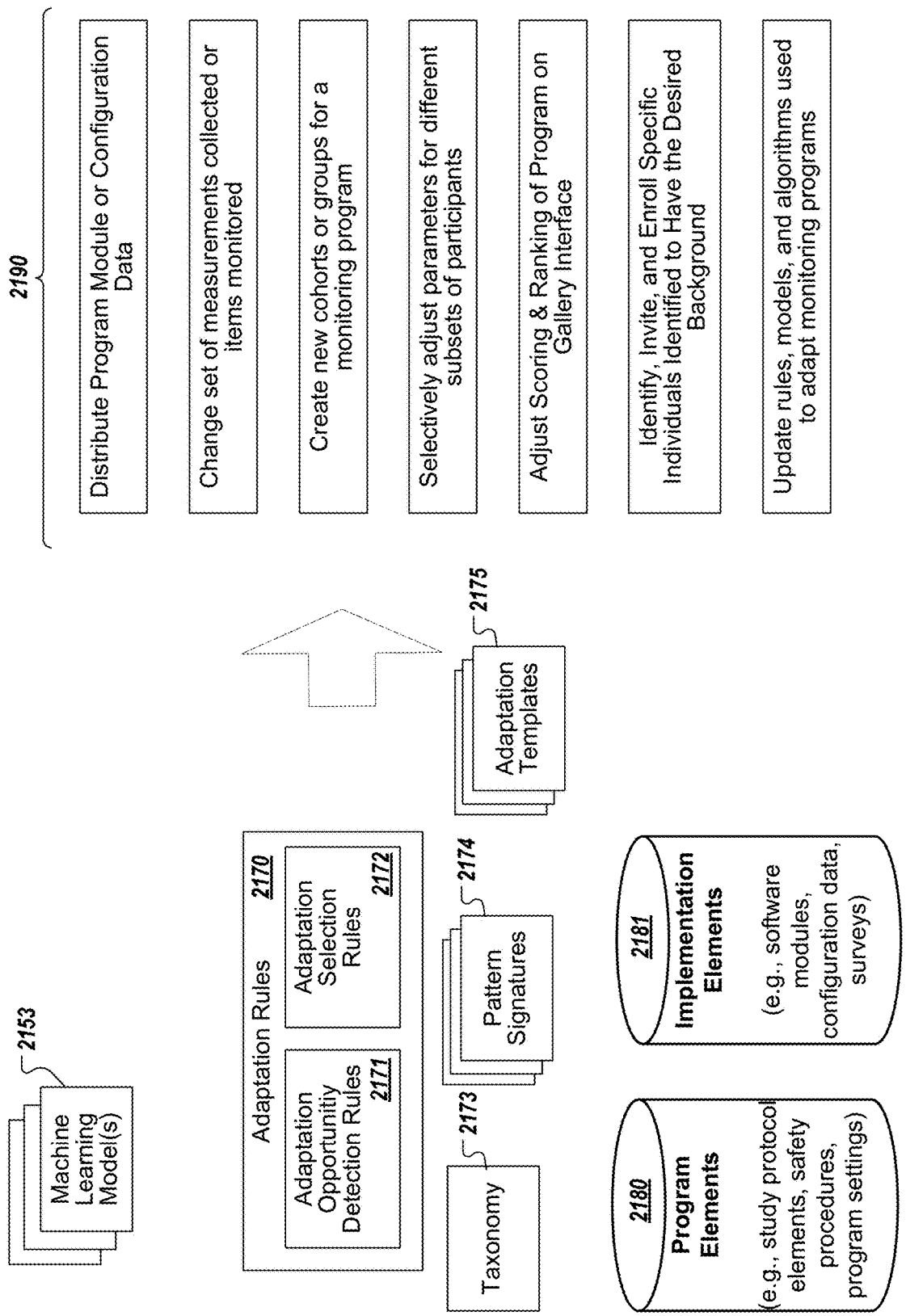
FIG. 21C is a diagram that illustrates further elements of the system that can be used to adapt monitoring programs.

FIG. 21C is a diagram that illustrates further elements of the computer system 210 that can be used to adapt monitoring programs. In particular, the example shows various elements that the computer system 210 can use to (i) detect opportunities to adapt a monitoring program, and (ii) generate or select specific adaptations (e.g., set adapted study parameters) that are appropriate to apply given the current status of the monitoring program. The computer system 210 can use various different approaches, including using scoring algorithms, rule-based approaches, pattern matching, and machine learning to carry out these functions. For all of these approaches, the computer system 210 can use historical data from many different monitoring programs, potentially both monitoring programs that the computer system 210 administered and monitoring programs that it did not administer. The historical data about the effects that different study parameters had, and effects that different adaptations had, can serve as source data for deriving rules and patterns, as well as serve as training data for machine learning models and adjusting algorithms. The example shows various implementation actions 2190 that can be used to carry out adaptations.

The adaptation rules 2170 can be used by the rule engine 2150 to evaluate the condition of a study. Adaptation opportunity detection rules 2171 can indicate conditions that, when present, indicate a significant opportunity to make an adaptation. Adaptation selection rules 2172 can indicate rules or mappings to indicate which types of adaptations, and which parameters or settings, should be used under which conditions. As an example, the detection rules 2171 may respectively specify conditions such as compliance decreasing by more than 5% in a week, diversity falling below a target level, prevalence of a side effect increasing or reaching a threshold level, and so on. The selection rules 2172 can then specify, for each of these conditions, one or more changes or settings to make. For example, when a decrease in compliance is the condition triggering adaptation, the selection rules 2172 may indicate certain steps, such as to change a reminder schedule and implement an alternative type of data collection to use instead of the one that has low compliance.

In some implementations, the computer system 210 identifies patterns or conditions that occur in monitoring programs which represent a need for adaptation, or represent conditions appropriate for specific adaptations. These patterns or conditions can be stored as pattern signatures 2174, and the rules engine 2150 can compare the current characteristics of a monitoring program with the defined pattern signatures 2174. When the characteristics of the monitoring program match or are within a threshold level of similarity to one of the pattern signatures, the computer system 210 can determine that adaptation is warranted, or even that particular adaptation related to the corresponding pattern signature is appropriate.

The computer system 210 may use a taxonomy 2180 that maps data types to categories, devices, software items, or configuration settings, to facilitate implementation of changes. For example, when adaptation to add heart rate measurement is selected, the taxonomy can indicate the software modules, settings, and devices that can provide that measurement. The computer system 210 can also retrieve stored implementation elements 2181 from a repository, where the software modules, configuration data, survey instruments, and other elements are stored and available to be retrieved and applied. A repository of program elements 2180 can also be maintained. These program elements 2180 can be stored for each of various types of adaptations, so that when an adaptation is selected, the corresponding protocol changes, safety procedures, and additional participant consent provisions can be retrieved and applied.

In some implementations, adaptation templates 2175 are provided, each with the basic framework for making a different type of adaptation defined. The template for adding a new type of monitoring can indicate the workflow or operations needed to make the adaptation. The template can be supplemented or completed with the combination of program elements 2180 and implementation elements 2181 specified for the particular type of monitoring (e.g., for resting heart rate detection). With the augmented template, the computer system 210 can carry out the changes and operations to implement the change. The computer system 210 can optionally store a registry or list that enumerates the many different types of adaptations that are possible, with each of these associated with conditions in which these are appropriate.

The computer system 210 can train and store machine learning models 2153 configured to detect when adaptation is present and/or to evaluate the appropriateness of specific adaptations. The machine learning models can be configured to receive input feature vectors having feature values for various different types of information about the monitoring program 2110 (e.g., research area, body systems affected, treatment actions, study objectives, elapsed time in the study, total duration scheduled, etc.), the monitoring group 2112 (e.g., amounts of participants in different categories, status with respect to diversity targets, total number of participants, target number of participants, compliance rates, etc.), and monitoring data 2114 (e.g., types of data monitored; distributions, averages, and clusters present in results for each monitored item; changes with respect to baseline values, etc.). These types of inputs can be used for training and for inference processing (e.g., prediction) after training. The training data can include examples of many different monitoring programs, as well as example data showing the state of each at many different time points during the monitoring programs. The specific examples of different time points or "snapshots" can each be labeled with scores or classifications as training targets, showing the level of appropriateness of adaptation in general, or of specific modifications, for the conditions represented by the example. The machine learning models 2153 can then be trained using the labeled training examples, so that the machine learning models 2153 learn to recognize (and can provide output scores or classifications indicating) when an input feature vector represents the conditions appropriate for adaptation.

For example, a model 2153 can be a neural network trained with an output layer having an output value for each of various different data types (e.g., resting heart rate, peak heart rate, respiration rate, step count, etc.). The output value corresponding to a data type can represent a likelihood (e.g., a score from 0 to 1.0) that a study as characterized by the input feature vector should collect that type of data. When the input for the program 2110 is provided, the model 2153 can indicate scores of 0.7 for resting heart rate, 0.2 for peak heart rate, 0.3 for respiration rate, 0.8 for step count, and so on. This indicates that resting heart rate and step count have a high predicted relevance to the study and the cohort, given the current state of data collection and the cohort characteristics. If these are not yet collected in the monitoring program 2110, the computer system 210 can select these as data types to add as an adaptation in the adapted program 2120. In a similar manner, other machine learning models 2153 can be trained to assess and provide outputs about whether other types of program features or changes are appropriate. For example, outputs of models can assess whether changes to eligibility are appropriate (e.g., general changes to broaden or narrow eligibility or more specific changes such as adding or removing specific criteria), whether addition of a new cohort or treatment arm is appropriate (and potentially also what changes to make in treatment, such as to increase dosage, decrease dosage, etc.), whether to increase study duration or change other study parameters, and so on.

FIG. 22 is a block diagram that illustrates another example of the system managing adaptive monitoring programs. In collecting data for research and clinical trials, systems recruit and enroll participants, as well as collect study participant data. An adaptive system, such as the computer system 210, can determine if eligibility and inclusion criteria should be expanded upon or narrowed based on information collected. Inclusion and exclusion criteria can be set or adjusted as function of diversity of the population and corresponding sampled data, whether the data is self-reported, biological, environmental, of another type. For example, values may be related to participant's mood propensity towards depression, biological genetic markers, or demographics (e.g., a participant's location, race, language, education level, climate, etc.).

The adaptive clinical trial system may either start with eligibility criteria that are broad or narrow, depending on the ability to recruit or tailor cohort characteristics for a particular study. A study that starts with narrow eligibility criteria may be attempting to identify new markers (e.g., biomarkers, digital markers, behavioral patterns, etc.) that will assist with developing a screening tool, e.g., a study to determine the risk-related identifiers associated with a marker. For example, the study start narrow with a cohort of participants in which an outcome or risk is known to be present, and as relationships are identified, the cohort can be expanded using a broader set of eligibility criteria to confirm that the identified relationships are predictive in broader settings (e.g., providing accurate positive indications and accurate negative indications).

A study that starts with narrow eligibility criteria may attempt to prove the sensitivity and specificity of the condition on a population to provide the evidence for a basis for safety and efficacy required for wide-scale adoption, such proving the safety of acetaminophen among a broad age range and set of health conditions. The study may begin with a narrow set of criteria to encompass populations where there is high likelihood or confidence that safety and efficacy are present, and adaptation can gradually or incrementally expand the eligibility in phases to encompass larger and larger portions of the overall population, as long as safety and efficacy continue to be shown as the group is expanded.

In the example of FIG. 22, the computer system 210 can create a variable number of cohorts within a monitoring program 2110. These cohorts may represent different treatment or control groups, different diversity categories, substudies, ancillary studies, or other divisions among the participants associated with the monitoring program 2110. The computer system 210 can dynamically
enable or disable the use of various of the cohorts when an appropriate criteria has been determined to be satisfied by the rules engine 2150. As an example, the data collection performed for one cohort or group can be enabled or ended on-demand.

As an example, the monitoring program 2110 can represent a study to develop a symptom screening tool for COVID-19. The study initially begins by using two cohorts, where (1) Cohort 1 includes participants who within 24 hours have tested positive with a COVID-19 antigen at-home test, and (2) Cohort 2 includes participants who within 24 hours have tested negative with a COVID antigen at-home test.

The assignment of participants to the two cohorts affects the comprehensive workflow for the participant. This includes screening and eligibility determination for recruitment, the registration and electronic consent ("eConsent") in the enrollment, and the survey and device data collection methodology used. The computer system 210 also collect information about the current COVID-19 case numbers and demographics across catchment areas.

In the example, the data collected for Cohort 1 includes participants' self-reported measures of symptoms first experienced and monitors their symptoms over time, detecting the diminishing measures as symptoms dissipate over time. The data collected for Cohort 2 similarly collects self-reported measures. However, it also measures PCR based test results as follow-up confirmation of the validity of the at-home measures. The commonality between Cohort 1 and 2 is that both are tested for other respiratory symptoms related to influenza and influenza-like illnesses (ILI) that can be excluded from the symptom's markers when COVID-19 is misreported as influenza.

Over the course of the monitoring program, as monitoring of symptoms is ongoing, the computer system 210 identifies a growing trend in the impact of the COVID-19 virus infecting Hispanic and Latino populations, especially in multi-generational households. Based on the rules applied by the rules engine 2150, when a trend of sufficient prevalence or magnitude is identified, the computer system 210 automatically enables a new cohort targeted to the population characteristics that are involved in the detected trend. As a result, the computer system 210 creates and enables a new cohort, Cohort 3, which includes participants who within 24 hours have tested positive with a COVID antigen at-home test and are also Hispanic or Latino and are living in a multi-generational household.

Although the rules engine 2150 did not have any specific rules in advance about Hispanic or Latino individuals or multi-generational households, the rules can nevertheless be used to detect when a trend reaches a magnitude or significance. For example, the original study definition did not specify that Hispanic or Latino participants should be evaluated separately, or that multi-generational households would represent a variable for adaptation. Nevertheless, the characteristics of the trend that emerged, e.g., the specific health factors or demographic factors involved in the trend, are derived from the monitoring data of the study itself. The adaptation action also, e.g., creating and enabling a new cohort within the monitoring program 2110, can be based on a template for this adaptation action, with the specific values or parameters (e.g., the specific participant attributes to target) inserted to carry out the adaptation. The computer system 210, by including general rules for detecting trends and conditions for adaptation and a library of templates or elements to use to perform adaptation, can respond and select adaptations for conditions and occurrences that are not predictable in advance and which are not identified as possible adaptations in the original monitoring program 2110.

In the example, the rules engine 2150 is shown having a set of adaptation rules 2170 and adaptation templates 2175. As discussed above, the adaptation rules 2170 can specify the conditions, triggers, thresholds, and other parameters that the rules engine 2150 checks to determine if there is sufficient reason for an adaptation. The adaptation templates 2175 can provide a base set of elements for making various types of adaptations (e.g., adding a cohort, adding an eligibility criterion, adding a new type of data collection, etc.), with the specific details (e.g., which characteristics for the new cohort, which values specify the new eligibility criterion, which of various types of data in a taxonomy to begin collection for, etc.), able to be defined later and incorporated in the appropriate template to implement an adaptation.

The computer system 210 sponsors Cohort 3 through the recruitment by identifying a select category for enrollment based on specified demographics. In some implementations, the computer system 210 may also disable additional recruitment for Cohort 1 (e.g., which has generalized, all-encompassing demographics), at least temporarily, to focus recruitment on the population most affected. With the computer system 210 now focused on a narrow recruitment, the identification of a statistical model is automatically presented and reported to the researchers. The computer system 210 can report the improved sensitivity and specificity to the identification with a specified population group.

As another example, the framework of FIG. 22 can be used to represent management and adaptation of a study for developing a treatment for cancer. The first example regarding COVID-19 symptoms (e.g., to identify the relationship of COVID-19 effects to specific demographics). In the cancer example, a specific cancer might be assessed by targeting a population having a specific hereditary measure. In order to localize the gene attribute and rate of occurrence in a specific population, the research study begins with a specific age range as well as a particular race or ethnicity. In this case, Cohort 1 may represent participants of a particular race, and initially the study may be limited to participants of that particular race, based on initial findings or prior research suggesting that the particular type of cancer is most prevalent among individuals of that particular race.

While analyzing the monitoring data, the computer system 210 detects a correlating statistical relevance of the cancer to 3 or 4 attributes that are common across Cohort 1. In correlating these attributes to a database of genetic or genomic information (e.g., a single-nucleotide polymorphism (SNP) database), the gene attributes are identified as common attributes that have relevance to other races. This signals broader applicability of the study beyond members of the particular race used to populate Cohort 1. In response, the computer system 210 can determine to adapt the study by creating or enabling one or more additional cohorts to gather information about other races in which the relevant genetic characteristics are present.

The computer system 210 can enable a second cohort, Cohort 2, to include participants of other race who with a strong hereditary history of the particular type of cancer being studied. Cohort 1 is left enabled, in order to added further statistical evidence. Cohort 2 is enabled as well to identify other potential overlapping gene attributes or environmental situations that may be affecting the broader population. With the study now broadened, the researchers will more likely be able to locate the remaining gene attribute(s) that can be targeted with gene therapy or gene replacement to potentially treat the risk of cancer in future generations.

In some implementations, a system is configured to create and administer monitoring programs that involve collection of data from remote devices over time. The monitoring programs can have different objectives and use different data collection techniques. For example, the system can provide a platform, such as a cloud-computing platform with a multi-tenant architecture, through which many different organizations can run separate monitoring programs that collect different types of data from different sets of remote devices. The system can enable an administrator to create a monitoring program to achieve a monitoring objective, where the administrator can specify parameters of the monitoring program such as types of data to collect from remote devices, frequency of data collection, the types of devices or specific sets of devices to be monitored, and so on.

One of the many features of the system is the ability to detect opportunities to adapt an ongoing monitoring program (e.g., a clinical trial, an adaptive clinical trial, a decentralized clinical trial, or other health research study). This can include initiating additional monitoring that can further the objectives of existing monitoring program. To make the monitoring efficient and effective, the system can extend or build onto existing monitoring programs. For example, where an ongoing monitoring program is configured to collect data from a set of one hundred devices and their users, the system can identify potential opportunities to extend monitoring with additional monitoring.

Beyond identifying the opportunities for adapting monitoring programs, the system can evaluate the viability or suitability of adaptations, e.g., evaluating or predicting the effectiveness and results that would be achieved if adaptations were to be conducted. For example, the system can assess the importance or significance of adaptation opportunities, filtering out opportunities that would not add sufficiently different data from the original monitoring study or those that do not have sufficient relevance to the objectives of the original monitoring program. The system can also use predictive models and other analysis to determine predicted rates that new candidates for the adapted monitoring program would enroll, be retained, comply with requirements of the adapted monitoring program, provide data of the needed data quality, and so on. These predictions allow the system to assess whether adapting the monitoring program would be appropriate and beneficial if initiated. This analysis allows the system to initiate or recommend new monitoring program adaptations conditionally, based on the likelihood that the adaptation enhance key measures needed for success (e.g., minimum number of retained participants, minimum level of statistical power, etc.). The system can use the predictions to selectively recommend or initiate adaptations to monitoring programs, doing so only when the prediction provides at least a minimum likelihood that the size, composition, and behavior of the altered monitoring group (e.g., cohort of devices and/or participants) will result in greater likelihood of completion of the objectives of the monitoring program.

The system's ability to evaluate monitoring programs and conditionally initiate or recommend adaptations is important to achieving high efficiency. Many monitoring programs, including clinical trials and other research studies, begin and ultimately fail to achieve the scope and quality of monitoring needed due to participants failing to remain in the programs, participants failing to comply with program requirements, the participants in a cohort lacking an appropriate level of diversity, and other factors. When these monitoring programs fail, the computational resources of the client devices, servers, and networks involved are all effectively wasted, and many times the programs need to be re-designed and re-run. However, the techniques described herein can use predictive modeling to consider many factors that cause monitoring programs to fail and assess their impact on the eventual results of particular, individual monitoring program adaptation opportunities. The system can provide predictions that are highly accurate, customized for the specific requirements of a monitoring program and the specific set of candidates or participants available. This enables the system to automatically generate and carry out monitoring program adaptations predicted to have high likelihoods of success, while filtering out and not conducting adaptations that are less likely to improve the likelihood of success of the monitoring program.

The system can use the same techniques and predictions in other ways besides evaluating adaptation opportunities that the system discovers. The system can assess adaptations that users request or initiate, prior to carrying out those changes. For example, the system can provide alerts, notifications, scores, and other data indicating the predicted likelihood of success of an adaptation being designed, for the study overall and/or for specific factors (e.g., statistical power, diversity among participants, retention, compliance, data quality, etc.). The same techniques can be used to assess and provide information about ongoing monitoring programs, e.g., to alert researchers of risks to success of a monitoring program over time as the monitoring programs progress and as data from participants is collected.

The systems and techniques discussed herein enable a system to manage a monitoring program and automatically adapt the monitoring program to efficiently leverage the infrastructure and arrangements of the original monitoring program. This can enable the system to carry out the objective of an original monitoring program and achieve further objectives with high efficiency. During the monitoring program, the system monitors the data collected and the overall progress of monitoring (e.g., retention of participants, compliance with program requirements, data quality, health outcomes of participants, etc.). The system detects conditions that indicate potential for adaptation, e.g., further monitoring or a change to the composition or characteristics of the cohort. When the system identifies one of various conditions that signals opportunity for adaptation (e.g., a monitored outcome of significant frequency or significance, and a change in the group of participants monitored or type of monitoring would be needed to test the factors related to that outcome), the system can design and carry out an adaptation to the monitoring program. In many cases, this allows the system to automatically focus monitoring to examine the relationships discovered over time between outcomes and specific contexts, participant attributes, environmental factors, and so on. This adaptation enables monitoring programs to capture data have been measured or identify outcomes would not have occurred in the course of the original monitoring program without adaptation.

This can provide much greater efficiency than an entirely new program for several reasons. One is that the system can take advantage of the existing set of configured client devices (e.g., user devices such as smart phones) used in the original monitoring program, as well as the set of users of those devices who are already enrolled. The level of compliance of these individuals with requirements of the original monitoring program, and the data quality levels achieved, is known from their participation in the original monitoring program. This provides high confidence about the compliance and retention for the adapted monitoring program, increasing the likelihood that the adapted monitoring program will be successful and thus be an effective use of computing resources. This efficiency is very likely to be achieved especially because many follow-on monitoring programs represent incremental additions to the requirements of the original monitoring program, such as addition of new data to be collected to an existing research study protocol, and so the compliance level for the majority of requirements of the new study is likely to stay consistently at or near the level observed in the original monitoring program.

In some cases, the original monitoring program from which data is used to identify further monitoring opportunities is a principal research study. The principal research study can be a clinical trial or other research study that involves remote monitoring of a group of devices and users (e.g., using sensors, surveys, devices, and other data collection techniques). The adaptation to the monitoring program can involve creation of a sub-study, ancillary study, follow-on study, or other extension of the original research study or principal research study. A sub-study can refer to an add-on study to the main protocol of the original research study, which can be designed to ask a separate research question or address different circumstances or conditions than the original study. The sub-study can include new data collection from some or all of the trial participants participating in the main protocol. The sub-study often involves a subgroup or sub-population of the participants in the principal trial, and it may involve additional types of measurements or types of data collection and/or data collection under circumstances or procedures that different from those of the original research study. As discussed below, the systems and techniques discussed herein can be used to automatically detect the opportunity for a sub-study or other adaptation, generate the parameters for a adaptation including selecting the types of data collection to perform and the set of participants to involve, and initiate the monitoring needed for the adaptation, whether automatically or in response to a researcher's confirmation or input about a recommendation for a adaptation.

To adapt a monitoring program, the system can start with the original monitoring program's parameters (e.g., types of data to collect, the devices and software used by participants, actions performed by participants, duration of monitoring, etc.) and adjust the parameters as needed to measure the specific factors related to the outcomes or conditions that prompted the adaptation. The system then can alter the parameters to better address the specific factors or outcomes that prompted the adaptation. For example, the changes can include adding additional types of data to collect, changing the data quality level for data collected (e.g., accuracy, precision, etc.), changing the frequency of data collection, changing the devices or software used to perform the data collection, changing activities of participants (e.g., change a medication used, change a medication dosage, change behavior factors such as sleep, exercise, diet, etc.), and so on.

The system can also update or alter the monitoring group as part of an adaptation. The group of monitored devices and/or their associated users are referred to as the monitoring group for a monitoring program. The system can leverage the monitoring group for an existing or original monitoring program, as well as expand it by adding participants or even new cohorts. This can occur in several ways, including selecting a subset of the original monitoring group (e.g., fewer than all of the members of the original monitoring group) that are selected for having characteristics that are suited for evaluating a factor that prompted the adaptation. For example, if the original monitoring program monitors diet and exercise, and a particular health outcome is identified in some participants (e.g., fatigue reported), then participants reporting that health outcome or others with similar attributes can be selected for further monitoring (or at least can be selected as candidates eligible for the new monitoring program, to whom the system can send invitations to enroll in the new monitoring program).

As a research study is ongoing, the system can analyze and assess the potential for a variety of adaptations, which would test different outcomes, conditions, or patterns from the data collected for the research study. As an example, a principal research study may indicate sleep characteristics of 1000 people, showing a distribution of outcomes including the rate and severity of sleep disorders over a period of time. The study can include answers to survey questions and collection of sensor data, and the collected data is received and processed by the system. From the data collected for the principal study, the system determines that 100 participants report a sleep disorder. The system can detect this through analysis of collected data even if the purpose of the principal study is not to study sleep as the main objective. For example, the study may be a clinical trial for a pharmaceutical, and the sleep disorder may be a patient-reported side effect. The system can identify that the reported occurrence of the sleep disorder meets criteria for significance, e.g., at least a one of a minimum amount of participants are affected, a minimum duration that the effect continues, a minimum severity of the effect, minimum reliability of collected data, and so on, and potentially combinations of these and other factors. When the appropriate criteria are met, the system determines that this presents the opportunity for adapting the principal study to investigate this sleep disorder and the factors that contribute to it, especially as they relate to the conditions of the principal study (e.g., to the use of a pharmaceutical by the participants or to another therapy or behavior tested in the principal study). The system can assess related factors potentially contributing to the sleep disorder (e.g., age, exercise, diet, etc.), based on analysis of the collected data for the principal research study, other research studies (which may show factors identified in other groups of participants), and other data sources (e.g., database of clinically relevant factors, electronic medical records, etc.). The system then defines the characteristics of the adapted study, including both the protocol to be used (e.g., data to be collected, manner of collecting data, activities of participants, etc.) and the cohort to be used (e.g., the cohort of the principal study and potentially other individuals added). At least some of the parameters or characteristics for the adapted study can be selected to test the factors identified as potentially relevant to the sleep disorder.

The systems discussed herein can use information collected in one or more monitoring programs (e.g., ongoing or completed) to efficiently and effectively adapt monitoring programs and corresponding groups of devices to be monitored. The opportunity for adapting monitoring programs and the characteristics of those programs can be determined from the patterns of data collected in earlier programs. For adapted monitoring programs, the monitored groups of remote devices can be, or can at least include, proper subsets of the monitored groups of other monitoring programs. For example, if at least a minimum number of monitored devices provide data that shows a certain outcome, the system can use this to trigger an adaptation of the monitoring program focused on evaluating that outcome and factors that may contribute to it. The devices in the original monitoring group can be retained, and others can be added that may have similar characteristics or context to those that experienced the outcome, in order to better explore the outcome, e.g., frequency, likelihood, intensity or severity, etc. of the outcome under a set of conditions.

The system can also dynamically detect opportunities for adapting monitoring programs and monitoring groups. For example, the system can analyze data that is collected as part of a monitoring program and determine when certain conditions occur. These conditions may be a pattern or similarity in data collected for a subset of the devices in a monitoring group of a monitoring program. To identify when potential for new monitoring programs arises, the system can analyze the incoming data received from devices involved in a monitoring program on an ongoing or repeated basis. The system can then determine when the data sets for different devices show a pattern or commonality or meet other criteria, which may be predetermined or dynamically determined. The system can then analyze various factors to determine whether adaptation of the monitoring program is warranted, such as the relevance or importance of the outcome detected to the objective of the study, the number of times the outcome is observed (e.g., number of participants or devices showing the outcome, or how frequently the outcome occurs), predicted effects on the viability of the monitoring program if the adaptation if performed, and other factors.

Figure 23A:
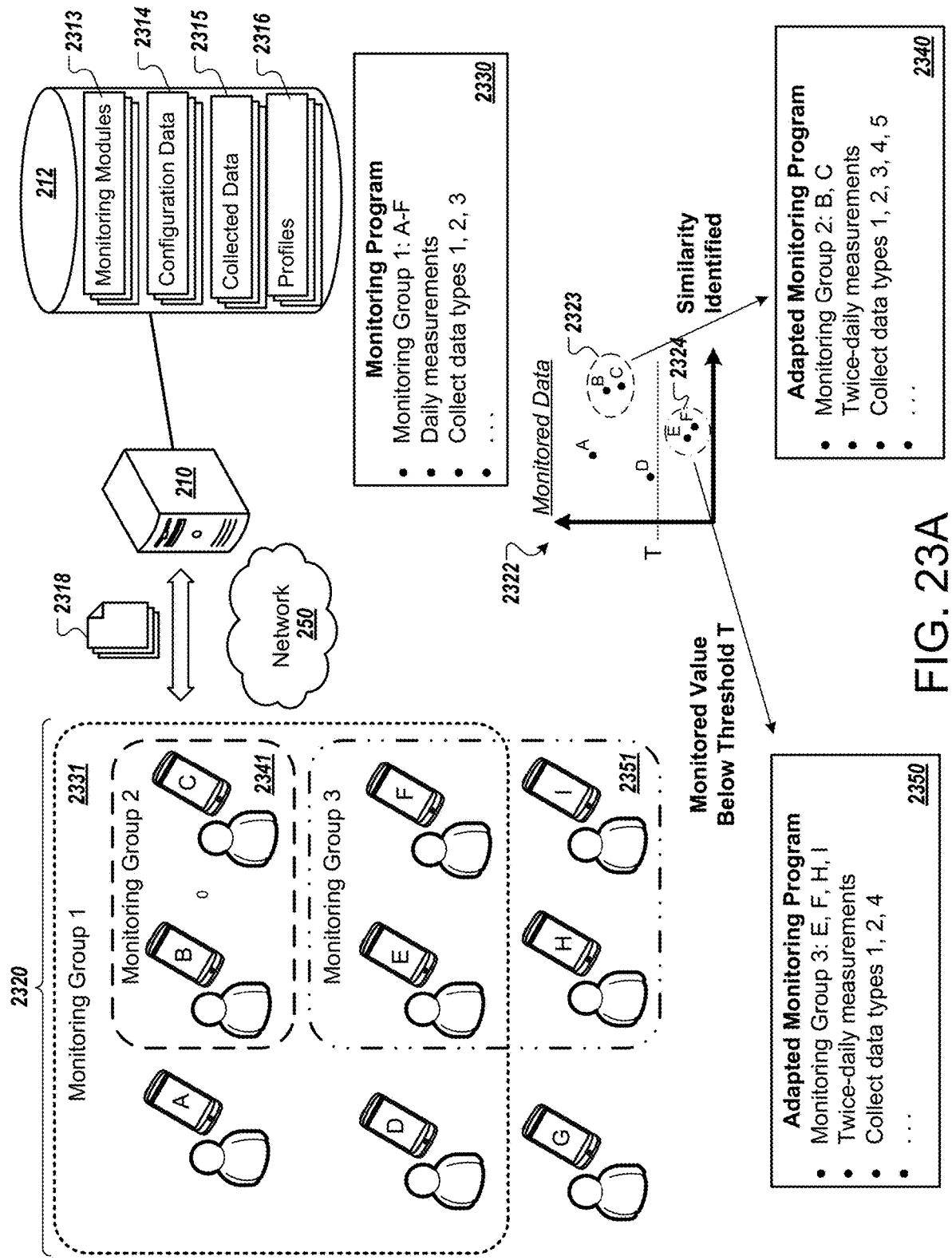
FIG. 23A is a diagram showing an example of a system for creating and carrying out monitoring programs involving remote devices, including adapting those monitoring programs.

FIG. 23A is a diagram showing an example of a system 100 for managing and adapting monitoring programs involving remote devices. The system 100 includes a computer system 210, which can be implemented using a server, a collection of servers, a cloud-computing platform, or other computing resources. The computer system 210 manages monitoring programs that involve different sets of data collection procedures and different monitoring groups (e.g., sets of devices and/or users from which to collect data).

The computer system 210 can provide many different functions, including monitoring and research using adaptive monitoring groups, such as adaptive cohorts that the computer system 210 can adaptively expand, contract, split, combine, or otherwise adjust in response to monitored outcomes. The computer system 210 can provide features to enable the automatic, conditional adaptations of a primary study. For example, the computer system 210 can automatically detect conditions and data patterns that indicate the opportunity for a useful adaptation as well as define and implement the adaptation. The computer system 210 includes capability for predictive modeling, including evaluation of the value of additional information that a potential adaptation would provide and the likelihood that a potential adaptation can increase the likelihood of desirable results (e.g., improved retention, compliance, data gathering completeness, data quality, etc.). The computer system 210 can be used for automatic creation, measurement, and adaptation of research studies and their corresponding cohorts, as well as generation and distribution of software modules, configuration data, and other content so that remote devices perform the needed monitoring.

One of the major benefits of the computer system 210 is the ability to identify, from an existing monitoring program (e.g., research study) and monitoring group (e.g., cohort of participants), additional research questions that can allow a researcher to adapt and improve a research study. This can include analyzing the data collected as part of a monitoring program, including monitoring the stream of incoming data as the monitoring program is ongoing, to detect events and conditions that merit further analysis. There are many types of events and conditions that the computer system 210 detect to consider an adaptation to a research study. One may be a detected commonality among multiple participants in the monitoring group, e.g., a behavior or outcome seen for multiple members of a monitoring group, a pattern or progression observed among some participants, a clustering of participants based on measured properties, and so on. Another may be based on measured properties or outcomes, e.g., identifying results that are outliers or anomalies relative to other participants, identifying results that are in certain ranges or classifications, identifying results that are positive (e.g., managing a disease effectively, a medication achieving its desired effect, improved health, etc.), identifying results that are negative (e.g., failure to effectively manage a disease, a serious side effect of a medication, decreased health, etc.), and so on. Another may be based on levels of compliance of participants with requirements of the monitoring program, e.g., a subset with high compliance that are expected to provide high-quality data for further monitoring, a subset with low compliance that may need different monitoring parameters or supplemental members in the cohort to be monitored effectively, etc. The detection of an opportunity for adapting a monitoring program may be based on identifying at least a minimum number of participants of an existing study that exhibit a certain outcome, characteristic, or pattern. This can indicate both the significance of the detected item (e.g., multiple occurrences show that it is not a random or unrelated occurrence) and the viability of achieving good results to study the topic or issue prompting the adaptation (e.g., there is a sufficient group of candidates to explore the detected item and the circumstances in which it arose). When evaluating the collected data, the computer system 210 can monitor the data with respect to objective references (e.g., predetermined thresholds, predetermined classifications, normal or expected ranges, etc.) or relative references (e.g., averages, distributions, clusters based on data collected for a primary study, which may vary as data continues to be collected during the study).

The ability of the computer system 210 to identify and carry out adaptations helps researchers quickly and efficiently expand and extend their research. The computer system 210 can use an existing study and cohort as a starting point, then generates adaptations to add capability to monitor on specific factors or outcomes that the computer system 210 detects as significant based on collected data for the original study. This provides a high efficiency for monitoring, because the system can focus monitoring on specific types of participants and specific factors or outcomes, allowing new monitoring objectives with relatively small groups of participants. The computer system 210 also provides a high likelihood of success and low risk because the adapted monitoring programs involve participants whose level of compliance with requirements is known and can be expected to continue similar rates. Similarly, the adapted research study often builds on the previous data collection activities, so the participants are often already accustomed to providing much of the data needed for the adapted research study—the adaptation can be an incremental change that many participants may not even notice. The adapted study can thus provide an opportunity to acquire valuable additional data, under conditions that the computer system 210 can predict with confidence will result in high compliance and high data quality, with small or even minimal changes to the configurations of the devices used in the monitoring.

Researchers commonly focus on the total recruitment number as a primary metric of success with their research project. However, with any research study that requires stratification of research (e.g., sub-studies or sub-cohorts), it is necessary to understand the composition of the cohort as well as the raw size of the cohort. To this end, the computer system 210 can increase efficiency by proactively identifying areas of risk and opportunity to the researcher, potentially even in real time or near real time by monitoring incoming data streams from participants, and then provide the information via an online dashboard or other end user interface. The added advantage that the computer system 210 provides with this research design tool allows for ongoing assessment and adaptation of monitoring programs. For example, the computer system 210 can provide a researcher metrics, predictions, and recommendations for iterative course corrections for study parameters, participant selection criteria, and so on during a participant accrual process (e.g., when recruitment of participants occurs), which can make better use of limited resources and obtain a cohort more quickly. The computer system 210 can not only optimize opportunities to make adaptations to a study but also optimizes the investment of resources over time, with the computer system 210 recommending adaptations that may direct or "branch off" certain types of monitoring in directions of highest value and highest likelihood of success, while warning of risks to success in the main study overall. The computer system 210 can run analysis to avoid adaptations that are unhelpful to a research objective, duplicative, or not sufficiently likely to improve outcomes for the study.

The computer system 210 can be used to create adapted criteria and parameters for a monitoring program. For example, the computer system 210 can assist a researcher to administer a study with a first set of participants. The computer system 210 can determine an area to focus or adjust the first study, such as to add tracking of sleep. The determination can be made based on the system's analysis of data collected in the study or in response to a user input indicating that additional sleep tracking is desired, or that an adaptation in general is desired. The computer system 210 can create the new parameters and program elements that would adapt the study to add sleep tracking, with the computer system 210 defining parameters for participant actions and data collection (e.g., an adapted study protocol).

The computer system 210 can distribute changes that adapt a study some or all of participants of an existing cohort, while also considering additional cohorts or a new cohort based on identified criteria, interest, and viability. As part of this process, the computer system 210 can generate and send software and configuration data to devices of individuals selected for the cohort. The software and/or configuration data can cause the receiving devices to initiate measurements or other data collection, e.g., presenting surveys, performing passive sensing (e.g., using sensors such as accelerometers, GPS sensors, light sensors, etc.), performing active sensing, providing instructions for a user to make a measurement, communicating with other devices (e.g., a watch or other wearable, a weight scale, a glucometer, a blood pressure cuff, etc.). To generate the correct set of configuration data or software, the computer system 210 can store, in a database or other storage, software elements or configuration settings corresponding to each of the different measurements for which that the computer system 210 supports collection. The computer system 210 then accesses the parameters for a sub-study, including the types of data to collect and the frequency, timing, accuracy, and other settings for the measurements. The computer system 210 then retrieves, for each of the measurements or data types to be collected, the corresponding settings or software elements that instruct the needed measurement and data collection. The computer system 210 aggregates the settings or software selected for performing the needed data collection into a data package that the computer system 210 then distributes to the devices of participants in the cohort for the sub-study. The receiving devices save and install the data package, carrying out the instructions and settings indicated to perform the data collection needed. In some implementations, the data package can be based on, or operate together with, the software or configuration data for the original study.

The computer system 210 then collects data from participants in the adapted study, receiving responses to surveys, measurements from sensors, results of interactions with the user's devices, EMR/EHR, and other data. The computer system 210 measures the performance and value of the adaptation, both to participants and researchers. For example, on an ongoing basis, the computer system 210 can determine whether an adapted study is collecting data with a trend or pattern that is likely to result in successfully completion (e.g., complying with sub-study protocol requirements for user behavior and data collection, as well as providing appropriate data quality, through the end of a period of time set for conducting the sub-study). If the pattern indicates a low or decreasing likelihood of successfully completion, the computer system 210 can notify the researcher and indicate areas where compliance or data quality is low or trending downward. The computer system 210 can also evaluate and select further adaptations predicted to improve characteristics of the study.

The computer system 210 can use examples of previous studies and adaptations to those studies to learn which research topics, data collected, and study parameters are most valuable. The computer system 210 can select or adapt study parameters based on criteria defined by researchers. For example, the system can predict the needs of a researcher based on characteristics of a previous study or study adaptation, either for that researcher or for other researchers. For example, the computer system 210 may use information about the parameters of studies (e.g., duration, cohort size, levels of participant diversity, etc.) and any elements of study protocols to determine which elements or ranges of parameters are most popular. Similarly, the computer system 210 can determine which data types and data collection methods are preferred, from the frequency with which they are selected or entered by researchers. The computer system 210 can make the determinations topic-dependent or context-dependent by analyzing the frequency or popularity of different elements based on the topic or context, e.g., identifying different study characteristics and data types are most applicable for different types of study objectives (e.g., investigating safety vs investigating efficacy vs investigating dose response), for different diseases (e.g., diabetes, lung cancer, heart disease, etc.), for different body systems or areas of medicine (e.g., neurology, cardiology, etc.), and so on. As a result, by comparing the characteristics of a study (e.g., study objectives, parameters, topics studied, etc.) with characteristics of other studies, the computer system 210 can identify which adaptions have been made for the other studies, and the conditions in which those adaptations took place, and then recommend similar sub-studies when similar conditions arise. For example, during data collection for a principal study investigating a drug for heart disease, the computer system 210 may determine that other studies for heart disease drugs often implemented adaptations involving lower-dose treatment groups and also included adaptations that combined the drug with certain dietary modifications. Based on these records of prior adaptations that were made, the computer system 210 can recommend an adaptation for a lower-dose administration of the drug, at least among one subgroup or new cohort, and an adaptation that involves dietary modifications.

The computer system 210 can also learn iteratively from researchers' responses to the sub-study recommendations that the computer system 210 itself provides. For example, the computer system 210 may identify and recommend three adaptation opportunities to investigate incidents of low blood pressure, sleep disturbance, and weight gain that the computer system 210 detected in participants of a principal study. Although each of these may have passed the system's 110 thresholds for importance and viability, the researcher my respond by electing only to adapt the study to investigate low blood pressure, as it has the greatest impact on safety. Based on the user selecting one adaptation and declining the others, the computer system 210 can prioritize low blood pressure as a higher-priority topic for adaptation than sleep disturbance and weight gain, and can adjust the weightings or importance scores for potential studies involving these factors accordingly. Over many different interactions, with feedback about many different adaptation recommendations by the computer system 210, the computer system 210 can incremental learn or infer which topics—as well as objectives, study protocol elements, and other parameters—are considered to be of highest importance or value, leading to more focused ranking and filtering of new adaptations before they are recommended or implemented. As with other factors assessed by the computer system 210, the scoring and selection can be dependent on context, e.g., learning how the types of adaptations needed from Phase I clinical trials differ from types of adaptations needed for Phase II clinical trials, or how the types of adaptations important for pharmaceutical studies may be different from those that are important for medical device studies, digital therapeutics studies, behavior change studies, and others.

Referring still to FIG. 23A, the computer system 210 is shown carrying out a monitoring program 2330 (e.g., an adaptive clinical trial, a decentralized clinical trial, or other research study) that involves ongoing, repeated data collection from a monitoring group 2331. As data is received over the course of the monitoring program 2330, the computer system 210 analyzes the collected data and determines when events or conditions occur that give rise for adaptation of the monitoring program 2330. In particular, the computer system 210 determines when outcomes, clusters of measured data, patterns in the data, or other signals indicate that there are additional contexts, outcomes, factors, or relationships that can be more effectively assessed through additional monitoring or which may need to be assessed to achieve a desired objective of monitoring. From this analysis, the computer system 210 creates one or more adaptations to the monitoring program, which may involve changing the monitoring group of individuals and devices to be monitored. In example of FIG. 1A, the computer system 210 identifies two new adaptation opportunities. These can be implemented as sub-studies or extensions of the monitoring program 2330. These adaptations 2340, 2350 that have monitoring groups 2341, 2351, which can be derived at least in part from the original monitoring group 2331 for the original monitoring program 2330.

The computer system 210 creates, manages, and administers monitoring programs. The computer system 210 does this on behalf of one or more administrators or organizations that use the monitoring platform that the computer system 210 provides. In some implementations, the computer system 210 is implemented as a cloud computing service, for example, software as a service (SaaS) or platform as a service (PaaS). The computer system 210 can be a tool to assist in adapting studies for researchers, including the automatic conditional creation of epidemiological sub-studies.

The computer system 210 can be used to conduct monitoring in various different fields. Examples include network intrusion detection, quality of service monitoring, telecommunications monitoring, reliability monitoring, power and usage monitoring, scientific research, health research, manufacturing process control, and so on. In many of these fields, there are more devices or endpoints in the system then can be reasonably monitored. Further, monitoring all devices in a large system can unnecessarily consume network bandwidth, battery power, local computing resources, and other limited resources in the system. As a result, monitoring is often most effective when it is done for a sampling of devices or individuals out of the overall population. In addition to providing enhanced efficiency of monitoring, this also gives the opportunity to target the monitoring to the specific subjects for which monitoring is most valuable, e.g., subjects having the greatest risk or need, or those in situations where the collected data will be most useful in determining relationships or meeting a monitoring objective.

The computer system 210 has an associated data storage in the database 212 that includes many different types of data used by the system. The computer system 210 includes monitoring modules 2313 for the various monitoring programs that the computer system 210 manages. These modules can include software and other content that the computer system 210 distributes over the network 250 to devices involved in the monitoring program, so that the devices are configured to perform the needed monitoring actions. In some cases, the monitoring modules 2313 supplement or configure an application that has already been installed on the devices to be monitored. The platform allows a single base application to be installed on the remote devices to be monitored, and then monitoring modules 2313, configuration data 2314, or other content specific to the monitoring program can be provided over the network 250. The computer system 210 can generate monitoring modules 2313 and configuration data 2314 for each monitoring program that it creates and managers. For example, the monitoring program 2330 can have an associated set of configuration data 2314 and the monitoring module 2313 that, when received by and installed at a remote device, enable the remote device to participate in the modeling program. The remote device is configured to collect the types of data needed for the monitoring program 2330, using the timing and techniques specified for that monitoring program 2330, as well as report collected data to the computer system 210 over the network 250. The monitoring module 2313 configuration data 2314 and reported data back to the computer system 210 can be associated with an identifier for the monitoring program 2330 allowing data sets for many different remote devices to be associated with the correct monitoring program. The monitoring module 2313 and configuration data 2314 can also specify, for example, which servers or network addresses to send data to and receive instructions from. They can configure a remote device to receive ongoing communications that may adjust how the remote device collects data from its sensors, from other devices connected to the device, from user input (e.g., by presenting prompts, surveys, interactive user interfaces, notifications, and other elements), and so on.

The database 212 includes the collected data 2315 that is received over the course of administering monitoring programs. The computer system 210 obtains data from many remote devices which may be involved in different monitoring programs. The computer system 210 maintains separate data sets for the different monitoring programs of different organizations or users of the computer system 210. The computer system 210 compiles this information over time as additional data is received during monitoring. For example, monitored devices can send messages 2318 that include monitoring results. These results may include regular, periodic information, schedule transfers, or asynchronous, submissions sent in response to user input at the remote devices or detection by the remote devices of and event or condition. for example, the monitoring modules and configuration data for a monitoring program may instruct a device to send a message 2318 with user input or sensor data in response to detecting the value of a measurement satisfies certain criteria, if a number of interactions is detected, if an amount of data to be gathered exceeds a minimum level, and so on.

The data storage 2312 also includes profiles 2316 of subjects involved in monitoring or who are candidates for monitoring. The computer system 210 can store profile information for many different candidates which could be the subjects of monitoring. This includes attributes of the subject, history, behavior data, and more. For example, the profile may indicate information such as location, device type, device model, device identifier, device capabilities (processing power, memory, battery life, typical load levels or usage levels, and so on), context, application or use of the device, owner of the device, and so on. For an individual, the profile can indicate various types of information such as demographics information, user preferences, historical compliance with previous monitoring programs, retention in prior monitoring programs, and more. To facilitate health research, the profile can indicate medical history, EMR/EHR, physiological attributes (height, weight, health conditions present, blood pressure, etc.), family medical history, and so on. Subjects can be enrolled in a database of the computer system 210 as potential candidates for monitoring, and the computer system 210 can use the profiles 116 to select monitoring groups for monitoring programs. Based on the profiles 2316, this computer system 210 can identify the groups of subjects that best meet the needs of a given monitoring program, for example, which meet the selection criteria that a user of the system or the computer system 210 itself sets for a monitoring program. As subjects participate in monitoring programs, the computer system 210 updates the profiles 2316 for the subjects based on the patterns of behavior of the subjects and the content of the data collected.

In FIG. 23A, a large group of candidates 2320 is represented. These represent geographically distributed devices and their users who are candidates for various types of monitoring. In FIG. 23A, a large group of candidates 2320 is represented. These represent geographically distributed devices and their users that are candidates for various types of monitoring. Profiles 2316 for these devices and/or users are stored in the database 212.

In the example of FIG. 12A, and administrator or researcher has set up a first monitoring program 2330 which includes a monitoring group 2331 that includes devices A through F and their corresponding users. The monitoring group 2331 has been selected to meet certain criteria, such as certain location, attributes, patterns, health status, and so on. The monitoring program 2330 also specifies measurement of certain types of data, as well as the manner of collecting it (e.g., time of day, frequency, precision needed, sensors to use, surveys to provide, and so on). The devices A through F have each received the appropriate monitoring module 2313 and/or set of configuration data 2314 that was generated for the monitoring program 2330, and so each of the devices a through F is configured to collect the data needed for the monitoring program 2330.

As the computer system 210 receives messages 2318 with additional monitoring data from the devices A through F, the computer system 210 compiles it into the collected data 2315 for the monitoring program 130. The computer system 210 analyzes the collected data 2315, as a whole or in part, to detect conditions that may indicate that an additional monitoring program is needed or is useful. The computer system 210 has several techniques that it can use to do this. For example, the data defining the program 2330 may set certain thresholds or ranges of acceptable or desirable measurements, and data received outside these criteria may signal that additional information may be needed through further monitoring.

As another example, the reference data may be dynamically determined based on the data collected for the monitoring group 2331 as a whole, such as an average, a distribution, or another measure of data for the subjects in the monitoring group. In other words, the data for individual members of the group 2331 may be compared with aggregations of data of other members of the group 2331. This way, each individual's results can be compared relative to the aggregate of the group, so that the reference data is represents average or typical data for the group rather than absolute levels or values. Similarly, reference data can be derived from information about a larger group, such as a population as a whole from which the monitoring group 2331 was selected, from aggregate data for one or more other monitoring programs, and so on. The computer system 210 may also look for patterns or progressions in the data in addition to or instead of specific measurements or outcomes. For example, the monitoring program may show a pattern of decreasing health for some members of the group 2331, or lack of improvement for certain members of the group 2331 compared to the rest of the group 2331. In general, the computer system 210 may use any of various observations about the group 2331, including about individuals, subsets, or the group as a whole to determine when a situation or condition of interest has occurred.

FIG. 23A shows a graphical representation of data analysis in a chart 2322. The chart 2322 shows that monitored data for the various devices A through F places them at different positions along a graph. The computer system 210 uses statistical analysis and machine learning analysis to identify data sets of individual members of the group 2331 that may warrant additional or different monitoring.

The analysis can include clustering analysis, where the computer system 210 identifies subgroups within the group 2331 for which the collected data has similarities. An example includes K-means clustering to identify clusters within the monitoring group 2331 based on the collected data. The criteria used for clustering may be specified in advance or may be determined by the computer system 210 from among the various types of data in the profiles 2316 and collected data 2315. In the example, the computer system 210 identifies a subgroup 2323, representing the data sets collected for devices B and C, which have similarities among they are collected data for monitored properties that are of interest to the monitoring program. For example, the two devices B and C may provide data that shows both have above average results or below average results for some measure or status indicator.

The analysis can also include comparison with specific references. In the example, the computer system 210 applies a threshold T and determines that the data sets for devices E and F both fall below the threshold T. As a result, the computer system 210 identifies these two examples as a potential opportunity for an additional monitoring program.

Based on the analysis of the collected data and the subgroups 2323 and 2324, The computer system 210 performs further evaluation to determine if additional monitoring programs are warranted. For example, the computer system 210 determines whether the significance of the observation or commonality identified meets a threshold level. This can include determining whether the magnitude, frequency, number of examples, and so on for an observed condition meets the minimum level. In other words, the computer system 210 can determine not only if a member of the group 2331 has a value outside a desired range, but also assess whether it is so far outside the range that it represents a new situation or the need for different monitoring techniques (e.g., monitoring with different devices, monitoring of different types of data, monitoring at a different frequency, monitoring with a different mode such as passive sensing vs. a survey, etc.). Similarly, the computer system 210 considers whether an outlier data point represents a temporary condition (in which case the computer system 210 may ignore it or wait for further confirming data) or a more significant condition (e.g., a repeated or permanent condition, or one that has persisted for at least a minimum amount of time). The system considers as well as if there are enough examples, among the group 2331 or among a broader set of candidates 2320, to show that the outlier is more than random chance, or has a significant enough correlation with the other monitored data to be explored and further monitoring.

The computer system 210 can perform various other analysis to assess the viability of studying the outcomes, contexts, and patterns exhibited by the subgroups 2323 and 2324. As discussed below, this can include assessing the overall pool of candidates 2320 and their profiles 2316 to predict the feasibility of monitoring subjects that would be similar to those of the subgroups 2323 and 2324. For example, the subgroup 2324 may include devices having a certain combination of properties or context factors, and using statistical analysis or machine learning models the computer system 210 can predict the compliance of devices having those properties in providing the types of data needed. If the computer system 210 determines that an adaptation involving those types of devices, or even the specific set of devices in a subgroup 2323 or 2324, would result in an acceptable monitoring program outcome or improvement to the likely outcome of the original study (e.g., compliance with data collection of 80% or more, retention of monitored subjects at 70% or higher, data quality of at least a minimum level, etc.), then the computer system 210 can make a determination to proceed with recommending or initiating adaptation of the monitoring program based on outcomes determined based on monitoring data for the subsets 2323 or 2324.

The computer system 210 can design an adaptation for the monitoring program based on the original monitoring program 130 and the identified factors that cause the subgroup 123 or 124 to stand out. As an example, the computer system 210 may use the parameters of the monitoring program 2330 as a starting point, and modify them to assess the actions or characteristics that caused the subgroup 2323 to be clustered together. As an example, this results in a second monitoring program 2340 where measurements are performed more frequently (e.g., twice daily instead of once daily), and additional types of data are monitored (e.g. data types one through five instead of data types one through three for the original monitoring program 130).

To determine which types of data to monitor and which techniques to use, the computer system 210 can have a database that includes a mapping between different parameters and different monitoring program elements. For example, a database, table, mapping, set of rules, or other data representation can include a list of measurable items. For device, this could include things like battery level, network bandwidth utilization, CPU usage, memory usage, applications currently running, error history, uptime, and so on. For monitoring health of an individual, these could include items like blood pressure, heart rate, diet, sleep characteristics, exercise measurements, blood glucose level, pulse oxygenation, mood, and many other aspects that can be measured with sensors, surveys, device interactions, games, and other methodologies. For each of the data types or potential measurements, the database or table can map to one or more techniques or study elements for acquiring that data. For example, it may indicate devices, software, configuration data, device drivers, user interface elements, third-party services, and more that can provide the associated type of data. The computer system 210 can then select from among the mapped monitoring program elements to build a monitoring program, along with the device configuration data, software, devices, and content that can achieve the type of monitoring desired.

In the example of FIG. 23A, the subset 2323 can represent two individuals or devices in the monitoring group 2331 that are identified as having very good results. As a result, the computer system 210 can generate the monitoring program 2340 to further assess the factors that contributed to those results. For example, in a clinical trial involving a medication, where the users of devices B and C were identified as showing a very good response to the medication, the computer system 210 may create the monitoring program 2340 to assess whether a lower dosage would still provide good results. The monitoring program 2340 can include a different set of actions by members of the corresponding monitoring group 2341, such as taking a medication less frequently or taking a lower dosage then was involved in the monitoring program 2330. In addition, the types of data to be measured may be different, in this case, more data types are monitored. Because the monitoring group 2341 includes the users of devices B and C, the computer system 210 can efficiently initiate the new monitoring program 2340 and have a high confidence that the monitoring program 2340 will be carried out successfully, based on the pattern of behavior of the users of devices B and C from their participation in the monitoring program 130, and potentially from other information in the profiles 116. Additionally, the devices B and C have already been configured for the monitoring program 2330, allowing the system to generate and provide additional monitoring modules 2313 or configuration data 2314 to easily and even seamlessly transition from the first monitoring program 130 to the adapted monitoring program 2340, or to carry out both at the remote devices B and C concurrently.

The system also generates another adapted monitoring program 2350, which may be an alternative adaptation or may represent an adaptation for a different sub-group than program 2340. This program 2350 is based on the observations for devices E and F that did not meet the threshold T. This may represent that the subgroup 2324 shows performance that did not meet expectations, or involved a safety concern, or showed a symptom or side effect. After determining that the difference with respect to the threshold is significant in magnitude and persistent over at least a minimum amount of time, as well as determining that the measurement with respect to the threshold is significant to the objective of monitoring for monitoring program 2330, the computer system 210 determines to create a monitoring program to focus on the factors and contexts and outcomes observed for the subset 2324. The computer system 210 includes the users of devices E and F in a new monitoring group 2351 and also adds additional users and devices, users of devices H and I, to create the monitoring group 2351, which may be a sub-study, sub-cohort, treatment arm, or other part of the study 2330.

As part of defining the characteristics of adapted monitoring program 2350, the computer system 210 may use the characteristics of the subgroup 2324 to define selection criteria for the monitoring group 2351. For example, the system may determine that there are commonalities among the members of the subgroup 2324, especially attributes or contextual factors that are different from those of other members of the monitoring group 2331 or rare in the other members of the monitoring group 2331, and which may be correlated with the outcomes that placed the members of the subgroup 2324 below the threshold. For example, parameters or values determined by clustering users into subgroups or by analysis of members of subgroups and comparison of members of subgroups with the broader set monitored can indicate potential factors leading to the outcomes observed for the subset 2324. For example, the subset 2324 may include devices of users who are over age 50 and live in a rural area, while other members of the monitoring group 2331 may be typically younger or live in urban or suburban areas. From the analysis of these attributes, the computer system 210 can identify selection criteria to find other individuals similar to those in the subgroup 2324 that may be recruited into the monitoring group 2351 to further explore whether being over age 50 and living in a rural area is, in fact, a contributing factor to the outcome observed.

As part of the monitoring program 2350, the computer system 210 may change or include aspects other than merely monitoring conditions that occur and collecting data. For example, the monitoring program 2350 may include a change in behaviors that users are expected to perform, a change in medication or treatment, and so on. As a result, the monitoring program 2350 may involve changes with respect to monitoring program 130 for what participants are asked to do for sleep, diet, exercise, taking medication, interactions on their devices, and more.

FIG. 23B provides a table 2360 of examples of conditions that, if detected, may prompt the computer system 210 to evaluate potential for a adapting monitoring program. The computer system 210 can store rules and conditions that it uses to assess the data collected for ongoing research studies. Application of the rules, or checking if the conditions are present, can indicate when an opportunity for a sub-study has occurred. Those shown in the table 2360 are simply examples, and more specific conditions can be set for individual studies. For example, each monitoring program can have its own set of data collected, with each type of measurement having a corresponding normal range or baseline used for comparison. When received data deviates from expected values or the normal range, that can be identified as a sub-study opportunity.

In the table 160, examples of conditions that the computer system 210 may detect to identify potential for an adaptation include: a desired effect detected (e.g., a positive effect of a medication, a health improvement, etc.), for which a sub-study may investigate dose response, persistence of the effect, etc.; a desired effect not being detected; an adverse event (e.g., side effects, toxicity, etc.); high compliance with the study protocol, indicating a good subset of individuals for more detailed monitoring; occurrence of a predetermined condition or attribute (e.g., physiological, behavioral, psychological, etc.); data received or outcomes generated that match, or have a minimum level of similarity to, a predetermined pattern; similarity identified in attributes, outcomes, events, or conditions monitored; a measured characteristic outside an expected range; a measured characteristic differs by a minimum amount from a target or typical level for the monitoring group; a cluster of participants identified having at least a minimum difference from other clusters; and so on.

More generally, the criteria for identifying an adaptation opportunity can include detecting patterns or conditions related to physiological attributes, behavior, lifestyle, genomics and epigenetics, demographics, social activities, and technology use (e.g., manner of usage of a particular participant engagement tool, such as a device or software specified to be used by participants in the primary study). The computer system 210 can analyze received data for individuals to detect biomarkers, digital markers, or other markers, whether or not the primary study specifies the markers as types of data to assess and record. In this manner, the computer system 210 may identify markers for unexpected results that were not anticipated and thus not built into the study protocol or the researcher's analysis process. Markers can relate to many different areas, such as mood related measures, cognition, mental health, trust and fear measures, sleep disruptors, stress, among other health indicators.

The system can also assess digital measures or measurements. The system can use information collected through an array of wearable, passive, invisible, or instantaneous sensor measures; laboratory blood and urine testing, polymerase chain reaction (PCR) and serology results; and more. A few example measurements that can be determined using remote devices include average sleep per night, average resting heart rate, average number of steps per day, physiological measures like blood pressure, and so on. Other data, such as EMR/EHR data, genomics information, environmental data (e.g., air quality), and so on can be obtained from medical caregivers, third-party systems, and other data sources.

The computer system 210 can collect and use self-reported Information, obtaining information such as demographic profile, technographic profiles, age, ethnicity, occupation, education, life events and decision making, health history, family history, region, location, time of day, times per day, number of people, and varying survey's across field entries and Likert scales Operational data, such as data that describes the context or manner in which a participant uses a device for a study, e.g., number of days of data collected, mobile device status, network-related data (e.g., connection type, bandwidth, etc.), average reporting time during the day, etc. All of these different sources of data, as well as any others that the primary study may specify, can be used to identify patterns, anomalies, clusters, expected outcomes, unexpected outcomes, or other conditions that can signal a topic to study in a sub-study or a set of participants that may be suitable for a sub-study.

The process of detecting opportunities for adaptation can be performed repeatedly, on an ongoing basis for active studies. As additional data is collected, the computer system 210 reviews and analyzes the data to identify new opportunities to assess. Once adaptations are applied, collected data from the adapted studies are also monitored and analyzed in the same way, to identify opportunities for further adaptation.

FIG. 23C illustrates a table 2370 that illustrates types of analysis that the computer system 210 can use to assess whether the system should proceed with recommending or implementing an adaptation opportunity, e.g., whether the changes to the protocol, cohort, and other elements should be generated, whether to recommend the adaptation, whether to distribute and begin use of adapted parameters, etc. Many of the elements in table 170 relate to assessing the viability of the adapted study, or a portion thereof (such as a new potential sub-study, treatment group, or cohort to be added). The computer system 210 can assess criteria to ensure a desired level or likelihood of improvement due to the adaptation (e.g., a minimum likelihood of meeting objectives or standards for results that would be achieved). Viability analysis can address various factors including cohort size, enrollment rate, retention rate, compliance rate, data quality, statistical power, and more. The computer system 210 can assess viability and potential likelihood of success of an adapted study using various different techniques, such as statistical analysis, rule-based analysis, and machine learning, using these alone or together in combination.

The table 170 shows an example of various items that the computer system 210 can evaluate to determine whether an identified adaptation opportunity should be pursued (e.g., started or recommended). For example, the system 100 can determine if a number of affected participants (e.g., those having an outcome or characteristic prompting the potential adaptation) satisfies a minimum threshold. This can be a check to verify that a minimum amount of participants (e.g., 2, 5, 10, etc., or 1%, 5%, etc.) are available for the adapted study to test the item detected. The computer system 210 can determine, based on a database with information about data collection methods, if the data needed to meet the objective of the adaptation can be collected with available methods (e.g., available devices, software, surveys, etc.). The computer system 210 can determine whether importance scores for the topic or outcome to be tested more extensively in the adapted study satisfies a minimum threshold. For example, there may be a significant number of people in a cohort for a primary study that have a skin rash, but the skin rash may be of minor importance. The machine-learning-generated scores discussed below can be used and compared to minimum thresholds or other references also.

The computer system 210 can use predictions about the behavior of potential participants (e.g., candidates or an already-selected cohort) to assess viability. For example, rather than use simply the starting number of eligible participants, the computer system 210 can predict enrollment rates, retention rates, protocol compliance rates, data quality results, and other results that can be expected for the adapted study. The predictions can be made using the details about the proposed adaptation—the types or categories of individuals, the requirements of the sub-study protocol that would be used (e.g., including parameters such as amount of time required of participants, duration of the sub-study, requirements for behavior such as taking medication, completing surveys, using monitoring devices, etc.). This allows for accurate predictions that are tailored or customized as much as possible for the adapted study that would be run. In some cases, if specific individuals are identified as candidates or cohort members for the adapted study, the computer system 210 can determine likelihoods of enrollment, compliance, retention, etc. can be determined, and the computer system 210 can aggregate the predictions to determine cohort-level predictions. As discussed below, the predictions can be made using machine learning models (e.g., classifiers, neural networks, etc.) that are trained to make those types of predictions.

The effect of enrollment rates, compliance rates, and retention rates have a significant effect on the viability or desirability of an adaptation. For example, an adaptation opportunity to add a sub-study or cohort has 100 candidates from the primary study that experienced a particular health condition. This sample size, if all enrolled and complied with the sub-study protocol to the end, might be expected to provide a statistical power of 0.85 or 85%. However, if the rates of enrollment (e.g., proportion of those eligible and invited that actually enroll), compliance (e.g., those enrolled that meet the minimum requirements to have their data considered in the study), and retention (e.g., those complying participants that continue to the end of the study) are 90% each, then the sub-study would be likely to end up with only about 73 that whose data can be used by the end of the sub-study. This may reduce the statistical power significantly, most likely well below the a threshold of 0.8 or 80%. If a researcher knew the sub-study was unlikely to meet key measures of validity, such as statistical power below a desired level, the researcher probably would decline to conduct the sub-study. The computer system 210 can thus generate predictions for the enrollment, compliance, and retention of participants, and potentially other factors such as data quality, and factor those into the predicted viability of the sub-study. The computer system 210 can also perform power analysis to determine, for example, the statistical power expected based on the expected final cohort size predicted for the end of the sub-study or a final cohort size needed to achieve a desired level of statistical power. These values can then be compared to corresponding thresholds to determine whether the predicted statistical power or predicted final cohort size would satisfy the requirements for the sub-study or adapted study. The computer system 210 can use the predictions and power calculations to rank or filter adaptation opportunities, thereby avoiding the inefficiency of creating and distributing chances to studies that would be unable to meet their requirements and so would waste resources of servers, networks, and participants' client devices.

The computer system 210 can inform researchers of the predictions it makes, e.g., rates of enrollment, compliance, and retention, as well as expected sample sizes that result from them. The computer system 210 can also provide results of power analysis, for example, (i) the statistical power expected based on the expected final cohort size predicted, (ii) a final cohort size needed to achieve a desired level of statistical power, and (iii) a starting cohort size that, given the predicted enrollment, compliance, and/or retention, would be needed to reach the desired level of statistical power. The computer system 210 can also perform the same predictions and calculations for primary studies and adaptation that researchers manually initiate. For example, as the researcher enters or adjusts parameters of a research study, the computer system 210 can update the predictions and power calculations and show updated values. Similarly, even when the values are not provided for display, the computer system 210 can detect when the predictions or calculations do not satisfy minimum levels, and can send notifications that specify the identified problem. For example, example notifications include "Given predicted compliance and retention, the planned sub-study would have a statistical power of 0.72, which is less than the target of 0.8" or "Alert: At the end of the planned sub-study, the cohort size is expected to be 62, which is less than the minimum of 75."

Referring to the table 170, the computer system 210 can determine if a predicted level of retention meets at least minimum amount of participants. This can take into account predicted enrollment rates, predicted attrition rates, etc., whether determined generally for other monitoring programs and applied or when determined for specific participant types (e.g., participants meeting certain profiles for age ranges, locations, etc.) or for specific individuals (e.g., based on each individual's attributes and history, and based on the attributes, history, and retention results for other similar individuals). In a similar manner, the computer system 210 can determine if predicted compliance with requirements of the monitoring program is above a minimum level, and if predicted data quality satisfies standards for the monitoring program.

The system can perform power analysis for the predicted set of complying participants at the end of the monitoring program. Rather than assessing the sample size for the monitoring group available at the beginning of a study, the system can identify the predicted sample size that will result at the end of the study, given the historical trends and patterns seen in other studies. Thus, the system can predict the end-of-study cohort characteristics, based on the expected rates of attrition, lack of compliance, etc., and determine whether that group has at least a minimum level of statistical power.

The system 100 also assess whether diversity criteria satisfied, for example, whether the set of retained, complying participants at the end of the study is predicted likely to provide needed levels of diversity. Diversity can be assessed over any of various dimensions, such as demographic characteristics such as age, race, sex, residence location, etc. but can also be assessed for other criteria (e.g., diversity in health status, comorbidities, genetic variants, etc.).

As shown in FIG. 1C, the computer system 210 can assess each of the different factors and filter out candidate adaptations that do not meet the required elements for viability (e.g., which do not provide a sufficient improvement or benefit to the monitoring program). For example, the proposed adaptation 1 meets all the criteria and so is selected by the computer system 210 to be recommended or implemented. The proposed adaptation 2 does not meet the requirements, and so will not be provided as a recommendation to a researcher and will not be initiated. Of course, the factors shown in FIG. 1C do not need to be assessed in a binary or yes/no manner. For example, the system may determine a numerical score for different factors, combine the different scores, and then compare the combined score to a threshold.

Predicted effects of a potential adaptation can be assessed based on parameters imposed by the researcher, e.g., limits that the researcher may specify in advance as minimum levels deemed necessary in order to start a sub-study (e.g., a target composition of a cohort, a minimum number of eligible candidates, a minimum expected statistical power, etc.). By generating and evaluating measures of viability, the system can use a researcher-created list of criteria in that can be assessed to determine the statistical significance needed in order to start a new sub-study. In the absence of researcher-specified preferences, the system can use default values for these standards. Viability analysis may address more than the basic need for sub-study creation. For example, the same analysis can assist when a researcher indicates a desire to monitor for side effects of a given therapeutic or as self-reported medication and dietary information. The computer system 210 can assess the viability of a study to achieve the objectives (e.g., whether the selected devices can accurately capture the data desired, whether the procedures defined in the study protocol adequately can meet the objective of the sub-study, etc.)

In some implementations, effects or suitability of an adaptation can be assessed using a machine learning algorithm. The computer system 210 can review data from participants regularly. Data associated with various areas like sleep, mental health, cognition, disease conditions, can each be assessed, e.g., to detect anomalies, patterns, or clusters in the data. The system 210 can correlate various data trends and data sources to identify opportunities. The system 210 can assign scores to the different identified opportunities based on output of a machine learning model. The computer system 210 can use the scores to prioritize a list of opportunities for sub-studies, e.g., to rank or filter the list based on the scores.

For example, the computer system 210 can train a model based on examples of different studies conducted or adaptations approved by researchers. The input to the model, for training and later for inference, can include factors such as characteristics of a primary study and characteristics of a potential study or adaptation (e.g., topic, data to be collected, disease condition to address, objectives, health outcomes that prompted the sub-study, etc.). In training, the input feature data indicating characteristics of a study and corresponding adaptation can be paired with a training target, which can be assigned as "1" or other classification label for adaptations that were approved or actually conducted. Other examples can assign an input feature data vector a training target of "0" or other classification label for adaptations that were suggested by the computer system 210 but were rejected by researchers (e.g., not elected to be performed). With both positive and negative examples, the computer system 210 can iteratively train a machine learning model to classify adaptation opportunities and indicate when they are appropriate.

In many cases the system can use a confidence score or probability value generated by the model for scoring opportunities for adaptations. For example, the computer system 210 can determine, for each identified adaptation opportunity, a confidence score indicating how likely the trained model considers the input data set to fit the criteria for the classification of a high-value, viable adaptation (e.g., those give a training target of "1"). In effect, the model in this way indicates a score indicating the similarity between the situation indicated by the input data (e.g., describing a proposed adaptation and its underlying study), and the situations for other adaptations that were selected and/or actually used. The confidence score can be a value on a scale from 0 to 1, where the higher the value indicates higher importance.

Variations can be made to address other factors, including the success of different adaptations in achieving their respective objectives, e.g., addressing the reasons that triggered them to be recommended (e.g., correcting low diversity, validating a correlation among health factors, etc.). For example, an additional or alternative training target may specify whether an adaptation achieved desired improvement in levels for, e.g., enrollment, retention, compliance, data quality, or other characteristics. As another example, a model can be trained with training targets of statistical power achieved or other measures of outcomes achieved by the different example studies in the training data set. Thus the model can be trained to predict the success or viability that would be achieved at the end of the study if the adaptation were implemented, not just whether the adaptation represents a topic of interest or whether researchers have expected the adaptation to be useful. In addition to training models with different training targets and output types, the information provided as input can be different in some implementations, such as to provide more information about the potential new adaptation, e.g., number of eligible candidates or cohort members, parameters or requirements of the adaptation, etc.

Other types of machine learning can be used to evaluate and score study adaptation opportunities. For example, a clustering model can be trained, based on the same training data examples and input feature data vectors discussed above, to cluster adaptation opportunities into different groups, e.g., opportunities accepted by researchers, opportunities rejected by researchers, opportunities accepted that met their requirements (e.g., for enrollment, retention, statistical power, etc.), opportunities accepted that did not meet their requirements, and so on. The parameters determined for the clusters can then be used to cluster different new potential adaptation opportunities, with scores assigned based on how close the input feature data vector for a new adaptation opportunity is to a cluster representing a desirable adaptation (e.g., distance from a centroid for a cluster of conducted adaptations that were labeled successful).

In addition, statistical techniques and machine learning models can be used to predicting the compliance rate or success probability of the an adaptation providing value. The results of any of the machine learning models can be provided as output to researchers, e.g., over a communication network for display in a user interface or in a notification.

Figure 24:
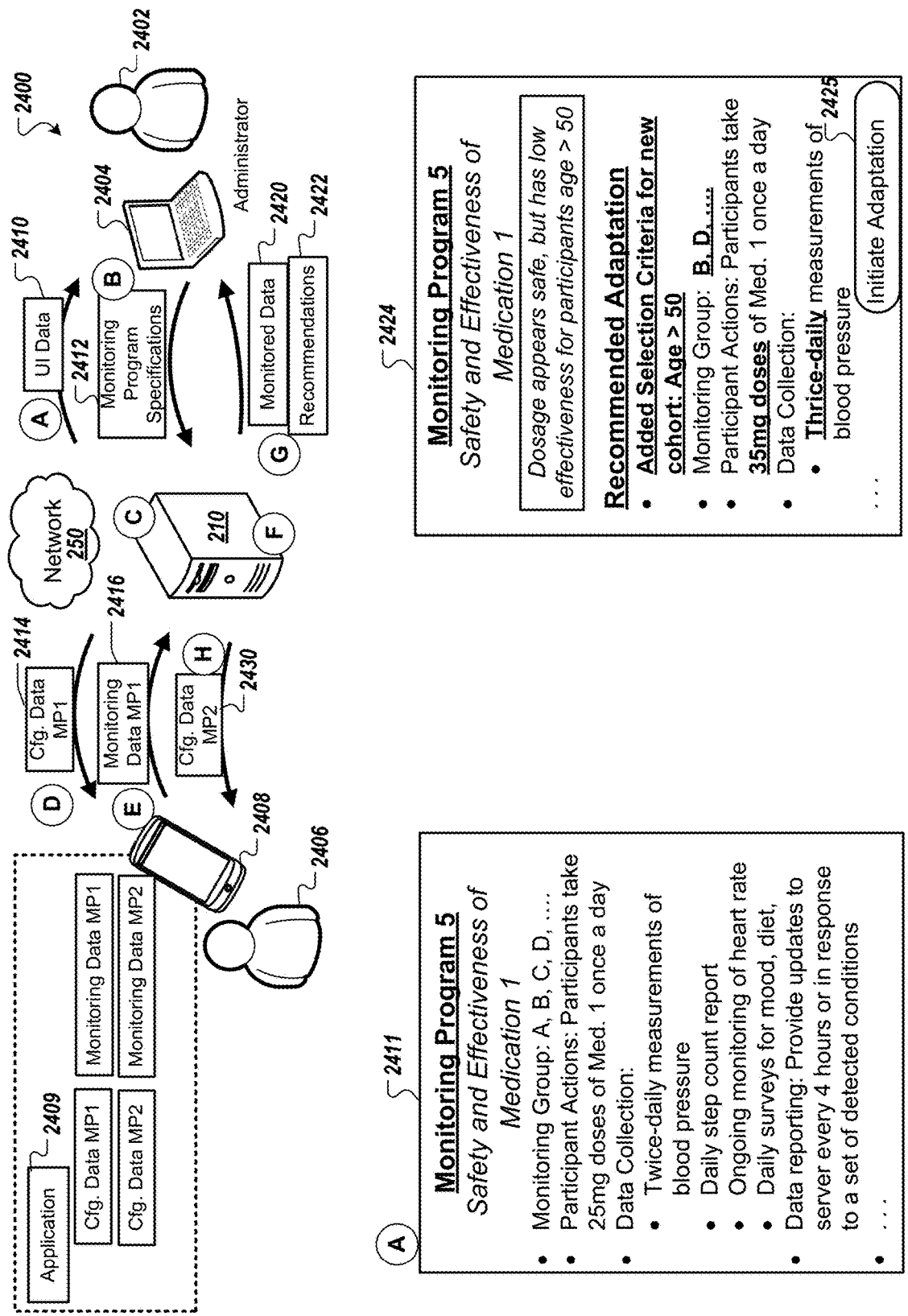
FIG. 24 is a diagram showing another example of the system and showing the system selecting and providing configuration data to configure remote devices for monitoring programs.

FIG. 24 is a diagram showing another example of the system and showing the system 210 selecting and providing configuration data to configure remote devices for monitoring programs. FIG. 24 shows an example with additional detail about how devices are configured to perform the monitoring programs managed by the computer system 210. As an example, an administrator 2402 uses a device 2404 to communicate with the computer system 210 over the network 250 to create a monitoring program. The system generates and sends configuration data 2414 to a device 2408 of a participant 2406 in the monitoring group. The system 210 then assesses the collected data for the establish monitoring program and recommends an adaptation for the monitoring program 2411.

The computer system 210 provides user interface data 2210 of a participant 2206 in the monitoring group. The computer system 210 then assesses the collected data for the establish monitoring program and recommends a new monitoring program, e.g., a sub-study of a clinical trial.

In stage (A), the computer system 210 provides user interface data 210 to the device 2204 of the administrator 2202. An example user interface is shown as UI 2211.

In stage (B), The administrator 2202 provides input and establishes the parameters of the monitoring program, which in this case as an objective to study the safety and effectiveness of a medication. With the assistance of the computer system 210, the interface enables the administrator 2402 to specify selection criteria for choosing devices and or individuals to use in the monitoring, such as a cohort of individuals to participate in a study over the course of a period of time e.g. three months, six months, a year, and so on. The interface also provides features to select specific individuals that meet the selection criteria, for example, to search for and receive results indicating individuals that have the desired attributes. Many other parameters of the study can be specified by the administrator 2402 or recommended or filled in by the computer system 210. For example, the administrator made directly indicate types of monitoring to perform in the monitoring program, or the administrator may specify topics and keywords, and the computer system 210 can build a program from elements in a database.

In stage (C), the computer system 210 uses the input from the administrator's device 2404 to finalize the monitoring program. For example, this may involve finalizing a study protocol for a research study. The computer system 210 also translates the parameters of the study into configuration data and software that will cause the appropriate type of monitoring at remote devices of participants in the monitoring program. and some implementations, participants download an application 2409 that is used for monitoring, and each monitoring program has a separate set of configuration data that includes instructions, content, device settings, And so on that implement they needed monitoring at the client device. In the example, the system 210 generates a set of configuration data 2414 for the newly generated monitoring program.

In stage (D), the computer system 210 sends the configuration data 2414 to the device 2408 of a participant 2406 in the monitoring program. The configuration data 2414 can be provided to all of the participants' devices, so that each of the remote devices of participants in the study is configured to collect, process, and report back to the server 110 the data needed for the monitoring program.

In stage (E), the device 2408 received the configuration data 2414 and applies it to adjust the application 2409 and cause it to perform the needed monitoring for the monitoring program. This can include acquiring data with sensors of the device 2408, acquiring measurement results and other data from other devices (e.g., a glucometer, a weight scale, a blood pressure cuff, etc.), acquiring data through surveys presented to the user 2406, and so on. The configuration data 2414 also specifies characteristics of the data to provide, including an identifier for the monitoring program, network addresses and data formats do use in sending the data collected, and so on.

With the configuration data applied, the device 2408 is configured to perform the ongoing monitoring tasks needed for the participant 2406. The device 2408 collects measurement results, activity tracking data, context data, survey responses and other inputs and then provides them to the computer system 210 as monitoring data 2416. Over the course of the monitoring program, the device 2408 provides many different messages or data packages to the computer system 210, for example on a periodic basis or in response to detecting certain conditions.

In stage (F), the computer system 210 analyzes the monitoring data received from the participant 2406 and other participants. The computer system 210 determines whether there are conditions that are appropriate for an additional, more focused monitoring program. The computer system 2410 can store a variety of rules, reference thresholds, reference ranges, representative data patterns, and so on the each correspond to different types of potential further monitoring programs or situations where monitoring programs can be valuable. As discussed above, many different observations about the collective data can indicate that there is value in a further monitoring program. This can include high compliance by the monitoring group showing that additional monitoring would likely be successful, low compliance with monitoring indicating that a different approach with different data collection techniques may be needed, positive results showing that it may be possible to decrease treatment or dosage and still achieve valuable results or that the attributes and background of certain individuals may be indicative of or predictive of those good results, negative results which may show that enhanced dosage or treatment may be necessary or that may indicate backgrounds to explore in further monitoring that may be indicative of our predictive of for outcomes, safety concerns or health conditions are rising that may show that summer all actions of the study may need to be changed or discontinued, symptoms or side effects exhibited by a subset of individuals monitored which may indicate an opportunity to explore the prevalence, magnitude or severity, and overall risk of the side effects in this group or groups of Individuals identified as having similar backgrounds, and so on.

In the example, the computer system 210 identifies that the dosage of the medication used in the primary monitoring program appears to be safe, but that it has a low effectiveness for at least some of participants over age 50. The computer system 210 verifies the importance of this finding, and because measuring effectiveness of the medication is a primary objective of the study, exploring the reasons for lower effectiveness and potential changes to improve effectiveness are highly relevant to the original monitoring objective. The system 210 generates parameters to adapt the monitoring program, with changes to the parameters to add a new cohort or sub-group to focus on the type of individuals for which effectiveness was low. The change parameters include additional selection criteria for the this portion of the adapted study, where participants are selected to be over age 50 in addition to other criteria used to select participants in the cohort for the primary study. This results in a different monitoring group within the study, which can include subset of the original monitoring group and may include additional other, newly-recruited participants. The new cohort also changes the dosage of the medication from 25 mg to 35 mg, as part of testing whether increase dosage will improve effectiveness. The new proposed cohort also includes changes to the data collection and monitoring procedures to be carried out by remote devices of participants in the cohort. For example, blood pressure measurements are set to be performed three times a day instead of twice a day. Other changes can be made such as monitoring different physiological parameters, using different questions or surveys, using different sensors or devices, and so on, and these changes can be specified in newly generated monitoring program data that the computer system 210 creates for the new cohort.

In stage (G), the computer system 210 provides monitoring data 220 for the monitoring group of the original study, allowing the administrator to have an up-to-date view of the progress and results for the monitoring program. The computer system 210 also provides recommendations 222 for carrying out the adaptation, e.g., the new cohort that the computer system 210 identified and created. This is illustrated in the user interface 224, which shows the parameters for a recommended cohort that focuses on monitoring a group selected with more specific selection criteria then the original selection criteria.

In some implementations, the administrator can approve or confirm that the new proposed adaptation (e.g., additional cohort with changed treatment parameters) should proceed. The interface 2424 shows a control 2425 that an administrator 2402 can interact with to cause the computer system 2410 to initiate the sub-study among remote devices.

In general, the process to identify adaptations begins with the type of cohort for a given research study. There are two main types, a generalizable cohort, which measures health across a large population, and a specialized cohort, which measures more specific conditions within a subset of the generalizable cohort.

For a generalizable cohort, this type of cohort is open to everyone and allows participant to share information across many topic areas as defined by the survey instrument by the researcher. For this type of the cohort, the following process would occur when identifying an adaptation. If a researcher is interested in the category of sleep, such as sleep disruptors; either across the entire united states or a region or area like the West Coast, state or local city or campus. The computer system 210 performs the following:

The computer system 210 receives cohort criteria to measure—related to sleep, this includes survey instruments, measurable data from the participant using a wearable or a bed sensor, and previously recorded data from electronic health records (EHR).

The computer system 210 compares data in the geographic region of the West Coast related to the participants, and statistically determines overlapping measures of interest that show population measures where environment is having an impact.

The computer system 210 automatically creates an adaptation around individuals that have overlapping environment related measures, physiological measures (such as low resting heart as healthy indicators, potential sleep disruptors as digital markers, etc.), and city or state related demographics.

The computer system 210 automatically distributes the changed elements for the adaptation (e.g., software, configuration data, etc.) to the devices of the individuals to measure relevant items for people most affected by environment in terms of sleep disruption The computer system 210 collects data from the adapted study from remote devices of the individuals selected for the cohort. This data can be collected using sensors, and self-reported measures to better understand several factors that could impact a person's sleep patterns and sleep disruptions.

Some of the soft aspects not limited to could include position of the bedroom, the impact of sunlight, noise levels, vibrations, among many other factors. Where those whose bedrooms face the sun during sunset show an abnormal amount of VOC, the chemical significance of this is further exacerbated when air conditioning isn't working, or the bedroom is above the garage.

The computer system 210 may further adapt the study to continue to measure a variety of correlating factors about the impacts of sleep disruption, such as the sunlight, noise, vibration, and health related outcomes like a high or low BMI, etc.

For a specialized cohort, this type of cohort is limited to specific inclusion-related criteria. For this type of cohort, the following would occur in managing studies that may lead to a more expanded generalized cohort. If a researcher is interested in measuring social interventions in cancer survivorship, while learning about cancer research specifically, interest is found in determining that there are more generalizable social considerations. The computer system 210 performs the following:

The computer system 210 receives cohort criteria to measure, e.g., related to cancer survivorship, and how mobile tools can support cancer patients as participants of the study.

The computer system 210 compares data across participants and determines that there are more generalizable social considerations—for instance, its discovered that while delivering an intervention that social engagement is low during specific times and specific locations indicating that texting individuals use a phone as a personal device in a personal space, and are less prone to engage in visible social activity.

The computer system 210 creates an adaptation specific to better measurements with mobile technology with the intent of improving an intervention in the study.

The computer system 210 the system distributes the adapted study elements potentially to a larger cohort or multiple cohorts in order to acquire the necessary statistical measures to show relevance The computer system 210 collects data from the adapted study, including, for example, measures through sensors a participant's proximity to others, heart rate variability, scheduling time along with demographic reported data like age. In this case, the adaptation aims to identify improved response time for participants as a virtual social situation. Insights are capture that describe changes in the heart rate variability as a digital marker of stress and its variance in virtual social situations; when collecting distance from home during an activity like walking, or the proximity to others along with self-reported measures. Where solitude, such as classification around a library or a personal office provide, decreases in stress and physical proximity to others may indicate increased acceptance and duration of virtual social engagements.

The computer system 210 adapt the study further to continue to add additional details around locations and classifications with metadata consistent with environment, densities around number of people present based on crowdsourced proximity cataloging.

Figure 25:
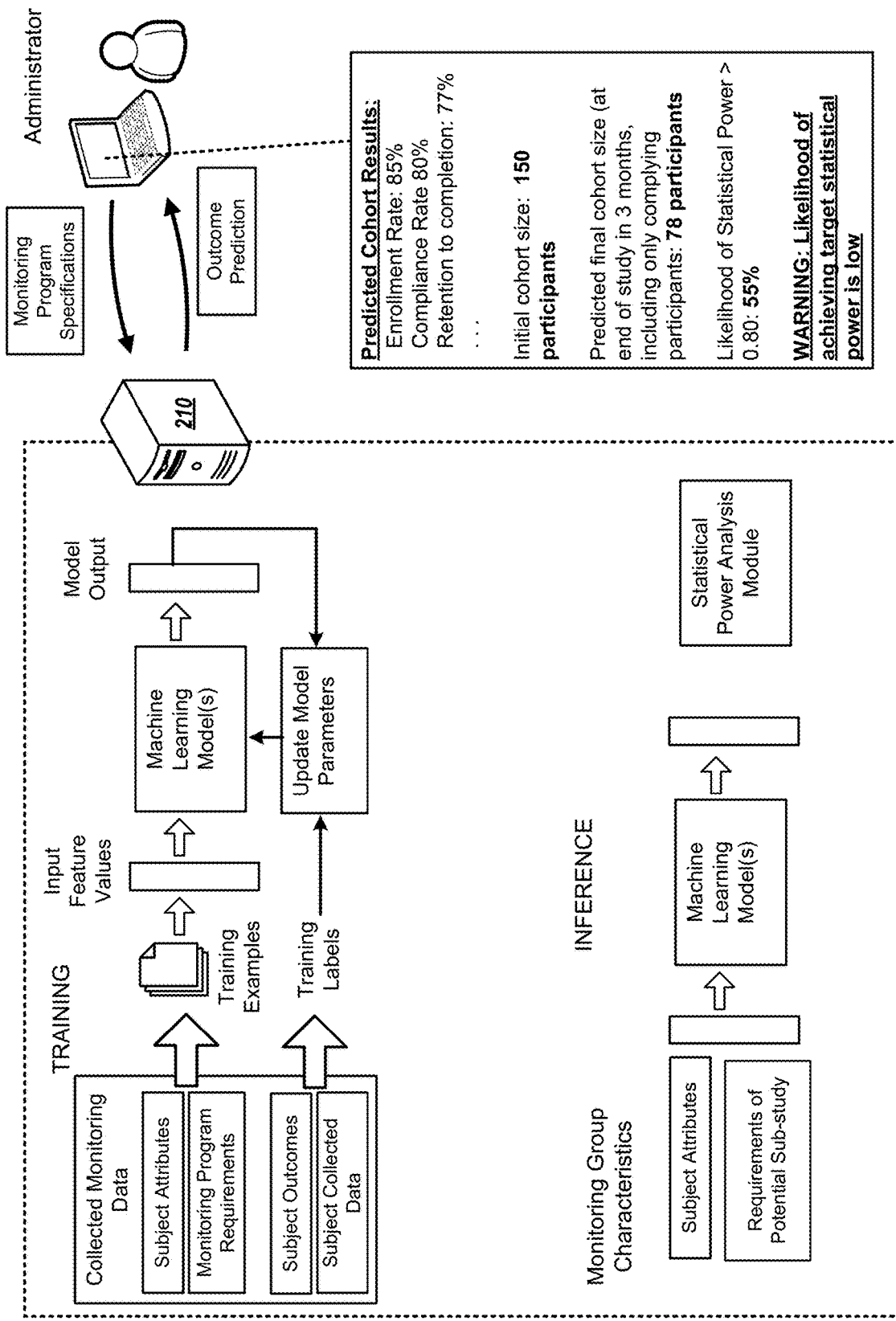
FIG. 25 is a diagram showing an example of the system and showing the system training and using machine learning models to determine predicted outcomes of monitoring programs, including potential adapted monitoring programs to recommend.

FIG. 25 is a diagram showing an example of the system and showing the system training and using machine learning models to determine predicted outcomes of monitoring programs. FIG. 25 shows a model training phase in which collected monitoring data for various studies is used as training examples to train machine learning models such as neural networks, classifiers, or other models. The models can be trained to protect any of various different outcomes, including enrollment likelihoods or rates, compliance with different sets of requirements for participants, retention of the participants to the end of a study, and more. In the training phase, the outcomes that have been observed in those prior studies for enrollment, compliance, retention, and so on are used to generate training labels they're used as training targets. Once input feature values for an example are provided as input to a machine learning model and are propagated to generate a model output, the computer system 210 compares the model output with the training target and then adjusts the model parameters to incrementally improve the predictions of the models. For example, the computer system 210 can use backpropagation of error and similar techniques to adjust the node weights for different layers of a neural network.

Training of the machine learning models can be done for individuals, so that the models predict the compliance of an individual based on the individual's attributes, behaviors, history, and other data that the computer system 210 is collected. In other implementations, models can be trained to make predictions or assessments of monitoring groups as a whole. For example, instead of receiving attributes of a single individual, the model can be trained to receive and process aggregate data about the entire group, using averages, distributions, and other measures of the characteristics of the group.

Once the machine learning models have been trained, the models can be used to predict the enrollment, compliance, retention, and other characteristics of potential cohorts for new sub studies. When evaluating a new potential adaptation, the monitoring group that is assessed can be an actual cohort selected or a candidate pool from which participants may be invited to participate. The predictions of the machine learning models can be provided for display to researchers, potentially Once the predictions from the machine learning models for enrollment rates, compliance rates, retention rates, rates of appropriate data quality, and other predictions are generated, the computer system 210 can determine a cohort size that is expected to be compliant with study requirements at the end of the study, if the adaptation were to be applied. The computer system 210 then provides this predicted study-end, complying-cohort-size to a statistical power analysis module that can perform power calculations to determine expected statistical power.

The computer system 210 can make predictions about the likelihood of a successful outcome for a study. The computer system 210 can identify patterns within historical study data (e.g., previously completed research studies) to determine whether a researcher's proposed study design, or proposed study adaptation, will succeed. For example, a researcher can input information for a proposed study, for example, into a user interface for designing or building a study. The input can include a research question to be addressed by the study or other parameters for the study (e.g., cohort size, data to be collected, devices or technology to be used in the study, duration of the study, protocols or procedures to be used, etc.). The system can use the information about prior studies (e.g., research questions and topics, study parameters, and study outcomes) to evaluate whether the study being designed is likely to achieve one or more outcomes, such as completion of the study by at least a minimum number of participants, achieving a level of statistical validity, achieving a desired level of precision, and so on. The system may generate a likelihood, for example, a confidence score, for each of one or more types of potential study outcomes. This can be done by comparing the proposed parameters for the new study being designed with the parameters of the prior studies to determine how similar the proposed parameters are to studies that achieved the outcomes or those that did not achieve the outcomes. To better assess the likelihood, the system can also examine the variability in outcomes, and the correlations among different outcomes and different study parameters or combinations of study parameters. One way the system can provide this functionality is to train a machine learning model to predict the outcome of a study based on study parameters, where training is based on the examples of prior studies and their outcomes.

The computer system 210 can use machine learning in a variety of ways. For example, machine learning models to classify individuals with respect to different outcomes. For example, models can be trained to predict, from input about an individual's attributes, whether the individual will really remain engaged in and be retained in the study until completion of the study. Models can be trained based on the examples of profile data in the database. Models can be trained to make predictions about a variety of outcomes, such as whether individuals will respond to different types of communication (e.g., email, SMS text messages, cell phone notifications, phone calls, etc.), whether they will answer different surveys or even individual questions, and so on.

Moreover, using the examples of user attributes and other characteristics in a database, the computer system 210 can predict which types of users are most likely to perform which types of actions. For example younger users might be more likely to download and install an app on their phones, while older individuals who have more regular doctor. Appointments may be more likely to provide or obtain blood test information. The computer system 210 can use these predictions in determining the likely rates of compliance, retention etc., to expect for a current study and for an adapted study.

The computer system 210 can track attributes or activities of each of multiple subjects over a period of time, as well as changes in the multiple subjects over the period of time. The computer system 210 can the train various types of models based on the data in the database, as discussed further below. By tracking many variables (e.g., subject attributes, subject activities, context of the subject and activities, etc.) for many subjects and storing the data in the database 122, the computer system 210 can obtain a rich data set with which to discover elements that have relevance to the potential actions of the subjects, including their levels of engagement and retention for participating in research studies. This data, whether used for machine learning training or through direct analysis and extraction of relationships by the computer system 210, can be used to identify which features are predictive of different types of outcomes (e.g., different actions by the subjects or outcomes of subjects during research studies) and to generate models that can be used to make predictions based on those features.

The computer system 210 may use the parameters of the study being designed to tailor the predictions regarding outcomes for individuals. For example, each study may have its own set of protocols and requirements, so that different studies require different levels of active engagement by participants. For example, some studies may require in-person meetings and others may not. Similarly, different studies require different types of data to be collected using different techniques. Predictions of likelihoods of outcomes can be based on the study protocols and requirements, so that the predictions of outcomes for a study are tailored for the particular types of actions and the overall burden imposed by that study.

For example, a machine learning model can be configured to receive, as input, (i) feature scores that indicate the study requirements (e.g., study duration, types of responses needed from subjects, types of hardware and software used, type and frequency of data collection, etc.) and (ii) feature scores that indicate a variety of attributes of an individual (e.g., demographic information, survey responses, and other data about the individual), including potentially actions that the individual has performed in the past (e.g., successfully completing appointments, failing to complete appointments, use of a medical device or an application, participation in a prior study, etc.). From these inputs, the machine learning model may provide one or more scores that indicate likelihood of the user performing different actions. For example, there may be a score predicting a likelihood of being retained in the study until the end, a score predicting a likelihood of the individual providing a particular type of data, a score predicting a likelihood of the individual responding to e-mail or another type of communication, and so on. The machine learning model may be, for example, a neural network, a support vector machine, a classifier, a regression model, a reinforcement learning model, a clustering model, a decision tree, a random forest model, a genetic algorithm, a Bayesian model, or a Gaussian mixture model. The machine learning model may be trained by using the many individuals whose data is in the database as training examples. For example, for participants of prior studies, the computer system 210 can use the database to determine outcomes for those participants, the study requirements for the studies they participated in, and the attributes of the participants. The outcomes can then be used as training targets for different training iterations to adjust the parameters of the machine learning model (such as weights for an artificial neural network) to predict the outcomes.

The computer system 210 can generate a prediction of a likelihood that the particular individual will perform the behavior using the one or more machine learning models. The computer system 210 may generate a prediction of a likelihood that the particular individual will perform a certain behavior using the machine learning models. The behavior may vary depending on the type of prediction being performed. For example, in some instances, the computer system 210 predicts a likelihood that the particular individual will complete a participant survey to be subsequently provided to the individual while the research studying is being conducted. In this example, the prediction can be based on historical activity data indicating whether the particular individual has completed surveys in research studies that he/she has previously participated, a user's preferences for different survey types. In other instances, the computer system 210 predicts a likelihood that the particular individual will successfully complete the entire research study (e.g., that the individual will not drop out of the research study). In this example, the prediction can be based on historical data indicating the completion rates of other individuals in similar research studies, or specifically, historical data of the individual's participation in previous research studies.

Figure 26:
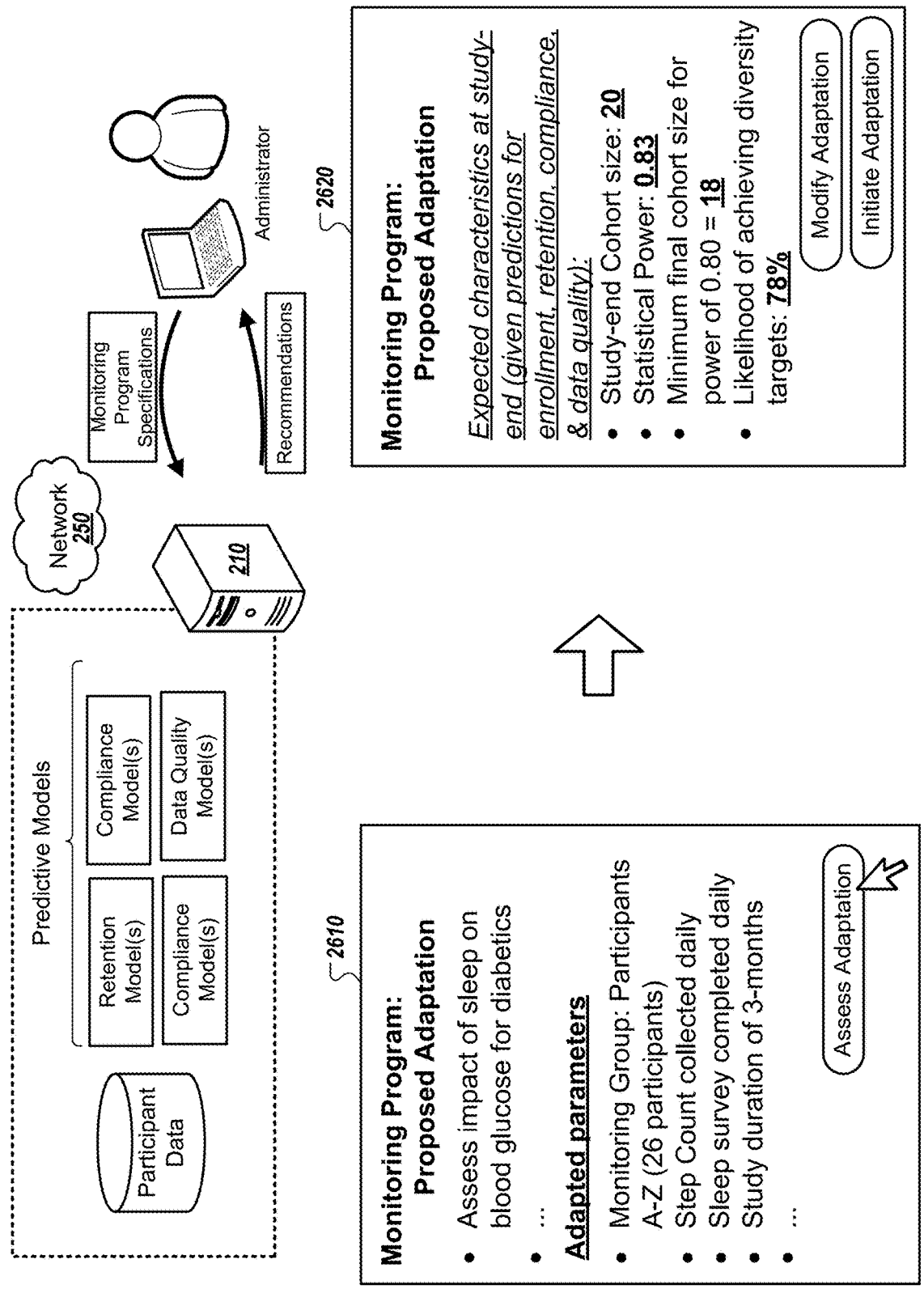
FIG. 26 is a diagram showing an example of the system and showing the system providing tools to design and implement or adapt a monitoring program.

FIG. 26 is a diagram showing an example of the system and showing the system providing tools to design and implement a monitoring program. The computer system 210 can use various predictive models, determined as discussed above, to assess the characteristics of a proposed monitoring program, such as one entered by a user in the user interface 2610 or one that the computer system 210 generates automatically. Using the models, the computer system 210 generates predictions about expected characteristics of results of the proposed adaptation, including how the predicted level of engagement among the participants, including their expected levels of compliance with the specific requirements of the study, will affect the validity and viability of the study to meet criteria for successful completion. Those criteria may include statistical power above a minimum level, a number of participants complying to the end of the study, and so on. Those predictions can be provided, as shown in user interface 2620.

Based on the predictions of the models, the system can determine one or more scores that indicate the probability of successful levels of engagement in the proposed adaptation (e.g., with the current cohort or candidate pool, and with the current requirements or study protocol considered for the adaptation). The engagement probability information helps a researcher determine if it would be worth conducting the study, e.g., whether the expected data quality and engagement is sufficient. In some cases, the computer system 210 shows study parameters on a user interface, and the researcher can vary the parameters and see the how the changes increase or decrease the likelihood of having a viable study. Through a combination of assessing the particular study requirements, compliance predictions, and power analysis results, the computer system 210 provides an evidence-based way to predict how different requirements affect compliance results.

Figure 27:
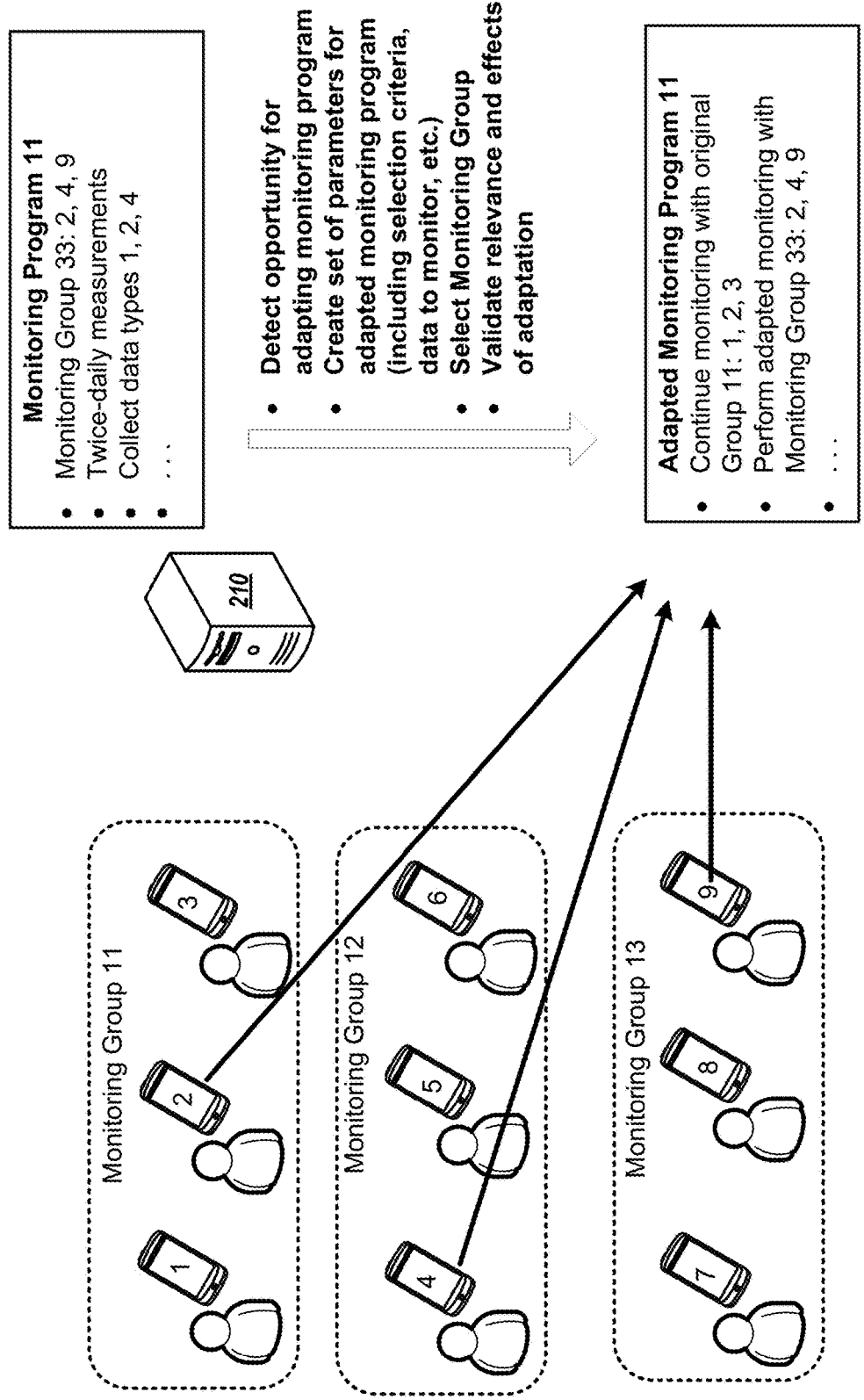
FIG. 27 is a diagram showing an example of the system and showing the system generating monitoring groups having devices selected from multiple monitoring groups for other monitoring programs.

FIG. 27 is a diagram showing an example the system 210 generating monitoring groups having devices selected from multiple monitoring groups for other monitoring programs.

The computer system 210 can provide a unique comparative tool across participants in a research study and combines the ability to identify trends to predict information and the overall statistical quantity and resources necessary to launch related studies. The computer system 210 can broaden study outcomes by evaluating the existing study cohort, researchers are able to identify opportunities to extend the study by a deeper understanding of existing AIMs and providing opportunities to learn more about related study artifacts. The computer system 210 can determine new study initiatives by evaluating the existing study cohort, researchers are able to identify opportunities for completely new research unrelated to the original study measures and expected research potentials. The computer system 210 can provide protocol definition support when considering new studies, guidance as to the qualitative and quantitative measures are provided to associate new measures and what or if any existing measures can be reused. The computer system 210 can provide cohort retention strategies by delivering sub-studies to participants, researchers are provided reoccurring engagement opportunities and encourage retention by enabling participants to contribute to new study efforts and reports.

Figure 28:
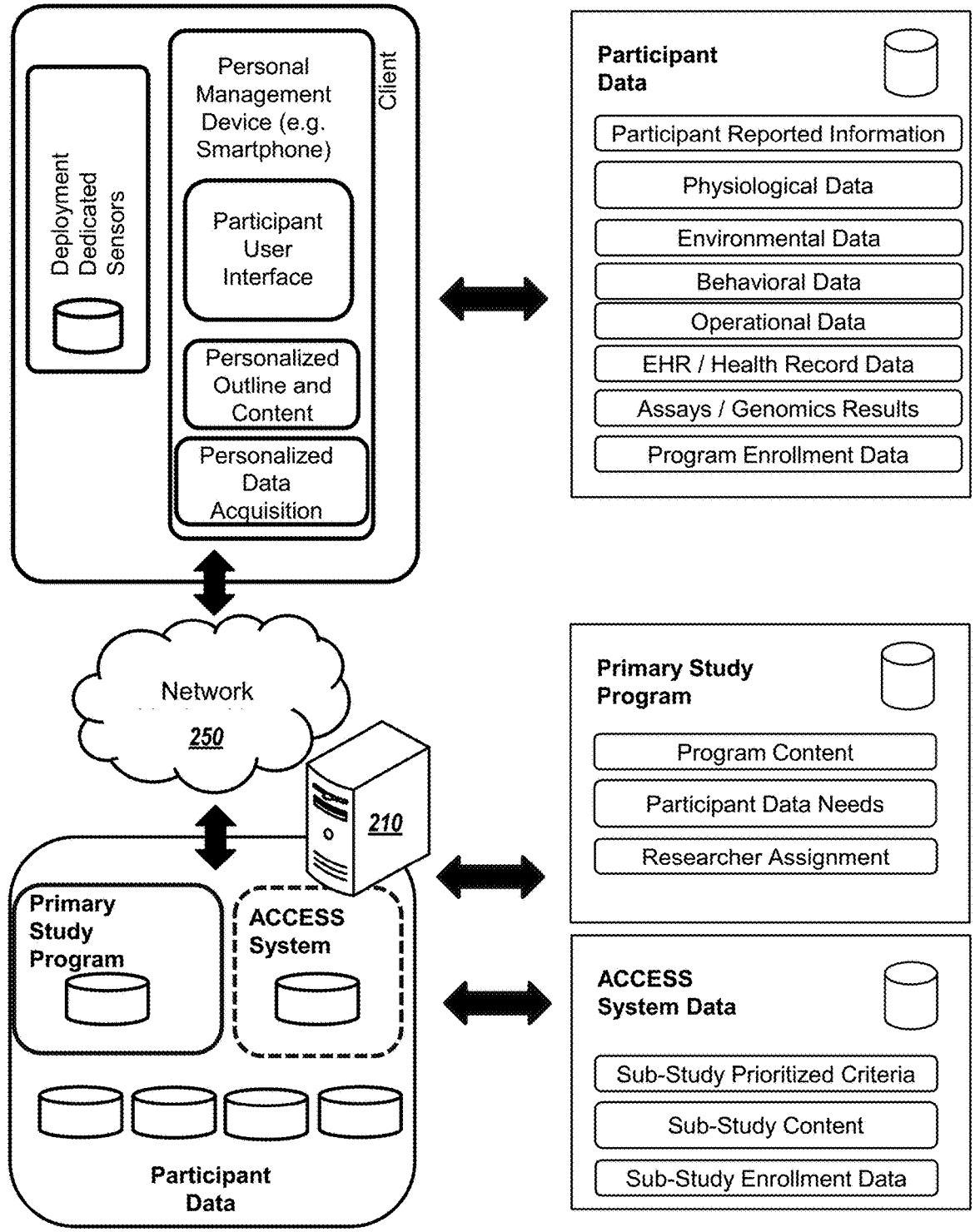
FIG. 28 is a diagram showing an example of the system and showing various devices and data sources used by the system.

FIG. 28 is a diagram showing an example of the system 100 and showing various devices and data sources used by the system. FIG. 28 shows various components of the system 100, including the computer system 210 and a client device 2810 in which participant data is collected or observed and reported to the computer system 210. The data from the client device 710 is then passed to the backend system through the network 250, e.g., through a server network interface. The computer system 210 stores the data and uses it for the corresponding monitoring program (e.g., a primary study) as well as to assess characteristics for further monitoring programs (e.g., sub-studies). The data received in a monitoring program can be used for further monitoring programs to determine a monitoring group to involve, configurations to set for remote devices, and content to provide to the devices.

Figure 29:
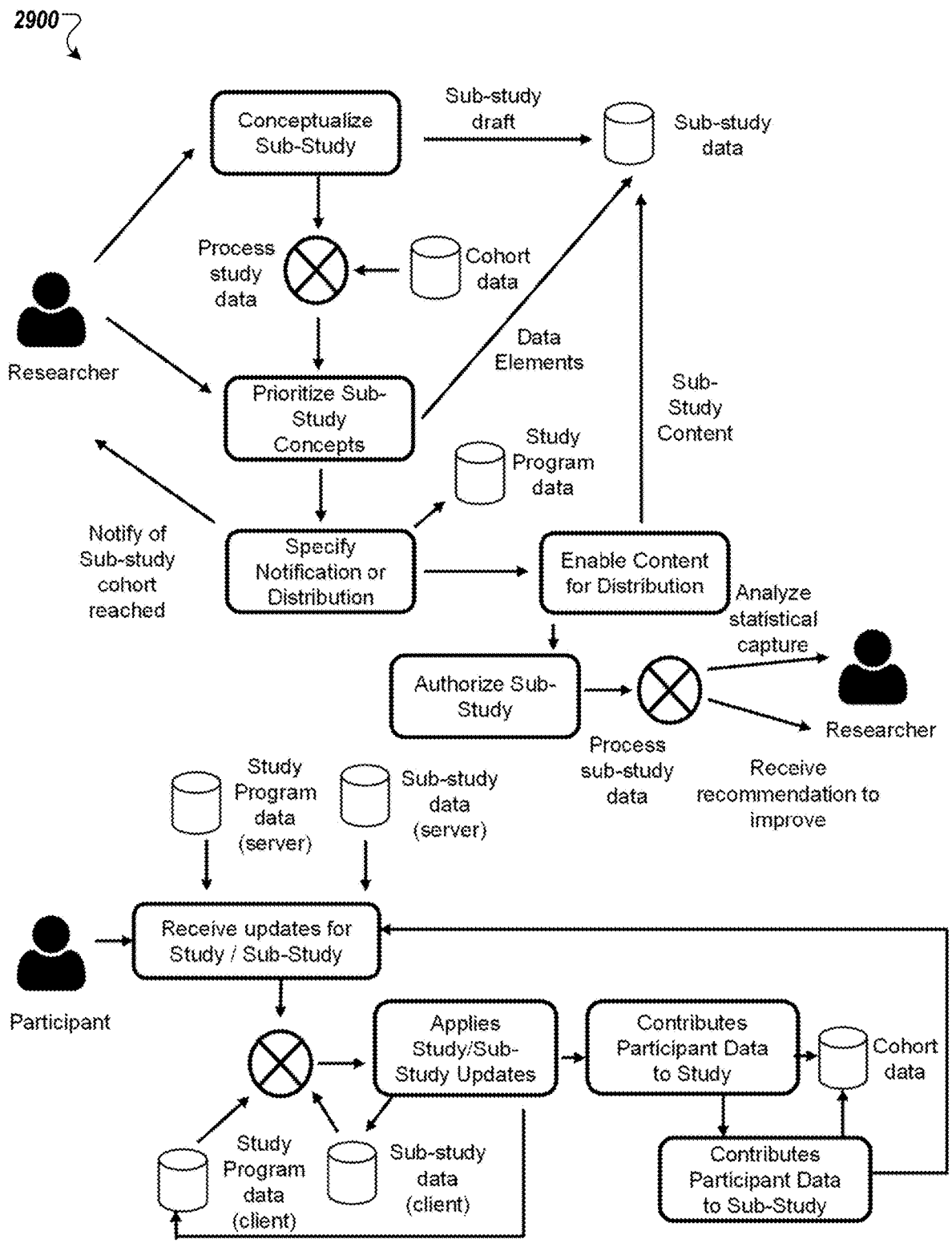
FIG. 29 is a diagram showing a flow of information that the system can use to carry out, assess, and adapt monitoring programs.

FIG. 29 is a diagram showing a flow of information 2900 that the system can use to carry out, assess, and create monitoring programs. FIG. 29 describes a workflow including actions performed by the computer system 210 to collect data from devices and participants enrolled in a monitoring program and to provide the data to a researcher. In the example, the adaptation is the creation and implementation of a new sub-study, but the same principles can be used to carry out other types of adaptations.

For the researcher workflow, the conceptualization of sub-studies from the analysis of cohort data is shown, where the researcher can enable distribution and monitor the participant engagement and data collection. For the participant, it shows the modification and changes applied based on adaptations to the original study and the collected data being used to update participant information.

A researcher accesses an online end user interface to enter the targets/goals for the cohort study including, for example: study timeline, target recruitment number, final number of retained participants, key composition indicators (e.g., ethnic/racial diversity, geographic distribution, age distribution, prevalence of a specific disease, prevalence of a specific belief/attitude, prevalence of a specific symptom, etc.), desired sub-cohort or sub-study composition and size, etc. The system can provide the capability to execute predictive modeling simulations based on the parameters and targets specified, e.g., using synthetic data or historical data from other studies, to understand whether any of the parameters should be adjusted at the outset.

The computer system 210 can provide a researcher an online dashboard with real-time predictive analytics that provides decision support given the current dataset. For example, the system can indicate progress of a candidate pool or of data collection within a primary study towards each of the targets and parameters identified by the researcher for a desired sub-study. The system can provide calculated probabilities for achieving the targets in specified timelines and estimated date for when each will be achieved (including target composition or diversity of the cohort of participants). The computer system 210 can provide alerts warning the researcher if the recruitment, retention and composition targets will likely not be achievable in the timeline specified. The computer system 210 can provide alerts notifying the researcher when a threshold probability has been reached to permit a reasonably likelihood of successful recruitment. This can indicate the beginning to recruit for a particular sub-study/sub-cohort as the researcher specified. The computer system 210 can send alerts notifying the researcher to change recruitment and/or retention study to meet desired sub-study/sub-cohort size or composition. The computer system 210 can indicate recommended sub-study/sub-cohort study design based on the dataset available at any time (and based on pre-defined research statistical best practices around power calculations).

Figure 30:
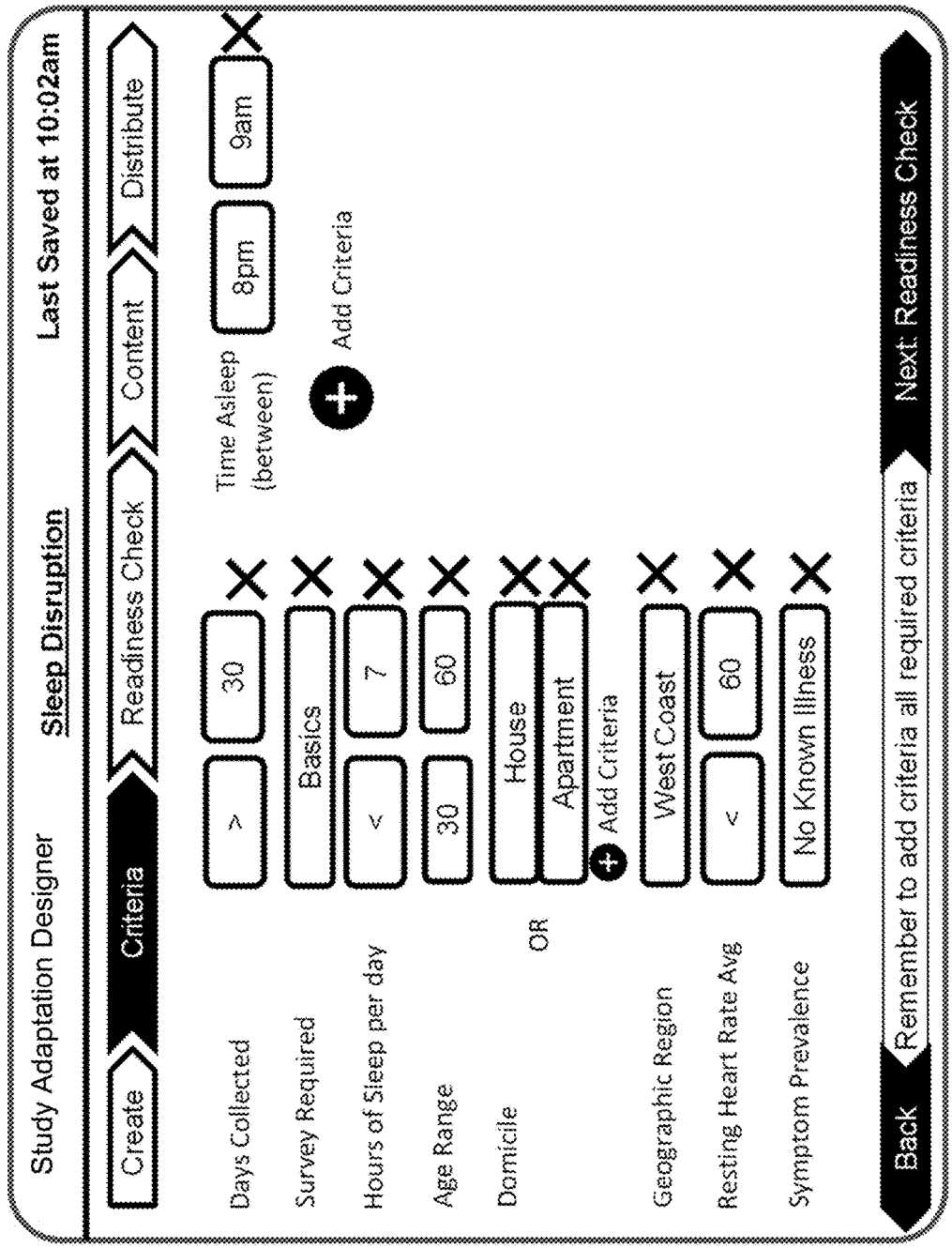
FIG. 30 is a user interface that the system can provide to guide adaptation of monitoring programs.

FIG. 30 is a user interface 3000 that the system can provide to guide creation of monitoring programs. The system 210 can provide user interfaces and other tools that enable a researcher or other administrator to initiate the creation of monitoring programs (e.g., a primary study and/or sub-studies). The tools can include an interface to design monitoring programs or specify adaptations to monitoring programs, where the interface provides interactive elements to receive user input specifying the objectives and characteristics desired for a monitoring program. In addition, the interface can provide information to assist the user in selecting parameters for the monitoring program, through recommendations, search results, statistics about candidate pools and database contents, etc. The system 210 can use the information a user provides about desired objectives and characteristics of a monitoring program, as well as historical data collected for other monitoring programs, to identify and recommend parameters that are predicted to facilitate meeting the objectives. The interface can provide predictions or measures to indicate the likely viability of a study being designed, such as the expected levels of data quality, participant retention, participant compliance with monitoring requirements, and so on given the sets of inputs that the user has provided.

The interface can guide the user through a series of view or operations in order to obtain the inputs and selections needed to complete the specification of a monitoring program or adaptation to a monitoring program. The process can include the system checking the viability of a monitoring program being designed (e.g., a primary study or a sub-study) to achieve certain outcomes, which can be determined by the system or can be specified by the user. The interface can also facilitate can loading or generation of content for the monitoring program and distribute the content to a group of selected participants from one or more monitoring groups (e.g., a cohort or multiple cohorts).

For example, the computer system 210 guides a user through various interfaces to specify the objective of a study (e.g., research question, topics, etc.) and parameters. This may include defining a study protocol, including recommending elements for the study protocol. The computer system 210 then receives criteria for selecting a cohort of participants, and the computer system 210 can recommend criteria to be used or adjustments to selection criteria, e.g., based on the sub-study characteristics the user indicated, based on data collected in the related primary study, based on historical data for many prior studies, and so on. The computer system 210 then assists the user in selecting participants to be included in a cohort for monitoring, determining which participants in a candidate pool are eligible according to the selection criteria defined for the sub-study. At each step in the process, the computer system 210 can evaluate the impact of the user's inputs and selections on the likely results of the sub-study being designed.

Figure 31:
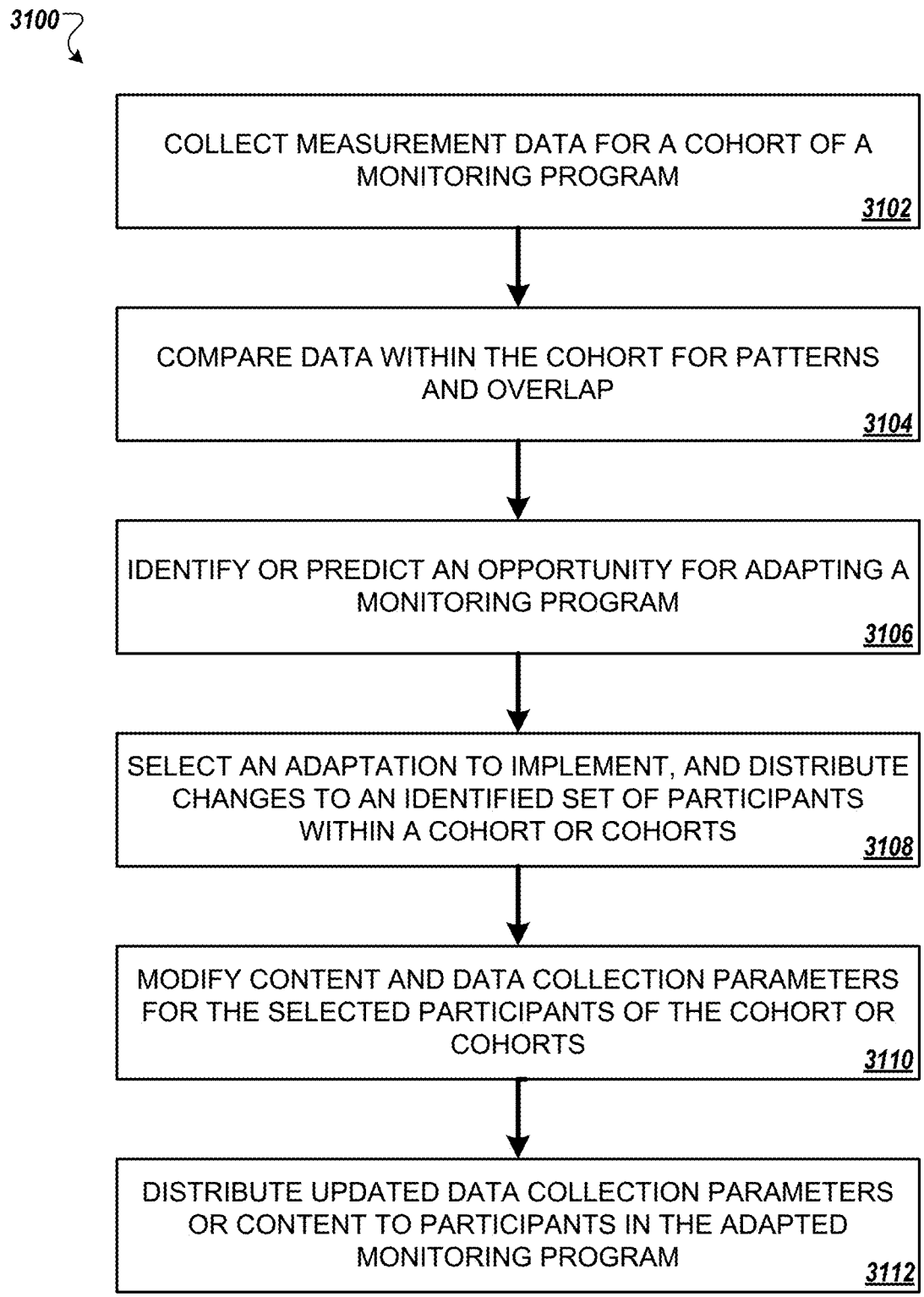
FIGS. 31-33 are flow diagrams showing example processes that the system can perform to create, manage, and adapt monitoring programs.

FIG. 31 is a flow diagram showing an example of a process 3100 that the system 100 can perform to create and manage monitoring programs. The process 3100 includes actions that the computer system 210 can perform, including collection of data for a monitoring program, analysis of the collected data to identify conditions for adapting a monitoring program, selection of adaptations to implement in the new monitoring program, adjustment or customization of the parameters of the monitoring program to carry out adaptation, and distribution of data packages to implement the adaptation to the monitoring program.

Figure 32:
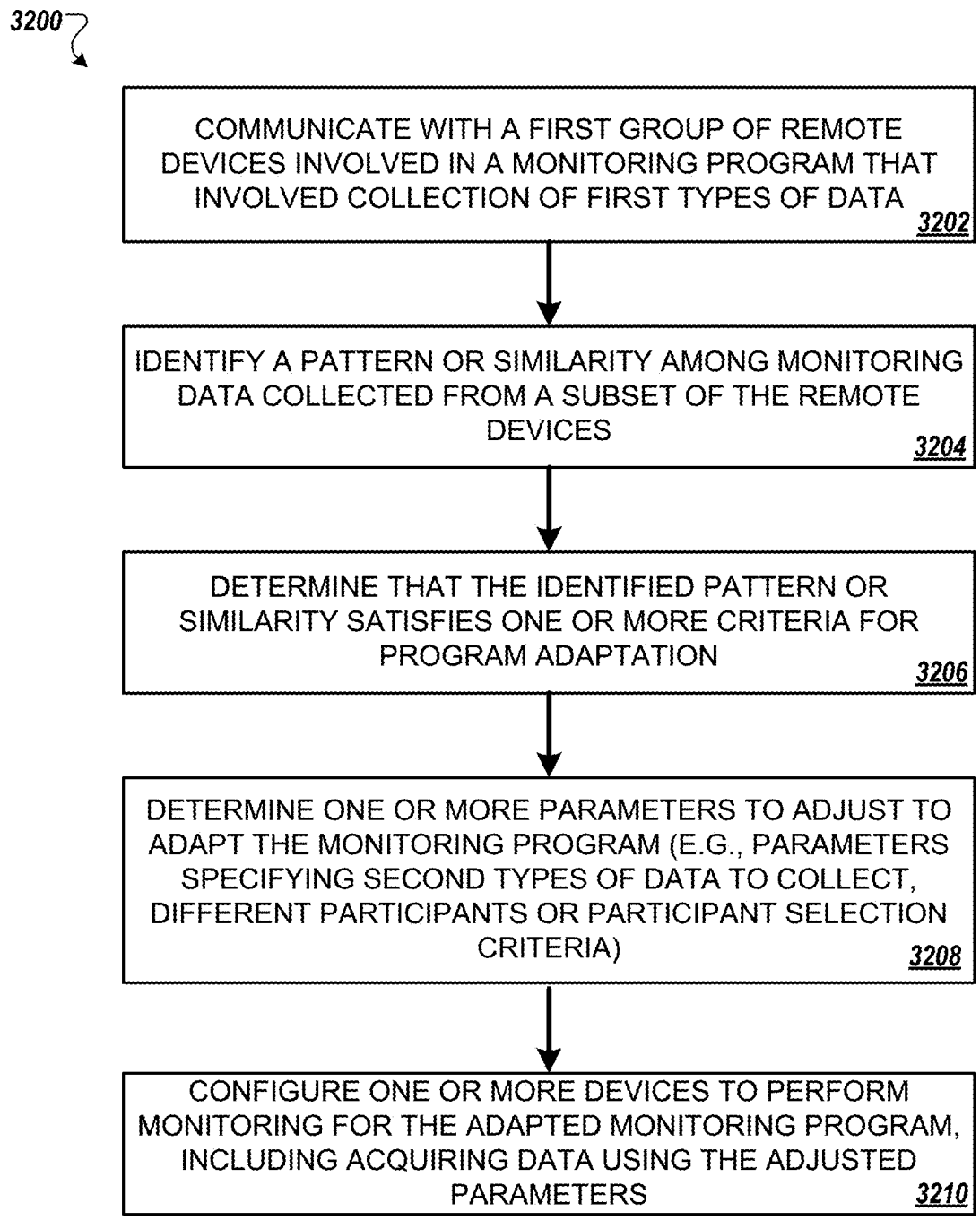

FIG. 32 is a flow diagram that illustrates a process 3200 for adapting monitoring programs. The process 3200 can improve the efficiency and effectiveness of monitoring using remote devices, including by adaptively changing monitoring to maximize monitoring coverage without the need to deploy or enroll large numbers of new devices. The process 3200 can be used by the system to leverage a set of existing monitoring devices, especially by expanding monitoring to a selected set that are predicted to provide or have demonstrated high data quality and reliability, which allows effective monitoring with fewer resources. Further, more intensive monitoring (e.g., which may require higher network bandwidth, higher power usage, greater user interaction, etc.) can optionally be limited by the system to the devices and contexts (e.g., environments, users, locations, etc.) that the computer system 210 determines are most likely to experience the events and conditions for which additional monitoring is needed. The events and conditions to monitor, as well as the factors that the computer system 210 uses to assess which devices are most likely to experience them, can be automatically detected by the computer system 210 from the monitoring data received and information about the devices and their users (e.g., device attributes, user attributes, device history, user history, etc.). These advantages can be provided without disruption to the original monitoring program, for example, by optionally layering in or integrating the further monitoring of a second monitoring program on top of the base level of monitoring provided by the original monitoring program.

Another way the computer system 210 contributes to high efficiency and effectiveness is by validating or verifying the likelihood of success of potential adaptations to monitoring programs, based on factors such as the likelihood of compliance by the available or selected devices and users (e.g., based on predictions or based on past history), the significance and relevance of the items to monitor, the statistical power that is expected to result from carrying out the adapted monitoring programs, and so on.

Beyond simply identifying significant items to monitor, the computer system 210 generates and implements the changes to monitoring by reconfiguring remote devices used for monitoring. This can enable transitions from one monitoring program to another, or to add a monitoring program, with little or no user action. For example, the computer system 210 can identify the types of data to be monitored in the second monitoring program and select the data collection techniques to be used. In general, "types of data" or "data types" herein refers to the characteristics or attributes to be monitored, e.g., the class or category of content to be detected or measured (e.g., heart rate, respiration rate, blood pressure, step count, etc.), not merely to the form of the data representation for that content (e.g., whether the data is expressed in binary, floating point, text, file type, media type, or other forms).

The computer system 210 can generate a program module or an update to a program module, comprising configuration data, device instructions, settings, software, communication profiles (e.g., Bluetooth profiles for connecting with other devices), and so on. The generated program module can specify types of data to collect, change sensor operation (e.g., activate or deactivate sensors, schedule sensor data collection, specify resolution or frequency of measurement, etc.), specify user interactions for the receiving device to perform (e.g., scheduled or context-driven interactions including notifications, media presentation, surveys, prompts, and so on). The computer system 210 can define criteria for selecting devices to participate in a second monitoring program, and select devices to participate in a second monitoring program based on the criteria, e.g., using a database that stores device profiles or user profiles that describe attributes, history, tracked monitoring compliance and performance, and so on. For the selected set of devices, the computer system 210 can deploy the generated program module or other configuration data over a network, such as the Internet, to cause the receiving devices to begin monitoring with the monitoring parameters for the second program module and continue to repeatedly perform monitoring and provide user interactions as specified in the program module and through further communication with the computer system 210 over the network.

The process 3200 can be performed by one or more computers, such as the computer system 210. The process 3200 shows how the computer system 210 can evaluate the monitoring data received for a monitoring program and detect results that are significant enough to justify further monitoring. The computer system 210 can then cause a change in monitoring, such as to initiate monitoring with changed parameters or under changed conditions for a subset of devices or users.

Monitoring programs can be designed by an administrator, such as a researcher. In general, the term monitoring program refers to a monitoring scheme that is designed and carried out, not to a computer program in particular. Nevertheless, one or more computer programs are often used to implement a monitoring program. A monitoring program is often defined and carried out using multiple components, such as program data, server-side components, and client-side components. The program data is stored by the computer system 210 and describes the monitoring to be done and the purpose for monitoring. The server-side components can include rules, content, software, and other elements that the computer system 210 uses to communicate with remote devices and process data collected from the remote devices. The server-side components can be used by the computer system 210 to cause remote devices to provide interactions with users or an environment, e.g., to present a survey for a user or to make a measurement with a sensor.

Each monitoring program can be different, for example, having its own objectives for monitoring (e.g., observation, testing safety, testing efficacy, testing dose response, etc.), selection criteria (e.g., defining which devices and users can participate), set of monitoring parameters (e.g., types of data to collect, procedures for collecting data, etc.), monitoring group (e.g., set of devices and/or users), content provided, user interfaces, etc. As a result, the computer system 210 can evaluate the collected data for each program with respect to the characteristics and objectives of the program to determine whether additional monitoring is warranted and, if so, how and for which participants the additional monitoring should be conducted.

For each monitoring program, the computer system 210 stores program data (e.g., a study protocol for a research study) that defines the monitoring program or describes aspects of the monitoring program. The program data, like a study protocol, can specify the reasons for performing monitoring and the manner in which data will be collected. In many cases, the program data can include or be derived from a study protocol. The program data can include items such as a research question, monitoring objectives, and methodology. This can include types of data to be collected, methods or techniques for collecting the data (e.g., types of devices or software to use), parameters for collecting data (e.g., data collection schedules, frequency of data collection, etc.), and so on. The program data can also indicate activities that participants are requested to perform, such as completing an in-office doctor visit, taking a certain medication (and potentially dose and schedule), performing various behaviors (e.g., parameters for sleep, exercise, diet, etc.), and so on. The program data can also indicate requirements for the monitoring program, such as selection criteria for participants (e.g., eligibility criteria, ineligibility criteria), targets or requirements for diversity among participants, constraints for numbers of participants (e.g., minimums, maximums, etc.), compliance levels needed for participants to comply with the various requirements, data quality needed, and so on.

The computer system 210 can the program data for various different purposes. For example, the computer system 210 can use any or all of the items in the program data to determine the relevance or importance of detected events and conditions, to gauge whether new or unusual items justify investigation with further monitoring. For example, measuring heart rate may have varying degrees of relevance to different programs, such as for those that study exercise (e.g., where heart rate is directly related to objectives of the monitoring program), a medication's safety (e.g., medium relevance, where changes in heart rate may be a side effect or health risk even if not a desired or expected effect of the medication), and diet (e.g., low relevance, as not related to the purpose of the program). The relevance of different measured items can be determined based on keywords and topics in the program data, from a class or category of objective of the program, from the set of items to be measured, and so on.

In some implementations, the program data may include or be part of a profile for a program, and the profile may include predetermined scores for the relevance of different topics, measurements, data types, data collection instruments (e.g., different surveys), and so on, and the computer system 210 uses the scores to evaluate whether discovered events, conditions, and relationships, when weighted according to the scores, are significant enough to justify proceeding with current monitoring. For example, headaches may be indicated to have a low relevance for a first monitoring program (e.g., a score of 2), so a few intermittent headaches reported may not meet the threshold for importance to justify adapting the study. For a second program, headaches may be given a higher relevance score (e.g., 8), and so the same level or of frequency of headaches may be sufficiently relevant to justify a targeted adaptation to further assess that that symptom.

In addition, the description of the program and its requirements can be used by the computer system 210 to determine the level of compliance with the requirements among participants. The requirements for data collection and participant activities provide the standard by which the computer system 210 can evaluate compliance of each individual with respect to their enrolled program(s). The program data for a monitoring program can also be used as a starting point from which to adapt the monitoring programs, so that that computer system 210 adapts monitoring programs for at least a subset of participants by applying changes to the current program data of the monitoring program (e.g., changing participant selection criteria, changing participant activities such as the dose of a medication to take, changing the types of data to be collected through sensors and surveys, etc.). The requirements for the number of participants and statistical validity can inform the system's decision of a number of participants to include in an adapted portion of a study, or whether an adaptation would be effective or suitable. In short, the program data can be used to determine whether to change monitoring or initiate new monitoring, which participants to involve in the new monitoring, what should be monitored in the new monitoring, and how the monitoring should occur, as well as in carrying out the adapted monitoring.

The process 3200 includes communicating with a set of remote devices involved in a monitoring program (3202).

The monitoring program involves collection of data from the remote devices over a communication network such as the Internet.

At the beginning of a monitoring program or at other times as needed, the computer system 210 can send a program module that includes software, configuration data, instructions, and other content that causes receiving devices to configure themselves to perform the types of monitoring needed for the program. This can include initiating sensor measurements, activating different sensors on a schedule, recording certain types of data, presenting surveys and other interactions for a user, transmitting data in a specified format or schedule to the computer system 210 or another server over the network, and so on. The program module can be received and processed by an operating system of a remote device or an application installed at the remote device. As a result, the remote devices involved in a program begin ongoing monitoring for a period of time, often for weeks or months, including repeated sensor measurements, surveys, and other interactions. The modules can be or can include modules as discussed in U.S. Pat. No. 9,858,063, issued on Jan. 2, 2018 and titled "Publishing Customized Application Modules," which is incorporated herein by reference. The modules can be or can include form data packages as discussed in U.S. Pat. No. 9,928,230, issued on Mar. 27, 2018 and titled "Variable and Dynamic Adjustments to Electronic Forms," which is incorporated herein by reference.

The communication can include the initial configuration of devices for a monitoring program, including the transfer of the configuration elements (e.g., configuration data, software, instructions, settings, etc.) that cause or enable the remote devices to perform the needed types of monitoring for the program. The provided program module can include rules, software, instructions, and content that enable the remote device to respond to different conditions and trigger notifications, sensor measurements, user interface, and other actions. The computer system 210 can also process the collected data from different devices and send further instructions to the remote devices to perform these and other actions.

The monitoring program can be configured for the remote devices to acquire and report data collected for first types of data specified by the first monitoring program. For example, a monitoring program may specify that remote devices should measure step count, GPS location, resting heart rate, and user-reported mood. The computer system 210 can receive, from each of the remote devices over the communication network, a series of messages including monitoring data collected by the remote device at different times for first types of data specified by the first monitoring program. For example, devices may send messages with the various measurements they determine as the measurements are made or as a batch once an amount of data or a time threshold is reached. For example, each of a set number of devices (e.g., devices of participants in a cohort for a research study) can send one or more messages daily to provide the data that the respective devices have collected.

The process 3200 includes identifying a pattern or similarity among monitoring data collected from a subset of the remote devices involved in the monitoring program (3204). The computer system 210 can be configured to use the monitoring data received to identify or detect any of various types of items that may prompt further monitoring, e.g., through an additional monitoring program such as a substudy for a principal research study. The evaluation of monitoring data can be done periodically (e.g., hourly, daily, weekly, etc.) or in response to each new data item received for the monitoring group. For example, for each of multiple monitoring programs that the computer system 210 administers, the computer system 210 may monitor the incoming data streams of monitoring data from remote devices in the monitoring group for the program and detect when events, conditions, patterns, similarities, or other items occur.

Many different types of items may be used by the computer system 210 to prompt the analysis of whether additional monitoring is appropriate. The types of items that prompt further monitoring can be events, conditions, relationships, contexts, situations, and more. For example, the values for monitored data items can be compared with thresholds to determine whether individual participants have experienced an event or condition that indicates further monitoring is appropriate. The detection to trigger further monitoring can be based on a single monitored item (e.g., a single type of sensor data) or a combination of multiple monitored items (e.g., a combination of multiple types of sensor data and/or survey responses). As a simple example, determining that three patients in a clinical trial experienced sleep disturbances or reduced sleep quality may provide the pattern or similarity to trigger an adaptation to measure sleep effects for participants having similar attributes as the three that reported the symptom (e.g., similar health status, same age range or age category, etc.). As discussed above, a wide variety of different monitored parameters and outcomes may be used to evaluate the potential for further monitoring, including detection of or absence of biomarkers, behaviors or changes in behaviors, physiological attributes or changes in physiological attributes, treatment side effects, symptoms, subjective reports from a participant, levels of efficacy of treatment, level of compliance with monitoring program requirements by patients, and more. The computer system 210 can be configured to look for events, conditions, and data patterns using any or all of the parameters measured for users, such as attributes of behavior (e.g., sleep, diet, exercise, social activity, travel, etc.) and user physiology (e.g., blood pressure, heart rate, respiration rate, blood oxygenation level, blood glucose levels, etc.), as well as combinations of these with each other and with contextual factors (e.g., time of day, location, user device movement or orientation, etc.), other user attributes (e.g., age, sex, race, ethnicity, etc.), and patient history.

As another example, a clinical trial for a medication may receive monitoring data indicating that, separate from the typical results of the main group of participants, a first subset showed a high effect of the medication and a second subset showed a low effect of the medication. As a result, after confirming other criteria are met (e.g., factors for significance of effect, sufficient cohort size, predicted compliance rate above a minimum, etc.), the computer system 210 can trigger an adaptation to monitor a set of participants that showed or are likely to show high effect from the medication, for example, to monitor additional factors (e.g., environmental, behavioral, etc.) that were not monitored as part of the original monitoring program but which may help explain the reason for the high effect. To facilitate this, the adapted or additional cohort can be selected by the computer system 210 to include an appropriate control group, such as individuals that experienced average medication effect. Other types of adaptations that may be designed to verify the results or rule out complications with more intensive monitoring, to monitor the patients after instructing a change to the medication regimen (e.g., to lower the dose of the medication, to change administration frequency, etc.), to combine the medication with a change in behavior (e.g., to instruct a behavior and test whether the behavior affects the outcome). Similarly, the computer system 210 can trigger another adaptation for a set of participants that showed or are likely to show the lower effect from the medication, for example, to monitor potentially causative factors for the low effect, to monitor other new effects or conditions that may be related (e.g., in related body systems), to verify the results, to rule out complications, to monitor effects of higher dose or other change in the medication, to monitor effects of a behavior change instructed to the participants, etc.

In addition to or instead of detecting predetermined types of conditions or events, the computer system 210 can identify conditions and events that arise even though these are not specifically or previously defined as triggering the assessment for further monitoring. For example, the computer system 210 can identify a pattern among the collected data of different participants, a similarity or commonality among participants and their collected data, trends indicated by the collected data for individuals and the overall set of participants, outliers among the collected data, and so on. These elements provide the computer system 210 versatility to identify the occurrence of unusual or unexpected situations.

The computer system 210 has multiple techniques that it can use to detect or identify items to evaluate further as triggers for potential adaptation and new monitoring. In some cases, the pattern or similarity detected may be as simple as determining that at least a minimum number of participants experienced a certain outcome, such as a certain event, monitored result, behavior measure or physiological measure in a certain range or category, etc. In other cases, the pattern or similarity may be more complex, such as detecting a trend or progression in measured values that differs from the rest of the monitoring group, determining that each of multiple attributes and outcomes are shared among a subset of the monitoring group, and so on.

One technique is simply for the computer system 210 to look for patterns or similarities among the received monitoring data that are different from the expected or desired results of the monitoring program. For example, in a study about exercise and diet, a small number of participants may have data that indicates declining sleep quality or may report sleep disturbances. Whether or not the original program was configured to monitor sleep for participants, the computer system 210 can detect the sleep changes or sleep problems for multiple individuals as a potential reason for further monitoring with additional emphasis on the interaction of sleep and potentially other sleep-related factors with the elements of the monitoring program.

Another technique is to compare monitoring data with reference levels, which can be determined from data sources outside the monitoring results for the current program, e.g., standard ranges for physiological measurements and behavior which may be from other research studies. References (e.g., thresholds, ranges, etc.) can be set for any or all of the types of data measured in a monitoring program (e.g., heart rate, blood pressure, respiration rate, self-reported pain levels, mood levels, etc.), and the references may be tailored to the context of the monitoring program (e.g., studying diabetes, or hypertension, or other situations) or to the participants (e.g., taking into account the participants' individual or average attributes such as age, sex, height, weight, etc.).

Another technique is the comparison of collected data among the participants in a monitoring program. Even if a participant has monitoring result that is within a normal range for the general population, the values still may be significantly different from other individuals in the same monitoring program. Comparison with monitoring results of others participating in the monitoring program may uncover valuable information, such as sets of participants that have higher or lower response to a medication, participants that may have different health risk profiles than others, participants with significantly different environments or contexts, and so on. The computer system 210 can evaluate a distribution of measured results and identify those with the highest and lowest values for different parameters. The difference in measured results between the groups or individuals with the highest and lowest results with respect to the rest of the group of participants can indicate. For example, a group of participants in a cohort having results that are at least a threshold amount (e.g. 20%, 50%, etc.) above or below the average for a cohort can trigger evaluation whether this occurrence justifies a sub-study to evaluate the result further or explore the causes or related effects.

Accordingly, the computer system 210 can determine the aggregate measures for a monitoring for each of different measured parameters (e.g., those in the first set of data specified by the first monitoring program). This can include determining averages (e.g., mean, median, etc.), characterizing a distribution of results (e.g., expected value, standard deviation, variance, etc.), determining a histogram for values, and so on. Another way the computer system 210 compares monitoring results among the monitoring group is through clustering. The computer system 210 can perform different clustering operations, based on different types of data collected or combinations of them, to cluster the participants according to the measured outcomes and/or characteristics of the participants, then compare the clusters to identify outcomes or subgroups of participants for further monitoring. For example, the computer system 210 can cluster participants based on any of various sensor measurements, survey responses, compliance levels (e.g., amount or rate of compliance with requirements for data collection or participant activities), health results, device performance, or other characteristics or outcomes of a device or user. The computer system 210 can then evaluate the size and composition of the clusters, especially to compare the aggregate data for the respective clusters (e.g., average values for outcomes or participant characteristics, characteristics of distributions of values for devices or users within the clusters, consistency or variance for values within the cluster, etc.). When the differences between the clusters reaches a threshold level of significance (e.g., such at least a minimum percentage difference in average measured value for a smaller cluster compared to an average cluster or the largest cluster), the system can identify a potential opportunity for adaptation to perform further monitoring.

In some cases, the identified features that resulted in the clustering may, at least in part, provide a pattern or similarity that triggers further monitoring. For example, a program may use the size of a cluster or other characteristics of a cluster as a basis for identifying a new reason for a monitoring program.

The computer system 210 can use the longitudinal data collection for individuals and the set of groups as a whole, comparing recent monitoring results with previous values. The measured values for an individual can be compared with previously measured values for the individual. For example, the computer system 210 can look at each individual's prior reported data an establish a baseline level or a trend for the individual, for each of various monitored items. The computer system 210 can then detect when the individual's own monitoring data subsequently deviates significantly (e.g., more than a predetermined threshold amount) from the baseline or when the trend changes. The computer system 210 can compare the baseline levels and trends for different participants to identify whether further monitoring is needed. For example, if the majority of the monitoring group shows a gradual upward trend for a monitored parameter (e.g., step count) but a subset of participants shows a different trend (e.g., flat, downward, etc.), the computer system 210 may determine that the less-common trends may justify adaptation of the study and further monitoring.

While many of the examples discuss using occurrences involving a minority of individuals as a basis for further monitoring (e.g., those with measured effects outside a normal range or outside a main grouping of results, outliers, etc.), this is not always the case. For example, the computer system 210 can also be used to determine additional monitoring programs to evaluate variations of the entire monitoring program, including for those that are experiencing good health outcomes and normal monitoring results. For example, the computer system 210 can identify a majority of participants that are responding well to a medication, and so share this similar outcome. The computer system 210 can also identify a subset from this group that has a high rate of compliance or high data quality, which makes them ideal candidates for further monitoring. The further monitoring may simply be to acquire a more detailed data set, e.g., with more frequent measurement and/or more types of measurements, than is obtained from the original monitoring program. As another example, the computer system 210 may make adaptations that alter one or more parameters of study protocol, to test different changes (e.g., incrementally higher medication dosage, incrementally lower medication dosage, combination with another medication, changed medication frequency, added or removed constraints on user behavior, added or removed user activities as part of the monitoring program, etc.). The types of changes to be made can be based on a range given by a researcher, such as a researcher indicating a desire to test various dosages from 10 mg to 50 mg daily, and the computer system 210 automatically identifying appropriate subsets of participants and timing to generate and begin the sub-studies to gradually reach those goals (e.g., while the computer system 210 also confirms that safety and efficacy requirements continue to be met). Other reasons for a sub-study can be determined by the computer system 210 based on factors tested in other studies and related sub-studies (e.g., adding in measurement of factors measured in other research), or based on databases with data indicating relationships between factors such as behavior, medication, patient attributes, and health effects (e.g., to extract factors and items to measure that are known to have relevance to a topic or portion of the monitoring program).

The computer system 210 can use a defined set of markers in its evaluation of whether an appropriate commonality or similarity prompting further monitoring has occurred. For example, the occurrence of certain markers among participants, or a set of participants each exhibiting a marker, can be triggers to perform adaptation of a cohort or of monitoring methodology. If the measured values or contexts for a marker are present, the computer system 210 can assess whether to perform further monitoring for that marker and potentially other related items. For example, if a marker for fatigue occurs due to decreased movement, decreased mood, or other measured parameters, the computer system 210 can perform analysis whether to perform further monitoring for a broader range of data types or markers related to fatigue and potentially other conditions as well (e.g., additionally measuring sleep quality and exercise levels to examine potential causes or related items). The computer system 210 can store a set of marker data that specifies different markers and the data types and values for those data types (e.g., threshold levels, ranges of values, combinations of conditions) that cause a marker to be present. A general set of markers can apply to all programs, or sets of markers can apply to certain categories or types of programs, or individual programs can have specific markers that are relevant specified for them. In addition to or instead of looking at the measured data directly, the monitoring data can be used to determine the presence or absence of different markers at different times for the participants, and the computer system 210 can use the similarity or commonality of the marker occurrences for the participants as a basis for further monitoring.

The computer system 210 may look for the occurrence of predetermined types of events or conditions, such as indicators of safety risks or symptoms or predetermined markers. These may include events or conditions that are relevant generally across multiple or all programs or are specified particularly for a specific program. The detection may include comparison of collected data (e.g., physiological parameters, survey responses, etc.) with corresponding references, which again may be defined generally (e.g., a standard range for healthy blood pressure) or specifically for a program.

The process 3200 includes determining that the identified pattern or similarity satisfies one or more criteria for program adaptation (3206). Not every detected commonality or similarity justifies enhanced monitoring and accompanying additional power usage, CPU usage, storage utilization, user burden, and other impacts. In addition, there are practical limits to the number of participants, cohorts, and data types to monitor that are feasible and desirable. As a result, the process 3200 can include filtering the many adaptation options to remove those that do not meet minimum requirements. This helps the computer system 210 to ensure efficiency and effectiveness by eliminating adaptation options that would not provide sufficiently valuable monitoring data or have a low likelihood of successfully achieving their monitoring objectives. The computer system 210 can score and rank different sub-studies based on their estimated value or likelihood of success, for sub-studies options that the computer system 210 identifies and to evaluate adaptations that researchers propose (e.g., providing likelihood of success or classifying the value of expected results from an adaptation defined by parameters a user specifies).

Many different factors can be used to evaluate an adaptation opportunity. For example, the criteria can include constraints based on the nature of the event or condition that prompted potential further monitoring, for example, minimum thresholds for (1) relevance or importance of event or condition (e.g., a sleep disturbance) that provides the new adaptation opportunity, (2) frequency or consistency of the event or condition (e.g., whether the event is repeated for participants affected, and how often), (3) severity or intensity of the event or condition (e.g., magnitude of sleep disturbance, amount of change in sleep per night, level of discomfort patients report the sleep disturbance causes, amount of difference from the average in the monitoring group, etc.), (4) prevalence of the event or condition (e.g., how many participants experienced the sleep disturbance, a percentage of the participants that experienced it, etc.), and/or (5) reliability or accuracy of the data indicating the event or condition (e.g., accuracy and precision levels for the participants generally and for those that report sleep disturbances). The computer system 210 can set minimum thresholds for these or other factors and filter out new adaptation opportunities that have measures or scores for the factors that do not meet one or more of the minimums. The minimums or other thresholds for these factors can be based on general reference levels, such as general behavior and health standards or norms (e.g., average or typical sleep characteristics for a large population or as established in medical research). As another example, the thresholds can be based relative to baselines or measures for the other members in the monitoring group, e.g., setting thresholds for sleep characteristics and other parameters based on the aggregate measures for a research study cohort and comparing As another example, the computer system 210 can use a holistic scoring method that takes a weighted average of scores for the various factors as a combined score for the adaptation opportunity. Then the computer system 210 can filter out opportunities that are assigned combined scores that are below a threshold, or the computer system 210 can rank opportunities according to the combined scores and select only a highest-ranked subset to proceed with evaluating and potentially implementing. As a simple example, scores for relevance, prevalence, and intensity can be determined for each identified pattern or similarity, with each score being set on a scale of 0 to 10. The component scores can be added to get the combined score. The computer system 210 may set a minimum combined score threshold of 20 that needs to be reached before the computer system 210 recommends a new monitoring program or generates a monitoring program. The relevance score can indicate a degree of match between the topic or type of data in the pattern (e.g., sleep disturbances reported) and the objective of the study. This can be done by using relevance weights for topics and data types that are set in a profile for the program. Another option is for the computer system 210 to store a general-use taxonomy that specifies levels of connection between different topics (e.g., sleep, exercise, diabetes, etc.) and data items (e.g., sleep duration, sleep quality score, resting heart rate, etc.). The computer system 210 can use the weights or scores for connections in the taxonomy (e.g., as weights for edges between nodes for different topics or data items) to determine the closeness or relevance of the topics and data types involved in the pattern to the objectives of the original monitoring program. The score for prevalence could be a percentage of the members of the cohort that experienced the effect, capped at 10. The score for intensity could be based on user self-reports of severity (e.g., pain on a scale of 1-10, level of sleep disturbance on a similar scale, etc.) or may be determined based on mapping differences in measured parameters to a scale. For example, based on a baseline 7 hours of sleep, recorded sleep amounts of 7, 6, 5, and 4 may be assigned intensity scores of 0, 2, 5, and 8, respectively, to give higher scores for increasingly large deviations from the baseline.

The computer system 210 can also use machine learning to evaluate different types of events, conditions, and other patterns and similarities identified. For example, as different patterns occur in monitoring data, the computer system 210 can provide information to researchers and ask the researchers to rate their importance or suitability for new monitoring. Similarly, the computer system 210 can indicate the identified results and propose new monitoring based on them. The researchers ratings of importance and/or decisions whether or not to pursue adaptation or additional monitoring for those features can serve as input to train or adapt the models that evaluate the different monitoring results in the future.

The models can be machine learning models, rule-based models, statistical models, or other types of models. As the computer system 210 receives additional input through cycles of informing researchers of monitoring opportunities and receiving the feedback about which justify further monitoring, the computer system 210 trains the models to increasingly learn the characteristics of data patterns that represent strong monitoring opportunities, so the computer system 210 can score new identified outcome patterns or classify how well the identified patterns fit the examples of those determined to justify adaptation before. For example, the model can be a classifier that, in response to receiving input feature values about an identified pattern (e.g., frequency of a condition, severity, intensity, etc.) and potentially the nature of the primary study (e.g., topic, objectives, key words, types of measurements made, etc.), the classifier outputs a score indicating how likely the event is to justify a follow-on monitoring program (e.g., a sub-study). For example, the classifier can output a confidence score indicating a level of similarity between the input set of features values and examples sets of input feature values that were labeled as representing adaptations that were accepted and applied.

The computer system 210 can perform this learning in the context of the parameters and aggregate results of the monitoring program. For example, a primary research study about a diabetes medication may result in 5 sleep disturbances reported in a certain time period, such as the first week. When a researcher determines to perform an adaptation or sub-study based on these events, the computer system 210 includes in the training data for the example the objectives, monitoring procedures, medications taken, cohort characteristics, study protocol contents, and other aspects of the primary research study. As a result, the computer system 210 can train and use models that learn not only the factors and characteristics that make further monitoring suitable generally but also the differences in importance of the factors for different types of studies. This allows the computer system 210 to make context-dependent evaluations, using factors such as the topic of the primary study, the objectives of the research study, the number of current or previous sub-studies, and so on. When evaluating potential for adaptations for a particular study, the evaluation can thus be made to emphasize or give higher weight to the examples of adaptations performed, or to examples of adaptation opportunities rejected, for studies most similar to the particular study for which results are being evaluated. The computer system 210 may learn that, for example, adaptations involving sleep are particular important for studies regarding exercise, or that adaptations are most often initiated for cardiology research when a symptom persists for more than a day, or that further monitoring is initiates most often after one month but before three months in diet-related studies. These relationships within the models can enable more accurate, customized identification of the reasons that would justify adaptation for different monitoring programs.

The process 3200 includes, in response to determining that the identified pattern or similarity satisfies the one or more criteria, determining one or more parameters to adjust in order to adapt the monitoring program (3208). Having identified a condition that likely justifies an adaptation (such as further monitoring or a change in cohort characteristics), the computer system 210 can select parameters that specify how the adapted program will operate. The parameters can indicate changes or differences for data collection with respect to the original monitoring program or the most recent set of parameters used in the program if previously adapted. The parameters can specify the types of data to be collected in the adapted program, including the physiological and behavioral attributes to be measured. The parameters can also specify the manner of collecting the data, e.g., data collection mode (e.g., active sensing, passive sensing, user input, etc.), which tools or instruments to use (e.g., different devices, software, sensors, surveys, etc.), timing of data collection, frequency of data collection, etc.

As an example, a research study about diet and exercise may involve collection of daily step count and twice-daily resting heart rate with a wrist-worn activity tracker, as well as collection of daily responses for a surveys about diet and general health. From the result data received in the first month, the computer system 210 may detect that a small group of participants experienced increases in resting heart rate significantly different from the trend of the other participants. With the set of results having sufficient commonality and relevance, the computer system 210 can determine that the criteria for considering further monitoring is met, and so the computer system 210 can determine monitoring parameters to better characterize the outcomes detected as well as potential causes and other potentially-related effects. For example, the computer system 210 can determine to increase the frequency of resting heart rate measurement to once an hour and also add a survey about mood (e.g., to determine if anxiety or other conditions may be involved).

The computer system 210 can use several techniques to identify types of data to monitor and the parameters to use for monitoring. The types of data involved in the outcome that prompted further monitoring (e.g., heart rate in the example above) can be included and the level of monitoring (e.g., frequency, accuracy, precision, etc.) can be increased. In addition, the computer system 210 can access a taxonomy of data types and topics (e.g., symptoms, diseases, body systems, etc.) and their relationships. For example, the taxonomy can be a graph in which different topics and data types are nodes, and connections among the nodes have weights that indicate the strength of the relationship. For example, the data types of heart rate and blood pressure can have strong connections with exercise, cardiology, heart disease, etc., moderate-strength connections with topics like headaches, migraines, fatigue, etc., and low-strength connections with even less-related items such as sleep quality, diabetes, etc. Given the identified pattern relating to heart rate in a study about diet and exercise, the computer system 210 can look up the connection scores branching out from the heart rate, exercise, and diet nodes and select data types based on the strength of the connections, e.g., those that have a connection greater than a minimum threshold or a distance less than a maximum threshold.

As another option, the computer system 210 may store tables or other data structures that map different topics or data types to others. These can provide predetermined sets of data to obtain or predetermined levels of monitoring to perform to investigate the causes and effects of different outcomes. For example, the parameter heart rate, like many others, can be mapped to a corresponding set of data types to acquire that represent factors known to be related to heart rate, such as diet, fitness level, medications, etc. The parameters and procedures for acquiring these types of data can also be retrieved in the same way, e.g., to determine a particular survey to assess diet, a survey for medication usage, a set of movement or actigraphy tracking measurements for fitness information, etc.

For example, a small group of participants in a monitoring program may exhibit symptoms of depression, e.g., low or decreased measures mood, social activity, and travel from surveys and sensor data. The computer system 210 can store data that specifies markers for different health conditions or risks, including markers that can be defined in terms of one or more of physiological measurements, self-reported survey parameters, monitored behavior, device usage, and so on. Using the marker data, the computer system 210 can determine that the collected data includes markers for depression for a subset of participants. Using the program data that describes the nature and objective of the monitoring program, the computer system 210 then determines that the criteria for further monitoring are met (e.g., depression is sufficiently relevant to the program, the markers are detected among at least a minimum number of individuals and with at least a threshold level of reliability and duration, etc.). The computer system 210 can then access mapping data that maps various items (e.g., topics, health conditions, health risks, etc.) with measurement parameters and measurement techniques. For example, the mapping data can associate the topic of depression with one or more surveys to present, as well as recommended timing to present the surveys (e.g., daily, or triggered in response to a detected context or pattern, etc.).

In some cases, the additional data types are expanded beyond those known or expected to be related to the outcome prompting further monitoring. For example, if a heart rate increase is detect in a study involving a medication, this could be a sign of potential toxicity, and so the computer system 210 may select data types to monitor that would capture multiple other potential signals of toxicity, even if these are not related to cardiology or heart rate in particular.

In addition to setting data types to be monitored and the techniques and parameters for carrying out the monitoring, the computer system 210 can set other requirements for participant activities. For example, the computer system 210 can determine changes to medication dosage, diet, exercise, sleep, and other behaviors. These changes can be based on predetermined rules that indicate variations of participant activities that may be required. For example, one rule may indicate that, for a group in which safety criteria are met and effectiveness is low, an incremental increase in dosage (e.g., 25% increase, as long as it is within predetermined limits) is appropriate for an adaptation (e.g., for an additional treatment arm or sub-study for the monitoring program). Similarly, another rule may indicate that where safety criteria are met and effectiveness is high, an incremental decrease in dosage (e.g., a 25% decrease, as long as safety criteria are met) is appropriate for an adaptation. Different sub-studies can be evaluated or generated for different purposes and some, such as evaluating dose response, may include changes to participant activities while other study types may instead simply focus on more extensive monitoring or different monitoring with the same participant activities.

The computer system 210 can determine many other parameters for further monitoring besides the data collection types and procedures. When the computer system 210 determines that an identified pattern or similarity among the monitoring data meets the criteria discussed above, the computer system 210 can perform various other steps to evaluate the potential for conducting further monitoring, inform researchers, and, if appropriate, generate the new monitoring program that can conduct the monitoring needed. For example, the computer system 210 can perform actions such as:

evaluate similarities in attributes and history of users and devices involved in outcomes prompting further monitoring, generate selection criteria that indicate criteria for determining eligible participants, use the selection criteria to select particular users and/or devices as candidates for a new monitoring program (e.g., selecting a sub-study cohort), make predictions regarding monitoring program characteristics and outcomes, evaluate the viability of the potential new monitoring program, generate the new monitoring program (e.g., study protocols, software and configuration data, parameters such as participant activities, duration, cohort size, etc.)

communicate information about the new monitoring program to researchers and other program administrators, and update models with feedback from researchers and results of monitoring programs.

In some implementations, the computer system 210 can evaluate similarities among the devices and users involved in the outcomes that prompted the opportunity for adaptation. As a factor in assessing whether the identified pattern is suitable for triggering an adaptation, the computer system 210 can assess the distribution of different attributes among the set of users or devices involved in the pattern. For example, if 10 participants out of 200 experience sleep disturbances, the computer system 210 can identify similarities among the attributes of the 10 participants that may be correlated with the sleep disturbances experienced. The result may be similarities in demographic attributes, health status, history, behavior, context, or other aspects. By examining the similarities among the subset of the monitoring group involved in the pattern, the computer system 210 can evaluate whether there are shared attributes or combinations of attributes that set the members of the subset apart from others in the monitoring group and may make the outcomes in the identified pattern more likely. If so, the shared or similar attributes can provide the computer system 210 an opportunity to narrow the focus of the adapted monitoring on the participant types, device types, contexts, or other factors that are most likely to experience the outcomes in the pattern of interest. If similarities or correlations among the subset are not found, then further monitoring may still be performed, but a more general set of selection criteria may be needed, and consequently a larger cohort may also be needed to investigate the pattern of interest.

In selecting participants to monitor in an adapted monitoring program, the computer system 210 can include a variety of candidates in addition to those who experienced the outcomes that prompted additional monitoring. For example, if five people in a clinical trial experience sleep disturbances, those five people may be included in a sleep-related sub-study, but the computer system 210 can additionally expand the sub-study to others who have characteristics in common with or similar to the five that experienced the sleep disturbance. As a result, the sub-study may include fifty people from the original study who are in a same category for age, health status, etc. Expanding the sub-study in this way allows the computer system 210 to provide monitoring that is more likely to capture information describing the onset of events and conditions that prompted the adaptation, providing information to characterize the environmental factors, user actions, behavioral factors, context, etc., and the progression of health parameters over time that make the event or condition more likely or less likely. This technique also provides a larger representative sample, allowing the system to better characterize the frequency or likelihood that the event or condition will occur. In some cases, the computer system 210 may apply other criteria to the selection of the subset for the sub-study, which may cause some or all of the five people that experienced the sleep disturbance to be omitted. Examples include requiring a minimum level of historical or predicted compliance with study requirements, a minimum historical or predicted data quality from monitoring, device compatibility with the requirements of the sub-study (e.g., whether a user's phone, watch, activity tracker, etc. have the sensors, software compatibility, or networking capabilities, etc. to participate), health requirements for a participant, meeting eligibility criteria, etc. Thus, even one of the participants whose experiences or monitoring data lead to the creation of the sub-study may be omitted if, for example, the participant's compliance history is poor or the participant does meet one of the criteria for inclusion in the cohort.

The computer system 210 can determine selection criteria with which to select devices or users for the new monitoring program. The computer system 210 can start with the selection criteria for the existing monitoring program, which may set various conditions for participant attributes (e.g., age, health status, physiological measurements in certain ranges, etc.), for device capabilities (e.g., a requirement for users to have a smartphone, an activity tracker, or other technology), behavior, history, etc. The selection criteria can include inclusion criteria (e.g., attributes that participants are required to have) as well as exclusion criteria (e.g., attributes that, if present, disqualify a candidate from participating). From the original selection criteria, the computer system 210 can apply additional restrictions to narrow the scope of the selection criteria, to focus in on the attributes and context for which the pattern or similarity occurred which prompted monitoring. For example, a study cohort may include 200 people in an age range from 18 to 67 years old. Of the cohort, a subset 10 people may experience sleep disturbances or some other symptom or difference in outcome compared to the rest of the cohort. The computer system 210 may determine commonalities or similarities among the subset, such as that they each were over age 40 and had low levels of physical exercise. From this, the computer system 210 generate selection criteria tailored to address this context or set of attributes, by adding additional selection criteria that participants for the new monitoring program should be over age 40 and have low exercise levels. This allows the new monitoring program to include participants of the same or similar type as those that experience an outcome of interest, to monitor the likelihood or occurrence of that outcome in a context where it seems likely to occur. The computer system 210 can include the participants for whom the outcome has already been detected (e.g., the 10 with the sleep disturbance). The selection criteria enables selection of others that have similar backgrounds and characteristics, and so monitoring them can investigate the onset of the outcome in the context where it is most likely, as well as assess the prevalence or likelihood at which the outcome occurs in a systematic way, with more detailed monitoring than in the monitoring program prior to adaptation.

In some implementations, the computer system 210 may set selection criteria that includes more than just the range of backgrounds linked to the pattern of outcomes to be measured. For example, one or more shared attributes can be set as requirements for selection, while one or more other shared attributes are not required, so that the new monitoring program cohort can collect data that allows the contrast between the results of the two groups to be determined. For example, even if the sleep disturbance symptoms occurred mostly in people that had low exercise, the computer system 210 may not restrict eligibility based on exercise, to allow a range of exercise levels that can help determine the impact of those different levels on the outcome.

Another factor that the computer system 210 can consider in setting the selection criteria is the size of the candidate pools and the quality of candidates (e.g., historical and predicted levels of enrollment, retention/study completion, compliance, data quality, etc.) for different combinations of the attributes that may be restricted. For example, if a subset experiencing a symptom has three different similarities identified, e.g., most of the subset is in a particular age range, has a certain gene variant, and has high social activity. The computer system 210 can determine, for each of these three factors and for the different possible combinations of them, the number of candidates (or specifically high-quality candidates with good predicted retention, compliance, etc.) that would meet the criteria from among the cohort for the original monitoring program. For example, out of 1000 people in the original cohort, 300 may be in the appropriate age range, 15 may have the gene variant, and 234 may have high social activity. Only 7 individuals may have all three factors. Optionally, the computer system 210 can expand the search for candidates outside the cohort for the original cohort, such as to find candidates in other cohorts or from a database of potential participants. The computer system 210 can compare the number of candidates identified for the different sets of possible selection criteria with a minimum threshold, such as a minimum of 50 individuals needed. This minimum can be a predetermined level or can be calculated by the computer system 210 to determine a level needed to achieve a desired statistical power. The computer system 210 can then select selection criteria determined to leave enough qualifying candidates to allow the new monitoring program to meet the minimum levels. When there are similar numbers of candidates available for different combinations of selection criteria, the computer system 210 may prioritize individual requirements (e.g., age requirement vs. gene variant) according to the degree of correlation to the outcome to be investigated. For example, if the age distribution is relatively wide but the presence of the gene variant is in nearly all members of the subset, the computer system 210 can determine to prioritize the gene variant criterion over the age criterion as it is more linked to the outcome to be investigated.

In some implementations, when determining selection criteria, the computer system 210 may expand the selection criteria to be broader in some respects than the original selection criteria for the monitoring program. For example, a research study may detect a symptom for a subset of people in which a majority have a particular gene variant or other attribute. The selection criteria for the primary monitoring program may limit participants to those residing in a certain geographical area or who have certain factors in their medical history. The computer system 210 may omit these requirements from the selection criteria for the new monitoring program, to expand the pool of potential candidates.

With the proposed cohort(s) for the adapted study, the computer system 210 can evaluate the likely results using historical data, statistical models, machine learning models, and so on. For example, given the attributes of the participants in the cohort(s), the computer system 210 can make predictions regarding the composition of the cohort(s) that would be enrolled (e.g., size, diversity of participants (such as distribution across different attributes of interest), etc.), composition of the portion of the cohort(s) expected to comply with the protocol requirements, and other factors.

The computer system 210 can evaluate the viability of the potential adapted monitoring program, based on the characteristics of the new monitoring program (e.g., data types to collect, parameters specifying how to collect the data, participant activities, etc.), the pool of candidates, and/or a specific set of candidates identified for the new monitoring group. For example, given the attributes and backgrounds of the people in a proposed cohort, the computer system 210 can assess: whether expected rates of enrollment, retention/completion, compliance, and sufficient data quality meet minimums; whether the proposed cohort meets the minimum size constraints; whether the cohort provides at least a target level of statistical power; and whether the cohort provides sufficient diversity for attributes of interest (e.g., age, sex, race, comorbidities, geographic location, etc.). For example, the computer system 210 can consider whether there are sufficient candidates to support the adapted study in the monitoring group for the original monitoring program or in other pools of candidates (e.g., in cohorts for other research studies, in a database of historical research study participants, in a database of individuals indicating interest in participating in research, etc. Even if a pattern of outcomes warrants further monitoring, if the pool of candidates is too small support a successful study (e.g., 7 people meeting needed criteria and 50 needed to provide a usable data set), the computer system 210 may determine that the adaptation is not viable and so should not be recommended or conducted.

The computer system 210 can also determine if the set of requirements of the new monitoring program can be met by technology available to be used in the adapted monitoring program, such as whether devices associated with the proposed cohort members are capable of performing the functions needed. The computer system 210 can evaluate the capabilities of user devices and select technology options to be used in a new monitoring program using the techniques discussed in U.S. patent application Ser. No. 16/877,162, filed on May 18, 2020 and titled "Monitoring Technology Usage and Performance," which is incorporated herein by reference.

To evaluate different monitoring opportunities, the computer system 210 may use machine learning and other modeling techniques to learn the characteristics of adaptations that provide high value and successful monitoring results in different situations. For example, in research literature or shared databases of research data, adaptations that researchers designed and used provide examples of adaptations that were considered worthwhile. In addition, the examples of adaptations can be labeled or scored based on the types of results achieved, e.g., levels of completion achieved by participants (e.g., retention, compliance, etc.), data quality achieved, statistical power achieved, whether the sub-study achieve its objectives or addressed the corresponding research question, etc. With these examples, the computer system 210 generates or trains models that can classify the data describing a proposed adaptation (e.g., the pattern or outcomes that prompted further monitoring, the data to be collected, the requirements for participants to meet, the composition and attributes of the proposed cohort, etc.) based on its similarity to the adaptations selected and/or were labelled as successful. In some cases, rather than processing data about the new adaptation alone, the models can process input describing both the proposed adapted study as well as the original study. This way, the models can evaluate how similar a current study/proposed adapted study pair is to the examples of study/adapted study pairs that were successful.

Any or all parameters of a study can be extracted for use in training models and evaluating adaptations, e.g., topic of study, field of study, disease or health aspects involved, research question keywords, type of study (e.g., medical device vs. medication vs. digital therapeutics; Phase 0, Phase I, Phase II, Phase III, etc.), objectives for the study (e.g., safety testing, efficacy testing, observation, toxicity testing, dose response testing, etc.), cohort size, data types collected, frequency of measurement, participant selection criteria, study duration, devices used, study protocol content, participant activities, and so on. The parameters of the original and adapted studies, showing the type of adaptation that was defined as well as the characteristics of the primary study that represent the context in which the adaptation occurs. In some cases, other aspects of context can also be used, such as the point in time that the adaptation occurs (e.g., after a month, after two months, one month before termination of the primary study, etc.). This can help the computer system 210 assess whether the timing for a proposed adaptation is appropriate or if the preference in a field of research is to initiate certain types of adaptations at certain times. The machine learning model can thus be trained with these examples to (i) evaluate input feature values characterizing a study and a proposed adaptation, and (ii) output one or more scores indicating the suitability of the adaptation, such as similarity of the input feature values to sets representing successful study adaptations.

In many cases, for a given study, the computer system 210 may generate multiple different proposed adaptations with different sets of parameters, e.g., variations of data to collect, different sets of participant activities, different participant selection criteria and different proposed cohorts, etc. The computer system 210 can evaluate each of these proposed adaptations using the models to score them on how similar they are to the selected adaptations, and thus how likely the proposed adaptations are to be selected and implemented by a researcher. Scores for the different proposed adaptations can be used to filter or rank the different proposed adaptations, so that the computer system 210 recommends or implements only the adaptations with the highest value and highest likelihood of success. The computer system 210 can generate and evaluate different proposed adaptations repeatedly for each study, such as periodically (e.g., weekly, monthly, etc.), in response to detecting certain conditions (e.g., such as a pattern or similarity in outcomes that rises to the minimum criteria for relevance and significance), or on demand (such as in response to a user request for adaptation recommendations or a user action to access a adaptation generation interface).

The computer system 210 can perform various actions to inform researchers or administrators of monitoring programs of the adaptation opportunities that the computer system 210 identifies. The computer system 210 can cause a notification to be sent to a device associated with a researcher when a high-scoring adaptation opportunity is determined, e.g., as an email, text message, mobile device notification, notice through a user interface of a study management tool, etc. The computer system 210 can provide, for display, information showing the pattern or similarity that provided the new adaptation opportunity, similarities and differences between the sub-study and the primary study, scores and predictions regarding the effectiveness of the adapted study, characteristics of the adaptation (e.g., data to be collected, data collection parameters, participant activities, selection criteria, proposed cohort, etc.).

In some cases, the computer system 210 can provide a list of new adaptation options for display in an interface that a user can browse and view the factors in monitoring data that prompted the opportunity, the topic or question to be addressed in the new monitoring program, the parameters for the monitoring program (e.g., cohort size, duration, participant activities, data to be collected, participant selection criteria, etc.), the set of users or devices selected to be in the monitoring group for the new monitoring program, and so on. The computer system 210 can indicate the scores for each adaptation opportunity, for the potential new monitoring program overall and/or with respect to the individual factors (e.g., enrollment likelihood, compliance likelihood, retention or completion likelihood, expected data quality, expected statistical power, sensor or other technology requirements for participants, etc.). The user interface can enable a researcher or other user to browse the different opportunities, filter the opportunities (e.g., filter by topic, keyword, score range, types of data measured, etc.), and view details for each. The user interface can also provide features to view information about proposed members of the monitoring group and edit the group, such as by adding or removing members manually. Similarly, the user interface can provide controls for altering the participant selection criteria the computer system 210 proposed or to alter the pools of candidates from which the monitoring group is derived (e.g., from the a single primary research study in progress, from a different study, from a combination of multiple studies, from one or more databases or pools of candidates, from different combinations of candidate pools, etc.). After the user adjusts the parameters for participant selection, the computer system 210 can automatically adjust the proposed monitoring group, removing members that no longer meet the criteria or adding additional individuals that do meet the criteria.

In some implementations, the computer system 210 provides data for a user interface of an application, web application, native application, or other functionality at a researcher's device. The user interface can include controls that enable the researcher to select a new adaptation opportunity and confirm that it should be conducted. The computer system 210 can also update models and scoring algorithms based on feedback from researchers (e.g., which recommended sub-studies were accepted and conducted and which were ignored or rejected) and results of adaptations themselves (e.g., updating models and data sets on based on the received monitoring data).

In response to user selection or confirmation to carry out an adaptation to a monitoring program, the computer system 210 can generate the various components needed to carry out the adapted monitoring program. In some implementations, no confirmation may be needed, and the computer system 210 may automatically and adaptively generate adapted monitoring programs, such with appropriate configuration data and software to initiate monitoring. Generating or configuring an adapted monitoring program can include altering a study protocol, software and configuration data, content to be provided to users, and more. For example, the computer system 210 can store templates for portions of monitoring programs that include the documents and software needed for different types of monitoring. The computer system 210 can then use the parameters determined for the adaptation (e.g., data to be collected, participant activities, cohort selection criteria, etc.) to select from a repository of content to build the server-side and client-side components needed to carry out the adapted monitoring program. For example, according to the monitoring determined for the adapted monitoring program, the computer system 210 can set the timing of messages to participants, set the configuration settings to enable and disable sensors for making measurements, select surveys and other content to present to users, and so on. The information can be compiled into program data that the computer system 210 uses to send instructions to the devices involved in the study to prompt action from time to time during the study (e.g., sending message just-in-time to cause a device to send a notification or show a survey). In addition or as an alternative, the computer system 210 can generate configuration data that causes a receiving device to change an ongoing monitoring plan that is managed by an application on the device (e.g., configuration data that instructs an application to perform daily measurements of the parameters needed for the adapted monitoring program).

The process 3200 includes configuring one or more devices to perform monitoring for the second monitoring program (3210). The computer system 210 can store user profiles that indicate device identifiers, phone numbers, electronic addresses, and other information for communicating with user devices over a communication network such as the Internet. With this profile information, the computer system 210 can send invitations to devices associated with the participants selected for a cohort of the adapted monitoring program as discussed above. The computer system 210 can receive user consent information and confirmation that the users agree to participate in the new sub-study. The computer system 210 can then send configuration data that causes the devices of the new participants to perform the monitoring actions of the adapted monitoring program (e.g., initiating recurring sensor measurements, presenting surveys for user input, reporting data collected to the computer system 210 over a network, etc.).

The monitoring that the devices in the second group performs includes acquiring data for second types of data specified by the adapted monitoring program and providing the acquired data to a server, such as the computer system 210, over the communication network. This step enables the computer system 210 to cause reconfiguration of the remote devices in the monitoring group for the adapted monitoring program.

The computer system 210 can configure devices and cause them to acquire data for the second types of data and providing the acquired data to a server over the communication network. This can include distributing a program module for the adapted monitoring program or other configuration data to remote devices associated with users selected for the adapted program's cohort(s). Distributing the configuration data can include transmitting, to each of the one or more devices, configuration data configured to adjust operation of the remote devices to set or change sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements.

The configuration data can set parameters for operating and using various types of sensors including accelerometers, gyroscope sensors, inertial measurement units, GPS receivers, cameras, microphones, pressure sensors, heart rate sensors, EKG sensors, and more. The configuration data can also instruct measurements to be performed using connected devices, such as weight scales, glucometers, blood pressure cuffs, and so on.

The configuration data can be configured to adjust operation of the remote devices to set or change data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements.

The configuration data can be configured to adjust operation of the remote devices to set or change network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data.

The configuration data can cause remote devices to perform various changes or configuration actions, often without requiring user action once the user enrolls in the program. The actions can include: enabling or disabling a sensor of the remote device or a device communicatively coupled to the remote device; setting or changing sensor parameters used by the remote device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements; setting or changing data storage parameters used by the remote device to format or store data acquired for the program to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements; setting or changing network communication parameters used by the remote device to report data acquired for the program to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data; setting or changing power usage parameters of the remote device, including changing a device power state or sleep setting of the remote device; altering a user interface of an application installed at the remote device, including changing a set of interactive user input controls presented in the user interface; setting or changing interactive content to be presented by the remote device as part of the program, the interactive content including at least one survey, prompt, or electronic form; or setting or changing parameters for presenting the interactive content that includes at least one of timing, frequency, format, triggers, or contexts for providing the interactive content.

Figure 33:
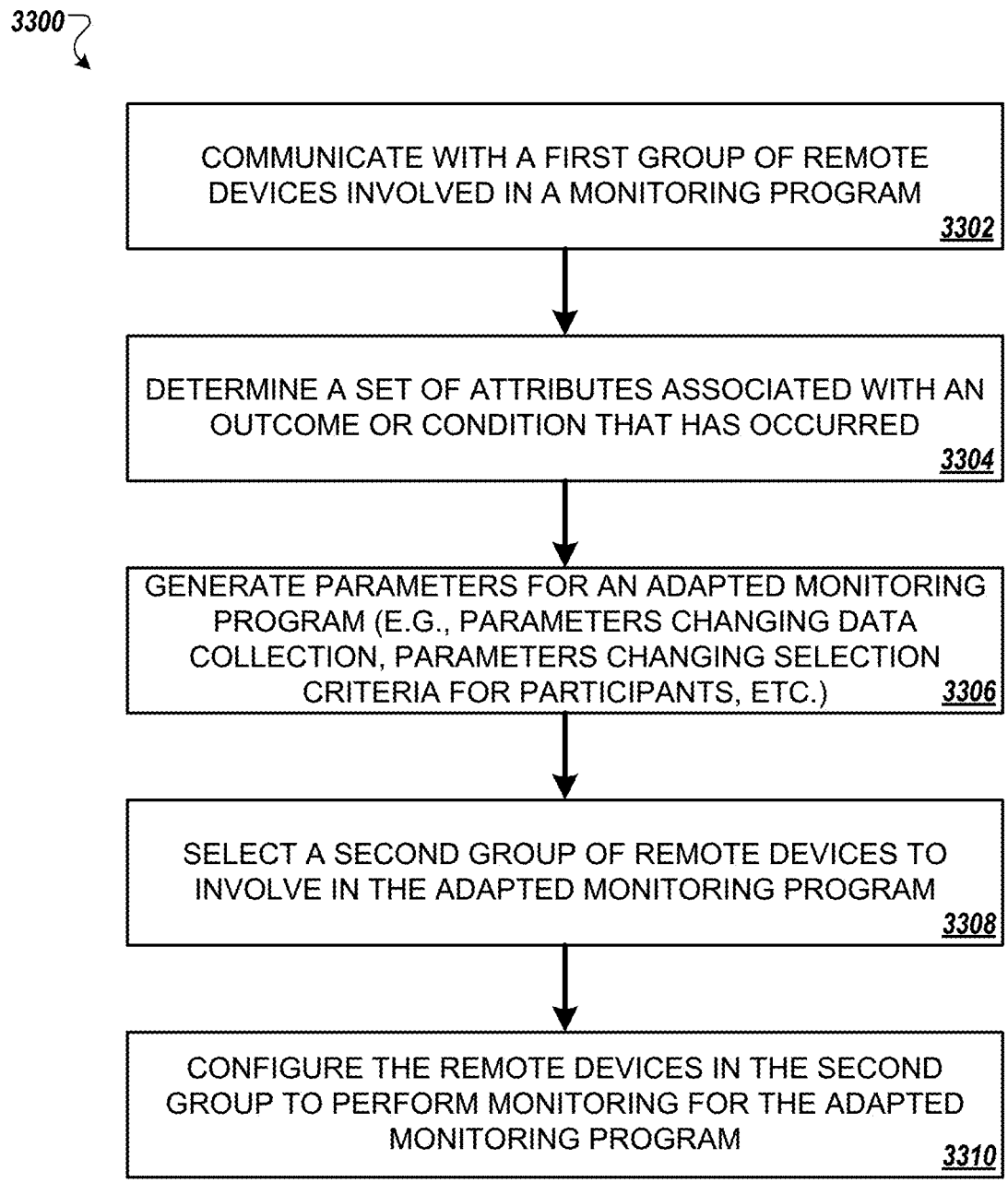

FIG. 33 is a flow diagram that illustrates a process 3300 for managing and adapting monitoring programs. The process 3300 can improve the efficiency and effectiveness of monitoring using remote devices, including by adaptively changing monitoring to maximize monitoring coverage without the need to deploy or enroll large numbers of new devices. The process 3300 can be performed by one or more computers, such as the computer system 210. The process 3300 can optionally include features of the process 3200 and other functions discussed above.

The process 3300 includes communicating with a first group of remote devices involved in a monitoring program that involves collection of data from the remote devices over a communication network (3302). This can include receiving, from each of the remote devices over the communication network, a series of messages including monitoring data collected by the remote device at different times for first types of data specified by the monitoring program. The communication can include other features as discussed above for step 3202 of the process 3200 and as discussed above generally.

The process 3300 includes determining, based on the data collected from the remote devices, a set of attributes associated with an outcome or condition that has occurred for multiple of the remote devices (3304). The computer system 210 can evaluate similarities among the devices and users involved in the outcomes that represent an opportunity for further monitoring. If the computer system 210 detects an outcome of interest (e.g., outliers in monitoring data, low compliance with study requirements, a symptom reported, etc.), the computer system 210 analyzes the subset from among the monitoring group (e.g., primary study cohort) that have that outcome. The computer system 210 can assess the distribution of different attributes among the subset for which an outcome or condition has occurred, and determine which attributes are most highly shared or most similar among the subset. In this process, the computer system 210 can also compare the subset or cluster of participants associated with the outcomes with those that do not experience the outcome, to determine which attribute values or ranges are most correlated with the outcome and which are not.

For example, if 10 participants out of 200 participants in a cohort experience sleep disturbances, the computer system 210 can identify similarities among the attributes of the 10 participants that experienced the sleep disturbances. The similarities may be in many different types of attributes, e.g., in demographic attributes, health status, health history, family medical history, history, behavior, context (e.g., time, locations, activities performed, etc.), or other aspects. By examining the similarities among the subset of the monitoring group involved in the pattern, the computer system 210 can evaluate whether there are shared attributes or combinations of attributes that set the members of the subset apart from others in the monitoring group, and so may make the outcomes or conditions of interest more likely. If so, the shared or similar attributes can provide the computer system 210 a basis for creating customized selection criteria to select for the participant types and situations in which the outcome of interest occurs. As a result, the system can use the similarities among the attributes of members of the subset to identify the participant types, device types, contexts, or other factors that are most likely to lead to the outcomes or conditions to be investigated.

The process 3300 includes generating parameters for an adapted monitoring program (3306). The parameters include selection criteria to select devices to provide data in the second monitoring program. For example, the computer system 210 can select participants and their devices (e.g., user devices such as smart phones) that have the set of attributes associated with the outcome.

The computer system 210 may determine determining, for a particular attribute (e.g., height, weight, age, heart rate, etc.) a range of attribute values based on a range or distribution of attribute values for the particular attribute among the attributes associated with the respective devices in the subset, and then determine the selection criteria to include devices or users having attribute values for the particular attribute in the determined range. In other words the computer system 210 can add a constraint to the selection criteria of a primary research study, where the constraint is determined based on and would encompass a majority of the devices or users in the subset.

In selecting devices and participants to monitor in a adapted monitoring program, the computer system 210 can include a variety of candidates in addition to those who experienced the outcomes that prompted adaptation. For example, if five people in a clinical trial experience sleep disturbances, those five people may be included in a sleep-related cohort, but the computer system 210 can additionally expand the cohort to others who have characteristics in common with or similar to the five that experienced the sleep disturbance. As a result, the cohort may include fifty people from the original study who are in a same category for age, health status, etc. Expanding the sub-study in this way allows the computer system 210 to provide monitoring that is more likely to capture information describing the onset of events and conditions that prompted the adaptation or adjustment to a cohort, providing information to characterize the environmental factors, user actions, behavioral factors, context, etc., and the progression of health parameters over time that make the event or condition more likely or less likely. This technique also provides a larger representative sample, allowing the system to better characterize the frequency or likelihood that the event or condition will occur. In some cases, the computer system 210 may apply other criteria to the selection of the cohort for the adapted monitoring program, which may cause some or all of the five people that experienced the sleep disturbance to be omitted. Examples include requiring a minimum level of historical or predicted compliance with study requirements, a minimum historical or predicted data quality from monitoring, device compatibility with the requirements of the sub-study (e.g., whether a user's phone, watch, activity tracker, etc. have the sensors, software compatibility, or networking capabilities, etc. to participate), health requirements for a participant, meeting eligibility criteria, etc. Thus, even one of the participants whose experiences or monitoring data lead to an adaptation may be omitted if, for example, the participant's compliance history is poor or the participant does meet one of the criteria for inclusion in the cohort.

The computer system 210 can determine selection criteria with which to select participants or devices for the adapted monitoring program. The computer system 210 can start with the selection criteria for the original monitoring program, which may set various conditions for participant attributes (e.g., age, health status, physiological measurements in certain ranges, etc.), for device capabilities (e.g., a requirement for users to have a smartphone, an activity tracker, or other technology), behavior, history, etc. The selection criteria can include inclusion criteria (e.g., attributes that participants are required to have) as well as exclusion criteria (e.g., attributes that, if present, disqualify a candidate from participating). From the original selection criteria, the computer system 210 can apply additional restrictions to narrow the scope of the selection criteria, to focus in on the attributes and context for which the outcome or condition occurred which prompted monitoring. For example, a study cohort may include 200 people in an age range from 18 to 67 years old. Of the cohort, a subset 10 people may experience sleep disturbances or some other symptom or difference in outcome compared to the rest of the cohort. The computer system 210 may determine commonalities or similarities among the subset, such as that they each were over age 40 and had low levels of physical exercise. From this, the computer system 210 generate selection criteria tailored to address this context or set of attributes, by adding additional selection criteria that new participants for a new cohort or monitoring group in the adapted monitoring program should be over age 40 and have low exercise levels. This allows the adapted monitoring program to include participants of the same or similar type as those that experience an outcome of interest, to monitor the likelihood or occurrence of that outcome in a context where it seems likely to occur. The computer system 210 can include the participants for whom the outcome has already been detected (e.g., the 10 with the sleep disturbance). The selection criteria enables selection of others that have similar backgrounds and characteristics, and so monitoring them can investigate the onset of the outcome in the context where it is most likely, as well as assess the prevalence or likelihood at which the outcome occurs in a in a systematic way with more detailed monitoring than in the original monitoring program.

In some implementations, the computer system 210 may set selection criteria that include more than just the range of backgrounds linked to the outcomes or conditions to be investigated. For example, one or more shared attributes can be set as requirements for selection, while one or more other shared attributes are not required, so that the new monitoring program cohort can collect data that allows the contrast between the results of the two groups to be determined. For example, even if the sleep disturbance symptoms occurred mostly in people that had low exercise, the computer system 210 may not restrict eligibility based on exercise, to allow a range of exercise levels that can help determine the impact of those different levels on the outcome.

Another factor that the computer system 210 can consider in setting the selection criteria is the size of the candidate pools and the quality of candidates (e.g., historical and predicted levels of enrollment, retention/study completion, compliance, data quality, etc.) for different combinations of the attributes that may be restricted. For example, if a subset experiencing a symptom has three different similarities identified, e.g., most of the subset is in a particular age range, has a certain gene variant, and has high social activity. The computer system 210 can determine, for each of these three factors and for the different possible combinations of them, the number of candidates (or specifically high-quality candidates with good predicted retention, compliance, etc.) that would meet the criteria from among the cohort for the original monitoring program. For example, out of 1000 people in the original cohort, 300 may be in the appropriate age range, 15 may have the gene variant, and 234 may have high social activity. Only 7 individuals may have all three factors. Optionally, the computer system 210 can expand the search for candidates outside the cohort for the original cohort, such as to find candidates in other cohorts or from a database of potential participants. The computer system 210 can compare the number of candidates identified for the different sets of possible selection criteria with a minimum threshold, such as a minimum of 50 individuals needed. This minimum can be a predetermined level or can be calculated by the computer system 210 to determine a level needed to achieve a desired statistical power. The computer system 210 can then select selection criteria determined to leave enough qualifying candidates to allow the new monitoring program to meet the minimum levels. When there are similar numbers of candidates available for different combinations of selection criteria, the computer system 210 may prioritize individual requirements (e.g., age requirement vs. gene variant) according to the degree of correlation to the outcome to be investigated. For example, if the age distribution is relatively wide but the presence of the gene variant is in nearly all members of the subset, the computer system 210 can determine to prioritize the gene variant criterion over the age criterion as it is more linked to the outcome to be investigated.

In some implementations, when determining selection criteria, the computer system 210 may expand the selection criteria to be broader in some respects than selection criteria for the primary monitoring program. For example, a research study may detect a symptom for a subset of people in which a majority have a particular gene variant or other attribute. The selection criteria for the primary monitoring program may limit participants to those residing in a certain geographical area or who have certain factors in their medical history. The computer system 210 may omit these requirements from the selection criteria for the new monitoring program, to expand the pool of potential candidates.

The computer system 210 can use the selection criteria to select particular users and/or devices as candidates for an adapted monitoring program. For example, the computer system 210 can use user profiles for members of a the original study cohort to determine which members satisfy the selection criteria for an added cohort or portion of an adapted monitoring program. The computer system 210 can also rank or filter the candidates based on quality measures (e.g., historical or predicted likelihoods of completion/retention, compliance, enrollment if invited, etc.). The computer system 210 can identify individuals and associated devices (e.g., user devices such as phones of candidates) that can then be included in a proposed cohort for the sub-study.

The process 3300 includes selecting a second group of remote devices to involve in the adapted monitoring program based on profiles or sets of attributes associated with the remote devices (3308). The computer system 210 can use the selection criteria to select particular users and/or devices as candidates for the adapted monitoring program. For example, the computer system 210 can use user profiles for members of a primary study's cohort to determine which members satisfy the selection criteria for the adapted monitoring program. The computer system 210 can also rank or filter the candidates based on quality measures (e.g., historical or predicted likelihoods of completion/retention, compliance, enrollment if invited, etc.). The computer system 210 can identify individuals and associated devices (e.g., user devices such as phones of candidates) that can then be included in a proposed cohort for the adapted monitoring program.

With the proposed adapted monitoring program cohort, the computer system 210 can evaluate the likely results using historical data, statistical models, machine learning models, and so on. For example, given the attributes of the participants in the adapted monitoring program cohort, the computer system 210 can make predictions regarding the composition of the adapted monitoring program cohort that would be enrolled (e.g., size, diversity of participants (such as distribution across different attributes of interest), etc.), composition of the portion of the adapted monitoring program cohort expected to comply with the requirements of the adapted monitoring program, and other factors.

The computer system 210 can evaluate the viability of the potential adapted monitoring program, based on the characteristics of the adapted monitoring program (e.g., data types to collect, parameters specifying how to collect the data, participant activities, etc.), the pool of candidates, and/or a specific set of candidates identified for the new monitoring group. For example, given the attributes and backgrounds of the people in a proposed cohort for the adapted monitoring program, the computer system 210 can assess: whether expected rates of enrollment, retention/completion, compliance, and sufficient data quality meet minimums; whether the proposed cohort meets the minimum size constraints; whether the cohort provides at least a target level of statistical power; and whether the cohort provides sufficient diversity for attributes of interest (e.g., age, sex, race, comorbidities, geographic location, etc.). For example, the computer system 210 can consider whether there are sufficient candidates to support the adapted monitoring program in the monitoring group for the original monitoring program or in other pools of candidates (e.g., in cohorts for other research studies, in a database of historical research study participants, in a database of individuals indicating interest in participating in research, etc. Even if a pattern of outcomes warrants further monitoring, if the pool of candidates is too small support a successful adapted monitoring program (e.g., 7 people meeting needed criteria and 50 needed to provide a usable data set), the computer system 210 may determine that the sub-study is not viable and so should not be recommended or conducted.

As discussed for process 3200 of FIG. 32, the computer system 210 can evaluate the set of devices and/or users selected for the proposed adapted monitoring program cohort, to assess the expected outcomes of performing the adapted monitoring program with the selected cohort (e.g., expected rates of enrollment and retention/completion, rates and levels of compliance with adapted monitoring program requirements, expected data quality, expected statistical power, diversity among different categories of participants at the end of the sub-study, and so on). The computer system 210 can score these different expected outcomes and rank or filter a set of different adaptation options to determine the best one or more adaptations to recommend, to provide information about in a message or user interface (such as the UI of a research study creation or management tool). The computer system 210 can provide information about all of these evaluations, including expected results and comparisons to reference values and similar example studies, to researchers over a network such as through a web page, web application, native application, etc.

The computer system 210 can also provide, to a device of a researcher over a network, information indicating any or all of the parameters of the proposed adaptation, such as the data types to be collected, the data collection techniques and other methodology, participant activities (including medication administration), the cohort selection criteria determined, and so on. The interface can enable the researcher to edit and adjust the parameters for an adapted monitoring program and save the results to be implemented.

The computer system 210 can provide functionality for researchers to select an adaptation, edit or alter the parameters, confirm that the adaptation should be carried out. Of course, in some implementations the computer system 210 may be enabled to automatically create and implement adaptations with or without user confirmation, for example, if the criteria meets predetermined standards that a researcher has set or approved.

The process 3300 includes configuring the remote devices in the selected second group to perform monitoring for the adapted monitoring program (3310). This can include features as discussed for step 3210 above.

The data collected by the computer system 210 in monitoring programs such as research studies and used in any of the examples and implementations discussed above can include a variety of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected in monitoring programs and used by the computer system 210 (e.g., to collect from participants in monitoring programs, to generate feature values, to train models, to detect opportunities for sub-studies, etc.) can include various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g. data from spirometers, pulse oximeters);

Neurological-related biodata (e.g. data from EEG monitors);

Behavior data (e.g. movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data and other scales/reporting mechanism);

Positioning and location data (e.g., GPS data, gyroscope, altimeter, accelerometer, linear acceleration, received signal strength indicator from nearby emitters such as WiFi access points, Bluetooth sensors and sensor networks and Cellular towers); Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., IsopropylC$_3$H$_8$O or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a cathode ray tube or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

The invention claimed is:

1. A method performed by one or more computers, the method comprising:

communicating, by one or more computers, with a group of remote devices involved in a research study that involves collection of data from the remote devices over a communication network, each of the remote devices corresponding to a different participant in a cohort of the research study, wherein communicating with the remote devices comprises receiving, from each of the remote devices over the communication network, a series of messages including monitoring data collected by the remote device at different times for one or more types of data specified by the research study;

based on the data collected from the remote devices, determining, by the one or more computers, that an outcome or condition has occurred for a first subset of participants in the cohort during a period of time, wherein the first subset comprises multiple participants in the cohort, and wherein the cohort includes a second subset of participants for which the outcome or condition was not detected to occur during the period of time; and based on determining that the outcome or condition has occurred for the first subset of participants:

generating, by the one or more computers, parameters to adapt monitoring performed for participants in the cohort, wherein the parameters change a procedure for collecting the one or more types of data or add an additional type of data to collect from participants in the cohort; and configuring, by the one or more computers, the remote devices of at least some of the participants in the cohort to perform adapted monitoring according to the generated parameters, such that (i) the remote devices of the participants in the first subset and the second subset are configured to perform the adapted monitoring and (ii) acquired data generated using the adapted monitoring is provided to a server over the communication network.

2. The method of claim 1, wherein generating the parameters and configuring the remote devices are performed based on a prevalence of a health outcome among the participants in the cohort of the research study.

3. The method of claim 1, further comprising:
based on determining that the outcome or condition has occurred for the first subset of participants, determining, by the one or more computers, selection criteria to select additional participants to include in the cohort for the research study, including:
determining, for a particular attribute, a range of attribute values based on a range or distribution of attribute values for the particular attribute among the participants in the first subset; and
determining the selection criteria to specify addition of participants to the cohort having attribute values for the particular attribute that are in the determined range.

4. The method of claim 1, wherein the generated parameters specify collection of a second type of data that is different from the one or more types of data specified by the research study; and
wherein configuring the remote devices comprises distributing, to the one or more devices, a software module or configuration data over the communication network, wherein the software module or configuration data is configured to cause the one or more devices to collect data of the second type of data.

5. The method of claim 4, wherein the second type of data comprises measurements made using one or more sensors.

6. The method of claim 5, wherein the measurements comprise one or more physiological or behavioral measurements.

7. A system comprising:
one or more computers; and
one or more computer-readable media storing instructions that are operable, when executed by the one or more computers, to cause the system to perform operations comprising:
communicating, by one or more computers, with a group of remote devices involved in a research study that involves collection of data from the remote devices over a communication network, each of the remote devices corresponding to a different participant in a cohort of the research study, wherein communicating with the remote devices comprises receiving, from each of the remote devices over the communication network, a series of messages including monitoring data collected by the remote device at different times for one or more types of data specified by the research study;
based on the data collected from the remote devices, determining, by the one or more computers, that an outcome or condition has occurred for a first subset of participants in the cohort during a period of time, wherein the first subset comprises multiple participants in the cohort, and wherein the cohort includes a second subset of participants for which the outcome or condition was not detected to occur during the period of time; and
based on determining that the outcome or condition has occurred for the first subset of participants:
generating, by the one or more computers, parameters to adapt monitoring performed for participants in the cohort, wherein the parameters change a procedure for collecting the one or more types of data or add an additional type of data to collect from participants in the cohort; and
configuring, by the one or more computers, the remote devices of at least some of the participants in the cohort to perform adapted monitoring according to the generated parameters, such that (i) the remote devices of the participants in the first subset and the second subset are configured to perform the adapted monitoring and (ii) acquired data generated using the adapted monitoring is provided to a server over the communication network.

8. The system of claim 7, wherein generating the parameters and configuring the remote devices are performed based on a prevalence of a health outcome among the participants in the cohort of the research study.

9. The system of claim 7, wherein the operations further comprise:
based on determining that the outcome or condition has occurred for the first subset of participants, determining, by the one or more computers, selection criteria to select additional participants to include in the cohort for the research study, including:
determining, for a particular attribute, a range of attribute values based on a range or distribution of attribute values for the particular attribute among the participants in the first subset; and
determining the selection criteria to specify addition of participants to the cohort or users having attribute values for the particular attribute that are in the determined range.

10. The system of claim 7, wherein the generated parameters specify collection of a second type of data that is different from the one or more types of data specified by the research study; and
wherein configuring the remote devices comprises distributing, to the one or more devices, a software module or configuration data over the communication network, wherein the software module or configuration data is configured to cause the one or more devices to collect data of the second type of data.

11. The system of claim 10, wherein the second type of data comprises measurements made using one or more sensors.

12. The system of claim 11, wherein the measurements comprise one or more physiological or behavioral measurements.

13. One or more non-transitory computer-readable media storing instructions that are operable, when executed by one or more computers, to cause the one or more computers to perform operations comprising:
communicating, by one or more computers, with a group of remote devices involved in a research study that involves collection of data from the remote devices over a communication network, each of the remote devices corresponding to a different participant in a cohort of the research study, wherein communicating with the remote devices comprises receiving, from each of the remote devices over the communication network, a series of messages including monitoring data collected by the remote device at different times for one or more types of data specified by the research study;
based on the data collected from the remote devices, determining, by the one or more computers, that an outcome or condition has occurred for a first subset of participants in the cohort during a period of time, wherein the first subset comprises multiple participants in the cohort, and wherein the cohort includes a second subset of participants for which the outcome or condition was not detected to occur during the period of time; and based on determining that the outcome or condition has occurred for the first subset of participants:

generating, by the one or more computers, parameters to adapt monitoring performed for participants in the cohort, wherein the parameters change a procedure for collecting the one or more types of data or add an additional type of data to collect from participants in the cohort; and configuring, by the one or more computers, the remote devices of at least some of the participants in the cohort to perform adapted monitoring according to the generated parameters, such that (i) the remote devices of the participants in the first subset and the second subset are configured to perform the adapted monitoring and (ii) acquired data generated using the adapted monitoring is provided to a server over the communication network.

14. The method of claim 1, wherein configuring the remote devices of at least some of the participants in the cohort comprises configuring a remote device of each of the participants in the cohort to perform the adapted monitoring.

15. The method of claim 1, comprising determining, by the one or more computers, selection criteria to select additional participants to include in the cohort for the research study; and selecting, by the one or more computers, one or more additional participants for the cohort based on the determined selection criteria.

16. The method of claim 15, wherein determining the selection criteria is based at least in part among levels of diversity among attribute values of the participants in the cohort.

17. The method of claim 1, further comprising, based on determining that the outcome or condition has occurred for the first subset of participants, adjusting treatment parameters of the research study to alter treatment provided to participants in the first subset and the second subset.

18. The method of claim 1, wherein the outcome or condition is a health result.

19. The method of claim 1, wherein the outcome or condition is a level of data quality achieved.

20. The method of claim 1, wherein the outcome or condition is a compliance status indicating a level of compliance in performing actions that participants are requested to perform as part of participation in the research study.

21. The method of claim 1, wherein the monitoring data is generated at least in part through an initial set of participant activities that a study protocol for the research study specifies for participants in the research study to perform; and wherein the parameters specify a set of participant activities for participants in the research study that is different from the initial set of participant activities that the study protocol for the research study specifies.

22. The method of claim 1, further comprising, based on determining that the outcome or condition has occurred for the first subset of participants, adapting parameters of the research study to change a structure of the research study from an initial state specified by a study protocol for the research study, including by changing at least one of:

a duration of the research study;
a number of cohorts in the research study; or
a size of one or more cohorts of the research study.

23. The method of claim 1, wherein the method includes changing a study protocol for the research study to indicate the generated parameters for the adapted monitoring.

24. The method of claim 1, wherein a study protocol for the research study specifies a constraint that specifies a predetermined scope of adaptations permitted for the research study; and wherein generating the parameters to adapt monitoring comprises generating the parameters, based on the constraint in the study protocol, to maintain the parameters for the adapted monitoring within the predetermined scope of adaptations permitted for the research study.

* * * * *